(12) United States Patent
Nygren

(10) Patent No.: US 10,774,375 B2
(45) Date of Patent: Sep. 15, 2020

(54) METHODS AND COMPOSITIONS FOR THE QUANTITATION OF MITOCHONDRIAL NUCLEIC ACID

(71) Applicant: Agena Bioscience, Inc., San Diego, CA (US)

(72) Inventor: Anders Olof Herman Nygren, San Diego, CA (US)

(73) Assignee: Agena Bioscience, Inc., San Diego, CA (US)

( * ) Notice: Subject to any disclaimer, the term of this patent is extended or adjusted under 35 U.S.C. 154(b) by 691 days.

(21) Appl. No.: 15/268,058

(22) Filed: Sep. 16, 2016

(65) Prior Publication Data

US 2017/0101673 A1   Apr. 13, 2017

Related U.S. Application Data

(60) Provisional application No. 62/220,749, filed on Sep. 18, 2015, provisional application No. 62/295,804, filed on Feb. 16, 2016.

(51) Int. Cl.
*C12Q 1/6851* (2018.01)
*C12Q 1/686* (2018.01)
(Continued)

(52) U.S. Cl.
CPC .......... *C12Q 1/6851* (2013.01); *C12Q 1/686* (2013.01); *C12Q 1/6848* (2013.01);
(Continued)

(58) Field of Classification Search
CPC .. C12Q 1/6848; C12Q 1/6851; C12Q 1/6858; C12Q 1/686; C12Q 2523/122; C12Q 2535/125; C12Q 2600/156
See application file for complete search history.

(56) References Cited

U.S. PATENT DOCUMENTS 6,344,322 B1   2/2002 Polyak et al.
6,605,433 B1   8/2003 Fliss et al.
(Continued)

FOREIGN PATENT DOCUMENTS

WO   WO 2008/117027   10/2008
WO   WO 2009/046445   4/2009
(Continued)

OTHER PUBLICATIONS

International Preliminary Report on Patentability dated Mar. 20, 2018 for International Application No. PCT/US2016/052279, filed on Sep. 16, 2016 and published as WO 2017/049180 on Mar. 23, 2017.

(Continued)

*Primary Examiner* — Jeremy C Flinders
(74) *Attorney, Agent, or Firm* — Grant IP, Inc.

(57) ABSTRACT

Provided herein are products and processes for the quantitation of mitochondrial nucleic acid in a sample from a subject. In certain aspects are multiplex methods for determining dosage of mitochondrial nucleic acid relative to genomic nucleic acid for a sample from a subject including amplifying sets of mitochondrial polynucleotides and genomic polynucleotides from nucleic acid for a sample under amplification conditions. In certain aspects are multiplex methods for determining dosage of mitochondrial nucleic acid relative to genomic nucleic acid for a sample from a subject including amplifying sets of mitochondrial polynucleotides and amplifying sets of nuclear polynucleotides from nucleic acid for a sample under amplification conditions.

19 Claims, 1 Drawing Sheet

Specification includes a Sequence Listing.

(51) Int. Cl.
    *C12Q 1/6848*   (2018.01)
    *C12Q 1/6858*   (2018.01)
(52) U.S. Cl.
    CPC ..... *C12Q 1/6858* (2013.01); *C12Q 2535/122* (2013.01); *C12Q 2535/125* (2013.01); *C12Q 2600/156* (2013.01)

(56) References Cited

U.S. PATENT DOCUMENTS

| | | | |
|---|---|---|---|
| 6,750,021 | B2 | 6/2004 | Polyak et al. |
| 8,003,317 | B2 | 8/2011 | Beaulieu et al. |
| 8,349,566 | B2 | 1/2013 | Beaulieu et al. |
| 2005/0287533 | A1 | 12/2005 | Ehrich et al. |
| 2005/0287592 | A1 | 12/2005 | Kless |
| 2009/0026082 | A1 | 1/2009 | Rothberg et al. |
| 2009/0029377 | A1 | 1/2009 | Lo et al. |
| 2011/0091900 | A1* | 4/2011 | Williams ............ C12Q 1/6851 435/6.16 |
| 2013/0237428 | A1 | 9/2013 | Beaulieu et al. |
| 2016/0203260 | A1 | 7/2016 | Lo et al. |

FOREIGN PATENT DOCUMENTS

| | | |
|---|---|---|
| WO | WO 2010/004265 | 1/2010 |
| WO | WO 2017/049180 | 3/2017 |

OTHER PUBLICATIONS

Beaucage and Caruthers, "Deoxynucleoside Phosphoramidites—A New Class of Key Intermediates for Deoxypolynucleotide Synthesis," (1981) Tetrahedron Letts. 22:1859-1862.

Cantsilieris et al., "Correlating Multiallelic Copy Number Polymorphisms with Disease Susceptibility" Human Mutation (2012) 34:1-13.

Cote et al., "Changes in mitochondrial DNA as a marker of nucleoside toxicity in HIV-Infected patients" New England Journal of Medicine (2002) 346(11):811-820.

Ellinger et al., "Circulating mitochondrial DNA in serum: A universal diagnostic biomarker for patients with urological malignancies" Urologic Oncology: seminars and Original Investigations (2012) 30:509-515.

Fernandez-Jimenez et al., "Accuracy in copy number calling by qPCR and PRT: a matter of DNA" PLoS One (2011) 6(12):e28910.

Goidts et al., "Identification of large-scale human-specific copy number differences by inter-species array comparative genomic hybridization" Hum. Genet. (2006) 119(1-2):185-198, abstract only.

Harris et al., "Single-Molecule DNA Sequencing of a Viral Genome," Science 320:106-109 (2008).

Hosgood III et al., "Mitochondrial DNA copy number and lung cancer risk in a prospective cohort study" Carcinogenesis (2010) 31(5):847-849.

Jurinke et al., "MALDI-TOF mass spectrometry: a versatile tool for high-performance DNA analysis", Mol. Biotechnol. 26, 147-164 (2004).

Kampira et al., "Peripheral blood mitochondrial DNA/nuclear DNA (mtDNA/nDNA) ratio as a marker of mitochondrial toxicities of stavudine containing antiretroviral therapy in HIV-infected Malawian patients" OMICS (2014) 18(7):438-445.

Kim et al., "Role of Mitochondrial Dysfunction in Insulin Resistance" Circulation Research (2008) 102:401-414.

Malik et al., "Is mitochondrial DNA content a potential biomarker of mitochondrial dysfunction?" Mitochondrion (2012) 13(5):481-492.

Margulies et al., "Genome sequencing in microfabricated high-density picolitre reactors," Nature 437:376-380 (2005).

Metzker, "Sequencing technologies—the next generation," Nature Rev 11:31-46 (2010).

Moudrianakis et al., "Base Sequence Determination in Nucleic Acids with the Electron Microscope, III. Chemistry and Microscopy of Guaninie-Labeled DNA," Proc Natl Acad Sci USA. Mar. 1965; 53:564-71.

Needham-Van Devanter et al. "Characterization of an adduct between CC-1065 and defined oligodeoxynucleotide," (1984) Nucleic Acids Res. 12:6159-6168.

Pearson and Regnier "High-Performance Anion-Exchange Chromatography of Oligonucleotides," (1983) J. Chrom. 255:137-149.

Phillips et al., "Simultaneous quantification of mitochondrial DNA copy number and deletion ratio: A multiplex real-time PCR assay" Scientific Reports (2014) 4:DOI: 10.1038/srep03887.

Pierce et al., "Comparison of the GenMark Diagnostics eSensor Respiratory Viral Panel to Real-Time PCR for Detection of Respiratory Viruses in Children" J. Clin. Microbiol. (2012) 50(11):3458-3465.

Pinto and Moraes, "Mitochondrial genome changes and neurodegenerative diseases" Biochimica et Biophysica Acta (2014) 1842:1198-1207.

Quispe-Tintaya et al., "Fast mitochondrial DNA isolation from mammalian cells for next-generation sequencing" BioTechniques (2013) 55:133-136.

Schon et al., Human mitochondrial DNA: roles of inherited and somatic mutations Nature Reviews Genetics (2012) 13:878-890.

Van Gisbergen et al., "How do changes in the mtDNA and mitochondrial dysfunction influence cancer and cancer therapy? Challenges, opportunities and models" Mutation Research (2015) 764:16-30.

Veal et al., "Automated design of paralogue ratio test assays for the accurate and rapid typing of copy number variation" Bioinformatics (2013) 29(16):1997-2003.

Volkerding et al. "Next-generation sequencing: from basic research to diagnostics," Clin Chem 55:641-658 (2009).

Walker et al., "Multiplex paralogue ratio tests for accurate measurement of multiallelic CNVs" Genomics (2009) 93:98-103.

International Search Report and Written Opinion dated Feb. 3, 2017 for International Application No. PCT/US2016/052279, filed on Sep. 16, 2016 and published as WO 2017/049180 on Mar. 23, 2017.

* cited by examiner

METHODS AND COMPOSITIONS FOR THE QUANTITATION OF MITOCHONDRIAL NUCLEIC ACID

RELATED APPLICATIONS

This patent application claims the benefit of U.S. Provisional Patent Application No. 62/295,804, filed Feb. 16, 2016, entitled METHODS AND COMPOSITIONS FOR THE QUANTITATION OF MITOCHONDRIAL NUCLEIC ACID, naming Anders Nygren as inventor. This patent application also claims the benefit of U.S. Provisional Application No. 62/220,749, filed Sep. 18 2015, entitled METHODS AND COMPOSITIONS FOR THE QUANTITATION OF MITOCHONDRIAL NUCLEIC ACID, naming Anders Nygren as inventor. The subject matter of each of these applications is incorporated in its entirety by reference thereto, including texts, tables and drawings.

SEQUENCE LISTING

The instant application contains a Sequence Listing which has been submitted electronically in ASCII format and is hereby incorporated by reference in its entirety. Said ASCII copy, created on Dec. 16, 2016, is named AGB-7003-UT_SL.txt and is 332,274 bytes in size.

SUMMARY

Mitochondria are the energy center of the cell. Every cell has about 100 to 200 mitochondria and every mitochondria contains 1-10 copies of mitochondrial DNA. Qualitative changes in mitochondrial DNA (mtDNA), such as mutations and deletions, have been implicated in many diseases such as diabetes mellitus and cancer. Mitochondria are also vulnerable to oxidative stress.

Provided are methods and kits for determining dosage of mitochondrial nucleic acid relative to genomic nucleic acid.

Provided in certain aspects are multiplex methods for determining dosage of mitochondrial nucleic acid relative to genomic nucleic acid for a sample from a subject including: (a) amplifying sets of mitochondrial polynucleotides and genomic polynucleotides from nucleic acid for a sample under amplification conditions, wherein: (i) each set comprises a mitochondrial polynucleotide and a genomic polynucleotide; (ii) the mitochondrial polynucleotide and the genomic polynucleotide are native; (iii) the mitochondrial polynucleotide of a set differs from the mitochondrial polynucleotide of the other sets and the genomic polynucleotide of a set differs from the genomic polynucleotide of the other sets; (iv) the mitochondrial polynucleotide and the genomic polynucleotide of a set are defined by formula $^{5'}X\text{-}V\text{-}Y^{3'}$; (v) $^{5'}X\text{-}V\text{-}Y^{3'}$ represents a contiguous sequence of nucleotides present in the mitochondrial polynucleotide and the genomic polynucleotide; (vi) X and Y of the mitochondrial polynucleotide are identical to X and Y, respectively, of the genomic polynucleotide in each set; (vii) V is one or more nucleotide positions at which a nucleotide of the mitochondrial polynucleotide differs from the corresponding nucleotide of the genomic polynucleotide in a set; thereby providing a plurality of amplified sets each comprising amplicons corresponding to all or a portion of the mitochondrial polynucleotide and amplified genomic polynucleotide in the set; (b) comparing (i) the amplicons corresponding to the mitochondrial polynucleotide, to (ii) the amplicons corresponding to the genomic polynucleotide for each set, thereby generating a comparison; and (c) determining the relative dosage of mitochondrial nucleic acid to genomic nucleic acid in the sample based on the comparison.

Provided in other aspects, are kits including amplification primer pairs that comprise polynucleotides chosen from polynucleotides in Table 2 and Table 4, or portions thereof.

Provided in another aspect, is a multiplex method for determining dosage of extrachromosomal nucleic acid relative to genomic nucleic acid for a sample from a subject including: (a) amplifying sets of extrachromosomal polynucleotides and genomic polynucleotides from nucleic acid for a sample under amplification conditions, wherein: (i) each set comprises an extrachromosomal polynucleotide and a genomic polynucleotide; (ii) the extrachromosomal polynucleotide and the genomic polynucleotide are native; (iii) the extrachromosomal polynucleotide of a set differs from the extrachromosomal polynucleotide of the other sets and the genomic polynucleotide of a set differs from the genomic polynucleotide of the other sets; (iv) the extrachromosomal polynucleotide and the genomic polynucleotide of a set are defined by formula $^{5'}X\text{-}V\text{-}Y^{3'}$; (v)$^{5'}X\text{-}V\text{-}Y^{3'}$ represents a contiguous sequence of nucleotides present in the extrachromosomal polynucleotide and the genomic polynucleotide; (vi) X and Y of the extrachromosomal polynucleotide are identical to X and Y, respectively, of the genomic polynucleotide in each set; (vii) V is one or more nucleotide positions at which a nucleotide of the extrachromosomal polynucleotide differs from the corresponding nucleotide of the genomic polynucleotide in a set; thereby providing a plurality of amplified sets each comprising amplicons corresponding to all or a portion of the extrachromosomal polynucleotide and amplified genomic polynucleotide in the set; (b) comparing (i) the amplicons corresponding to the extrachromosomal polynucleotide, to (ii) the amplicons corresponding to the genomic polynucleotide for each set, thereby generating a comparison; and (c) determining the relative dosage of extrachromosomal nucleic acid to genomic nucleic acid in the sample based on the comparison.

Provided in another aspect, is a multiplex method for determining dosage of extrachromosomal nucleic acid relative to genomic nucleic acid for a sample from a subject including: (a) amplifying sets of extrachromosomal polynucleotides and genomic polynucleotides from nucleic acid for a sample under amplification conditions, wherein: (i) each set comprises an extrachromosomal polynucleotide and a genomic polynucleotide; (ii) the extrachromosomal polynucleotide and the genomic polynucleotide are native; (iii) the extrachromosomal polynucleotide of a set differs from the extrachromosomal polynucleotide of the other sets and the genomic polynucleotide of a set differs from the genomic polynucleotide of the other sets; (iv) the extrachromosomal polynucleotide and the genomic polynucleotide of a set are defined by formula $^{5'}X\text{-}V\text{-}Y^{3'}$; (v) the $^{5'}X\text{-}V\text{-}Y^{3'}$ represents a contiguous sequence of nucleotides present in the extrachromosomal polynucleotide and the genomic polynucleotide; (vi) X and Y of the extrachromosomal polynucleotide are identical to X and Y, respectively, of the genomic polynucleotide in each set; (vii) V is one or more nucleotide positions at which a nucleotide of the extrachromosomal polynucleotide differs from the corresponding nucleotide of the genomic polynucleotide in a set; thereby providing a plurality of amplified sets each comprising amplicons corresponding to all or a portion of the extrachromosomal polynucleotide and amplified genomic polynucleotide in the set; (b) comparing (i) the amplicons corresponding to the extrachromosomal polynucleotide, to (ii) the amplicons corresponding to the genomic polynucleotide for each set, thereby generating a comparison; and (c) determining the relative dosage of extrachromosomal nucleic acid to genomic nucleic acid in the sample based on the comparison.

Provided in another aspect, is a multiplex method for determining dosage of mitochondrial nucleic acid relative to nuclear nucleic acid for a sample from a subject, including: (a) contacting nucleic acid of a sample from a subject comprising nucleic acid of a first species comprising a nuclear genome and a mitochondrial genome with nucleic acid of a second species comprising nucleic acid of a nuclear genome and a mitochondrial genome for which the copy number of the mitochondrial genome and the copy number of the nuclear genome are known, wherein the nuclear genome of the first species has regions that are paralogous to regions of the nuclear genome of the second species and the mitochondrial genome of the first species has regions that are paralogous to regions of the mitochondrial genome of the second species; (b) amplifying sets of nuclear polynucleotides of paralogous regions of the nuclear genome of the first species and the nuclear genome of the second species and sets of mitochondrial polynucleotides of paralogous regions of the mitochondrial genome of the first species and the mitochondrial genome of the second species from the nucleic acid of (a) under amplification conditions, wherein: (i) each set comprises a polynucleotide of the nuclear genome of the first species and a polynucleotide of the nuclear genome of the second species or each set comprises a polynucleotide of the mitochondrial genome of the first species and a polynucleotide of the mitochondrial genome of the second species; (ii) the mitochondrial polynucleotides and the nuclear polynucleotides are native; (iii) the mitochondrial polynucleotides of a set differ from the mitochondrial polynucleotides of the other sets and the nuclear polynucleotides of a set differ from the nuclear polynucleotides of the other sets; (iv) the mitochondrial polynucleotides of a set and the nuclear polynucleotides of a set are defined by formula $^{5'}$J-V-K$^{3'}$; (v) $^{5'}$J-V-K$^{3'}$ represents a contiguous sequence of nucleotides present in the mitochondrial polynucleotides or in the nuclear polynucleotides; (vi) J and K of the mitochondrial polynucleotides of a set are identical and J and K of the nuclear polynucleotides of a set are identical; and (vii) V is one or more nucleotide positions at which a nucleotide of the mitochondrial polynucleotides of the first and second species of a set differ or V is one or more nucleotide positions at which a nucleotide of the nuclear polynucleotides of the first and second species of a set differ; thereby providing a plurality of amplified sets each comprising amplicons corresponding to all or a portion of the mitochondrial polynucleotides of a set or amplicons corresponding to all or a portion of the amplified nuclear polynucleotides of a set; (c) comparing the amplicons corresponding to the mitochondrial polynucleotide of the second species to the amplicons corresponding to mitochondrial polynucleotide of the first species in a set and comparing the amplicons corresponding to the nuclear polynucleotide of the second species to the amplicons corresponding to the nuclear polynucleotide of the first species in a set, thereby generating comparisons; and (d) determining the relative dosage of mitochondrial nucleic acid to the nuclear nucleic acid in the sample from the subject based on comparisons of (c) for all sets. In certain embodiments, the comparisons in (c) are a ratio of the amount of the amplicons corresponding to the polynucleotide of the mitochondrial genome of the second species to the amount of amplicons corresponding to polynucleotide of the mitochondrial genome of the first species in a set and a ratio of the amount of the amplicons corresponding to the polynucleotide of the nuclear genome of the second species to the amount of amplicons corresponding to the polynucleotide of the nuclear genome of the first species in a set, and determining the relative dosage of mitochondrial nucleic acid to nuclear nucleic acid in the sample from the subject in (d) is based on the ratios. In certain aspects, the first species is human. In some aspects, the second species is chimpanzee.

Provided in other aspects, are kits including amplification primer pairs that comprise polynucleotides chosen from polynucleotides in Table 7, or portions thereof.

Certain embodiments are described further in the following description, examples, claims and drawings.

BRIEF DESCRIPTION OF THE DRAWINGS

The drawings illustrate certain embodiments of the technology and are not limiting. For clarity and ease of illustration, the drawings are not made to scale and, in some instances, various aspects may be shown exaggerated or enlarged to facilitate an understanding of particular embodiments.

DETAILED DESCRIPTION

Figure 1A:
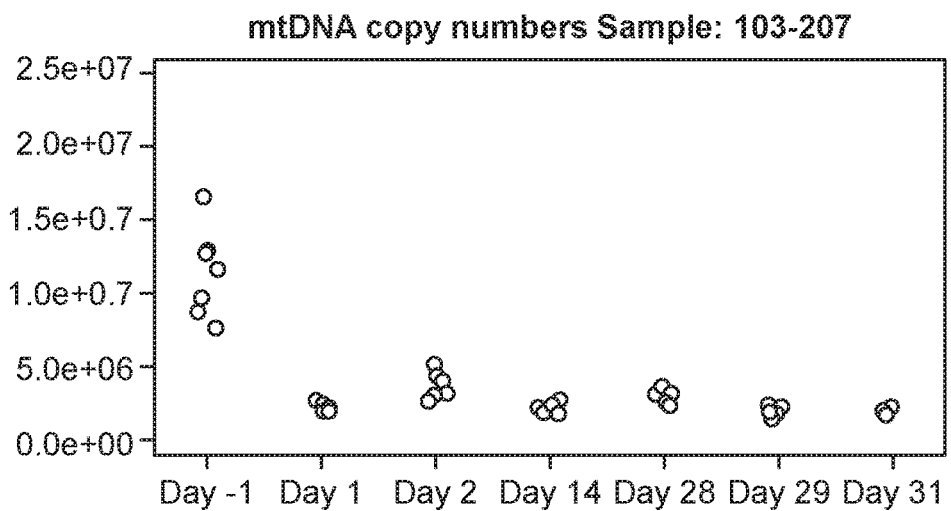
FIG. 1A-C show mitochondria copy numbers (FIG. 1A), nuclear copy numbers (FIG. 1B) mitochondrial vs nuclear ratios (FIG. 1C) calculated based on a multiplex assay targeting human and chimpanzee paralogs for a single subject over a period of time.

Certain of methods and kits provided herein enable the interrogation of both mitochondrial nucleic acid and genomic nucleic acid in a single reaction and do not require control samples or internal standards in order to compare amplicons representing these species. Certain methods and kits provided herein also do not require positive controls.

Certain of methods and kits provided herein enable the interrogation of both mitochondrial nucleic acid and nuclear (genomic) nucleic acid in a single reaction and utilize an internal standard that simulates the huge difference in copy number between the mitochondrial genome and the nuclear genome, as well as allowing for multiplex assays requiring little to no optimization. Certain methods and kits provided herein also utilize an internal standard.

The multiplex methods and kits provided herein by examining multiple regions of the mitochondrial DNA genome allow for both the determination of mitochondrial dosage and the detection of mitochondrial deletions in a single reaction. The examination of multiple locations of the mitochondrial genome also minimizes technical variability, allowing for a more accurate assessment of mitochondrial dosage.

Technology described herein can be utilized to assess a state of a cell, tissue, body function, medical condition (e.g., disease) or disorder, progression of a medical condition or disorder or treatment of a medical condition or disorder, for example. Certain embodiments of the technology are useful for (i) determining the likelihood a test subject has a medical condition or disorder or is pre-disposed to having a medical condition or disorder, (ii) determining the presence or absence of a progression of a medical condition or disorder in a test subject, (iii) determining the presence or absence of a response to a therapy administered to a test subject having the medical condition or disorder, (iv) determining whether a dosage of a therapeutic agent administered to a test subject should be increased, decreased or maintained; the like or combination of the foregoing. Various aspects and embodiments of the technology are described hereafter.

Nucleic Acid

Provided in part herein are methods for nucleic acid quantification. The terms "nucleic acid", "nucleic acid molecule" and "polynucleotide" may be used interchangeably throughout the disclosure. Non-limiting examples of nucleic acid include deoxyribonucleic acid (DNA, e.g., complementary DNA (cDNA), genomic DNA (gDNA) also referred to as nuclear DNA, mitochondrial DNA (mtDNA), episomal DNA, and the like), ribonucleic acid (RNA, e.g., message RNA (mRNA), short inhibitory RNA (siRNA), ribosomal RNA (rRNA), transfer RNA (tRNA), microRNA, RNA highly expressed by the fetus or placenta, and the like), DNA or RNA analogs (e.g., containing base analogs, sugar analogs and/or a non-native backbone and the like), RNA/DNA hybrids and polyamide nucleic acids (PNAs). A nucleic acid can be in single-stranded or double-stranded form, and unless otherwise limited, can encompass known analogs of natural nucleotides that can function in a similar manner as naturally occurring nucleotides.

A nucleic acid can be in any form useful for conducting processes herein (e.g., linear, circular, supercoiled, single-stranded, double-stranded and the like). A nucleic acid may be, or may be from, mitochondria, a plasmid, phage, virus, an episomal or extrachromosomal element, a chloroplast, a plastid, autonomously replicating sequence (ARS), centromere, artificial chromosome, chromosome, or other nucleic acid able to replicate or be replicated in vitro or in a host cell, a cell, a cell nucleus or cytoplasm of a cell, in certain embodiments. A nucleic acid in some embodiments can be from a single chromosome (e.g., a nucleic acid sample may be from one chromosome of a sample obtained from a diploid organism). The term also may include, as equivalents, derivatives, variants and analogs of RNA or DNA synthesized from nucleotide analogs, single-stranded (e.g., "sense" or "antisense", "plus" strand or "minus" strand, "forward" reading frame or "reverse" reading frame) and double-stranded polynucleotides. Deoxyribonucleotides include deoxyadenosine, deoxycytidine, deoxyguanosine and deoxythymidine. For RNA, the base thymine is replaced with uracil. A nucleic acid may be prepared using a nucleic acid obtained from a subject.

Circulating Cell-Free Nucleic Acid

Nucleic acid can be circulating cell-free nucleic acid in certain embodiments. The terms "circulating cell-free nucleic acid," "extracellular nucleic acid" and "cell free nucleic acid" as used herein refer to nucleic acid isolated from a source having substantially no cells. Circulating cell-free nucleic acid (ccfNA, ccfDNA) can be present in and obtained from blood. Circulating cell-free nucleic acid often includes no detectable cells and may contain cellular elements or cellular remnants. Non-limiting examples of acellular sources for extracellular nucleic acid are blood, blood plasma, blood serum, cerebrospinal fluid, spinal fluid, and urine. Obtaining circulating cell-free nucleic acid includes obtaining a sample directly (e.g., collecting a sample, e.g., a test sample) or obtaining a sample from another who has collected a sample. Without being limited by theory, circulating cell-free nucleic acid may be a product of cell apoptosis and cell breakdown, which provides basis for extracellular nucleic acid often having a series of lengths across a spectrum (e.g., a "ladder").

Circulating cell-free nucleic acid can include different nucleic acid species, and therefore is referred to herein as "heterogeneous." For example, blood serum or plasma from a person having cancer can include nucleic acid from cancer cells and nucleic acid from non-cancer cells. In another non-limiting example, blood serum or plasma from a pregnant female can include maternal nucleic acid and fetal nucleic acid. In another non-limiting example, blood serum or plasma from a pregnant female can include maternal nucleic acid, placental nucleic acid and fetal nucleic acid. In another non-limiting example, blood serum or plasma can include nuclear or genomic nucleic acid and mitochondrial nucleic acid. At least two different nucleic acid species can exist in different amounts in circulating cell-free nucleic acid and sometimes are referred to as minority species and majority species. In certain instances, a minority species of nucleic acid is from an affected cell type (e.g., cancer cell, wasting cell, cell attacked by immune system). In some instances, a minority species of circulating cell-free nucleic acid sometimes is about 1% to about 40% of the overall nucleic acid (e.g., about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40% of the nucleic acid is minority species nucleic acid). In circulating cell-free nucleic acid mitochondrial nucleic acid can be present in greater amounts than genomic or nuclear nucleic acid and can be considered the majority species. In some embodiments, a minority species of circulating cell-free nucleic acid is of a length of about 500 base pairs or less (e.g., about 80, 85, 90, 91, 92, 93, 94, 95, 96, 97, 98, 99 or 100% of minority species nucleic acid is of a length of about 500 base pairs or less). In some embodiments, a minority species of circulating cell-free nucleic acid is of a length of about 300 base pairs or less (e.g., about 80, 85, 90, 91, 92, 93, 94, 95, 96, 97, 98, 99 or 100% of minority species nucleic acid is of a length of about 300 base pairs or less). In some embodiments, a minority species of circulating cell-free nucleic acid is of a length of about 200 base pairs or less (e.g., about 80, 85, 90, 91, 92, 93, 94, 95, 96, 97, 98, 99 or 100% of minority species nucleic acid is of a length of about 200 base pairs or less). In some embodiments, a minority species of circulating cell-free nucleic acid is of a length of about 150 base pairs or less (e.g., about 80, 85, 90, 91, 92, 93, 94, 95, 96, 97, 98, 99 or 100% of minority species nucleic acid is of a length of about 150 base pairs or less). In some embodiments, the majority nucleic acid species of circulating cell-free nucleic acid (mitochondrial) is of a length that is less than the length of the minority nucleic acid species of circulating cell-free nucleic acid (nuclear or genomic). In some embodiments, the length of the majority nucleic acid species (mitochondrial) is about 50 base pairs and the length of the minority nucleic acid species (genomic or nuclear) is about 166 base pairs.

Cellular Nucleic Acid

Nucleic acid can be cellular nucleic acid in certain embodiments. The term "cellular nucleic acid" as used herein refers to nucleic acid isolated from a source having intact cells. Non-limiting examples of sources for cellular nucleic acid are blood cells, tissue cells, organ cells, tumor cells, hair cells, skin cells, and bone cells.

In some embodiments, nucleic acid is from peripheral blood mononuclear cells (PBMC). A PBMC is any blood cell having a round nucleus, such as, for example, lymphocytes, monocytes or macrophages. These cells can be extracted from whole blood, for example, using ficoll, a hydrophilic polysaccharide that separates layers of blood, with PBMCs forming a buffy coat under a layer of plasma. Additionally, PBMCs can be extracted from whole blood using a hypotonic lysis which preferentially lyses red blood cells and leaves PBMCs intact, and/or can be extracted using a differential centrifugation process known in the art.

Mitochondrial DNA can be extracted from whole blood using standard methods for DNA extraction from whole blood. Mitochondrial DNA can be enriched using a protocol as described in BioTechniques 55:133-136 (September 2013), hereby incorporated in its entirety by reference.

Using standard methods of DNA extraction both mitochondrial and nuclear DNA can be obtained from a sample. For example, standard DNA extraction kits can be used with buffy coat or buccal swaps for both mitochondrial and nuclear DNA and the corresponding kits when targeting circulating cell free DNA.

Nucleic Acid for Internal Standard

In some embodiments the copy number or genomic equivalents of the mitochondrial genome and the nuclear genome of nucleic acid of a second species is known or can be determined. The known equivalents of the mitochondrial genome and the nuclear genome for the nucleic acid of the second species serve as internal standards that can be used in conjunction with paralog assay results in determining the copy number of the mitochondrial genome and the copy number of the nuclear genome of the nucleic acid of the first species. The copy number of the mitochondrial nucleic acid and the copy number of the nuclear nucleic acid can be used to determine the mitochondrial/nuclear ratio for the nucleic acid of the sample from a subject (i.e., dosage). The exact amounts of mitochondrial and nuclear genomic equivalents or copy numbers for the nucleic acid of a second species (e.g., chimpanzee) that is utilized in an assay can be determined using methods such digital PCR. In some embodiments, the method is digital droplet PCR with a mitochondrial specific primer pair and a nuclear specific primer pair. In certain embodiments, ratios for mitochondrial to nuclear genomic equivalents for the internal standard species can be from approximately 500 to approximately 5000. A standard ratio for a chimpanzee is approximately 1200. As described below the nucleic acid for the internal standard is obtained from a genome (species) with regions in its mitochondrial and nuclear genome that are paralogs with regions of the mitochondrial and nuclear genome of the nucleic acid of the sample from a subject.

Samples

Nucleic acid in or from a suitable sample can be utilized in a method described herein. A mixture of nucleic acids can comprise two or more nucleic acid fragment species having different nucleotide sequences, different fragment lengths, different origins (e.g., genomic origin, mitochondrial vs nuclear (genomic) origin, fetal vs. maternal origin, cell or tissue origin, cancer vs. non-cancer origin, tumor vs. non-tumor origin, sample origin, subject origin, and the like), or combinations thereof. In some embodiments, nucleic acid is analyzed in situ (e.g., in a sample; in a subject), in vivo, ex vivo or in vitro.

Nucleic acid often is isolated from a sample obtained from a subject. A subject can be any living or non-living organism, including but not limited to a human, a non-human animal, a plant, a bacterium, a fungus or a protist. Any human or non-human animal can be selected, including but not limited to mammal, reptile, avian, amphibian, fish, ungulate, ruminant, bovine (e.g., cattle), equine (e.g., horse), caprine and ovine (e.g., sheep, goat), swine (e.g., pig), camelid (e.g., camel, llama, alpaca), monkey, ape (e.g., gorilla, chimpanzee), ursid (e.g., bear), poultry, dog, cat, mouse, rat, fish, dolphin, whale and shark. A subject may be male or female.

Nucleic acid may be isolated from any type of suitable biological specimen or sample (e.g., a test sample). A sample or test sample can be any specimen that is isolated or obtained from a subject (e.g., a human subject, a pregnant female or a non-human subject). Non-limiting examples of specimens include fluid or tissue from a subject, including, without limitation, cerebrospinal fluid, spinal fluid, lavage fluid (e.g., bronchoalveolar, gastric, peritoneal, ductal, ear, arthroscopic), urine, feces, sputum, saliva, nasal mucous, prostate fluid, lavage, semen, lymphatic fluid, bile, tears, sweat, breast milk, breast fluid, biopsy sample (e.g., cancer biopsy), cell or tissue sample (e.g., from the liver, lung, spleen, pancreas, colon, skin, bladder, eye, brain, esophagus, head, neck, ovary, testes, prostate, the like or combination thereof). In some embodiments, a biological sample may be blood and sometimes a blood fraction (e.g., plasma or serum). As used herein, the term "blood" encompasses whole blood or any fractions of blood, such as serum and plasma as conventionally defined, for example. Blood or fractions thereof often comprise nucleosomes (e.g., maternal and/or fetal nucleosomes). Nucleosomes comprise nucleic acids and are sometimes cell-free or intracellular. Blood also comprises buffy coats. Buffy coats sometimes are isolated by utilizing a ficoll gradient. Buffy coats can comprise white blood cells (e.g., leukocytes, T-cells, B-cells, platelets, and the like). In some embodiments, buffy coats comprise maternal and/or fetal nucleic acid. Blood plasma refers to the fraction of whole blood resulting from centrifugation of blood treated with anticoagulants. Blood serum refers to the watery portion of fluid remaining after a blood sample has coagulated. Fluid or tissue samples often are collected in accordance with standard protocols hospitals or clinics generally follow. For blood, an appropriate amount of peripheral blood (e.g., between 3-40 milliliters) often is collected and can be stored according to standard procedures prior to or after preparation. A fluid or tissue sample from which nucleic acid is extracted may be acellular (e.g., cell-free). In some embodiments, a fluid or tissue sample may contain cellular elements or cellular remnants. In some embodiments cancer cells may be included in the sample.

Nucleic Acid Isolation and Processing

Nucleic acid can be isolated using any suitable technique. Cell lysis procedures and reagents are known in the art and may generally be performed by chemical (e.g., detergent, hypotonic solutions, enzymatic procedures, and the like, or combination thereof), physical (e.g., French press, sonication, and the like), or electrolytic lysis methods. Any suitable lysis procedure can be utilized. For example, chemical methods generally employ lysing agents to disrupt cells and extract the nucleic acids from the cells, followed by treatment with chaotropic salts. Physical methods such as freeze/thaw followed by grinding, the use of cell presses and the like also are useful. High salt lysis procedures also are commonly used. For example, an alkaline lysis procedure may be utilized. The latter procedure traditionally incorporates the use of phenol-chloroform solutions, and an alternative phenol-chloroform-free procedure involving three solutions can be utilized. In the latter procedures, one solution can contain 15 mM Tris, pH 8.0; 10 mM EDTA and 100 ug/ml Rnase A; a second solution can contain 0.2N NaOH and 1% SDS; and a third solution can contain 3M KOAc, pH 5.5. These procedures can be found in Current Protocols in Molecular Biology, John Wiley & Sons, N.Y., 6.3.1-6.3.6 (1989), incorporated herein in its entirety.

Nucleic acid may be isolated at a different time point as compared to another nucleic acid, where each of the samples is from the same or a different source. A nucleic acid may be from a nucleic acid library, such as a cDNA or RNA library, for example. A nucleic acid may be a result of nucleic acid purification or isolation and/or amplification of nucleic acid molecules from the sample. Nucleic acid provided for processes described herein may contain nucleic acid from one sample or from two or more samples (e.g., from 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, or 20 or more samples).

Nucleic acid may be provided for conducting methods described herein without processing of the sample(s) containing the nucleic acid, in certain embodiments. In some embodiments, nucleic acid is provided for conducting methods described herein after processing of the sample(s) containing the nucleic acid. For example, a nucleic acid can be extracted, isolated, purified, partially purified or amplified from the sample(s). The term "isolated" as used herein refers to nucleic acid removed from its original environment (e.g., the natural environment if it is naturally occurring, or a host cell if expressed exogenously), and thus is altered by human intervention (e.g., "by the hand of man") from its original environment. The term "isolated nucleic acid" as used herein can refer to a nucleic acid removed from a subject (e.g., a human subject). An isolated nucleic acid can be provided with fewer non-nucleic acid components (e.g., protein, lipid) than the amount of components present in a source sample. A composition comprising isolated nucleic acid can be about 50% to greater than 99% free of non-nucleic acid components. A composition comprising isolated nucleic acid can be about 90%, 91%, 92%, 93%, 94%, 95%, 96%, 97%, 98%, 99% or greater than 99% free of non-nucleic acid components. The term "purified" as used herein can refer to a nucleic acid provided that contains fewer non-nucleic acid components (e.g., protein, lipid, carbohydrate) than the amount of non-nucleic acid components present prior to subjecting the nucleic acid to a purification procedure. A composition comprising purified nucleic acid may be about 80%, 81%, 82%, 83%, 84%, 85%, 86%, 87%, 88%, 89%, 90%, 91%, 92%, 93%, 94%, 95%, 96%, 97%, 98%, 99% or greater than 99% free of other non-nucleic acid components. The term "purified" as used herein can refer to a nucleic acid provided that contains fewer nucleic acid species than in the sample source from which the nucleic acid is derived. A composition comprising purified nucleic acid may be about 90%, 91%, 92%, 93%, 94%, 95%, 96%, 97%, 98%, 99% or greater than 99% free of other nucleic acid species. For example, cancer cell nucleic acid can be purified from a mixture comprising cancer cell and non-cancer cell nucleic acid. In certain examples, nucleosomes comprising small fragments of cancer cell nucleic acid can be purified from a mixture of larger nucleosome complexes comprising larger fragments of non-cancer nucleic acid.

Mitochondrial and Genomic (Nuclear) Nucleic Acid

Provided herein are methods to determine the dosage of mitochondrial nucleic acid relative to genomic (nuclear) nucleic acid in a sample. In some embodiments, the nucleic acid is DNA.

Mitochondrial/Genomic (Nuclear) Paralogs

In some embodiments, mitochondrial and genomic polynucleotides are analyzed in sets of polynucleotides. In some embodiments the mitochondrial polynucleotide and the genomic polynucleotide of a set are referred to as a mitochondrial/genomic (nuclear) paralog. A mitochondrial/genomic (nuclear) paralog is a region in the mitochondrial genome with a similar or nearly identical region in the nuclear genome. The paralogous sequence can be any size but must contain one or more regions that are identical in the mitochondrial genome and the nuclear genome and one or more nucleotides that are different in the mitochondria genome and the nuclear genome. In some embodiments, the paralogous sequence includes one or two base pair mismatches.

As used herein, the term "set" can refer to a mitochondrial polynucleotide and a corresponding genomic polynucleotide (paralogs) that have the following characteristics: (i) a set comprises a mitochondrial polynucleotide and a genomic polynucleotide; (ii) the mitochondrial polynucleotide and the genomic polynucleotide of a set are native; (iii) the mitochondrial polynucleotide is different from the genomic polynucleotide in a set; (iv) the mitochondrial polynucleotide and the genomic polynucleotide of a set are defined by formula $5'X\text{-}V\text{-}Y3'$ and (v) the mitochondrial polynucleotide of a set differs from the mitochondrial polynucleotide of the other sets and the genomic polynucleotide of a set differs from the genomic polynucleotide of the other sets.

The term "native" as used herein refers to the sequence of nucleotides as it is present in a mitochrondrial genome or nuclear genome and that has not been modified, altered or rearranged.

As used herein the term "multiplex" refers to the analysis of more than one set of a mitochondrial polynucleotide and a genomic polynucleotide in a single reaction. The polynucleotides represent distinct and different regions of the mitochondrial genome and distinct and different regions of the nuclear genome.

In some embodiments, $5'X\text{-}V\text{-}Y3'$ represents a contiguous sequence of nucleotides present in the mitochondrial polynucleotide and the genomic polynucleotide and X and Y of the mitochondrial polynucleotide are identical to X and Y, respectively, of the genomic polynucleotide in each set. V is one or more nucleotide positions at which a nucleotide of the mitochondrial polynucleotide differs from the corresponding nucleotide of the genomic polynucleotide in a set (e.g., a mismatch, single nucleotide polymorphisms (SNPs)). V can also be an insertion or a deletion. In certain embodiments, V is a single nucleotide position.

As used herein, the term "identical" refers to defined portions (specific length) of mitochondrial and genomic polynucleotides for which the nucleotide sequence does not differ at any position. $5'X\text{-}V\text{-}Y3'$ can be any length or number of nucleotides. In some embodiments, $5'X\text{-}V\text{-}Y^3$ is about 30 to about 300 base pairs in length.

In some embodiments "dosage" is determined based on a comparison of mitochondrial nucleic acid (from mitochondrial genome) to genomic nucleic acid. In some embodiments "dosage" is a ratio of mitochondrial DNA to genomic DNA for a sample. In some embodiments "dosage" is a ratio of the amount of mitochondrial DNA to the amount of genomic DNA for a sample. In some embodiments, the comparison is a ratio of (i) the amount of the amplicons corresponding to the mitochondrial polynucleotide, to (ii) the amount of the amplicons corresponding to the genomic polynucleotide, in each set. A ratio could be either a comparison of the amount of the amplicons corresponding to the mitochondrial polynucleotide to the amount of the amplicons corresponding to the genomic polynucleotide or a comparison of the amount of the amplicons corresponding to the genomic polynucleotide to the amount of the amplicons corresponding to the mitochondrial polynucleotide. Sometimes dosage represents the copy number of mitochondrial DNA relative to the copy number of genomic DNA in a sample.

The term "amount" as used herein with respect to amplicons refers to any suitable measurement, including, but not limited to, copy number, weight (e.g., grams) and concentration (e.g., grams per unit volume (e.g., milliliter); molar units). In some embodiments, "amount" is determined based on analysis of a detectable parameter that correlates with amount; such as the quantification of a specific nucleotide at a defined position in a mitochondrial or a genomic polynucleotide (e.g., "V").

Mitochondrial/Mitochondrial Paralogs-Nuclear/Nuclear Paralogs

In some embodiments, mitochondrial polynucleotides of a first species present in a sample and mitochondrial polynucleotides of a second species provided as an internal standard are analyzed in sets of polynucleotides and nuclear polynucleotides of a first species present in a sample and nuclear polynucleotides of a second species provided as an internal standard are analyzed in sets of polynucleotides. In some embodiments, the mitochondrial polynucleotides of a set are referred to as a mitochondrial/mitochondrial paralog. In some embodiments, the nuclear polynucleotides of a set are referred to as a nuclear/nuclear paralog. A mitochondrial/mitochondrial paralog is a region in the mitochondrial genome of a first species with a similar or nearly identical region in the mitochondrial genome of a second species. A nuclear/nuclear paralog is a region in the nuclear genome of a first species with a similar or nearly identical region in the nuclear genome of a second species. The paralogous sequence can be any size but must contain one or more regions that are identical in the two mitochondrial genomes and one or more nucleotides that are different in the two mitochondrial genomes. For nuclear genomes, the paralogous sequence can be any size but must contain one or more regions that are identical in the two nuclear genomes and one or more nucleotides that are different in the two nuclear genomes. In some embodiments, the paralogous sequence includes one or two base pair mismatches.

The species of polynucleotides of a set can represent any two species where paralog regions occur in the mitochondrial genomes of the two species and where paralog regions occur in the nuclear genomes of the two species. In certain embodiments, the first species is human and second species is non-human. In some embodiments, the second species is chimpanzee. In certain embodiments, the nucleic acid of a sample from a subject is the first species and the nucleic acid providing an internal standard is the second species.

The term "set" can refer to a mitochondrial polynucleotide of a first species and a corresponding mitochondrial polynucleotide of a second species (paralogs) or can refer to a nuclear polynucleotide of a first species and a corresponding nuclear polynucleotide of a second species (paralogs) that have the following characteristics: (i) each set comprises a polynucleotide of the nuclear genome of the first species and a polynucleotide of the nuclear genome of the second species or each set comprises a polynucleotide of the mitochondrial genome of the first species and a polynucleotide of the mitochondrial genome of the second species; (ii) the mitochondrial polynucleotides and the nuclear polynucleotides are native; (iii) the mitochondrial polynucleotides of a set differ from the mitochondrial polynucleotides of the other sets and the nuclear polynucleotides of a set differ from the nuclear polynucleotides of the other sets; (iv) the mitochondrial polynucleotides of a set and the nuclear polynucleotides of a set are defined by formula $5'J\text{-}V\text{-}K3'$; (v) $5'J\text{-}V\text{-}K3'$ represents a contiguous sequence of nucleotides present in the mitochondrial polynucleotides or in the nuclear polynucleotides; (vi) J and K of the mitochondrial polynucleotides of a set are identical and J and K of the nuclear polynucleotides of a set are identical; and (vii) V is one or more nucleotide positions at which a nucleotide of the mitochondrial polynucleotides of the first and second species of a set differ or V is one or more nucleotide positions at which a nucleotide of the nuclear polynucleotides of the first and second species of a set differ.

The term "native" as used herein refers to the sequence of nucleotides as it is present in a mitochrondrial genome or nuclear genome and that has not been modified, altered or rearranged.

The term "multiplex" refers to the analysis of more than one set of a mitochondrial polynucleotide of a first species and a corresponding mitochondrial polynucleotide of a second species in a single reaction or more than one set of a nuclear polynucleotide of a first species and a corresponding nuclear polynucleotide of a second species in a single reaction. In some embodiments, the more than one set of mitochondrial polynucleotides and the more than one set of nuclear polynucleotides are in a single reaction. In some embodiments, the more than one set of mitochondrial polynucleotides and the more than one set of nuclear polynucleotides are in different reactions.

The mitochondrial polynucleotides of a set of a mitochondrial polynucleotide of a first species and a corresponding mitochondrial polynucleotide of a second species differs from the mitochondrial polynucleotides of other sets of mitochondrial polynucleotides. The nuclear polynucleotides of a set of a nuclear polynucleotide of a first species and a corresponding nuclear polynucleotide of a second species differs from the nuclear polynucleotides of other sets of nuclear polynucleotides. The polynucleotides represent distinct and different regions of the mitochondrial genomes and distinct and different regions of the nuclear genomes.

In some embodiments, $5'J\text{-}V\text{-}K3'$ represents a contiguous sequence of nucleotides present in the mitochondrial polynucleotides and J and K of the mitochondrial polynucleotides are identical in each set. In some embodiments, $5'J\text{-}V\text{-}K3'$ represents a contiguous sequence of nucleotides present in the nuclear polynucleotides and J and K of the nuclear polynucleotides are identical in each set. V is one or more nucleotide positions at which a nucleotide of the mitochondrial polynucleotides in a set differ or one or more nucleotide positions at which a nucleotide of the nuclear polynucleotides in a set differ. In some aspects V can be a mismatch or single nucleotide polymorphism (SNP). V can also be an insertion or a deletion. In certain embodiments, V is a single nucleotide position.

As used herein, the term "identical" refers to defined portions (specific length) of mitochondrial polynucleotides of a set or nuclear polynucleotides of a set for which the nucleotide sequences do not differ at any position.

$5'J\text{-}V\text{-}K3'$ can be any length or number of nucleotides. In some embodiments, $5'J\text{-}V\text{-}K3'$ is about 30 to about 300 base pairs in length.

In certain embodiments, a first species/second species paralog are analyzed together in an assay. In some embodiments, assays target nuclear paralogs. In some embodiments, assays target mitochondrial paralogs. In some embodiments, the first species/second species paralogs are human/chimpanzee paralogs. In some embodiments, an assay consists of a set of a mitochondrial polynucleotide of a first species and a corresponding mitochondrial polynucleotide of a second species that analyzed together. In some embodiments, an assay consists of set of a nuclear polynucleotide of a first species and a corresponding nuclear polynucleotide of a second species that are analyzed together. Certain ratios are based on the amounts of amplicons of a first and a second species determined in the assays that target mitochondrial paralogs. Certain ratios are based on the amounts of amplicons of a first and a second species determined in the assays that target nuclear paralogs.

In some embodiments "dosage" is determined based on a comparison of mitochondrial nucleic acid (from the mitochondrial genome) to nuclear nucleic acid (from the nuclear genome) for a first species. In some embodiments "dosage" is a ratio of mitochondrial DNA to nuclear DNA for a sample from a subject. In some embodiments "dosage" is a ratio of the amount of mitochondrial DNA to the amount of nuclear DNA for a sample from a subject. In some embodiments "dosage" is a ratio of the copy number of mitochondrial DNA to the copy number of nuclear DNA for a sample from a subject (e.g., first species or human). In some embodiments, the mitochondrial copy number for the nucleic acid of a first species can be derived based on the ratio of the amount of the mitochondrial polynucleotide of the first species and the amount of the mitochondrial polynucleotide of the second species as determined by assays targeting mitochondrial paralogs, in conjunction with the known value for the copy number of the mitochondrial nucleic acid (genome) of the second species. In some embodiments, the nuclear copy number for the nucleic acid of a first species can be derived based on the ratio of the amount of the nuclear polynucleotide of the first species and the amount of the nuclear polynucleotide of the second species as determined by assays targeting nuclear paralogs, in conjunction with the known value for the copy number of the nuclear nucleic acid (genome) of the second species.

In some embodiments, the subject is human and accordingly the nucleic acid of the first species is human and the nucleic acid of the second species is chimpanzee.

The term "amount" as used herein with respect to amplicons refers to any suitable measurement, including, but not limited to, copy number, weight (e.g., grams) and concentration (e.g., grams per unit volume (e.g., milliliter); molar units). In some embodiments, "amount" is determined based on analysis of a detectable parameter that correlates with amount; such as the quantification of a specific nucleotide at a defined position in a mitochondrial or a nuclear polynucleotide (e.g., "V").

Identification of Paralogs

The mitochondrial genome is a circular genome of about 16.5 Kb and contains 37 genes, 13 of which encode proteins. The mitochondrial genome can be is divided into short fragments of any length that is amenable to carrying out sequence comparison (e.g., 100 bp). Alignment techniques and sequence identity assessment methodology are known. Such analyses can be performed by using mathematical algorithms.

Mitochondrial/Genomic (Nuclear) Paralogs ($^5$'X-V-Y$^{3'}$)

Fragments of the mitochondrial genome are aligned with and compared to regions of a human genome based on defined criteria, such as, but not limited to, the number of mismatches that are allowed in the sequence (e.g., 1 mismatch, 2 mismatches, 5 mismatches, 10 mismatches, 15 mismatches, 20 mismatches, 25 mismatches) to identify similar or nearly identical regions. From these regions, those regions that fulfil the criteria specified for ($^5$'X-V-Y$^{3'}$) and the other criteria that define a set, as discussed above, are selected. A sufficient number of regions are chosen from different locations in the mitochondrial genome in order to span the mitochondrial genome and to provide a sufficient number of measurements to minimize technical variability. In some embodiments, regions are chosen so that at least one region is located in specific mitochondrial genes of interest. In some embodiments the number of sets is about 2 sets to about 20 sets. In some embodiments the number of sets is about 2 sets to about 10 sets. In some embodiments the number of sets is 10 sets. In some embodiments the number of sets is a least 5 sets.

In some embodiments, sets of mitochondrial and genomic polynucleotides are described in Table 1.

Mitochondrial/Mitochondrial Paralogs-Nuclear/Nuclear Paralogs ($^5$'J-V-K$^{3'}$)

Fragments of a mitochondrial genome of a first species are aligned with and compared to regions of a mitochondrial genome of a second species and fragments of a nuclear genome of a first species are aligned with and compared to regions of a nuclear genome of a second species based on defined criteria, such as, but not limited to, the number of mismatches that are allowed in the sequence (e.g., 1 mismatch, 2 mismatches, 5 mismatches, 10 mismatches, 15 mismatches, 20 mismatches, 25 mismatches) to identify similar or nearly identical regions. From these regions, those regions that fulfil the criteria specified for ($^5$'J-V-K$^{3'}$) and the other criteria that define a set, as discussed above, are selected. A sufficient number of regions are chosen from different locations in the mitochondrial genome in order to span the mitochondrial genome and to provide a sufficient number of measurements to minimize technical variability. In some embodiments, regions are chosen so that at least one region is located in specific mitochondrial genes of interest. A sufficient number of regions are chosen from different locations in the nuclear genome in order to provide a sufficient number of measurements to minimize technical variability. In some embodiments the number of sets of mitochondrial/mitochondrial paralogs and nuclear/nuclear paralogs are each about 2 sets to about 20 sets. In some embodiments, the number of sets of mitochondrial/mitochondrial paralogs and nuclear/nuclear paralogs are each about 2 sets to about 10 sets. In some embodiments, the number of sets is 10 sets. In some embodiments, the number of sets is a least 5 sets. In other embodiments, the number of sets of nuclear/nuclear paralogs is greater than the number of sets of mitochondrial/mitochondrial paralogs. For example, the number of sets of mitochondrial/mitochondrial paralogs and nuclear/nuclear paralogs are each about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475 or 500 sets, in some embodiments.

In some embodiments, sets of mitochondrial paralogs are described in Table 6.

Amplification

Often sets of mitochondrial polynucleotides and genomic polynucleotides from nucleic acid for a sample are amplified and then analyzed. Sometimes only a portion of a paralog $^5$'X-V-Y$^{3'}$ is amplified. In some embodiments, the length of an amplicon is about 30 base pairs to about 300 base pairs. An amplicon often includes at least a portion of X and Y regions and includes V. In some embodiments, an amplicon includes regions of a polynucleotide 5' of X and 3' of Y. In some embodiments, sets of mitochondrial polynucleotides and sets of nuclear polynucleotides from nucleic acid for a sample and an added internal standard are amplified and then analyzed. Sometimes only a portion of a paralog $^5$'J-V-K$^{3'}$ is amplified. In some embodiments, the length of an amplicon is about 30 base pairs to about 300 base pairs. An amplicon often includes at least a portion of J and K regions and includes V.

Amplification primers are chosen as described below. In some embodiments, amplifying is by a polymerase chain reaction (PCR) process.

Amplification conditions are known and can be selected for a particular nucleic acid that will be amplified. Amplification conditions include certain reagents some of which can include, without limitation, nucleotides (e.g., nucleotide triphosphates), modified nucleotides, oligonucleotides (e.g., primer oligonucleotides for polymerase-based amplification and oligonucleotide building blocks for ligase-based amplification), one or more salts (e.g., magnesium-containing salt), one or more buffers, one or more polymerizing agents (e.g., ligase enzyme, polymerase enzyme), one or more nicking enzymes (e.g., an enzyme that cleaves one strand of a double-stranded nucleic acid) and one or more nucleases (e.g., exonuclease, endonuclease, RNase). Any polymerase suitable for amplification may be utilized, such as a polymerase with or without exonuclease activity, DNA polymerase and RNA polymerase, mutant forms of these enzymes, for example. Any ligase suitable for joining the 5' of one oligonucleotide to the 3' end of another oligonucleotide can be utilized. Amplification conditions also can include certain reaction conditions, such as isothermal or temperature cycle conditions. Methods for cycling temperature in an amplification process are known, such as by using a thermocycle device. The term "cycling" refers to amplification (e.g. an amplification reaction or extension reaction) utilizing a single amplification primer pair or multiple amplification primer pairs where temperature cycling is used. In some embodiments, about 25 PCR amplification cycles to about 45 PCR amplification cycles are performed in. Amplification conditions also can, in some embodiments, include an emulsion agent (e.g., oil) that can be utilized to form multiple reaction compartments within which single nucleic acid molecule species can be amplified. Amplification is sometimes an exponential product generating process and sometimes is a linear product generating process.

Any suitable amplification technique and amplification conditions can be selected for a particular nucleic acid for amplification. Known amplification processes include, without limitation, polymerase chain reaction (PCR), extension and ligation, ligation amplification (or ligase chain reaction (LCR)) and amplification methods based on the use of Q-beta replicase or template-dependent polymerase (see US Patent Publication Number US20050287592). Also useful are strand displacement amplification (SDA), thermophilic SDA, nucleic acid sequence based amplification (3SR or NASBA) and transcription-associated amplification (TAA). Reagents, apparatus and hardware for conducting amplification processes are commercially available, and amplification conditions are known and can be selected for the target nucleic acid at hand.

Amplification Primers

Primers useful for amplification of mitochondrial and genomic polynucleotides are provided. In some embodiments primers are used in sets, where a set contains at least a pair. In some embodiments a plurality of primer sets, each set comprising pair(s) of primers, may be used. The term "primer" as used herein refers to a nucleic acid that comprises a nucleotide sequence capable of hybridizing or annealing to a polynucleotide, at or near (e.g., adjacent to) a specific region of interest. A primer may be naturally occurring or synthetic. The term "specific" or "specificity", as used herein, refers to the binding or hybridization of one molecule to another molecule, such as a primer for a polynucleotide. That is, "specific" or "specificity" refers to the recognition, contact, and formation of a stable complex between two molecules, as compared to substantially less recognition, contact, or complex formation of either of those two molecules with other molecules. As used herein, the term "anneal" refers to the formation of a stable complex between two molecules. The terms "primer", "oligo", or "oligonucleotide" may be used interchangeably throughout the document, when referring to primers.

A primer nucleic acid can be designed and synthesized using suitable processes, and may be of any length suitable for hybridizing to a nucleotide sequence of interest (e.g., where the nucleic acid is in liquid phase or bound to a solid support) and performing analysis processes described herein. Primers may be designed based upon a target nucleotide sequence. A primer in some embodiments may be about 10 to about 100 nucleotides, about 10 to about 70 nucleotides, about 10 to about 50 nucleotides, about 15 to about 30 nucleotides, or about 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95 or 100 nucleotides in length. A primer may be composed of naturally occurring and/or non-naturally occurring nucleotides (e.g., labeled nucleotides), or a mixture thereof. Primers suitable for use with embodiments described herein, may be synthesized and labeled using known techniques. Oligonucleotides (e.g., primers) may be chemically synthesized according to the solid phase phosphoramidite triester method first described by Beaucage and Caruthers, Tetrahedron Letts., 22:1859-1862, 1981, using an automated synthesizer, as described in Needham-VanDevanter et al., Nucleic Acids Res. 12:6159-6168, 1984. Purification of oligonucleotides can be effected by native acrylamide gel electrophoresis or by anion-exchange high-performance liquid chromatography (HPLC), for example, as described in Pearson and Regnier, J. Chrom., 255:137-149, 1983.

All or a portion of a primer nucleic acid sequence (naturally occurring or synthetic) may be substantially complementary to a target nucleic acid, in some embodiments. As referred to herein, "substantially complementary" with respect to sequences refers to nucleotide sequences that will hybridize with each other. The stringency of the hybridization conditions can be altered to tolerate varying amounts of sequence mismatch. Included are regions of counterpart, target and capture nucleotide sequences 55% or more, 56% or more, 57% or more, 58% or more, 59% or more, 60% or more, 61% or more, 62% or more, 63% or more, 64% or more, 65% or more, 66% or more, 67% or more, 68% or more, 69% or more, 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more or 99% or more complementary to each other.

Primers that are substantially complimentary to a target nucleic acid sequence are also substantially identical to the compliment of the target nucleic acid sequence. That is, primers are substantially identical to the anti-sense strand of the nucleic acid. As referred to herein, "substantially identical" with respect to sequences refers to nucleotide sequences that are 55% or more, 56% or more, 57% or more, 58% or more, 59% or more, 60% or more, 61% or more, 62% or more, 63% or more, 64% or more, 65% or more, 66% or more, 67% or more, 68% or more, 69% or more, 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more or 99% or more identical to each other. One test for determining whether two nucleotide sequences are substantially identical is to determine the percent of identical nucleotide sequences shared.

Amplification primer sequence, primer length and mismatches with the target nucleic acid are some of the parameters that affect amplification primer annealing to target nucleic acid sequences. By adjusting these parameters and others amplification primers can be designed that minimize annealing and accordingly inhibit elongation.

As used herein, the phrase "hybridizing" or grammatical variations thereof, refers to binding of a first nucleic acid molecule to a second nucleic acid molecule under nucleic acid synthesis conditions. Hybridizing can include instances where a first nucleic acid molecule binds to a second nucleic acid molecule, where the first and second nucleic acid molecules are complementary. As used herein, "specifically hybridizes" refers to preferential hybridization under nucleic acid synthesis conditions of a primer, to a nucleic acid molecule having a sequence complementary to the primer compared to hybridization to a nucleic acid molecule not having a complementary sequence. For example, specific hybridization includes the hybridization of a primer to a target nucleic acid sequence that is complementary to the primer.

A primer, in certain embodiments, may contain a modification such as inosines, abasic sites, locked nucleic acids, minor groove binders, duplex stabilizers (e.g., acridine, spermidine), Tm modifiers or any modifier that changes the binding properties of the primers or probes.

In some embodiments, amplification primers are designed to result in amplicons of about 30 base pairs to about 300 base pairs. In some embodiments, when the sample comprises circulating cell free nucleic acid, amplification primers are designed to result in amplicons greater than about 50 base pairs and less than about 166 pairs. Circulating cell free genomic nucleic acid (DNA) is less degraded (the mean is about 166 bp) than circulating cell free mitochondrial nucleic acid (DNA) (the mean is about 50 bp), Designing primers so amplicons are in the size range of greater than about 50 base pairs to less than about 166 base pairs results in amplification of a large portion of circulating cell free genomic nucleic acid and amplification of a smaller portion of the circulating cell free mitochondrial nucleic acid. This selective amplification can allow for the detection and quantitation of genomic nucleic acid in the same assay as mitochondrial nucleic acid. In some embodiments, the size of the amplicons is greater than about 60 bp and less than about 100 bp. In some embodiments, the size of the amplicons is greater than about 70 bp and less than about 100 bp.

In some embodiments, amplification primers are designed to amplify a paralog $5'X$-$V$-$Y3'$ and the mitochondrial polynucleotide and the genomic polynucleotide of a set are reproducibly amplified relative to each other by a single pair of amplification primers that hybridize to an internal polynucleotide within X and Y. One primer in the pair hybridizes to a polynucleotide within X and the other primer in the pair hybridizes to another polynucleotide within Y. The mitochondrial polynucleotide of a set is co-amplified with the genomic polynucleotide of a set using a single primer pair that binds to regions upstream and downstream of V. In some embodiments, mitochondrial and genomic polynucleotides are amplified under conditions that amplify each species at a "substantially reproducible level". In certain embodiments, a "substantially reproducible level" varies by about 1% or less. In some embodiments, a substantially reproducible level varies by 10%, 5%, 4%, 3%, 2%, 1.5%, 1%, 0.5%, 0.1%, 0.05%, 0.01%, 0.005% or 0.001%. Unbiased amplification of the mitochondrial and genomic polynucleotides of a set allows for a direct comparison of the amplicons in a single reaction and without the need for an internal standard. In some embodiments, determining the identity and quantity of the nucleotide at V is a good marker for relative copy number quantification.

In some embodiments, amplification primers are designed so the mitochondrial polynucleotide and the genomic polynucleotide of a set are amplified by different species specific pairs of amplification primers. The amplification primers are designed to hybridize to flanking polynucleotides that are 5' to X and 3' to Y. The flanking polynucleotides are different at one or more nucleotide positions between mitochondrial and genomic polynucleotides. The regions upstream and downstream of X and Y should have enough differences to allow for design of amplification primer pairs that are specific for mitochondrial polynucleotides or genomic polynucleotides. The mitochondrial polynucleotide amplification primers will not bind the genomic polynucleotide and vice versa. In some embodiments, methods employing amplification primers specific for mitochondrial polynucleotides can be used to reduce the amplification of the abundant mitochondrial polynucleotide relative to the amplification of the less abundant genomic polynucleotide.

In some embodiments, the amplification primer that is specific for the mitochondrial polynucleotide is designed not to hybridize as well to amplification primer binding site (e.g., binding site contains nucleotide mismatches and/or nucleotides that have reduced hydrogen binding) as does the amplification primer that is specific for the genomic polynucleotide in a set. The amplicons corresponding to the mitochondrial polynucleotide are reduced with respect to the amplicons corresponding to the genomic polynucleotide in each set.

In some embodiments, the amplification primers that specifically hybridize to the mitochondrial polynucleotide are provided at a lower concentration than the concentration of the amplification primers that specifically hybridize to the genomic polynucleotide. The amplicons corresponding to the mitochondrial polynucleotide are reduced with respect to the amplicons corresponding to the genomic polynucleotide in each set. In some embodiments, the concentration of the amplification primers that specifically hybridize to the mitochondrial polynucleotide is about 2 times to about 30 times lower than the concentration of amplification primers that specifically hybridize to the genomic polynucleotide in a set. The concentration of the amplification primer for the mitochondrial polynucleotide relative to the concentration of the amplification primer for the genomic polynucleotide can be optimized to try to achieve equal signal strength based on the following scheme, for example.

| | Pool 1 | Pool 2 | Pool 3 | Pool 4 | Pool 5 | Pool 6 | Pool 7 | Pool 8 | Pool 9 | Pool 10 |
|---|---|---|---|---|---|---|---|---|---|---|
| gDNA primers | 100 nM | 100 nM | 100 nM | 100 nM | 100 nM | 100 nM | 100 nM | 100 nM | 100 nM | |

-continued

|  | Pool 1 | Pool 2 | Pool 3 | Pool 4 | Pool 5 | Pool 6 | Pool 7 | Pool 8 | Pool 9 | Pool 10 |
|---|---|---|---|---|---|---|---|---|---|---|
| mDNA primers |  | 100 nM | 75 nM | 50 nM | 35 nM | 25 nM | 12.5 nM | 6.25 nM | 3.125 nM | 100 nM |

In some embodiments, the two approaches can be used together.

In some embodiments, amplification primers are designed to amplify a paralog $5'X\text{-}V\text{-}Y^{3'}$ in which the mitochondrial polynucleotide and the genomic polynucleotide of such a set are amplified by an amplification primer that hybridizes to a polynucleotide within X and two different amplification primers that hybridize to flanking polynucleotides that are 3' to Y. The amplification primers that hybridize to X are the same for the mitochondrial and genomic polynucleotide, as X is identical for the mitochondrial and genomic polynucleotide. The amplification primers that hybridize to flanking polynucleotides 3' to Y are different for the mitochondrial and genomic polynucleotide. In some embodiments, amplification primers are designed to amplify a paralog $5'X\text{-}V\text{-}Y^{3'}$ in which the mitochondrial polynucleotide and the genomic polynucleotide of such a set are amplified by an amplification primer that hybridizes to a polynucleotide within Y and two different amplification primers that hybridize to flanking polynucleotides that are 5' to X. The amplification primers that hybridize to Y are the same for the mitochondrial and genomic polynucleotide, as Y is identical for the mitochondrial and genomic polynucleotide. The amplification primers that hybridize to flanking polynucleotides 5' to X are different for the mitochondrial and genomic polynucleotide. Having at least one amplification primer for the mitochondrial and genomic polynucleotides that is different allows for an assay to be designed so the amplification of the mitochondrial polynucleotide of a set is reduced relative to the amplification of the genomic polynucleotide of the set. The concentration of the amplification primer specific for the mitochondrial polynucleotide can be made lower than the concentration of the amplification primer specific for the genomic polynucleotide. In some embodiments, the forward amplification primers specifically hybridize to and amplify either mitochondrial or genomic polynucleotides are at different concentrations relative to each other (e.g., 0.1 (mitochondrial) and 1.0 (genomic)) and the reverse amplification primer is universal and hybridizes and amplifies both species of polynucleotides (mitochondrial and genomic) is at the same relative concentration as the genomic specific forward amplification primer (e.g., 1.0). In some embodiments, the reverse amplification primers specifically hybridize to and amplify either mitochondrial or genomic polynucleotides are at different concentrations relative to each other (e.g., 0.1 (mitochondrial) and 1.0 (genomic)) and the forward amplification primer is universal and hybridizes and amplifies both species of polynucleotides (mitochondrial and genomic) is present at the same relative concentration as the genomic specific reverse amplification primer (e.g., 1.0). In some embodiments, the concentration of the amplification primer that specifically hybridizes to the mitochondrial polynucleotide is about 2 times to about 30 times lower than the concentration of the amplification primer that specifically hybridizes to the genomic polynucleotide in a set. Optimization of concentration of amplification primers is as described above. Forward and reverse amplification primers and their relative concentrations can be chosen based on the sequence of the polynucleotides that are to be amplified using known principles of PCR.

Alternatively, a primer binding site for the amplification primer specific for the mitochondrial polynucleotide can be selected so that the amplification primer for the mitochondrial polynucleotide does not hybridize to its primer binding site as well (e.g., binding site contains nucleotide mismatches and/or nucleotides that have reduced hydrogen binding) as the amplification primer specific for the genomic polynucleotide.

In some embodiments, the two approaches can be used together.

In some embodiments, amplification primers are designed so a paralog $5'J\text{-}V\text{-}K^{3'}$ of the mitochondrial polynucleotides of a set or a paralog $5'J\text{-}V\text{-}K^{3'}$ of the nuclear polynucleotides of a set are reproducibly amplified relative to each other by a single pair of amplification primers that hybridize to an internal polynucleotide within J and K. One primer in the pair hybridizes to a polynucleotide within J and the other primer in the pair hybridizes to another polynucleotide within K. The mitochondrial polynucleotides of a set are co-amplified using a single primer pair that binds to regions upstream and downstream of V. The nuclear polynucleotides of a set are co-amplified using a single primer pair that binds to regions upstream and downstream of V. In some embodiments, mitochondrial polynucleotides of a set are amplified under conditions that amplify each polynucleotide at a "substantially reproducible level". In some embodiments, nuclear polynucleotides of a set are amplified under conditions that amplify each polynucleotide at a "substantially reproducible level." In certain embodiments, a "substantially reproducible level" varies by about 1% or less. In some embodiments, a substantially reproducible level varies by 10%, 5%, 4%, 3%, 2%, 1.5%, 1%, 0.5%, 0.1%, 0.05%, 0.01%, 0.005% or 0.001%. Unbiased amplification of the mitochondrial polynucleotides of a set allow for a direct comparison of the amplicons in a single reaction. Unbiased amplification of nuclear polynucleotides of a set allow for a direct comparison of the amplicons in a single reaction. In some embodiments, determining the identity and quantity of the nucleotide at V is a good marker for relative copy number quantification.

Quantitation of Amplicons

In some embodiments, amplicons corresponding to the mitochondrial polynucleotide of a set and amplicons corresponding to the genomic polynucleotide of a set are quantified. In some embodiments amplicons are quantified by determining the amount of a nucleotide at V in the amplicons corresponding to the mitochondrial polynucleotide of a set and the amount of the nucleotide at V in the amplicons corresponding to the genomic polynucleotide of a set is determined. Based on the amount of a nucleotide at V in the amplicons corresponding to the mitochondrial polynucleotide of a set and the amount of the nucleotide at V in the amplicons corresponding to the genomic polynucleotide of a set a ratio of the amount of a mitochondrial polynucleotide relative to the amount of a genomic polynucleotide can be obtained and used to determine the dosage of mitochondrial nucleic acid relative to genomic nucleic acid.

In some embodiments, amplicons corresponding to the mitochondrial polynucleotides of a set are quantified and amplicons corresponding to the nuclear polynucleotides of a set are quantified. In some embodiments amplicons are quantified by determining the amount of a nucleotide at V in the amplicons corresponding to each of the mitochondrial polynucleotides of a set (e.g., first and second species, human and chimpanzee). In some embodiments amplicons are quantified by determining the amount of a nucleotide at V in the amplicons corresponding to each of the nuclear polynucleotides of a set (e.g., first and second species, human and chimpanzee).

Any suitable technology can be used to detect and/or quantify amplicons. Non-limiting examples of technologies that can be utilized to detect and/or quantify amplicons include primer extension assays, amplification (e.g., digital PCR, quantitative polymerase chain reaction (qPCR)), sequencing (e.g., nanopore sequencing, massive parallel sequencing), mass spectrometry, array hybridization (e.g., microarray hybridization; gene-chip analysis), flow cytometry, gel electrophoresis (e.g., capillary electrophoresis), cytofluorimetric analysis, fluorescence microscopy, confocal laser scanning microscopy, laser scanning cytometry, affinity chromatography, manual batch mode separation, electric field suspension, the like and combinations of the foregoing. Further detail is provided hereafter for certain amplicon detection and/or quantification technologies.

Primer Extension Reactions

In some embodiments, determining the amount of a nucleotide at V in the amplicons corresponding to the mitochondrial polynucleotide of a set and the amount of the nucleotide at V in the amplicons corresponding to the genomic polynucleotide of a set is by a primer extension reaction process. In some embodiments, determining the amount of a nucleotide at V in the amplicons corresponding to each of the mitochondrial polynucleotides of a set and the amount of the nucleotide at V in the amplicons corresponding to each of the nuclear polynucleotides of a set is by a primer extension reaction process. An extension reaction is conducted under extension conditions, and a variety of such conditions are known and selected for a particular application. Extension conditions can include certain reagents, including without limitation, one or more oligonucleotides, extension nucleotides (e.g., nucleotide triphosphates (dNTPs)), chain terminating reagents or nucleotides (e.g., one or more dideoxynucleotide triphosphates (ddNTPs) or acyclic terminators), one or more salts (e.g., magnesium-containing salt), one or more buffers (e.g., with beta-NAD, Triton X-100), and one or more polymerizing agents (e.g., DNA polymerase, RNA polymerase).

Extension can be conducted under isothermal conditions or under non-isothermal conditions (e.g., thermocycled conditions), in certain embodiments. One or more nucleic acid species can be extended in an extension reaction and one or more molecules of each nucleic acid species can be extended. A nucleic acid can be extended by one or more nucleotides, and in some embodiments, the extension product is about 10 nucleotides to about 10,000 nucleotides in length, about 10 to about 1000 nucleotides in length, about 10 to about 500 nucleotides in length, 10 to about 100 nucleotides in length, and sometimes about 10, 11, 12, 13, 14, 15, 16, 17, 18, 19, 20, 25, 30, 35, 40, 45, 50, 55, 60, 65, 70, 75, 80, 80, 85, 90, 95, 100, 125, 150, 175, 200, 225, 250, 275, 300, 325, 350, 375, 400, 425, 450, 475, 500, 600, 700, 800, 900 or 1000 nucleotides in length. Incorporation of a terminating nucleotide (e.g., ddNTP), the hybridization location, or other factors, can determine the length to which the oligonucleotide is extended. In certain embodiments, amplification and extension processes are carried out in the same detection procedure.

In some embodiments an extension reaction includes multiple temperature cycles repeated to amplify the amount of extension product in the reaction. In some embodiments the extension reaction is cycled 2 or more times. In some embodiments the extension reaction is cycled 10 or more times. In some embodiments the extension reaction is cycled about 10, 15, 20, 50, 55, 60, 65, 70, 75, 80, 85, 90, 95, 100, 200, 300, 400, 500 or 600 or more times. In some embodiments the extension reaction is cycled 20 to 50 times. In some embodiments the extension reaction is cycled 20 to 100 times. In some embodiments the extension reaction is cycled 20 to 300 times. In some embodiments the extension reaction is cycled 200 to 300 times. In certain embodiments, the extension reaction is cycled at least 50, 55, 60, 65, 70, 75, 80, 85, 90, 95 or 100 times.

Primer extension processes include methods such as iPLEX™ or homogeneous MassExtend® (hME) (see, for example, U.S. Published Patent Application No. 2013/0237428 A1, U.S. Pat. Nos. 8,349,566, and 8,003,317, the contents of which are incorporated in their entirety by reference herein), in which a mixture of minor nucleic acid species (e.g., mutant alleles) and major nucleic acid species (e.g., wild type alleles) are subjected to a polymerase chain reaction (PCR) amplification using a set of amplification primers, a polymerase and deoxynucleotides (dNTPs), thereby generating amplicons of the wild type and mutant species. After treatment with shrimp alkaline phosphatase (SAP) to dephosphorylate unincorporated dNTPs, the amplicon mixture is extended using extension primers (unextended primers or UEPs), a polymerase and a termination mix that includes chain terminating reagents (e.g., dideoxynucleotides or ddNTPs). The UEPs hybridize to the amplicons and are extended either up to the site of variance between the mutant and wild type species (i.e., extension stops at the mutation site where there is a difference in bases between the mutant and wild type species to generate single base extension products or SBEs, as in iPLEX™) or a few bases (e.g., 2-3 bases) past the site of variance (as in, for example, the hME method). The resulting extension products can then be processed (e.g., by desalting prior to mass spectrometry) and analyzed for the presence of the mutant alleles based on a difference in detection signal (e.g., mass) relative to the wild type allele.

The above-described iPLEX™ and homogeneous MassExtend® (hME) methods use an equimolar mixture of ddNTPs in the extension step for generating extension products corresponding to wild type and mutant species. Thus, in the iPLEX™ and homogeneous MassExtend® (hME) methods, all other factors being equal with the exception of the major nucleic acid species being present in a large excess relative to the minor nucleic acid species, the majority of the UEPs hybridize to the major nucleic acid species and are extended using the chain terminating reagent specific for the major nucleic acid species. Relatively few molecules of UEP are available for hybridization and extension of the minor nucleic acid species. This compromises the magnitude of the detection signal corresponding to the minor nucleic acid species, which is overshadowed by the predominant detection signal from the major nucleic acid species and may be subsumed by background noise.

In certain embodiments, the extension step uses a limiting concentration of chain terminating reagent specific for the mitochondrial polynucleotide, relative to the chain terminating reagent specific for the genomic polynucleotide.

Amplicons are contacted with extension primers under extension conditions with chain terminating reagents. The chain terminating reagent that is specific for the amplicons corresponding to the mitochondrial polynucleotide is not specific for the amplicons corresponding to genomic polynucleotide and the chain terminating reagent specific for the amplicons corresponding to the genomic polynucleotide is not specific for the amplicons corresponding to mitochondrial polynucleotide. The extension primers are extended up to V, thereby generating chain terminated extension products corresponding to the mitochondrial polynucleotide or the genomic polynucleotide. The concentration of the chain terminating reagent specific for the mitochondrial polynucleotide is less than the concentration of the chain terminating reagent specific for the genomic polynucleotide.

In some embodiments, the ratio of the amount of extension product corresponding to the mitochondrial polynucleotides relative to the amount of extension product corresponding to the genomic polynucleotide is determined and the amount of mitochondrial nucleic acid relative to the amount of genomic nucleic acid in the sample is determined based on the ratio and based on the concentration of the chain terminating reagent specific for the mitochondrial polynucleotide relative to the concentration of the chain terminating reagent specific for genomic polynucleotide.

In certain embodiments, the concentration of the chain terminating reagent specific for a mitochondrial polynucleotide is between about 1% to about 20% of the concentration of the chain terminating reagent specific for a genomic polynucleotide. The concentration of the chain terminating reagent specific for a mitochondrial polynucleotide generally being between about 0.5% to less than about 20% of the concentration of the chain terminating reagent specific for a genomic polynucleotide, about 0.5% to less than about 15%, about 1% to about 15%, about 1% to about 10%, about 2% to about 10% or about 1%, 1.5%, 2%, 2.5%, 3%, 3.5%, 4%, 4.5%, 5%, 5.5%, 6%, 6.5%, 7%, 7.5%, 8%, 8.5%, 9%, 9.5% or 10% of the concentration of the chain terminating reagent specific for a genomic polynucleotide.

In certain embodiments, the extension step uses an equimolar concentration of chain terminating reagents specific for each of the mitochondrial polynucleotides of a set or an equimolar concentration of chain terminating reagents specific for each of the nuclear polynucleotides of a set. Amplicons are contacted with extension primers under extension conditions with chain terminating reagents. The chain terminating reagent that is specific for the amplicons corresponding to the mitochondrial polynucleotide of the first species is not specific for the amplicons corresponding to the mitochondrial polynucleotide of the second species; and the chain terminating reagent specific for the amplicons corresponding to the nuclear polynucleotide of the first species is not specific for the amplicons corresponding to the nuclear polynucleotide of the second species. The primers are extended up to V, thereby generating chain terminated extension products corresponding to the mitochondrial polynucleotide of the first species, the mitochondrial polynucleotide of the second species, the nuclear polynucleotide of the first species and the nuclear polynucleotide of the second species.

In some embodiments, a ratio of the amount of extension product corresponding to the mitochondrial polynucleotide of the second species to the amount of extension product corresponding to the mitochondrial polynucleotide of the first species is determined.

In some embodiments, a ratio of the amount of extension product corresponding to the nuclear polynucleotide of the second species to the amount of extension product corresponding to the nuclear polynucleotide of the first species and the amount of mitochondrial nucleic acid relative to the amount of nuclear nucleic acid in the sample is determined based on the ratios.

The term "up to" as used herein includes nucleotide position V.

In some embodiments, the chain terminating reagents are chain terminating nucleotides. In some embodiments, the chain terminating nucleotides independently are selected from among ddATP, ddGTP, ddCTP, ddTTP and ddUTP. In some embodiments, the chain terminating reagents comprise one or more acyclic terminators. In some embodiments, one or more of the chain terminating reagents comprises a detectable label. In some embodiments, the label is a fluorescent label or dye. In some embodiments, the label is a mass label and detection is by mass spectrometry.

Any suitable extension reaction can be selected and utilized. An extension reaction can be utilized, for example, to discriminate the nucleotide of a mitochondrial polynucleotide from the nucleotide of a genomic polynucleotide at V, to discriminate the nucleotide of a mitochondrial polynucleotide of a first species from the nucleotide of a mitochondrial polynucleotide of a second species at V or to discriminate the nucleotide of a nuclear polynucleotide of a first species from the nucleotide of a nuclear polynucleotide of a second species at V by the incorporation of deoxynucleotides and/or dideoxynucleotides to an extension oligonucleotide that hybridizes to a region adjacent to V in the amplicon. The primer often is extended with a polymerase. In some embodiments, the oligonucleotide is extended by only one deoxynucleotide or dideoxynucleotide complementary to the V site. In some embodiments, an oligonucleotide may be extended by dNTP incorporation and terminated by a ddNTP, or terminated by ddNTP incorporation without dNTP extension in certain embodiments. Extension may be carried out using unmodified extension oligonucleotides and unmodified dideoxynucleotides, unmodified extension oligonucleotides and biotinylated dideoxynucleotides, extension oligonucleotides containing a deoxyinosine and unmodified dideoxynucleotides, extension oligonucleotides containing a deoxyinosine and biotinylated dideoxynucleotides, extension by biotinylated dideoxynucleotides, or extension by biotinylated deoxynucleotide and/or unmodified dideoxynucleotides, in some embodiments.

The extension products corresponding to the mitochondrial polynucleotide and the genomic polynucleotide of a set, the mitochondrial polynucleotide of a first species and the mitochondrial polynucleotide of a second species of a set or the nuclear polynucleotide of a first species and the nuclear polynucleotide of a second species of a set that are obtained by the methods provided herein can be detected by a variety of methods. For example, the extension primers (UEPs) and/or the chain terminating reagents may be labeled with any type of chemical group or moiety that allows for detection of a signal and/or quantification of the signal including, but not limited to, mass labels, radioactive molecules, fluorescent molecules, antibodies, antibody fragments, haptens, carbohydrates, biotin, derivatives of biotin, phosphorescent moieties, luminescent moieties, electrochemiluminescent moieties, moieties that generate an electrochemical signal upon oxidation or reduction, e.g., complexes of iron, ruthenium or osmium (see, for example, eSensor technology used by Genmark Diagnostics, Inc. e.g., as described in Pierce et al., J. Clin. Micribiol., 50(11):3458-3465 (2012)), chromatic moieties, and moieties having a detectable electron spin resonance, electrical capacitance, dielectric constant or electrical conductivity, or any combination of labels thereof.

The labeled extension products corresponding to the mitochondrial polynucleotide and the genomic polynucleotide of a set, the mitochondrial polynucleotide of a first species and the mitochondrial polynucleotide of a second species of a set or the nuclear polynucleotide of a first species and the nuclear polynucleotide of a second species of a set can be analyzed by a variety of methods including, but not limited to, mass spectrometry, MALDI-TOF mass spectrometry, fluorescence detection, DNA sequencing gel, capillary electrophoresis on an automated DNA sequencing machine, microchannel electrophoresis, and other methods of sequencing, mass spectrometry, time of flight mass spectrometry, quadrupole mass spectrometry, magnetic sector mass spectrometry, electric sector mass spectrometry infrared spectrometry, ultraviolet spectrometry, palentiostatic amperometry, measurement of current/electrochemical signal or by DNA hybridization techniques including Southern Blots, Slot Blots, Dot Blots, and DNA microarrays, wherein DNA fragments would be useful as both "probes" and "targets," ELISA, fluorimetry, Fluorescence Resonance Energy Transfer (FRET), SNP-IT, GeneChips, HuSNP, BeadArray, TaqMan assay, Invader assay, MassExtend®, or MassCleave® method.

In some embodiments, a chain terminating reagent or chain terminating nucleotide includes one detectable label. In some embodiments, a first chain terminating reagent or chain terminating nucleotide includes a detectable label that is different from the detectable label of a second chain terminating reagent or chain terminating nucleotide. In some embodiments, an extension composition includes one or more chain terminating reagents or chain terminating nucleotides where each chain terminating reagent or chain terminating nucleotide includes a different detectable label. In some embodiments, an extension composition includes one or more chain terminating reagents or chain terminating nucleotides where each contains the same detection label. In some embodiments, an extension composition includes a chain terminating reagent or chain terminating nucleotide and an extension nucleotide (e.g., dNTP) and one or more of the nucleotides (e.g. terminating nucleotides and/or extension nucleotides) includes a detection label. In some embodiments, the relative amount (frequency or copy number, e.g.) of a mitochondrial polynucleotide to that of a genomic polynucleotide can be determined by the proportions of their detection signals relative to the ratio of the concentration of the chain terminating reagents specific for the mitochondrial polynucleotide to the concentration of the chain terminating reagents specific for genomic polynucleotide, using a normalization coefficient. In some embodiments the amount (e.g. copy number, concentration, percentage) of mitochondrial polynucleotide is quantified by normalizing the ratio of the signal for the genomic polynucleotide to the signal for the mitochondrial polynucleotide, using a coefficient. This coefficient is inversely proportional to the fraction of concentration of the chain terminating reagent or nucleotide specific for the mitochondrial polynucleotide compared to the concentration of the chain terminating reagent or nucleotide specific for genomic polynucleotide (i.e., the lower the fraction of mitochondrial polynucleotide-specific chain terminating reagent relative to the chain terminating reagent specific for the genomic polynucleotide, the larger the coefficient).

In some embodiments, a normalization coefficient is not required as the ratio for a sample is either compared to a population or to samples obtained from the same subject over a period of time.

Mass Spectrometry

Mass spectrometry methods typically are used to determine the mass of a molecule. In some embodiments, mass spectrometry is used to detect and/or quantify the primer extension product based on its unique mass. The relative signal strength, e.g., mass peak on a spectra, for the nucleic acid nucleic acid can indicate the relative population of the species amongst other nucleic acids in the sample (see e.g., Jurinke et al. (2004) Mol. Biotechnol. 26, 147-164).

Mass spectrometry generally works by ionizing chemical compounds to generate charged molecules or molecule fragments and measuring their mass-to-charge ratios. A typical mass spectrometry procedure involves several steps, including (1) loading a sample onto a mass spectrometry instrument followed by vaporization, (2) ionization of the sample components by any one of a variety of methods (e.g., impacting with an electron beam), resulting in charged particles (ions), (3) separation of ions according to their mass-to-charge ratio in an analyzer by electromagnetic fields, (4) detection of ions (e.g., by a quantitative method), and (5) processing of ion signals into mass spectra.

Mass spectrometry methods are known, and include without limitation quadrupole mass spectrometry, ion trap mass spectrometry, time-of-flight mass spectrometry, gas chromatography mass spectrometry and tandem mass spectrometry can be used with a method described herein. Processes associated with mass spectrometry are generation of gas-phase ions derived from the sample, and measurement of ions. Movement of gas-phase ions can be precisely controlled using electromagnetic fields generated in the mass spectrometer, and movement of ions in these electromagnetic fields is proportional to the mass to charge ratio (m/z) of each ion, which forms the basis of measuring m/z and mass. Movement of ions in these electromagnetic fields allows for containment and focusing of the ions which accounts for high sensitivity of mass spectrometry. During the course of m/z measurement, ions are transmitted with high efficiency to particle detectors that record the arrival of these ions. The quantity of ions at each m/z is demonstrated by peaks on a graph where the x axis is m/z and the y axis is relative abundance. Different mass spectrometers have different levels of resolution (i.e., the ability to resolve peaks between ions closely related in mass). Resolution generally is defined as R=m/delta m, where m is the ion mass and delta m is the difference in mass between two peaks in a mass spectrum. For example, a mass spectrometer with a resolution of 1000 can resolve an ion with a m/z of 100.0 from an ion with a m/z of 100.1.

Certain mass spectrometry methods can utilize various combinations of ion sources and mass analyzers which allows for flexibility in designing customized detection protocols. In some embodiments, mass spectrometers can be programmed to transmit all ions from the ion source into the mass spectrometer either sequentially or at the same time. In some embodiments, a mass spectrometer can be programmed to select ions of a particular mass for transmission into the mass spectrometer while blocking other ions.

Several types of mass spectrometers are available or can be produced with various configurations. In general, a mass spectrometer has the following major components: a sample inlet, an ion source, a mass analyzer, a detector, a vacuum system, and instrument-control system, and a data system. Difference in the sample inlet, ion source, and mass analyzer generally define the type of instrument and its capabilities. For example, an inlet can be a capillary-column liquid chromatography source or can be a direct probe or stage such as used in matrix-assisted laser desorption. Common ion sources are, for example, electrospray, including nanospray and microspray or matrix-assisted laser desorption. Mass analyzers include, for example, a quadrupole mass filter, ion trap mass analyzer and time-of-flight mass analyzer.

An ion formation process generally is a starting point for mass spectrum analysis. Several ionization methods are available and the choice of ionization method depends on the sample used for analysis. For example, for the analysis of polypeptides a relatively gentle ionization procedure such as electrospray ionization (ESI) can be desirable. For ESI, a solution containing the sample is passed through a fine needle at high potential which creates a strong electrical field resulting in a fine spray of highly charged droplets that is directed into the mass spectrometer. Other ionization procedures include, for example, fast-atom bombardment (FAB) which uses a high-energy beam of neutral atoms to strike a solid sample causing desorption and ionization. Matrix-assisted laser desorption ionization (MALDI) is a method in which a laser pulse is used to strike a sample that has been crystallized in an UV-absorbing compound matrix (e.g., 2,5-dihydroxybenzoic acid, alpha-cyano-4-hydroxycinammic acid, 3-hydroxypicolinic acid (3-HPA), di-ammoniumcitrate (DAC) and combinations thereof). Other ionization procedures known in the art include, for example, plasma and glow discharge, plasma desorption ionization, resonance ionization, and secondary ionization.

A variety of mass analyzers are available that can be paired with different ion sources. Different mass analyzers have different advantages as known in the art and as described herein. The mass spectrometer and methods chosen for detection depends on the particular assay, for example, a more sensitive mass analyzer can be used when a small amount of ions are generated for detection. Several types of mass analyzers and mass spectrometry methods are described below.

Ion mobility mass (IM) spectrometry is a gas-phase separation method. IM separates gas-phase ions based on their collision cross-section and can be coupled with time-of-flight (TOF) mass spectrometry. IM-MS methods are known in the art.

Quadrupole mass spectrometry utilizes a quadrupole mass filter or analyzer. This type of mass analyzer is composed of four rods arranged as two sets of two electrically connected rods. A combination of rf and dc voltages are applied to each pair of rods which produces fields that cause an oscillating movement of the ions as they move from the beginning of the mass filter to the end. The result of these fields is the production of a high-pass mass filter in one pair of rods and a low-pass filter in the other pair of rods. Overlap between the high-pass and low-pass filter leaves a defined m/z that can pass both filters and traverse the length of the quadrupole. This m/z is selected and remains stable in the quadrupole mass filter while all other m/z have unstable trajectories and do not remain in the mass filter. A mass spectrum results by ramping the applied fields such that an increasing m/z is selected to pass through the mass filter and reach the detector. In addition, quadrupoles can also be set up to contain and transmit ions of all m/z by applying a rf-only field. This allows quadrupoles to function as a lens or focusing system in regions of the mass spectrometer where ion transmission is needed without mass filtering.

A quadrupole mass analyzer, as well as the other mass analyzers described herein, can be programmed to analyze a defined m/z or mass range. Since the desired mass range of nucleic acid fragment is known, in some instances, a mass spectrometer can be programmed to transmit ions of the projected correct mass range while excluding ions of a higher or lower mass range. The ability to select a mass range can decrease the background noise in the assay and thus increase the signal-to-noise ratio. Thus, in some instances, a mass spectrometer can accomplish a separation step as well as detection and identification of certain mass-distinguishable nucleic acid fragments.

Ion trap mass spectrometry utilizes an ion trap mass analyzer. Typically, fields are applied such that ions of all m/z are initially trapped and oscillate in the mass analyzer. Ions enter the ion trap from the ion source through a focusing device such as an octapole lens system. Ion trapping takes place in the trapping region before excitation and ejection through an electrode to the detector. Mass analysis can be accomplished by sequentially applying voltages that increase the amplitude of the oscillations in a way that ejects ions of increasing m/z out of the trap and into the detector. In contrast to quadrupole mass spectrometry, all ions are retained in the fields of the mass analyzer except those with the selected m/z. Control of the number of ions can be accomplished by varying the time over which ions are injected into the trap.

Time-of-flight mass spectrometry utilizes a time-of-flight mass analyzer. Typically, an ion is first given a fixed amount of kinetic energy by acceleration in an electric field (generated by high voltage). Following acceleration, the ion enters a field-free or "drift" region where it travels at a velocity that is inversely proportional to its m/z. Therefore, ions with low m/z travel more rapidly than ions with high m/z. The time required for ions to travel the length of the field-free region is measured and used to calculate the m/z of the ion.

Gas chromatography mass spectrometry often can a target in real-time. The gas chromatography (GC) portion of the system separates the chemical mixture into pulses of analyte and the mass spectrometer (MS) identifies and quantifies the analyte.

Tandem mass spectrometry can utilize combinations of the mass analyzers described above. Tandem mass spectrometers can use a first mass analyzer to separate ions according to their m/z in order to isolate an ion of interest for further analysis. The isolated ion of interest is then broken into fragment ions (called collisionally activated dissociation or collisionally induced dissociation) and the fragment ions are analyzed by the second mass analyzer. These types of tandem mass spectrometer systems are called tandem in space systems because the two mass analyzers are separated in space, usually by a collision cell. Tandem mass spectrometer systems also include tandem in time systems where one mass analyzer is used, however the mass analyzer is used sequentially to isolate an ion, induce fragmentation, and then perform mass analysis.

Mass spectrometers in the tandem in space category have more than one mass analyzer. For example, a tandem quadrupole mass spectrometer system can have a first quadrupole mass filter, followed by a collision cell, followed by a second quadrupole mass filter and then the detector. Another arrangement is to use a quadrupole mass filter for the first mass analyzer and a time-of-flight mass analyzer for the second mass analyzer with a collision cell separating the two mass analyzers. Other tandem systems are known in the art including reflectron-time-of-flight, tandem sector and sector-quadrupole mass spectrometry.

Mass spectrometers in the tandem in time category have one mass analyzer that performs different functions at different times. For example, an ion trap mass spectrometer can be used to trap ions of all m/z. A series of rf scan functions are applied which ejects ions of all m/z from the trap except the m/z of ions of interest. After the m/z of interest has been isolated, an rf pulse is applied to produce collisions with gas molecules in the trap to induce fragmentation of the ions. Then the m/z values of the fragmented ions are measured by the mass analyzer. Ion cyclotron resonance instruments, also known as Fourier transform mass spectrometers, are an example of tandem-in-time systems.

Several types of tandem mass spectrometry experiments can be performed by controlling the ions that are selected in each stage of the experiment. The different types of experiments utilize different modes of operation, sometimes called "scans," of the mass analyzers. In a first example, called a mass spectrum scan, the first mass analyzer and the collision cell transmit all ions for mass analysis into the second mass analyzer. In a second example, called a product ion scan, the ions of interest are mass-selected in the first mass analyzer and then fragmented in the collision cell. The ions formed are then mass analyzed by scanning the second mass analyzer. In a third example, called a precursor ion scan, the first mass analyzer is scanned to sequentially transmit the mass analyzed ions into the collision cell for fragmentation. The second mass analyzer mass-selects the product ion of interest for transmission to the detector. Therefore, the detector signal is the result of all precursor ions that can be fragmented into a common product ion. Other experimental formats include neutral loss scans where a constant mass difference is accounted for in the mass scans.

For quantification, controls may be used which can provide a signal in relation to the amount of the nucleic acid fragment, for example, that is present or is introduced. A control to allow conversion of relative mass signals into absolute quantities can be accomplished by addition of a known quantity of a mass tag or mass label to each sample before detection of the nucleic acid fragments. Any mass tag that does not interfere with detection of the fragments can be used for normalizing the mass signal. Such standards typically have separation properties that are different from those of any of the molecular tags in the sample, and could have the same or different mass signatures.

A separation step sometimes can be used to remove salts, enzymes, or other buffer components from the nucleic acid sample. Several methods well known in the art, such as chromatography, gel electrophoresis, or precipitation, can be used to clean up the sample. For example, size exclusion chromatography or affinity chromatography can be used to remove salt from a sample. The choice of separation method can depend on the amount of a sample. For example, when small amounts of sample are available or a miniaturized apparatus is used, a micro-affinity chromatography separation step can be used. In addition, whether a separation step is desired, and the choice of separation method, can depend on the detection method used. Salts sometimes can absorb energy from the laser in matrix-assisted laser desorption/ionization and result in lower ionization efficiency. Thus, the efficiency of matrix-assisted laser desorption/ionization and electrospray ionization sometimes can be improved by removing salts from a sample.

Nanopores

In some embodiments, amplicons of mitochondrial and genomic (nuclear) polynucleotides are detected and/or quantified using a nanopore process. In some embodiments, determining the amount of a nucleotide at V in the amplicons corresponding to the mitochondrial polynucleotide of a set and the amount of the nucleotide at V in the amplicons corresponding to the genomic polynucleotide of a set is by using a nanopore process. In some embodiments, determining the amount of a nucleotide at V in the amplicons corresponding to the mitochondrial polynucleotide of the first species and the second species of a set and determining the amount of a nucleotide at V in the amplicons corresponding to the nuclear polynucleotide of the first species and the second species of a set is by a nanopore process.

A nanopore can be used to obtain nucleotide sequencing information for the amplicons. In some embodiments, amplicons are detected and/or quantified using a nanopore without obtaining nucleotide sequences. A nanopore is a small hole or channel, typically of the order of 1 nanometer in diameter. Certain transmembrane cellular proteins can act as nanopores (e.g., alpha-hemolysin). Nanopores can be synthesized (e.g., using a silicon platform). Immersion of a nanopore in a conducting fluid and application of a potential across it results in a slight electrical current due to conduction of ions through the nanopore. The amount of current which flows is sensitive to the size of the nanopore. As a nucleic acid fragment passes through a nanopore, the nucleic acid molecule obstructs the nanopore to a certain degree and generates a change to the current. In some embodiments, the duration of current change as the nucleic acid fragment passes through the nanopore can be measured.

In some embodiments, nanopore technology can be used in a method described herein for obtaining nucleotide sequence information for nucleic acid fragments. Nanopore sequencing is a single-molecule sequencing technology whereby a single nucleic acid molecule (e.g. DNA) is sequenced directly as it passes through a nanopore. As described above, immersion of a nanopore in a conducting fluid and application of a potential across it results in a slight electrical current due to conduction of ions through the nanopore. The amount of current which flows is sensitive to the size of the nanopore. As a DNA molecule passes through a nanopore, each nucleotide on the DNA molecule obstructs the nanopore to a different degree and generates characteristic changes to the current. The amount of current which can pass through the nanopore at any given moment therefore varies depending on whether the nanopore is blocked by an A, a C, a G, a T, or sometimes methyl-C. The change in the current through the nanopore as the DNA molecule passes through the nanopore represents a direct reading of the DNA sequence. In some embodiments, a nanopore can be used to identify individual DNA bases as they pass through the nanopore in the correct order (e.g., International Patent Application No. WO2010/004265).

There are a number of ways that nanopores can be used to sequence nucleic acid molecules. In some embodiments, an exonuclease enzyme, such as a deoxyribonuclease, is used. In this case, the exonuclease enzyme is used to sequentially detach nucleotides from a nucleic acid (e.g. DNA) molecule. The nucleotides are then detected and discriminated by the nanopore in order of their release, thus reading the sequence of the original strand. For such an embodiment, the exonuclease enzyme can be attached to the nanopore such that a proportion of the nucleotides released from the DNA molecule is capable of entering and interacting with the channel of the nanopore. The exonuclease can be attached to the nanopore structure at a site in close proximity to the part of the nanopore that forms the opening of the channel. In some embodiments, the exonuclease enzyme can be attached to the nanopore structure such that its nucleotide exit trajectory site is orientated towards the part of the nanopore that forms part of the opening.

In some embodiments, nanopore sequencing of nucleic acids involves the use of an enzyme that pushes or pulls the nucleic acid (e.g. DNA) molecule through the pore. In this case, the ionic current fluctuates as a nucleotide in the DNA molecule passes through the pore. The fluctuations in the current are indicative of the DNA sequence. For such an embodiment, the enzyme can be attached to the nanopore structure such that it is capable of pushing or pulling the target nucleic acid through the channel of a nanopore without interfering with the flow of ionic current through the pore. The enzyme can be attached to the nanopore structure at a site in close proximity to the part of the structure that forms part of the opening. The enzyme can be attached to the subunit, for example, such that its active site is orientated towards the part of the structure that forms part of the opening.

In some embodiments, nanopore sequencing of nucleic acids involves detection of polymerase bi-products in close proximity to a nanopore detector. In this case, nucleoside phosphates (nucleotides) are labeled so that a phosphate labeled species is released upon the addition of a polymerase to the nucleotide strand and the phosphate labeled species is detected by the pore. Typically, the phosphate species contains a specific label for each nucleotide. As nucleotides are sequentially added to the nucleic acid strand, the bi-products of the base addition are detected. The order that the phosphate labeled species are detected can be used to determine the sequence of the nucleic acid strand.

Probes

In some embodiments, amplicons are detected and/or quantified using one or more probes. In some embodiments, quantification comprises quantifying target nucleic acid (mitochondrial amplicon and/or genomic amplicon, mitochondrial amplicon of a first species, mitochondrial amplicon of a second species, nuclear amplicon of a first species, nuclear amplicon of a second species) specifically hybridized to the probe. In some embodiments, quantification comprises quantifying the probe in the hybridization product. In some embodiments, quantification comprises quantifying target nucleic acid specifically hybridized to the probe and quantifying the probe in the hybridization product. In some embodiments, quantification comprises quantifying the probe after dissociating from the hybridization product. Quantification of hybridization product, probe and/or nucleic acid target can comprise use of, for example, mass spectrometry, MASSARRAY and/or MASSEXTEND technology, as described herein.

In some embodiments, probes are designed such that they each hybridize to a nucleic acid of interest in a sample. For example, a probe may comprise a polynucleotide sequence that is complementary to a nucleic acid of interest or may comprise a series of monomers that can bind to a nucleic acid of interest. Probes may be any length suitable to hybridize (e.g., completely hybridize) to one or more nucleic acid fragments of interest. For example, probes may be of any length which spans or extends beyond the length of a nucleic acid fragment to which it hybridizes. Probes may be about 10 bp or more in length. For example, probes may be at least about 20, 30, 40, 50, 60, 70, 80, 100, 200, 300, 400, 500, 600, 700, 800, 900 or 1000 bp in length. In some embodiments, a detection and/or quantification method is used to detect and/or quantify probe-nucleic acid fragment duplexes.

Probes may be designed and synthesized according to methods known in the art and described herein for oligonucleotides (e.g., capture oligonucleotides). Probes also may include any of the properties known in the art and described herein for oligonucleotides. Probes herein may be designed such that they comprise nucleotides (e.g., adenine (A), thymine (T), cytosine (C), guanine (G) and uracil (U)), modified nucleotides (e.g., mass-modified nucleotides, pseudouridine, dihydrouridine, inosine (I), and 7-methylguanosine), synthetic nucleotides, degenerate bases (e.g., 6H,8H-3,4-dihydropyrimido[4,5-c][1,2]oxazin-7-one (P), 2-amino-6-methoxyaminopurine (K), N6-methoxyadenine (Z), and hypoxanthine (I)), universal bases and/or monomers other than nucleotides, modified nucleotides or synthetic nucleotides, mass tags or combinations thereof.

In some embodiments, probes are dissociated (i.e., separated) from their corresponding nucleic acid fragments. Probes may be separated from their corresponding nucleic acid fragments using any method known in the art, including, but not limited to, heat denaturation. Probes can be distinguished from corresponding nucleic acid fragments by a method known in the art or described herein for labeling and/or isolating a species of molecule in a mixture. For example, a probe and/or nucleic acid fragment may comprise a detectable property such that a probe is distinguishable from the nucleic acid to which it hybridizes. Non-limiting examples of detectable properties include mass properties, optical properties, electrical properties, magnetic properties, chemical properties, and time and/or speed through an opening of known size. In some embodiments, probes and sample nucleic acid fragments are physically separated from each other. Separation can be accomplished, for example, using capture ligands, such as biotin or other affinity ligands, and capture agents, such as avidin, streptavidin, an antibody, or a receptor. A probe or nucleic acid fragment can contain a capture ligand having specific binding activity for a capture agent. For example, fragments from a nucleic acid sample can be biotinylated or attached to an affinity ligand using methods well known in the art and separated away from the probes using a pull-down assay with steptavidin-coated beads, for example. In some embodiments, a capture ligand and capture agent or any other moiety (e.g., mass tag) can be used to add mass to the nucleic acid fragments such that they can be excluded from the mass range of the probes detected in a mass spectrometer. In some embodiments, mass is added to the probes, addition of a mass tag for example, to shift the mass range away from the mass range for the nucleic acid fragments. In some embodiments, a detection and/or quantification method is used to detect and/or quantify dissociated nucleic acid fragments. In some embodiments, detection and/or quantification method is used to detect and/or quantify dissociated probes.

Quantitative PCR

In certain embodiments quantitation of amplicons is by quantitative PCR (qPCR). In some embodiments, determining the amount of a nucleotide at V in the amplicons corresponding to the mitochondrial polynucleotide of a set and the amount of the nucleotide at V in the amplicons corresponding to the genomic polynucleotide of a set is by a process that comprises qPCR using the TAQman biochemistry with two fluorescent probes each specific for either the mitochondrial or genomic nucleotide at V.

In some embodiments, determining the amount of a nucleotide at V in the amplicons corresponding to the mitochondrial polynucleotide of the first species and the second species of a set is by a qPCR process comprising two fluorescent probes specific for the nucleotide at V of the mitochondrial polynucleotide of either the first or second species or a digital PCR process. In some embodiments, determining the amount of a nucleotide at V in the amplicons corresponding to the nuclear polynucleotide of the first species and the second species of a set is by a qPCR process comprising two fluorescent probes specific for the nucleotide at V of the nuclear polynucleotide of either the first or second species or a digital PCR process. In certain embodiments, the qPCR uses TAQman biochemistry.

Digital PCR

In some embodiments, amplicons are detected and/or quantified using digital PCR technology. Digital polymerase chain reaction (digital PCR or dPCR) can be used, for example, to directly identify and quantify nucleic acids in a sample. Digital PCR can be performed in an emulsion, in some embodiments. For example, individual nucleic acids are separated, e.g., in a microfluidic chamber device, and each nucleic acid is individually amplified by PCR. Nucleic acids can be separated such that there is no more than one nucleic acid per well. In some embodiments, different probes can be used to distinguish amplicons corresponding to the mitochondrial polynucleotide of a set and amplicons corresponding to the genomic polynucleotide of a set. In certain embodiments, different probes can be used to distinguish amplicons corresponding to the mitochondrial polynucleotide of the first species and the mitochondrial polynucleotide of the second species of a set or the nuclear polynucleotide of the first species and the nuclear polynucleotide of the second species of a set.

Nucleic Acid Sequencing

In certain embodiments quantitation of amplicons is by sequencing amplicons of mitochondrial and genomic (nuclear) polynucleotides. In some embodiments, the sequencing process is massive parallel sequencing. In some embodiments, the amount of a nucleotide at V in the amplicons corresponding to the mitochondrial polynucleotide of a set and the amount of the nucleotide at V in the amplicons corresponding to the genomic polynucleotide of a set is determined by the amount of the nucleotide at V is by a massive parallel sequencing process. In some embodiments, the amount of a nucleotide at V in the amplicons corresponding to the mitochondrial polynucleotide of the first species and the second species of a set and/or the amount of a nucleotide at V in the amplicons corresponding to the nuclear polynucleotide of the first species and the second species of a set is determined by a massive parallel sequencing process. Sometimes the sequencing is by a sequencing by synthesis process. In some embodiments, a sequence tag or barcode is attached to one or more amplification primers in each amplification primer pair. The term "sequence tagging" refers to incorporating a recognizable and distinct sequence into a nucleic acid or population of nucleic acids.

In some embodiments, a full or substantially full sequence is obtained and sometimes a partial sequence is obtained. Sequencing, mapping and related analytical methods are known in the art (e.g., United States Patent Application Publication US2009/0029377, incorporated by reference). Certain aspects of such processes are described hereafter.

Certain sequencing technologies generate nucleotide sequence reads. As used herein, "reads" (i.e., "a read", "a sequence read") are short nucleotide sequences produced by any sequencing process described herein or known in the art. Reads can be generated from one end of nucleic acid fragments ("single-end reads"), and sometimes are generated from both ends of nucleic acids (e.g., paired-end reads, double-end reads).

In some embodiments the nominal, average, mean or absolute length of single-end reads sometimes is about 20 contiguous nucleotides to about 50 contiguous nucleotides, sometimes about 30 contiguous nucleotides to about 40 contiguous nucleotides, and sometimes about 35 contiguous nucleotides or about 36 contiguous nucleotides. In some embodiments, the nominal, average, mean or absolute length of single-end reads is about 20 to about 30 bases in length. In some embodiments, the nominal, average, mean or absolute length of single-end reads is about 24 to about 28 bases in length. In some embodiments, the nominal, average, mean or absolute length of single-end reads is about 21, 22, 23, 24, 25, 26, 27, 28 or about 29 bases in length.

In certain embodiments, the nominal, average, mean or absolute length of the paired-end reads sometimes is about 10 contiguous nucleotides to about 50 contiguous nucleotides (e.g., about 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 nucleotides in length), sometimes is about 15 contiguous nucleotides to about 25 contiguous nucleotides, and sometimes is about 17 contiguous nucleotides, about 18 contiguous nucleotides, about 20 contiguous nucleotides, about 25 contiguous nucleotides, about 36 contiguous nucleotides or about 45 contiguous nucleotides.

Reads generally are representations of nucleotide sequences in a physical nucleic acid. For example, in a read containing an ATGC depiction of a sequence, "A" represents an adenine nucleotide, "T" represents a thymine nucleotide, "G" represents a guanine nucleotide and "C" represents a cytosine nucleotide, in a physical nucleic acid. Sequence reads obtained from the blood of a pregnant female can be reads from a mixture of fetal and maternal nucleic acid. A mixture of relatively short reads can be transformed by processes described herein into a representation of a genomic nucleic acid present in the pregnant female and/or in the fetus. A mixture of relatively short reads can be transformed into a representation of a copy number variation (e.g., a maternal and/or fetal copy number variation), genetic variation or an aneuploidy, for example. Reads of a mixture of maternal and fetal nucleic acid can be transformed into a representation of a composite chromosome or a segment thereof comprising features of one or both maternal and fetal chromosomes. In certain embodiments, "obtaining" nucleic acid sequence reads of a sample from a subject and/or "obtaining" nucleic acid sequence reads of a biological specimen from one or more reference persons can involve directly sequencing nucleic acid to obtain the sequence information. In some embodiments, "obtaining" can involve receiving sequence information obtained directly from a nucleic acid by another.

Sequence reads can be mapped and the number of reads or sequence tags mapping to a specified nucleic acid region (e.g., a chromosome, a bin, a genomic section) are referred to as counts. In some embodiments, counts can be manipulated or transformed (e.g., normalized, combined, added, filtered, selected, averaged, derived as a mean, the like, or a combination thereof). In some embodiments, counts can be transformed to produce normalized counts. Normalized counts for multiple genomic sections can be provided in a profile (e.g., a genomic profile, a chromosome profile, a profile of a segment of a chromosome). One or more different elevations in a profile also can be manipulated or transformed (e.g., counts associated with elevations can be normalized) and elevations can be adjusted.

In some embodiments, one nucleic acid sample from one individual is sequenced. In certain embodiments, nucleic acid samples from two or more biological samples, where each biological sample is from one individual or two or more individuals, are pooled and the pool is sequenced. In the latter embodiments, a nucleic acid sample from each biological sample often is identified by one or more unique identification tags.

In some embodiments, a fraction of the genome is sequenced, which sometimes is expressed in the amount of the genome covered by the determined nucleotide sequences (e.g., "fold" coverage less than 1). When a genome is sequenced with about 1-fold coverage, roughly 100% of the nucleotide sequence of the genome is represented by reads. A genome also can be sequenced with redundancy, where a given region of the genome can be covered by two or more reads or overlapping reads (e.g., "fold" coverage greater than 1). In some embodiments, a genome is sequenced with about 0.01-fold to about 100-fold coverage, about 0.2-fold to 20-fold coverage, or about 0.2-fold to about 1-fold coverage (e.g., about 0.02-, 0.03-, 0.04-, 0.05-, 0.06-, 0.07-, 0.08-, 0.09-, 0.1-, 0.2-, 0.3-, 0.4-, 0.5-, 0.6-, 0.7-, 0.8-, 0.9-, 1-, 2-, 3-, 4-, 5-, 6-, 7-, 8-, 9-, 10-, 15-, 20-, 30-, 40-, 50-, 60-, 70-, 80-, 90-fold coverage).

In certain embodiments, a subset of nucleic acid fragments is selected prior to sequencing. In certain embodiments, hybridization-based techniques (e.g., using oligonucleotide arrays) can be used to first select for nucleic acid sequences from certain regions of the mitochondrial and/or nuclear genome. In some embodiments, nucleic acid can be fractionated by size (e.g., by gel electrophoresis, size exclusion chromatography or by microfluidics-based approach). In some embodiments, a portion or subset of a pre-selected set of nucleic acid fragments is sequenced randomly. In some embodiments, the nucleic acid is amplified prior to sequencing. In some embodiments, a portion or subset of the nucleic acid is amplified prior to sequencing.

In some embodiments, a sequencing library is prepared prior to or during a sequencing process. Methods for preparing a sequencing library are known in the art and commercially available platforms may be used for certain applications. Certain commercially available library platforms may be compatible with certain nucleotide sequencing processes described herein. For example, one or more commercially available library platforms may be compatible with a sequencing by synthesis process. In some embodiments, a ligation-based library preparation method is used (e.g., ILLUMINA TRUSEQ, Illumina, San Diego Calif.). Ligation-based library preparation methods typically use a methylated adaptor design which can incorporate an index sequence at the initial ligation step and often can be used to prepare samples for single-read sequencing, paired-end sequencing and multiplexed sequencing. In some embodiments, a transposon-based library preparation method is used (e.g., EPICENTRE NEXTERA, Illumina, Inc., California). Transposon-based methods typically use in vitro transposition to simultaneously fragment and tag DNA in a single-tube reaction (often allowing incorporation of platform-specific tags and optional barcodes), and prepare sequencer-ready libraries.

Any sequencing method suitable for conducting methods described herein can be utilized. In some embodiments, a high-throughput sequencing method is used. High-throughput sequencing methods generally involve clonally amplified DNA templates or single DNA molecules that are sequenced in a massively parallel fashion within a flow cell (e.g. as described in Metzker M Nature Rev 11:31-46 (2010); Volkerding et al. Clin Chem 55:641-658 (2009)). Such sequencing methods also can provide digital quantitative information, where each sequence read is a countable "sequence tag" or "count" representing an individual clonal DNA template, a single DNA molecule, bin or chromosome. Next generation sequencing techniques capable of sequencing DNA in a massively parallel fashion are collectively referred to herein as "massively parallel sequencing" (MPS). Certain MPS techniques include a sequencing-by-synthesis process. High-throughput sequencing technologies include, for example, sequencing-by-synthesis with reversible dye terminators, sequencing by oligonucleotide probe ligation, pyrosequencing and real time sequencing. Non-limiting examples of MPS include Massively Parallel Signature Sequencing (MPSS), Polony sequencing, Pyrosequencing, Illumina (Solexa) sequencing, SOLiD sequencing, Ion semiconductor sequencing, DNA nanoball sequencing, Helioscope single molecule sequencing, single molecule real time (SMRT) sequencing, nanopore sequencing, ION Torrent and RNA polymerase (RNAP) sequencing.

Systems utilized for high-throughput sequencing methods are commercially available and include, for example, the Roche 454 platform, the Applied Biosystems SOLID platform, the Helicos True Single Molecule DNA sequencing technology, the sequencing-by-hybridization platform from Affymetrix Inc., the single molecule, real-time (SMRT) technology of Pacific Biosciences, the sequencing-by-synthesis platforms from 454 Life Sciences, Illumina/Solexa and Helicos Biosciences, and the sequencing-by-ligation platform from Applied Biosystems. The ION TORRENT technology from Life technologies and nanopore sequencing also can be used in high-throughput sequencing approaches.

In some embodiments, first generation technology, such as, for example, Sanger sequencing including the automated Sanger sequencing, can be used in a method provided herein. Additional sequencing technologies that include the use of developing nucleic acid imaging technologies (e.g. transmission electron microscopy (TEM) and atomic force microscopy (AFM)), also are contemplated herein. Examples of various sequencing technologies are described below.

A nucleic acid sequencing technology that may be used in a method described herein is sequencing-by-synthesis and reversible terminator-based sequencing (e.g. Illumina's Genome Analyzer; Genome Analyzer II; HISEQ 2000; HISEQ 2500 (Illumina, San Diego Calif.)). With this technology, millions of nucleic acid (e.g. DNA) fragments can be sequenced in parallel. In one example of this type of sequencing technology, a flow cell is used which contains an optically transparent slide with 8 individual lanes on the surfaces of which are bound oligonucleotide anchors (e.g., adaptor primers). A flow cell often is a solid support that can be configured to retain and/or allow the orderly passage of reagent solutions over bound analytes. Flow cells frequently are planar in shape, optically transparent, generally in the millimeter or sub-millimeter scale, and often have channels or lanes in which the analyte/reagent interaction occurs.

In certain sequencing by synthesis procedures, for example, template DNA (e.g., circulating cell-free DNA (ccfDNA)) sometimes can be fragmented into lengths of several hundred base pairs in preparation for library generation. In some embodiments, library preparation can be performed without further fragmentation or size selection of the template DNA (e.g., ccfDNA). Sample isolation and library generation may be performed using automated methods and apparatus, in certain embodiments. Briefly, template DNA is end repaired by a fill-in reaction, exonuclease reaction or a combination of a fill-in reaction and exonuclease reaction. The resulting blunt-end repaired template DNA is extended by a single nucleotide, which is complementary to a single nucleotide overhang on the 3' end of an adapter primer, and often increases ligation efficiency. Any complementary nucleotides can be used for the extension/overhang nucleotides (e.g., A/T, C/G), however adenine frequently is used to extend the end-repaired DNA, and thymine often is used as the 3' end overhang nucleotide.

In certain sequencing by synthesis procedures, for example, adapter oligonucleotides are complementary to the flow-cell anchors, and sometimes are utilized to associate the modified template DNA (e.g., end-repaired and single nucleotide extended) with a solid support, such as the inside surface of a flow cell, for example. In some embodiments, the adapter also includes identifiers (i.e., indexing nucleotides, or "barcode" nucleotides (e.g., a unique sequence of nucleotides usable as an identifier to allow unambiguous identification of a sample and/or chromosome)), one or more sequencing primer hybridization sites (e.g., sequences complementary to universal sequencing primers, single end sequencing primers, paired end sequencing primers, multiplexed sequencing primers, and the like), or combinations thereof (e.g., adapter/sequencing, adapter/identifier, adapter/identifier/sequencing). Identifiers or nucleotides contained in an adapter often are six or more nucleotides in length, and frequently are positioned in the adaptor such that the identifier nucleotides are the first nucleotides sequenced during the sequencing reaction. In certain embodiments, identifier nucleotides are associated with a sample but are sequenced in a separate sequencing reaction to avoid compromising the quality of sequence reads. Subsequently, the reads from the identifier sequencing and the DNA template sequencing are linked together and the reads de-multiplexed. After linking and de-multiplexing the sequence reads and/or identifiers can be further adjusted or processed as described herein.

In certain sequencing by synthesis procedures, utilization of identifiers allows multiplexing of sequence reactions in a flow cell lane, thereby allowing analysis of multiple samples per flow cell lane. The number of samples that can be analyzed in a given flow cell lane often is dependent on the number of unique identifiers utilized during library preparation and/or probe design. Non limiting examples of commercially available multiplex sequencing kits include Illumina's multiplexing sample preparation oligonucleotide kit and multiplexing sequencing primers and PhiX control kit (e.g., Illumina's catalog numbers PE-400-1001 and PE-400-1002, respectively). A method described herein can be performed using any number of unique identifiers (e.g., 4, 8, 12, 24, 48, 96, or more). The greater the number of unique identifiers, the greater the number of samples and/or chromosomes, for example, that can be multiplexed in a single flow cell lane. Multiplexing using 12 identifiers, for example, allows simultaneous analysis of 96 samples (e.g., equal to the number of wells in a 96 well microwell plate) in an 8 lane flow cell. Similarly, multiplexing using 48 identifiers, for example, allows simultaneous analysis of 384 samples (e.g., equal to the number of wells in a 384 well microwell plate) in an 8 lane flow cell.

In certain sequencing by synthesis procedures, adapter-modified, single-stranded template DNA is added to the flow cell and immobilized by hybridization to the anchors under limiting-dilution conditions. In contrast to emulsion PCR, DNA templates are amplified in the flow cell by "bridge" amplification, which relies on captured DNA strands "arching" over and hybridizing to an adjacent anchor oligonucleotide. Multiple amplification cycles convert the single-molecule DNA template to a clonally amplified arching "cluster," with each cluster containing approximately 1000 clonal molecules. Approximately $1 \times 10^9$ separate clusters can be generated per flow cell. For sequencing, the clusters are denatured, and a subsequent chemical cleavage reaction and wash leave only forward strands for single-end sequencing. Sequencing of the forward strands is initiated by hybridizing a primer complementary to the adapter sequences, which is followed by addition of polymerase and a mixture of four differently colored fluorescent reversible dye terminators. The terminators are incorporated according to sequence complementarity in each strand in a clonal cluster. After incorporation, excess reagents are washed away, the clusters are optically interrogated, and the fluorescence is recorded. With successive chemical steps, the reversible dye terminators are unblocked, the fluorescent labels are cleaved and washed away, and the next sequencing cycle is performed. This iterative, sequencing-by-synthesis process sometimes requires approximately 2.5 days to generate read lengths of 36 bases. With $50 \times 10^6$ clusters per flow cell, the overall sequence output can be greater than 1 billion base pairs (Gb) per analytical run.

Another nucleic acid sequencing technology that may be used with a method described herein is 454 sequencing (Roche). 454 sequencing uses a large-scale parallel pyrosequencing system capable of sequencing about 400-600 megabases of DNA per run. The process typically involves two steps. In the first step, sample nucleic acid (e.g. DNA) is sometimes fractionated into smaller fragments (300-800 base pairs) and polished (made blunt at each end). Short adaptors are then ligated onto the ends of the fragments. These adaptors provide priming sequences for both amplification and sequencing of the sample-library fragments. One adaptor (Adaptor B) contains a 5'-biotin tag for immobilization of the DNA library onto streptavidin-coated beads. After nick repair, the non-biotinylated strand is released and used as a single-stranded template DNA (sstDNA) library. The sstDNA library is assessed for its quality and the optimal amount (DNA copies per bead) needed for emPCR is determined by titration. The sstDNA library is immobilized onto beads. The beads containing a library fragment carry a single sstDNA molecule. The bead-bound library is emulsified with the amplification reagents in a water-in-oil mixture. Each bead is captured within its own microreactor where PCR amplification occurs. This results in bead-immobilized, clonally amplified DNA fragments.

In the second step of 454 sequencing, single-stranded template DNA library beads are added to an incubation mix containing DNA polymerase and are layered with beads containing sulfurylase and luciferase onto a device containing pico-liter sized wells. Pyrosequencing is performed on each DNA fragment in parallel. Addition of one or more nucleotides generates a light signal that is recorded by a CCD camera in a sequencing instrument. The signal strength is proportional to the number of nucleotides incorporated. Pyrosequencing exploits the release of pyrophosphate (PPi) upon nucleotide addition. PPi is converted to ATP by ATP sulfurylase in the presence of adenosine 5' phosphosulfate. Luciferase uses ATP to convert luciferin to oxyluciferin, and this reaction generates light that is discerned and analyzed (see, for example, Margulies, M. et al. Nature 437:376-380 (2005)).

Another nucleic acid sequencing technology that may be used in a method provided herein is Applied Biosystems' SOLiD™ technology. In SOLiD™ sequencing-by-ligation, a library of nucleic acid fragments is prepared from the sample and is used to prepare clonal bead populations. Wth this method, one species of nucleic acid fragment will be present on the surface of each bead (e.g. magnetic bead). Sample nucleic acid (e.g. genomic DNA) is sheared into fragments, and adaptors are subsequently attached to the 5' and 3' ends of the fragments to generate a fragment library. The adapters are typically universal adapter sequences so that the starting sequence of every fragment is both known and identical. Emulsion PCR takes place in microreactors containing all the necessary reagents for PCR. The resulting PCR products attached to the beads are then covalently bound to a glass slide. Primers then hybridize to the adapter sequence within the library template. A set of four fluorescently labeled di-base probes compete for ligation to the sequencing primer. Specificity of the di-base probe is achieved by interrogating every 1st and 2nd base in each ligation reaction. Multiple cycles of ligation, detection and cleavage are performed with the number of cycles determining the eventual read length. Following a series of ligation cycles, the extension product is removed and the template is reset with a primer complementary to the n−1 position for a second round of ligation cycles. Often, five rounds of primer reset are completed for each sequence tag. Through the primer reset process, each base is interrogated in two independent ligation reactions by two different primers. For example, the base at read position 5 is assayed by primer number 2 in ligation cycle 2 and by primer number 3 in ligation cycle 1.

Another nucleic acid sequencing technology that may be used in a method described herein is Helicos True Single Molecule Sequencing (tSMS). In the tSMS technique, a polyA sequence is added to the 3' end of each nucleic acid (e.g. DNA) strand from the sample. Each strand is labeled by the addition of a fluorescently labeled adenosine nucleotide. The DNA strands are then hybridized to a flow cell, which contains millions of oligo-T capture sites that are immobilized to the flow cell surface. The templates can be at a density of about 100 million templates/cm2. The flow cell is then loaded into a sequencing apparatus and a laser illuminates the surface of the flow cell, revealing the position of each template. A CCD camera can map the position of the templates on the flow cell surface. The template fluorescent label is then cleaved and washed away. The sequencing reaction begins by introducing a DNA polymerase and a fluorescently labeled nucleotide. The oligo-T nucleic acid serves as a primer. The polymerase incorporates the labeled nucleotides to the primer in a template directed manner. The polymerase and unincorporated nucleotides are removed. The templates that have directed incorporation of the fluorescently labeled nucleotide are detected by imaging the flow cell surface. After imaging, a cleavage step removes the fluorescent label, and the process is repeated with other fluorescently labeled nucleotides until the desired read length is achieved. Sequence information is collected with each nucleotide addition step (see, for example, Harris T. D. et al., Science 320:106-109 (2008)).

Another nucleic acid sequencing technology that may be used in a method provided herein is the single molecule, real-time (SMRT™) sequencing technology of Pacific Biosciences. With this method, each of the four DNA bases is attached to one of four different fluorescent dyes. These dyes are phospholinked. A single DNA polymerase is immobilized with a single molecule of template single stranded DNA at the bottom of a zero-mode waveguide (ZMW). A ZMW is a confinement structure which enables observation of incorporation of a single nucleotide by DNA polymerase against the background of fluorescent nucleotides that rapidly diffuse in an out of the ZMW (in microseconds). It takes several milliseconds to incorporate a nucleotide into a growing strand. During this time, the fluorescent label is excited and produces a fluorescent signal, and the fluorescent tag is cleaved off. Detection of the corresponding fluorescence of the dye indicates which base was incorporated. The process is then repeated.

Another nucleic acid sequencing technology that may be used in a method described herein is ION TORRENT (Life Technologies) single molecule sequencing which pairs semiconductor technology with a simple sequencing chemistry to directly translate chemically encoded information (A, C, G, T) into digital information (0, 1) on a semiconductor chip. ION TORRENT uses a high-density array of micro-machined wells to perform nucleic acid sequencing in a massively parallel way. Each well holds a different DNA molecule. Beneath the wells is an ion-sensitive layer and beneath that an ion sensor. Typically, when a nucleotide is incorporated into a strand of DNA by a polymerase, a hydrogen ion is released as a byproduct. If a nucleotide, for example a C, is added to a DNA template and is then incorporated into a strand of DNA, a hydrogen ion will be released. The charge from that ion will change the pH of the solution, which can be detected by an ion sensor. A sequencer can call the base, going directly from chemical information to digital information. The sequencer then sequentially floods the chip with one nucleotide after another. If the next nucleotide that floods the chip is not a match, no voltage change will be recorded and no base will be called. If there are two identical bases on the DNA strand, the voltage will be double, and the chip will record two identical bases called. Because this is direct detection (i.e. detection without scanning, cameras or light), each nucleotide incorporation is recorded in seconds.

Another nucleic acid sequencing technology that may be used in a method described herein is the chemical-sensitive field effect transistor (CHEMFET) array. In one example of this sequencing technique, DNA molecules are placed into reaction chambers, and the template molecules can be hybridized to a sequencing primer bound to a polymerase. Incorporation of one or more triphosphates into a new nucleic acid strand at the 3' end of the sequencing primer can be detected by a change in current by a CHEMFET sensor. An array can have multiple CHEMFET sensors. In another example, single nucleic acids are attached to beads, and the nucleic acids can be amplified on the bead, and the individual beads can be transferred to individual reaction chambers on a CHEMFET array, with each chamber having a CHEMFET sensor, and the nucleic acids can be sequenced (see, for example, U.S. Patent Application Publication No. 2009/0026082).

Another nucleic acid sequencing technology that may be used in a method described herein is electron microscopy. In one example of this sequencing technique, individual nucleic acid (e.g. DNA) molecules are labeled using metallic labels that are distinguishable using an electron microscope. These molecules are then stretched on a flat surface and imaged using an electron microscope to measure sequences (see, for example, Moudrianakis E. N. and Beer M. Proc Natl Acad Sci USA. 1965 March; 53:564-71). In some embodiments, transmission electron microscopy (TEM) is used (e.g. Halcyon Molecular's TEM method). This method, termed Individual Molecule Placement Rapid Nano Transfer (IMPRNT), includes utilizing single atom resolution transmission electron microscope imaging of high-molecular weight (e.g. about 150 kb or greater) DNA selectively labeled with heavy atom markers and arranging these molecules on ultra-thin films in ultra-dense (3 nm strand-to-strand) parallel arrays with consistent base-to-base spacing. The electron microscope is used to image the molecules on the films to determine the position of the heavy atom markers and to extract base sequence information from the DNA (see, for example, International Patent Application No. WO 2009/046445).

Other sequencing methods that may be used to conduct methods herein include digital PCR and sequencing by hybridization. In sequencing by hybridization, the method involves contacting a plurality of polynucleotide sequences with a plurality of polynucleotide probes, where each of the plurality of polynucleotide probes can be optionally tethered to a substrate. The substrate can be a flat surface with an array of known nucleotide sequences, in some embodiments. The pattern of hybridization to the array can be used to determine the polynucleotide sequences present in the sample. In some embodiments, each probe is tethered to a bead, e.g., a magnetic bead or the like. Hybridization to the beads can be identified and used to identify the plurality of polynucleotide sequences within the sample.

In some embodiments, chromosome-specific sequencing is performed. In some embodiments, chromosome-specific sequencing is performed utilizing DANSR (digital analysis of selected regions). Digital analysis of selected regions enables simultaneous quantification of hundreds of loci by cfDNA-dependent catenation of two locus-specific oligonucleotides via an intervening 'bridge' oligo to form a PCR template. In some embodiments, chromosome-specific sequencing is performed by generating a library enriched in chromosome-specific sequences. In some embodiments, sequence reads are obtained only for a selected set of chromosomes. In some embodiments, sequence reads are obtained only for chromosomes 21, 18 and 13.

The length of the sequence read often is associated with the particular sequencing technology.

High-throughput methods, for example, provide sequence reads that can vary in size from tens to hundreds of base pairs (bp). Nanopore sequencing, for example, can provide sequence reads that can vary in size from tens to hundreds to thousands of base pairs. In some embodiments, the sequence reads are of a mean, median, mode or average length of about 4 bp to 900 bp long (e.g. about 5 bp, about 10 bp, about 15 bp, about 20 bp, about 25 bp, about 30 bp, about 35 bp, about 40 bp, about 45 bp, about 50 bp, about 55 bp, about 60 bp, about 65 bp, about 70 bp, about 75 bp, about 80 bp, about 85 bp, about 90 bp, about 95 bp, about 100 bp, about 110 bp, about 120 bp, about 130, about 140 bp, about 150 bp, about 200 bp, about 250 bp, about 300 bp, about 350 bp, about 400 bp, about 450 bp, or about 500 bp. In some embodiments, the sequence reads are of a mean, median, mode or average length of about 1,000 bp or more.

Distinguishable Labels and Release

As used herein, the terms "distinguishable labels" and "distinguishable tags" refer to types of labels or tags that can be distinguished from one another and used to identify the nucleic acid (e.g., amplicon or primer extension product) to which the tag is attached. A variety of types of labels and tags may be selected and used for multiplex methods provided herein. For example, oligonucleotides, amino acids, small organic molecules, light-emitting molecules, light-absorbing molecules, light-scattering molecules, luminescent molecules, isotopes, enzymes and the like may be used as distinguishable labels or tags. In certain embodiments, oligonucleotides, amino acids, and/or small molecule organic molecules of varying lengths, varying mass-to-charge ratios, varying electrophoretic mobility (e.g., capillary electrophoresis mobility) and/or varying mass also can be used as distinguishable labels or tags. Accordingly, a fluorophore, radioisotope, colormetric agent, light emitting agent, chemiluminescent agent, light scattering agent, and the like, may be used as a label. The choice of label may depend on the sensitivity required, ease of conjugation with a nucleic acid, stability requirements, and available instrumentation. The term "distinguishable feature," as used herein with respect to distinguishable labels and tags, refers to any feature of one label or tag that can be distinguished from another label or tag (e.g., mass and others described herein). In some embodiments, label composition of the distinguishable labels and tags can be selected and/or designed to result in optimal flight behavior in a mass spectrometer and to allow labels and tags to be distinguished at high multiplexing levels.

For methods used herein, a particular target (mitochondrial or genomic, nuclear)) nucleic acid species, amplicon species and/or extended oligonucleotide species often is paired with a distinguishable detectable label species, such that the detection of a particular label or tag species directly identifies the presence of and/or quantifies a particular target minor or nucleic acid species, amplicon species and/or extended oligonucleotide species in a particular composition. Accordingly, one distinguishable feature of a label species can be used, for example, to identify one target nucleic acid species in a composition, as that particular distinguishable feature corresponds to the particular target nucleic acid. Labels and tags may be attached to a nucleic acid (e.g., oligonucleotide) by any known methods and in any location (e.g., at the 5' of an oligonucleotide). Thus, reference to each particular label species as "specifically corresponding" to each particular target nucleic acid species, as used herein, refers to one label species being paired with one target species. When the presence of a label species is detected, then the presence of the target nucleic acid species associated with that label species thereby is detected and/or quantified, in certain embodiments.

The term "mass distinguishable label" as used herein refers to a label that is distinguished by mass as a feature. A variety of mass distinguishable labels can be selected and used, such as for example a compomer, amino acid and/or a concatemer. Different lengths and/or compositions of nucleotide strings (e.g., nucleic acids, compomers), amino acid strings (e.g., peptides, polypeptides, compomers) and/or concatemers can be distinguished by mass and be used as labels. Any number of units can be utilized in a mass distinguishable label, and upper and lower limits of such units depends in part on the mass window and resolution of the system used to detect and distinguish such labels. Thus, the length and composition of mass distinguishable labels can be selected based in part on the mass window and resolution of the detector used to detect and distinguish the labels.

The term "compomer" as used herein refers to the composition of a set of monomeric units and not the particular sequence of the monomeric units. For a nucleic acid, the term "compomer" refers to the base composition of the nucleic acid with the monomeric units being bases. The number of each type of base can be denoted by $B_n$ (i.e., $A_aC_cG_gT_t$, with $A_0C_0G_0T_0$ representing an "empty" compomer or a compomer containing no bases). A natural compomer is a compomer for which all component monomeric units (e.g., bases for nucleic acids and amino acids for polypeptides) are greater than or equal to zero. In certain embodiments, at least one of A, C, G or T equals 1 or more (e.g., $A_0C_0G_1T_0$, $A_1C_0G_1T_0$, $A_2C_1G_1T_2$, $A_3C_2G_1T_5$). For purposes of comparing sequences to determine sequence variations, in the methods provided herein, "unnatural" compomers containing negative numbers of monomeric units can be generated by an algorithm utilized to process data. For polypeptides, a compomer refers to the amino acid composition of a polypeptide fragment, with the number of each type of amino acid similarly denoted. A compomer species can correspond to multiple sequences. For example, the compomer $A_2G_3$ corresponds to the sequences AGGAG, GGGAA, AAGGG, GGAGA and others. In general, there is a unique compomer corresponding to a sequence, but more than one sequence can correspond to the same compomer. In certain embodiments, one compomer species is paired with (e.g., corresponds to) one target nucleic acid species, amplicon species and/or oligonucleotide species. Different compomer species have different base compositions, and distinguishable masses, in embodiments herein (e.g., $A_0C_0G_5T_0$ and $A_0C_5G_0T_0$ are different and mass-distinguishable compomer species). In some embodiments, a set of compomer species differ by base composition and have the same length. In certain embodiments, a set of compomer species differ by base compositions and length.

A nucleotide compomer used as a mass distinguishable label can be of any length for which all compomer species can be detectably distinguished, for example about 1 to 15, 5 to 20, 1 to 30, 5 to 35, 10 to 30, 15 to 30, 20 to 35, 25 to 35, 30 to 40, 35 to 45, 40 to 50, or 25 to 50, or sometimes about 55, 60, 65, 70, 75, 80, 85, 90, 85 or 100, nucleotides in length. A peptide or polypeptide compomer used as a mass distinguishable label can be of any length for which all compomer species can be detectably distinguished, for example about 1 to 20, 10 to 30, 20 to 40, 30 to 50, 40 to 60, 50 to 70, 60 to 80, 70 to 90, or 80 to 100 amino acids in length. As noted above, the limit to the number of units in a compomer often is limited by the mass window and resolution of the detection method used to distinguish the compomer species.

The terms "concatamer" and "concatemer" are used herein synonymously (collectively "concatemer"), and refer to a molecule that contains two or more units linked to one another (e.g., often linked in series; sometimes branched in certain embodiments). A concatemer sometimes is a nucleic acid and/or an artificial polymer in some embodiments. A concatemer can include the same type of units (e.g., a homoconcatemer) in some embodiments, and sometimes a concatemer can contain different types of units (e.g., a heteroconcatemer). A concatemer can contain any type of unit(s), including nucleotide units, amino acid units, small organic molecule units (e.g., trityl), particular nucleotide sequence units, particular amino acid sequence units, and the like. A homoconcatemer of three particular sequence units ABC is ABCABCABC, in an embodiment. A concatemer can contain any number of units so long as each concatemer species can be detectably distinguished from other species. For example, a trityl concatemer species can contain about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 80, 85, 90, 95, 100, 125, 150, 175, 200, 225, 250, 275, 300, 325, 350, 375, 400, 425, 450, 475, 500, 600, 700, 800, 900 or 1000 trityl units, in some embodiments.

A distinguishable label can be released from a nucleic acid product (e.g., an extended oligonucleotide) in certain embodiments. The linkage between the distinguishable label and a nucleic acid can be of any type that can be transcribed and cleaved, cleaved and allow for detection of the released label or labels, thereby identifying and/or quantifying the nucleic acid product (e.g., U.S. patent application publication no. US20050287533A1, entitled "Target-Specific Compomers and Methods of Use," naming Ehrich et al.). Such linkages and methods for cleaving the linkages ("cleaving conditions") are known. In certain embodiments, a label can be separated from other portions of a molecule to which it is attached. In some embodiments, a label (e.g., a compomer) is cleaved from a larger string of nucleotides (e.g., extended oligonucleotides). Non-limiting examples of linkages include linkages that can be cleaved by a nuclease (e.g., ribonuclease, endonuclease); linkages that can be cleaved by a chemical; linkages that can be cleaved by physical treatment; and photocleavable linkers that can be cleaved by light (e.g., o-nitrobenzyl, 6-nitroveratryloxycarbonyl, 2-nitrobenzyl group). Photocleavable linkers provide an advantage when using a detection system that emits light (e.g., matrix-assisted laser desorption ionization (MALDI) mass spectrometry involves the laser emission of light), as cleavage and detection are combined and occur in a single step.

In certain embodiments, a label can be part of a larger unit, and can be separated from that unit prior to detection. For example, in certain embodiments, a label is a set of contiguous nucleotides in a larger nucleotide sequence, and the label is cleaved from the larger nucleotide sequence. In such embodiments, the label often is located at one terminus of the nucleotide sequence or the nucleic acid in which it resides. In some embodiments, the label, or a precursor thereof, resides in a transcription cassette that includes a promoter sequence operatively linked with the precursor sequence that encodes the label. In the latter embodiments, the promoter sometimes is a RNA polymerase-recruiting promoter that generates an RNA that includes or consists of the label. An RNA that includes a label can be cleaved to release the label prior to detection (e.g., with an RNase).

In certain embodiments, a distinguishable label or tag is not cleaved from an extended oligonucleotide, and in some embodiments, the distinguishable label or tag comprises a capture agent. In certain embodiments, detecting a distinguishable feature includes detecting the presence or absence of an extended oligonucleotide, and in some embodiments an extended oligonucleotide includes a capture agent.

Detection and Degree of Multiplexing

The term "detection" of a label as used herein refers to identification of a label species. Any suitable detection device can be used to distinguish label species in a sample. Detection devices suitable for detecting mass distinguishable labels, include, without limitation, certain mass spectrometers and gel electrophoresis devices. Examples of mass spectrometry formats include, without limitation, Matrix-Assisted Laser Desorption/Ionization Time-of-Flight (MALDI-TOF) Mass Spectrometry (MS), MALDI orthogonal TOF MS (OTOF MS; two dimensional), Laser Desorption Mass Spectrometry (LDMS), Electrospray (ES) MS, Ion Cyclotron Resonance (ICR) MS, and Fourier Transform MS. Methods described herein are readily applicable to mass spectrometry formats in which analyte is volatized and ionized ("ionization MS," e.g., MALDI-TOF MS, LDMS, ESMS, linear TOF, OTOF). Orthogonal ion extraction MALDI-TOF and axial MALDI-TOF can give rise to relatively high resolution, and thereby, relatively high levels of multiplexing. Detection devices suitable for detecting light-emitting, light absorbing and/or light-scattering labels, include, without limitation, certain light detectors and photodetectors (e.g., for fluorescence, chemiluminescence, absorption, and/or light scattering labels).

Multiplex Assay Design

The methods provided herein can be adapted to a multiplexed format to amplify and quantitate polynucleotides of a plurality of sets. Multiplexing can be performed in a single reaction vessel, compartment or container. In some embodiments, paralogs are chosen and assays are designed so that the nucleotide at V for the mitochondrial polynucleotides and genomic polynucleotides for a number of sets can be distinguished and quantified in a single reaction. The following are examples of multiplex reaction schemes and are not meant to be limiting. For example, paralogs with a combination of either C (mitochondrial) and T (genomic) or G (mitochondrial) and A (genomic) are selected. Single base extension reactions to probe C/A would be carried out in the forward direction and reactions to probe G/A in the reverse direction, i.e. at C/T. Thus enabling a plurality of sets to be examined in a single reaction vessel. This approach could be applied to sets of paralogs having C as the nucleotide at V for mitochondrial polynucleotides and A/G/T as the nucleotide at V for genomic polynucleotides. Another possible combination of sets of paralogs that could be plexed in a single reaction vessel has V as C/T, C/A, G/A, G/T, where C and G are mitochondrial and A and T are genomic. An alternative multiplex assay has paralog sets that share a common V nucleotide for the mitochondrial polynucleotides and have any of the other three nucleotides as the V nucleotide for genomic polynucleotides. Additional liberty in design can is obtained for any of the assays by allowing reverse design, i.e., probing a sequence on the opposite stand.

In some embodiments, mitochondrial paralogs are chosen and assays are designed for co-amplification of different sets of mitochondrial paralogs and so that the nucleotide at V for the mitochondrial polynucleotides of a number of sets can be distinguished and quantified in a single reaction. In some embodiments, nuclear paralogs are chosen and assays are designed for co-amplification of different sets of nuclear paralogs and so that the nucleotide at V for the nuclear polynucleotides for a number of sets can be distinguished and quantified in a single reaction. In certain embodiments, assays targeting nuclear paralogs and assays targeting mitochondrial paralogs can be performed in the same reaction. In certain embodiments, assays targeting nuclear paralogs are performed in a separate reaction from assays targeting mitochondrial paralogs (both amplification and single base extension). In some embodiments, amplification of nuclear paralogs and amplification of mitochondrial paralogs are carried out in separate reactions and then combined to carry out single base extension reactions.

Design methods for achieving resolved mass spectra with multiplexed assays can include primer and oligonucleotide design methods, relative concentrations of reagents such as chain terminating reagents, choice of detection labels and other reaction design methods. For primer and oligonucleotide design in multiplexed assays, the same general guidelines for primer design applies for uniplexed reactions, such as avoiding false priming and primer dimers, only more primers are involved for multiplex reactions. In addition, for analysis by mass spectrometry, analyte peaks in the mass spectra for one assay are sufficiently resolved from a product of any assay with which that assay is multiplexed, including pausing peaks and any other by-product peaks. Also, analyte peaks optimally fall within a user-specified mass window, for example, within a range of 5,000-8,500 Da. Extension oligonucleotides can be designed with respect to target sequences of a given V (e.g., SNP) strand, in some embodiments. In such embodiments, the length often is between limits that can be, for example, user-specified (e.g., 17 to 24 bases or 17-26 bases) and often do not contain bases that are uncertain in the target sequence. Hybridization strength sometimes is gauged by calculating the sequence-dependent melting (or hybridization/dissociation) temperature, $T_m$. A particular primer choice may be disallowed, or penalized relative to other choices of primers, because of its hairpin potential, false priming potential, primer-dimer potential, low complexity regions, and problematic subsequences such as GGGG. Methods and software for designing extension oligonucleotides (e.g., according to these criteria) are known, and include, for example, SpectroDESIGNER™ (Sequenom).

Mitochondrial Dosage

Mitochondrial/Genomic (Nuclear) Paralogs

In certain embodiments, the ratios for a plurality of sets are combined and the relative dosage of mitochondrial nucleic acid to genomic nucleic acid for the sample is determined based on the combined ratio. In some embodiments, the combined ratio is an average ratio or a median ratio. The term "average" as used herein is meant a value that is calculated by adding the value of the ratios for each of a number of sets and then dividing by the total number of sets. The term "median" as used herein is meant a value for a ratio that is at the midpoint of the frequency distribution of observed values of the ratios for the sets examined, such that there is an equal probability of falling above or below it.

In some embodiments, the ratio of each set is compared to an average or median ratio based on the plurality of sets and an outlier or cluster that deviates from the average or median ratio is an indication of a mitochondrial deletion. In other embodiments, the ratio of a set representing one region of the mitochondrial genome is compared to the ratio of each of the other sets representing different regions of the mitochondrial genome and the presence of one or more deletions in the mitochondrial genome is determined based on a difference in the ratio for the one region compared with the ratios for one or more other regions of the mitochondrial genome.

Mitochondrial/Mitochondrial Paralogs-Nuclear/Nuclear Paralogs

In some embodiments, the ratios for a plurality of sets of mitochondrial polynucleotides are combined and the ratios for a plurality of sets of nuclear polynucleotides are combined and the mitochondrial/nuclear ratio for the sample is determined based on using the combined ratios. In some embodiments, the combined ratio is an average ratio or a median ratio. Variability can be minimized by using the results of multiple independent assays targeting nuclear paralogs and multiple independent assays targeting mitochondrial paralogs to derive Ratio X and Ratio Y.

In some embodiments, the ratio of a set of a mitochondrial paralog representing one region of the mitochondrial genome is compared to an average or median ratio based on the plurality of sets of mitochondrial paralogs and an outlier or cluster that deviates from the average or median ratio is an indication of a mitochondrial deletion.

In certain embodiments, the ratio of a set of a mitochondrial paralog representing one region of the mitochondrial genome is compared to the ratio of each of the other sets of a mitochondrial paralog representing different regions of the mitochondrial genome and the presence of one or more deletions in the mitochondrial genome is determined based on a difference in the ratio of the set representing the one region compared with the ratios for one or more sets representing other regions of the mitochondrial genome.

Baseline Mitochondrial Dosage

The number of mitochondria in a sample can exhibit differences based on the tissue of origin, the genetics of a subject, as well as fitness of the subject. In some embodiments, a baseline mitochondrial dosage is determined for an individual subject and/or population and the dosage determined for the sample is compared to or adjusted relative to the baseline dosage. For example, a baseline mitochondrial dosage for a subject can be based on a sample from the subject obtained at multiple points in time. A baseline mitochondrial dosage for a population can be determined for a sample from individuals that do not have or are not pre-disposed to having a disease, disorder or symptoms associated with an increase or decrease in the dosage of mitochondria nucleic acid or a deletion in the mitochondrial genome. The baseline mitochondrial dosage for a population can be used as the baseline for a subject when the subject and the population share one or more of the following exemplary characteristics: tissue of origin for which the mitochondria are examined, sex, ethnicity, age and activity level. Other relevant characteristics can be utilized depending on the subject and the population. If there are differences, such as tissue of origin, adjusts are made to normalize the samples.

Diseases and Disorders

An increase or decrease in mitochondrial dosage has be associated with a number of diseases, disorder, conditions and symptoms, including, but not limited to the following examples.

Neurodegenerative Disease

Non-limiting examples include: Parkinson's, Alzheimers, Friedreich's Ataxia, Amyotropic lateral sclerosis and Multiple sclerosis (MS).

Diseases Associated with nDNA Mutations that Cause mtDNA Stability

POLG associated diseases are most common (POLG is a gene that codes for the catalytic subunit of the mitochondrial DNA polymerase, called DNA polymerase gamma). Non-limiting examples include: Opthalmoplegia, Alper's syndrome and Leigh's syndrome.

Diseases Associated with mtDNA Deletions/Mutations

Non-limiting examples include: Kearns-Sayre syndrome (KSS), Leber's heredity optic neuropathy (LHON), Mitochondiral encephalomyopathy, lactic acidosis, stroke like episodes (MELAS) and Myoclonic Epilepsy with Ragged Red Fibers (MERRF).

Cancer

Non-limiting examples include: gastric cancer, hepatocellular carcinoma (HCC), HPV associated cancer, breast cancer and Ewing's Sarcoma, pancreatic cancer, liver cancer, testicular cancer, prostate cancer, renal cell carcinoma (RCC), bladder cancer, and ovarian cancer.

Metabolic Disease

Non-limiting examples include: obesity, diabetes, pre-diabetes and diabetic retinopathy.

Cardiovascular Disease

Non-limiting examples include: diabetic cardiomyopathies and coronary heart disease.

Sepsis

Non-limiting examples include: sepsis caused by bacterial, viral or fungal infection.

In some embodiments, the dosage of mitochondrial nucleic acid relative to genomic nucleic acid for the sample from the subject is used in determining the likelihood the subject has or is pre-disposed to having a disease, disorder or symptoms associated with an increase or decrease in the dosage of mitochondria nucleic acid or a deletion in the mitochondrial genome. In some embodiments, the disease or disorder is a neurodegenerative disease, a cancer, a disease or disorder associated with mitochondrial stability, a disease or disorder associated with a mitochondrial deletion, a metabolic disease or disorder, a cardiovascular disease or disorder, a disease or disorder associated with oxidative stress, a disease or disorder associated with infertility or a disease or disorder associated with sepsis.

In some embodiments, the disease, disorder or condition is Parkinson's disease, Alzheimers disease, Friedreich's Ataxia, Amyotropic lateral sclerosis, Multiple sclerosis (MS), POLG associated diseases, Opthalmoplegia, Alper's syndrome, Leigh's syndrome, Kearns-Sayre syndrome (KSS), Leber's heredity optic neuropathy (LHON), Mitochondiral encephalomyopathy, lactic acidosis, stroke like episodes (MELAS), Myoclonic Epilepsy with Ragged Red Fibers (MERRF), gastric cancer, hepatocellular carcinoma (HCC), HPV associated cancer, breast cancer, Ewing's Sarcoma, pancreatic cancer, liver cancer, testicular cancer, prostate cancer, renal cell carcinoma (RCC), bladder cancer, ovarian cancer, obesity, diabetes, pre-diabetes, diabetic retinopathy, diabetic cardiomyopathies coronary heart disease and sepsis.

In some embodiments, the dosage of mitochondrial nucleic acid relative to genomic nucleic acid for the sample from the subject can be used to monitor the efficacy of treatment of the subject for a disease, disorder or symptoms associated with an increase or decrease in the dosage of mitochondria nucleic acid or a deletion in the mitochondrial genome.

Kits

In some embodiments, provided are kits for carrying out methods described herein. Kits often comprise one or more containers that contain one or more components described herein. A kit comprises one or more components in any number of separate containers, packets, tubes, vials, multi-well plates and the like, or components may be combined in various combinations in such containers. One or more of the following components, for example, may be included in a kit: (i) one or more nucleotides (e.g., terminating nucleotides and/or non-terminating nucleotides); one or more of which can include a detection label; (ii) one or more oligonucleotides, one or more of which can include a detection label (e.g., amplification primers, one or more extension primers (UEPs)); (iii) one or more enzymes (e.g., a polymerase, endonuclease, restriction enzyme, etc.); (iv) one or more buffers and (vii) printed matter (e.g. directions, labels, etc). In some embodiments, a kit comprises amplification primer pairs that comprise polynucleotides chosen from polynucleotides in Table 2 and Table 4, or portions thereof. In some embodiments, a kit also comprises extension primers comprising polynucleotides chosen from polynucleotides in Table 2 and Table 4 or portions thereof.

In some embodiments, a kit comprises amplification primer pairs that comprise polynucleotides chosen from polynucleotides in Table 7, or portions thereof. In some embodiments, a kit also comprises extension primers comprising polynucleotides chosen from polynucleotides in Table 7 or portions thereof.

A kit sometimes is utilized in conjunction with a process, and can include instructions for performing one or more processes and/or a description of one or more compositions. A kit may be utilized to carry out a process described herein. Instructions and/or descriptions may be in tangible form (e.g., paper and the like) or electronic form (e.g., computer readable file on a tangle medium (e.g., compact disc) and the like) and may be included in a kit insert. A kit also may include a written description of an internet location that provides such instructions or descriptions.

EXAMPLES

The examples set forth below illustrate, and do not limit, the technology.

Example 1—Identification of Mitochondrial/Genomic (Nuclear) Paralogs

Mitochondrial/genomic (nuclear) paralogs were identified using a R-based algorithm. Utilizing the Biostrings library from the Bioconductor open source software for bioinformatics matched the sequences to the UCSC hg19 build. Bioconductor contains memory efficient string containers, string matching algorithms, and other utilities, for fast manipulation of large biological sequences or sets of sequences. When paralog regions were identified these were verified using the BLAST algorithm from NCBI.

An exemplary protocol is as follows:
1) The mitochondrial genome was split into shorter fragments (in the case here 100 bp) and given a name, here Seq-1 is the mitochondrial genome nt 1-100 and Seq-2 is nucleotides 101-200.
2) Each sequence was aligned against the human genome and a certain number of mismatches are allowed in this case 20 mismatches per sequence. Results are displayed in Table 1. Shown are sequence number, chromosome number, start of alignment, end of alignment, regions that are suitable for use as amplicons (potential amplification primer binding regions) and sequence. Dashes indicate matches in the nuclear sequence (genomic) and letter mismatches in the nuclear sequence (genomic).
3) Sequences that do not have a paralog (using the settings in 2) in the nuclear genome will only retrieve the mitochondrial match (Chr=M). Examples here are sequences Seq-3 to Seq-6a.
4) Sequences with multiplex alignments can be identified from sequences with only one or two nuclear alignments.
5) All sequence mismatches can be used for paralog detection (V) as long as the upstream/downstream regions X and Y and regions 5' to X and regions 3' to Y fit the strategy for amplification as described below.
6) For Co-amplification of mitochondrial and genomic polynucleotides with a single amplification primer pair—select a region V (denoted by "$" above the sequence) surrounded by regions X and Y (denoted by "*" above the sequence), where X and Y are identical in both the nuclear and mitochondrial genome. Examples are Seq-1 and Seq-41. Another example is sequence Seq-51 where perfect alignment is identified to chromosome 17 with a single mismatch but the alignments to chromosome 2 and 17 are different enough to enable amplification of chromosome 1 and M only. Amplification primers are designed to bind to a region within X and Y, for amplification of both mitochondrial and genomic polynucleotides. Amplicon produced with these amplification primers will include V. The nucleotide at V is analyzed to distinguish an amplicon of a mitochondrial polynucleotide from an amplicon of a genomic polynucleotide.
7) Amplification of mitochondrial polynucleotides with a mitochondrial specific amplification primer pair and amplification of genomic polynucleotides with a genomic specific amplification primer pair—select a region V (denoted by "$" above the sequence) surrounded by regions X and Y, where regions 5' to X and 3' to Y (denoted by "+" above the sequence) are not identical in both the genomic and mitochondrial genome. Example is sequence Seq-1. Mitochondrial specific amplification primers are designed to bind to a region outside of X and Y, region 5' to X and region 3' to Y. Genomic specific amplification primers are designed to bind to a region outside of X and Y, region 5' to X and region 3' to Y. Amplicon produced with these amplification primers will include V. The nucleotide at V is analyzed to distinguish an amplicon of a mitochondrial polynucleotide from an amplicon of a genomic polynucleotide.
8) Amplification with one amplification primer binding to both mitochondrial and genomic paralogs in region X and the other amplification primer being a pair of primers that binds to a region 3' to Y where one primer is mitochondrial specific and the other is genome specific—select a region V (denoted by "$" above the sequence) surrounded by regions X and Y (denoted by "*" above the sequence), where regions 5' to X and 3' to Y (denoted by "+" above the sequence) are not identical in both the genomic and mitochondrial genome. Regions will be selected that are hybrids from 6) and 7). Example is Seq-1 and Seq-95. One amplification primer is designed to bind to a region within X, for use in the amplification of a mitochondrial polynucleotide or a genomic polynucleotide. Two corresponding amplification primers, one specific for a mitochondrial polynucleotide and one specific for a genomic polynucleotide are designed to bind to a region '3 of Y that has one or more mismatches between mitochondrial and genomic polynucleotides of a set. Amplicon produced with these amplification primers will include V. The nucleotide at V is analyzed to distinguish an amplicon of a mitochondrial polynucleotide from an amplicon of a genomic polynucleotide.

TABLE 1

Mitochondrial and Genomic (Nuclear) Paralogs

| Seq. No. | Chr | Start | End | Length | SEQ ID NO: | Sequence |
|---|---|---|---|---|---|---|
| Seq-1 | M | 1 | 100 | 100 | 1 | GATCACAGGTCTATCACCCTATTAACCACTCACGGGAGCTCTCCATGCATTTGGTATTTTCGTCTGGGGGGTGTGCACGGATAGCATTGCGAGACGCTG |
| Seq-1 | 17 | 22020727 | 22020826 | 100 | 2 | ------T--G---------------------------------AA---------------------T--A--- |
| Seq-2 | M | 101 | 200 | 100 | 3 | GAGCCGAGCACCCTATGTCGCAGTATCGTCTTTGATTCCTGCCTCATTCTATTATTTATCGCACCTACGTTCAATATTACAGGCGAACATACCTACTA |
| Seq-2 | 17 | 22020827 | 22020926 | 100 | 4 | --CC--A-------------------------G-----------------------A------CC-----G-------TC- |
| Seq-3 | M | 201 | 300 | 100 | 5 | AAGTGTGTTAATTAATAATGCTTGTAGGACATAATAATAACAATTGAATGTCTGCACAGCCGCTTTCCACACAGACATCATAACAAAAAATTTCACCA |
| Seq-4 | M | 301 | 400 | 100 | 6 | AACCCCCCCCTCCCCCGCTTCTGGCCACAGCACTTAAACAGTCACACACCCAAAAACAAATCCTGCCAAAACCCATCCTACTACTAATCTCATCAGATTTCAAAT |
| Seq-5 | M | 401 | 500 | 100 | 7 | TTTATCTTTAGGGGTATGCACAGCAGCACACAGTCACTTTTAACAGTCACTTTTAAAACATCATTATTTCCCCTCCCACTACCCCCACAGTTTATGTAGCTTACCTCCTCA |
| Seq-6 | M | 501 | 600 | 100 | 8 | GCCCATCCTACCCAGCACCGGCTCACATGGCTAACACTGCTAAACCCGAACCACAACAAATAGGTTTGGTCCTAGCCTTTCTATTAGCTCTTAGTAAGATTACACATGC |
| Seq-7 | M | 601 | 700 | 100 | 9 | AAGCAAATACACTGAAAATGTTTAGACGGGCTCACATCACCCCATAAACAAAAAGGTTTGGTCCTAGCCTTTCTATTAGCTCTTAGTAAGATTACACATGC |
| Seq-7 | 2 | 83048020 | 83048119 | 100 | 10 | -----------G-----------------C----T----TC-----CA---------G----------C--------T-----------G |
| Seq-7 | 2 | 117778792 | 117778891 | 100 | 11 | -----------G-----------------C---TT----TC-----C----G-G------G---------T-------- |
| Seq-7 | 3 | 106617467 | 106617566 | 100 | 12 | ---A--GG---------------------C-C--A-ATT---G-A-T---------C------------G------T-G-----A---- |
| Seq-7 | 4 | 117218921 | 117219020 | 100 | 13 | -----------G-----------------C----T-ATC-G--CA---T--------G-G---------T--C-----T |
| Seq-7 | 5 | 120366903 | 120367002 | 100 | 14 | -----------G-----------------C-G-T------C------CTG----------CA----------G-T |
| Seq-7 | 7 | 142373034 | 142373133 | 100 | 15 | -----------G-----------------C----T-----T-T-CAG------G-C-TC---------G------A |
| Seq-7 | 8 | 32868986 | 32869085 | 100 | 16 | -----------G-----------------C----T----TCTG--CA--------G--------GA----T-----CT- |
| Seq-7 | 9 | 33656634 | 33656733 | 100 | 17 | -----------G-----------------A-C--T-----T-T-CAG------G-C-----------A |
| Seq-7 | 17 | 19501896 | 19501995 | 100 | 18 | -----------G-----------------C----T----TCTG--CAT------G-T----------------T----C- |
| Seq-7 | 17 | 22021387 | 22021486 | 100 | 19 | -----------G-----------------A-C--T-----CT---CTG-----G-------------A--- |
| Seq-7 | 17 | 125865728 | 125865827 | 100 | 20 | -----------G-----------------C----T----TCTG--CA--AT-----C-----------A---- |
| Seq-7 | 23 | 8234672 | 8234771 | 100 | 21 | -----------G-----------------C----T----TCT-G-CA-T-----C--A---A-------A-C--------A--- |
| Seq-8 | M | 701 | 800 | 100 | 22 | AAGCATCCCGTTCCAGTGAGTTCACCCTCAGTGAGTTCACCCTCTAAATCACCACGATCAAGGACACGACAATGCAGCAGCATCAAGCAGCATCAAAGGAAAACCGCTCAAAACCGTCAAAACGCTTAGCGCTTAGCGCC |

TABLE 1-continued

Mitochondrial and Genomic (Nuclear) Paralogs

| Seq. No. | Chr | Start | End | Length | SEQ ID NO: | Sequence |
|---|---|---|---|---|---|---|
| Seq-8 | 9 | 33656734 | 33656833 | 100 | 23 | ----------A-C-------AAGT------TT-----T---CA-------A--T---C--- |
| Seq-8 | 17 | 22021487 | 22021586 | 100 | 24 | ------G-ACC-TG-----AA-A------T--A----AGT---T-------A--T------ |
| | | | | | | +++++++++++++++++++++++++++$+++++++++++++++++++++ |
| Seq-9 | M | 801 | 900 | 100 | 25 | ACACCCCACGGGAAACAGCAGTGATTAACCTTTAGCAATAAACGAAAGTTTAACTAAGCTATACTAACCCCAGGGTTGGTCAATTCGTGCCAGCCACC |
| Seq-9 | 17 | 22021587 | 22021686 | 100 | 26 | -------------------G---------A--------------------------TTT----T---A-------------------------- |
| Seq-10 | M | 901 | 1000 | 100 | 27 | GCGGTCAACGATTAACCCAAGTCAATAGAAGCCGGCGTAAAGAGTGTTTTAGATCACCCCTCCCAATAAAGCTAAAACTCACCTGAGTTGTAAAAAA |
| Seq-11 | M | 1001 | 1100 | 100 | 28 | CTCCAGTTGACACAAAATAGACTACGAAAGTGGCTTTAACATATCTGAACACACAAATAGTCTAAGACCCAAACTGGGATTAGATACCCCACTATGCTTAGC |
| Seq-11 | 1 | 9634769 | 9634868 | 100 | 29 | -C-T--C---A-T---G------A----T---G-------T-CT---------T----------------- |
| Seq-11 | 4 | 56194364 | 56194463 | 100 | 30 | ------------C------T---------A---------G-----------------G-------G------GGCTCA |
| Seq-11 | 5 | 123096916 | 123097015 | 100 | 31 | -C-T--C---A-T-------A-------G--AA----T--T---GG------- |
| Seq-11 | 7 | 142373430 | 142373529 | 100 | 32 | -C-GG-C---A-T-------A-------G--T--G-A-------T-CT--------G------- |
| Seq-11 | 17 | 22021783 | 22021882 | 100 | 33 | -C-T------T-T-----C-A------------T---T------G---TT------C--- |
| Seq-12 | M | 1101 | 1200 | 100 | 34 | CCTAAACCTCAACAGTTAAATCAACAAACTGCTCGCCAGAACACTACGAGCCACACAGCTTAAAACTCAAAGGACCTGGCGTGCTTCATATCCCTCTAGA |
| Seq-12 | 1 | 142792707 | 142792806 | 100 | 35 | T-------TCA--T------G------A-------T--A----T----------A--- |
| Seq-12 | 1 | 143344785 | 143344884 | 100 | 36 | T-------TCG--T------G------A-------T--A----T----------A--- |
| Seq-12 | 4 | 117219422 | 117219521 | 100 | 37 | --------TCT--T------C--TG-G-----CAT-----A-------T----------A--- |
| Seq-12 | 5 | 123097016 | 123097115 | 100 | 38 | --------TC----T------------AT-A--------A--A-T------T----------A--- |
| Seq-12 | 7 | 142373530 | 142373629 | 100 | 39 | --------TC----T------------AT--C-------A--A-T------T----------A--- |
| Seq-12 | 9 | 33657133 | 33657232 | 100 | 40 | --------TC----T------G-----AT--A-------A--A-T------T----------A--- |
| Seq-12 | 17 | 19502389 | 19502488 | 100 | 41 | --------TCT--T------C--T------CAT-----GT----A-------T----------A--- |
| Seq-12 | 17 | 22021883 | 22021982 | 100 | 42 | -------------T-------------------------G---A-------T-----C------ |
| Seq-12 | 21 | 9735630 | 9735729 | 100 | 43 | T-------TCG--T------G-----------------T----A-------T----------A--- |
| Seq-12 | 24 | 13290257 | 13290356 | 100 | 44 | --------TCG--T------G----------------------A-------T--T---T-C-------A--- |
| Seq-13 | M | 1201 | 1300 | 100 | 45 | GGAGCCTGTTCTGTAATCGATAAACCCGATCAACCTTCACCACCCTCTTGCTCAGCCTATATACCGCCATCTTCAGCAAACCCTGATGAAGGCTACAAAGT |

TABLE 1-continued

Mitochondrial and Genomic (Nuclear) Paralogs

| Seq. No. | Chr | Start | End | Length | SEQ ID NO: | Sequence |
|---|---|---|---|---|---|---|
| Seq-13 | 1 | 142792807 | 142792906 | 100 | 46 | ------------------A------------------------------A--TT-----------C---------------A------------GAA-G-CTGCAG-GTA |
| Seq-13 | 1 | 143344885 | 143344984 | 100 | 47 | ---------G--------A------------------------------A--TT--------------------------------A-------GAA-G-C-GCAG-GTA |
| Seq-13 | 7 | 142373630 | 142373729 | 100 | 48 | ------------------A---------G--------------------A--TT---------AT-------------------------AT---AG-A--A-TC----- |
| Seq-13 | 9 | 33657233 | 33657332 | 100 | 49 | ------------------A---------G---------A--A-TTG-----------------A-TG-----------------------G----AGCA----------- |
| Seq-13 | 17 | 22021983 | 22022082 | 100 | 50 | ------------------A---------------------A--TC-------------------A---C---------CA-----C--------- |
| Seq-13 | 21 | 9735730 | 9735829 | 100 | 51 | ------G----------A-----------------------A--TT------------------A-------------------A-T--------GAA-G-C-GCAG-GTA |
| Seq-14 | M | 1301 | 1400 | 100 | 52 | AAGCGCAAGTACCCCACGTAAAGACGTTAGGTCAAGGTGTAGCCCATGAGGTGGCAAGAATGGGCTACATTTTCTACCCAGAAAACTACGATAGCCCTT |
| Seq-14 | 7 | 142373730 | 142373829 | 100 | 53 | ---------A-----T-T-A--A--A-------C-T---------------A-CAG---A-CTC--C-A--- |
| Seq-14 | 9 | 5092100 | 5092199 | 100 | 54 | ------A-----AAT--A--A------------C-T--------------C-------------------TCT-ACG-CAA--C- |
| Seq-14 | 17 | 22022083 | 22022182 | 100 | 55 | ---------A-----T-T-A--A-T----------------T----------------------T-CTACA-TAA--CC |
| Seq-15 | M | 1401 | 1500 | 100 | 56 | ATGAAACTTAAGGGTCGAAGGTGATTTAGCAGTAAACTGAGAGTAGAGTGCTTAGTTGAACAGGGCCCTGAAGCGCGTACACCGCCGTCACCCTCC |
| Seq-15 | 1 | 142793009 | 142793108 | 100 | 57 | ---------TC-----A-----CTC--A----------------C------T--A----T-A-----A------AT-C- |
| Seq-15 | 1 | 143345087 | 143345186 | 100 | 58 | ---------TC-----A-----CTC--A----------------C------T--A----T-A-----A------AT-C- |
| Seq-15 | 4 | 117219730 | 117219829 | 100 | 59 | ------C-G---------A-----CTC--A------------CA--C-C---G-----T-A-----A------AT-C- |
| Seq-15 | 5 | 123097321 | 123097420 | 100 | 60 | ---------C-------------C------------------T-AG-----C-----T--A-----A-A-----AT-C- |
| Seq-15 | 9 | 33657434 | 33657533 | 100 | 61 | ---------TC------A----CTC--A------------C-T-A------C---TGA---A-A--A-C--- |
| Seq-15 | 17 | 19502693 | 19502792 | 100 | 62 | ------C-TC------------CTC---------------CA---------G-----T-A-----A------AT-C- |
| Seq-15 | 17 | 22022185 | 22022284 | 100 | 63 | ---------TC-----A-----CTC--A------------T-A--AC----------T-----AA------A------AT-C- |
| Seq-15 | 21 | 9735932 | 9736031 | 100 | 64 | ---------TC-----A-----CTC--A-------------C---------T--A-----A------AT-C- |
| Seq-15 | 24 | 13290559 | 13290658 | 100 | 65 | ---------TC-----A-----CTC--A-------------C---------T--A-----A--C--------T------A------ |
| | | | | | | +++++++++++++++++++++$$ +++++++++++++++++++++ |
| Seq-16 | M | 1501 | 1600 | 100 | 66 | TCAAGTATACTTCAAAGGACATTTAACTAAAACCCCTACGCATTTATAGAGGAGACAAGTCGTAACATGGTAAGTGTACTGGAAAGTGCACTTGGACG |
| Seq-16 | 9 | 33657536 | 33657635 | 100 | 67 | AA-TA-TACT--AG-GATTAG---------------TT-------------------A--------------------T- |
| Seq-17 | M | 1601 | 1700 | 100 | 68 | AACCAGAGTGTAGCTTAACACAAAGCACCCAACTTACTTAGGAGATTTCAACTTAACTTGACCGCTCTGAGCTAAACTAGCCCCAAACCCACTCCAC |

TABLE 1-continued

Mitochondrial and Genomic (Nuclear) Paralogs

| Seq. No. | Chr | Start | End | Length | SEQ ID NO: | Sequence |
|---|---|---|---|---|---|---|
| Seq-17 | 7 | 145694412 | 145694511 | 100 | 69 | --TA-T-AA-G-----T------------------------------------------------------------------------ |
| Seq-17 | 17 | 22022353 | 22022452 | 100 | 70 | -----AG------T------TG---C-G-------T----A-C----TT--------ACTA-T $$$$$$$$$$$$$$$$$$$$$$$$$$$$$$ |
| Seq-18 | M | 1701 | 1800 | 100 | 71 | CTTACTACCAGACAACCTTAGCCAACCATTTACCCAAATAAGTATAGGCCAATAGATAAGTAGTACCGCAAGGAAGA |
| Seq-18 | 17 | 22022453 | 22022552 | 100 | 72 | TC--------A-T----C-A-T--A---------------------------------------GAT-T-TC--A-------C--A------G-T------- |
| Seq-19 | M | 1801 | 1900 | 100 | 73 | TGAAAAATTATAACCAAGCATATATATAGCAAGGACTAACCCTATACCTTTGCATAATGAATTAACTAGAAATAACTTTGCAAGGAGCCAAAGCTAA |
| Seq-19 | 7 | 142374229 | 142374328 | 100 | 74 | ATG----AGT-------A----A---------TAG---T-----------------------A--CA----A------C-- |
| Seq-20 | 17 | 22022553 | 22022652 | 100 | 75 | --------AC-----AGT---------A--------A---A----------------------A----A----A------C-- |
| Seq-20 | M | 1901 | 2000 | 100 | 76 | GACCCCCGAAAACAGACGAGCTACCTAAGAACACAGCTAAAAGAGCACACCCGTCTATGTAGCAAAAATAGTGGGAAGATTTATAGGTAGAGGCGACAAACCT |
| Seq-20 | 2 | 117780085 | 117780184 | 100 | 77 | -T----T------T------C--------AC------G----G--G-- |
| Seq-20 | 3 | 40294119 | 40294218 | 100 | 78 | -T----T-A-----G-----C------T-AC------GC--GA---C--TC----G-- |
| Seq-20 | 7 | 142374329 | 142374428 | 100 | 79 | -G---------A--------C------A-----------C--GA---T--T--T--G-- |
| Seq-20 | 9 | 33657935 | 33658034 | 100 | 80 | -G----TA---------G------A------T--------C--GA--C--CA-T--T-CG-- |
| Seq-20 | 14 | 84637760 | 84637859 | 100 | 81 | -T-------AG-------C---T------G------A---------C--GA----C--T----GG-- |
| Seq-20 | 17 | 19503190 | 19503289 | 100 | 82 | -T---------A-----------T---------G--------C--GA----CA----T--G-- |
| Seq-20 | 17 | 22022653 | 22022752 | 100 | 83 | -----------------G----------A-----------C---------T----G-- |
| Seq-21 | M | 2001 | 2100 | 100 | 84 | ACCGAGCCTGGTGATAGCTGGTTGTCCAAGATAGAATCTAGTTCAACTTTAAATTTGCCCACAGAACCCTCTAAATCCCCTTGTAAATTTAACTGTTAG |
| Seq-21 | 3 | 160665516 | 160665615 | 100 | 85 | T--A----------------------------A--T-----ACT--T-----GTA-T--A-CTGT-AGT |
| Seq-21 | 23 | 142519115 | 142519214 | 100 | 86 | ---A----------------TGA-A------------A--T-----AC----TC-TAT-GT---G----T------ |
| Seq-22 | M | 2101 | 2200 | 100 | 87 | TCCAAAGAGGAACAGCTCTTTGGACACTAGGAAAAATTAACACCCATAGTAGGCCTAAAAGCAGCCACCAATTAAGA |
| Seq-22 | 17 | 22022852 | 22022951 | 100 | 88 | --T------G----------A------------A---TT--A--T----A---G--A--G-T------ |
| Seq-23 | M | 2201 | 2300 | 100 | 89 | AAGCGTTCAAGCTCAACACCCACTACCTAAAAATCCAAAAAATCACTCCTCACACATATAACTGAACTCTCACCCTATGAAGAGAACTAA |
| Seq-24 | M | 2301 | 2400 | 100 | 90 | TGTTAGTATAAGTAACATGAAAACATTCTCCTCCGCATAAGCCTGCGTCAGATCAAAAACATTGCAATGACAATTAACAGCCCAATATCTACAATCAACCA |

TABLE 1-continued

Mitochondrial and Genomic (Nuclear) Paralogs

| Seq. No. | Chr | Start | End | Length | SEQ ID NO: | Sequence |
|---|---|---|---|---|---|---|
| Seq-24 | 17 | 22023053 | 22023152 | 100 | 91 | ----------------G----C----------------------A-A------T---TC-------T--AT--T-- |
| | | | | | | ++++++++++++++++++++++++++++++++ |
| Seq-M | M | 2401 | 2500 | 100 | 92 | ACAAGTCATTATTACCCTCACTGTCAACCCACCAGCATGTCTCATAAGGAAAGGTTAAAAAAGTAAAGGAACTCGGCAAACCTTACCCGCCTGTT |
| Seq-M | 6 | 62283999 | 62284098 | 100 | 93 | -TG-AA-TG--------T-CT--------------------------------C---C----------T------------------------ |
| Seq-M | 7 | 45291551 | 45291650 | 100 | 94 | ----AC-GG-GC-----AT-----------T--------------------------------------------------------------- |
| Seq-M | 7 | 142374830 | 142374929 | 100 | 95 | CA--T-T--------GAT-------T--T----TA-G-A--G-T-A-----T-------------------TT-------T------------- |
| Seq-M | 17 | 22023154 | 22023253 | 100 | 96 | TG--AC---------A--------T-C-----T---------------------------A--G--T-------T-------- |
| Seq-M | M | 2501 | 2600 | 100 | 97 | TACCAAAAACATCACCTTCTAGCATCACCAGTATTAGAGGCACCGCTGCCCAGTGACACATGTTTAACGGCCGCGTACCCTAACCGTGCAAAGGTAGCA |
| Seq-26 | 2 | 117780688 | 117780787 | 100 | 98 | -------------------------T-A---------------T-----------T----A-A----T--G--A----C------------- |
| Seq-26 | 3 | 40294719 | 40294818 | 100 | 99 | -------------------------------------------T-----------T-----CG-T-----A----T--G-T----------- |
| Seq-26 | 4 | 117220823 | 117220922 | 100 | 100 | ----------------------------------T--T-----T------G---T-----C--T-----T----T--G------------- |
| Seq-26 | 6 | 62284099 | 62284198 | 100 | 101 | -------------------------------------------T-----------T-----A---------AT--T--G------------- |
| Seq-26 | 7 | 45291651 | 45291750 | 100 | 102 | -------------------------------------------T----G-T---------TT------C----A-A-CA--T--G--T---A-- |
| Seq-26 | 8 | 32870812 | 32870911 | 100 | 103 | -------------------------------------------T-----------T-G----------CTTT----CGTC--CT--GG--CT--TG |
| Seq-26 | 8 | 77114212 | 77114311 | 100 | 104 | -------------------------------------------T-----------T-----A----A-T--T-------- |
| Seq-26 | 9 | 5093284 | 5093383 | 100 | 105 | -------------------------------------------T-----------T-----C----A--A-CA--T--G--T-------A-- |
| Seq-26 | 9 | 33658532 | 33658631 | 100 | 106 | -------T-TT-------------------------G-T----T-----------T-----C----A--A-A------G-G------------ |
| Seq-26 | 10 | 20035756 | 20035855 | 100 | 107 | ---------------------------A---------------T-----------T-----C----A--T-T-----T--G----------- |
| Seq-26 | 10 | 57359526 | 573596M | 100 | 108 | ----------------C---------TG-T------------T-----------T-----G-TT------T--G-A--T------------- |
| Seq-26 | 14 | 84638370 | 84638469 | 100 | 109 | -------------------------------------------T-----------T-----C----TG-T--T---G--------G-TAGCAT |
| Seq-26 | 17 | 19504108 | 19504207 | 100 | 110 | -------------------------------------------T-----------T-----C----A--T--G--A--T-G-TAGCAT |
| Seq-26 | 17 | 22023254 | 22023353 | 100 | 111 | -T---------------------------C------------T------------T------------T----T-------- |
| Seq-26 | 23 | 62061037 | 62061136 | 100 | 112 | -------------------GA--A--T-------TA-------T-----------T-----A----A-AA--T--G--A--T---------- |
| Seq-26 | 23 | 142519695 | 142519794 | 100 | 113 | --------------------T--T---CC------AT----A---------GT-------G---T----T-G--A---------------C |

TABLE 1-continued

Mitochondrial and Genomic (Nuclear) Paralogs

| Seq. No. | Chr | Start | End | Length | SEQ ID NO: | Sequence |
|---|---|---|---|---|---|---|
| Seq-27 | M | 2601 | 2700 | 100 | 114 | TAATCACTTGTTCCTTAAATAGGGACCTGTATGAATGGCTCCACGAGGGTTCAGCTGTCTCTTACTTTTAACCAGTGAAATTGACCTGCCCGTGAAGAGG |
| Seq-27 | 3 | 40294819 | 40294918 | 100 | 115 | ---------------C---------T-----CAT-T--A-------------T------------------------------------------ATT-- |
| Seq-27 | 4 | 117220923 | 117221022 | 100 | 116 | -----------------G-------T-----ACA--A-------------T-------------------------------------------AT-T- |
| Seq-27 | 6 | 62284199 | 62284298 | 100 | 117 | -G-----------------------T-----------------G------T------------C---C--C------------------------- |
| Seq-27 | 7 | 142375029 | 142375128 | 100 | 118 | -------------------------------------A-C---------------------------CC---------------T---------- |
| Seq-27 | 8 | 32870912 | 32871011 | 100 | 119 | -------------------------C-----T-A---------CA-T-----T--------------C-----------------G-AT--A---A--- |
| Seq-27 | 9 | 33658632 | 33658731 | 100 | 120 | -------------------------C-----------------T------------------------CC-------------------A-----C--- |
| Seq-27 | 10 | 57359626 | 573597M | 100 | 121 | -----------C----G--------T-----CA---C--------------------------------C---------------------A--TA--- |
| Seq-27 | 14 | 84638469 | 84638568 | 100 | 122 | -------------------------T-----A--CA--A-----G-----T-------------------------------------------AT-A- |
| Seq-27 | 17 | 22023354 | 22023453 | 100 | 123 | -----------------------T-C------------------------------------------C--------------------------- |
| Seq-27 | 23 | 62061137 | 62061236 | 100 | 124 | ----T----------CA------G-A--T-CC------CT--A-------G-----T-AT-------------------------AT-T---G--- |
| Seq-27 | 23 | 142519795 | 142519894 | 100 | 125 | ------G--T-----CC-------------CA--A---CTGAT--------C---GT--A---------------------------A---A---- |
| Seq-28 | M | 2701 | 2800 | 100 | 126 | CGGGCATGACACAGCAAGACGAAGAGACCCTATGGAGCTTTAATTATTAATGCAAACAGTACCTACAAACCCACAGTCCTAAACTACCAAACCTGCA |
| Seq-28 | 6 | 62284299 | 62284398 | 100 | 127 | ------------------------------A---------C--------AC--C--T--G--------CT---C---------------------- |
| Seq-28 | 17 | 22023454 | 22023553 | 100 | 128 | ---A--A-T--A---------A--------------------AG--A--T-GG--G---C-----G------G |
| Seq-29 | M | 2801 | 2900 | 100 | 129 | TTAAAAATTTCGTTGGGCGACCTCGGAGCAGAACCCAACCTCCGAGACTACATGCTAAGACTTCACCAGTCAAAGCGAACTACTATACTCAATTGAT |
| Seq-29 | 6 | 62284399 | 62284498 | 100 | 130 | -------C---------------T-T-----------T--------AC-T--G---A----GT--C-CGTA------------------------- |
| Seq-29 | 17 | 22023554 | 22023653 | 100 | 131 | ----C----------------A----T----------T--------AC-T------G----AT----G----TAT-C-C-TA------C |
| Seq-30 | M | 2901 | 3000 | 100 | 132 | CCAATAACTTGACCAACGAACAAGTTACCCTAGGADATAACGCGCAATCCATATCAACAATAGGGTTTACGACCTCGATGTTGGAT |
| Seq-30 | 2 | 117781085 | 117781184 | 100 | 133 | ---G-T-C-T--A--T---------------T--------G-------T---------------G--------------------- |
| Seq-30 | 3 | 40295118 | 40295217 | 100 | 134 | -----------T----------T--------------C---T--A--AG--TG--------A----A---------- |
| Seq-30 | 7 | 142375331 | 142375430 | 100 | 135 | ----T-----T---------T------------------TG-------- |
| Seq-30 | 8 | 32871202 | 32871301 | 100 | 136 | ----T-T----T--------------TG-----T----------G-G-------A-G-T--------C-A---- |

TABLE 1-continued

Mitochondrial and Genomic (Nuclear) Paralogs

| Seq. No. | Chr | Start | End | Length | SEQ ID NO: | Sequence |
|---|---|---|---|---|---|---|
| Seq-30 | 9 | 33658934 | 33659033 | 100 | 137 | ------T---T------------------------------------A------------------------G-------------------- |
| Seq-30 | 10 | 57360227 | 57360326 | 100 | 138 | ----T-CT-T---A-G-T------G------CA-------------T------- |
| Seq-30 | 13 | 57262611 | 57262710 | 100 | 139 | ----------TT--G--T------------A----------G------G----- |
| Seq-30 | 17 | 19504821 | 19504920 | 100 | 140 | ----------T-------T----------------------T------G-G--- |
| Seq-30 | 17 | 22023654 | 22023753 | 100 | 141 | ----------T---------------T------TA---------G--C--G--CA-A- |
| Seq-30 | 23 | 62061579 | 62061678 | 100 | 142 | -A-G--GT----G---T------C-------TA-----A--G---G--T--A--- |
| Seq-30 | 23 | 1425204M | 142520524 | 100 | 143 | -A-----GT---------T--G-----A-A-G------TG-T---T----- |
| Seq-31 | M | 3001 | 3100 | 100 | 144 | CAGGACATCCCGATGGTGCAGCCGCTATTAAGGTTCGTTGTTCAACGATTAAAGTCCTACGTGATCTGAGTTCAGACCGAGTAATCCAGGTCGGTTT |
| Seq-31 | 2 | 117781185 | 117781284 | 100 | 145 | ----------AA-----T-----A------G---T--C---------T--------TA-----------C---- |
| Seq-31 | 4 | 93623185 | 93623284 | 100 | 146 | ----------TA-----T-------T-----T--C--G--T-----A---------------A---- |
| Seq-31 | 4 | 117221300 | 117221399 | 100 | 147 | G---------TA------------T-------T--G----G--------T----T---------- |
| Seq-31 | 7 | 142375431 | 142375530 | 100 | 148 | ----------TA----------G-----T--T-----C------A------T-----C--G------T-G-A |
| Seq-31 | 8 | 32871302 | 32871401 | 100 | 149 | ---------TTTA----C--G--------GA--T----------------A------A--A-----A--C |
| Seq-31 | 9 | 5093795 | 5093894 | 100 | 150 | ----------TA----------------------G-----A-A--------T--------A-----T---- |
| Seq-31 | 9 | 33659034 | 33659133 | 100 | 151 | ----------TA-----T--T--G-C--G--------T------------C-----------T-G-A |
| Seq-31 | 10 | 57360328 | 57360427 | 100 | 152 | GG-ACATC-TAA---------T---------G-A--A-----T-----A-----A--C---T---- |
| Seq-31 | 14 | 84638867 | 84638966 | 100 | 153 | GG---TA-------G----T---------A--A------T------C------A----A---- |
| Seq-31 | 17 | 19504921 | 19505020 | 100 | 154 | ----------TA-----------------G-----T-----C--------T-----G-A------T---- |
| Seq-31 | 17 | 22023754 | 22023853 | 100 | 155 | -------A------------------------------G----T---------------------- |
| Seq-31 | 24 | 8239395 | 8239494 | 100 | 156 | A-------G-TA-----T---AG-----------G-A--T------------GT-----A------T---- |
| Seq-32 | M | 3101 | 3200 | 100 | 157 | CTATCTACTTCAAATTCCTCCCTGTACGAAAGGACAAGAGAAATAAGGCCTACTTCACAAAGCGCCTTCCCCCGTAAATGATATCATCTCAACTTAGTAT |
| Seq-33 | M | 3201 | 3300 | 100 | 158 | TATACCCACACCCAAGAACAGGGTTTGTTAAGATGCAGAGCCCGGTAATCGCATAAAACTTACAGTCAGAGGTTCAATTCCTCTTCT |
| Seq-33 | 2 | 117781387 | 117781486 | 100 | 159 | C--CA-ACACA-T-TT---------A---------------A-C--T-------T-A-------G-C-------- |
| Seq-33 | 9 | 5093993 | 5094092 | 100 | 160 | G-A-T-AC---A---------------------------C-------G-----T--C--A-------A--A--------C--C-- |

TABLE 1-continued

Mitochondrial and Genomic (Nuclear) Paralogs

| Seq. No. | Chr | Start | End | Length | SEQ ID NO: | Sequence |
|---|---|---|---|---|---|---|
| Seq-33 | 17 | 22023955 | 22024054 | 100 | 161 | -G---------------------------------T-------------------AC-----------------CC----------------- |
| Seq-34 | M | 3301 | 3400 | 100 | 162 | TAACAACATACCCATGGCCAACCTCCTACTCCTCATTGTACCCATTCTAATGCGCAATGGCATTCCTAATGCTTACCGAACGAAAAATTCTAGGCTATATA |
| Seq-34 | 17 | 22024055 | 22024154 | 100 | 163 | ----------GT----AA-T-------T--C-------------C-----------------A-T--T-------C---------C--G |
| Seq-35 | M | 3401 | 3500 | 100 | 164 | CAACTACCCAAAGGCCCAACGTTGTAGGCCCCTACTACAACCCCTTGCTGACGGCTACTACAAACCTTCACCAAAGAGCCCTAAAACCCGCCA |
| Seq-35 | 4 | 93623586 | 93623685 | 100 | 165 | --------------------T------AT----T---------TA--T-------T-A--T-T----------A---------T-AT |
| Seq-35 | 8 | 32871692 | 32871791 | 100 | 166 | --------------------T------------------A-T--A-----G--T-----AG---T--A-------T------GG--T-A- |
| Seq-35 | 17 | 22024155 | 22024254 | 100 | 167 | --------------------G------TA----------------TA---G---T------T----C-T-------AT-T-------T-A- |
| Seq-36 | M | 3501 | 3600 | 100 | 168 | CATCTCTACCATCACCCTCTACATCACCGCCCCGACCTTAGCTCTCACCATGCTCTTCTACTATGAACCCCCCTCCCCATACCCAACCCCCTGGTCAACCT |
| Seq-36 | 17 | 22024255 | 22024354 | 100 | 169 | -G--A--TG-T---------------T---A-----------C----T-T--T--C-------------T---------A--T--T----- |
| Seq-37 | M | 3601 | 3700 | 100 | 170 | CAACCTAGGCCTCCTATTTATTCTAGCCACCTCTAGCCTAGCCGTTTACTCAATCCTCTGATCAGGGTGAGCATCAAACTACGCCCTGATCGGC |
| Seq-37 | 9 | 5094368 | 5094467 | 100 | 171 | T--TA---------T--------------------A--A-------A-C-T--A----------C--T--T-TA--------------- |
| Seq-37 | 17 | 19505863 | 19505962 | 100 | 172 | T--TA---------------------------A----------A------------T--A----------T-T--T-A--A---------- |
| Seq-37 | 17 | 22024355 | 22024454 | 100 | 173 | T-------------T-------T-----C-----G-T-A--C-----------T-C-------------A-----------T---------- |
| Seq-38 | M | 3701 | 3800 | 100 | 174 | GCACTGCGAGCAGTAGCCCAAACAATTCATATGAAGTCATCACCCTAGCCATCATTCTACTATCAACATTACTAATAAGTGGCTCCTTAACCTCTCACCC |
| Seq-38 | 17 | 22024455 | 22024554 | 100 | 175 | ---T-AT------------T------------C-----T----------C--T--G-TCC-------CAA--C-T---G-----------CCCC |
| Seq-39 | M | 3801 | 3900 | 100 | 176 | TTATCACAACAAGACACCTCTGATTACTCCTGCCATCATGACCCTTGGCCATATATGATTATTCTCCACACTAGCCCATATATGATTTATCTGAGAGACCAACCGAACCCCCTT |
| Seq-39 | 9 | 5094564 | 5094663 | 100 | 177 | GC--------TG-C----TTA------CCG--------A----------------A---------T--------A-A--T----G--T--- |
| Seq-39 | 15 | 35688444 | 35688543 | 100 | 178 | ----------TG----TT------GCCG--------A----------TC---------G--G-----A-T---A-G--A--- |
| Seq-39 | 17 | 19506063 | 19506162 | 100 | 179 | --C-----------TT----------C-G-------A---C-G-G-A-T------A------C----------A-T-----G---T--- |
| Seq-39 | 17 | 22024555 | 22024654 | 100 | 180 | --C-T-G----------------C-G----------AA----------C------C-A-A--T-----------A---T-----G---T--- |
| Seq-40 | M | 3901 | 4000 | 100 | 181 | CGACCTTGCCGAAGGGGAGTCCGAACTAGTCTCAGGCTTCAACATCGAATACGCCGAGGCCCCTCGCCCTATTCTTCATGAGCCGAATACACAAACATT |
| Seq-40 | 1 | 564450 | 564549 | 100 | 182 | TC-G-AA-GTC--A------------------------A---------------------------------A---------T-G-T--- |
| Seq-40 | 17 | 22024655 | 22024754 | 100 | 183 | T------A-T------A--A-------------------------------------------T-----T----------T---T--C |

TABLE 1-continued

Mitochondrial and Genomic (Nuclear) Paralogs

| Seq. No. | Chr | Start | End | Length | SEQ ID NO: | Sequence |
|---|---|---|---|---|---|---|
| Seq-41 | M | 4001 | 4100 | 100 | 184 | ATTATAATAAACACCCTCACCACTACAATCTTCCTAGGAACAACATATTTGACGCACTCTCCCCTGAACTCTACACAACATATTTGTCACCAAGACCCTAC |
| Seq-41 | 1 | 564550 | 564649 | 100 | 185 | ---------------------------------------------A-------------------------------------------------------- |
| Seq-42 | M | 4101 | 4200 | 100 | 186 | TTCTAACCTCCCCTGTTCTTATGAATTCGAACAGCATACCCCCGATTCCGCTACGACCAACTCATACACCTTCCTATGAAAAACTTCCTACCACTCACCCT |
| Seq-42 | 1 | 564650 | 564749 | 100 | 187 | -----G------------------------------------------------------------------------------------------------ |
| Seq-42 | 2 | 131029682 | 131029781 | 100 | 188 | -CT--------------A--T-------------T--T--A-----T--TT---T--T---------------T-------------T--T---A------ |
| Seq-42 | 7 | 57253751 | 57253850 | 100 | 189 | -CT--------------A--T-------------T--T--A--T------C--------------------------------T-----T--T---A---- |
| Seq-42 | 17 | 19506363 | 19506462 | 100 | 190 | -----------G-----A--T-------------------A---------T-T------------------------------T-----T--AA------- |
| Seq-42 | 17 | 22024855 | 22024954 | 100 | 191 | -C---------------------C--------------------T--GT--A--------T------GT-T--T------------T--T--T--A----- |
| Seq-43 | M | 4201 | 4300 | 100 | 192 | AGCATTACTTATATGATATGTCTCCATTACAATCTCCAGCATTCCCCTCAAACCTAAGAAATATGTCGATAAAAGAGTTACTTTGATAGAGT |
| Seq-43 | 1 | 564750 | 564849 | 100 | 193 | ------------------------------------------------------------------------------------------------------ |
| Seq-43 | 2 | 131029782 | 131029881 | 100 | 194 | ---CTG----CA---A----------------C-T---------------C----------G---------C-------------C---A----------- |
| Seq-43 | 7 | 57253851 | 57253950 | 100 | 195 | ---CTG--------C--A------A--------CCT---------C--A--------TG-----------C-G-----------C-------A-------- |
| Seq-43 | 13 | 36639618 | 36639717 | 100 | 196 | CTATA-TT-C--------A-T--A--T--------C--------C--A--C--TG-----------------C------------------------A--- |
| Seq-43 | 17 | 22024955 | 22025054 | 100 | 197 | ---C------CA----A--T--GC----------A--T--GC--------CT--T----------C-------G--------------------------- |
| Seq-44 | M | 4301 | 4400 | 100 | 198 | AAATAATAGGAGCTTAAACCCCCTTATTTCTAGGACTATGAGAATCGAACCCATCCTGAGAATCCAAAATTCTCCGTGCCACCTATCACACCCATCCT |
| Seq-44 | 1 | 564850 | 564949 | 100 | 199 | ----------------------T------T------------------------------------------------------------------------ |
| Seq-44 | 2 | 131029882 | 131029981 | 100 | 200 | ---C---C--AG-T-G--T--T--A----------------AG---T-----------------------------A--T----------------A-G-- |
| Seq-44 | 3 | 106620849 | 106620948 | 100 | 201 | ---T------AG-T----GT--T-------G--A-T--AG-------T-C---------------------AT---T-----------A------------ |
| Seq-44 | 7 | 57253951 | 57254050 | 100 | 202 | ---C---C--AG-A--TC-A--T----------A-------AG-------------C--------------C-A---T-------------A-G------- |
| Seq-44 | 13 | 36639718 | 36639817 | 100 | 203 | ----G------AG--T------------------C------AG-----------------T-A-----------A--T--G--------A----------- |
| Seq-44 | 17 | 19506558 | 19506657 | 100 | 204 | ---AG-T--A-T---G--T--------------A-------AG-------------T--C-----------A------------A----T---------- |
| Seq-44 | 17 | 22025055 | 22025154 | 100 | 205 | ---AG-T----G--T----------------C-AG---------------T--------------------T------G-G---------T--------- |
| Seq-45 | M | 4401 | 4500 | 100 | 206 | AAAGTAAGGTCAGCTAAATAAGCTATCGGGCCCATAACCCCGAAAATGTTGGTTATACCCTTCCCGTACTAATTAATCCCTGGCCCAACCCGTCATCTAC |

TABLE 1-continued

Mitochondrial and Genomic (Nuclear) Paralogs

| Seq. No. | Chr | Start | End | Length | SEQ ID NO: | Sequence |
|---|---|---|---|---|---|---|
| Seq-45 | 1 | 564950 | 565049 | 100 | 207 | ----------------------------T----------------------------------------------------------------------- |
| Seq-45 | 2 | 117782580 | 117782679 | 100 | 208 | -G-------------C-----------------A-C---A-A----------T---------T----TTA-T--TACT |
| Seq-45 | 2 | 131029982 | 131030081 | 100 | 209 | -----------------------------------------A---------------C-----A-------C-TAT-A--T-G-TTA- |
| Seq-45 | 7 | 57254051 | 57254150 | 100 | 210 | -G------------------------------A----------------C----------C-ATAA-GT---TTA-T--T-TA |
| Seq-45 | 8 | 32872717 | 32872816 | 100 | 211 | -G---------------G-T--------------------------C---------A-GGC------T-A-T----TT-T--T-C- |
| Seq-45 | 10 | 20036681 | 20036780 | 100 | 212 | -G--C---------------------T-AC-------A---------C------------------T-A-T----TTAGT--T-CT |
| Seq-45 | 17 | 19506658 | 19506757 | 100 | 213 | ------------------------------A-------------------C-----------AT-A--TTGG--TTA-TAT-TT |
| Seq-45 | 17 | 22025155 | 22025254 | 100 | 214 | GG-----------A-----------------------T-----------------------A-------------T--- |
| Seq-45 | 24 | 8240212 | 8240311 | 100 | 215 | ---T----------A-TA------------------T---------------AA-G----AT-A-TT----TTA-T---C- |
| Seq-46 | M | 4501 | 4600 | 100 | 216 | TCTACCATCTTTGCAGGCACACTCATCACAGCGCTAAGCTCGACACTGATTTTTACCTGAGTAGGCCTAGAATAAACATGCTAGCTTTTATTCCAGTTC |
| Seq-46 | 1 | 565050 | 565149 | 100 | 217 | ------------------------------------------------------------------------------------------------ |
| Seq-47 | M | 4601 | 4700 | 100 | 218 | TAACCAAAAATAAACCCTGTTCCACAGAAGCTGCCATCAAGTATTTCCTCACGCAAGCCATCCATAATCCTTCTAATAGCTATCCTCTTCAA |
| Seq-47 | 1 | 565150 | 565249 | 100 | 219 | -----------G-------------------------------------------------------------------- |
| Seq-47 | 17 | 22025355 | 22025454 | 100 | 220 | ---TT---------C--C--T------A--C--T------AT----$----A---T------CA---------------C-- |
| Seq-48 | M | 4701 | 4800 | 100 | 221 | CAATATACTCTCCGGACAATGAACCATAACCAATACTAATCCATAATCTCATCATTAATAATCATAATGGCTATAGCAATAAACTAGGAATAGCCCCC |
| Seq-48 | 1 | 565250 | 565349 | 100 | 222 | -------C-------------C--------------------------------------************************ |
| Seq-48 | 17 | 22025455 | 22025554 | 100 | 223 | -----G-------------C-----C--CA------------------C--CA--CC--T---------------T+++++++++ |
| Seq-49 | M | 4801 | 4900 | 100 | 224 | TTTCACTTCTGAGTCCCAGAGGTTACCCAAGGCACCCCTCTGACATCCGGCCTGCTTCTTCTCACATGACAAAAACTAGCCCCCATCCAATCATATACC |
| Seq-49 | 1 | 565350 | 565449 | 100 | 225 | -----------------------------------------------------C------------------------------- |
| Seq-49 | 1 | 50482956 | 50483055 | 100 | 226 | AGG--------A--TT----A-T--T--A-A----C-T---------T-----G-T-----TT- |
| Seq-49 | 2 | 117782984 | 117783083 | 100 | 227 | ----------A----A-TT-T-T-A-----T-TA-A----T------------T-----G-----G-TT- |
| Seq-49 | 2 | 131030381 | 131030480 | 100 | 228 | ----T---A--A-----A-TT----A----A-A-------C--------G-----A--T--T----TCA-T-A |
| Seq-49 | 8 | 32873109 | 32873208 | 100 | 229 | ----C-T-A-----AA---T--A-TT-T--A-A---C-------------------T----G-T-TT- |

TABLE 1-continued

Mitochondrial and Genomic (Nuclear) Paralogs

| Seq. No. | Chr | Start | End | Length | SEQ ID NO: | Sequence |
|---|---|---|---|---|---|---|
| Seq-49 | 9 | 5095554 | 5095653 | 100 | 230 | ----------C---------A--A-----G--A--TT---A-TG--T---A-A------C---------------T-----TT- |
| Seq-49 | 17 | 22025555 | 22025654 | 100 | 231 | --C-GT------------------A--C--T-----A-T---A-----CC---------T--T---T---T---------- ++++++++++++++++++++++++++++++++++++++$++++++++++++++++++++++ ******* |
| Seq-50 | M | 4901 | 5000 | 100 | 232 | AATCTCTCCCTCACTAAACGTAAGCCTTCTCCTCACTCTCTCAATCTTATCCATCATAGCAGGCAGTTGAGTGATTAAACCAAACCCAGCTACGCAA |
| Seq-50 | 1 | 565450 | 565549 | 100 | 233 | ---T-----T------------------------T-----G--------A------ ******************** ******************** |
| Seq-51 | M | 5001 | 5100 | 100 | 234 | AATCTTAGCATACTCCTCAATTACCCACATAGGATGAATAATAGCAGTTCTACCGTACAACCCTAAACATAACCATTCTTAATTTAACTATTTATATTATC |
| Seq-51 | 1 | 565550 | 565649 | 100 | 235 | --------------C--------------------------------------------------------------- |
| Seq-51 | 2 | 212642076 | 212642175 | 100 | 236 | ---------C--T---------T---------------A---ATT--TG---A-----T-----C---A---C-G-T-------CC------- |
| Seq-51 | 17 | 22025749 | 22025848 | 100 | 237 | ---------C-----T--------C------------A---G-A-------A-GT--C-------T-C--CC---TC--C-----C--T *********** $ ******************* |
| Seq-52 | M | 5101 | 5200 | 100 | 238 | CTAACTACTACCGCCATTCCTACTACTCAACTTAAACTCCAGCACCACCGACCCTATCTCGCACCTGAAACAAGCTAACATGACTAACACCCCTTAA |
| Seq-52 | 1 | 565650 | 565749 | 100 | 239 | -----------------------A------------------------------A----------------C----------------- |
| Seq-52 | 2 | 68487950 | 68488049 | 100 | 240 | -----A-----T------GC-----TC-G--T--A--------AG------T---C-A-G-----A--------T--T-A----- |
| Seq-52 | 17 | 22025849 | 22025948 | 100 | 241 | -----A-C-----A-------GG--------G-----T----G-GC-------T-A-------C--------T-A-----T--C------- *********** ******************** |
| Seq-53 | M | 5201 | 5300 | 100 | 242 | TTCCATCCACCCCTCCTCTCCCTAGGAGAGCCTGCCCCCCGCTACCGGCTTTTTGCCCAAATGGGCCATTATCGAAGAATTCACAAAAAACAATAGCCTCAT |
| Seq-53 | 1 | 565750 | 565849 | 100 | 243 | -----------------A-----------------------------A--------T----------C-A--------------------- |
| Seq-53 | 17 | 22025949 | 22026048 | 100 | 244 | -C-----T---A--A-------------------T--------ATTT--C--T--------T--C-A----- $ $ *********** ******************** |
| Seq-54 | M | 5301 | 5400 | 100 | 245 | CATCCCCACCACCATCATAGCCACCATCACCCTCCTTAACCTCTACTTCTACCTACGCCTAATCTACTCCACCTACTCCCCATATCTAACAAC |
| Seq-54 | 1 | 565850 | 565949 | 100 | 246 | -------T----------------------------G---------------------T--------------------- |
| Seq-54 | 17 | 22026049 | 22026148 | 100 | 247 | T-----T-C--------TT-T--T-------A--T--T---A------T-----------TG-T----T-------C--------- |
| Seq-55 | M | 5401 | 5500 | 100 | 248 | GTAAAAATAAAATAAAATCTCCCCACATTCCTCCCCACACTCGCCCTTACCACGCTACTCCTACCTATCTCCCCTTTTATAC |
| Seq-55 | 1 | 565950 | 566049 | 100 | 249 | ---------C----------------------------A--G-----------G- |
| Seq-55 | 17 | 22026149 | 22026248 | 100 | 250 | ----------A---------A-----T--A---C--T---------CT-T-------A-----T-AC---C-- |

TABLE 1-continued

Mitochondrial and Genomic (Nuclear) Paralogs

| Seq. No. | Chr | Start | End | Length | SEQ ID NO: | Sequence |
|---|---|---|---|---|---|---|
| Seq-56 | M | 5501 | 5600 | 100 | 251 | TAATAATCTTATAGAAATTTAGTTAAATACAGACCAAGAGCCTTCAAAGCCCTCAGTAAGTTGCAATACTTAATTTCTGCAACAGCTAAGGACTGCAAA |
| Seq-56 | 1 | 566050 | 566149 | 100 | 252 | ------------------------------------------------------------------------------------------- |
| Seq-57 | M | 5601 | 5700 | 100 | 253 | ACCCCACTCTGCATCAACTGAACGCAAATCAGCCACTTTAATTAAGCCCTTACTAGACCAATGGGACTTAAACCCACAAACACTTAGTAACAGC |
| Seq-57 | 1 | 566150 | 566249 | 100 | 254 | ------------------------------------------------------------------------------------------- |
| Seq-57 | 2 | 131031172 | 131031271 | 100 | 255 | -TT-T---------T-----------------AT-----------------------------TTG-----------------G---T---A-------A |
| Seq-57 | 2 | 212642676 | 212642775 | 100 | 256 | --T-T-T--------GT-----------------A-A--------------------------TGG---A-T-C---A---G-A-T--------T |
| Seq-57 | 7 | 57255247 | 57255346 | 100 | 257 | --TGT-T---------T-----------------AT-----------------------------TGT----------------TG--A-T---C- |
| Seq-57 | 8 | 134767787 | 134767886 | 100 | 258 | --T-T-T---------T-----------------A---C-----------------------A-GG-----------G---------TTCGCA-A-T-C--------- |
| Seq-57 | 9 | 5096353 | 5096452 | 100 | 259 | --T-T-T--------GT-----------------A----------------------------T---G------T-GG---A-T-C--------- |
| Seq-57 | 17 | 22026350 | 22026449 | 100 | 260 | ------T-T-------T-----------------------------------------G-------T---------------A-T-G--------- |
| Seq-58 | M | 5701 | 5800 | 100 | 261 | TAAGCACCCTAATCAACTGGCTTCAATCTACTTCTCCCGCGCGGGAAAAAGGCGGGAGAAGCCCCCGCAGGTTTGAAGCTGCTCTTCGAATTGCA |
| Seq-58 | 1 | 566250 | 566349 | 100 | 262 | **********************************$$$$$$$$$$$$$$$$$$$$$$$$************************* |
| Seq-59 | M | 5801 | 5900 | 100 | 263 | ATTCAATATGAAAATCACCTCGGAGCTGGTAAAAGAGAGCCTAACCCTGTCTTTAGATTTACAGTCCATTTACCTCACCCCC |
| Seq-59 | 1 | 566350 | 566449 | 100 | 264 | -------------------------A---------------------------------T----------------------------- |
| Seq-59 | 21 | 10493045 | 10493045 | 100 | 265 | -------------------------A---------------------------------T----------------------------AGA |
| Seq-60 | M | 5901 | 6000 | 100 | 266 | ACTGATGTTCGCCGACCGTTGACTATTCTCACAAACCACAAAGACATTGGAACACTATACCTATTATTCGGCGCATGAGCTGGAGTCCTAGGCACAGCT |
| Seq-60 | 1 | 566450 | 566549 | 100 | 267 | ------------------------------------------------------------------------------------------- |
| Seq-60 | 17 | 22026634 | 22026733 | 100 | 268 | ---A---------A---------A------------------A----------A--------TT----G-T---------T-G-T------C |
| Seq-61 | M | 6001 | 6100 | 100 | 269 | CTAAGCCTCCTTATTCGAGCCGAGCTGGGCCAGCCAACCTTCTAGGTAACGACCAACATCTACACGTTATCGTCACAGCCCATGCATTTGTAATAA |
| Seq-61 | 1 | 566550 | 566649 | 100 | 270 | ----------------------------------A----------------------------------------------------- |
| Seq-61 | 17 | 22026734 | 22026833 | 100 | 271 | T-------AGA-T--A--A--T-A-T--------------C-------------------------------CA----CT-C------- |
| Seq-62 | M | 6101 | 6200 | 100 | 272 | TCTTTCTTCATAGTAATACCCATCATAATCGGAGGCTTTGGCAACTGACTAGTTCCCCTAATAATCGGTGCCCCCGATATGGCGTTTCCCCGCATAAACAA |
| Seq-62 | 1 | 566650 | 566749 | 100 | 273 | ------------------------------------------------------------------------------------------- |

TABLE 1-continued

Mitochondrial and Genomic (Nuclear) Paralogs

| Seq. No. | Chr | Start | End | Length | SEQ ID NO: | Sequence |
|---|---|---|---|---|---|---|
| Seq-62 | 8 | 134768284 | 134768383 | 100 | 274 | ---------------A--------T-G--T-C------AG--C--T-----A---C----G----TT- |
| Seq-62 | 17 | 19508954 | 19509053 | 100 | 275 | -A-------T-G-----A-------T---------T------------T-----A-------A-A----T----- |
| Seq-62 | 17 | 22026834 | 22026933 | 100 | 276 | ---T-----------GT-T---------T-------GT-T---T----G--C------T-C----A----T-G----T----- |
| Seq-62 | M | 6201 | 6300 | 100 | 277 | CATAAGCTTCTGACTCTTACCTCCCTCTCCTACTCTGCTCGCATCTGCTATAGTGGAGGCCGGAGCAGGAACAGTTGAACAGTCTACCCTCCCTTA |
| Seq-63 | 1 | 566750 | 566849 | 100 | 278 | ****************************-C-----------T-------------------------C---------------G |
| Seq-64 | M | 6301 | 6400 | 100 | 279 | GCAGGGAACTACTCCCACCCTGGAGCCTCCGTAGACCTAACCATCTCTCCTTACACCTAGCAGGTGTCTCCTATCTTAGGGGCCATCAATTTCATCA |
| Seq-64 | 1 | 566850 | 566949 | 100 | 280 | -------------------------A---------- |
| Seq-64 | 17 | 22027034 | 22027133 | 100 | 281 | ---------A-----T------T-A-AG---T-------------C-T-T-----TC----A--T--- |
| Seq-65 | M | 6401 | 6500 | 100 | 282 | CAACAATTATCAATATAAAACCCCTGCCATAACCAATACCCAATACCCATAACGCCCCCTCTTCGTCGATCCGTCCTAATCACAGCAGTCCTACTTCTCCTATCTCT |
| Seq-65 | 1 | 566950 | 567049 | 100 | 283 | -------T-------------------T----------------------T- |
| Seq-65 | 1 | 142791954 | 142792053 | 100 | 284 | -C---------A----------GT----T-C-A------A-----TA-----T-T-A----T-G-- |
| Seq-65 | 1 | 143344026 | 143344125 | 100 | 285 | -C---------A----------GT----T-C-A------A-----TA-----T-T-A----T-G-- |
| Seq-65 | 17 | 22027134 | 22027233 | 100 | 286 | -C-------------TAT---------T-C---------------G-------C-----C- |
| Seq-65 | 21 | 9734872 | 9734971 | 100 | 287 | -C---------A----------GT----T-C-A------A-----TA-----T-T-A----T-G-- |
| Seq-65 | 24 | 13289499 | 13289598 | 100 | 288 | -C---------A----------GT----T-C-A------A--A--TA-----T-T-A----T-G-- |
| Seq-66 | M | 6501 | 6600 | 100 | 289 | CCCAGTCCTAGCTGCTGGCATCACTATACTACTAACACGCCAACCTCAACACCACCTTCTCGACCCCGCCGGAGGAGGAGACCCCATTCTATACCAA |
| Seq-66 | 1 | 567050 | 567149 | 100 | 290 | -----------------C---------------T-----------A--------- |
| Seq-67 | M | 6601 | 6700 | 100 | 291 | CACCTATTCTGATTTTCGGTCACCCTGAAGTTTATATTCTTATCCTACCAGGCTTCGGAATAATCTCCATATTGTAACTTACTACTCCGGAAAAAAG |
| Seq-67 | 1 | 567150 | 567249 | 100 | 292 | -------------------C-------------------------------------G-----A |
| Seq-67 | 7 | 57256299 | 57256398 | 100 | 293 | ---T---------C-CT-------C----T-C------A-G---T-----CAC--A---T-- |
| Seq-67 | 9 | 5097351 | 5097450 | 100 | 294 | ---TT--------C--T------C-------------T-T-G-G-----G-C-G--T-----G- |
| Seq-67 | 17 | 22027333 | 22027432 | 100 | 295 | ---T---------C--T-------C-----------T--------T-T-C--C--C-A--T-------G-- |

TABLE 1-continued

Mitochondrial and Genomic (Nuclear) Paralogs

| Seq. No. | Chr | Start | End | Length | SEQ ID NO: | Sequence |
|---|---|---|---|---|---|---|
| Seq-67 | 23 | 15745953 | 15746052 | 100 | 296 | --TT---------------------T--------CA----C----------------------------A--T--T-----G--G--CTC |
| Seq-67 | 23 | 125605734 | 125605833 | 100 | 297 | -------------------------T--C---C--------------G-------------------------------------T--- |
| Seq-68 | M | 6701 | 6800 | 100 | 298 | AACCATTTGGATACATAGGTATGGTCTGAGCTATGATATCAATTGGCTTCCTAGGGTTTATCCGTGTGAGCACCATATATTTACAGTAGGAATAGACGT |
| Seq-68 | 1 | 567251 | 567350 | 100 | 299 | ------------------------------------------------------------------------------------------------ |
| Seq-68 | 2 | 131032284 | 131032383 | 100 | 300 | ------G--T--G--C--A--A-----C--A-------------A--G--C---------------------------------T-------- |
| Seq-68 | 2 | 167271100 | 167271199 | 100 | 301 | ------G-------G--C--------G----------G--A--C--T---------G--C-----G------------------A-------- |
| Seq-68 | 3 | 171252207 | 171252306 | 100 | 302 | -CGGG---C------T--G-A--A------------C----------------A------T--A--G--C----CC------------------ |
| Seq-68 | 7 | 57256399 | 57256498 | 100 | 303 | -G--------------G-------G--C--A--G-----C--A-------------T--A--G--T-----C--------C--T--T------ |
| Seq-68 | 8 | 104102235 | 104102334 | 100 | 304 | ---------------------------------T--T-----A------G------CG------T-----C-------AA--G--T-G----A |
| Seq-68 | 9 | 5097451 | 5097550 | 100 | 305 | ------G-------G--T--G--C--A--A-----C--A-------T--T-----C-------T--A--------------C-------A--- |
| Seq-68 | 11 | 73221764 | 73221863 | 100 | 306 | ----------------------------T----------------T---------------T--A-----------------G--------- |
| Seq-68 | 12 | 40680151 | 40680250 | 100 | 307 | ------G-------G--T--G-----A-G-A---C--AG----------G--C----T-G--------A--A--G-TC------T-------- |
| Seq-68 | 17 | 22027433 | 22027532 | 100 | 308 | -------G--------------G--A----------------------G----------A--------T--A-----C--T-----G------ |
| Seq-68 | 23 | 125605834 | 125605933 | 100 | 309 | ------C----------T-----------------------G----------A--------T-----T---------G--------------- |
| Seq-69 | M | 6801 | 6900 | 100 | 310 | AGACACACGAGCATATTTCACCCTCCGCTACCATAATCATCGCTATCCCACCGGCGTCAAAGTATTAGCTGACTCGCCACACTCCACGGAAGCAATATG |
| Seq-69 | 1 | 567351 | 567450 | 100 | 311 | ------------------------------------------------------------------------------------------------ |
| Seq-69 | 2 | 131032384 | 131032483 | 100 | 312 | ---T--T--------------T-----T-----T-----T--T--T-----C---------G--A--T-----T--A--C--T-G----C |
| Seq-69 | 3 | 171252307 | 171252406 | 100 | 313 | ---T-----------------C--C-------------T--------T-----T--------T-----T--G--------T--C--CC |
| Seq-69 | 17 | 51183076 | 51183175 | 100 | 314 | CTCATTGA-CTGC-GGGA-----------------------------------------------T-----------T------------- |
| Seq-69 | 23 | 125605934 | 125606033 | 100 | 315 | ------C-----------------------------A-------------------T-----A----------T---------------- |
| Seq-70 | M | 6901 | 7000 | 100 | 316 | AAATGATCTGCTGCTGCAGTGCTCTGAGCCCTAGGATTCATCTTTCTTTTCACCGTAGGTGGCCATTGGTATTAGCAAACTCATCACTAGACATCG |
| Seq-70 | 1 | 567451 | 567550 | 100 | 317 | ------------------------------------------T--T--------------------------------------------- |
| Seq-70 | 9 | 5097657 | 5097756 | 100 | 318 | ------C--C--A--T------A--------A--T--A-----------C----T--T-----------T--TA |

TABLE 1-continued

Mitochondrial and Genomic (Nuclear) Paralogs

| Seq. No. | Chr | Start | End | Length | SEQ ID NO: | Sequence |
|---|---|---|---|---|---|---|
| Seq-70 | 17 | 22027633 | 22027732 | 100 | 319 | -----G--CA-C----A--------------------------------------C------T-A-G--------A-G-A---------T------ |
| Seq-70 | 17 | 51183176 | 51183275 | 100 | 320 | ------------------G---------------G----------------------------T-------C-----A------------------ |
| Seq-70 | 23 | 125606034 | 125606133 | 100 | 321 | --G--------------------A-----G------------------------------C--------A-C------------------T----- |
| Seq-70 | M | 7001 | 7100 | 100 | 322 | TACTACACGACACGTACGTTGTAGCTCACTTCCACTATGTCCTATCAATAGGAGCTGTATTTGCCATCATAGAGGCTTCATTCACTGATTTCCCCT |
| Seq-71 | 1 | 567551 | 567650 | 100 | 323 | ---------------------------------------C-------------------------------------------------------- |
| Seq-71 | 2 | 203478989 | 203479088 | 100 | 324 | -CT-----------------A--T-----------------GC--T----------------C-G--------------TG-C---------C--C |
| Seq-71 | 2 | 212644050 | 212644149 | 100 | 325 | CCT----T--------A--T-------------C--T-------------------A--C-C-------------TG-C------------CT--T |
| Seq-71 | 7 | 57256697 | 57256796 | 100 | 326 | -TT-----T--------A--T-------T-A--C---------------------C-----T--T---------------TG-C-----------C |
| Seq-71 | 17 | 22027733 | 22027832 | 100 | 327 | -----------T-T-A--T-------G--C-------------C------------G--CA-------G--G--------------------T--- |
| Seq-71 | 17 | 51183276 | 51183375 | 100 | 328 | --------------------A---------------C----------------------C----------G------------------------- |
| Seq-71 | 23 | 125606134 | 125606233 | 100 | 329 | --------A----------------C---T--C---------------------------C----T------------------------------ |
| Seq-72 | M | 7101 | 7200 | 100 | 330 | AATTCTCAGGCTACACCCTAGACCAAACCTACGCCAAAATCCATTTCACTATCATATTCATCGGCGTAAATCTAACTTTCTCCCACAACACTTTCTGGC |
| Seq-72 | 1 | 567651 | 567750 | 100 | 331 | -----------------G-------------------------------G----------------------------------------- |
| Seq-72 | 17 | 22027833 | 22027932 | 100 | 332 | --A-C-G-------A--G-T-T--------T--C--TG-C---------T--C--TG-A-------C----G--G----------- |
| Seq-72 | 17 | 51183376 | 51183475 | 100 | 333 | ----------------T---------------G--------------------------------T------------------------ |
| Seq-73 | M | 7201 | 7300 | 100 | 334 | CTATCCGGAATGCCCCGACGTTACTCGGACTACCCCCGATGCATACACCACATGAAACATCCTATCATCTGTAGGCTTCATTCATTTCTAACAGCAGTAA |
| Seq-73 | 1 | 567751 | 567850 | 100 | 335 | ------------------T---------------T------------------T----------------------------------------- |
| Seq-73 | 3 | 120440919 | 120441018 | 100 | 336 | T----T------A--------T-T-------C------G----T-TT---------T-TT-------------C--CT--------- |
| Seq-73 | 7 | 57256899 | 57256998 | 100 | 337 | ----------------T--------CA-T---T-----------T--TA-T----CAG--------T------C----------- |
| Seq-73 | 7 | 67562742 | 67562841 | 100 | 338 | ----A-T----TT--------C--T--T-T-----------T--TA-C-----------T-C-A------T----- |
| Seq-73 | 17 | 22027933 | 22028032 | 100 | 339 | ----T-AG---T----------T-------------G----T----------T-TT--------C--C---A---------G |
| Seq-73 | 17 | 51183476 | 51183575 | 100 | 340 | ----T-------A---------A------------------T-----------------------T------C--------- |
| Seq-73 | 23 | 125606333 | 125606432 | 100 | 341 | ----T-------A----------------------------T-----------------------T------C--------- |

TABLE 1-continued

Mitochondrial and Genomic (Nuclear) Paralogs

| Seq. No. | Chr | Start | End | Length | SEQ ID NO: | Sequence |
|---|---|---|---|---|---|---|
| Seq-74 | M | 7301 | 7400 | 100 | 342 | TATTAATAATTTCATGATTTGAGAAGCCTTCGCTTCGAAGCGAAAAGTCCTAATAGTAGAAGAACCCTCCATAAACCTGGAGTGACTATATGGATGCCC |
| Seq-74 | 1 | 567851 | 567950 | 100 | 343 | ---------------------------A------------------------------------------------------------------------ |
| Seq-74 | 17 | 22028033 | 22028132 | 100 | 344 | -GC----------A-CC------GA------------AAT-GC---T-----CT---A-----G--G--G--------------- |
| Seq-74 | 17 | 51183576 | 51183675 | 100 | 345 | ------------------------A---------------------------A----------------------------G- |
| Seq-75 | M | 7401 | 7500 | 100 | 346 | CCCACCCTACCACACATTCGAAGAACCCGTATACATAAAATCTAGACAAAAAGGAATCGAACCCCCAAAGCTGGTTTCAAGCCAACCCCATGGC |
| Seq-75 | 1 | 567951 | 568050 | 100 | 347 | ---------------------------------------------------------------------------------------------- |
| Seq-75 | 3 | 120441119 | 120441218 | 100 | 348 | T-----------T-G-T-------A--C---------C-----------T--A---------------------T--AA- |
| Seq-75 | 17 | 22028133 | 22028232 | 100 | 349 | T-----------TA----------A--C---------C-----------T--T-G---------------G--T--AA- |
| Seq-76 | M | 7501 | 7600 | 100 | 350 | CTCCATGACTTTTTCAAAAAGGTATTAGAGAAAAACCATTTCATAACTTTGTCAAAGTTAAATCCTATATATCTTAATGGCACATGCAGC |
| Seq-76 | 1 | 568051 | 568150 | 100 | 351 | ------------------A--------------------------------------------------------------------- |
| Seq-76 | 2 | 131033079 | 131033178 | 100 | 352 | ---TG------------C-------A-------TG---TT---------G-----T--GC-G-------C---A---T |
| Seq-76 | 3 | 120441219 | 120441318 | 100 | 353 | ---T-------------C-------A-------TT---------------G-----T--G---C----------C---- |
| Seq-76 | 7 | 57257199 | 57257298 | 100 | 354 | ---T-CA-G--------C--G-T--A-------T-----------------G-----T--GC-------------C---T |
| Seq-76 | 9 | 5098255 | 5098354 | 100 | 355 | ---TG------------C--G-T--A-------TT---A-G---------T------T---------G--T---C---T |
| Seq-76 | 11 | 39788483 | 39788582 | 100 | 356 | ---T-------------C--C--G-T--A-------TT---AT-------T------T---------G--T---C---T |
| Seq-76 | 13 | 97349967 | 97350066 | 100 | 357 | ---T-------------G--T--A---------TT---------C------T------------A-T---G---C---- |
| Seq-76 | 17 | 22028233 | 22028332 | 100 | 358 | -C-T----------C--A--------G------T--------------G-----C--T---CG------C------ |
|  |  |  |  |  |  | ***************************** $ ***************************** ***************************** |
| Seq-77 | M | 7601 | 7700 | 100 | 359 | GCAAGTAGGTCTACAAGACGCTACTTCCCCTATCATAGAAGAGCTTATCACCTTTCATGATCACGCCCCTCATAATCATTTCCTTATCTGCTTCCTAGTC |
| Seq-77 | 1 | 568151 | 568250 | 100 | 360 | ------------------------------------------T------------------------------------------------------ |
| Seq-77 | 3 | 120441319 | 120441418 | 100 | 361 | C-----C-----T----C-T-----C-A---------A-C--------A-T---AT-A---T |
| Seq-77 | 17 | 22028333 | 22028432 | 100 | 362 | C--GC-----T-----------------C-------A-G-----C-------C-----T---A---- |
| Seq-78 | M | 7701 | 7800 | 100 | 363 | CTGTATGCCCTTTTCCTAACACTCACAACAAAACTAACATCTCAGACGCTCAGGAAATAGAAACCGTCTGAACTATCCTGCCCGCCATCA |
| Seq-78 | 1 | 568251 | 568350 | 100 | 364 | ---------------C------------------------------------------------------------------------- |
|  |  |  |  |  |  | ***************************** |

TABLE 1-continued

Mitochondrial and Genomic (Nuclear) Paralogs

| Seq. No. | Chr | Start | End | Length | SEQ ID NO: | Sequence |
|---|---|---|---|---|---|---|
| Seq-79 | M | 7801 | 7900 | 100 | 365 | TCCTAGTCCTCATCGCCCTCCCATCCCTACGCATCCTTTACATAAGACGAGGTCAACGATCCCTCCTTACCATCAAATCAATTGGCCACCAATGTA |
| Seq-79 | 1 | 568351 | 568450 | 100 | 366 | ------------------------------T------------------------------------------------------T---------- |
| Seq-79 | 17 | 22028529 | 22028628 | 100 | 367 | ---------A--T----------T-------G--G---------T--AA------T---C--T--TT-------C---A------A---------- $ ****************** |
| Seq-80 | M | 7901 | 8000 | 100 | 368 | CTGAACCTACGAGTACACCGACTACGGCGGACTAATCTTCAACTCCTACATATTCCCCCATTATTCCTAGAACCAGGCGACCTGCGACTCCTTGACGTT |
| Seq-80 | 1 | 568451 | 568550 | 100 | 369 | ---------A---------------------------------------------------------------------------------------- |
| Seq-80 | 17 | 22028629 | 22028728 | 100 | 370 | ----------------T--A------A-T--T--A------T------T--------A-----C----T-----A-T------T-----T--A-A-- |
| Seq-81 | M | 8001 | 8100 | 100 | 371 | GACAATCGAGTAGTACTCCCGATTGAAGCCCCCATTCGTATATATAATTACATCACAGACGTCTTGCACTCATGAGCTGTCCCACATTAGGCTTAAAA |
| Seq-81 | 1 | 568551 | 568650 | 100 | 372 | --------G----------------------------------------------------------------------------------------- |
| Seq-81 | 17 | 22028729 | 22028828 | 100 | 373 | ---T---------C-T--A-----------TG--A----------C-A----A--------- |
| Seq-82 | M | 8101 | 8200 | 100 | 374 | CAGATGCAATTCCCGGACGTCTAAACCAACCACTTTCACCGCTACACGGGGTATACTACGGTCAATGCTCTGAAATCGTGTGGAGCAAACCACAG |
| Seq-82 | 1 | 568651 | 568750 | 100 | 375 | -------------------------------------T----------A----------C-----------------------------GTT |
| Seq-82 | 17 | 8969862 | 8969961 | 100 | 376 | -----------------------C---------------------A--------C---------G--A---------CA-----T-G-------- |
| Seq-82 | 17 | 22028829 | 22028928 | 100 | 377 | ---T-------------C-------------------A--------C-T------A-------------A----------C------TG---T-- |
| Seq-83 | M | 8201 | 8300 | 100 | 378 | TTTCATGCCCATCGTCCTAGAATTAATTCCCTAAAATCTTTGAAATAGGGCCCGTATTACCTATAGCACCCCCCTCTACCCCCTCTAGAGCCCACTG |
| Seq-83 | 1 | 568749 | 568848 | 100 | 379 | ---T------------------------------------------------------------------------****************** |
| Seq-84 | M | 8301 | 8400 | 100 | 380 | TAAAGCTAACTTAGCATTAACCTTTTAAGTTAAAGATTAAGAGAACCAACACCTTCTTTACAGTGAAATGCCCCAACTAAATACTACCGTATGCCACCA |
| Seq-84 | 1 | 568849 | 568948 | 100 | 381 | ----------------------------------------------------------------------------A-------------------- |
| Seq-84 | 2 | 88124395 | 88124494 | 100 | 382 | CCGCCGCCG-CGCA---------------------------------------------G----------------C-------T------------ |
| Seq-84 | 17 | 22029031 | 22029130 | 100 | 383 | -G-----G--CC--------------------C-------T-GCT-T--------C---------T----G-C--C---A----A----T------- $$$$$$ |
| Seq-85 | M | 8401 | 8500 | 100 | 384 | TAATTACCCCCATACTCCTTACACTATTCCTCATCACCCAACTAAAAATATTTAAACAACAAACTACCACCTCCCTACCTCCCCAAAGCCCATAAAATAAA |
| Seq-85 | 1 | 568949 | 569048 | 100 | 385 | -------------------------------T-------------------T-------------- |
| Seq-85 | 2 | 88124495 | 88124594 | 100 | 386 | -----G------------------------------T----------------T-----------T----C-------- |

TABLE 1-continued

Mitochondrial and Genomic (Nuclear) Paralogs

| Seq. No. | Chr | Start | End | Length | SEQ ID NO: | Sequence |
|---|---|---|---|---|---|---|
| Seq-86 | M | 8501 | 8600 | 100 | 387 | AAATTATAACAAACCCTGAGAACCAAAATGAACGAAAATCTGTTCGCTTCATTCATTGCCCCACAATCCTAGGCCTACCCGCCGCAGTACTGATCATTC |
| Seq-86 | 1 | 569049 | 569148 | 100 | 388 | ---C------------------------------A--------------------------------------------------------------- |
| Seq-86 | 2 | 88124595 | 88124694 | 100 | 389 | ---C----GT---------G---------------------T-G--------------------------------------------------- |
| Seq-86 | 2 | 131034053 | 131034152 | 100 | 390 | ---AC------C--T----------T------A-----A-C----T--C----GT----A-A---C----A-----CT |
| Seq-86 | 6 | 92436501 | 92436600 | 100 | 391 | ---C-C--T-----------G--------T-A--A---------A---------------------T--T-----CA----C |
| Seq-86 | 7 | 57234880 | 57234979 | 100 | 392 | ---AC-----C--T-----------C----------T---C-A-C-----T-C-------G--------C--TT-----A----C-----A-----CT |
| Seq-86 | 17 | 22029231 | 22029330 | 100 | 393 | ---CC-C--T--T--T--GT---------------------TA-----------------T-----------T-A--T----G-CA----G-- |
| Seq-87 | M | 8601 | 8700 | 100 | 394 | TATTTCCCCTCTTATTGATCCCCACCTCCAAATATCTCATCAACAACCGACTAATCACCACCCCAAATGACTAATCAAACTAACCTCAAAACAAATGAT |
| Seq-87 | 1 | 569149 | 569248 | 100 | 395 | ------------------------------------------T------------------------C------------------------------ |
| Seq-87 | 2 | 88124695 | 88124794 | 100 | 396 | --------------------------------C---------T------------------------C------------------------------ |
| Seq-87 | 6 | 92436601 | 92436700 | 100 | 397 | ---CT-C--G-T--A-TT-------C-----------T------------------C-T--T------A-- |
| Seq-88 | M | 8701 | 8800 | 100 | 398 | AGCCATACACAACCACCGCTAAAGGACGAACCTGATCTCTTATACTAGTATCTTAATCATTTTATTGCCACAACTAACCTCCTGGACTCCTGCCTCACTCA |
| Seq-88 | 1 | 569249 | 569348 | 100 | 399 | ------------------------G----------------------------------------------------------------------- |
| Seq-88 | 2 | 88124795 | 88124894 | 100 | 400 | --------------------G--------------------------------------------T--T------G------A-GC-GAGGC |
| Seq-88 | 8 | 20408741 | 20408840 | 100 | 401 | -ATG------------T--G--------------G-C--------T-----------------G--T---------T-A--C--- |
| Seq-88 | 17 | 22029431 | 22029530 | 100 | 402 | -A-A---A-T-------T-----------------C--G---A-------T-C-C------T-----C-------G--T----C-- |
| Seq-89 | M | 8801 | 8900 | 100 | 403 | TTTACACCAACCACCCACTATAAACCTATAAACCTAGCCATGGCCATCCCCCTTATGAGCGGGCGCAGTGATTATAGGCTTTCGCTCTAAGATTAAAATGCCC |
| Seq-89 | 1 | 569349 | 569448 | 100 | 404 | -------------------------------------------T------------------------------------------------------- |
| Seq-89 | 2 | 131034350 | 131034449 | 100 | 405 | ------------T-----------C------A-----------T--CA--A-----------A--A----A-C------C------T--A-C-----CT--T |
| Seq-90 | M | 8901 | 9000 | 100 | 406 | TAGCCCCACTTCTTACCCACCAAGGCACACCTAGTTATTATCGAAACCATCAGCTACTCATTCAACCATATAGCCCTGGCCGT |
| Seq-90 | 1 | 569449 | 569548 | 100 | 407 | --------T--------------------------------------T---------------T----T---------T----T-------G--A-CA--T-- |
| Seq-90 | 2 | 203480860 | 203480959 | 100 | 408 | --T----T---------C---------T----A-------T--G---G-C-T------T------T---------T-------G--A-CA--T-- |
| Seq-90 | 7 | 57235280 | 57235379 | 100 | 409 | -------------C-T--TA---C------T----A-C---A--------T----CT--T-------T--------G--A--A--T-- |

TABLE 1-continued

Mitochondrial and Genomic (Nuclear) Paralogs

| Seq. No. | Chr | Start | End | Length | SEQ ID NO: | Sequence |
|---|---|---|---|---|---|---|
| Seq-90 | 9 | 5099929 | 5100028 | 100 | 410 | -G--TGG---T--------------TG-A---------T--------A--C--T-----------T-T--------AT-A--T-- |
| Seq-90 | 17 | 22029630 | 22029729 | 100 | 411 | ------TC---G---------------CT------------A-----------C--T--------T-T--C---------A--A- <br> ************************************************************************************ |
| Seq-91 | M | 9001 | 9100 | 100 | 412 | ACGCCTAACCGCTAACATTACTGCAGGCCACTCATGCCAGCTAATTGAAGCGCCACCTAGCAATATCAACCATTAACCTTCCCTCTACACTTATC |
| Seq-91 | 1 | 569549 | 569648 | 100 | 413 | ---------------------------------------------A-----------------T-------------------- |
| Seq-92 | M | 9101 | 9200 | 100 | 414 | ATCTTCACAATTCTAATTCTACTGACTATCCTAGAAATCGCTGTCGCCTTAATCCAAGCGCCTACGTTTTCACACTTCTAGTAAGCCTCTACCTGCACGACA |
| Seq-92 | 1 | 569649 | 569748 | 100 | 415 | ----------------------------------T--------------------------------------T--------- |
| Seq-92 | 17 | 22029830 | 22029929 | 100 | 416 | -----------T-G--T---------T-G--T-C---------------C-G--T--T--------C-----G------A--T-- |
| Seq-93 | M | 9201 | 9300 | 100 | 417 | ACACATAATGACCACCACCAATCACATGCCTATCATATAGTAAAACCCAGCCCTACATCATGACCCCTAACAGGGCCCCTCTCAGCCCTCCTAATGACCTTCCGGCCTA |
| Seq-93 | 1 | 569749 | 569848 | 100 | 418 | ------------------------------G----------------------------------------------------- |
| Seq-93 | 2 | 120969296 | 120969395 | 100 | 419 | ------------------A-------C-G---------C--------C--------GA--G-----A--T----------T-------G |
| Seq-93 | 2 | 131034750 | 131034849 | 100 | 420 | -T--------------A---CA---------T--C---------AT----------T----------A--A--------C |
| Seq-93 | 2 | 203481159 | 203481258 | 100 | 421 | -T-TA--------------C--------------A----------A--------T-----T-T---------A--A--T-----G |
| Seq-93 | 3 | 72632514 | 72632613 | 100 | 422 | -T------------A-----C-----C-----T--G----------T-G--AT--------A--A--T---- |
| Seq-93 | 9 | 5100229 | 5100328 | 100 | 423 | -T-----------A---T-GC-----------A------------A-----------AA--T-----T--A--A--T-----G |
| Seq-93 | 9 | 94871288 | 94871387 | 100 | 424 | -T------------GA---------C---G--TGT--T-----T----------A-------G--T----A--A--T------- |
| Seq-93 | 17 | 22029930 | 22030029 | 100 | 425 | -T-----G--T--++++++++++++++++++++++++++++--C----------T------------T-------A------- <br> **************************$********* |
| Seq-94 | M | 9301 | 9400 | 100 | 426 | GCCATGTGATTCACTTCCACTCCATAACGCTCCTACTAACGCCTCCATATAGGCCTCATACTCCTATACTAACCACACTATACCAATGCTGGCCGATGTAACACGAGAAA |
| Seq-94 | 1 | 569849 | 569948 | 100 | 427 | --------------------C--C-------++++++++++++++++++++++++--A------------------------- <br> **************** |
| Seq-95 | M | 9401 | 9500 | 100 | 428 | GCACATACCAAGGCCACCACAACACCACCTGTCCAAAAAGGCCTTCGATACGGATAATCCTATTATTACCTCAGAAGTTTTTTCTTCGCAGGATTTTT |
| Seq-95 | 1 | 569949 | 570048 | 100 | 429 | --------------------------------G-------------------------------------------------- |
| Seq-95 | 2 | 120969496 | 120969595 | 100 | 430 | -T----------TT-------T--------T---A--GT------------T-------C-A---G--A----T---------A--A---C----T--T--C-- |
| Seq-95 | 6 | 153988650 | 153988749 | 100 | 431 | ------------------T--T--ATC---------------A--A---------T-----CG--TT------G--T--C----T--C--C-- |

TABLE 1-continued

Mitochondrial and Genomic (Nuclear) Paralogs

| Seq. No. | Chr | Start | End | Length | SEQ ID NO: | Sequence |
|---|---|---|---|---|---|---|
| Seq-95 | 7 | 57235773 | 57235872 | 100 | 432 | -T---TT------T--A-AT------T--A---AT--T-A--G-A------T------A------T-T----- |
| Seq-95 | 13 | 24340119 | 24340218 | 100 | 433 | -T-----TT-----A------A-A-CA-------CT---T-A-----------C------A------C------ |
| Seq-95 | 17 | 22030130 | 22030229 | 100 | 434 | -T------------A---------------GT-----C--------G-T-A-----TT---C-C-T-------C------T------ |
| Seq-95 | 17 | 61470777 | 61470876 | 100 | 435 | -T-------------G--AT---------------A------A-----GT-C-C-----TT-------C------T-C- |
| Seq-96 | M | 9501 | 9600 | 100 | 436 | CTGAGCCCTTTTACCACTCCAGCCTAGCCCTACCCCCAACTAGGAGGCATCCCCGTAAATCCCCTAGAAGTCCCACTC |
| Seq-96 | 1 | 570049 | 570148 | 100 | 437 | -----------------------T--C---------G-A------ |
| Seq-96 | 17 | 22030230 | 22030329 | 100 | 438 | ------A-C-********** -----C----T-------A-----C-------T-A-C--C-********** |
| Seq-97 | M | 9601 | 9700 | 100 | 439 | CTAAACACATCCGTATACTCGCATCAGGAGTATCAATCACCTGAGTCTCACCATAGTCTAATAGAAAACAACCAAATAATTCAAGCACTGCTTA |
| Seq-97 | 1 | 570149 | 570248 | 100 | 440 | ---------------------G---------- |
| Seq-97 | 2 | 131035150 | 131035249 | 100 | 441 | -G---------------T-------G-T------C-T-C-CA--------T-T----A---G--------A---T |
| Seq-97 | 7 | 57235973 | 57236072 | 100 | 442 | -CG--T-----------T-------G-T------C-T-C-C---------T-----A-----------A----- |
| Seq-97 | 7 | 57259246 | 57259345 | 100 | 443 | -CG--T------------------G-T------C-T-C-----------T-T---A------------A----- |
| Seq-97 | 17 | 22030330 | 22030429 | 100 | 444 | --------------T-C----------------T--------C--------G-----TT-T--T--GC------A----- |
| Seq-98 | M | 9701 | 9800 | 100 | 445 | TTACAAATTTTACTGGGTCTCTATTTTACCCTCCTACAGAGCCTCAGAGTACTTCCTTCCACCATTTCCGACGGCATCTACGGCTCAACATTTT |
| Seq-99 | M | 9801 | 9900 | 100 | 446 | TGTAGCCACAGGCTTCCACGGACTTCACGTCATTATTGGCTCAACTTCCTACTATGCTTCATCCGCCAACTAATATTTCACTTTACATCCAACAT |
| Seq-99 | 2 | 95567160 | 95567259 | 100 | 447 | -A-----T------T--A---------T--------TA--------G------C-TC-------T---A-AC-------T-GT-- |
| Seq-99 | 2 | 120970252 | 120970351 | 100 | 448 | -A-----T--------T-------------CA-A---A--------C---C-T--A--C--------C---C-- |
| Seq-99 | 2 | 131035350 | 131035449 | 100 | 449 | -A------TT-T-----------A-------------A----T--------C-TC--T---A-AC--------GC-- |
| Seq-99 | 2 | 203481748 | 203481847 | 100 | 450 | -AC--------T-----T-T-----------T------A-------------C--------A---T--A--C---T-C |
| Seq-99 | 15 | 58442575 | 58442674 | 100 | 451 | -A----------A----T-T--------------C-G-----A-------T------A-------T-C-C |
| Seq-99 | 17 | 22030530 | 22030629 | 100 | 452 | ----------T-G---------G-C---C------T---------T------A-------T--A-----T----GT-C |
| Seq-100 | M | 9901 | 10000 | 100 | 453 | CACTTTGGCTTCGAAGCCGCCGCCCTGATACTGGCATTTTGTAGATGTGGTTTGACATATTTCTGTATGTCTCCATCATTGATGAGGGTCTTACTCTTTA |
| Seq-100 | 1 | 143245677 | 143245776 | 100 | 454 | -----C----T----------A-T-----TCAA--C------------CT-------T--T------A------ |

TABLE 1-continued

Mitochondrial and Genomic (Nuclear) Paralogs

| Seq. No. | Chr | Start | End | Length | SEQ ID NO: | Sequence |
|---|---|---|---|---|---|---|
| Seq-100 | 2 | 95567260 | 95567359 | 100 | 455 | ------C----T----GT--T-------A-------T-A-C--CA------A------CT----------A-T-T--- |
| Seq-100 | 2 | 120970352 | 120970451 | 100 | 456 | -----------T--------------------T-----------T-A-C--CA------A-AG----CT-A-C------TT--C--- |
| Seq-100 | 2 | 131035450 | 131035549 | 100 | 457 | --T-----------------------------A---------T-A-C-A--------A-A------CTCA----A-T--T------ |
| Seq-100 | 2 | 203481848 | 203481947 | 100 | 458 | ------C----T--------------TT-----G----------T-A-C---------A------CT-A---------T------- |
| Seq-100 | 4 | 49248466 | 49248565 | 100 | 459 | -----------T---------------T-----------------TC-A-C---------A------CT-----------T------C--- |
| Seq-100 | 6 | 143398978 | 143399077 | 100 | 460 | -----------T----------A-T-A---T-AA---C--G----A-A------CT----------T-----A--- |
| Seq-100 | 6 | 153989150 | 153989249 | 100 | 461 | T-T----AA--T-------G-------------C--------CA-A--A-T------C--A-T------T------A--- |
| Seq-100 | 7 | 57236273 | 57236372 | 100 | 462 | -----------T---A------------------------T-A-C----------A--------A-T--T--C---------A--- |
| Seq-100 | 7 | 57259547 | 57259646 | 100 | 463 | -----------T------TG------------T-A-C--------A-A-------T-----------A--- |
| Seq-100 | 9 | 5107065 | 5107164 | 100 | 464 | -----------T--------------A-T----------GT-A-C---------A------CT-C--A-T--T--C------A--- |
| Seq-100 | 11 | 81262696 | 81262795 | 100 | 465 | -----------A--T----------T-A--GC-C-C---------A-A------T-A-CA---------C--- |
| Seq-100 | 15 | 58442675 | 58442774 | 100 | 466 | -----------T----------T-----------A-C--CA-------A-A-AA------CT-A---------T-----A--- |
| Seq-100 | 17 | 22030630 | 22030729 | 100 | 467 | ------C----T--T-----------A-----------C--A-----------T--C--G--A------ |
| | | | | | | $$$$$$$$$$$ $$$$$$$$$$$$$$$$$$$ |
| Seq-101 | M | 10001 | 10100 | 100 | 468 | GTATAAATAGTACCGTTAACTTCCAATTAACATTCAAAAAAGAGTAATAAACTTCGCCTTAATTTAATAATCAACACCCTCCTAGC |
| Seq-101 | 17 | 22030730 | 22030829 | 100 | 469 | -----G-C-----AC--G-------------------C--T-----C---C-G--AC--GCCC---G---- |
| Seq-102 | M | 10101 | 10200 | 100 | 470 | CTTACTACTAATAATTATTACATTTTGACTACCACAACTCAACGGCTACATAGAAAAATCCACCCCTTACGAGTGCGGCTTCGACCCTATATCCCCGCC |
| | | | | | | ++++++++++ +++++++++++++++++++++++++++++++ |
| Seq-103 | M | 10201 | 10300 | 100 | 471 | CGCGTCCCTTTCCTCCATAAAATTCTCTTAGTAGCTATTACCTTCTTATTATTTGATCTAGAAATTGCCCTCCTTTTACCCTACCATGAGCCCTACAAA |
| Seq-103 | 17 | 22030929 | 22031028 | 100 | 472 | ---A-T--C-------GA-T---C-----T-----C----------AT-AC------G------C--- |
| Seq-104 | M | 10301 | 10400 | 100 | 473 | CAACTAACCTGCCACTAATAGTTTAAACAAAACGGTTGTCATCCTCTATTAATCATCCTAGCCTAGTCTGGCCTATGAGTGACTACAAAAGGATTAGAC |
| Seq-105 | M | 10401 | 10500 | 100 | 474 | CGAATTGGTATATATCTTAAACAAAACGAATGATTTCGACTCATTAATTATGATAATCATATTACCAAATGCCCCTCATTTACATTAAATATTATACTA |
| Seq-106 | M | 10501 | 10600 | 100 | 475 | GCATTACCATCTCACTTCTAGAAATACTAGTATATCGCTCACACCTCATATCCTCCCTACTATGCCTAGAAGGAATAATACTATCGCTGTTCATTATAG |
| Seq-106 | 6 | 92436907 | 92437006 | 100 | 476 | ---T-----T-G----------A-C--CT---------A----------G-----G----A-A----C--A |
| Seq-106 | 7 | 57260142 | 57260241 | 100 | 477 | ---A--------A---------G--G--T-A-C---T-A--C-----------T--AT-A----C---A |

TABLE 1-continued

Mitochondrial and Genomic (Nuclear) Paralogs

| Seq. No. | Chr | Start | End | Length | SEQ ID NO: | Sequence |
|---|---|---|---|---|---|---|
| Seq-106 | 17 | 22031232 | 22031331 | 100 | 478 | ------------T-C------GT-------A-C-----------------G-G-----T---T-A-----CG--A |
| Seq-107 | M | 10601 | 10700 | 100 | 479 | CTACTCTCATAACCCTCAACACCCCTCACTCCTCTTAGCCAATATTGTGCCTATTGCCATAGTCTTTGCCGCCTGCGAAGCAGGCGGTGGGCCTAGCCCT |
| Seq-107 | 23 | 125606708 | 125606807 | 100 | 480 | G-GTAA---------------------------A------------T---A-G----A--A--------- |
| Seq-108 | M | 10701 | 10800 | 100 | 481 | ACTAGTCTTCAATCTCCAACACATATGGCCTAGACTAGTACATAACCTACTCCAATGCTAAAACTAAACTAATCGTCCCAACAATTATATTACTACCAC |
| Seq-108 | 2 | 120971147 | 120971246 | 100 | 482 | ---------T---------------T---------T---------A-----C-T---T----A-T-TA-T------------C-GT-----A |
| Seq-108 | 2 | 131036246 | 131036345 | 100 | 483 | ---------T----------------------------T-A--T-G---------TT---T-G-C-G----A-T--A-T-----------C-G------A |
| Seq-108 | 7 | 57237053 | 57237152 | 100 | 484 | ---------T---C-------------------------T---------TT---T-G------A-T--TA-T-----------C-G------A |
| Seq-108 | 9 | 94873087 | 94873186 | 100 | 485 | C--------------G--A-------------------TT---T--------C------A-T--TA-T-----------C-GT---A-T |
| Seq-108 | 15 | 58443461 | 58443560 | 100 | 486 | ---------T----------CA-----------------TT---T--------------G-T--TA-T-----------C-GT--- |
| Seq-108 | 17 | 22031432 | 22031531 | 100 | 487 | ---------T---------T-T---G----C--T---T-------------T-----TA--T-----------C----T--A |
| Seq-108 | 23 | 125606808 | 125606907 | 100 | 488 | --------T----------------------G-------------------------A----C-------- |
| Seq-108 | 23 | | | | | ++++++++++++++++++++++++++++++++ $ |
| Seq-109 | M | 10801 | 10900 | 100 | 489 | TGACATGACTTTCCAAAAAGCACATATTTGAATCAACACCACCCCACAGCCTAATTATTAGCATCATCCCCCTACTATTTTTAACCAAATCAACAA |
| Seq-109 | 23 | 125606908 | 125607007 | 100 | 490 | -A------T-C-------A-T-------------------------T-----------C----------- |
| Seq-109 | 23 | | | | | ++++++++++++++++++ $ |
| Seq-110 | M | 10901 | 11000 | 100 | 491 | CAACCTATTTAGCTGTGTCCCCAACCTTTTCCTCCGACCCCCCTAACAACCCCCCTAATACTAACTACCTGACTCTCCTACCCCTCACAATCATGGCAAGC |
| Seq-110 | 23 | 125607008 | 125607107 | 100 | 492 | -------------C-----T-T---C-----------------------------T-- |
| Seq-110 | 23 | | | | | ++++++++++++++++++++++++++ |
| Seq-111 | M | 11001 | 11100 | 100 | 493 | CAACGCCACTTATCCAGCGAACCACTACGAAAAAACTCTACCTCTATACTAATCTCCCTACAAATCTCCTTAATTATTATAACATTCACAGCCACAG |
| Seq-111 | 23 | 125607108 | 125607207 | 100 | 494 | --G------G---------A-----------------------G------------C------------G |
| Seq-112 | M | 11101 | 11200 | 100 | 495 | AACTAATCATATATTTATATCTTCTTCGAAACCACACTTATCCCCACCTTGGCTATCATCACCCGATGAGGCAACCAGCCAGAACGCCTGAACGCAGGCAC |
| Seq-112 | 2 | 131036647 | 131036746 | 100 | 496 | -------T-----------------TC-----T---T---G-T-----------AAT---T-T----A-----T--C-T--A--- |
| Seq-112 | 7 | 57260746 | 57260845 | 100 | 497 | -------T-----------------TC-----T---T---G-T-----------AAT---G------CC----T----A--------C-T--A-T- |
| Seq-113 | M | 11201 | 11300 | 100 | 498 | ATACTTCCTATTCTACACCCCTAGTAGGCTCCCTTCCCCTACTCATCGCACTAATTACACTCACAACACCCCTAGGCTCACTAAACATTCTACTACTCACT |
| Seq-114 | M | 11301 | 11400 | 100 | 499 | CTCACTGCCCAAGAACTATCAACTTCCTGAGCCAACAATTAATATGACTAGCTTACAACATTCTTTATAGTAAAGATACCTCTTTACGGACTCCACT |

TABLE 1-continued

Mitochondrial and Genomic (Nuclear) Paralogs

| Seq. No. | Chr | Start | End | Length | SEQ ID NO: | Sequence |
|---|---|---|---|---|---|---|
| Seq-115 | M | 11401 | 11500 | 100 | 500 | TATGACTCCCTAAAGCCCATGTCGAAGCCCCCATCGCTGGGTCAATAGTACTTGCCGCAGTACTCTTAAACTAGGCGGCTATGGTATAATACGCCTCAC |
| Seq-115 | 2 | 120971832 | 120971931 | 100 | 501 | -G-------------------C--A-------T-AC--C------------A----T----------C-----G-------G------T-G--T--- |
| Seq-115 | 2 | 131036946 | 131037045 | 100 | 502 | ----T-----------------------------A---A----T----A-C--G------A-----------------C-----A---T-A----- |
| Seq-115 | 6 | 153990666 | 153990765 | 100 | 503 | -G----------------C--A---------------T-------T----C----------------TA----------C--A-G--T-G------ |
| Seq-115 | 7 | 57237751 | 57237850 | 100 | 504 | -T---------------------------T--T--T-A--C----------AGA--T-----------------A----C--C---T-G--T--- |
| Seq-115 | 7 | 57261048 | 57261147 | 100 | 505 | ----T---------------AC----------T--T-A--C---------------A----------C----------C-------GG-T----- |
| Seq-115 | 9 | 5108562 | 5108661 | 100 | 506 | -G-----------------A--------------T--C--C----------A-G---------------C--------GC--------G-T---- |
| Seq-115 | 11 | 81264219 | 81264318 | 100 | 507 | --------------------C---------GA-A----------C----G---C-----A-------------A------GCA-----TAG-T-- |
| Seq-115 | 14 | 84639220 | 84639319 | 100 | 508 | ------------------C-----------T-C--A------TT--T-CA-C-------------------G--------T--------T-G-T- |
| Seq-115 | 15 | 58443978 | 58444077 | 100 | 509 | ---------------------C--G----------T-----------C------------------A-AG----------G-------T----- |
| Seq-116 | M | 11501 | 11600 | 100 | 510 | ACTCATTCTCAACCCCTGACAAACATAGCTACCCCTCCTTGTACTATCCCTATGAGGCATAATTATAACAGCTCCATCTGCCTACGACAAACA |
| Seq-116 | 2 | 120971932 | 120972031 | 100 | 511 | C--T--C----G-----A---G-T------------A---------A-----CA-T---------A-GG-----G---------T-T--T------C |
| Seq-116 | 9 | 94873853 | 94873952 | 100 | 512 | C-----------------------A--T-G--T-T--------------------CA--------A----G-----------T-T--T--A---T |
| Seq-116 | 11 | 81264319 | 81264418 | 100 | 513 | C--T--C-------A---G----T----------------T-------T-CA----T--------------G------------T-CT--T-G----G-C |
| Seq-117 | M | 11601 | 11700 | 100 | 514 | GACCTAAAAATGCTCATTGCATACTCTTCAATCAGCCACATAGCCCTCGTAGTAACAGCCCATTCTCCAAACCCCTGAAGCTTCACCGGCGCAGTCA |
| Seq-118 | M | 11701 | 11800 | 100 | 515 | TTTCTCATAATGCCCACGGACTTTCGCCCTCCTAGCAAACTCAAACTACGAACGCACTCACAGTCGCATCATATCCTCTCTCAAGG |
| Seq-119 | M | 11801 | 11900 | 100 | 516 | ACTTCAAACTCTACTCCCACTAATAGAGCTTTTTGATGACTTCTAGCAAGCCTCGCCTTACCCCACTATTAACTACTGGGAGAACTCTCT |
| Seq-119 | 2 | 120972232 | 120972331 | 100 | 517 | C-----TA-G--T----------------C--C--------------------AT--A-------T------------T--C---T--G-A--T------T-- |
| Seq-119 | 2 | 156167597 | 156167696 | 100 | 518 | C----------G-T---------------C-------------------AT--A-C------T----------C------T--C---T---AGA------- |
| Seq-119 | 7 | 57238151 | 57238250 | 100 | 519 | G------A--------------------------AG------AT-TAT--------------C------T------A--------T-- |
| Seq-119 | 7 | 57261448 | 57261547 | 100 | 520 | T------A-----------------------------TA-----A--TA--------------C--C---T---A--------T-- |
| Seq-120 | M | 11901 | 12000 | 100 | 521 | GTGCTAGTAACCACGTTCTCCTGATCAAATATCACTCTTCCTTACGAGACTCAACATACTAGTCACAGCCCTATACTCCCTACATATTTACCACAA |
| Seq-121 | M | 12001 | 12100 | 100 | 522 | CACAATGGGGCTTACTCACCACCACCACCACACATTAAACAACATTAAACCCTCATGTTCATACACCTATCCCCCATTCTCCTCCT |

TABLE 1-continued

Mitochondrial and Genomic (Nuclear) Paralogs

| Seq. No. | Chr | Start | End | Length | SEQ ID NO: | Sequence |
|---|---|---|---|---|---|---|
| Seq-122 | M | 12101 | 12200 | 100 | 523 | ATCCCTCAACCCCGACATCATTACCGGGTTTCCTCTGTAAATATAGTTTAACCAAAACATCAGATTGTGAATCTGACAACAGAGGCTTACGACCCCTT |
| Seq-123 | M | 12201 | 12300 | 100 | 524 | AATTACCGAGAAAGCTCACAAGAACTGCTAACTCATGCCCCCATGTCTAACAACATGGCTTTCTCAACTTTTAAAGGATAACAGCTATCCATTGGTCTTA |
| Seq-123 | 1 | 181391978 | 181392077 | 100 | 525 | G-C--------------TGT-----------------C-----------G-----------------------T-G--TC------G--------------- |
| Seq-123 | 2 | 83042710 | 83042809 | 100 | 526 | --C--TG----------TAIGTG----------T--T--------------------------------------G-G--TC-----AG------------ |
| Seq-123 | 2 | 120972629 | 120972728 | 100 | 527 | --C----A--------TTA-G---G-A-----TG---------------------------------------A--T-G--T-G--T-------------- |
| Seq-123 | 2 | 131037731 | 131037830 | 100 | 528 | -------A--------TGTG-----------------C-G--T-----------G---------------------G--------TG-------C-------- |
| Seq-123 | 2 | 156167996 | 156168095 | 100 | 529 | --C----A--------TATG---------------------A--A----C-----------------------G--T-G--TC-----T-------------- |
| Seq-123 | 7 | 57238545 | 57238644 | 100 | 530 | -------T--------TATG----------T-----------------TG--C-----------G-G--G------------G------------------- |
| Seq-123 | 7 | 57261844 | 57261943 | 100 | 531 | -------T--------TATG-------------------------------------------------G-G--G-----------G---------------C |
| Seq-123 | 9 | 5109356 | 5109455 | 100 | 532 | --C----A--------TATG------------------C------------T-----------------TGG--TC-----G----C-------------- |
| Seq-123 | 11 | 81265012 | 81265111 | 100 | 533 | --C----A--------TTATG--------------C-----------------------------------A--T-G--G--------------------- |
| Seq-123 | 14 | 84640014 | 84640113 | 100 | 534 | -A-G--A--------TATGT-------------------------------------------------T-G--T--------------------------- |
| Seq-123 | 16 | 69392576 | 69392675 | 100 | 535 | --C--TG--------TATCTG--C-----------T-----------------------------CT-G--TC-----C--A-------------------- |
| Seq-123 | 19 | 57433652 | 57433751 | 100 | 536 | --C------------TATG-----------------G--------------A--------------T-G--T--A------A------------------- |
| Seq-124 | M | 12301 | 12400 | 100 | 537 | GGCCCCAAAAATTTGGTGCAACTCCAAATAAAAGTAATAACCATGCACACTACTATAACCCTAACCCTGACTCCCTAATTCCCCCATCCTTACC |
| Seq-1M | M | 12401 | 12500 | 100 | 538 | ACCCTCGTTAACCCTAACAAAAAAACTCATACCCCCATTATGTAAAATCATGTCCGCATCCACCTTTATTATCAGTCTCTTCCCCACAACAATATTCA |
| Seq-126 | M | 12501 | 12600 | 100 | 539 | TGTGCCTAGACCAAGAAGTTATTATCTCGAACTGACACTGAGCGAGCCACACAACCAGCTCTCCCTAAGCTTCAAACTAGACTACTTCTCCATAAT |
| Seq-126 | 14 | 84640221 | 84640320 | 100 | 540 | -A---AC--------C----------A------T---TA-----A------TCT-A-A---A-------C------------------------------- |
| Seq-127 | M | 12601 | 12700 | 100 | 541 | ATTCATCCCTGTAGCATTGTTCGTTACATGGTCCATCATAGAATTCTCACTGTGATATAAACTCAGACCCAAACATTAATCAGTTCTTCAAATATCTA |
| Seq-127 | 2 | 83043109 | 83043208 | 100 | 542 | ---T----------C----A-------C-A-----C--A----T--TG--A---------------------A---------T------CA--T-------T-- |
| Seq-127 | 7 | 57262230 | 57262329 | 100 | 543 | ---T----------A-------C-A--T-C--C--A--T-T-G-----------------AA--G------A---A-T-------C--------------T-- |
| Seq-127 | 11 | 81265410 | 81265509 | 100 | 544 | G-T-----------A-------G-A--T----------C--A--T--TG------------------------------------------------------CT-- |
| Seq-127 | 15 | 58445062 | 58445161 | 100 | 545 | ---T----A-G---C-A--T-------C--A--T--TG-----G----------G-A-A-------------------T----T-C-----------A--T------T-- |
| Seq-128 | M | 12701 | 12800 | 100 | 546 | CTCATTTTCCTAATTACCATACATAATCTTAGTTACCGCTAACAACCTATTCCAACTGTTCATCGGCTGAGAGGGCGTAGGAATTATATCCTTCTGCTCA |

TABLE 1-continued

Mitochondrial and Genomic (Nuclear) Paralogs

| Seq. No. | Chr | Start | End | Length | SEQ ID NO: | Sequence |
|---|---|---|---|---|---|---|
| Seq-128 | 5 | 93903199 | 93903298 | 100 | 547 | -T----------------TC----C-----T--C------C--G-T--C-A--- |
| | | | | | | ++++++++++++++++++++$$$$$$$$$$$$$$$$$$$$++++++++++++++++++++ |
| Seq-129 | M | 12801 | 12900 | 100 | 548 | TCAGTTGATGATACGCCCGAGCAGATGCCAACACAGCAGTCCTATACAACCTATCGGCGATATCGGTTTCATCCTCGCCTTAGCATG |
| Seq-129 | 5 | 93903299 | 93903398 | 100 | 549 | -G------G-T--T---A---------------------------T---C--T--C-----A----C--- |
| Seq-130 | M | 12901 | 13000 | 100 | 550 | ATTTATCCTACACTCCAACTCATGAGACCCAACACAATAGCCCTTCTAAACGCTAATCCAAGCCTCCCCTACTAGGCCTCCTCCTAGCAGCA |
| Seq-130 | 5 | 93903399 | 93903498 | 100 | 551 | ---CC----------A-----CT--C----A--C-TGA-T-TT--------TT----T--- |
| Seq-131 | M | 13001 | 13100 | 100 | 552 | GGCAAATCAGCCCCAATTAGGTCTCCACCCCTGACTCCCCTCAGCCATAGAAGGCCCCACCCCAGTCTCCAGCCCTACTCCAAGCACTATAGTTGTAG |
| Seq-131 | 2 | 83043509 | 83043608 | 100 | 553 | --A--G------T-----C--C-----TA----T-A-CA-------C------A--- |
| Seq-131 | 2 | 120973719 | 120973818 | 100 | 554 | --A--G----TA----CAAC-----A-------------G------G--- |
| Seq-131 | 2 | 131038518 | 131038617 | 100 | 555 | --A--G-----A----C-T--C-----T-----T--C----AG--T-----T-A--C--G--- |
| Seq-131 | 2 | 156168791 | 156168890 | 100 | 556 | --A--G------CA-----T-----T-A-T-TG-T----A--G---T------C--- |
| Seq-131 | 3 | 106618267 | 106618366 | 100 | 557 | --A----------T-----A-------A--TT--G---T-A--- |
| Seq-131 | 5 | 93903499 | 93903598 | 100 | 558 | --A-----------T---CA------T---C-C--- |
| Seq-131 | 7 | 57239333 | 57239432 | 100 | 559 | --A--G------T--------CT-T--C-----T-A---------T--G--G--- |
| Seq-131 | 7 | 57262633 | 57262732 | 100 | 560 | --A--G------T-----T--T--CA-----A------------T--- |
| Seq-131 | 9 | 5110127 | 5110226 | 100 | 561 | --A--G------TA----C--C-----T-A--C-----A-----------G------C--- |
| Seq-131 | 10 | 2277871 | 2277970 | 100 | 562 | A--CTCAA-TAG--G--T----------T-----G-T-----T-----G------C--- |
| Seq-131 | 11 | 81265806 | 81265905 | 100 | 563 | --A--G-----T-G--CA-C---------AG-----G------G--- |
| Seq-131 | 13 | 85096902 | 85097001 | 100 | 564 | A-----------T----------A---TG----C--AG-A--CA-------T-----A---G--- |
| Seq-131 | 14 | 84640720 | 84640819 | 100 | 565 | --A--G------T-----T-A-GC-----T-AA----AC--------C--- |
| Seq-131 | 15 | 46633609 | 46633708 | 100 | 566 | --A--G-----T-----CA-C------A---------------AT--- |
| Seq-131 | 15 | 58445461 | 58445560 | 100 | 567 | --A--G------T--T--CA-TG-------A-------T-------C |
| Seq-132 | M | 13101 | 13200 | 100 | 568 | CAGGAATCTTCTTACTCATCCGTTCACCCCTAGCAGAGAAAATAGCCCACTAATCCAAACTCTAACACTATGCTTAGGCGTATCACCACTCTGTTCGC |
| Seq-132 | 4 | 17063502 | 17063601 | 100 | 569 | -T---G------T--G----C-A------AC------C---C-C--T--C----T--- |

TABLE 1-continued

| Seq. No. | Chr | Start | End | Length | SEQ ID NO: | Sequence | Mitochondrial and Genomic (Nuclear) Paralogs | | | | | | | | | |
|---|---|---|---|---|---|---|---|---|---|---|---|---|---|---|---|---|
| Seq-132 | 5 | 93903599 | 93903698 | 100 | 570 | -T--GG----TC------A----------T-----------A-----C-C------C-------- |
| Seq-133 | M | 13201 | 13300 | 100 | 571 | AGCAGTCTGCGCGCCCTTACACAAAAATGACATCAAAAAATCGTAGCCTTCTCCACTTCAAGTCAACTAGGACTCATAATAGTTACAATCGGCATCAACCAA |
| Seq-133 | 2 | 131038717 | 131038816 | 100 | 572 | ---A---T--TT-A----------T-TG-------AC-----------C----T-G---ACC-----T---T-T-- |
| Seq-133 | 4 | 17063602 | 17063701 | 100 | 573 | ---T--T----------------C-----------T------------G-C-------T---G----T----------G |
| Seq-133 | 5 | 93903699 | 93903798 | 100 | 574 | ---T--T-----------------------------------T------------C---T-----GG-----C-------- |
| Seq-133 | 7 | 57239533 | 57239632 | 100 | 575 | ---A-T--T--A---------TG-----C----------A-----------CC----T-----G-----AG--T-- |
| Seq-133 | 7 | 57262833 | 57262932 | 100 | 576 | ---A-T--T--A---------TT-----C--------------------------C---T-----CT----T-- |
| Seq-133 | 7 | 112012836 | 112012935 | 100 | 577 | --GA----------T--G----T-TT---A-----G------------C---G--C--T------T-- |
| Seq-133 | 9 | 5110327 | 5110426 | 100 | 578 | ---A---------T-A------A---A-----------G------G---C--T-CG--------T-T--G |
| Seq-133 | 13 | 85097102 | 85097201 | 100 | 579 | ---A--A-T--A-------AT------T-G--A-T-T---C-G--T----------T-T-T----- |
| Seq-133 | 13 | 96344942 | 96345041 | 100 | 580 | ---A--T--A----------T-----C--G------AC--------AC-T-C----C--T-A--T-T-- |
| Seq-134 | M | 13301 | 13400 | 100 | 581 | CCACACCTAGCATTCCTGCACATCGTGACCCACGCGCCTTCTCAAAGCCATATATTTATGTGCTCCGGTCCATCATCCACACCTAACAATGAACAAG |
| Seq-134 | 2 | 120974184 | 120974283 | 100 | 582 | -------------------T----------C-T---------T-AA------T------A-T-A--C-----T-----C-TG---------- |
| Seq-134 | 2 | 131038817 | 131038916 | 100 | 583 | -------------------A--------C-----------T------T------A-T--A-------T-----G--C---G-------- |
| Seq-134 | 2 | 202422542 | 202422641 | 100 | 584 | -------T---------T-C-T------A-T-A------TT---T-------T-G-G----A-------T---TG----C--G- |
| Seq-134 | 5 | 93903799 | 93903898 | 100 | 585 | -------T----------A----------T------T-----------A---------T-T--C-------- |
| Seq-134 | 7 | 57239633 | 57239732 | 100 | 586 | ----------------A----------T-C---------A--T--T---------AA-T-A--A--------C---------A-------- |
| Seq-134 | 7 | 57262933 | 57263032 | 100 | 587 | G------T--G--C----------A-T---------T----T-CT------T------AA-T--A--A------C---T------C---G-------- |
| Seq-134 | 9 | 5110427 | 5110526 | 100 | 588 | -------T----------A----------T------T--------------------A---C----------T--C-TG-------- |
| Seq-134 | 11 | 47345580 | 47345679 | 100 | 589 | --T-T-----------------------------T-----------T-----------C--A------A-T-----C----T--------- |
| Seq-134 | 11 | 81266104 | 81266203 | 100 | 590 | -------T----------T--------------TA--------------A-T--A-------T-T--C-TG-------- |
| Seq-134 | 14 | 84641019 | 84641118 | 100 | 591 | -------------TT--T------T--GT--------A-T--A----T-G--C-TG--------C |
| Seq-135 | M | 13401 | 13500 | 100 | 592 | ATATTCGAAAAATAGGAGGACTACTCAAACCATACCTCTCACTTCAACCTCCTGGCACTACTCCCCACCATTGGCAGCCTAGCATTAGCAGGAATACCTTCCTCACAGG |

TABLE 1-continued

Mitochondrial and Genomic (Nuclear) Paralogs

| Seq. No. | Chr | Start | End | Length | SEQ ID NO: | Sequence |
|---|---|---|---|---|---|---|
| Seq-135 | 5 | 93903899 | 93903998 | 100 | 593 | -C------------------------------------------------TT---C------------------G--C-T------G--C----G--- |
| Seq-135 | 15 | 58445848 | 58445947 | 100 | 594 | -C--CT------------------------T------G--TC---TC------------CT------------------CA--C-TA----T--G--- |
| Seq-136 | M | 13501 | 13600 | 100 | 595 | TTTCTACTCCAAAGACCACATCATCGAAACCGAAACATATCATACAAAGCCCTGAGCCCTATCTATTACTCTCATCGCTACCTCCCTGACAAGCGCC |
| Seq-136 | 2 | 120974384 | 120974483 | 100 | 596 | C--T--------------------TT------------------T----------C----------------------T--T---C----TTT-A---GCT-T- |
| Seq-136 | 5 | 93903999 | 93904098 | 100 | 597 | C-------------------------------T-----A------------T------------------------------C--T-----A--------- |
| Seq-136 | 15 | 58445948 | 58446047 | 100 | 598 | C--T--T--T----------------T--T--T--------C------------------T----------------T------A------GCT-T- |
| Seq-137 | M | 13601 | 13700 | 100 | 599 | TATAGCACTGCGAATAATTCTTCTCCACCCTAAGGTCAACCCTTACTACAGATTAACGAAAATAACCCCACCCTACTAAACCCCATTA |
| Seq-137 | 5 | 93904099 | 93904198 | 100 | 600 | A-----------------------------------C---------------C----------A----C--------C-------T------G-------C--- |
| Seq-138 | M | 13701 | 13800 | 100 | 601 | AACGCCCTGGCAGCCGGAAGCCTATTCGCAGAGATTTCTCATTACTAATAACACAATTTCCCCGCATCCCCCCTTCCAAACAACAATCCCCTCTACCTAAAACT |
| Seq-138 | 5 | 93904199 | 93904298 | 100 | 602 | ------AA--AT-------------------------------------------T----A----AT-CC-----A--TC--T--------------- |
| | | | | | | +++++++++++++++++++$+++++++++++++++++++++++ |
| Seq-139 | M | 13801 | 13900 | 100 | 603 | CACAGCCCTCGCTGTCACTTTCCTAGGACTTCTAACGCCTCAACTACCTAACCTAAAATAAATAAAATCCCACTATGCACATTTTAT |
| Seq-139 | 5 | 93904299 | 93904398 | 100 | 604 | ------A-GCA-----C------------G----------------T---------------C--------AA-----G--T------C-C |
| Seq-140 | M | 13901 | 14000 | 100 | 605 | TTCTCCAACATACTCGGATTCTACCCTAGCCTATTCTTACGAGCCAAAACCTGCCCCTACTCCTCCTAGACC |
| | | | | | | $ |
| Seq-141 | M | 14001 | 14100 | 100 | 606 | TRACCTGACTAGAAAAGCTATTACCTAAAAACAATTTCACAGCACCCAAATCTCCACCTCCATCATCACCTCCAAAAAGGCATAATTAAACTTTACTT |
| Seq-141 | 5 | 93904499 | 93904598 | 100 | 607 | ----T---------A--A------------------------------CC-----T---C--G------------T------------C--------- |
| | | | | | | +++++++++++++++++++++++++ $ +++ |
| Seq-142 | M | 14101 | 14200 | 100 | 608 | CCTCTCTTCTTCTTCCCACTCATCCTAACCCTCCTAATCACATAACCTATTCCCCGAGCAATCTCAATTACATATATACACCAACAAACAATGT |
| Seq-142 | 5 | 93904597 | 93904696 | 100 | 609 | TTC----------------C--------------C--------G-A---------------------C---------------------G- |
| | | | | | | +++++++++++++++++++++++++ |
| Seq-143 | M | 14201 | 14300 | 100 | 610 | TCAACCAGTAACCACTACTAATCAATCATCATACAAAGCCCCCGACCAATAGGATCCTCCCGAATCAACCCTGACCCCTCCTTCATAAATT |
| Seq-143 | 2 | 131039713 | 131039812 | 100 | 611 | -----------C----C--------A--T------T--G-------A---------C-C--A--T-A-----G-------A--C--A---- |
| Seq-143 | 5 | 93904697 | 93904796 | 100 | 612 | ----------T--C--C---------T-----G--T-------------------------------TG--G-----C--------- |
| Seq-143 | 9 | 80580108 | 80580207 | 100 | 613 | ----------T--C--C--------A-------------------------T-------A-----T------A--C---A---CC |
| Seq-143 | 23 | 5087007 | 5087106 | 100 | 614 | ----------T--C-------G---AT----------A--------T---------A-----------A--A---A---C |

TABLE 1-continued

Mitochondrial and Genomic (Nuclear) Paralogs

| Seq. No. | Chr | Start | End | Length | SEQ ID NO: | Sequence |
|---|---|---|---|---|---|---|
| Seq-144 | M | 14301 | 14400 | 100 | 615 | ATTCAGCTTCCTACACTATTAAAGTTTACCACAACCACCCCATCATACTCTTTCACCCACAGACCAATCCTACCTCCATCGCTAACCCCACTAAAA |
| Seq-144 | 5 | 93904797 | 93904896 | 100 | 616 | -----A-----A--C--------------------T-T---T-A--T-C--C--T--T--- |
| Seq-145 | M | 14401 | 14500 | 100 | 617 | CACTCACCAAGACCCTCAACCCCTGACCCCATGCCTCAGGATACTCCTCAATAGCCCTGCTGTAGTATATCCAAAGACAACCATCATTCCCCTAAATA |
| Seq-145 | 5 | 93904897 | 93904996 | 100 | 618 | ---T--T-----------------T----------------T--T-----G--C---A-----T-A--- |
| Seq-145 | 7 | 57264010 | 57264109 | 100 | 619 | A-G-TC-T--A-----TA-T--T--T-----------A-C-C------A-------C----C---- |
| Seq-145 | 7 | 153665815 | 153665914 | 100 | 620 | ---C-T--A-T----TG------T-----A-----C-TG--T--T----------A------T---G-GC--C--- |
| Seq-145 | 17 | 22018556 | 22018655 | 100 | 621 | -------TT-------T--------T-CA---------------A---------G--- |
| Seq-146 | M | 14501 | 14600 | 100 | 622 | AATTAAAAAAACTATTAAACCTATATAACCTCCCCCCAAAATTCAGAATAATAACACACCCGCTAACATCAGTACTAAACCCCCATAAATA |
| Seq-146 | 5 | 93904998 | 93905097 | 100 | 623 | -T--------C-------T---T--T-A-----G-T-------A-------AC-----G----- |
| Seq-146 | 17 | 22018657 | 22018756 | 100 | 624 | -T-A--------C--------T----------A-T----A---T--- |
| Seq-147 | M | 14601 | 14700 | 100 | 625 | GGAGAAGGCTTAGAGAAACCCCACAAACCCATTACTAAACCACACTCAACAGAAACAAAGCATACATCATTATTCTCGACGGACTACAACCACGA |
| Seq-147 | 5 | 93905098 | 93905197 | 100 | 626 | -------------T----------A-----T----A--T------TG--- |
| Seq-147 | 17 | 22018757 | 22018856 | 100 | 627 | ---------------T----G------T----------TG-G---A--C-A--T--- |
| Seq-148 | M | 14701 | 14800 | 100 | 628 | CCAATGATATGAAAACCATCGTTGTATTCAACTACAAGAACACCATGACCCCATAATAACGCAAAATTAACCCCTAATAAAATTATTAACCACTCATT |
| Seq-148 | 2 | 131040206 | 131040305 | 100 | 629 | -T------T-CA---------T--------AT--------T---CA-T--A-----A-C----TT-T--C |
| Seq-148 | 5 | 93905198 | 93905297 | 100 | 630 | ---------------T------C--CC---T-GT |
| Seq-148 | 15 | 58447112 | 58447211 | 100 | 631 | -T-------G--------A---------T-----AA----T--C--CGC---TG-----A-T----GT--T--- |
| Seq-148 | 17 | 22018857 | 22018956 | 100 | 632 | -G-------A-T---------G------T------C-T--T--C--T-A--G-----A----C------C |
| Seq-149 | M | 14801 | 14900 | 100 | 633 | CATCGAACTTCCCCACCCCATCCCGCATGATGAAACTTCGGCTCACTCCTTGGCGCCTGCCTGATGAAACTTCCAAATCACCAGGACTATTCCTA |
| Seq-149 | 5 | 93905298 | 93905397 | 100 | 634 | T-T--T--T--------A-------C---------T-----T----------A-C-A-T---G-T--- |
| Seq-149 | 13 | 96346876 | 96346975 | 100 | 635 | T-T--T----A-------TA--------T------T--T-A-T----G-C-T------T---T--G |
| Seq-149 | 17 | 22018957 | 22019056 | 100 | 636 | T------T-----G--------AT-------G---A--TG-T------T-A-C--T----T-TT-------- |
| Seq-149 | 23 | 5087606 | 5087705 | 100 | 637 | -------T--T----TAT-----------C--T------A-------T-AT----T----G-------- |

TABLE 1-continued

Mitochondrial and Genomic (Nuclear) Paralogs

| Seq. No. | Chr | Start | End | Length | SEQ ID NO: | Sequence |
|---|---|---|---|---|---|---|
| Seq-150 | M | 14901 | 15000 | 100 | 638 | GCCATACACTACTCACCAGAGCGCCTCAACGCCCTTTCATCAATCGCCCACATCACTCGAGACGTAAATTATGGCTGAATCATCCGCTACCTTCACGCCA |
| Seq-150 | 5 | 93905398 | 93905497 | 100 | 639 | ---------------------A-----------T--T-------------------------------CC------------------C-------T- |
| Seq-150 | 17 | 22019057 | 22019156 | 100 | 640 | --T---------Q-------------------C--C--G---T-------C-------T--------------------------------C----T- |
| Seq-150 | 23 | 5087706 | 5087805 | 100 | 641 | -----------------A-------A--A--T-------C--T-----G-----T-A-------T-G-C----------T-------A--T--C--A-T- |
| Seq-151 | M | 15001 | 15100 | 100 | 642 | ATGGCGCCTCAATATTCTTTATCTGCCTCTTCCTACACATCGGGCGAGGCCTATATTACGGATCATTTCTACTCAGAAACCTGAAACATCGGCATTAT |
| Seq-151 | 2 | 156170798 | 156170897 | 100 | 643 | -------T--C----------------TG-T--C-----T-----C--------A-A-T-CT------------------T--T-ATT--T- |
| Seq-151 | 5 | 8619543 | 8619642 | 100 | 644 | ------T--C---------------------T--CT------C--T---------ACA-TTCT-------------T------ |
| Seq-151 | 5 | 93905498 | 93905597 | 100 | 645 | -C--T--------------------C----------C----------C--T--C--------CT--------------T--T- |
| Seq-151 | 7 | 57241291 | 57241390 | 100 | 646 | ----C--T----C--------T---------T----G----CG---------T-G---CG-AC-T-T------A----CT---- |
| Seq-151 | 7 | 112014629 | 112014728 | 100 | 647 | ------T--T----------------T--C-A--GT------C----G------A-A-T-C----------T--T-- |
| Seq-151 | 17 | 22019157 | 22019256 | 100 | 648 | ---------T--C---------------T--C-------G--C-T---CT------T-----C- |
| Seq-151 | 23 | 5087806 | 5087905 | 100 | 649 | ---A---T--------T--TA-C------T--C-----T--C--CA-A---T-----T-A------ |
| Seq-151 | 23 | 125863340 | 125863439 | 100 | 650 | -----T---------------T--C-A----------T-----C--T--G----C--A-TTCT----T--T- |
| Seq-152 | M | 15101 | 15200 | 100 | 651 | CCTCCTGCTTGCAACTATAGCAACAGCCTTCATAGGCTATGTCCTCCCGTGAGGCCAAATATCATTCTGAGGGGCCACAGTAATTACAAACTTACTATCC |
| Seq-152 | 2 | 83045608 | 83045707 | 100 | 652 | ----T-A--CA------G------A-----CC-G---A---------T-------------TC------G |
| Seq-152 | 2 | 131040606 | 131040705 | 100 | 653 | T--T------A----C-C------G--T--A-----------CC----------C--A---A |
| Seq-152 | 5 | 8619643 | 8619742 | 100 | 654 | ----A--CA------G------A---G---------C--G-----T--------G-------TC------A |
| Seq-152 | 5 | 93905598 | 93905697 | 100 | 655 | ----T-AT-CA------C------A-----------TC----A-----G---------G--TC--T-G--- |
| Seq-152 | 7 | 57241391 | 57241490 | 100 | 656 | ----A--CAT--C-C------A-T------------CA-T----C-----------C-------A |
| Seq-152 | 7 | 57264700 | 57264799 | 100 | 657 | G---A--CA--C-C------A-T------------CA-T--C--CC---------C-------A |
| Seq-152 | 7 | 112014729 | 112014828 | 100 | 658 | T----AT-CA------A-A---A------------G---------CA-T----------T-------A |
| Seq-152 | 8 | 18707079 | 18707178 | 100 | 659 | ----A--CA------G------A----------------C--------G---------T-----TC-------A |
| Seq-152 | 11 | 81267892 | 81267991 | 100 | 660 | ----C--CA------C------A-----------G---------T--T------T--C--TCC--A |
| Seq-152 | 14 | 84643115 | 84643214 | 100 | 661 | -TA-------CA---------A--A---C--A--A-CA-G-----A-----G------------TC--------A |

TABLE 1-continued

Mitochondrial and Genomic (Nuclear) Paralogs

| Seq. No. | Chr | Start | End | Length | SEQ ID NO: | Sequence |
|---|---|---|---|---|---|---|
| Seq-152 | 23 | 5087906 | 5088005 | 100 | 662 | TG------CA------A-T------C-T------A |
| Seq-152 | 23 | 125863441 | 125863540 | 100 | 663 | -TC-TACT-AA------A------C-G------T-T------TA |
| Seq-153 | M | 15201 | 15300 | 100 | 664 | GCCATCCCATACATTGGGACAGACCTAGTTCAATGAATCTGAGGAGGCTACTCAGTAGACAGTCCCACCCTCACACGATTCTTTACCTTTCACTTCATCT |
| Seq-153 | 5 | 93905698 | 93905797 | 100 | 665 | -----T------C--A------C------T------A--A------C-----TC |
| Seq-153 | 7 | 57264800 | 57264899 | 100 | 666 | -----T------T--A-T------G-----T--A-TTC----T--T------AAG------T------CG------C |
| Seq-153 | 7 | 112014829 | 112014928 | 100 | 667 | -----T------T--A-T------G--A-T------T--T------AAG------T--G------C-T |
| Seq-153 | 15 | 58447613 | 58447712 | 100 | 668 | -----T-G--T------A-T--G------T--A-TT------AAG------T------G------C-T |
| Seq-154 | M | 15301 | 15400 | 100 | 669 | TACCCTTCATTATTGCAGCCCTAGCAGCACTCCACCCTCCTATTCTTCACGAAACGGATCAAACAACCCCTAGGAATCACCTCCCATTCGATAAAAT |
| Seq-154 | 5 | 93905798 | 93905897 | 100 | 670 | -G------A----T-A--A-C--A------T------C--A------TA------T--T----C------C |
| Seq-155 | M | 15401 | 15500 | 100 | 671 | CACCCTTCCACCCTTACTACACAATCAAAGAGCCCCTCGGCTTACTTCCTCCTTAATGACATTAACACTATTCTCACCAGACCTCCTAGGC |
| Seq-155 | 5 | 93905898 | 93905997 | 100 | 672 | T------AT--A--C-T-C--T------C--A--C--T-A---C--GT------G-- |
| Seq-156 | M | 15501 | 15600 | 100 | 673 | GACCCAGACAATATACCTAGCACAACCCTAGCCAACCCCCTCCCCACATCAGCCCGAATGATATTTCGTATTCGCCTACACAATTCTCCGATCCGTCC |
| Seq-156 | 5 | 93905998 | 93906097 | 100 | 674 | ---C--C----GA-T------C------A------G------A-T- |
| Seq-157 | 6 | 133471815 | 133471914 | 100 | 675 | ---------------------C------------------C-------A------T-A------T-C-T------G----C-A-G--A-T- |
| Seq-157 | M | 15601 | 15700 | 100 | 676 | CTAACAAACTAGGAGGCGTCCTTGCCCTATTACTATCCATCCTAGCAATATCCCATCCTCCATATATCCAAACAACAAAGCATAATATTTCG |
| Seq-157 | 5 | 93906098 | 93906197 | 100 | 677 | ---C--T------A-T-A------TC------GC--T--T-A------C------A |
| Seq-157 | 17 | 22019755 | 22019854 | 100 | 678 | -C------A--G----CC------A------GC------CA--T--C-G------CT- |
| Seq-158 | M | 15701 | 15800 | 100 | 679 | CCCACTAAGCCAATCACTTATTGACTCCTAGCCGCAGACCTCCTCATTCTAACCTGAATCGGAGGACAACCAGTAGCTACCCTTTTACCATCATTGGA |
| Seq-158 | 5 | 93906198 | 93906297 | 100 | 680 | -----T------TC--A------T------A------T--T-CC------T------G-A------C--T-C--C |
| Seq-159 | M | 15801 | 15900 | 100 | 681 | CAAGTAGCATCCGTACTATACTTCACACAATCCTAATACCAACTATCTCCAATTGAAAACAAAATACTCAAATGGGCCTGTCCTTGTAGTA |
| Seq-159 | 5 | 93906298 | 93906397 | 100 | 682 | ---G------TT------G-C-C----TC--C---T------A---C----C |
| Seq-160 | M | 15901 | 16000 | 100 | 683 | TAAACTAATACACCAGTCTTGTAAACCGGAGACGAAATCAGAGAAAAAGTCTTTAACTCCACCATTAGCACCCAAAGCTAA |

TABLE 1-continued

Mitochondrial and Genomic (Nuclear) Paralogs

| Seq. No. | Chr | Start | End | Length | SEQ ID NO: | Sequence |
|---|---|---|---|---|---|---|
| Seq-160 | 5 | 93906398 | 93906497 | 100 | 684 | ------C-------G----------T---A-T---G-T-CC------------AC--G---T------C------- |
| Seq-160 | 17 | 22020055 | 22020154 | 100 | 685 | ------C---T-TTG---------A-A-T-G-G--TC-C-C--------C-------------AC--G---T------C------- |
| Seq-161 | M | 16001 | 16100 | 100 | 686 | GATTCTAATTAAACTATTCTCTGTTCTTTCATGGGAAGCAGATTTGGGTACCACCCAAGTATTGACTCACCCATCAACACCGCTATGTATTTCGTAC |
| Seq-162 | M | 16101 | 16200 | 100 | 687 | ATTACTGCCAGCCACCATGAATATTGTACGGTACCATAAATACTTGACCACCTGTAGTACATAAAAACCCACCCATCAAACCCCCCCCCCATGCT |
| Seq-163 | M | 16201 | 16300 | 100 | 688 | TACAAGCAAGTACAGCAATCAACCTTCAACTATCACACATCAACTGCAACTCCAAAGCCACCCTCCACACTAGGATACAACAAAACTACCACCCTT |
| Seq-164 | M | 16301 | 16400 | 100 | 689 | AACAGTACATAGTACATAAAGTCATTTACCGTACATAGCACATTACAGTACACATCAAATCCCTTCCTCCGTCCCCATGATGACCCCCCTCAGATAGGGGTCCCTTG |
| Seq-165 | M | 16401 | 16500 | 100 | 690 | ACCACCATCCTCCGTGAAATCAATATCCCGACAAGAGTGCTACTCTCCGCTCCGGGCCCATAACACTTGGGGTAGCTAAAGTGAACTGTATCCGAC |
| Seq-165 | 17 | 22020556 | 22020655 | 100 | 691 | TT----------T---------T--G---------T-----T-T-A---A--T-------T-A--------G- |

Example 2—Amplification and Primer Extension

An exemplary protocol used in Examples 3 and 4 is provided.

PCR Amplification

PCR was performed in a 5 µL volume reaction using Agena Bioscience's iPLEX Pro PCR kit, consisting of 2 µL DNA template, 0.5 µL 10×PCR Buffer, 0.4 µL 25 mM MgCl2, 0.1 µL dNTP/dUTP mix, 0.125 µL Uracyl-N-Glycosylase (New England Biolabs®, Ipswich, Mass., USA), 0.2 µL DNA polymerase. For a strategy using the same PCR primer for both mitochondrial and nuclear DNA a concentration of 100 nM was used. For a strategy of template specific primer combinations a set of different combinations was used (Table A). Finally for the hybrid strategy of one universal PCR forward primer and a template specific pair of reverse primers, 100 nM of the universal primer was used and the combinations in Table A was used for the reverse primers. Alternatively, a hybrid strategy can use one universal PCR reverse primer and a template specific pair of forward primers with 100 nM of the universal primer and the combinations in Table A was used for the forward primers. Thermal cycling consisted of an initial incubation at 30° C. for 10 minutes followed by denaturation at 94° C. for 2 minutes; 30 cycles of 94° C. for 30 seconds, 60° C. for 30 seconds, and 72° C. for 1 minute; followed by a final extension of 5 minutes at 72° C. Following PCR, the reactions were treated with a 2 µL SAP mastermix consisting of 0.5 U shrimp alkaline phosphatase (SAP) and 0.17 µL 10×SAP Buffer. Samples were incubated for 20 minutes at 37° C., followed by SAP enzyme denaturation for 10 minutes at 85° C. Thermal cycling and incubation were performed in a GeneAmp® PCR System 9700 (Thermo Fisher). All reagents used were obtained from Agena Bioscience unless otherwise stated.

Single Base Extension

Single base extension was performed by adding 2 µL of a master mix consisting of 0.2× iPLex Buffer, 0.2× Termination Mix, 5-15 µM extension primer mix, and 0.00615 U iPLEX® Pro enzyme. Reaction parameters consisted of an initial incubation at 94° C. for 30 seconds followed by 20 cycles at 94° C. for 5 seconds with five nested cycles of 52° C. for 5 seconds followed by 80° C. for 5 seconds. A final extension was performed at 72° C. for 3 minutes. Thermal cycling was performed in a GeneAmp PCR System 9700.

Maldi-TOF Analysis

After 41 ul of water addition and desalting by the addition of 15 mg Clean Resin, 15 nL of each extend mixture was transferred to a SpectroCHIP® II-G384 and Mass spectra were recorded using a MassARRAY System. Spectra were acquired using SpectroAcquire software (Agena Bioscience, San Diego). The software parameters were set to acquire 20 shots from each of 5 raster positions. The resulting mass spectra were summed and peak detection and intensity analysis performed using Typer 4 software (Agena Bioscience, San Diego).

Example 3—Amplification Using Species Specific Amplification Primers and iPLEX

Table 2: ADF1 Assay design using strategy of species specific PCR primers but same extension primer, please note that each PCR primer has a 10 bp tag to move them out of the MassARRAY window 3500-9000 m/z Table 3: The alignment showing each primer pair alignment and the sequence of the amplicons (-g=nuclear specific primers, -mt=mitochondrial specific primers)

TABLE A

| PCR primer combination sets | | | | | | | | | | |
|---|---|---|---|---|---|---|---|---|---|---|
| | Pool 1 | Pool 2 | Pool 3 | Pool 4 | Pool 5 | Pool 6 | Pool 7 | Pool 8 | Pool 9 | Pool 10 |
| gDNA primers | 100 nM | 100 nM | 100 nM | 100 nM | 100 nM | 100 nM | 100 nM | 100 nM | 100 nM | |
| mDNA primers | | 100 nM | 75 nM | 50 nM | 35 nM | 25 nM | 12.5 nM | 6.25 nM | 3.125 nM | 100 nM | gDNA = nucleic DNA specific PCR primers,
mDNA = mitochondrial specific PCR primers

TABLE 2

Assay Design ADF1 Different PCR same UEP

| WELL | SNP_ID | SEQ ID NO: | 2nd-PCRP | SEQ ID NO: | 1st-PCRP | UEP_DIR | UEP_MASS | UEP_SEQ | SEQ ID NO: | EXT1_CALL | EXT1_MASS |
|---|---|---|---|---|---|---|---|---|---|---|---|
| W1 | MitoQ-001 | 692 | acgttggatgGGTCTATTACCCTAT TAATCAG | 693 | acgttggatgTCTGGGCCAGCGTTTCA | R | 5439.6 | GCGTGCATACCCCCCAGA | 694 | G | 5686.8 |
| W1 | | 695 | acgttggatgAGGTCTATCACCCTA TTAACCAC | 696 | acgttggatgTCCGGCTCCAGCGTCTCG | | | | | | |
| W1 | MitoQ-024 | 697 | acgttggatgGCCTACATCAGACCA AAATACTTC | 698 | acgttggatgAACAGTGTGGGTAAATAAT GGTTTCA | F | 7891.2 | ACTGACAATTAACAGCCCAATATCTA | 699 | C | 8138.4 |
| W1 | | 700 | acgttggatgCTGCGTCAGATCAAA ACACTGA | 701 | acgttggatgGACAGTGAGGGTAAATAAT GACTTGT | | | | | | |
| W1 | MitoQ-050 | 702 | acgttggatgTCATATATACCAAATTT CTCCCTCAT | 703 | acgttggatgGAGTATGCTAAGATTTTGC GTAGT | F | 5032.3 | AGCCTTCTCCTCACTCT | 704 | C | 5279.5 |
| W1 | | 705 | acgttggatgTCATATACCAAATCT CTCCCTCAC | 706 | acgttggatgGAGTATGCTAAGATTTTGC GTAGC | | | | | | |
| W1 | MitoQ-065 | 707 | acgttggatgCCTATCTCTCCCAGT CCTAGCC | 708 | acgttggatgAATGGGGTCTCCTCCTCC GGCT | F | 6960.6 | ATCACTATACTACTAACAGACCG | 709 | C | 7207.7 |
| W1 | | 710 | acgttggatgCCTATCTCTCCCAGT CCTAGCT | 711 | acgttggatgAATGGGGTCTCCTCCTCCG GCG | | | | | | |
| W1 | MitoQ-073 | 712 | acgttggatgCTCCCTAAAAGCAGT AGTGC | 713 | acgttggatgCTACAGCCACTCTAGGTTAG | R | 6377.2 | TACTATTAGGACTTTTCGCTT | 714 | G | 6624.3 |
| W1 | | 715 | acgttggatgCATTCATTTCTCTAAC AGCAGTAATAT | 716 | acgttggatgCATCCATATAGTCACTCCA GGTTTA | | | | | | |
| W1 | MitoQ-094 | 717 | acgttggatgGATTTCACTTCCACT CCACAACC | 718 | acgttggatgTCCCGTATCGAAGGCCTTTC | R | 5804.8 | ggCTGTTACATCGCGCCA | 719 | G | 6052 |
| W1 | | 720 | acgttggatgGATTTCACTTCCACT CCATAACG | 721 | acgttggatgTCCCGTATCGAAGGCCTTTT | | | | | | |
| W1 | MitoQ-110 | 722 | acgttggatgTAGCTGCTCCCTATC CTTC | 723 | acgttggatgTTCGTTGGATAGGTGGCGC | F | 7504.9 | caCTCCTAATACTAACTACCTGACT | 724 | C | 7752.1 |
| W1 | | 725 | acgttggatgTAGCTGTTCCCCAAC CTTT | 726 | acgttggatgTTCGCTGGATAAGTGCGT | | | | | | |
| W1 | MitoQ-129 | 727 | acgttggatgCGGTTGATGGTATG AGGGCT | 728 | acgttggatgTGTAGGAGGAATCATGCT | F | 7330.8 | ggAAGCATTCCTATACAACCGTAT | 729 | C | 7578 |
| W1 | | 730 | acgttggatgCAGTTGATGATACGC CCGAG | 731 | acgttggatgTGTAGGATAAATCATGCTA AGGCG | | | | | | |
| W1 | MitoQ-139 | 732 | acgttggatgCACAGCCCTAGGCAT CACC | 733 | acgttggatgGTGAAATGTCACAGTGG GTT | F | 5990.9 | CAGCCCTAGACCTCAACTAC | 734 | C | 6238.1 |
| W1 | | 735 | acgttggatgCACAGCCCTCGCTGT CACT | 736 | acgttggatgATAAAATGTGCATAGTGG GGA | | | | | | |

TABLE 2-continued

| WELL | SNP_ID | Assay Design | | | ADF1 | Different PCR | same UEP | | |
|---|---|---|---|---|---|---|---|---|---|
| W1 | MitoQ-156 | acgttggatgcCCAGACAACTACAC CCTGACT | 737 | acgttggatgGCCTCCTAGTTTATTGGGA AT | 738 | R | 6518.3 | GAATAGGAAATATCATTCGGG | 739 |
| W1 | | acgttggatgcCCAGACAATTATAC CCTAGCC | 740 | acgttggatgGCCTCCTAGTTTGTTAGGG AC | 741 | | | | |

| WELL | SNP_ID | EXT1_SEQ | SEQ ID NO: | EXT2_CALL | EXT2_MASS | EXT2_SEQ | SEQ ID NO: | EXT3_CALL | EXT3_MASS | EXT3_SEQ | EXT4_CALL | EXT4_MASS | EXT4_SEQ |
|---|---|---|---|---|---|---|---|---|---|---|---|---|---|
| W1 | MitoQ-001 | GCGTGCAIACCCCCCAGAC | 742 | A | 5766.7 | GCGTGCAIACCCCCCAGAT | 743 | | | | | | |
| W1 | MitoQ-024 | ACTGACAATTAACAGCCCAATATCTAC | 744 | T | 8218.3 | ACTGACAATTAACAGCCCAATAT CTAT | 745 | | | | | | |
| W1 | MitoQ-050 | AGCCTTCTCCTCACTCTC | 746 | T | 5359.4 | AGCCTTCTCCTCACTCTT | 747 | | | | | | |
| W1 | MitoQ-065 | ATCACTATATACTAACAGACCGC | 748 | T | 7287.7 | ATCACTATATACTACTAACAGACCGT | 749 | | | | | | |
| W1 | MitoQ-073 | TACTATTAGGACTTTTCGCTTC | 750 | A | 6704.3 | TACTATTAGGACTTTTCGCTTT | 751 | | | | | | |
| W1 | MitoQ-094 | ggCGTGTTACATCGGCCAC | 752 | A | 6131.9 | ggCGTGTTACATCGCGCCAT | 753 | | | | | | |
| W1 | MitoQ-110 | caCTCCTAATACTAACTACCTGACTC | 754 | T | 7832 | caCTCCTAATACTAACTACCTGAC TT | 755 | | | | | | |
| W1 | MitoQ-129 | ggAAGCAITCCTATACAACCGTATC | 756 | T | 7657.9 | ggAAGCAITCCTATACAACCGTAT CT | 757 | | | | | | |
| W1 | MitoQ-139 | CAGCCCTAGACCTCAACTACC | 758 | T | 6318 | CAGCCCTAGACCTCAACTACT | 759 | | | | | | |
| W1 | MitoQ-156 | GAATAGGAAATATCATTCGGGC | 760 | A | 6845.4 | GAATAGGAAATATCATTCGGGT | 761 | | | | | | |

TABLE 3

| Assay | Chr | Start | End | Length | Amplicon |
|---|---|---|---|---|---|
| MitoQ-001-g | chr17 | 22020734 | 22020834 | 101 | GGTCTATTACCCTATTAATCAGTCACGGGAGCTCTCCATGCATTTGGTATTTTAATCTGGGGGGTGTGCACGCGATAGCATTGTGAAACGCTGGCCCCAGA |
| MitoQ-001-mt | chrM | 7 | 108 | 102 | AGGTCTATCACCCTATTAACCACTCACGGGAGCTCTCCATGCATTTGGTATTTTCGTCTGGGGGGTGTGCACGCGATAGCATTGCGAGACGCTGGAGCCGGA |
| MitoQ-024-g | chr17 | 22023093 | 22023178 | 86 | GCCTACATCAGACCAAAATACTTCACTGACAATTAACAGCCCAATATCTATAAATAATCAATGAAACCATTATTACCCACACTGTT |
| MitoQ-024-mt | chrM | 2343 | 2425 | 83 | CTGCGTCAGATCAAAACACTGAACTGACAATTAACAGCCCAATATCTACAATCAACCAACAAGTCATTATTACCCTCACTGTC |
| MitoQ-050-g | chr1 | 565441 | 565564 | 124 | TCATATACCAAATTTCTCCCTCATTAAACGTAAGCCTTCTCCTCACTCTTTCAATCTTATCCATCATGGCAGGCAGTTGAGGTGGATTAAACCAAACCCAACTACGCAAAATCTTAGCATACTC |
| MitoQ-050-mt | chrM | 4892 | 5015 | 124 | TCATATACCAAATCTCTCCCTCACTAAACGTAAGCCTTCTCCTCACTCTCTCAATCTTATCCATCATAGCAGGCAGTTGAGGTGGATTAAACCAAACCCAGCTACGCAAAATCTTAGCATACTC |
| MitoQ-065-g | chr1 | 567041 | 567141 | 101 | CCTATCTCTCCCAGTCCTAGCCGCTGGCATCACTATACTACTAACAGACCGTAACCTCAACACCACCTTCTTCGACCCAGCCGGAGGAGGAGACCCCATTC |
| MitoQ-065-mt | chrM | 6492 | 6591 | 100 | CCTATCTCTCCCAGTCCTAGCTGCTGGCATCACTATACTACTAACAGACCGCAACCTCAACACCACCTTCTTCGACCCCGCCGGAGGAGGAGACCCCATT |
| MitoQ-073-g | chr17 | 22028016 | 22028124 | 109 | CTCCCTAAAAGCAGTAGTGCTAATAATTTTCATAACCTGAGAGACCTTCGCTTCAAAGCGAAAAGTCCTAATAAATGAGCAACCTTCCACTAACCTAGAGTGGCTGTAG |
| MitoQ-073-mt | chr1 | 567827 | 567947 | 121 | CATTCATTTCTCTAACAGCAGTAATATTAATAATTTTCATAATTTGAGAAGCCTTCGCTTCGAAGCGAAAAGTCCTAATAGTAGAAGAACCCTCCATAAACCTGGAGTGACTATATGGATG |
| MitoQ-073-mt | chrM | 7277 | 7397 | 121 | CATTCATTTCTCTAACAGCAGTAATATTAATAATTTTCATGATTTGAGAAGCCTTCGCTTCGAAGCGAAAAGTCCTAATAGTAGAAGAACCCTCCATAAACCTGGAGTGACTATATGGATG |
| MitoQ-094-g | chr1 | 569856 | 570002 | 147 | GATTTCACTTCCACTCCACAACCCTCCTCATACTAGGCCTACTAACCAACACACTAACCATATACCAATGATGGCGCGATGTAACACGAGAAAGCACATACCAAGGCCACCACACACCACCTGTCCAGAAAGGCCTTCGATACGGGA |
| MitoQ-094-mt | chrM | 9308 | 9454 | 147 | GATTTCACTTCCACTCCATAACGCTCCTCATACTAGGCCTACTAACCAACACACTAACCATATACCAATGGTGGCGCGATGTAACACGAGAAAGCACATACCAAGGCCACCACACACCACCTGTCCAAAAAGGCCTTCGATACGGGA |
| MitoQ-110-g | chrX | 125607017 | 125607128 | 112 | TAGCTGCTCCCTATCCTTCTCCTCCGACCCCCTAACGACCCCCCTCCTAATACTAACTACCTGACTTCTACCCCTCACAATCATGGCAAGCCAGCGCCACCTATCCAACGAA |
| MitoQ-110-mt | chrM | 10910 | 11021 | 112 | TAGCTGTTCCCCAACCTTTTCCTCCGACCCCCTAACAACCCCCCTCCTAATACTAACTACCTGACTCCTACCCCTCACAATCATGGCAAGCCAACGCCACTTATCCAGCGAA |
| MitoQ-129-g | chr5 | 93903300 | 93903410 | 111 | CGGTTGATGGTATGCTCGAACAGATGCCAACACAGCAGCCATCCCAGCAATCCTATACAACCGTATTGGCGACATTGGCTTCATCCTAGCCCTAGCATGATTCCTCCTACA |
| MitoQ-129-mt | chrM | 12802 | 12912 | 111 | CAGTTGATGATACGCCCGAGCAGATGCCAACACAGCAGCCATTCAAGCAGTCCTATACAACCGTATCGGCGATATCGGTTTCATCCTCGCCTTAGCATGATTTATCCTACA |
| MitoQ-139-g | chr5 | 93904299 | 93904398 | 100 | CACAGCCCTAGGCATCACCTTCCTAGGACTTCTGACAGCCCTAGACCTCAACTACTTAACCAACAAACTCAAAATAAAAAACCCACTGTGTACATTTCAC |

TABLE 3-continued

Alignment Using ADF1

| | | | | | |
|---|---|---|---|---|---|
| MitoQ-139-mt | chrM | 13801 | 13900 | 100 | CACAGCCCTCGCTGTCACTTTCCTAGGACTTCTAACAGCCCTAGACCTCAACTACCTAACCAACAAACTTAAAATAAAATCCCCACTATGCACATTTTAT |
| MitoQ-156-g | chr5 | 93906000 | 93906114 | 115 | CCCAGACAACTACACCCTGACTAACCCCCTAAACACCCCACCCCACATCAAACCCGAATGATATTTCCTATTCGCCTACGCAATTCTCCGATCCATTCCCAATAAACTAGGAGGC |
| MitoQ-156-mt | chrM | 15503 | 15617 | 115 | CCCAGACAATTATACCCTAGCCAACCCCTTAAACACCCCTCCCCACATCAAGCCCGAATGATATTTCCTATTCGCCTACACAATTCTCCGATCCGTCCCTAACAAACTAGGAGGC |

| Assay | Chr | SEQ ID NO:UEP | | SEQ ID NO:Direction | | Nucleotide | WTExtension |
|---|---|---|---|---|---|---|---|
| MitoQ-001-g | chr17 | 762 | TCTGGGGGGTNTGCACGC | 763 | Reverse | 22020789 | A |
| MitoQ-001-mt | chrM | 764 | TCTGGGGGGTNTGCACGC | 765 | Reverse | 63 | G |
| MitoQ-024-g | chr17 | 766 | ACTGACAATTAACAGCCCAATATCTA | 767 | Forward | 22023144 | T |
| MitoQ-024-mt | chrM | 768 | ACTGACAATTAACAGCCCAATATCTA | 769 | Forward | 2392 | C |
| MitoQ-050-g | chr1 | 770 | AGCCTTCTCCTCACTCT | 771 | Forward | 565491 | T |
| MitoQ-050-mt | chrM | 772 | AGCCTTCTCCTCACTCT | 773 | Forward | 4942 | C |
| MitoQ-065-g | chr1 | 774 | ATCACTATACTACTAACAGACCG | 775 | Forward | 567093 | T |
| MitoQ-065-mt | chrM | 776 | ATCACTATACTACTAACAGACCG | 777 | Forward | 6544 | C |
| MitoQ-073-g | chr17 | 778 | AAGCGAAAAGTCCTAATAGTA | 779 | Reverse | 22028071 | A |
| MitoQ-073-mt | chr1 | 780 | AAGCGAAAAGTCCTAATAGTA | 781 | Reverse | 567889 | G |
| MitoQ-073-mt | chrM | 782 | AAGCGAAAAGTCCTAATAGTA | 783 | Reverse | 7339 | G |
| MitoQ-094-g | chr1 | 784 | TGGCGCGATGTAACACG | 785 | Reverse | 569927 | A |
| MitoQ-094-mt | chrM | 786 | TGGCGCGATGTAACACG | 787 | Reverse | 9379 | G |
| MitoQ-110-g | chrX | 788 | CTCCTAATACTAACTACCTGACT | 789 | Forward | 125607084 | T |
| MitoQ-110-mt | chrM | 790 | CTCCTAATACTAACTACCTGACT | 791 | Forward | 10977 | C |
| MitoQ-129-g | chr5 | 792 | AAGCANTCCTATACAACCGTAT | 793 | Forward | 93903367 | T |
| MitoQ-129-mt | chrM | 794 | AAGCANTCCTATACAACCGTAT | 795 | Forward | 12869 | C |
| MitoQ-139-g | chr5 | 796 | CAGCCCTAGACCTCAACTAC | 797 | Forward | 93904355 | T |
| MitoQ-139-mt | chrM | 798 | CAGCCCTAGACCTCAACTAC | 799 | Forward | 13857 | C |
| MitoQ-156-g | chr5 | 800 | CCCGAATGATATTTCCTATTC | 801 | Reverse | 93906052 | A |
| MitoQ-156-mt | chrM | 802 | CCCGAATGATATTTCCTATTC | 803 | Reverse | 15555 | G |

Example 4—Amplification Using Same Amplification Primer and iPLEX

Table 4: ADF2 Assay design using strategy of universal PCR primers and the same extension primer, please note that each PCR primer has a 10 bp tag to move them out of the MassARRAY window 3500-9000 m/z Table 5: The alignment showing each primer pair aligning both on nuclear as well as mitochondrial DNA All samples are set up in 25 uL PCR reactions.

TABLE 4

| WELL | TERM | Forward PCR primer | Reverse PCR primer | SEQ ID NO: 1st-PCRP | Assay Design ADF2 SEQ ID NO: Comment 1 | Same PCR same UEP AMP_LEN | UP_CONF | MP_CONF | Tm(NN) | PoGC | PWARN | UEP_DIR | UEP_MASS |
|---|---|---|---|---|---|---|---|---|---|---|---|---|---|
| W1 | iPLEX | Mito-019 | ACGTTGGATGGATCT AAAACACTCTTTAC | 804 ACGTTGGATGTCACA CGATTAACCCAAGTC | 805 new FP | 74 | 82.7 | 98.9 | 51.1 | 47.4 | h | R | 5757 |
| W1 | iPLEX | Mito-081 | ACGTTGGATGTGTG TAGAGTTCAGGGGAG | 806 ACGTTGGATGCTACA ATCTTCCTAGGAACA | 807 | 75 | 92.8 | 98.9 | 53.5 | 58.8 | g | R | 5307 |
| W1 | iPLEX | Mito-100 | ACGTTGGATGGAGGA GTATGCTAAGATTTT | 808 ACGTTGGATGCAGTT GAGGTGGATTAAACC | 809 | 75 | 90.2 | 98.9 | 45.7 | 35 | h | R | 6162 |
| W1 | iPLEX | Mito-108 | | 810 ACGTTGGATGCTACTCCACCTCAATCACAC | 811 new RP ATTTTTACGTTGTTAGA | 75 | 84.3 | 98.9 | 46.6 | 50 | | F | 5324 |
| W1 | iPLEX | Mito-129 | | 812 ACGTTGGATGAGGCCATCAATTTCATCACA ATGGCAGGGGTT | 813 new FP and RP | 73 | 93.6 | 98.9 | 45.5 | 21.7 | G | F | 6950 |
| W1 | iPLEX | Mito-138 | | 814 ACGTTGGATGATTTC ATATTGCTTCCGTGG | 815 | 75 | 95.2 | 98.9 | 46.6 | 44.4 | | F | 5490 |
| W1 | iPLEX | Mito-162 | | 816 ACGTTGGATGTAATA ATTACATCACAAGAC | 817 new FP | 74 | 90 | 98.9 | 49.7 | 58.8 | g | F | 5275 |
| W1 | iPLEX | Mito-172 | | 818 ACGTTGGATGGAATG ATCAGTACTGCGGCG | 819 | 75 | 95.6 | 98.9 | 52.2 | 64.7 | | R | 5100 |
| W1 | iPLEX | Mito-184 | | 820 ACGTTGGATGCGCCTTAATCCAAGCTAC TAGAGGCTTACTAGA | 821 | 75 | 95.6 | 98.9 | 46.3 | 41.2 | h | F | 5120 |
| W1 | iPLEX | Mito-204 | | 822 ACGTTGGATGGGGATATAGGGTCGAAGC CATAGAAAATCCAC | 823 new FP and RP | 74 | 93.7 | 98.9 | 53.7 | 52.6 | G | R | 5862 |

| Forward PCR primer | SEQ ID NO: | UEP_SEQ | SEQ ID NO: | EXT1_CALL | EXT1_MASS | EXT1_SEQ | SEQ ID NO: | EXT2_CALL | EXT2_MASS | EXT2_SEQ |
|---|---|---|---|---|---|---|---|---|---|---|
| Mito-019 | 824 | AAAACACTCTT TACGCCGG | 825 | G | 6004 | AAAACACT CTTTACGCC GGC | 826 | A | 6083.9 | AAAACACTC TTTACGCCG GT |
| Mito-081 | 828 | TTCAGGGGAG AGTGCGT | 829 | G | 5553.6 | TTCAGGGG AGAGTGCG TC | 830 | A | 5633.5 | TTCAGGGGA GAGTGCGTT |
| Mito-100 | 832 | TATGCTAAGAT TTTGCGTAG | 833 | G | 6409.2 | TATGCTAA GATTTTGC GTAGC | 834 | A | 6489.1 | TATGCTAAG ATTTTGCGT AGT |

TABLE 4-continued

| Assay Design ADF2 | | Same PCR same UEP | | | | | | | |
|---|---|---|---|---|---|---|---|---|---|
| Mito-108 | ACGTTGGATGCTACTCCACCTCAATCACAC | 836 | CTCAATCACTACTCCC | 837 | CTCAATCACACTACTCCCC | 838 | T | 5650.6 | CTCAATCACACTACTCCCT |
| Mito-129 | ACGTTGGATGAGGCCATCAATTTCATCACA | 840 | ATCAATTTCATCACACAATTAT | 841 | ATCAATTTCATCACAAATTATC | 842 | T | 7276.7 | ATCAATTTCATCACAACAATTATT |
| Mito-138 | ACGTTGGATGCCGGCGTCAAAGTATTTAGC | 844 | AGTATTTAGCTGACTCGC | 845 | AGTATTTAGCTGACTCGCC | 846 | T | 5816.7 | AGTATTTAGCTGACTCGCT |
| Mito-162 | ACGTTGGATGGCCTAATGTGGGACAGC | 848 | GGGACAGCTCATGAGTG | 849 | GGGACAGCTCATGAGTGC | 850 | A | 5602.5 | GGGACAGCTCATGAGTGT |
| Mito-172 | ACGTTGGATGCTTCATTCATTGCCCCCACA | 852 | GCCCCCACAATCCTAGG | 853 | GCCCCCACAATCCTAGGC | 854 | T | 5427.4 | GCCCCCACAATCCTAGGT |
| Mito-184 | ACGTTGGATGCGCCTTAATCCAAGCCTAC | 856 | ATCCAAGCCTACGTTTT | 857 | ATCCAAGCCTACGTTTTC | 858 | T | 5447.4 | ATCCAAGCCTACGTTTTT |
| Mito-204 | ACGTTGGATGGGGATATAGGGTCGAAGCCG | 860 | ATATAGGGTCGAAGCCGCA | 861 | ATATAGGGTCGAAGCCGCAC | 862 | A | 6188.9 | ATATAGGGTCGAAGCCGCAT |

| | Forward PCR primer SEQ ID NO: | EXT3_CALL | EXT3_MASS | EXT3_SEQ | EXT4_CALL | EXT4_MASS | EXT4_SEQ |
|---|---|---|---|---|---|---|---|
| Mito-019 | 827 | | | | | | |
| Mito-081 | 831 | | | | | | |
| Mito-100 | 835 | | | | | | |
| Mito-108 | 839 | | | | | | |
| Mito-129 | 843 | | | | | | |
| Mito-138 | 847 | | | | | | |
| Mito-162 | 851 | | | | | | |
| Mito-172 | 855 | | | | | | |
| Mito-184 | 859 | | | | | | |
| Mito-204 | 863 | | | | | | |

TABLE 5

| | | | | | | SEQ ID NO: |
|---|---|---|---|---|---|---|
| Assay | Chr | Start | End | Length | Amplicon | |
| Mito-019 | chr5 | 79947581 | 79947633 | 53 | TGATCTAAAACACTCTTTACGCCGGTTTCTATTGACTTGGGTTAATCGTGTGA | 864 |
| Mito-019 | chr11 | 10531450 | 10531502 | 53 | TGATCTAAAACACTCTTTATGCCGGTTTCTATTGACTTGGGTTAATCGTGTGA | 866 |
| Mito-019 | chrM | 905 | 957 | 53 | TCACACGATTAACCCAAGTCAATAGAAGCCGGCGTAAAGAGTGTTTTAGATCA | 868 |
| Mito-081 | chr1 | 564572 | 564625 | 54 | CTACAATCTTCCTAGGAACAACATATAACGCACTCTCCCCTGAACTCTACACAA | 870 |
| Mito-081 | chrM | 4023 | 4076 | 54 | CTACAATCTTCCTAGGAACAACATATGACGCACTCTCCCCTGAACTCTACACAA | 872 |
| Mito-100 | chr1 | 565514 | 565567 | 54 | CAGTTGAGGTGGATTAAACCAAACCCAACTACGCAAAATCTTAGCATACTCCTC | 874 |
| Mito-100 | chrM | 4965 | 5018 | 54 | CAGTTGAGGTGGATTAAACCAAACCCAGCTACGCAAAATCTTAGCATACTCCTC | 876 |
| Mito-108 | chr1 | 565910 | 565963 | 54 | CTACTCCACCTCAATCACACTACTCCCTATATCTAACAACGTAAAATAAAATG | 878 |
| Mito-108 | chrM | 5361 | 5414 | 54 | CTACTCCACCTCAATCACACTACTCCCCATATCTAACAACGTAAAAATAAAATG | 880 |
| Mito-129 | chr1 | 566934 | 566985 | 52 | GCCATCAATTTCATCACAACAATTATTAATATAAAACCCCCTGCCATAACCC | 882 |
| Mito-129 | chrM | 6385 | 6436 | 52 | GCCATCAATTTCATCACAACAATTATCAATATAAAACCCCCTGCCATAACCC | 884 |
| Mito-138 | chr1 | 567401 | 567454 | 54 | CCGGCGTCAAAGTATTTAGCTGACTCGCCACACTCCACGGAAGCAATATGAAAT | 886 |
| Mito-138 | chr17 | 51183126 | 51183179 | 54 | CCGGCGTCAAAGTATTTAGCTGACTCGCTACACTCCACGGAAGCAATATGAAAT | 888 |
| Mito-138 | chrM | 6851 | 6904 | 54 | CCGGCGTCAAAGTATTTAGCTGACTCGCCACACTCCACGGAAGCAATATGAAAT | 890 |
| Mito-162 | chr1 | 568591 | 568643 | 53 | TAATAATTACATCACAAGACGTCTTACACTCATGAGCTGTCCCCACATTAGGC | 892 |
| Mito-162 | chr18 | 45379691 | 45379743 | 53 | GCCTAATGTGGGGACAGCTCATGAGTGTAAGACGTCTTGTGATGTAATTATTA | 894 |
| Mito-162 | chrM | 8041 | 8093 | 53 | TAATAATTACATCACAAGACGTCTTGCACTCATGAGCTGTCCCCACATTAGGC | 896 |
| Mito-172 | chr1 | 569095 | 569148 | 54 | CTTCATTCATTGCCCCCACAATCCTAGGCCTACCCGCCGCAGTACTGATCATTC | 898 |
| Mito-172 | chr2 | 88124641 | 88124694 | 54 | CTTCATTCATTGCCCCCACAATCCTAGGTCTGCCCGCCGCAGTACTGATCATTC | 900 |
| Mito-172 | chrM | 8547 | 8600 | 54 | CTTCATTCATTGCCCCCACAATCCTAGGCCTACCCGCCGCAGTACTGATCATTC | 902 |
| Mito-184 | chr1 | 569689 | 569742 | 54 | CTGTCGCCTTAATCCAAGCCTACGTTTTTACACTTCTAGTAAGCCTCTACCTGC | 904 |
| Mito-184 | chrM | 9141 | 9194 | 54 | CTGTCGCCTTAATCCAAGCCTACGTTTTCACACTTCTAGTAAGCCTCTACCTGC | 906 |
| Mito-204 | chr17 | 42075087 | 42075139 | 53 | TACATAGAAAATCCACCCCTTACGAATGCGGCTTCGACCCTATATCCCCCGC | 908 |
| Mito-204 | chrM | 10147 | 10199 | 53 | TACATAGAAAATCCACCCCTTACGAGTGCGGCTTCGACCCTATATCCCCCGC | 910 |

TABLE 5-continued

Alignment Using ADF2

| Assay | Chr | UEP | SEQ ID NO: | Direction | Nucleotide | WTExtension |
|---|---|---|---|---|---|---|
| Mito-019 | chr5 | AAAACACTCTTTACGCCGG | 865 | Forward | 79947607 | T |
| Mito-019 | chr11 | AAAACACTCTTTACGCCGG | 867 | Forward | 10531476 | T |
| Mito-019 | chrM | CCGGCGTAAAGAGTGTTTT | 869 | Reverse | 933 | G |
| Mito-081 | chr1 | ACGCACTCTCCCCTGAA | 871 | Reverse | 564599 | A |
| Mito-081 | chrM | ACGCACTCTCCCCTGAA | 873 | Reverse | 4050 | G |
| Mito-100 | chr1 | CTACGCAAAATCTTAGCATA | 875 | Reverse | 565542 | A |
| Mito-100 | chrM | CTACGCAAAATCTTAGCATA | 877 | Reverse | 4993 | G |
| Mito-108 | chr1 | CTCAATCACACTACTCCC | 879 | Forward | 565938 | T |
| Mito-108 | chrM | CTCAATCACACTACTCCC | 881 | Forward | 5389 | C |
| Mito-129 | chr1 | ATCAATTTCATCACAACAATTAT | 883 | Forward | 566961 | T |
| Mito-129 | chrM | ATCAATTTCATCACAACAATTAT | 885 | Forward | 6412 | C |
| Mito-138 | chr1 | AGTATTTAGCTGACTCGC | 887 | Forward | 567430 | C |
| Mito-138 | chr17 | AGTATTTAGCTGACTCGC | 889 | Forward | 51183155 | T |
| Mito-138 | chrM | AGTATTTAGCTGACTCGC | 891 | Forward | 6880 | C |
| Mito-162 | chr1 | CACTCATGAGCTGTCCC | 893 | Reverse | 568617 | A |
| Mito-162 | chr18 | GGGACAGCTCATGAGTG | 895 | Forward | 45379719 | T |
| Mito-162 | chrM | CACTCATGAGCTGTCCC | 897 | Reverse | 8067 | G |
| Mito-172 | chr1 | GCCCCCACAATCCTAGG | 899 | Forward | 569124 | C |
| Mito-172 | chr2 | GCCCCCACAATCCTAGG | 901 | Forward | 88124670 | T |
| Mito-172 | chrM | GCCCCCACAATCCTAGG | 903 | Forward | 8576 | C |
| Mito-184 | chr1 | ATCCAAGCCTACGTTTT | 905 | Forward | 569718 | T |
| Mito-184 | chrM | ATCCAAGCCTACGTTTT | 907 | Forward | 9170 | C |
| Mito-204 | chr17 | TGCGGCTTCGACCCTATAT | 909 | Reverse | 42075114 | A |
| Mito-204 | chrM | TGCGGCTTCGACCCTATAT | 911 | Reverse | 10174 | G |

Example 5—Identification of Chimpanzee Mitochondrial/Human Mitochondrial Paralogs and Chimpanzee Nuclear/Human Nuclear Paralogs Chimpanzee mitochondrial/human mitochondrial paralogs were identified using a R-based algorithm. Utilizing the Biostrings library from the Bioconductor open source software aligned small fragments (50-100 bps) of the human (Homo sapiens) mitochondrial genome (UCSC hg19 build) against the chimpanzee (Pan troglodytes) mitochondrial genome (P. troglodytes 2013 assembly). Bioconductor contains memory efficient string containers, string matching algorithms, and other utilities, for fast manipulation of large biological sequences or sets of sequences. Similar nucleotide regions containing at least one mismatch were selected and assays were designed based on these regions. When paralog regions were identified these were verified using the BLAST algorithm from NCBI.

An exemplary protocol is as follows:
1. The mitochondrial genome was split into shorter fragments (in the case here 75 bp) and given a name, e.g., Seq-1 is the mitochondrial genome nt 1-75 and Seq-2 is nucleotides 76-150.
2. Each sequence was aligned against the chimpanzee mitochondrial genome and a certain number of mismatches are allowed in this case 15 mismatches per sequence. Results are displayed in Table 6. Shown are sequence number, direction of DNA (strand) match, start of alignment, end of alignment, length of alignment (Width) finally regions that are suitable for use as amplicons (potential amplification primer binding regions) and sequence. Dashes indicate matches in the sequences and letters mismatches in the sequences. The human mitochondria is labelled with hchrM and the chimpanzee is labelled chrM.

3. All sequence mismatches can be used for paralog detection (V) as long as the upstream/downstream regions J and K fit the strategy for amplification as described below.
4. For Co-amplification of chimpanzee and human mitochondrial polynucleotides with a single amplification primer pair—a region V surrounded by regions J and K, where V is different between the chimpanzee and human mitochondrial genomes and J and K are identical in both the chimpanzee and human mitochondrial genomes was selected. Amplification primers were designed to bind to a region within J and K, for amplification of both chimpanzee and human polynucleotides. Amplicons produced with these amplification primers include V. The nucleotide at V was analyzed to distinguish an amplicon of a chimpanzee mitochondrial polynucleotide from an amplicon of a human mitochondrial polynucleotide.

The human and chimpanzee nuclear genomes are 99% identical, therefore there are numerous suitable paralog regions. Suitable chimpanzee nuclear/human nuclear paralogs were determined in the same manner as mitochondrial paralogs, e.g., by blasting portions of the human genome against the chimpanzee genome.

TABLE 6

Chimpanzee and Human Mitochondrial Paralogs
chrM = Chimpanzee mitochondrial DNA, hchrM = *Homo Sapiens* mitochondrial DNA,
(−) = Alignment Match, Letter (ACGT) = Corresponding chimpanzee mismatch

| fragment | chr | strand | start | end | width | SEQ ID NO: | amplicon |
|---|---|---|---|---|---|---|---|
| Seq-1 | chrM | Sense | 15986 | 16060 | 75 | 912 | ---------------------------G----------CT-------<br>-----------------------G-- |
| Seq-1 | hchrM | Sense | 1 | 75 | 75 | 913 | GATCACAGGTCTATCACCCTATTAACCACTCACGGGAGCTCTCCATGC<br>ATTTGGTATTTTCGTCTGGGGGGTATG |
| Seq-2 | chrM | Sense | 16061 | 16135 | 75 | 914 | -------------------A-------CC--------------------<br>---------------------C---T |
| Seq-2 | hchrM | Sense | 76 | 150 | 75 | 915 | CACGCGATAGCATTGCGAGACGCTGGAGCCGGAGCACCCTATGTCGCA<br>GTATCTGTCTTTGATTCCTGCCTCATC |
| Seq-3 | chrM | Sense | 16136 | 16210 | 75 | 916 | G-------------------------------GAC-T-G-----C---<br>-----------G--------------- |
| Seq-3 | hchrM | Sense | 151 | 225 | 75 | 917 | CTATTATTTATCGCACCTACGTTCAATATTACAGGCGAACATACTTAC<br>TAAAGTGTGTTAATTAATTAATGCTTG |
| Seq-4 | hchrM | Sense | 226 | 300 | 75 | 918 | TAGGACATAATAATAACAATTGAATGTCTGCACAGCCACTTTCCACAC<br>AGACATCATAACAAAAAATTTCCACCA |
| Seq-5 | chrM | Sense | 16281 | 16355 | 75 | 919 | C--AAA---C---TTC-CC-C------------C-----A--------<br>----------------------AG-- |
| Seq-5 | hchrM | Sense | 301 | 375 | 75 | 920 | AACCCCCCCTCCCCCGCTTCTGGCCACAGCACTTAAACACATCTCTGC<br>CAAACCCCAAAAACAAAGAACCCTAAC |
| Seq-6 | chrM | Sense | 16356 | 16430 | 75 | 921 | G--------G-----C---------C------A----------------<br>--------------T---T-----TGCC |
| Seq-6 | hchrM | Sense | 376 | 450 | 75 | 922 | ACCAGCCTAACCAGATTTCAAATTTTATCTTTTGGCGGTATGCACTTT<br>TAACAGTCACCCCCCAACTAACACATT |
| Seq-7 | hchrM | Sense | 451 | 525 | 75 | 923 | ATTTTCCCCTCCCACTCCCATACTACTAATCTCATCAATACAACCCCC<br>GCCCATCCTACCCAGCACACACACACC |
| Seq-8 | hchrM | Sense | 526 | 600 | 75 | 924 | GCTGCTAACCCCATACCCCGAACCAACCAAACCCCAAAGACACCCCCC<br>ACAGTTTATGTAGCTTACCTCCTCAAA |
| Seq-9 | chrM | Sense | 25 | 99 | 75 | 925 | --------------------C------T-T-------------------<br>-C------------------------ |
| Seq-9 | hchrM | Sense | 601 | 675 | 75 | 926 | GCAATACACTGAAAATGTTTAGACGGGCTCACATCACCCCATAAACAA<br>ATAGGTTTGGTCCTAGCCTTTCTATTA |
| Seq-10 | hchrM | Sense | 676 | 750 | 75 | 927 | GCTCTTAGTAAGATTACACATGCAAGCATCCCCGTTCCAGTGAGTTCA<br>CCCTCTAAATCACCACGATCAAAAGGA |
| Seq-11 | chrM | Sense | 173 | 247 | 75 | 928 | -----T-------------------------------------------<br>--------------G-----------A |
| Seq-11 | hchrM | Sense | 751 | 825 | 75 | 929 | ACAAGCATCAAGCACGCAGCAATGCAGCTCAAAACGCTTAGCCTAGCC<br>ACACCCCACGGGAAACAGCAGTGATT |
| Seq-12 | chrM | Sense | 248 | 322 | 75 | 930 | --------------------------------------C---------T----<br>-----------------T--------- |

TABLE 6-continued

Chimpanzee and Human Mitochondrial Paralogs
chrM = Chimpanzee mitochondrial DNA, hchrM = Homo Sapiens mitochondrial DNA,
(−) = Alignment Match, Letter (ACGT) = Corresponding chimpanzee mismatch

| fragment | chr | strand | start | end | width | SEQ ID NO: | amplicon |
|---|---|---|---|---|---|---|---|
| Seq-12 | hchrM | Sense | 826 | 900 | 75 | 931 | AACCTTTAGCAATAAACGAAAGTTTAACTAAGCTATACTAACCCCAGG GTTGGTCAATTTCGTGCCAGCCACCGC |
| Seq-13 | chrM | Sense | 323 | 397 | 75 | 932 | -----T----------------------A-------------------- ------------C-ATA--GCT-AAAT |
| Seq-13 | hchrM | Sense | 901 | 975 | 75 | 933 | GGTCACACGATTAACCCAAGTCAATAGAAGCCGGCGTAAAGAGTGTTT TAGATCACCCCCTCCCCAATAAAGCTA |
| Seq-14 | chrM | Sense | 394 | 468 | 75 | 934 | --T-----------------------C---T--------A----- ----------------C-------T-- |
| Seq-14 | hchrM | Sense | 976 | 1050 | 75 | 935 | AAACTCACCTGAGTTGTAAAAAACTCCAGTTGACACAAAATAGACTAC GAAAGTGGCTTTAACATATCTGAACAC |
| Seq-15 | chrM | Sense | 469 | 543 | 75 | 936 | ------------------------------------------------- -------T-------------T----- |
| Seq-15 | hchrM | Sense | 1051 | 1125 | 75 | 937 | ACAATAGCTAAGACCCAAACTGGGATTAGATACCCCACTATGCTTAGC CCTAAACCTCAACAGTTAAATCAACAA |
| Seq-16 | chrM | Sense | 544 | 618 | 75 | 938 | ------------------------------------------------- -------------------------- |
| Seq-16 | hchrM | Sense | 1126 | 1200 | 75 | 939 | AACTGCTCGCCAGAACACTACGAGCCACAGCTTAAAACTCAAAGGACC TGGCGGTGCTTCATATCCCTCTAGAGG |
| Seq-17 | chrM | Sense | 619 | 693 | 75 | 940 | -----------------------------------------G-------- -------------------------- |
| Seq-17 | hchrM | Sense | 1201 | 1275 | 75 | 941 | AGCCTGTTCTGTAATCGATAAACCCCGATCAACCTCACCACCTCTTGC TCAGCCTATATACCGCCATCTTCAGCA |
| Seq-18 | chrM | Sense | 694 | 768 | 75 | 942 | --------------T------------A--------------------- ------------------T-------- |
| Seq-18 | hchrM | Sense | 1276 | 1350 | 75 | 943 | AACCCTGATGAAGGCTACAAAGTAAGCGCAAGTACCCACGTAAAGACG TTAGGTCAAGGTGTAGCCCATGAGGTG |
| Seq-19 | chrM | Sense | 769 | 843 | 75 | 944 | ----------------------------------T-------A----- -------C--------A---------- |
| Seq-19 | hchrM | Sense | 1351 | 1425 | 75 | 945 | GCAAGAAATGGGCTACATTTTCTACCCCAGAAAACTACGATAGCCCTT ATGAAACTTAAGGGTCGAAGGTGGATT |
| Seq-20 | chrM | Sense | 844 | 918 | 75 | 946 | ------------------------------------------------- -------------------------- |
| Seq-20 | hchrM | Sense | 1426 | 1500 | 75 | 947 | TAGCAGTAAACTAAGAGTAGAGTGCTTAGTTGAACAGGGCCCTGAAGC GCGTACACACCGCCCGTCACCCTCCTC |
| Seq-21 | hchrM | Sense | 1501 | 1575 | 75 | 948 | AAGTATACTTCAAAGGACATTTAACTAAAACCCCTACGCATTTATATA GAGGAGACAAGTCGTAACATGGTAAGT |
| Seq-22 | chrM | Sense | 995 | 1069 | 75 | 949 | ------------------------------------------------T---- -------------------------- |
| Seq-22 | hchrM | Sense | 1576 | 1650 | 75 | 950 | GTACTGGAAAGTGCACTTGGACGAACCAGAGTGTAGCTTAACACAAAG CACCCAACTTACACTTAGGAGATTTCA |
| Seq-23 | chrM | Sense | 1070 | 1144 | 75 | 951 | ---C---------A--------C-------------------C------ -C--------A---------A------ |
| Seq-23 | hchrM | Sense | 1651 | 1725 | 75 | 952 | ACTTAACTTGACCGCTCTGAGCTAAACCTAGCCCCAAACCCACTCCAC CTTACTACCAGACAACCTTAGCCAAAC |
| Seq-24 | chrM | Sense | 1145 | 1219 | 75 | 953 | ------------------------------------T--A-C------- ----C--------------------- |
| Seq-24 | hchrM | Sense | 1726 | 1800 | 75 | 954 | CATTTACCCAAATAAAGTATAGGCGATAGAAATTGAAACCTGGCGCAA TAGATATAGTACCGCAAGGGAAAGATG |

TABLE 6-continued

Chimpanzee and Human Mitochondrial Paralogs
chrM = Chimpanzee mitochondrial DNA, hchrM = Homo Sapiens mitochondrial DNA,
(—) = Alignment Match, Letter (ACGT) = Corresponding chimpanzee mismatch

| fragment | chr | strand | start | end | width | SEQ ID NO: | amplicon |
|---|---|---|---|---|---|---|---|
| Seq-25 | chrM | Sense | 1220 | 1294 | 75 | 955 | ----------C------------C------------------G------T------------------------ |
| Seq-25 | hchrM | Sense | 1801 | 1875 | 75 | 956 | AAAAATTATAACCAAGCATAATATAGCAAGGACTAACCCCTATACCTT CTGCATAATGAATTAACTAGAAATAAC |
| Seq-26 | chrM | Sense | 1295 | 1369 | 75 | 957 | --------A----A----------------------------------------------------- |
| Seq-26 | hchrM | Sense | 1876 | 1950 | 75 | 958 | TTTGCAAGGAGAGCCAAAGCTAAGACCCCCGAAACCAGACGAGCTACC TAAGAACAGCTAAAAGAGCACACCCGT |
| Seq-27 | chrM | Sense | 1370 | 1444 | 75 | 959 | ------------------------------------------------------------------------- |
| Seq-27 | hchrM | Sense | 1951 | 2025 | 75 | 960 | CTATGTAGCAAAATAGTGGGAAGATTTATAGGTAGAGGCGACAAACCT ACCGAGCCTGGTGATAGCTGGTTGTCC |
| Seq-28 | chrM | Sense | 1445 | 1519 | 75 | 961 | -------------------------------A--T-------------- -------------C------------- |
| Seq-28 | hchrM | Sense | 2026 | 2100 | 75 | 962 | AAGATAGAATCTTAGTTCAACTTTAAATTTGCCCACAGAACCCTCTAA ATCCCCTTGTAAATTTAACTGTTAGTC |
| Seq-29 | chrM | Sense | 1520 | 1594 | 75 | 963 | --------------------A--------------------A----- --------------------------- |
| Seq-29 | hchrM | Sense | 2101 | 2175 | 75 | 964 | CAAAGAGGAACAGCTCTTTGGACACTAGGAAAAAACCTTGTAGAGAGA GTAAAAAATTTAACACCCATAGTAGGC |
| Seq-30 | chrM | Sense | 1595 | 1669 | 75 | 965 | ---------------------------------------------A- ---T---G------------C---C- |
| Seq-30 | hchrM | Sense | 2176 | 2250 | 75 | 966 | CTAAAAGCAGCCACCAATTAAGAAAGCGTTCAAGCTCAACACCCACTA CCTAAAAAATCCCAAACATATAACTGA |
| Seq-31 | chrM | Sense | 1670 | 1744 | 75 | 967 | ------T---------------------T----C-------------- --------------------------- |
| Seq-31 | hchrM | Sense | 2251 | 2325 | 75 | 968 | ACTCCTCACACCCAATTGGACCAATCTATCACCCTATAGAAGAACTAA TGTTAGTATAAGTAACATGAAAACATT |
| Seq-32 | chrM | Sense | 1745 | 1819 | 75 | 969 | -----------------A-A-----CC----T-T-A------------- ------T-------------------- |
| Seq-32 | hchrM | Sense | 2326 | 2400 | 75 | 970 | CTCCTCCGCATAAGCCTGCGTCAGATTAAAACACTGAACTGACAATTA ACAGCCCAATATCTACAATCAACCAAC |
| Seq-33 | chrM | Sense | 1820 | 1894 | 75 | 971 | ---C-----------C-G----T------------------C--C--- --------------------------- |
| Seq-33 | hchrM | Sense | 2401 | 2475 | 75 | 972 | AAGTCATTATTACCCTCACTGTCAACCCAACACAGGCATGCTCATAAG GAAAGGTTAAAAAAAGTAAAAGGAACT |
| Seq-34 | chrM | Sense | 1895 | 1969 | 75 | 973 | ------------------------------------------------ T------------------------G |
| Seq-34 | hchrM | Sense | 2476 | 2550 | 75 | 974 | CGGCAAATCTTACCCCGCCTGTTTACCAAAAACATCACCTCTAGCATC ACCAGTATTAGAGGCACCGCCTGCCCA |
| Seq-35 | chrM | Sense | 1970 | 2044 | 75 | 975 | ------T----------------------------------------- -------------------------T |
| Seq-35 | hchrM | Sense | 2551 | 2625 | 75 | 976 | GTGACACATGTTTAACGGCCGCGGTACCCTAACCGTGCAAAGGTAGCA TAATCACTTGTTCCTTAAATAGGGACC |
| Seq-36 | chrM | Sense | 2045 | 2119 | 75 | 977 | ------------------------T----------------C------ ------------A-------------- |
| Seq-36 | hchrM | Sense | 2626 | 2700 | 75 | 978 | TGTATGAATGGCTCCACGAGGGTTCAGCTGTCTCTTACTTTTAACCAG TGAAATTGACCTGCCCGTGAAGAGGCG |

TABLE 6-continued

Chimpanzee and Human Mitochondrial Paralogs
chrM = Chimpanzee mitochondrial DNA, hchrM = *Homo Sapiens* mitochondrial DNA,
(-) = Alignment Match, Letter (ACGT) = Corresponding chimpanzee mismatch

| fragment | chr | strand | start | end | width | SEQ ID NO: | amplicon |
|---|---|---|---|---|---|---|---|
| Seq-37 | chrM | Sense | 2120 | 2194 | 75 | 979 | ---------T-A-----------------------------C----<br>----------A---T---------T--- |
| Seq-37 | hchrM | Sense | 2701 | 2775 | 75 | 980 | GGCATAACACAGCAAGACGAGAAGACCCTATGGAGCTTTAATTTATTA<br>ATGCAAACAGTACCTAACAAACCCACA |
| Seq-38 | chrM | Sense | 2195 | 2269 | 75 | 981 | ------------TT-----------------------------<br>-------C----------------A- |
| Seq-38 | hchrM | Sense | 2776 | 2850 | 75 | 982 | GGTCCTAAACTACCAAACCTGCATTAAAAATTTCGGTTGGGGCGACCT<br>CGGAGCAGAACCCAACCTCCGAGCAGT |
| Seq-39 | chrM | Sense | 2270 | 2344 | 75 | 983 | ------------C----------------T-----C-TC--------<br>-----G-------------------- |
| Seq-39 | hchrM | Sense | 2851 | 2925 | 75 | 984 | ACATGCTAAGACTTCACCAGTCAAAGCGAACTACTATACTCAATTGAT<br>CCAATAACTTGACCAACGGAACAAGTT |
| Seq-40 | chrM | Sense | 2345 | 2419 | 75 | 985 | -------------------------------C------------------<br>-------------------------- |
| Seq-40 | hchrM | Sense | 2926 | 3000 | 75 | 986 | ACCCTAGGGATAACAGCGCAATCCTATTCTAGAGTCCATATCAACAAT<br>AGGGTTTACGACCTCGATGTTGGATCA |
| Seq-41 | chrM | Sense | 2420 | 2494 | 75 | 987 | ---------------------------------------------<br>-------------------------- |
| Seq-41 | hchrM | Sense | 3001 | 3075 | 75 | 988 | GGACATCCCGATGGTGCAGCCGCTATTAAAGGTTCGTTTGTTCAACGA<br>TTAAAGTCCTACGTGATCTGAGTTCAG |
| Seq-42 | hchrM | Sense | 3076 | 3150 | 75 | 989 | ACCGGAGTAATCCAGGTCGGTTTCTATCTACNTTCAAATTCCTCCCTG<br>TACGAAAGGACAAGAGAAATAAGGCCT |
| Seq-43 | chrM | Sense | 2569 | 2643 | 75 | 990 | --------------------AA----------T-------T----<br>CGCC--G-A--------T---------A |
| Seq-43 | hchrM | Sense | 3151 | 3225 | 75 | 991 | ACTTCACAAAGCGCCTTCCCCCGTAAATGATATCATCTCAACTTAGTA<br>TTATACCCACACCCACCCAAGAACAGG |
| Seq-44 | chrM | Sense | 2644 | 2718 | 75 | 992 | ----------------------------T-------------------<br>---A---------------------- |
| Seq-44 | hchrM | Sense | 3226 | 3300 | 75 | 993 | GTTTGTTAAGATGGCAGAGCCCGGTAATCGCATAAAACTTAAAACTTT<br>ACAGTCAGAGGTTCAATTCCTCTTCTT |
| Seq-45 | chrM | Sense | 2719 | 2793 | 75 | 994 | G------C-------A----------------------------C---<br>---------A--------------A--- |
| Seq-45 | hchrM | Sense | 3301 | 3375 | 75 | 995 | AACAACATACCCATGGCCAACCTCCTACTCCTCATTGTACCCATTCTA<br>ATCGCAATGGCATTCCTAATGCTTACC |
| Seq-46 | chrM | Sense | 2794 | 2868 | 75 | 996 | --------------------C-----------------T------A--<br>-----T-T---------T----G--- |
| Seq-46 | hchrM | Sense | 3376 | 3450 | 75 | 997 | GAACGAAAAATTCTAGGCTATATACAACTACGCAAAGGCCCCAACGTT<br>GTAGGCCCCTACGGGCTACTACAACCC |
| Seq-47 | chrM | Sense | 2869 | 2943 | 75 | 998 | -------------------------T-----A---T--------T--<br>--T--A-----T--------------- |
| Seq-47 | hchrM | Sense | 3451 | 3525 | 75 | 999 | TTCGCTGACGCCATAAAACTCTTCACCAAAGAGCCCCTAAAACCCGCC<br>ACATCTACCATCACCCTCTACATCACC |
| Seq-48 | chrM | Sense | 2944 | 3018 | 75 | 1000 | -----A---C----C--------T--C--CT----------------<br>-----------------A-----T-T |
| Seq-48 | hchrM | Sense | 3526 | 3600 | 75 | 1001 | GCCCCGACCTTAGCTCTCACCATCGCTCTTCTACTATGAACCCCCCTC<br>CCCATACCCAACCCCCTGGTCAACCTC |
| Seq-49 | chrM | Sense | 3019 | 3093 | 75 | 1002 | ---T----------------------------C---------------<br>-------------------------- |

TABLE 6-continued

Chimpanzee and Human Mitochondrial Paralogs
chrM = Chimpanzee mitochondrial DNA, hchrM = Homo Sapiens mitochondrial DNA,
(—) = Alignment Match, Letter (ACGT) = Corresponding chimpanzee mismatch

| fragment | chr | strand | start | end | width | SEQ ID NO: | amplicon |
|---|---|---|---|---|---|---|---|
| Seq-49 | hchrM | Sense | 3601 | 3675 | 75 | 1003 | AACCTAGGCCTCCTATTTATTCTAGCCACCTCTAGCCTAGCCGTTTAC TCAATCCTCTGATCAGGGTGAGCATCA |
| Seq-50 | chrM | Sense | 3094 | 3168 | 75 | 1004 | -----G---------T-A-----T-----A-------------------- ---------C---------T--------T |
| Seq-50 | hchrM | Sense | 3676 | 3750 | 75 | 1005 | AACTCAAACTACGCCCTGATCGGCGCACTGCGAGCAGTAGCCCAAACA ATCTCATATGAAGTCACCCTAGCCATC |
| Seq-51 | chrM | Sense | 3169 | 3243 | 75 | 1006 | --C-----G-----GC-------------------C--T-----T--- ---G-------------G--------- |
| Seq-51 | hchrM | Sense | 3751 | 3825 | 75 | 1007 | ATTCTACTATCAACATTACTAATAAGTGGCTCCTTTAACCTCTCCACC CTTATCACAACACAAGAACACCTCTGA |
| Seq-52 | chrM | Sense | 3244 | 3318 | 75 | 1008 | C--A---------A---------C---------------------T--- --------------------T------ |
| Seq-52 | hchrM | Sense | 3826 | 3900 | 75 | 1009 | TTACTCCTGCCATCATGACCCTTGGCCATAATATGATTTATCTCCACA CTAGCAGAGACCAACCGAACCCCCTTC |
| Seq-53 | chrM | Sense | 3319 | 3393 | 75 | 1010 | ------A-T-----A-A-T-----------------T--T----- G--T--------------T--------T |
| Seq-53 | hchrM | Sense | 3901 | 3975 | 75 | 1011 | GACCTTGCCGAAGGGGAGTCCGAACTAGTCTCAGGCTTCAACATCGAA TACGCCGCAGGCCCCTTCGCCCTATTC |
| Seq-54 | chrM | Sense | 3394 | 3468 | 75 | 1012 | ----------------T-----------------------TG-- ----------------G-------CA-T |
| Seq-54 | hchrM | Sense | 3976 | 4050 | 75 | 1013 | TTCATAGCCGAATACACAAACATTATTATAATAAACACCCTCACCACT ACAATCTTCCTAGGAACAACATATGAC |
| Seq-55 | chrM | Sense | 3469 | 3543 | 75 | 1014 | A-T-A-----------------G-----------------AG-T--- ------------------C-------- |
| Seq-55 | hchrM | Sense | 4051 | 4125 | 75 | 1015 | GCACTCTCCCCTGAACTCTACACAACATATTTTGTCACCAAGACCCTA CTTCTAACCTCCCTGTTCTTATGAATT |
| Seq-56 | chrM | Sense | 3544 | 3618 | 75 | 1016 | -----------T--------T-----------G---------------- -------------------------- |
| Seq-56 | hchrM | Sense | 4126 | 4200 | 75 | 1017 | CGAACAGCATACCCCCGATTCCGCTACGACCAACTCATACACCTCCTA TGAAAAAACTTCCTACCACTCACCCTA |
| Seq-57 | chrM | Sense | 3619 | 3693 | 75 | 1018 | ----C---C-G------A------------C--------------- C------------------------- |
| Seq-57 | hchrM | Sense | 4201 | 4275 | 75 | 1019 | GCATTACTTATATGATATGTCTCCATACCCATTACAATCTCCAGCATT CCCCCTCAAACCTAAGAAATATGTCTG |
| Seq-58 | chrM | Sense | 3694 | 3768 | 75 | 1020 | --------A--------------------------T-C---T----- ---------------A----------T |
| Seq-58 | hchrM | Sense | 4276 | 4350 | 75 | 1021 | ATAAAAGAGTTACTTTGATAGAGTAAATAATAGGAGCTTAAACCCCCT TATTTCTAGGACTATGAGAATCGAACC |
| Seq-59 | chrM | Sense | 3769 | 3843 | 75 | 1022 | ------------------------------------------------ -------------------------- |
| Seq-59 | hchrM | Sense | 4351 | 4425 | 75 | 1023 | CATCCCTGAGAATCCAAAATTCTCCGTGCCACCTATCACACCCCATCC TAAAGTAAGGTCAGCTAAATAAGCTAT |
| Seq-60 | chrM | Sense | 3844 | 3918 | 75 | 1024 | ---------------------------C-------------------- -------A---------A--------- |
| Seq-60 | hchrM | Sense | 4426 | 4500 | 75 | 1025 | CGGGCCCATACCCCGAAAATGTTGGTTATACCCTTCCCGTACTAATTA ATCCCCTGGCCCAACCCGTCATCTACT |
| Seq-61 | chrM | Sense | 3919 | 3993 | 75 | 1026 | --------C--A--------G-----T--------------A------- ----C--------------------- |

TABLE 6-continued

Chimpanzee and Human Mitochondrial Paralogs
chrM = Chimpanzee mitochondrial DNA, hchrM = *Homo Sapiens* mitochondrial DNA,
(—) = Alignment Match, Letter (ACGT) = Corresponding chimpanzee mismatch

| fragment | chr | strand | start | end | width | SEQ ID NO: | amplicon |
|---|---|---|---|---|---|---|---|
| Seq-61 | hchrM | Sense | 4501 | 4575 | 75 | 1027 | CTACCATCTTTGCAGGCACACTCATCACAGCGCTAAGCTCGCACTGAT TTTTTACCTGAGTAGGCCTAGAAATAA |
| Seq-62 | chrM | Sense | 3994 | 4068 | 75 | 1028 | -T---A-----------C---A-C-----------------G---C--C- ----------C---------A--C--T- |
| Seq-62 | hchrM | Sense | 4576 | 4650 | 75 | 1029 | ACATGCTAGCTTTTATTCCAGTTCTAACCAAAAAATAAACCCTCGTT CCACAGAAGCTGCCATCAAGTATTTCC |
| Seq-63 | chrM | Sense | 4069 | 4143 | 75 | 1030 | ----A--------T--G--------T--C--G--------------C-- ---GC--------------------- |
| Seq-63 | hchrM | Sense | 4651 | 4725 | 75 | 1031 | TCACGCAAGCAACCGCATCCATAATCCTTCTAATAGCTATCCTCTTCA ACAATATACTCTCCGGACAATGAACCA |
| Seq-64 | chrM | Sense | 4144 | 4218 | 75 | 1032 | -----------------------------------------T--------A- -G----------------------- |
| Seq-64 | hchrM | Sense | 4726 | 4800 | 75 | 1033 | TAACCAATACTACCAATCAATACTCATCATTAATAATCATAATAGCTA TAGCAATAAAACTAGGAATAGCCCCCT |
| Seq-65 | chrM | Sense | 4219 | 4293 | 75 | 1034 | -------T-----T-----A-----------------C--A-T----- ----A--C--C--------------T |
| Seq-65 | hchrM | Sense | 4801 | 4875 | 75 | 1035 | TTCACTTCTGAGTCCCAGAGGTTACCCAAGGCACCCCTCTGACATCCG GCCTGCTTCTTCTCACATGACAAAAAC |
| Seq-66 | chrM | Sense | 4294 | 4368 | 75 | 1036 | -------T--T-----T---------------CT-A-----G------- A------------C--T---------G- |
| Seq-66 | hchrM | Sense | 4876 | 4950 | 75 | 1037 | TAGCCCCCATCTCAATCATATACCAAATCTCTCCCTCACTAAACGTAA GCCTTCTCCTCACTCTCTCAATCTTAT |
| Seq-67 | chrM | Sense | 4369 | 4443 | 75 | 1038 | ----T-----------C-----C---C-------------A-------- -----C----------------C---- |
| Seq-67 | hchrM | Sense | 4951 | 5025 | 75 | 1039 | CCATCATAGCAGGCAGTTGAGGTGGATTAAACCAAACCCAGCTACGCA AAATCTTAGCATACTCCTCAATTACCC |
| Seq-68 | chrM | Sense | 4444 | 4518 | 75 | 1040 | -------C---------------C-----A--T----------------- -------------C-----C--C---- |
| Seq-68 | hchrM | Sense | 5026 | 5100 | 75 | 1041 | ACATAGGATGAATAATAGCAGTTCTACCGTACAACCCTAACATAACCA TTCTTAATTTAACTATTTATATTATCC |
| Seq-69 | chrM | Sense | 4519 | 4593 | 75 | 1042 | ----------------T--G-------------------------A- --------------------------- |
| Seq-69 | hchrM | Sense | 5101 | 5175 | 75 | 1043 | TAACTACTACCGCATTCCTACTACTCAACTTAAACTCCAGCACCACGA CCCTACTACTATCTCGCACCTGAAACA |
| Seq-70 | chrM | Sense | 4594 | 4668 | 75 | 1044 | -----------T----T---C------------------------- -------A-----A-----T-----C- |
| Seq-70 | hchrM | Sense | 5176 | 5250 | 75 | 1045 | AGCTAACATGACTAACACCCTTAATTCCATCCACCCTCCTCTCCCTAG GAGGCCTGCCCCCGCTAACCGGCTTTT |
| Seq-71 | chrM | Sense | 4669 | 4743 | 75 | 1046 | -A--------A-TT-C--------------------T---------- --------------------T----- |
| Seq-71 | hchrM | Sense | 5251 | 5325 | 75 | 1047 | TGCCCAAATGGGCCATTATCGAAGAATTCACAAAAAACAATAGCCTCA TCATCCCACCATCATAGCCACCATCA |
| Seq-72 | chrM | Sense | 4744 | 4818 | 75 | 1048 | -T-------------T------------------------------- -T--------T-----------T---- |
| Seq-72 | hchrM | Sense | 5326 | 5400 | 75 | 1049 | CCCTCCTTAACCTCTACTTCTACCTACGCCTAATCTACTCCACCTCAA TCACACTACTCCCCATATCTAACAACG |
| Seq-73 | chrM | Sense | 4819 | 4893 | 75 | 1050 | ----------------A--C--------------------C------- -T---------A-----------A--G- |

TABLE 6-continued

Chimpanzee and Human Mitochondrial Paralogs
chrM = Chimpanzee mitochondrial DNA, hchrM = Homo Sapiens mitochondrial DNA,
(—) = Alignment Match, Letter (ACGT) = Corresponding chimpanzee mismatch

| fragment | chr | strand | start | end | width | SEQ ID NO: | amplicon |
|---|---|---|---|---|---|---|---|
| Seq-73 | hchrM | Sense | 5401 | 5475 | 75 | 1051 | TAAAAATAAAATGACAGTTTGAACATACAAAACCCACCCCATTCCTCC CCACACTCATCGCCCTTACCACGCTAC |
| Seq-74 | chrM | Sense | 4894 | 4968 | 75 | 1052 | -T-----C--------C--C------------------------ ---GC--------------------- |
| Seq-74 | hchrM | Sense | 5476 | 5550 | 75 | 1053 | TCCTACCTATCTCCCCTTTTATACTAATAATCTTATAGAAATTTAGGT TAAATACAGACCAAGAGCCTTCAAAGC |
| Seq-75 | chrM | Sense | 4969 | 5043 | 75 | 1054 | ------C-----A----------------C----A------------- --------------------------- |
| Seq-75 | hchrM | Sense | 5551 | 5625 | 75 | 1055 | CCTCAGTAAGTTGCAATACTTAATTTCTGTAACAGCTAAGGACTGCAA AACCCCACTCTGCATCAACTGAACGCA |
| Seq-76 | chrM | Sense | 5044 | 5118 | 75 | 1056 | ----------------------------------------TT---------- --------------T-------------- |
| Seq-76 | hchrM | Sense | 5626 | 5700 | 75 | 1057 | AATCAGCCACTTTAATTAAGCTAAGCCCTTACTAGACCAATGGGACTT AAACCCACAAACACTTAGTTAACAGCT |
| Seq-77 | chrM | Sense | 5119 | 5193 | 75 | 1058 | --A-------------------------------------AA-A-- --------------------------- |
| Seq-77 | hchrM | Sense | 5701 | 5775 | 75 | 1059 | AAGCACCCTAATCAACTGGCTTCAATCTACTTCTCCCGCCGCCGGGAA AAAAGGCGGGAGAAGCCCCGGCAGGTT |
| Seq-78 | chrM | Sense | 5194 | 5268 | 75 | 1060 | ----------------------------------------A-- -----------------T---------- |
| Seq-78 | hchrM | Sense | 5776 | 5850 | 75 | 1061 | TGAAGCTGCTTCTTCGAATTTGCAATTCAATATGAAAATCACCTCGGA GCTGGTAAAAGAGGCCTAACCCCTGT |
| Seq-79 | hchrM | Sense | 5851 | 5925 | 75 | 1062 | CTTTAGATTTACAGTCCAATGCTTCACTCAGCCATTTTACCTCACCCC CACTGATGTTCGCCGACCGTTGACTAT |
| Seq-80 | chrM | Sense | 5343 | 5417 | 75 | 1063 | --------------------T-------------------C-------T- ----------------G--------C- |
| Seq-80 | hchrM | Sense | 5926 | 6000 | 75 | 1064 | TCTCTACAAACCACAAAGACATTGGAACACTATACCTATTATTCGGCG CATGAGCTGGAGTCCTAGGCACAGCTC |
| Seq-81 | chrM | Sense | 5418 | 5492 | 75 | 1065 | ----T-----------G--T--A--A-----A------------C---- ----T--------------T--C---- |
| Seq-81 | hchrM | Sense | 6001 | 6075 | 75 | 1066 | TAAGCCTCCTTATTCGAGCCGAGCTGGGCCAGCCAGGCAACCTTCTAG GTAACGACCACATCTACAACGTTATCG |
| Seq-82 | chrM | Sense | 5493 | 5567 | 75 | 1067 | ----------------C---------------------G--T--T- ---------------------G---- |
| Seq-82 | hchrM | Sense | 6076 | 6150 | 75 | 1068 | TCACAGCCCATGCATTTGTAATAATCTTCTTCATAGTAATACCCATCA TAATCGGAGGCTTTGGCAACTGACTAG |
| Seq-83 | chrM | Sense | 5568 | 5642 | 75 | 1069 | -----T-G-----T-----------C-----A--C-------------- --------------G---C-G--C--T- |
| Seq-83 | hchrM | Sense | 6151 | 6225 | 75 | 1070 | TTCCCTAATAATCGGTGCCCCCGATATGGCGTTTCCCCGCATAAACA ACATAAGCTTCTGACTCTTACCTCCCT |
| Seq-84 | chrM | Sense | 5643 | 5717 | 75 | 1071 | ----------T--A--T---------C-----A--A------C--G---- --------------------------- |
| Seq-84 | hchrM | Sense | 6226 | 6300 | 75 | 1072 | CTCTCCTACTCCTGCTCGCATCTGCTATAGTGGAGGCCGGAGCAGGAA CAGGTTGAACAGTCTACCCTCCCTTAG |
| Seq-85 | chrM | Sense | 5718 | 5792 | 75 | 1073 | -G---A--------G--T--------------------------- -------T--G-----CA--------- |
| Seq-85 | hchrM | Sense | 6301 | 6375 | 75 | 1074 | CAGGGAACTACTCCCACCCTGGAGCCTCCGTAGACCTAACCATCTTCT CCTTACACCTAGCAGGTGTCTCCTCTA |

TABLE 6-continued

Chimpanzee and Human Mitochondrial Paralogs
chrM = Chimpanzee mitochondrial DNA, hchrM = Homo Sapiens mitochondrial DNA,
(—) = Alignment Match, Letter (ACGT) = Corresponding chimpanzee mismatch

| fragment | chr | strand | start | end | width | SEQ ID NO: | amplicon |
|---|---|---|---|---|---|---|---|
| Seq-86 | chrM | Sense | 5793 | 5867 | 75 | 1075 | --C----A-----T--C-----------------T----------T---------G--------------A---- |
| Seq-86 | hchrM | Sense | 6376 | 6450 | 75 | 1076 | TCTTAGGGGCCATCAATTTCATCACAACAATTATCAATATAAAACCCCCTGCCATAACCCAATACCAAACGCCCC |
| Seq-87 | chrM | Sense | 5868 | 5942 | 75 | 1077 | ---------------------------------T-------------C--------------------------C- |
| Seq-87 | hchrM | Sense | 6451 | 6525 | 75 | 1078 | TCTTCGTCTGATCCGTCCTAATCACAGCAGTCCTACTTCTCCTATCTCTCCCAGTCCTAGCTGCTGGCATCACTA |
| Seq-88 | chrM | Sense | 5943 | 6017 | 75 | 1079 | -----T-G-----T--T-----------T--------------A-----G-----------T--------T---- |
| Seq-88 | hchrM | Sense | 6526 | 6600 | 75 | 1080 | TACTACTAACAGACCGCAACCTCAACACCACCTTCTTCGACCCCGCCGGAGGAGGAGACCCCATTCTATACCAAC |
| Seq-89 | chrM | Sense | 6018 | 6092 | 75 | 1081 | --T-------------T--C-----C-----------------------------------T-----C---- |
| Seq-89 | hchrM | Sense | 6601 | 6675 | 75 | 1082 | ACCTATTCTGATTTTCGGTCACCCTGAAGTTTATATTCTTATCCTACCAGGCTTCGGAATAATCTCCCATATTG |
| Seq-90 | chrM | Sense | 6093 | 6167 | 75 | 1083 | -------T----------------------------T-----C-----T--------A---------------- |
| Seq-90 | hchrM | Sense | 6676 | 6750 | 75 | 1084 | TAACTTACTACTCCGGAAAAAAAGAACCATTTGGATACATAGGTATGGTCTGAGCTATGATATCAATTGGCTTCC |
| Seq-91 | chrM | Sense | 6168 | 6242 | 75 | 1085 | -----------------------------------------G--------------C-----C-------------- |
| Seq-91 | hchrM | Sense | 6751 | 6825 | 75 | 1086 | TAGGGTTTATCGTGTGAGCACACCATATATTTACAGTAGGAATAGACGTAGACACACGAGCATATTTCACCTCCG |
| Seq-92 | chrM | Sense | 6243 | 6317 | 75 | 1087 | --------------T-----T--T-------------------C----------T-----T---------------- |
| Seq-92 | hchrM | Sense | 6826 | 6900 | 75 | 1088 | CTACCATAATCATCGCTATCCCCACCGGCGTCAAAGTATTTAGCTGACTCGCCACACTCCACGGAAGCAATATGA |
| Seq-93 | chrM | Sense | 6318 | 6392 | 75 | 1089 | ----------C-----A---------------G--T--------C--------------A--C---------C |
| Seq-93 | hchrM | Sense | 6901 | 6975 | 75 | 1090 | AATGATCTGCTGCAGTGCTCTGAGCCCTAGGATTCATCTTTCTTTTCACCGTAGGTGGCCTGACTGGCATTGTAT |
| Seq-94 | chrM | Sense | 6393 | 6467 | 75 | 1091 | ---------------T----------G-----------A--------C-----------------C--T------- |
| Seq-94 | hchrM | Sense | 6976 | 7050 | 75 | 1092 | TAGCAAACTCATCACTAGACATCGTACTACACGACACGTACTACGTTGTAGCCCACTTCCACTATGTCCTATCAA |
| Seq-95 | chrM | Sense | 6468 | 6542 | 75 | 1093 | -------------C---------------------------C----------------T------------- |
| Seq-95 | hchrM | Sense | 7051 | 7125 | 75 | 1094 | TAGGAGCTGTATTTGCCATCATAGGAGGCTTCATTCACTGATTTCCCCTATTCTCAGGCTACACCCTAGACCAAA |
| Seq-96 | chrM | Sense | 6543 | 6617 | 75 | 1095 | ----T-----------A--TG-C-----G-----T--------C-----C-----------G-----C--T---- |
| Seq-96 | hchrM | Sense | 7126 | 7200 | 75 | 1096 | CCTACGCCAAAATCCATTTCACTATCATATTCATCGGCGTAAATCTAACTTTCTTCCCACAACACTTTCTCGGCC |
| Seq-97 | chrM | Sense | 6618 | 6692 | 75 | 1097 | ----T--G-----------------------------------TG----------C------- |
| Seq-97 | hchrM | Sense | 7201 | 7275 | 75 | 1098 | TATCCGGAATGCCCCGACGTTACTCGGACTACCCCGATGCATACACCACATGAAACATCCTATCATCTGTAGGCT |

TABLE 6-continued

Chimpanzee and Human Mitochondrial Paralogs
chrM = Chimpanzee mitochondrial DNA, hchrM = Homo Sapiens mitochondrial DNA,
(−) = Alignment Match, Letter (ACGT) = Corresponding chimpanzee mismatch

| fragment | chr | strand | start | end | width | SEQ ID NO: | amplicon |
|---|---|---|---|---|---|---|---|
| Seq-98 | chrM | Sense | 6693 | 6767 | 75 | 1099 | ----T--C--C--G-------------------------------T-----A--A---------- |
| Seq-98 | hchrM | Sense | 7276 | 7350 | 75 | 1100 | CATTCATTTCTCTAACAGCAGTAATATTAATAATTTTCATGATTTGAGAAGCCTTCGCTTCGAAGCGAAAAGTCC |
| Seq-99 | chrM | Sense | 6768 | 6842 | 75 | 1101 | -------------G------GC---------A-------------------------------------- |
| Seq-99 | hchrM | Sense | 7351 | 7425 | 75 | 1102 | TAATAGTAGAAGAACCCTCCATAAACCTGGAGTGACTATATGGATGCCCCCCACCCTACCACACATTCGAAGAAC |
| Seq-100 | chrM | Sense | 6843 | 6917 | 75 | 1103 | ----------------------------------------------T-----------------------A- |
| Seq-100 | hchrM | Sense | 7426 | 7500 | 75 | 1104 | CCGTATACATAAAATCTAGACAAAAAAGGAAGGAATCGAACCCCCCAAAGCTGGTTTCAAGCCAACCCCATGGCC |
| Seq-101 | chrM | Sense | 6918 | 6992 | 75 | 1105 | --------------------A-------------T-----------------------C---T---CC--C |
| Seq-101 | hchrM | Sense | 7501 | 7575 | 75 | 1106 | TCCATGACTTTTTCAAAAAGGTATTAGAAAAACCATTTCATAACTTTGTCAAAGTTAAATTATAGGCTAAATCCT |
| Seq-102 | chrM | Sense | 6993 | 7067 | 75 | 1107 | G-------------------------------------------T----------------------A-----T-T |
| Seq-102 | hchrM | Sense | 7576 | 7650 | 75 | 1108 | ATATATCTTAATGGCACATGCAGCGCAAGTAGGTCTACAAGACGCTACTTCCCCTATCATAGAAGAGCTTATCAC |
| Seq-103 | chrM | Sense | 7068 | 7142 | 75 | 1109 | ------C--C--T-----------T--C--T--C---------T--------A--C-------------------- |
| Seq-103 | hchrM | Sense | 7651 | 7725 | 75 | 1110 | CTTTCATGATCACGCCCTCATAATCATTTTCCTTATCTGCTTCCTAGTCCTGTATGCCCTTTTCCTAACACTCAC |
| Seq-104 | chrM | Sense | 7143 | 7217 | 75 | 1111 | --------------------GT--T--------C-------------------------------- |
| Seq-104 | hchrM | Sense | 7726 | 7800 | 75 | 1112 | AACAAAACTAACTAATACTAACATCTCAGACGCTCAGGAAATAGAAACCGTCTGAACTATCCTGCCCGCCATCAT |
| Seq-105 | chrM | Sense | 7218 | 7292 | 75 | 1113 | ---------T--T-----A---------G--T-------------------------C------T----T-- |
| Seq-105 | hchrM | Sense | 7801 | 7875 | 75 | 1114 | CCTAGTCCTCATCGCCCTCCCATCCCTACGCATCCTTTACATAACAGACGAGGTCAACGATCCCTCCCTTACCAT |
| Seq-106 | chrM | Sense | 7293 | 7367 | 75 | 1115 | T--------C-----T-----A--T-----------A-------------------G-------------------- |
| Seq-106 | hchrM | Sense | 7876 | 7950 | 75 | 1116 | CAAATCAATTGGCCACCAATGGTACTGAACCTACGAGTACACCGACTACGGCGGACTAATCTTCAACTCCTACAT |
| Seq-107 | chrM | Sense | 7368 | 7442 | 75 | 1117 | ---C-----------T------------T--T--A----------------T--C-----G--C-----AG---- |
| Seq-107 | hchrM | Sense | 7951 | 8025 | 75 | 1118 | ACTTCCCCCATTATTCCTAGAACCAGGCGACCTGCGACTCCTTGACGTTGACAATCGAGTAGTACTCCCGATTGA |
| Seq-108 | chrM | Sense | 7443 | 7517 | 75 | 1119 | -------G------------------------T--TC-A-----------T------------C------- |
| Seq-108 | hchrM | Sense | 8026 | 8100 | 75 | 1120 | AGCCCCCATTCGTATAATAATTACATCACAAGACGTCTTGCACTCATGAGCTGTCCCCACATTAGGCTTAAAAAC |
| Seq-109 | chrM | Sense | 7518 | 7592 | 75 | 1121 | ---C-------------C----------------------C---------A--A-----------C-------- |
| Seq-109 | hchrM | Sense | 8101 | 8175 | 75 | 1122 | AGATGCAATTCCCGGACGTCTAAACCAAACCACTTTCACCGCTACACGACCGGGGGTATACTACGGTCAATGCTC |

TABLE 6-continued

Chimpanzee and Human Mitochondrial Paralogs
chrM = Chimpanzee mitochondrial DNA, hchrM = Homo Sapiens mitochondrial DNA,
(−) = Alignment Match, Letter (ACGT) = Corresponding chimpanzee mismatch

| fragment | chr | strand | start | end | width | SEQ ID NO: | amplicon |
|---|---|---|---|---|---|---|---|
| Seq-110 | chrM | Sense | 7593 | 7667 | 75 | 1123 | A-------------------------T--A--------------------C--T------------------ |
| Seq-110 | hchrM | Sense | 8176 | 8250 | 75 | 1124 | TGAAATCTGTGGAGCAAACCACAGTTTCATGCCCATCGTCCTAGAATTAATTCCCCTAAAAATCTTTGAAATAGG |
| Seq-111 | hchrM | Sense | 8251 | 8325 | 75 | 1125 | GCCCGTATTTACCCTATAGCACCCCCTCTACCCCCTCTAGAGCCCACTGTAAAGCTAACTTAGCATTAACCTTTT |
| Seq-112 | chrM | Sense | 7744 | 7818 | 75 | 1126 | ------------------G---G---------------------------CG-------A-------- |
| Seq-112 | hchrM | Sense | 8326 | 8400 | 75 | 1127 | AAGTTAAAGATTAAGAGAACCAACACCTCTTTACAGTGAAATGCCCCAACTAAATACTACCGTATGGCCCACCAT |
| Seq-113 | chrM | Sense | 7819 | 7893 | 75 | 1128 | ------------------G--------T---G---------------------TT----T-----T-----C- |
| Seq-113 | hchrM | Sense | 8401 | 8475 | 75 | 1129 | AATTACCCCCATACTCCTTACACTATTCCTCATCACCCAACTAAAAATATTAAACACAAACTACCACCTACCTCC |
| Seq-114 | chrM | Sense | 7894 | 7968 | 75 | 1130 | ---------A-----------------C--C--T------------------------------A--------- |
| Seq-114 | hchrM | Sense | 8476 | 8550 | 75 | 1131 | CTCACCAAAGCCCATAAAAATAAAAATTATAACAAACCCTGAGAACCAAAATGAACGAAAATCTGTTCGCTTCA |
| Seq-115 | chrM | Sense | 7969 | 8043 | 75 | 1132 | ---GC--------------------T----------------A-----------C---------C--G-------T |
| Seq-115 | hchrM | Sense | 8551 | 8625 | 75 | 1133 | TTCATTGCCCCCACAATCCTAGGCCTACCCGCCGCAGTACTGATCATTCTATTTCCCCCTCTATTGATCCCCACC |
| Seq-116 | chrM | Sense | 8044 | 8118 | 75 | 1134 | --T---C--------------------T--------------------TC----G--------------A--- |
| Seq-116 | hchrM | Sense | 8626 | 8700 | 75 | 1135 | TCCAAATATCTCATCAACAACCGACTAATCACCACCCAACAATGACTAATCAAACTAACCTCAAAACAAATGATA |
| Seq-117 | chrM | Sense | 8119 | 8193 | 75 | 1136 | --T-------G-------------------------C---------------------------A-------C--T |
| Seq-117 | hchrM | Sense | 8701 | 8775 | 75 | 1137 | ACCATACACAACACTAAAGGACGAACCTGATCTCTTATACTAGTATCCTTAATCATTTTTATTGCCACAACTAAC |
| Seq-118 | chrM | Sense | 8194 | 8268 | 75 | 1138 | --T--T--G--T--A--C---------C---------------------T------C-- |
| Seq-118 | hchrM | Sense | 8776 | 8850 | 75 | 1139 | CTCCTCGGACTCCTGCCTCACTCATTTACACCAACCACCCAACTATCTATAAACCTAGCCATGGCCATCCCCTTA |
| Seq-119 | chrM | Sense | 8269 | 8343 | 75 | 1140 | -----A---G----AG-C-------------T-----C----------------------G--------- |
| Seq-119 | hchrM | Sense | 8851 | 8925 | 75 | 1141 | TGAGCGGGCACAGTGATTATAGGCTTTCGCTCTAAGATTAAAAATGCCCTAGCCCACTTCTTACCACAAGGCACA |
| Seq-120 | chrM | Sense | 8344 | 8418 | 75 | 1142 | ------------------------------C--------T--T------------------------T-A------ |
| Seq-120 | hchrM | Sense | 8926 | 9000 | 75 | 1143 | CCTACACCCCTTATCCCCATACTAGTTATTATCGAAACCATCAGCCTACTCATTCAACCAATAGCCCTGGCCGTA |
| Seq-121 | chrM | Sense | 8419 | 8493 | 75 | 1144 | --T---------------------------------------------A------T-------T |
| Seq-121 | hchrM | Sense | 9001 | 9075 | 75 | 1145 | CGCCTAACCGCTAACATTACTGCAGGCCACCTACTCATGCACCTAATTGGAAGCGCCACCCTAGCAATATCAACC |
| Seq-122 | chrM | Sense | 8494 | 8568 | 75 | 1146 | --C--T--A----A-G----C--T-----------------C-----------T-----G-----C--------- |

TABLE 6-continued

Chimpanzee and Human Mitochondrial Paralogs
chrM = Chimpanzee mitochondrial DNA, hchrM = Homo Sapiens mitochondrial DNA,
(—) = Alignment Match, Letter (ACGT) = Corresponding chimpanzee mismatch

| fragment | chr | strand | start | end | width | SEQ ID NO: | amplicon |
|---|---|---|---|---|---|---|---|
| Seq-122 | hchrM | Sense | 9076 | 9150 | 75 | 1147 | ATTAACCTTCCCTCTACACTTATCATCTTCACAATTCTAATTCTACTG ACTATCCTAGAAATCGCTGTCGCCTTA |
| Seq-123 | chrM | Sense | 8569 | 8643 | 75 | 1148 | -----------------T-----------G------------------- --------------------------- |
| Seq-123 | hchrM | Sense | 9151 | 9225 | 75 | 1149 | ATCCAAGCCTACGTTTTCACACTTCTAGTAAGCCTCTACCTGCACGAC AACACATAATGACCCACCAATCACATG |
| Seq-124 | chrM | Sense | 8644 | 8718 | 75 | 1150 | ----C--C--------------------------------- -G-----------A-----------G- |
| Seq-124 | hchrM | Sense | 9226 | 9300 | 75 | 1151 | CCTATCATATAGTAAAACCCAGCCCATGACCCCTAACAGGGGCCCTCT CAGCCCTCCTAATGACCTCCGGCCTAG |
| Seq-125 | chrM | Sense | 8719 | 8793 | 75 | 1152 | ----A-----C------T------C---A--A----C-------T--- ----T------T-G--------T---- |
| Seq-125 | hchrM | Sense | 9301 | 9375 | 75 | 1153 | CCATGTGATTTCACTTCCACTCCATAACGCTCCTCATACTAGGCCTAC TAACCAACACACTAACCATATACCAAT |
| Seq-126 | chrM | Sense | 8794 | 8868 | 75 | 1154 | ----A--------T-T-------G------------------ ----C-----------T--C-----T- |
| Seq-126 | hchrM | Sense | 9376 | 9450 | 75 | 1155 | GATGGCGCGATGTAACACGAGAAAGCACATACCAAGGCCACCACACAC CACCTGTCCAAAAAGGCCTTCGATACG |
| Seq-127 | chrM | Sense | 8869 | 8943 | 75 | 1156 | -------T--T------------------------T---------- -T-----T--C---------------- |
| Seq-127 | hchrM | Sense | 9451 | 9525 | 75 | 1157 | GGATAATCCTATTTATTACCTCAGAAGTTTTTTCTTCGCAGGATTTT TCTGAGCCTTTTACCACTCCAGCCTAG |
| Seq-128 | chrM | Sense | 8944 | 9018 | 75 | 1158 | -------------GC-------A-----------------T--T---- -A------------------------ |
| Seq-128 | hchrM | Sense | 9526 | 9600 | 75 | 1159 | CCCCTACCCCCCAATTAGGAGGGCACTGGCCCCCAACAGGCATCACCC CGCTAAATCCCCTAGAAGTCCCACTCC |
| Seq-129 | chrM | Sense | 9019 | 9093 | 75 | 1160 | ----------T-------------------------T--T-----C- -T--C--CT----------T------- |
| Seq-129 | hchrM | Sense | 9601 | 9675 | 75 | 1161 | TAAACACATCCGTATTACTCGCATCAGGAGTATCAATCACCTGAGCTC ACCATAGTCTAATAGAAAACAACCGAA |
| Seq-130 | chrM | Sense | 9094 | 9168 | 75 | 1162 | ----------------------G---C----A-----T---- ---------------------A--T- |
| Seq-130 | hchrM | Sense | 9676 | 9750 | 75 | 1163 | ACCAAATAATTCAAGCACTGCTTATTACAATTTTACTGGGTCTCTATT TTACCCTCCTACAAGCCTCAGAGTACT |
| Seq-131 | chrM | Sense | 9169 | 9243 | 75 | 1164 | ----A--C--T--T-----------T--------------------C- ------------------------C- |
| Seq-131 | hchrM | Sense | 9751 | 9825 | 75 | 1165 | TCGAGTCTCCCTTCACCATTTCCGACGGCATCTACGGCTCAACATTTT TTGTAGCCACAGGCTTCCACGGACTTC |
| Seq-132 | chrM | Sense | 9244 | 9318 | 75 | 1166 | -------------A---------------------C------------ -------------C------------- |
| Seq-132 | hchrM | Sense | 9826 | 9900 | 75 | 1167 | ACGTCATTATTGGCTCAACTTTCCTCACTATCTGCTTCATCCGCCAAC TAATATTTCACTTTACATCCAAACATC |
| Seq-133 | chrM | Sense | 9319 | 9393 | 75 | 1168 | ----C-----TC-------------------A--C--C--------A- -C-----------A--------T--T- |
| Seq-133 | hchrM | Sense | 9901 | 9975 | 75 | 1169 | ACTTTGGCTTCGAAGCCGCCGCCTGATACTGGCATTTTGTAGATGTGG TTTGACTATTTCTGTATGTCTCCATCT |
| Seq-134 | chrM | Sense | 9394 | 9468 | 75 | 1170 | -C--------A--------------------G----------------- -------------------------- |

TABLE 6-continued

Chimpanzee and Human Mitochondrial Paralogs
chrM = Chimpanzee mitochondrial DNA, hchrM = Homo Sapiens mitochondrial DNA,
(−) = Alignment Match, Letter (ACGT) = Corresponding chimpanzee mismatch

| fragment | chr | strand | start | end | width | SEQ ID NO: | amplicon |
|---|---|---|---|---|---|---|---|
| Seq-134 | hchrM | Sense | 9976 | 10050 | 75 | 1171 | ATTGATGAGGGTCTTACTCTTTTAGTATAAATAGTACCGTTAACTTCC AATTAACTAGTTTTGACAACATTCAAA |
| Seq-135 | chrM | Sense | 9469 | 9543 | 75 | 1172 | ------------------T-C--------------C---T-----T---- --C-------G---------C-----C- |
| Seq-135 | hchrM | Sense | 10051 | 10125 | 75 | 1173 | AAAGAGTAATAAACTTCGCCTTAATTTTAATAATCAACACCCTCCTAG CCTTACTACTAATAATTATTACATTTT |
| Seq-136 | chrM | Sense | 9544 | 9618 | 75 | 1174 | ------------------A-----------------T-----------A- -T------------------------ |
| Seq-136 | hchrM | Sense | 10126 | 10200 | 75 | 1175 | GACTACCACAACTCAACGGCTACATAGAAAAATCCACCCCTTACGAGT GCGGCTTCGACCCTATATCCCCCGCCC |
| Seq-137 | chrM | Sense | 9619 | 9693 | 75 | 1176 | -------C---------------T---C-------C--C------C--- -------C----------------A- |
| Seq-137 | hchrM | Sense | 10201 | 10275 | 75 | 1177 | GCGTCCCTTTCTCCATAAAATTCTTCTTAGTAGCTATTACCTTCTTAT TATTTGATCTAGAAATTGCCCTCCTTT |
| Seq-138 | chrM | Sense | 9694 | 9768 | 75 | 1178 | -G---T----T--------------GG-C-----A-----------C- CA----------------T-CT---- |
| Seq-138 | hchrM | Sense | 10276 | 10350 | 75 | 1179 | TACCCCTACCATGAGCCCTACAAACAACTAACCTGCCACTAATAGTTA TGTCATCCCTCTTATTAATCATCATCC |
| Seq-139 | chrM | Sense | 9769 | 9843 | 75 | 1180 | ----------C--C-----C--A---T----------G---------- ---------------------T---- |
| Seq-139 | hchrM | Sense | 10351 | 10425 | 75 | 1181 | TAGCCCTAAGTCTGGCCTATGAGTGACTACAAAAAGGATTAGACTGAA CCGAATTGGTATATAGTTTAAACAAAA |
| Seq-140 | chrM | Sense | 9844 | 9918 | 75 | 1182 | ------------------------------------------------- ----T-----T---------------- |
| Seq-140 | hchrM | Sense | 10426 | 10500 | 75 | 1183 | CGAATGATTTCGACTCATTAAATTATGATAATCATATTTACCAAATGC CCCTCATTTACATAAATATTATACTAG |
| Seq-141 | chrM | Sense | 9919 | 9993 | 75 | 1184 | ----------------------------------------------A- ----T---------------------- |
| Seq-141 | hchrM | Sense | 10501 | 10575 | 75 | 1185 | CATTTACCATCTCACTTCTAGGAATACTAGTATATCGCTCACACCTCA TATCCTCCCTACTATGCCTAGAAGGAA |
| Seq-142 | chrM | Sense | 9994 | 10068 | 75 | 1186 | ----------A---------C-----C--C--------------T--T- ---------------------A--C- |
| Seq-142 | hchrM | Sense | 10576 | 10650 | 75 | 1187 | TAATACTATCGCTGTTCATTATAGCTACTCTCATAACCCTCAACACCC ACTCCCTCTTAGCCAATATTGTGCCTA |
| Seq-143 | chrM | Sense | 10069 | 10143 | 75 | 1188 | -CA----------------T--------------A--A--T-----A- -------T--------T---------- |
| Seq-143 | hchrM | Sense | 10651 | 10725 | 75 | 1189 | TTGCCATACTAGTCTTTGCCGCCTGCGAAGCAGCGGTGGGCCTAGCCC TACTAGTCTCAATCTCCAACACATATG |
| Seq-144 | chrM | Sense | 10144 | 10218 | 75 | 1190 | --T--------------------------------------------- -A----G-------------------- |
| Seq-144 | hchrM | Sense | 10726 | 10800 | 75 | 1191 | GCCTAGACTACGTACATAACCTAAACCTACTCCAATGCTAAAACTAAT CGTCCCAACAATTATATTACTACCACT |
| Seq-145 | chrM | Sense | 10219 | 10293 | 75 | 1192 | A------T-C--T-------GT--------------------T-- ------------C----C---T--CT- |
| Seq-145 | hchrM | Sense | 10801 | 10875 | 75 | 1193 | GACATGACTTTCCAAAAAACACATAATTTGAATCAACACAACCACCCA CAGCCTAATTATTAGCATCATCCCTCT |
| Seq-146 | chrM | Sense | 10294 | 10368 | 75 | 1194 | ------------------T--------------C----------TGC- ---C------------T-------T-- |

TABLE 6-continued

Chimpanzee and Human Mitochondrial Paralogs
chrM = Chimpanzee mitochondrial DNA, hchrM = Homo Sapiens mitochondrial DNA,
(−) = Alignment Match, Letter (ACGT) = Corresponding chimpanzee mismatch

| fragment | chr | strand | start | end | width | SEQ ID NO: | amplicon |
|---|---|---|---|---|---|---|---|
| Seq-146 | hchrM | Sense | 10876 | 10950 | 75 | 1195 | ACTATTTTTAACCAAATCAACAACAACCTATTTAGCTGTTCCCCAAC CTTTTCCTCCGACCCCCTAACAACCCC |
| Seq-147 | chrM | Sense | 10369 | 10443 | 75 | 1196 | ----------T-----G-T-----T-----------------A----- ---G------C------AC-------- |
| Seq-147 | hchrM | Sense | 10951 | 11025 | 75 | 1197 | CCTCCTAATACTAACTACCTGACTCCTACCCCTCACAATCATGGCAAG CCAACGCCACTTATCCAGTGAACCACT |
| Seq-148 | chrM | Sense | 10444 | 10518 | 75 | 1198 | -----------------------C--G-----T-----C-------- ----------------T-G-------- |
| Seq-148 | hchrM | Sense | 11026 | 11100 | 75 | 1199 | ATCACGAAAAAAACTCTACCTCTCTATACTAATCTCCCTACAAATCTC CTTAATTATAACATTCACAGCCACAGA |
| Seq-149 | chrM | Sense | 10519 | 10593 | 75 | 1200 | G-----T-----------------------------------C- -----------------G--T----- |
| Seq-149 | hchrM | Sense | 11101 | 11175 | 75 | 1201 | ACTAATCATATTTTATATCTTCTTCGAAACCACACTTATCCCCACCTT GGCTATCATCACCCGATGAGGCAACCA |
| Seq-150 | chrM | Sense | 10594 | 10668 | 75 | 1202 | A--------------------T-----------------T-------- ----------C----------------- |
| Seq-150 | hchrM | Sense | 11176 | 11250 | 75 | 1203 | GCCAGAACGCCTGAACGCAGGCACATACTTCCTATTCTACACCCTAGT AGGCTCCCTTCCCCTACTCATCGCACT |
| Seq-151 | chrM | Sense | 10669 | 10743 | 75 | 1204 | ---C--T--C---------------------T--C---T------- ---T--AA----------------A- |
| Seq-151 | hchrM | Sense | 11251 | 11325 | 75 | 1205 | AATTTACACTCACAACACCCTAGGCTCACTAAACATTCTACTACTCAC TCTCACTGCCCAAGAACTATCAAACTC |
| Seq-152 | chrM | Sense | 10744 | 10818 | 75 | 1206 | -------------------------G-----G--G-----C--G-- ----A-----C---------------C- |
| Seq-152 | hchrM | Sense | 11326 | 11400 | 75 | 1207 | CTGAGCCAACAACTTAATATGACTAGCTTACACAATAGCTTTTATAGT AAAGATACCTCTTTACGGACTCCACTT |
| Seq-153 | chrM | Sense | 10819 | 10893 | 75 | 1208 | -------------------------------T--T--C--------G-- ------T---------------T---- |
| Seq-153 | hchrM | Sense | 11401 | 11475 | 75 | 1209 | ATGACTCCCTAAAGCCCATGTCGAAGCCCCCATCGCTGGGTCAATAGT ACTTGCCGCAGTACTCTTAAAACTAGG |
| Seq-154 | chrM | Sense | 10894 | 10968 | 75 | 1210 | T--------C-----------------C-----------A----- ---T--------T--------CA-GT- |
| Seq-154 | hchrM | Sense | 11476 | 11550 | 75 | 1211 | CGGCTATGGTATAATACGCCTCACACTCATTCTCAACCCCCTGACAAA ACACATAGCCTACCCCTTCCTTGTACT |
| Seq-155 | chrM | Sense | 10969 | 11043 | 75 | 1212 | G---T-------T-----C---------------------G-------- -----------------------C- |
| Seq-155 | hchrM | Sense | 11551 | 11625 | 75 | 1213 | ATCCCTATGAGGCATAATTATAACAAGCTCCATCTGCCTACGACAAAC AGACCTAAAATCGCTCATTGCATACTC |
| Seq-156 | chrM | Sense | 11044 | 11118 | 75 | 1214 | ----G--------------------------------------- ---------------------A-T-- |
| Seq-156 | hchrM | Sense | 11626 | 11700 | 75 | 1215 | TTCAATCAGCCACATAGCCCTCGTAGTAACAGCCATTCTCATCCAAAC CCCCTGAAGCTTCACCGGCGCAGTCAT |
| Seq-157 | chrM | Sense | 11119 | 11193 | 75 | 1216 | C-----------------A----------------T---C--------- ----------T--T--------C----- |
| Seq-157 | hchrM | Sense | 11701 | 11775 | 75 | 1217 | TCTCATAATCGCCCACGGGCTTACATCCTCATTACTATTCTGCCTAGC AAACTCAAACTACGAACGCACTCACAG |
| Seq-158 | chrM | Sense | 11194 | 11268 | 75 | 1218 | -------------T-----C------------------------ ---C------------C--G-------- |

TABLE 6-continued

Chimpanzee and Human Mitochondrial Paralogs
chrM = Chimpanzee mitochondrial DNA, hchrM = Homo Sapiens mitochondrial DNA,
(—) = Alignment Match, Letter (ACGT) = Corresponding chimpanzee mismatch

| fragment | chr | strand | start | end | width | SEQ ID NO: | amplicon |
|---|---|---|---|---|---|---|---|
| Seq-158 | hchrM | Sense | 11776 | 11850 | 75 | 1219 | TCGCATCATAATCCTCTCTCAAGGACTTCAAACTCTACTCCCACTAAT AGCTTTTTGATGACTTCTAGCAAGCCT |
| Seq-159 | chrM | Sense | 11269 | 11343 | 75 | 1220 | -------------C-------T--C-----T--C--A--G-------- C------------T-A----------- |
| Seq-159 | hchrM | Sense | 11851 | 11925 | 75 | 1221 | CGCTAACCTCGCCTTACCCCCCACTATTAACCTACTGGGAGAACTCTC TGTGCTAGTAACCACGTTCTCCTGATC |
| Seq-160 | chrM | Sense | 11344 | 11418 | 75 | 1222 | -----C------------C------T-----------A---------- G--------------G----------- |
| Seq-160 | hchrM | Sense | 11926 | 12000 | 75 | 1223 | AAATATCACTCTCCTACTTACAGGACTCAACATACTAGTCACAGCCCT ATACTCCCTCTACATATTTACCACAAC |
| Seq-161 | chrM | Sense | 11419 | 11493 | 75 | 1224 | ------A-----------------------T-G------G-------- ---------------T-----A--TT- |
| Seq-161 | hchrM | Sense | 12001 | 12075 | 75 | 1225 | ACAATGGGGCTCACTCACCCACCACATTAACAACATAAAACCCTCATT CACACGAGAAAACACCCTCATGTTCAT |
| Seq-162 | chrM | Sense | 11494 | 11568 | 75 | 1226 | ----------------C-----T-----------T--T--T-----C-- T--A--CA----C--------------- |
| Seq-162 | hchrM | Sense | 12076 | 12150 | 75 | 1227 | ACACCTATCCCCCATTCTCCTCCTATCCCTCAACCCCGACATCATTAC CGGGTTTTCCTCTTGTAAATATAGTTT |
| Seq-163 | chrM | Sense | 11569 | 11643 | 75 | 1228 | ----------------------------------------C--------- -----------------T-T------- |
| Seq-163 | hchrM | Sense | 12151 | 12225 | 75 | 1229 | AACCAAAACATCAGATTGTGAATCTGACAACAGAGGCTTACGACCCCT TATTTACCGAGAAAGCTCACAAGAACT |
| Seq-164 | chrM | Sense | 11644 | 11718 | 75 | 1230 | --------G-ATT------C------------------------- ----------T---------------- |
| Seq-164 | hchrM | Sense | 12226 | 12300 | 75 | 1231 | GCTAACTCATGCCCCCATGTCTAACAACATGGCTTTCTCAACTTTTAA AGGATAACAGCTATCCATTGGTCTTAG |
| Seq-165 | chrM | Sense | 11719 | 11793 | 75 | 1232 | --------------------------------------------T- TG----C---------T--G----A--- |
| Seq-165 | hchrM | Sense | 12301 | 12375 | 75 | 1233 | GCCCCAAAAATTTTGGTGCAACTCCAAATAAAAGTAATAACCATGCAC ACTACTATAACCACCCTAACCCTGACT |
| Seq-166 | chrM | Sense | 11794 | 11868 | 75 | 1234 | ---T----------------CGG-G-----A------------------ ----------------C--G------ |
| Seq-166 | hchrM | Sense | 12376 | 12450 | 75 | 1235 | TCCCTAATTCCCCCCATCCTTACCACCCTCGTTAACCCTAACAAAAAA AACTCATACCCCCATTATGTAAAATCC |
| Seq-167 | chrM | Sense | 11869 | 11943 | 75 | 1236 | ---A----------------C--T--C--T-------------------- --A---------------AC------- |
| Seq-167 | hchrM | Sense | 12451 | 12525 | 75 | 1237 | ATTGTCGCATCCACCTTTATTATCAGTCTCTTCCCCACAACAATATTC ATGTGCCTAGACCAAGAAGTTATTATC |
| Seq-168 | chrM | Sense | 11944 | 12018 | 75 | 1238 | -----------------A------------------A--------G--- --T-----------T----------C- |
| Seq-168 | hchrM | Sense | 12526 | 12600 | 75 | 1239 | TCGAACTGACACTGAGCCACAACCCAAACAACCCAGCTCTCCCTAAGC TTCAAACTAGACTACTTCTCCATAATA |
| Seq-169 | chrM | Sense | 12019 | 12093 | 75 | 1240 | --T-----C------C-------------A------------------- --A---------G----------C--- |
| Seq-169 | hchrM | Sense | 12601 | 12675 | 75 | 1241 | TTCATCCCTGTAGCATTGTTCGTTACATGGTCCATCATAGAATTCTCA CTGTGATATATAAACTCAGACCCAAAC |
| Seq-170 | chrM | Sense | 12094 | 12168 | 75 | 1242 | --C--C--A-----------CT----T---------------T------ ---C----C----------------- |

TABLE 6-continued

Chimpanzee and Human Mitochondrial Paralogs
chrM = Chimpanzee mitochondrial DNA, hchrM = *Homo Sapiens* mitochondrial DNA,
(—) = Alignment Match, Letter (ACGT) = Corresponding chimpanzee mismatch

| fragment | chr | strand | start | end | width | SEQ ID NO: | amplicon |
|---|---|---|---|---|---|---|---|
| Seq-170 | hchrM | Sense | 12676 | 12750 | 75 | 1243 | ATTAATCAGTTCTTCAAATATCTACTCATCTTCCTAATTACCATACTA ATCTTAGTTACCGCTAACAACCTATTC |
| Seq-171 | chrM | Sense | 12169 | 12243 | 75 | 1244 | -----C--------------A--------------------TC-A--- --T--C-----G---------A----- |
| Seq-171 | hchrM | Sense | 12751 | 12825 | 75 | 1245 | CAACTGTTCATCGGCTGAGAGGGCGTAGGAATTATATCCTTCTTGCTC ATCAGTTGATGATACGCCCGAGCAGAT |
| Seq-172 | chrM | Sense | 12244 | 12318 | 75 | 1246 | -----------------C---------------T-----------T--- --T-----TG----A---C-------- |
| Seq-172 | hchrM | Sense | 12826 | 12900 | 75 | 1247 | GCCAACACAGCAGCCATTCAAGCAATCCTATACAACCGTATCGGCGAT ATCGGTTTCATCCTCGCCTTAGCATGA |
| Seq-173 | chrM | Sense | 12319 | 12393 | 75 | 1248 | ---C---------------------T------------AT---C--- -GTA-----A--GA---T--T------ |
| Seq-173 | hchrM | Sense | 12901 | 12975 | 75 | 1249 | TTTATCCTACACTCCAACTCATGAGACCCACAACAAATAGCCCTTCTA AACGCTAATCCAAGCCTCACCCCACTA |
| Seq-174 | chrM | Sense | 12394 | 12468 | 75 | 1250 | ------T--------------------------T---C----C-- T------------------------- |
| Seq-174 | hchrM | Sense | 12976 | 13050 | 75 | 1251 | CTAGGCCTCCTCCTAGCAGCAGCAGGCAAATCAGCCCAATTAGGTCTC CACCCCTGACTCCCCTCAGCCATAGAA |
| Seq-175 | chrM | Sense | 12469 | 12543 | 75 | 1252 | -----T-----T--T----------------------C-----C--- ------------C-------------- |
| Seq-175 | hchrM | Sense | 13051 | 13125 | 75 | 1253 | GGCCCCACCCCAGTCTCAGCCCTACTCCACTCAAGCACTATAGTTGTA GCAGGAATCTTCTTACTCATCCGCTTC |
| Seq-176 | chrM | Sense | 12544 | 12618 | 75 | 1254 | T-------------G----A------------------C--G------ C----------------C--A------ |
| Seq-176 | hchrM | Sense | 13126 | 13200 | 75 | 1255 | CACCCCCTAGCAGAAAATAGCCCACTAATCCAAACTCTAACACTATGC TTAGGCGCTATCACCACTCTGTTCGCA |
| Seq-177 | chrM | Sense | 12619 | 12693 | 75 | 1256 | --------------C------------------------G------ -----------C--------------- |
| Seq-177 | hchrM | Sense | 13201 | 13275 | 75 | 1257 | GCAGTCTGCGCCCTTACACAAAATGACATCAAAAAAATCGTAGCCTTC TCCACTTCAAGTCAACTAGGACTCATA |
| Seq-178 | chrM | Sense | 12694 | 12768 | 75 | 1258 | --------------T--------------------------T------ --C--------T--------------- |
| Seq-178 | hchrM | Sense | 13276 | 13350 | 75 | 1259 | ATAGTTACAATCGGCATCAACCAACCACACCTAGCATTCCTGCACATC TGTACCCACGCCTTCTTCAAAGCCATA |
| Seq-179 | chrM | Sense | 12769 | 12843 | 75 | 1260 | -----C--A--------A-----T--T--------C--T-----G--- --C-----------------T----- |
| Seq-179 | hchrM | Sense | 13351 | 13425 | 75 | 1261 | CTATTTATGTGCTCCGGGTCCATCATCCACAACCTTAACAATGAACAA GATATTCGAAAAATAGGAGGACTACTC |
| Seq-180 | chrM | Sense | 12844 | 12918 | 75 | 1262 | -----------C-------------------------G--------- --------------C------------ |
| Seq-180 | hchrM | Sense | 13426 | 13500 | 75 | 1263 | AAAACCATACCTCTCACTTCAACCTCCCTCACCATTGGCAGCCTAGCA TTAGCAGGAATACCTTTCCTCACAGGT |
| Seq-181 | chrM | Sense | 12919 | 12993 | 75 | 1264 | -----------------T---------------T--------------- -------------------------- |
| Seq-181 | hchrM | Sense | 13501 | 13575 | 75 | 1265 | TTCTACTCCAAAGACCACATCATCGAAACCGCAAACATATCATACACA AACGCCTGAGCCCTATCTATTACTCTC |
| Seq-182 | chrM | Sense | 12994 | 13068 | 75 | 1266 | -----C-----T--------------C-----C--------C--C--- -------------------------A |

TABLE 6-continued

Chimpanzee and Human Mitochondrial Paralogs
chrM = Chimpanzee mitochondrial DNA, hchrM = Homo Sapiens mitochondrial DNA,
(-) = Alignment Match, Letter (ACGT) = Corresponding chimpanzee mismatch

| fragment | chr | strand | start | end | width | SEQ ID NO: | amplicon |
|---|---|---|---|---|---|---|---|
| Seq-182 | hchrM | Sense | 13576 | 13650 | 75 | 1267 | ATCGCTACCTCCCTGACAAGCGCCTATAGCACTCGAATAATTCTTCTC ACCCTAACAGGTCAACCTCGCTTCCCC |
| Seq-183 | chrM | Sense | 13069 | 13143 | 75 | 1268 | -----C--C--------------C---------T--GT----T------ ---------AA-CATT------T----T |
| Seq-183 | hchrM | Sense | 13651 | 13725 | 75 | 1269 | ACCCTTACTAACATTAACGAAAATAACCCCACCCTACTAAACCCCATT AAACGCCTGGCAGCCGGAAGCCTATTC |
| Seq-184 | hchrM | Sense | 13726 | 13800 | 75 | 1270 | GCAGGATTTCTCATTACTAACAACATTTCCCCCGCATCCCCCTTCCAA ACAACAATCCCCCTCTACCTAAAACTC |
| Seq-185 | chrM | Sense | 13219 | 13293 | 75 | 1271 | ---------A-GC--T----C--------------------------- --T----------G---G--C------ |
| Seq-185 | hchrM | Sense | 13801 | 13875 | 75 | 1272 | ACAGCCCTCGCTGTCACTTTCCTAGGACTTCTAACAGCCCTAGACCTC AACTACCTAACCAACAAACTTAAAATA |
| Seq-186 | chrM | Sense | 13294 | 13368 | 75 | 1273 | --------------AT------C-C-----T--T--------------- ----A---T-T-------T-G------ |
| Seq-186 | hchrM | Sense | 13876 | 13950 | 75 | 1274 | AAATCCCCACTATGCACATTTTATTTCTCCAACATACTCGGATTCTAC CCTAGCATCACACACCGCACAATCCCC |
| Seq-187 | chrM | Sense | 13369 | 13443 | 75 | 1275 | ------------------A-----------A---------T--T------ --G-----------G--A--------- |
| Seq-187 | hchrM | Sense | 13951 | 14025 | 75 | 1276 | TATCTAGGCCTTCTTACGAGCCAAAACCTGCCCCTACTCCTCCTAGAC CTAACCTGACTAGAAAAGCTATTACCT |
| Seq-188 | chrM | Sense | 13444 | 13518 | 75 | 1277 | ----------------T------------G-T-----T-C---------- -----------G--C--------T--- |
| Seq-188 | hchrM | Sense | 14026 | 14100 | 75 | 1278 | AAACAATTTCACAGCACCAAATCTCCACCTCCATCATCACCTCAACC CAAAAAGGCATAATTAAACTTTACTTC |
| Seq-189 | chrM | Sense | 13519 | 13593 | 75 | 1279 | ---------T---------T------T-----T----------------- ----------------------C-- |
| Seq-189 | hchrM | Sense | 14101 | 14175 | 75 | 1280 | CTCTCTTTCTTCTTCCCACTCATCCTAACCCTACTCCTAATCACATAA CCTATTCCCCCGAGCAATCTCAATTAC |
| Seq-190 | chrM | Sense | 13594 | 13668 | 75 | 1281 | ---G--------------------C---------------------C-- ---------------T--G-------- |
| Seq-190 | hchrM | Sense | 14176 | 14250 | 75 | 1282 | AATATATACACCAACAAACAATGTTCAACCAGTAACTACTACTAATCA ACGCCCATAATCATACAAAGCCCCCGC |
| Seq-191 | chrM | Sense | 13669 | 13743 | 75 | 1283 | -----------------------G-----G------C----------- ------A-----C--G--------A-- |
| Seq-191 | hchrM | Sense | 14251 | 14325 | 75 | 1284 | ACCAATAGGATCCTCCCGAATCAACCCTGACCCCTCTCCTTCATAAAT TATTCAGCTTCCTACACTATTAAAGTT |
| Seq-192 | chrM | Sense | 13744 | 13818 | 75 | 1285 | --------------T----------C----T-----T-A---T----- ------------C-GT--T-------- |
| Seq-192 | hchrM | Sense | 14326 | 14400 | 75 | 1286 | TACCACAACCACCACCCCATCATACTCTTTCACCCACAGCACCAATCC TACCTCCATCGCTAACCCCACTAAAAC |
| Seq-193 | chrM | Sense | 13819 | 13893 | 75 | 1287 | ---A-----A-------------------------------------- ---------A--C--------C----- |
| Seq-193 | hchrM | Sense | 14401 | 14475 | 75 | 1288 | ACTCACCAAGACCTCAACCCCTGACCCCCATGCCTCAGGATACTCCTC AATAGCCATCGCTGTAGTATATCCAAA |
| Seq-194 | chrM | Sense | 13894 | 13968 | 75 | 1289 | A--------T--------C------------------C---------T-- -------------T------A---G-- |
| Seq-194 | hchrM | Sense | 14476 | 14550 | 75 | 1290 | GACAACCATCATTCCCCCTAAATAAATTAAAAAAACTATTAAACCCAT ATAACCTCCCCCAAAATTCAGAATAAT |

TABLE 6-continued

Chimpanzee and Human Mitochondrial Paralogs
chrM = Chimpanzee mitochondrial DNA, hchrM = Homo Sapiens mitochondrial DNA,
(-) = Alignment Match, Letter (ACGT) = Corresponding chimpanzee mismatch

| fragment | chr | strand | start | end | width | SEQ ID NO: | amplicon |
|---|---|---|---|---|---|---|---|
| Seq-195 | chrM | Sense | 13969 | 14043 | 75 | 1291 | GG-------A--T-----A----------------------------<br>G------------------------ |
| Seq-195 | hchrM | Sense | 14551 | 14625 | 75 | 1292 | AACACACCCGACCACACCGCTAACAATCAATACTAAACCCCCATAAAT<br>AGGAGAAGGCTTAGAAGAAAACCCCAC |
| Seq-196 | chrM | Sense | 14044 | 14118 | 75 | 1293 | ------T--C-------T---------T-A---T--------TG----<br>-------------------------- |
| Seq-196 | hchrM | Sense | 14626 | 14700 | 75 | 1294 | AAACCCCATTACTAAACCCACACTCAACAGAAACAAAGCATACATCAT<br>TATTCTCGCACGGACTACAACCACGAC |
| Seq-197 | chrM | Sense | 14119 | 14193 | 75 | 1295 | ------------------------------------------------<br>------G-C---------T------A-- |
| Seq-197 | hchrM | Sense | 14701 | 14775 | 75 | 1296 | CAATGATATGAAAAACCATCGTTGTATTTCAACTACAAGAACACCAAT<br>GACCCCAATACGCAAAACTAACCCCCT |
| Seq-198 | chrM | Sense | 14194 | 14268 | 75 | 1297 | -----------------T--------T---------------------<br>---T-----------G----------- |
| Seq-198 | hchrM | Sense | 14776 | 14850 | 75 | 1298 | AATAAAATTAATTAACCACTCATTCATCGACCTCCCCACCCCATCCAA<br>CATCTCCGCATGATGAAACTTCGGCTC |
| Seq-199 | chrM | Sense | 14269 | 14343 | 75 | 1299 | ---T--C-----------A-----T-----T---------T-------<br>---T--A-------------------- |
| Seq-199 | hchrM | Sense | 14851 | 14925 | 75 | 1300 | ACTCCTTGGCGCCTGCCTGATCCTCCAAATCACCACAGGACTATTCCT<br>AGCCATGCACTACTCACCAGACGCCTC |
| Seq-200 | chrM | Sense | 14344 | 14418 | 75 | 1301 | ---------C--G--G--------------C------------C-----<br>T--G--------------C-----T-- |
| Seq-200 | hchrM | Sense | 14926 | 15000 | 75 | 1302 | AACCGCCTTTTCATCAATCGCCCACATCACTCGAGACGTAAATTATGG<br>CTGAATCATCCGCTACCTTCACGCCAA |
| Seq-201 | chrM | Sense | 14419 | 14493 | 75 | 1303 | C--------------T-------------------------C-----<br>T-----------C------------CT |
| Seq-201 | hchrM | Sense | 15001 | 15075 | 75 | 1304 | TGGCGCCTCAATATTCTTTATCTGCCTCTTCCTACACATCGGGCGAGG<br>CCTATATTACGGATCATTTCTCTACTC |
| Seq-202 | chrM | Sense | 14494 | 14568 | 75 | 1305 | ----------------T-------------T----CA----C--------<br>------T--G--------------A-- |
| Seq-202 | hchrM | Sense | 15076 | 15150 | 75 | 1306 | AGAAACCTGAAACATCGGCATTATCCTCCTGCTTGCAACTATAGCAAC<br>AGCCTTCATAGGCTATGTCCTCCCGTG |
| Seq-203 | chrM | Sense | 14569 | 14643 | 75 | 1307 | -------------C--------A-------------------C----G--<br>---T-----------C--A-------- |
| Seq-203 | hchrM | Sense | 15151 | 15225 | 75 | 1308 | AGGCCAAATATCATTCTGAGGGGCCACAGTAATTACAAACTTACTATC<br>CGCCATCCCATACATTGGGACAGACCT |
| Seq-204 | chrM | Sense | 14644 | 14718 | 75 | 1309 | G--C--G---G------------------------C--T-----T--<br>----------C-----C-----T----- |
| Seq-204 | hchrM | Sense | 15226 | 15300 | 75 | 1310 | AGTTCAATGAATCTGAGGAGGCTACTCAGTAGACAGTCCCACCCTCAC<br>ACGATTCTTTACCTTTCACTTCATCTT |
| Seq-205 | chrM | Sense | 14719 | 14793 | 75 | 1311 | A--------C--CA--------A-------T--T-----------A--<br>-------A---------T----------- |
| Seq-205 | hchrM | Sense | 15301 | 15375 | 75 | 1312 | GCCCTTCATTATTGCAGCCCTAGCAACACTCCACCTCCTATTCTTGCA<br>CGAAACGGGATCAAACAACCCCCTAGG |
| Seq-206 | chrM | Sense | 14794 | 14868 | 75 | 1313 | ------------C-----C-----T------------C-----------<br>------TAT---T------T-C--T-- |
| Seq-206 | hchrM | Sense | 15376 | 15450 | 75 | 1314 | AATCACCTCCCATTCCGATAAAATCACCTTCCACCCTTACTACACAAT<br>CAAAGACGCCCTCGGCTTACTTCTCTT |

TABLE 6-continued

Chimpanzee and Human Mitochondrial Paralogs
chrM = Chimpanzee mitochondrial DNA, hchrM = Homo Sapiens mitochondrial DNA,
(—) = Alignment Match, Letter (ACGT) = Corresponding chimpanzee mismatch

| fragment | chr | strand | start | end | width | SEQ ID NO: | amplicon |
|---|---|---|---|---|---|---|---|
| Seq-207 | chrM | Sense | 14869 | 14943 | 75 | 1315 | ---C--TAT-C---------------------------G---------<br>---T--------C-----------T-- |
| Seq-207 | hchrM | Sense | 15451 | 15525 | 75 | 1316 | CCTTCTCTCCTTAATGACATTAACACTATTCTCACCAGACCTCCTAGG<br>CGACCCAGACAATTATACCCTAGCCAA |
| Seq-208 | chrM | Sense | 14944 | 15018 | 75 | 1317 | ----C----------A--------T--A-----G-----C--T-----<br>T-----------C---------A---- |
| Seq-208 | hchrM | Sense | 15526 | 15600 | 75 | 1318 | CCCCTTAAACACCCCTCCCCACATCAAGCCCGAATGATATTTCCTATT<br>CGCCTACACAATTCTCCGATCCGTCCC |
| Seq-209 | chrM | Sense | 15019 | 15093 | 75 | 1319 | C--------------------C------C-------T-----A-----<br>-A--GC------TG-------C-C--- |
| Seq-209 | hchrM | Sense | 15601 | 15675 | 75 | 1320 | TAACAAACTAGGAGGCGTCCTTGCCCTATTACTATCCATCCTCATCCT<br>AGCAATAATCCCCATCCTCCATATATC |
| Seq-210 | chrM | Sense | 15094 | 15168 | 75 | 1321 | -------------------------------------CTG-----C--<br>----------A-------------C-- |
| Seq-210 | hchrM | Sense | 15676 | 15750 | 75 | 1322 | CAAACAACAAAGCATAATATTTCGCCCACTAAGCCAATCACTTTATTG<br>ACTCCTAGCCGCAGACCTCCTCATTCT |
| Seq-211 | chrM | Sense | 15169 | 15243 | 75 | 1323 | ---------------------------------C--C-T--C---C--<br>----A-----------T---------- |
| Seq-211 | hchrM | Sense | 15751 | 15825 | 75 | 1324 | AACCTGAATCGGAGGACAACCAGTAAGCTACCCTTTTACCATCATTGG<br>ACAAGTAGCATCCGTACTATACTTCAC |
| Seq-212 | chrM | Sense | 15244 | 15318 | 75 | 1325 | -----------------------TCGC----T-----C-----------<br>---TG----AA----C----------- |
| Seq-212 | hchrM | Sense | 15826 | 15900 | 75 | 1326 | AACAATCCTAATCCTAATACCAACTATCTCCCTAATTGAAAACAAAAT<br>ACTCAAATGGGCCTGTCCTTGTAGTAT |
| Seq-213 | chrM | Sense | 15319 | 15393 | 75 | 1327 | --------------G---------------A-C------T--C------<br>-------------------AA----- |
| Seq-213 | hchrM | Sense | 15901 | 15975 | 75 | 1328 | AAACTAATACACCAGTCTTGTAAACCGGAGATGAAAACCTTTTTCCAA<br>GGACAAATCAGAGAAAAAGTCTTTAAC |
| Seq-214 | chrM | Sense | 15394 | 15468 | 75 | 1329 | -T------C---------------------------------------<br>------------------A----A--- |
| Seq-214 | hchrM | Sense | 15976 | 16050 | 75 | 1330 | TCCACCATTAGCACCCAAAGCTAAGATTCTAATTTAAACTATTCTCTG<br>TTCTTTCATGGGAAGCAGATTTGGGT |
| Seq-215 | hchrM | Sense | 16051 | 16125 | 75 | 1331 | ACCACCCAAGTATTGACTCACCCATCAACAACCGCTATGTATTTCGTA<br>CATTACTGCCAGCCACCATGAATATTG |
| Seq-216 | hchrM | Sense | 16126 | 16200 | 75 | 1332 | TACGGTACCATAAATACTTGACCACCTGTAGTACATAAAAACCCAATC<br>CACATCAAAACCCCTCCCCATGCTTA |
| Seq-217 | hchrM | Sense | 16201 | 16275 | 75 | 1333 | CAAGCAAGTACAGCAATCAACCCTCAACTATCACACATCAACTGCAAC<br>TCCAAAGCCACCCCTCACCCACTAGGA |
| Seq-218 | chrM | Sense | 15692 | 15766 | 75 | 1334 | --------G-----T-TC-----G----A------------C-A----<br>AC------------------ |
| Seq-218 | hchrM | Sense | 16276 | 16350 | 75 | 1335 | TACCAACAAACCTACCCACCCTTAACAGTACATAGTACATAAAGCCAT<br>TTACCGTACATAGCACATTACAGTCAA |
| Seq-219 | chrM | Sense | 15767 | 15841 | 75 | 1336 | -C----C----C-----C-----CT-------------AA-------<br>GT------------------ |
| Seq-219 | hchrM | Sense | 16351 | 16425 | 75 | 1337 | ATCCTTCTCGTCCCCATGGATGACCCCCCTCAGATAGGGGTCCCTTG<br>ACCACCATCCTCCGTGAAATCAATATC |
| Seq-220 | chrM | Sense | 15840 | 15914 | 75 | 1338 | T-C-G--CA--A-TG--------------------TC-----<br>-------------------------- |

TABLE 6-continued

Chimpanzee and Human Mitochondrial Paralogs
chrM = Chimpanzee mitochondrial DNA, hchrM = *Homo Sapiens* mitochondrial DNA,
(−) = Alignment Match, Letter (ACGT) = Corresponding chimpanzee mismatch

| fragment | chr | strand | start | end | width | SEQ ID NO: | amplicon |
|---|---|---|---|---|---|---|---|
| Seq-220 | hchrM | Sense | 16426 | 16500 | 75 | 1339 | CCGCACAAGAGTGCTACTCTCCTCGCTCCGGGCCCATAACACTTGGGG GTAGCTAAAGTGAACTGTATCCGACAT |
| Seq-1 | chrM | Sense | 15986 | 16060 | 75 | 1340 | --------------------------G----------CT------- ----------------------G-- |
| Seq-1 | hchrM | Sense | 1 | 75 | 75 | 1341 | GATCACAGGTCTATCACCCTATTAACCACTCACGGGAGCTCTCCATGC ATTTGGTATTTTCGTCTGGGGGGTATG |

Example 6—Amplification and Primer Extension of Chimpanzee Mitochondrial/Human Mitochondrial Paralogs and Chimpanzee Nuclear/Human Nuclear Paralogs All samples were set up in 25 ul PCR reactions.

For circulating cell free DNA three parallel reactions were run using a different amount of chimpanzee DNA in each reaction, as the DNA concentration of the liquid biopsy sample is not known. Reactions were evaluated based on dynamic range. For each sample 3 wells were used. Each well had a different chimpanzee DNA amount (1 ng, 0.5 ng, and 0.125 ng total input).

1. Three concentrations of chimpanzee DNA; 0.0625 ng/uL, 0.125 ng/uL, and 0.5 ng/ul were prepared. Estimation of the number of chimpanzee nuclear and mitochondrial genomic equivalents (copy number) were carried out using the Biorad QX200 digital droplet PCR.
2. PCR Mastermix was prepared.

|  | Final Conc. | uL/rxn |
|---|---|---|
| RNAse-free Water | N/A | 3.375 |
| 10X PCR buffer with 20 mM MgCl2 | 1X (2 mM MgCl2) | 2.5 |
| MgCl2, 25 mM | 2 mM | 2 |
| dUTP/dNTP Mix, 25 mM | 500 uM | 0.5 |
| Primer Mix, 500 nM | 100 nM | 5 |
| UNG Enzyme (5 U/uL) | 0.125 U/uL | 0.625 |
| PCR Enzyme (5 U/uL) | 1 U/rxn | 1 |
| Mastermix Total |  | 15 |
| ccfDNA |  | 8 |
| Chimp DNA |  | 2 |
| Total |  | 25 |

PCR and single base extension primers are described in Table 7.

3. 8 uL ccfDNA & 2 uL Chimp DNA were added to wells of a 96-well plate.
4. 15 uL PCR Mix was added to each well.
5. Wells were mixed by vortexing the plate and spun down briefly.
6. Thermocycling was carried out using the following parameters.

| PCR Cycle | Cycling | Number of Cycles |
|---|---|---|
| Initial Incubation | 30° C. for 10:00 | 1 Cycle |
| Initial Denaturation | 95° C. for 2:00 | 1 Cycle |
| Cycled Template Denaturation | 95° C. for 0:30 | 45 Cycles |
| Cycled Primer Annealing | 56° C. for 0:30 |  |
| Cycled Primer Extension | 72° C. for 1:00 |  |
| Final Extension | 72° C. for 5:00 | 1 Cycle |
| Hold | 4° C. for ∞ |  |

7. Following completion of PCR, 5 uL from each well were transferred to a well of a new plate.
8. SAP Mastermix was prepared (see table below) and 2 uL SAP Mastermix was added to each reaction.

| SAP | Final Conc. | 7 uL rxn |
|---|---|---|
| Water | N/A | 1.53 |
| SAP Buffer | 10X | 0.17 |
| SAP Enzyme | 1.7 U/ul | 0.3 |

9. Thermocycling was carried out using the following parameters.

| SAP Cycle | Cycling Conditions | Number of Cycles |
|---|---|---|
| Initial Incubation | 37° C. for 40:00 | 1 Cycle |
| Cycled Template Denaturation | 85° C. for 5:00 | 1 Cycle |
| Hold | 4° C. for ∞ |  |

10. Single base extension was performed. Extend Mastermix was prepared (see table below) and 2 uL EXT Mastermix was added to each reaction.

| EXT | Final Conc. | 9 uL rxn |
|---|---|---|
| Water | N/A | 0.619 |
| iPLEX Buffer Plus (10X) | 0.222x | 0.2 |
| iPLEX Termination Mix | 0.222x | 0.2 |
| Primer Mix | Various | 0.94 |
| Thermosequenase | 0.15 U/uL | 0.041 |

11. Thermocycling was carried out using the following parameters.

| PCR Cycle | Cycling Conditions | Number of Cycles |
|---|---|---|
| Initial Denaturation | 95° C. for 0:30 | 1 Cycle |
| Cycled Template Denaturation | 95° C. for 0:05 | 40 Cycles |
| Cycled Primer Annealing | 52° C. for 0:05 | 5 Cycles |
| Cycled Primer Extension | 80° C. for 0:05 | |
| Final Denaturation | 72° C. for 3:00 | |
| Hold | 4° C. | |

12. Following completion of PCR, reactions were processed on the CPM or Nanodispenser and MA4 analyzer. After 41 ul of water addition and desalting by the addition of 15 mg Clean Resin, 15 nL of each extend mixture was transferred to a SpectroCHIP® II-G384 and Mass spectra were recorded using a MassARRAY System. Spectra were acquired using SpectroAcquire software (Agena Bioscience, San Diego). The software parameters were set to acquire 20 shots from each of 5 raster positions. The resulting mass spectra were summed and peak detection and intensity analysis performed using Typer 4 software (Agena Bioscience, San Diego).

TABLE 7

PCR and Primer Extension Primers

| SNIP_ID | Forward PCRprimer | SEQ ID NO: | Reverse PCRprimer | SEQ ID NO: | UEP_DIR | UEP_MASS | UEP | SEQ ID NO: |
|---|---|---|---|---|---|---|---|---|
| chr1_AtoC | ACGTTGGATGCAAGGCATGCCTGTATACTC | 1342 | ACGTTGGATGGTAACAACGCAGAGCTCAGG | 1343 | R | 8457 | agGCCTGTATACTCTCTCCTGTTATCCT | 1344 |
| chr10_AtoC | ACGTTGGATGGAAGCTCCTCCTTGCTCTTC | 1345 | ACGTTGGATGGGAAAAACTAGAGAAAGAGC | 1346 | R | 7053 | ggCTGCTGCAGGGCTTTTATTTC | 1347 |
| chr12_CtoG | ACGTTGGATGTAGAGGTGATACACTTACCG | 1348 | ACGTTGGATGGACCAAAGAAGTAAACACTG | 1349 | R | 5034 | CATTTCCCTCCAAACAC | 1350 |
| chr19_CtoG | ACGTTGGATGCCTCCCGGCCACAGAGTGTG | 1351 | ACGTTGGATGGGATGACAAAGATGCCAGGC | 1352 | F | 5944 | CCCGCCCTCCCTCAGAGCCA | 1353 |
| chr20_TtoA | ACGTTGGATGAAGGGAACAGGAGTGAGTG | 1354 | ACGTTGGATGTCTTCCAGTCCCTGATCTGG | 1355 | R | 8364 | tTAATGCCAACCATGGGATAGTGTGAG | 1356 |
| Mito-01240 | ACGTTGGATGGGGTTTGCTGAAGATGGCGG | 1357 | ACGTTGGATGCTGCTCGCCAGAACACTACG | 1358 | R | 7836 | GGCGGTATATAGGCTGAGCAAGAGG | 1359 |
| Mito-02522 | ACGTTGGATGGTCCCTATTTAAGGAACAAG | 1360 | ACGTTGGATGCTCGGCAAATCTTACCCCGC | 1361 | R | 7689 | gtCAGGCGGTGCCTCTAATACTGGT | 1362 |
| Mito-05747 | ACGTTGGATGGGTGATTTTCATATTGAATTG | 1363 | ACGTTGGATGCACCCTAATCAACTGGCTTC | 1364 | R | 7278 | gaCGGGGCTTCTCCCGCCTTTTTT | 1365 |
| Mito-07471 | ACGTTGGATGTTTTGAAAAAGTCATGGAGG | 1366 | ACGTTGGATGTGACTATATGGATGCCCCCC | 1367 | R | 5185 | GGCTTGAAACCAGCTTT | 1368 |
| Mito-09066 | ACGTTGGATGGCACACCTACACCCCTTATC | 1369 | ACGTTGGATGGTGGCGCTTCCAATTAGGTG | 1370 | F | 6294 | CTACTCATTCAACCAATAGCC | 1371 |
| Mito-10477 | ACGTTGGATGCTGAACCGAATTGGTATATAG | 1372 | ACGTTGGATGAGGTGTGAGCGATATACTAG | 1373 | F | 5394 | TATTTACCAAATGCCCCT | 1374 |
| Mito-13487 | ACGTTGGATGGTAATAGATAGGGCTCAGGC | 1375 | ACGTTGGATGCTCACTTCAACCTCCCTCAC | 1376 | R | 6833 | ctGAGTAGAAACCTGTGAGGAA | 1377 |
| Mito-16467 | ACGTTGGATGCACCATCCTCCGTGAAATC | 1378 | ACGTTGGATGGGTTAATAGGGTGATAGACC | 1379 | F | 5783 | gaGCTCCGGGCCCATAACA | 1380 |

| SNP_ID | Allele1_MASS | Allele 1 | SEQ ID NO: | Allele2_MASS | Allele 2 | SEQ ID NO: |
|---|---|---|---|---|---|---|
| chr1_AtoC | 8743.7 | agGCCTGTATACTCTCTCCTGTTATCCTG | 1381 | 8783.6 | agGCCTGTATACTCTCTCCTGTTATCCTT | 1382 |
| chr10_AtoC | 7339.8 | ggCTGCTGCAGGGCTTTTATTTCG | 1383 | 7379.7 | ggCTGCTGCAGGGCTTTTATTTCT | 1384 |

TABLE 7-continued

PCR and Primer Extension Primers

| | | | | | | |
|---|---|---|---|---|---|---|
| chr12_CtoG | 5281.5 | CATTTCCCTCCAAACACC | 1385 | 5321.5 | CATTTCCCTCCAAACACG | 1386 |
| chr19_CtoG | 6191 | CCCGCCCTCCCTCAGAGCCAC | 1387 | 6231.1 | CCCGCCCTCCCTCAGAGCCAG | 1388 |
| chr20_TtoA | 8634.7 | tTAATGCCAACCATGGGATAGTGTGAGA | 1389 | 8690.5 | tTAATGCCAACCATGGGATAGTGTGAGT | 1390 |
| Mito-01240 | 8083.3 | GGCGGTATATAGGCTGAGCAAGAGGC | 1391 | 8163.2 | GGCGGTATATAGGCTGAGCAAGAGGT | 1392 |
| Mito-02522 | 7960.2 | gtCAGGCGGTGCCTCTAATACTGGTA | 1393 | 7976.2 | gtCAGGCGGTGCCTCTAATACTGGTG | 1394 |
| Mito-05747 | 7524.9 | gaCGGGGCTTCTCCCGCCTTTTTC | 1395 | 7604.8 | gaCGGGGCTTCTCCCGCCTTTTTTT | 1396 |
| Mito-07471 | 5456.6 | GGCTTGAAACCAGCTTTA | 1397 | 5472.6 | GGCTTGAAACCAGCTTTG | 1398 |
| Mito-09066 | 6541.3 | CTACTCATTCAACCAATAGCCC | 1399 | 6621.2 | CTACTCATTCAACCAATAGCCT | 1400 |
| Mito-10477 | 5640.7 | TATTTACCAAATGCCCCTC | 1401 | 5720.6 | TATTTACCAAATGCCCCTT | 1402 |
| Mito-13487 | 7103.7 | ctGAGTAGAAACCTGTGAGGAAA | 1403 | 7119.7 | ctGAGTAGAAACCTGTGAGGAAG | 1404 |
| Mito-16467 | 6030 | gaGCTCCGGGCCCATAACAC | 1405 | 6109.9 | gaGCTCCGGGCCCATAACAT | 1406 |

Example 7 Quantification of the Mitochondrial/Nuclear Ratio Using a Multiplex Assay Targeting Human and Chimpanzee Paralogs Samples were obtained from a single subject over the course of 1 month. Samples were obtained prior to start of a treatment and additional samples were obtained at start, halfway and at the end of treatment. Circulating cell free DNA was extracted and subjected to co-amplification with a known amount of chimpanzee DNA. The DNA was subjected to multiplex amplification in a single reaction using a panel consisting of 7 mitochondrial and 5 nuclear amplicons. PCR and single base extension primers used are shown in Table 8.

TABLE 8

Assay Design MitoChimp

| WELL | TERM | SNP_ID | 2nd-PCRP | SEQ ID NO: | 1st-PCRP | SEQ ID NO: | AMP_LEN | UP_CONF | MP_CONF | Tm (NN) | PcGC |
|---|---|---|---|---|---|---|---|---|---|---|---|
| W1 | iPLEX | chr1_AtoC | ACGTTGGATGCAAGGCATGCCTGTATACTC | 1407 | ACGTTGGATGGTAACAACGCAGAGCTCAGG | 1408 | 141 | 94.5 | 98.2 | 55.3 | 46.2 |
| W1 | iPLEX | chr10_AtoC | ACGTTGGATGGAAGCTCCTCCTTGCTCTTC | 1409 | ACGTTGGATGGGAAAAACTAGAGAAAGAGC | 1410 | 127 | 88.1 | 98.2 | 52.8 | 47.6 |
| W1 | iPLEX | chr12_CtoG | ACGTTGGATGTAGAGGTGATACACTTACCG | 1411 | ACGTTGGATGGACCAAAGAAGTAAACACTG | 1412 | 133 | 88.6 | 98.2 | 45.4 | 47.1 |
| W1 | iPLEX | chr19_CtoG | ACGTTGGATGCCTCCCGGCCACAGAGTGTG | 1413 | ACGTTGGATGGGATGACAAAGATGCCAGGC | 1414 | 122 | 88.5 | 98.2 | 64 | 75 |
| W1 | iPLEX | chr20_TtoA | ACGTTGGATGAAGGGAACAGGAGTGAGTG | 1415 | ACGTTGGATGTCTTCCAGTCCCTGATCTGG | 1416 | 119 | 85.6 | 98.2 | 57.2 | 46.2 |
| W1 | iPLEX | Mito-01240 | ACGTTGGATGGGGTTTGCTGAAGATGGCGG | 1417 | ACGTTGGATGCTGCTCGCCAGAACACTACG | 1418 | 174 | 100 | 98.2 | 58.9 | 56 |

TABLE 8-continued

Assay Design MitoChimp

| | | | | | | | | | | | |
|---|---|---|---|---|---|---|---|---|---|---|---|
| W1 | iPLEX | Mito-02522 | ACGTTGGATGGTCCCTATTTAAGGAACAAG | 1419 | ACGTTGGATGCTCGGCAAATCTTACCCCGC | 1420 | 172 | 96.8 | 98.2 | 59 | 56.5 |
| W1 | iPLEX | Mito-05747 | ACGTTGGATGGGTGATTTTCATATTGAATTG | 1421 | ACGTTGGATGCACCCTAATCAACTGGCTTC | 1422 | 136 | 86.1 | 98.2 | 60.8 | 59.1 |
| W1 | iPLEX | Mito-07471 | ACGTTGGATGTTTTGAAAAAGTCATGGAGG | 1423 | ACGTTGGATGTGACTATATGGATGCCCCCC | 1424 | 156 | 93.6 | 98.2 | 48.3 | 47.1 |
| W1 | iPLEX | Mito-09066 | ACGTTGGATGGCACACCTACACCCCTTATC | 1425 | ACGTTGGATGGTGGCGCTTCCAATTAGGTG | 1426 | 160 | 98.7 | 98.2 | 48.7 | 42.9 |
| W1 | iPLEX | Mito-13487 | ACGTTGGATGGTAATAGATAGGGCTCAGGC | 1427 | ACGTTGGATGCTCACTTCAACCTCCCTCAC | 1428 | 154 | 97.3 | 98.2 | 49.1 | 45 |
| W1 | iPLEX | Mito-16467 | ACGTTGGATGCACCATCCTCCGTGAAATC | 1429 | ACGTTGGATGGGTTAATAGGGTGATAGACC | 1430 | 147 | 92.5 | 98.2 | 55.1 | 64.7 |

| GNP_ID | PWARN | UEP_DIR | UEP_MASS | UEP_SEQ | SEQ ID NO | EXT1_CALL | EXT1_MASS | EXT1_SEQ | SEQ ID NO: | EXT2_CALL |
|---|---|---|---|---|---|---|---|---|---|---|
| chr1_AtoC | | R | 8457 | agGCCTGTATACTCTCTCCTGTTATCCT | 1431 | C | 8744 | agGCCTGTATACTCTCTCCTGTTATCCTG | 1432 | A |
| chs10_AtoC | | R | 7053 | ggCTGCTGCAGGGCTTTTATTTC | 1433 | C | 7340 | ggCTGCTGCAGGGCTTTTATTTCG | 1434 | A |
| chr12_CtoG | | R | 5034 | CATTTCCCTCCAAACAC | 1435 | G | 5282 | CATTTCCCTCCAAACACC | 1436 | C |
| chr19_CtoG | h | F | 5944 | CCCGCCCTCCCTCAGAGCCA | 1437 | C | 6191 | CCCGCCCTCCCTCAGAGCCAC | 1438 | G |
| chr20_TtoA | h | R | 8364 | tTAATGCCAACCATGGGATAGTGTGAG | 1439 | T | 8635 | tTAATGCCAACCATGGGATAGTGTGAGA | 1440 | A |
| Mito-01240 | | R | 7836 | GGCGGTATATAGGCTGAGCAAGAGG | 1441 | G | 8083 | GGCGGTATATAGGCTGAGCAAGAGGC | 1442 | A |
| Mito-02522 | | R | 7689 | gtCAGGCGGTGCCTCTAATACTGGT | 1443 | T | 7960 | gtCAGGCGGTGCCTCTAATACTGGTA | 1444 | C |
| Mito-05747 | g | R | 7278 | gaCGGGGCTTCTCCCGCCTTTTTT | 1445 | G | 7525 | gaCGGGGCTTCTCCCGCCTTTTTTC | 1446 | A |
| Mito-07471 | | R | 5185 | GGCTTGAAACCAGCTTT | 1447 | T | 5457 | GGCTTGAAACCAGCTTTA | 1448 | C |
| Mito-09066 | | F | 6294 | CTACTCATTCAACCAATAGCC | 1449 | C | 6541 | CTACTCATTCAACCAATAGCCC | 1450 | T |
| Mito-13487 | h | R | 6833 | ctGAGTAGAAACCTGTGAGGAA | 1451 | T | 7104 | ctGAGTAGAAACCTGTGAGGAAA | 1452 | C |
| Mito-16467 | h | F | 5783 | gaGCTCCGGGCCCATAACA | 1453 | C | 6030 | gaGCTCCGGGCCCATAACAC | 1454 | T |

| SNP_ID | EXT2_MASS | EXT2_SEQ | SEQ ID NO: |
|---|---|---|---|
| chr1_AtoC | 8784 | agGCCTGTATACTCTCTCCTGTTATCCTT | 1455 |
| chr10_AtoC | 7380 | ggCTGCTGCAGGGCTTTTATTTCT | 1456 |
| chr12_CtoG | 5322 | CATTTCCCTCCAAACACG | 1457 |

TABLE 8-continued

Assay Design MitoChimp

| chr19_CtoG | 6231 | CCCGCCCTCCCTCAGAGCCAG | 1458 |
| --- | --- | --- | --- |
| chr20_TtoA | 8691 | tTAATGCCAACCATGGGATAGTGTGAGT | 1459 |
| Mito-01240 | 8163 | GGCGGTATATAGGCTGAGCAAGAGGT | 1460 |
| Mito-02522 | 7976 | gtCAGGCGGTGCCTCTAATACTGGTG | 1461 |
| Mito-05747 | 7605 | gaCGGGGCTTCTCCCGCCTTTTTTT | 1462 |
| Mito-07471 | 5473 | GGCTTGAAACCAGCTTTG | 1463 |
| Mito-09066 | 6621 | CTACTCATTCAACCAATAGCCT | 1464 |
| Mito-13487 | 7120 | ctGAGTAGAAACCTGTGAGGAAG | 1465 |
| Mito-16467 | 6110 | gaGCTCCGGGCCCATAACAT | 1466 |

Figure 1B:
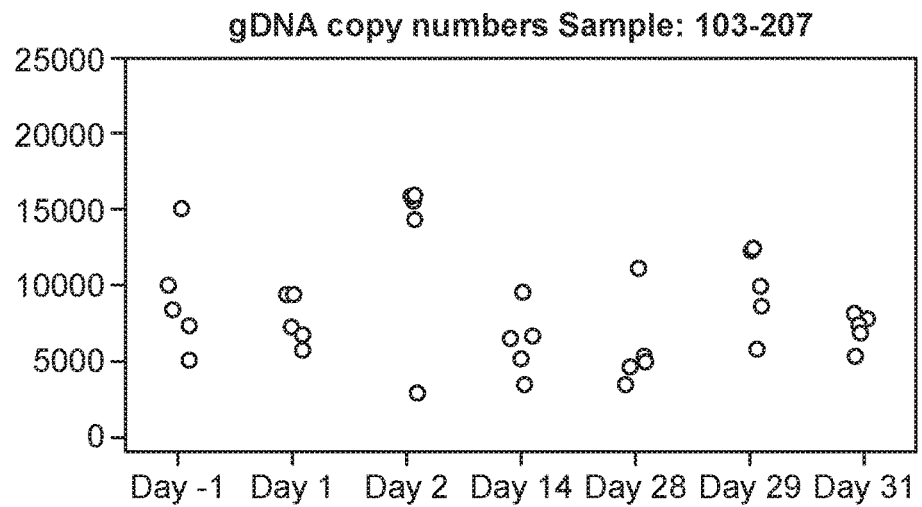
Figure 1C:
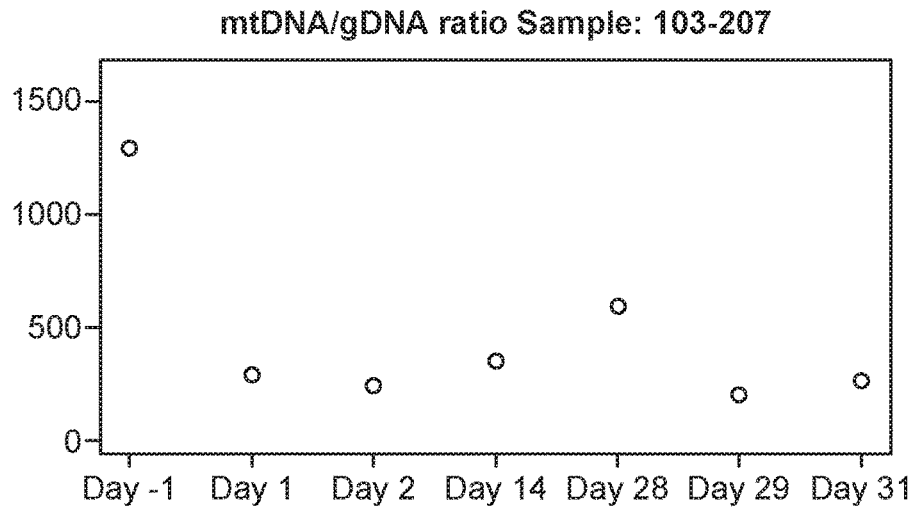

Mitochondria copy numbers (FIG. 1A) and nuclear copy numbers (FIG. 1B) were calculated and used for determining the mitochondrial vs nuclear ratio (FIG. 1C) at each time point. In order to minimize variance a mean of the calculated nuclear and mitochondrial copy numbers were used to determine the ratio. As can be seen in the FIG. 1A there was spike in mitochondrial copy numbers at time point day −1 after which the mitochondrial copy numbers for the subject stabilized.

Example 8—Non-Limiting Examples of Embodiments

Provided hereafter are non-limiting examples of certain embodiments of the technology.

A1. A multiplex method for determining dosage of mitochondrial nucleic acid relative to genomic nucleic acid for a sample from a subject, comprising:
  a. amplifying sets of mitochondrial polynucleotides and genomic polynucleotides from nucleic acid for a sample under amplification conditions, wherein: (i) each set comprises a mitochondrial polynucleotide and a genomic polynucleotide; (ii) the mitochondrial polynucleotide and the genomic polynucleotide are native; (iii) the mitochondrial polynucleotide of a set differs from the mitochondrial polynucleotide of the other sets and the genomic polynucleotide of a set differs from the genomic polynucleotide of the other sets; (iv) the mitochondrial polynucleotide and the genomic polynucleotide of a set are defined by formula $5'X\text{-}V\text{-}Y3'$; (v) $5'X\text{-}V\text{-}Y3'$ represents a contiguous sequence of nucleotides present in the mitochondrial polynucleotide and the genomic polynucleotide; (vi) X and Y of the mitochondrial polynucleotide are identical to X and Y, respectively, of the genomic polynucleotide in each set; (vii) V is one or more nucleotide positions at which a nucleotide of the mitochondrial polynucleotide differs from the corresponding nucleotide of the genomic polynucleotide in a set;
  thereby providing a plurality of amplified sets each comprising amplicons corresponding to all or a portion of the mitochondrial polynucleotide and amplified genomic polynucleotide in the set;
  b. comparing (i) the amplicons corresponding to the mitochondrial polynucleotide, to (ii) the amplicons corresponding to the genomic polynucleotide for each set, thereby generating a comparison; and
  c. determining the relative dosage of mitochondrial nucleic acid to genomic nucleic acid in the sample based on the comparison.

A1.1. The method of embodiment A1, wherein the comparison in (b) is a ratio of (i) the amount of the amplicons corresponding to the mitochondrial polynucleotide, to (ii) the amount of the amplicons corresponding to the genomic polynucleotide, in each set and determining the relative dosage of mitochondrial nucleic acid to genomic nucleic acid in the sample in (c) is based on the ratio.

A2. The method of embodiment A1 or A1.1, wherein the nucleic acid for the sample is DNA.

A3. The method of any one of embodiments of A1 to A2, wherein amplifying is by a polymerase chain reaction (PCR) process.

A4. The method of any one of embodiments A1 to A3, wherein V is a single nucleotide position.

A5. The method of any one of embodiments A1 to A4, wherein $5'X\text{-}V\text{-}Y3'$ is about 30 base pairs to about 300 base pairs in length.

A6. The method of any one of embodiments A1 to A5, wherein the lengths of the amplicons are about 30 base pairs to about 300 base pairs.

A7. The method of any one of embodiments A1 to A6, wherein the plurality of amplified sets is about 2 sets to about 20 sets.

A8. The method of any one of embodiments A1 to A7, wherein the plurality of amplified sets is about 2 sets to about 10 sets.

A9. The method of any one of embodiments A1 to A6, wherein the plurality of amplified sets is at least 5 sets.

A10. The method of any one of embodiments A1 to A9, wherein the mitochondrial polynucleotide and/or the genomic polynucleotide of a set comprise polynucleotides or portions thereof chosen from Table 1.

A11. The method of any one of embodiments A1 to A10, wherein the mitochondrial polynucleotide and the genomic polynucleotide of a set are reproducibly amplified relative to each other by a single pair of amplification primers that hybridize to a polynucleotide within X and Y.

A12. The method of any one of embodiments A1 to A10, wherein the mitochondrial polynucleotide and the genomic polynucleotide of a set are amplified by different species specific pairs of amplification primers.

A13. The method of embodiment A12, wherein amplification primers hybridize to flanking polynucleotides that are 5' to X and 3' to Y and are different between mitochondrial and genomic polynucleotides at one or more nucleotide positions.

A13.1. The method of any one of embodiments A1 to A10, wherein the amplification is by an amplification primer that hybridizes to a polynucleotide within X for both species and two species specific amplification primers that hybridize 3' to Y.

A13.2. The method of any one of embodiments A1 to A10, wherein the amplification is by an amplification primer that hybridizes to a polynucleotide within Y for both species and two species specific amplification primers that hybridize 5' to X.

A14. The method of any one of embodiments A12 to A13.2, wherein the amplification primer or primers that are specific for the mitochondrial polynucleotide hybridize less efficiently than the amplification primer or primers that are specific for the genomic polynucleotide in a set, whereby the amplicons corresponding to the mitochondrial polynucleotide are reduced with respect to the amplicons corresponding to the genomic polynucleotide in each set.

A15. The method of any one of embodiments A12 to A14, wherein the amplification primer or primers that specifically hybridize to the mitochondrial polynucleotides are provided at a lower concentration than the concentration of the amplification primer or primers that specifically hybridize to genomic polynucleotides, whereby the amplicons corresponding to the mitochondrial polynucleotide are reduced with respect to the amplicons corresponding to the genomic polynucleotide in each set.

A15.1 The method of embodiment A13.1, wherein the amplification primer that hybridizes to a polynucleotide within X is at the same concentration as the species specific amplification primer that hybridizes 3' to Y for a genomic polynucleotide and the species specific amplification primer that hybridizes 3' to Y for a mitochondrial polynucleotide is at a lower concentration.

A15.2 The method of embodiment A13.2, wherein the amplification primer that hybridizes to a polynucleotide within Y is at the same concentration as the species specific amplification primer that hybridizes 5' to X for a genomic polynucleotide and the species specific amplification primer that hybridizes 5' to X for a mitochondrial polynucleotide is at a lower concentration.

A16. The method of embodiment A15, wherein the concentration of the amplification primer or primers that specifically hybridize to the mitochondrial polynucleotide is about 2× to about 30× less than the concentration of amplification primer or primers that specifically hybridize to the genomic polynucleotide in a set.

A17. The method of any one of embodiments A1 to A16, wherein the nucleic acid for the sample comprises circulating cell free nucleic acid (ccfDNA) and the size of the amplicons is greater than about 50 bp and less than about 166 bp.

A18. The method of embodiment A17, wherein the size of the amplicons is greater than about 60 bp and less than about 100 bp.

A19. The method of embodiment A18, wherein the size of the amplicons is greater than about 70 bp and less than about 100 bp.

A20. The method of any one of embodiments A1 to A19, wherein (b) comprises determining the amount of a nucleotide at V in the amplicons corresponding to the mitochondrial polynucleotide of a set and the amount of the nucleotide at V in the amplicons corresponding to the genomic polynucleotide of a set.

A21. The method of embodiment A20, wherein determining the amount of a nucleotide at V in the amplicons corresponding to the mitochondrial polynucleotide of a set and the amount of the nucleotide at V in the amplicons corresponding to the genomic polynucleotide of a set is by massive parallel sequencing process.

A22. The method of embodiment A21, wherein the sequencing is by a sequencing by synthesis process.

A23. The method of embodiments A21 or A22, wherein a sequence tag or barcode is attached to one or more primers in each amplification primer pair.

A24. The method of embodiment A20, wherein determining the amount of a nucleotide at V in the amplicons corresponding to the mitochondrial polynucleotide of a set and the amount of the nucleotide at V in the amplicons corresponding to the genomic polynucleotide of a set is by a nanopore process.

A25. The method of embodiment A20, wherein (b) comprises determining the amount of amplicons corresponding to the mitochondrial polynucleotide of a set and the amount of amplicons corresponding to the genomic polynucleotide of a set by a qPCR process comprising two fluorescent probes each specific for either the mitochondrial or genomic nucleotide at V or a digital PCR process.

A26. The method of embodiment A20, wherein (b) comprises contacting the amplicons with extension primers under extension conditions comprising chain terminating reagents, wherein:
    (1) the chain terminating reagent that is specific for the amplicons corresponding to the mitochondrial polynucleotide is not specific for the amplicons corresponding to the genomic polynucleotide; and
    (2) the chain terminating reagent specific for the amplicons corresponding to the genomic polynucleotide is not specific for the amplicons corresponding to mitochondrial polynucleotide,
    whereby the primers are extended up to V, thereby generating chain terminated extension products corresponding to the mitochondrial polynucleotide and the genomic polynucleotide, respectively, wherein: (1) the concentration of each of the chain terminating reagents is known; and (2) the concentration of the chain terminating reagent specific for the mitochondrial polynucleotide is less than the concentration of the chain terminating reagent specific for the genomic polynucleotide.

A27. The method of embodiment A26, wherein (b) comprises determining a ratio of the amount of extension product corresponding to the mitochondrial polynucleotide to the amount of extension product corresponding to the genomic polynucleotide; and (c) comprises determining the amount of mitochondrial nucleic acid relative to the amount of genomic nucleic acid in the sample based on the ratio of (b).

A28. The method of any one of embodiments A1 to A27, wherein for the sets of a mitochondrial polynucleotides and a genomic polynucleotides (a) and (b) are performed in a single reaction vessel or a single reaction vessel compartment.

A29. The method of embodiment A26 or A27, wherein (a) and (b) are performed in at least two reaction vessels or at least two reaction vessel compartments and each reaction vessel or vessel compartment comprises at least two sets of mitochondrial and genomic polynucleotides.

A30. The method of any one of embodiments A26 to A29, wherein V is a single nucleotide position at which a nucleotide of the mitochondrial polynucleotide differs from the corresponding nucleotide of the genomic polynucleotide and the primers are extended up to the single nucleotide.

A31. The method of any one of embodiments A26 to A30, wherein the concentration of the chain terminating reagent specific for a mitochondrial polynucleotide is between about 1% to about 20% of the concentration of the chain terminating reagent specific for a genomic polynucleotide.

A32. The method of any one of embodiments A26 to A31, wherein the chain terminating reagents are chain terminating nucleotides.

A33. The method of embodiment A32, wherein the chain terminating nucleotides independently are selected from among ddATP, ddGTP, ddCTP, ddTTP and ddUTP.

A34. The method of any one of embodiments A26 to A33, wherein the chain terminating reagents comprise one or more acyclic terminators.

A35. The method of any one of embodiments A26 to A34, wherein one or more of the chain terminating reagents comprises a detectable label.

A36. The method of embodiment A35, wherein the label is a fluorescent label or dye.

A37. The method of embodiment A35, wherein the label is a mass label and detection is by mass spectrometry.

A38. The method of any one of embodiments A1-A37, comprising between about 25 to about 45 PCR amplification cycles in (a).

A39. The method of any one of embodiments A26 to A38, wherein the extension conditions in (b) comprise between about 20 to about 300 cycles.

A40. The method of any one of embodiments A1.1 to A39, wherein the ratios for a plurality of sets are combined and the relative dosage of mitochondrial nucleic acid to genomic nucleic acid for the sample is determined based on the combined ratio.

A41. The method of embodiment A40, wherein the combined ratio is an average ratio or a median ratio.

A42. The method of any one of embodiments A1.1 to A41, wherein the ratio of each set is compared to an average or median ratio based on the plurality of sets and an outlier or cluster that deviates from the average or median ratio is an indication of a mitochondrial deletion.

A42.1. The method of any one of embodiments A1.1 to A41, wherein the ratio of a set representing one region of the mitochondrial genome is compared to the ratio of each of the other sets representing different regions of the mitochondrial genome and the presence of one or more deletions in the mitochondrial genome is determined based on a difference in the ratio of the set representing the one region compared with the ratios for one or more sets representing other regions of the mitochondrial genome.

A43. The method of any one of embodiments A1 to A42, wherein a baseline value for the dosage of mitochondrial nucleic acid relative to genomic nucleic acid is determined for the subject or a population of subjects and the dosage of mitochondrial nucleic acid relative to genomic nucleic acid for the sample from the subject is compared to the baseline value.

A44. The method of any one of embodiments A1 to A43, wherein the dosage of mitochondrial nucleic acid relative to genomic nucleic acid for the sample from the subject is used in determining the likelihood the subject has or is predisposed to having a disease, disorder or symptoms associated with an increase or decrease in the dosage of mitochondria nucleic acid or a deletion in the mitochondrial genome.

A45. The method of embodiment A44, wherein the disease or disorder is a neurodegenerative disease, a cancer, a disease or disorder associated with mitochondrial stability, a disease or disorder associated with a mitochondrial deletion, a metabolic disease, a cardiovascular disease, a disease or disorder associated with oxidative stress, a disease or disorder associated with infertility or a disease or disorder associated with sepsis.

A45.1. The method of embodiment A44, wherein the disease or disorder is Parkinson's disease, Alzheimers disease, Friedreich's Ataxia, Amyotropic lateral sclerosis, Multiple sclerosis (MS), POLG associated diseases, Opthalmoplegia, Alper's syndrome, Leigh's syndrome, Kearns-Sayre syndrome (KSS), Leber's heredity optic neuropathy (LHON), Mitochondiral encephalomyopathy, lactic acidosis, stroke like episodes (MELAS), Myoclonic Epilepsy with Ragged Red Fibers (MERRF), gastric cancer, hepatocellular carcinoma (HCC) HPV related cancer, breast cancer, Ewing's Sarcoma, pancreatic cancer, liver cancer, testicular cancer, prostate cancer, renal cell carcinoma (RCC), bladder cancer, ovarian cancer, obesity, diabetes, pre-diabetes, diabetic retinopathy, diabetic cardiomyopathies, coronary heart disease and sepsis.

A45.2.2. The method of any one of embodiments A1 to A43, wherein the dosage of mitochondrial nucleic acid relative to genomic nucleic acid for the sample from the subject is used to monitor the efficacy of treatment of the subject for a disease, disorder or symptoms associated with an increase or decrease in the dosage of mitochondria nucleic acid or a deletion in the mitochondrial genome.

A46. The method of any one of embodiments A1 to A45, wherein the sample comprises circulating cell free nucleic acid.

A46.1. The method of embodiment A46, wherein the sample is chosen from blood plasma, blood serum, spinal fluid, cerebrospinal fluid and urine.

B1. A kit comprising amplification primer pairs that comprise polynucleotides chosen from polynucleotides of Table 2 and Table 4 or portions thereof.

B2. The kit of embodiment B1, further comprising extension primers that comprise polynucleotides chosen from polynucleotides of Table 2 and Table 4, or portions thereof.

C1. A multiplex method for determining dosage of extrachromosomal nucleic acid relative to genomic nucleic acid for a sample from a subject, comprising:
  a. amplifying sets of extrachromosomal polynucleotides and genomic polynucleotides from nucleic acid for a sample under amplification conditions, wherein: (i) each set comprises an extrachromosomal polynucleotide and a genomic polynucleotide; (ii) the extrachromosomal polynucleotide and the genomic polynucleotide are native; (iii) the extrachromosomal polynucleotide of a set differs from the extrachromosomal polynucleotide of the other sets and the genomic polynucleotide of a set differs from the genomic polynucleotide of the other sets; (iv) the extrachromosomal polynucleotide and the genomic polynucleotide of a set are defined by formula $5'X\text{-}V\text{-}Y3'$; (v) the $5'X\text{-}V\text{-}Y3'$ represents a contiguous sequence of nucleotides present in the extrachromosomal polynucleotide and the genomic polynucleotide; (vi) X and Y of the extrachromosomal polynucleotide are identical to X and Y, respectively, of the genomic polynucleotide in each set; (vii) V is one or more nucleotide positions at which a nucleotide of the extrachromosomal polynucleotide differs from the corresponding nucleotide of the genomic polynucleotide in a set;
  thereby providing a plurality of amplified sets each comprising amplicons corresponding to all or a portion of the extrachromosomal polynucleotide and amplified genomic polynucleotide in the set;

b. comparing (i) the amplicons corresponding to the extrachromosomal polynucleotide, to (ii) the amplicons corresponding to the genomic polynucleotide for each set, thereby generating a comparison; and c. determining the relative dosage of extrachromosomal nucleic acid to genomic nucleic acid in the sample based on the comparison.

D1. A multiplex method for determining dosage of mitochondrial nucleic acid relative to nuclear nucleic acid for a sample from a subject, comprising:

a. contacting nucleic acid of a sample from a subject comprising nucleic acid of a first species comprising a nuclear genome and a mitochondrial genome with nucleic acid of a second species comprising nucleic acid of a nuclear genome and a mitochondrial genome for which the copy number of the mitochondrial genome and the copy number of the nuclear genome are known, wherein the nuclear genome of the first species has regions that are paralogous to regions of the nuclear genome of the second species and the mitochondrial genome of the first species has regions that are paralogous to regions of the mitochondrial genome of the second species;

b. amplifying sets of nuclear polynucleotides of paralogous regions of the nuclear genome of the first species and the nuclear genome of the second species and sets of mitochondrial polynucleotides of paralogous regions of the mitochondrial genome of the first species and the mitochondrial genome of the second species from the nucleic acid of (a) under amplification conditions, wherein: (i) each set comprises a polynucleotide of the nuclear genome of the first species and a polynucleotide of the nuclear genome of the second species or each set comprises a polynucleotide of the mitochondrial genome of the first species and a polynucleotide of the mitochondrial genome of the second species; (ii) the mitochondrial polynucleotides and the nuclear polynucleotides are native; (iii) the mitochondrial polynucleotides of a set differ from the mitochondrial polynucleotides of the other sets and the nuclear polynucleotides of a set differ from the nuclear polynucleotides of the other sets; (iv) the mitochondrial polynucleotides of a set and the nuclear polynucleotides of a set are defined by formula $^{5'}$J-V-K$^{3'}$; (v)$^{5'}$J-V-K$^{3'}$ represents a contiguous sequence of nucleotides present in the mitochondrial polynucleotides or in the nuclear polynucleotides; (vi) J and K of the mitochondrial polynucleotides of a set are identical and J and K of the nuclear polynucleotides of a set are identical; and (vii) V is one or more nucleotide positions at which a nucleotide of the mitochondrial polynucleotides of the first and second species of a set differ or V is one or more nucleotide positions at which a nucleotide of the nuclear polynucleotides of the first and second species of a set differ; thereby providing a plurality of amplified sets each comprising amplicons corresponding to all or a portion of the mitochondrial polynucleotides of a set or amplicons corresponding to all or a portion of the amplified nuclear polynucleotides of a set;

c. comparing the amplicons corresponding to the mitochondrial polynucleotide of the second species to the amplicons corresponding to mitochondrial polynucleotide of the first species in a set and comparing the amplicons corresponding to the nuclear polynucleotide of the second species to the amplicons corresponding to the nuclear polynucleotide of the first species in a set, thereby generating comparisons; and d. determining the relative dosage of mitochondrial nucleic acid to the nuclear nucleic acid in the sample from the subject based on comparisons of (c) for all sets.

D1.1. The method of embodiment D1, wherein the comparisons in (c) are a ratio of the amount of the amplicons corresponding to the polynucleotide of the mitochondrial genome of the second species to the amount of amplicons corresponding to polynucleotide of the mitochondrial genome of the first species in a set and a ratio of the amount of the amplicons corresponding to the polynucleotide of the nuclear genome of the second species to the amount of amplicons corresponding to the polynucleotide of the nuclear genome of the first species in a set, and determining the relative dosage of mitochondrial nucleic acid to nuclear nucleic acid in the sample from the subject in (d) is based on the ratios.

D1.2 The method of embodiment D1 or D1.1, wherein the first species is human.

D1.3 The method of any one of embodiments D1 to D1.2, wherein the second species is chimpanzee.

D2. The method of any one of embodiments D1 or D1.3, wherein the nucleic acid for the sample is DNA.

D3. The method of any one of embodiments of D1 to D2, wherein amplifying is by a polymerase chain reaction (PCR) process.

D4. The method of any one of embodiments D1 to D3, wherein V is a single nucleotide position.

D5. The method of any one of embodiments D1 to D4, wherein $^{5'}$J-V-K$^{3'}$ is about 30 base pairs to about 300 base pairs in length.

D6. The method of any one of embodiments D1 to D5, wherein the lengths of the amplicons are about 30 base pairs to about 300 base pairs.

D7. The method of any one of embodiments D1 to D6, wherein the plurality of amplified sets of nuclear polynucleotides and the plurality of amplified sets of mitochondrial polynucleotides are each about 2 sets to about 20 sets.

D8. The method of any one of embodiments D1 to D7, wherein the plurality of amplified sets of nuclear polynucleotides and the plurality of amplified sets of mitochondrial polynucleotides are each about 5 sets to about 15 sets.

D9. The method of any one of embodiments D1 to D6, wherein the plurality of amplified sets of nuclear polynucleotides and the plurality of amplified sets of mitochondrial polynucleotides are each at least 5 sets.

D9.1 The method of any one of embodiments D1 to D9, wherein the mitochondrial polynucleotides are distributed throughout the mitochondrial genome.

D10. The method of any one of embodiments D1 to D9.1, wherein the mitochondrial polynucleotides of a set comprise polynucleotides or portions thereof chosen from Table 6.

D11. The method of any one of embodiments D1 to D10, wherein the mitochondrial polynucleotides of a set are reproducibly amplified relative to each other by a single pair of amplification primers that hybridize to a mitochondrial polynucleotide within J and K and the nuclear polynucleotides of a set are reproducibly amplified relative to each other by a single pair of amplification primers that hybridize to a nuclear polynucleotide within J and K.

D12. The method of any one of embodiments D1 to D11, wherein (c) comprises determining the amount of a nucleotide at V in the amplicons corresponding to the mitochondrial polynucleotide of the first species and the second species of a set and determining the amount of a nucleotide at V in the amplicons corresponding to the nuclear polynucleotide of the first species and the second species of a set.

D13. The method of embodiment D12, wherein determining the amount of a nucleotide at V in the amplicons corresponding to the mitochondrial polynucleotide of the first species and the second species of a set and determining the amount of a nucleotide at V in the amplicons corresponding to the nuclear polynucleotide of the first species and the second species of a set is by massive parallel sequencing process.

D14. The method of embodiment D13, wherein the sequencing is by a sequencing by synthesis process.

D15. The method of embodiments D13 or D14, wherein a sequence tag or barcode is attached to one or more primers in each amplification primer pair.

D16. The method of embodiment D12, wherein determining the amount of a nucleotide at V in the amplicons corresponding to the mitochondrial polynucleotide of the first species and the second species of a set and determining the amount of a nucleotide at V in the amplicons corresponding to the nuclear polynucleotide of the first species and the second species of a set is by a nanopore process.

D17. The method of embodiment D12, determining the amount of a nucleotide at V in the amplicons corresponding to the mitochondrial polynucleotide of the first species and the second species of a set is by a qPCR process comprising two fluorescent probes specific for the nucleotide at V of the mitochondrial polynucleotide of either the first or second species or a digital PCR process and determining the amount of a nucleotide at V in the amplicons corresponding to the nuclear polynucleotide of the first species and the second species of a set is by a qPCR process comprising two fluorescent probes specific for the nucleotide at V of the nuclear polynucleotide of either the first or second species or a digital PCR process.

D18. The method of embodiment D12, wherein (c) comprises contacting the amplicons with extension primers under extension conditions comprising chain terminating reagents, wherein:
  (1) the chain terminating reagent that is specific for the amplicons corresponding to the mitochondrial polynucleotide of the first species is not specific for the amplicons corresponding to the mitochondrial polynucleotide of the second species; and
  (2) the chain terminating reagent specific for the amplicons corresponding to the nuclear polynucleotide of the first species is not specific for the amplicons corresponding to the nuclear polynucleotide of the second species,
  whereby the primers are extended up to V, thereby generating chain terminated extension products corresponding to the mitochondrial polynucleotide of the first species, the mitochondrial polynucleotide of the second species, the nuclear polynucleotide of the first species and the nuclear polynucleotide of the second species.

D19. The method of embodiment D18, wherein (c) comprises determining a ratio of the amount of extension product corresponding to the mitochondrial polynucleotide of the second species to the amount of extension product corresponding to the mitochondrial polynucleotide of the first species and determining a ratio of the amount of extension product corresponding to the nuclear polynucleotide of the second species to the amount of extension product corresponding to the nuclear polynucleotide of the first species; and (d) comprises determining the amount of mitochondrial nucleic acid relative to the amount of nuclear nucleic acid in the sample based on the ratios of (c).

D20. The method of any one of embodiments D1 to D19, wherein the sets of mitochondrial polynucleotides and the sets of nuclear polynucleotides are in a single reaction vessel or a single reaction vessel compartment.

D20.1 The method of any one of embodiments D1 to D19, wherein the sets of mitochondrial polynucleotides and the sets of nuclear polynucleotides are in different separate reaction vessels or reaction vessel compartments.

D21. The method of any one of embodiments D18 to D20, wherein V is a single nucleotide position at which a nucleotide of the mitochondrial polynucleotide of the first species differs from the corresponding nucleotide of the mitochondrial polynucleotide of the second species and the primers are extended up to the single nucleotide.

D22. The method of any one of embodiments D18 to D20, wherein V is a single nucleotide position at which a nucleotide of the nuclear polynucleotide of the first species differs from the corresponding nucleotide of the nuclear polynucleotide of the second species and the primers are extended up to the single nucleotide.

D23. The method of any one of embodiments D18 to D22, wherein the chain terminating reagents are chain terminating nucleotides.

D24. The method of embodiment D23, wherein the chain terminating nucleotides independently are selected from among ddATP, ddGTP, ddCTP, ddTTP and ddUTP.

D25. The method of any one of embodiments D18 to D24, wherein the chain terminating reagents comprise one or more acyclic terminators.

D26. The method of any one of embodiments D18 to D25, wherein one or more of the chain terminating reagents comprises a detectable label.

D27. The method of embodiment D26, wherein the label is a fluorescent label or dye.

D28. The method of embodiment D26, wherein the label is a mass label and detection is by mass spectrometry.

D29. The method of any one of embodiments D1-D28, comprising between about 25 to about 45 PCR amplification cycles in (b).

D30. The method of any one of embodiments D18 to D25, wherein the extension conditions in (c) comprise between about 20 to about 300 cycles.

D31. The method of any one of embodiments D1.1 to D30, wherein the ratios for a plurality of sets mitochondrial polynucleotides and a plurality of sets of nuclear polynucleotides are combined and the relative dosage of mitochondrial nucleic acid to nuclear nucleic acid for the sample is determined based on the combined ratio.

D32. The method of embodiment D31, wherein the combined ratio is an average ratio or a median ratio.

D33. The method of any one of embodiments D1.1 to D32, wherein the ratio of each set is compared to an average or median ratio based on the plurality of sets and an outlier or cluster that deviates from the average or median ratio is an indication of a mitochondrial deletion.

D34. The method of any one of embodiments D1.1 to D32, wherein the ratio of a set of a mitochondrial paralog representing one region of the mitochondrial genome is compared to the ratio of each of the other sets of a mitochondrial paralog representing different regions of the mitochondrial genome and the presence of one or more deletions in the mitochondrial genome is determined based on a difference in the ratio of the set representing the one region compared with the ratios for one or more sets representing other regions of the mitochondrial genome.

D35. The method of any one of embodiments D1 to D34, wherein a baseline value for the dosage of mitochondrial nucleic acid relative to nuclear nucleic acid is determined for the subject or a population of subjects and the dosage of mitochondrial nucleic acid relative to nuclear nucleic acid for the sample from the subject is compared to the baseline value.

D36. The method of any one of embodiments D1 to D35, wherein the dosage of mitochondrial nucleic acid relative to nuclear nucleic acid for the sample from the subject is used in determining the likelihood the subject has or is predisposed to having a disease, disorder or symptoms associated with an increase or decrease in the dosage of mitochondria nucleic acid or a deletion in the mitochondrial genome.

D37. The method of embodiment D36, wherein the disease or disorder is a neurodegenerative disease, a cancer, a disease or disorder associated with mitochondrial stability, a disease or disorder associated with a mitochondrial deletion, a metabolic disease, a cardiovascular disease, a disease or disorder associated with oxidative stress, a disease or disorder associated with infertility or a disease or disorder associated with sepsis.

D38. The method of embodiment D37, wherein the disease or disorder is Parkinson's disease, Alzheimers disease, Friedreich's Ataxia, Amyotropic lateral sclerosis, Multiple sclerosis (MS), POLG associated diseases, Opthalmoplegia, Alper's syndrome, Leigh's syndrome, Kearns-Sayre syndrome (KSS), Leber's heredity optic neuropathy (LHON), Mitochondiral encophalomyopathy, lactic acidosis, stroke like episodes (MELAS), Myoclonic Epilepsy with Ragged Red Fibers (MERRF), gastric cancer, hepatocellular carcinoma (HCC) HPV related cancer, breast cancer, Ewing's Sarcoma, pancreatic cancer, liver cancer, testicular cancer, prostate cancer, renal cell carcinoma (RCC), bladder cancer, ovarian cancer, obesity, diabetes, pre-diabetes, diabetic retinopathy, diabetic cardiomyopathies, coronary heart disease and sepsis.

D39. The method of any one of embodiments D1 to D38, wherein the dosage of mitochondrial nucleic acid relative to nuclear nucleic acid for the sample from the subject is used to monitor the efficacy of treatment of the subject for a disease, disorder or symptoms associated with an increase or decrease in the dosage of mitochondria nucleic acid or a deletion in the mitochondrial genome.

D40. The method of any one of embodiments D1 to D39, wherein the sample comprises circulating cell free nucleic acid.

D41. The method of embodiment D40, wherein the sample is chosen from blood plasma, blood serum, spinal fluid, cerebrospinal fluid and urine.

E1. A kit comprising amplification primer pairs that comprise polynucleotides chosen from polynucleotides of Table 7 or portions thereof.

E2. The kit of embodiment E1, further comprising extension primers that comprise polynucleotides chosen from polynucleotides of Table 7 or portions thereof.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications may be made to the foregoing without departing from the basic aspects of the technology. Although the technology has been described in substantial detail with reference to one or more specific embodiments, those of ordinary skill in the art will recognize that changes may be made to the embodiments specifically disclosed in this application, yet these modifications and improvements are within the scope and spirit of the technology.

The technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the technology claimed. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" is about 1, about 2 and about 3). For example, a weight of "about 100 grams" can include weights between 90 grams and 110 grams. Thus, it should be understood that although the present technology has been specifically disclosed by representative embodiments and optional features, modification and variation of the concepts herein disclosed may be resorted to by those skilled in the art, and such modifications and variations are considered within the scope of this technology.

Embodiments of the technology are set forth in the claim(s) that follow(s).

What is claimed is:

1. A multiplex method for determining dosage of mitochondrial nucleic acid relative to nuclear nucleic acid for a sample from a subject, comprising:
   a. contacting nucleic acid of a sample from a subject comprising nucleic acid of a first species comprising a nuclear genome and a mitochondrial genome with nucleic acid of a second species comprising nucleic acid of a nuclear genome and a mitochondrial genome for which the copy number of the mitochondrial genome and the copy number of the nuclear genome are known, wherein the nuclear genome of the first species has regions that are paralogous to regions of the nuclear genome of the second species and the mitochondrial genome of the first species has regions that are paralogous to regions of the mitochondrial genome of the second species;
   b. amplifying sets of nuclear polynucleotides of paralogous regions of the nuclear genome of the first species and the nuclear genome of the second species and sets of mitochondrial polynucleotides of paralogous regions of the mitochondrial genome of the first species and the mitochondrial genome of the second species from the nucleic acid of (a) under amplification conditions, wherein: (i) each set comprises a polynucleotide of the nuclear genome of the first species and a polynucleotide of the nuclear genome of the second species or each set comprises a polynucleotide of the mitochondrial genome of the first species and a polynucleotide of the mitochondrial genome of the second species; (ii) the mitochondrial polynucleotides and the nuclear polynucleotides are native; (iii) the mitochondrial polynucleotides of a set differ from the mitochondrial polynucleotides of the other sets and the nuclear polynucleotides of a set differ from the nuclear polynucleotides of the other sets; (iv) the mitochondrial polynucleotides of a set and the nuclear polynucleotides of a set are defined by formula $5'J-V-K^{3'}$; (v) $5'J-V-K^{3'}$ represents a contiguous sequence of nucleotides present in the mitochondrial polynucleotides or in the nuclear polynucleotides; (vi) J and K of the mitochondrial polynucleotides of a set are identical and J and K of the nuclear polynucleotides of a set are identical; and (vii) V is one or more nucleotide positions at which a nucleotide of the mitochondrial polynucleotides of the first and second species of a set differ or V is one or more nucleotide positions at which a nucleotide of the nuclear polynucleotides of the first and second species of a set differ; thereby providing a plurality of amplified sets each comprising amplicons corresponding to all or a portion of the mitochondrial polynucleotides of a set or amplicons corresponding to all or a portion of the amplified nuclear polynucleotides of a set;
   c. comparing the amplicons corresponding to the mitochondrial polynucleotide of the second species to the amplicons corresponding to the mitochondrial polynucleotide of the first species in a set and comparing the amplicons corresponding to the nuclear polynucleotide of the second species to the amplicons corresponding to the nuclear polynucleotide of the first species in a set, thereby generating comparisons; and
   d. determining the relative dosage of mitochondrial nucleic acid to the nuclear nucleic acid in the sample from the subject based on comparisons of (c) for all sets.

2. The method of claim 1, wherein the comparisons in (c) are a ratio of the amount of the amplicons corresponding to the polynucleotide of the mitochondrial genome of the second species to the amount of amplicons corresponding to the polynucleotide of the mitochondrial genome of the first species in a set and a ratio of the amount of the amplicons corresponding to the polynucleotide of the nuclear genome of the second species to the amount of amplicons corresponding to the polynucleotide of the nuclear genome of the first species in a set, and determining the relative dosage of mitochondrial nucleic acid to nuclear nucleic acid in the sample from the subject in (d) is based on the ratios.

3. The method of claim 1, wherein the first species is human.

4. The method of claim 3, wherein the second species is chimpanzee.

5. The method of claim 1, wherein the nucleic acid for the sample is DNA.

6. The method of claim 1, wherein amplifying is by a polymerase chain reaction (PCR) process.

7. The method of claim 1, wherein V is a single nucleotide position.

8. The method of claim 1, wherein $5'J-V-K^{3'}$ is about 30 base pairs to about 300 base pairs in length.

9. The method of claim 1, wherein the plurality of amplified sets of nuclear polynucleotides and the plurality of amplified sets of mitochondrial polynucleotides are each about 2 sets to about 20 sets.

10. The method of claim 1, wherein the mitochondrial polynucleotides of each set comprise polynucleotides or portions thereof chosen from Table 6.

11. The method of claim 1, wherein the mitochondrial polynucleotides of each set are reproducibly amplified relative to each other by a single pair of amplification primers that hybridize to mitochondrial polynucleotides within J and K, respectively and the nuclear polynucleotides of each set are reproducibly amplified relative to each other by a single pair of amplification primers that hybridize to a nuclear polynucleotides within J and K, respectively.

12. The method of claim 1, wherein (c) comprises determining the amount of a nucleotide at V in the amplicons corresponding to the mitochondrial polynucleotide of the first species and the second species of a set and determining the amount of a nucleotide at V in the amplicons corresponding to the nuclear polynucleotide of the first species and the second species of a set.

13. The method of claim 12, wherein determining the amount of a nucleotide at V in the amplicons corresponding to the mitochondrial polynucleotide of the first species and the second species of a set and determining the amount of a nucleotide at V in the amplicons corresponding to the nuclear polynucleotide of the first species and the second species of a set is by a massive parallel sequencing process.

14. The method of claim 12, wherein (c) comprises contacting the amplicons with extension primers under extension conditions comprising chain terminating reagents, wherein:
  (1) the chain terminating reagent that is specific for the amplicons corresponding to the mitochondrial polynucleotide of the first species is not specific for the amplicons corresponding to the mitochondrial polynucleotide of the second species; and
  (2) the chain terminating reagent specific for the amplicons corresponding to the nuclear polynucleotide of the first species is not specific for the amplicons corresponding to the nuclear polynucleotide of the second species,
  whereby the primers are extended up to V, thereby generating chain terminated extension products corresponding to the mitochondrial polynucleotide of the first species, the mitochondrial polynucleotide of the second species, the nuclear polynucleotide of the first species and the nuclear polynucleotide of the second species.

15. The method of claim 14, wherein (c) comprises determining a ratio of the amount of extension product corresponding to the mitochondrial polynucleotide of the second species to the amount of extension product corresponding to the mitochondrial polynucleotide of the first species and determining a ratio of the amount of extension product corresponding to the nuclear polynucleotide of the second species to the amount of extension product corresponding to the nuclear polynucleotide of the first species; and (d) comprises determining the amount of mitochondrial nucleic acid relative to the amount of nuclear nucleic acid in the sample based on the ratios of (c).

16. The method of claim 1, wherein the sets of mitochondrial polynucleotides and the sets of nuclear polynucleotides are in a single reaction vessel or a single reaction vessel compartment.

17. The method of claim 2, wherein the ratios for a plurality of sets of mitochondrial polynucleotides and a plurality of sets of nuclear polynucleotides are combined and the relative dosage of mitochondrial nucleic acid to nuclear nucleic acid for the sample is determined based on the combined ratio.

18. The method of claim 1, wherein the sample comprises circulating cell free nucleic acid.

19. The method of claim 2, further comprising determining the presence or absence of a deletion in the mitochondrial genome of the subject by comparing the relative dosage of the mitochondrial nucleic acid to nuclear nucleic acid for a plurality of sets.

* * * * *

UNITED STATES PATENT AND TRADEMARK OFFICE
CERTIFICATE OF CORRECTION

PATENT NO. : 10,774,375 B2
APPLICATION NO. : 15/268058
DATED : September 15, 2020
INVENTOR(S) : Anders Olof Herman Nygren Page 1 of 1

It is certified that error appears in the above-identified patent and that said Letters Patent is hereby corrected as shown below:

In the Claims

In Claim 11 (Column 642, Line 64):
"to a nuclear" should be changed to --to nuclear--.

Signed and Sealed this
Twenty-seventh Day of April, 2021

Drew Hirshfeld
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 1466

<210> SEQ ID NO 1
<211> LENGTH: 100
<212> TYPE: DNA
<213> ORGANISM: Homo sapiens

<400> SEQUENCE: 1
gatcacaggt ctatcaccct attaaccact cacgggagct ctccatgcat ttggtatttt     60
cgtctggggg gtgtgcacgc gatagcattg cgagacgctg                          100
```

<210> SEQ ID NO 2
<211> LENGTH: 100
<212> TYPE: DNA
<213> ORGANISM: Homo sapiens

<400> SEQUENCE: 2
gatcacgggt ctattaccct attaatcagt cacgggagct ctccatgcat ttggtatttt    60
aatctggggg gtgtgcacgc gatagcattg tgaaacgctg                          100

<210> SEQ ID NO 3
<211> LENGTH: 100
<212> TYPE: DNA
<213> ORGANISM: Homo sapiens

<400> SEQUENCE: 3
gagccggagc accctatgtc gcagtatctg tctttgattc ctgcctcatt ctattattta    60
tcgcacctac gttcaatatt acaggcgaac atacctacta                          100

<210> SEQ ID NO 4
<211> LENGTH: 100
<212> TYPE: DNA
<213> ORGANISM: Homo sapiens

<400> SEQUENCE: 4
gccccagagc accctatgtc gcagtgtctg tctttgattc ctgccccatc ccattattga    60
tcacacctac attcaatatc ccaggcgagc atacctatca                          100

<210> SEQ ID NO 5
<211> LENGTH: 100
<212> TYPE: DNA
<213> ORGANISM: Homo sapiens

<400> SEQUENCE: 5
aagtgtgtta attaattaat gcttgtagga cataataata acaattgaat gtctgcacag    60
ccgctttcca cacagacatc ataacaaaaa atttccacca                          100

<210> SEQ ID NO 6
<211> LENGTH: 100
<212> TYPE: DNA
<213> ORGANISM: Homo sapiens

<400> SEQUENCE: 6 aaccccccc tcccccgct tctggccaca gcacttaaac acatctctgc caaacccaa       60 aaacaaagaa ccctaacacc agcctaacca gatttcaaat                          100

<210> SEQ ID NO 7
<211> LENGTH: 100
<212> TYPE: DNA
<213> ORGANISM: Homo sapiens

<400> SEQUENCE: 7
tttatcttta ggcggtatgc acttttaaca gtcacccccc aactaacaca ttattttccc    60
ctcccactcc catactacta atctcatcaa tacaaccccc                          100

<210> SEQ ID NO 8
<211> LENGTH: 100
<212> TYPE: DNA
<213> ORGANISM: Homo sapiens

<400> SEQUENCE: 8

```
gcccatccta cccagcacac acacaccgct gctaacccca taccccgaac caaccaaacc    60
ccaaagacac cccccacagt ttatgtagct tacctcctca                         100

<210> SEQ ID NO 9
<211> LENGTH: 100
<212> TYPE: DNA
<213> ORGANISM: Homo sapiens

<400> SEQUENCE: 9
aagcaataca ctgaaaatgt ttagacgggc tcacatcacc ccataaacaa ataggtttgg    60
tcctagcctt tctattagct cttagtaaga ttacacatgc                         100

<210> SEQ ID NO 10
<211> LENGTH: 100
<212> TYPE: DNA
<213> ORGANISM: Homo sapiens

<400> SEQUENCE: 10
aagcaagaca ctgaaaatgt ctagatgggt ccacacaacc ccataaacag ataggcttgg    60
tcctggcctt tttattacct cttattaaga ttacacatgg                         100

<210> SEQ ID NO 11
<211> LENGTH: 100
<212> TYPE: DNA
<213> ORGANISM: Homo sapiens

<400> SEQUENCE: 11
aagcaagaca ctgaaaatgt ctagttgggt ccacaccacc cgatgaacag ataggttttg    60
tcctggcctt tttattagct cttagtaaga ttaaacatgc                         100

<210> SEQ ID NO 12
<211> LENGTH: 100
<212> TYPE: DNA
<213> ORGANISM: Homo sapiens

<400> SEQUENCE: 12
aagaaaggca ctgaaaatgc tcagaagatt tcacgtaact ccataaacac ataggtttgg    60
tcctggcctt tttgttagtt cttagtaaga ttatacatgc                         100

<210> SEQ ID NO 13
<211> LENGTH: 100
<212> TYPE: DNA
<213> ORGANISM: Homo sapiens

<400> SEQUENCE: 13
aagcaagaca ctgaaaatgt ctagatggat ccgcacaacc ctataaacag agaggtttgg    60
tcctggcctt tttactagct cttagtaaga ttacacatgt                         100

<210> SEQ ID NO 14
<211> LENGTH: 100
<212> TYPE: DNA
<213> ORGANISM: Homo sapiens

<400> SEQUENCE: 14
aagcaatgca ctgaaaatgt ctggatgggc ccacactgcc ccataaacaa ataggtttca    60
tcctagcctt tctattggtt cttagtaaga ttacacactc                         100

<210> SEQ ID NO 15
```

```
<211> LENGTH: 100
<212> TYPE: DNA
<213> ORGANISM: Homo sapiens

<400> SEQUENCE: 15
aagcaagaca ctgaaaatgt ctagatgggc ttatacagcc ccataaacag acagtcttgg      60
tcctggcctt tctattaact cttagtaaga ttacacatgc                           100

<210> SEQ ID NO 16
<211> LENGTH: 100
<212> TYPE: DNA
<213> ORGANISM: Homo sapiens

<400> SEQUENCE: 16
aagcaagaca ctgaaaatat ctagatgggt ctgcacaacc ccataaacag ataggtttgg      60
ccctgacctt tttattagct cttagtaaga ttacacatgc                           100

<210> SEQ ID NO 17
<211> LENGTH: 100
<212> TYPE: DNA
<213> ORGANISM: Homo sapiens

<400> SEQUENCE: 17
aagcaagaca ctgaaaatgt ctagatgggc ttatacagcc ccgtaaacag acaggtttgg      60
tcctggcctt tctattaact cttagtaaga ttacacatgc                           100

<210> SEQ ID NO 18
<211> LENGTH: 100
<212> TYPE: DNA
<213> ORGANISM: Homo sapiens

<400> SEQUENCE: 18
aagcaagaca ctgaaaatgt ctagatgggt ctgcacatcc ccataaacag atatgtttgg      60
tcctggcctt tctattagct tttagtaaga ttacacacgc                           100

<210> SEQ ID NO 19
<211> LENGTH: 100
<212> TYPE: DNA
<213> ORGANISM: Homo sapiens

<400> SEQUENCE: 19
aagcaagaca ctgaaaatat ctagatgggc ctacactgcc ccatagacaa ataggtttgg      60
tcctagcctt tctattaact cttagtaaga ttacacaagc                           100

<210> SEQ ID NO 20
<211> LENGTH: 100
<212> TYPE: DNA
<213> ORGANISM: Homo sapiens

<400> SEQUENCE: 20
aagcaagaca ctgaaagtgt ctagacgggt ctgcacaaca tcataaacaa ataggcttgg      60
tcctggcctt tctattagct cttagtaaga ttacacatgc                           100

<210> SEQ ID NO 21
<211> LENGTH: 100
<212> TYPE: DNA
<213> ORGANISM: Homo sapiens

<400> SEQUENCE: 21
aagcaagaca ctgaaaatgt ctagatgggt ctagacaatc ccataaacaa acagatttag      60
```

```
tccaggcctt tctattagat cctagtaaga ttacacaagc                          100
```

<210> SEQ ID NO 22
<211> LENGTH: 100
<212> TYPE: DNA
<213> ORGANISM: Homo sapiens

<400> SEQUENCE: 22

```
aagcatcccc gttccagtga gttcaccctc taaatcacca cgatcaaaag ggacaagcat     60
caagcacgca gcaatgcagc tcaaaacgct tagcctagcc                          100
```

<210> SEQ ID NO 23
<211> LENGTH: 100
<212> TYPE: DNA
<213> ORGANISM: Homo sapiens

<400> SEQUENCE: 23

```
aagcatcccc atcccagtga aagtaccctc taaatcacct tgatcaaaag aagtaagtat     60
caagcatgca caaatgcagc tcaaaacact ttgcccagcc                          100
```

<210> SEQ ID NO 24
<211> LENGTH: 100
<212> TYPE: DNA
<213> ORGANISM: Homo sapiens

<400> SEQUENCE: 24

```
aagcatcgcc accctggtga aataaccctc taaatcacta caatcaaaag gagtaagtat     60
caagcacgca ttagtgcagc tcaaaacact ttgcctagcc                          100
```

<210> SEQ ID NO 25
<211> LENGTH: 100
<212> TYPE: DNA
<213> ORGANISM: Homo sapiens

<400> SEQUENCE: 25

```
acaccccac gggaaacagc agtgattaac ctttagcaat aaacgaaagt ttaactaagc      60
tatactaacc ccagggttgg tcaatttcgt gccagccacc                          100
```

<210> SEQ ID NO 26
<211> LENGTH: 100
<212> TYPE: DNA
<213> ORGANISM: Homo sapiens

<400> SEQUENCE: 26

```
acaccccac gggagacagc agtgataaac ctttagcaat aaacgaaagt ttaactgagc      60
tatactaact ttagggttgg ttaatttcat gccagccacc                          100
```

<210> SEQ ID NO 27
<211> LENGTH: 100
<212> TYPE: DNA
<213> ORGANISM: Homo sapiens

<400> SEQUENCE: 27

```
gcggtcacac gattaaccca agtcaataga agccggcgta aagagtgttt tagatcaccc     60
cctccccaat aaagctaaaa ctcacctgag ttgtaaaaaa                          100
```

<210> SEQ ID NO 28
<211> LENGTH: 100
<212> TYPE: DNA

<213> ORGANISM: Homo sapiens

<400> SEQUENCE: 28
ctccagttga cacaaaatag actacgaaag tggctttaac atatctgaac acacaatagc      60
taagacccaa actgggatta datacccac tatgcttagc                            100

<210> SEQ ID NO 29
<211> LENGTH: 100
<212> TYPE: DNA
<213> ORGANISM: Homo sapiens

<400> SEQUENCE: 29
ccctagctga aataaaataa actatgaagg tggctttaat acttctgaag acacaatagc      60
taagacccaa attgggatta datacccac tatgcttagc                            100

<210> SEQ ID NO 30
<211> LENGTH: 100
<212> TYPE: DNA
<213> ORGANISM: Homo sapiens

<400> SEQUENCE: 30
ctccagctga cataaaataa actacgaaag tggctttaac gtatctgaac acacaatagc      60
taagacccaa actgggatta dataccgcac tatgggctca                            100

<210> SEQ ID NO 31
<211> LENGTH: 100
<212> TYPE: DNA
<213> ORGANISM: Homo sapiens

<400> SEQUENCE: 31
ccctagctga aataaaataa actacgaagg tgaatttaat atttctgagg acacaatagc      60
taagacccaa actgggatta datacccac tatgcttagc                            100

<210> SEQ ID NO 32
<211> LENGTH: 100
<212> TYPE: DNA
<213> ORGANISM: Homo sapiens

<400> SEQUENCE: 32
cccgggctga aataaaataa actatgaagg aggctttaat acttctgaag acacaatagc      60
taagacccaa actgggatta datacccac taggcttagc                            100

<210> SEQ ID NO 33
<211> LENGTH: 100
<212> TYPE: DNA
<213> ORGANISM: Homo sapiens

<400> SEQUENCE: 33
ccctagttga tataaaacaa actacgaaag tggctttaat atttctgaat acacaatagc      60
gaagattcaa actgggatta datacccac tatgctcagc                            100

<210> SEQ ID NO 34
<211> LENGTH: 100
<212> TYPE: DNA
<213> ORGANISM: Homo sapiens

<400> SEQUENCE: 34
cctaaacctc aacagttaaa tcaacaaaac tgctcgccag aacactacga gccacagctt      60
aaaactcaaa ggacctggcg gtgcttcata tccctctaga                            100

<210> SEQ ID NO 35
<211> LENGTH: 100
<212> TYPE: DNA
<213> ORGANISM: Homo sapiens

<400> SEQUENCE: 35
tctaaactca aatagttaga tcaaaaaaac tgttcgccag aacactacaa gcaacagctt    60
aaaactcaaa ggacttggcg gtgctttata tccctctaaa                         100

<210> SEQ ID NO 36
<211> LENGTH: 100
<212> TYPE: DNA
<213> ORGANISM: Homo sapiens

<400> SEQUENCE: 36
tctaaactcg aatagttaga tcaacaaaac tgttcgccag aacactacaa gcaacagctt    60
aaaactcaaa ggacttggcg gtgctttata tccctctaaa                         100

<210> SEQ ID NO 37
<211> LENGTH: 100
<212> TYPE: DNA
<213> ORGANISM: Homo sapiens

<400> SEQUENCE: 37
cctaaactct aatagttaca ttgagaaaac cattcgccag agtactacaa gcaacagctt    60
aaaactcaaa ggacttggcg gtgctttata tccctctaga                         100

<210> SEQ ID NO 38
<211> LENGTH: 100
<212> TYPE: DNA
<213> ORGANISM: Homo sapiens

<400> SEQUENCE: 38
cctaaactcc aatagttaaa tcaacaaaac tattcaccag aacactacaa gcaatagctt    60
aaaactcaaa ggacttggcg gtgctttata tccctctaga                         100

<210> SEQ ID NO 39
<211> LENGTH: 100
<212> TYPE: DNA
<213> ORGANISM: Homo sapiens

<400> SEQUENCE: 39
cctaaactcc aatagttaaa tcaacaaaac tattccccag aacactacaa gcaatagctt    60
aaaactcaaa ggacttggca gtgctttata tccctctaga                         100

<210> SEQ ID NO 40
<211> LENGTH: 100
<212> TYPE: DNA
<213> ORGANISM: Homo sapiens

<400> SEQUENCE: 40
cctaaactcc aatagttaaa tcaacagaac tattcaccag aacactacaa gcaatagctt    60
aaaactcaaa ggacttggcg gtgctttata tccctctaga                         100

<210> SEQ ID NO 41
<211> LENGTH: 100
<212> TYPE: DNA
<213> ORGANISM: Homo sapiens

```
<400> SEQUENCE: 41
cctaaactct aatagttaca ttaacaaaac cattcgccag agtactacaa gcaacagctt     60
aaaactcaaa ggacttggca gtgctttata tccctctaga                          100

<210> SEQ ID NO 42
<211> LENGTH: 100
<212> TYPE: DNA
<213> ORGANISM: Homo sapiens

<400> SEQUENCE: 42
cctaaacttc aacagttaaa tcaacaaaac tgctcgccag aacactagga gcaacagctt     60
aaaactcaaa ggacctggcg gtgcttcaca tccctctaga                          100

<210> SEQ ID NO 43
<211> LENGTH: 100
<212> TYPE: DNA
<213> ORGANISM: Homo sapiens

<400> SEQUENCE: 43
tctaaactcg aatagttaga tcaacaaaac tgttcgccag aacactacaa gcaacagctt     60
aaaactcaaa ggacttggcg gtgctttata tccctctaaa                          100

<210> SEQ ID NO 44
<211> LENGTH: 100
<212> TYPE: DNA
<213> ORGANISM: Homo sapiens

<400> SEQUENCE: 44
cctaaactcg aatagttaga tcaacaaaac tgttcgccag aacactacaa gcaacagctt     60
aaaactcaaa ggactttgcg gtgctttaca tccctctaaa                          100

<210> SEQ ID NO 45
<211> LENGTH: 100
<212> TYPE: DNA
<213> ORGANISM: Homo sapiens

<400> SEQUENCE: 45
ggagcctgtt ctgtaatcga taaaccccga tcaacctcac cacctcttgc tcagcctata     60
taccgccatc ttcagcaaac cctgatgaag gctacaaagt                          100

<210> SEQ ID NO 46
<211> LENGTH: 100
<212> TYPE: DNA
<213> ORGANISM: Homo sapiens

<400> SEQUENCE: 46
ggagcctgtt ctataatcga taaaccccaa tttacctcac cacctcttgc ccagcctaaa     60 taccccatc ttcagcaaac cctggaaagg ctgcagagta                           100

<210> SEQ ID NO 47
<211> LENGTH: 100
<212> TYPE: DNA
<213> ORGANISM: Homo sapiens

<400> SEQUENCE: 47
ggaggctgtt ctataatcga taaaccccaa tttacctcac cacctcttgc ccagcctaaa     60
tacctccatc ttcagcaaac cctggaaagg ccgcagagta                          100
```

```
<210> SEQ ID NO 48
<211> LENGTH: 100
<212> TYPE: DNA
<213> ORGANISM: Homo sapiens

<400> SEQUENCE: 48
ggagcctgtt ctataatgga taaaccccaa tttacctcac cacttcttgc tcagcctata      60
taccatcatc ttcagcaaac cctagtaaaa gtcacaaagt                           100

<210> SEQ ID NO 49
<211> LENGTH: 100
<212> TYPE: DNA
<213> ORGANISM: Homo sapiens

<400> SEQUENCE: 49
ggagcctgtt ctataatgga taaaacccaa tttgcctcac cacctcttgc tcagcctata      60
taccactgtc ttcagcaaac cctagcaaag gctgcaaagt                           100

<210> SEQ ID NO 50
<211> LENGTH: 100
<212> TYPE: DNA
<213> ORGANISM: Homo sapiens

<400> SEQUENCE: 50
ggagcctgtt ctataatcga taaaccccaa ttcacctcac cacctcttgc tcaacccata      60
taccgccatc ttcagcaaac cctgacaaag gccacaaagt                           100

<210> SEQ ID NO 51
<211> LENGTH: 100
<212> TYPE: DNA
<213> ORGANISM: Homo sapiens

<400> SEQUENCE: 51
ggaggctgtt ctataatcga taaaccccaa tttacctcac cacctcttgc ccagcctaaa      60
tacctccatc ttcagcaaac cctggaaagg ccgcagagta                           100

<210> SEQ ID NO 52
<211> LENGTH: 100
<212> TYPE: DNA
<213> ORGANISM: Homo sapiens

<400> SEQUENCE: 52
aagcgcaagt acccacgtaa agacgttagg tcaaggtgta gcccatgagg tggcaagaaa      60
tgggctacat tttctacccc agaaaactac gatagccctt                           100

<210> SEQ ID NO 53
<211> LENGTH: 100
<212> TYPE: DNA
<213> ORGANISM: Homo sapiens

<400> SEQUENCE: 53
aagcacaagt atctacataa aaacattagg tcaaggtgta gcccatgagg cggtaagaaa      60
tgggctacat tttctacacc cagaaaatct cacaacccct                           100

<210> SEQ ID NO 54
<211> LENGTH: 100
<212> TYPE: DNA
<213> ORGANISM: Homo sapiens

<400> SEQUENCE: 54
```

```
aagcacaagt aaatacataa aaacgttagg tcaacgtgta gctcatgagg tggcaagaaa    60
tgggccacat tttctacccc agaaaatctc acgacaacct                          100

<210> SEQ ID NO 55
<211> LENGTH: 100
<212> TYPE: DNA
<213> ORGANISM: Homo sapiens

<400> SEQUENCE: 55
aagcacaagt atctacataa aaatgttagg tcaaggtgta gcctatgagg tggcaagaaa    60
tgggctacat tttctacccc agaaaattct acaataaccc                          100

<210> SEQ ID NO 56
<211> LENGTH: 100
<212> TYPE: DNA
<213> ORGANISM: Homo sapiens

<400> SEQUENCE: 56
atgaaactta agggtcgaag gtggatttag cagtaaactg agagtagagt gcttagttga    60
acagggccct gaagcgcgta cacaccgccc gtcaccctcc                          100

<210> SEQ ID NO 57
<211> LENGTH: 100
<212> TYPE: DNA
<213> ORGANISM: Homo sapiens

<400> SEQUENCE: 57
atgaaatcta agggctcaag gaggatttag caataaattg agagcagagt gtttaattga    60
ataaggccat gaagcatgca cacaccgccc atcaccctcc                          100

<210> SEQ ID NO 58
<211> LENGTH: 100
<212> TYPE: DNA
<213> ORGANISM: Homo sapiens

<400> SEQUENCE: 58
atgaaatcta agggctcaag gaggatttag caataaattg agagcagagt gtttaattga    60
ataaggccat gaagcatgca cacaccgccc gtcaccctcc                          100

<210> SEQ ID NO 59
<211> LENGTH: 100
<212> TYPE: DNA
<213> ORGANISM: Homo sapiens

<400> SEQUENCE: 59
atgaaatcta agggctcaag gaggatttag tagtaaacca agcgcagagt gcttggttga    60
ataaggccat gaagcatgca cacaccgctc atcaccctcc                          100

<210> SEQ ID NO 60
<211> LENGTH: 100
<212> TYPE: DNA
<213> ORGANISM: Homo sapiens

<400> SEQUENCE: 60
atgaaaccta agggcccaag gaggatttag cagtaaatta ggagcagagt gcttaattga    60
ataaggccat aaagcatgca cacactgcct gtcaccctcc                          100

<210> SEQ ID NO 61
<211> LENGTH: 100
```

```
<212> TYPE: DNA
<213> ORGANISM: Homo sapiens

<400> SEQUENCE: 61
atgaaatcta agggctcaag gaggatttag cagtacatta agagcagagt gcttaattga      60
atgaggccat aaagcacgca cacaatgccc gtcaccctcc                           100

<210> SEQ ID NO 62
<211> LENGTH: 100
<212> TYPE: DNA
<213> ORGANISM: Homo sapiens

<400> SEQUENCE: 62
atgacatcta agggctcaag gaggatttgg cagtaaacca agagcagagt gcttggttga      60
ataaggccat gaagcatgca cacaccgccc atcaccctcc                           100

<210> SEQ ID NO 63
<211> LENGTH: 100
<212> TYPE: DNA
<213> ORGANISM: Homo sapiens

<400> SEQUENCE: 63
atgaaacctg agggtccaag gaggatttag tagtaaatta agaacagagt gcttaattga      60
atagggccat aaagcacgca cacaccaccc atcaccctcc                           100

<210> SEQ ID NO 64
<211> LENGTH: 100
<212> TYPE: DNA
<213> ORGANISM: Homo sapiens

<400> SEQUENCE: 64
atgaaatcta agggctcaag gaggatttag caataaattg agagcagagt gtttaattga      60
ataaggccat gaagcatgca cacaccgccc gtcaccctcc                           100

<210> SEQ ID NO 65
<211> LENGTH: 100
<212> TYPE: DNA
<213> ORGANISM: Homo sapiens

<400> SEQUENCE: 65
atgaaatcta agggctcaag gaggatttag caataaattg agagcagagt gtttaattga      60
ataaggccat gaagcacgca cacaccgccc ttcaccctcc                           100

<210> SEQ ID NO 66
<211> LENGTH: 100
<212> TYPE: DNA
<213> ORGANISM: Homo sapiens

<400> SEQUENCE: 66
tcaagtatac ttcaaaggac atttaactaa aaccccctacg catttatata gaggagacaa     60
gtcgtaacat ggtaagtgta ctggaaagtg cacttggacg                           100

<210> SEQ ID NO 67
<211> LENGTH: 100
<212> TYPE: DNA
<213> ORGANISM: Homo sapiens

<400> SEQUENCE: 67
aaatattact ttagagatta gtttaactaa aaccccctact tatttatata gaggagacaa     60
```

```
gtcgtaacat ggtaagtgta ctagaaagtg cacttggatg                          100
```

<210> SEQ ID NO 68
<211> LENGTH: 100
<212> TYPE: DNA
<213> ORGANISM: Homo sapiens

<400> SEQUENCE: 68

```
aaccagagtg tagcttaaca caaagcaccc aacttacact taggagattt caacttaact    60
tgaccgctct gagctaaacc tagccccaaa cccactccac                         100
```

<210> SEQ ID NO 69
<211> LENGTH: 100
<212> TYPE: DNA
<213> ORGANISM: Homo sapiens

<400> SEQUENCE: 69

```
aataataaag gaggttaaca taaagcaccc aacttacact taggagattt caacttaact    60
tgaccgctct gagctaaacc tagccccaaa cccactccac                         100
```

<210> SEQ ID NO 70
<211> LENGTH: 100
<212> TYPE: DNA
<213> ORGANISM: Homo sapiens

<400> SEQUENCE: 70

```
aaccaaggtg tagcttaaca taaagcaccc tgcttacacc tgggagattt caatttaatt    60
tgaccaccct gagctaattc tagccccaaa cccaactaat                         100
```

<210> SEQ ID NO 71
<211> LENGTH: 100
<212> TYPE: DNA
<213> ORGANISM: Homo sapiens

<400> SEQUENCE: 71

```
cttactacca gacaacctta gccaaaccat ttacccaaat aaagtatagg cgatagaaat    60
tgaaacctgg cgcaatagat atagtaccgc aagggaaaga                         100
```

<210> SEQ ID NO 72
<211> LENGTH: 100
<212> TYPE: DNA
<213> ORGANISM: Homo sapiens

<400> SEQUENCE: 72

```
tctactacca aataacctca actaaaacat ttacccaaat aaagtatagg cgatagaaat    60
gatatctcgg cacaatagac ataataccgc gatggaaaga                         100
```

<210> SEQ ID NO 73
<211> LENGTH: 100
<212> TYPE: DNA
<213> ORGANISM: Homo sapiens

<400> SEQUENCE: 73

```
tgaaaaatta taaccaagca taatatagca aggactaacc cctataccttt ctgcataatg   60 aattaactag aaataacttt gcaaggagag ccaaagctaa                         100
```

<210> SEQ ID NO 74
<211> LENGTH: 100
<212> TYPE: DNA
<213> ORGANISM: Homo sapiens

<400> SEQUENCE: 74
atgaaaaagt taaccaagaa taaaatagca aggatagacc cttatacctt ctgcgtaatg    60
aattaactag aaataacttt acacagagaa ccaaagccaa                         100

<210> SEQ ID NO 75
<211> LENGTH: 100
<212> TYPE: DNA
<213> ORGANISM: Homo sapiens

<400> SEQUENCE: 75
tgaaaaaaca taaccaagca taaagtagca aggacaaacc cctatacctt ctgcataatg    60
aattaactag aaataacttt acaaagagaa ccaaagccaa                         100

<210> SEQ ID NO 76
<211> LENGTH: 100
<212> TYPE: DNA
<213> ORGANISM: Homo sapiens

<400> SEQUENCE: 76
gacccccgaa accagacgag ctacctaaga acagctaaaa gagcacaccc gtctatgtag    60
caaaatagtg ggaagattta taggtagagg cgacaaacct                         100

<210> SEQ ID NO 77
<211> LENGTH: 100
<212> TYPE: DNA
<213> ORGANISM: Homo sapiens

<400> SEQUENCE: 77
gtcccctgaa accagatgag ctacccaaga ataactgaaa gcgcacaccc acctatgtgg    60
caaaatagtg ggaagattga tgagtagggg ggacaagcct                         100

<210> SEQ ID NO 78
<211> LENGTH: 100
<212> TYPE: DNA
<213> ORGANISM: Homo sapiens

<400> SEQUENCE: 78
gtcccccgaa accagatgaa ctacccaaga acagctgaaa gagcacactc acctatgtgg    60
caaaatagtg ggaagatgca tgagtagcgg tcacaagcct                         100

<210> SEQ ID NO 79
<211> LENGTH: 100
<212> TYPE: DNA
<213> ORGANISM: Homo sapiens

<400> SEQUENCE: 79 ggccccaaa accagacgag ctacccaaga acagctaaaa gaacacaccc atctatgtag     60
taaaatagtg gggagattca tgagtagtgg tgataagcct                         100

<210> SEQ ID NO 80
<211> LENGTH: 100
<212> TYPE: DNA
<213> ORGANISM: Homo sapiens

<400> SEQUENCE: 80
ggcccctaaa accagacgag ctacccaaga acagcgaaaa gagcacaccc atctatgtag    60
taaaatagtg gggagattca tgagcagcag tgatacgcct                         100

```
<210> SEQ ID NO 81
<211> LENGTH: 100
<212> TYPE: DNA
<213> ORGANISM: Homo sapiens

<400> SEQUENCE: 81
gtcccccgaa accagacagg ctacccaaga atagctaaaa gagcacactc acctgtgtgg      60
caaaatagtg agaagattca tgagtagcgg tgacaaggct                          100

<210> SEQ ID NO 82
<211> LENGTH: 100
<212> TYPE: DNA
<213> ORGANISM: Homo sapiens

<400> SEQUENCE: 82
gtcccccaaa accagatgag ctacccaaga acagctgaaa gagcacaccc acctatgtgg      60
caaaataggg ggaagattca tgagtagcag cgataagcct                          100

<210> SEQ ID NO 83
<211> LENGTH: 100
<212> TYPE: DNA
<213> ORGANISM: Homo sapiens

<400> SEQUENCE: 83 gaccccgaa accagacgag ctacctaaga acagctgaaa gagcacaccc atctatgtag       60
caaaatagtg ggaagattca taggtagagg tgacaagcct                          100

<210> SEQ ID NO 84
<211> LENGTH: 100
<212> TYPE: DNA
<213> ORGANISM: Homo sapiens

<400> SEQUENCE: 84
accgagcctg gtgatagctg gttgtccaag atagaatctt agttcaactt taaatttgcc      60
cacagaaccc tctaaatccc cttgtaaatt taactgttag                          100

<210> SEQ ID NO 85
<211> LENGTH: 100
<212> TYPE: DNA
<213> ORGANISM: Homo sapiens

<400> SEQUENCE: 85
tccaagcctg gtgatagctg gttgtccaag atagaatctt agttcaactt taaatttacc      60 tacagaaacca cttaattccc ctgtaaattt aactgttagt                         100

<210> SEQ ID NO 86
<211> LENGTH: 100
<212> TYPE: DNA
<213> ORGANISM: Homo sapiens

<400> SEQUENCE: 86
accaagcctg gtgatagctg gttgtccaag atagaattga aattcaactt taaatttacc      60
tacagaacca cctaatccta ttgttaagtt taattgttag                          100

<210> SEQ ID NO 87
<211> LENGTH: 100
<212> TYPE: DNA
<213> ORGANISM: Homo sapiens

<400> SEQUENCE: 87
```

```
tccaaagagg aacagctctt tggacactag gaaaaaacct tgtagagaga gtaaaaaatt    60
taacacccat agtaggccta aaagcagcca ccaattaaga                          100

<210> SEQ ID NO 88
<211> LENGTH: 100
<212> TYPE: DNA
<213> ORGANISM: Homo sapiens

<400> SEQUENCE: 88
tctaaagagg gacagctctt tagacactag gaaaaaacct tgtagagaga gtaaaaaata    60
taacttccaa agttggccta gaagaagcga tcaattaaga                          100

<210> SEQ ID NO 89
<211> LENGTH: 100
<212> TYPE: DNA
<213> ORGANISM: Homo sapiens

<400> SEQUENCE: 89
aagcgttcaa gctcaacacc cactacctaa aaaatcccaa acatataact gaactcctca    60
cacccaattg gaccaatcta tcaccctata gaagaactaa                          100

<210> SEQ ID NO 90
<211> LENGTH: 100
<212> TYPE: DNA
<213> ORGANISM: Homo sapiens

<400> SEQUENCE: 90
tgttagtata agtaacatga aaacattctc ctccgcataa gcctgcgtca gatcaaaaca    60
ctgaactgac aattaacagc ccaatatcta caatcaacca                          100

<210> SEQ ID NO 91
<211> LENGTH: 100
<212> TYPE: DNA
<213> ORGANISM: Homo sapiens

<400> SEQUENCE: 91
tgttagtata agtgacatgc aaacattctc ctccgcataa gcctacatca gaccaaaata    60
cttcactgac aattaacagc ccaatatcta taaataatca                          100

<210> SEQ ID NO 92
<211> LENGTH: 100
<212> TYPE: DNA
<213> ORGANISM: Homo sapiens

<400> SEQUENCE: 92
acaagtcatt attaccctca ctgtcaaccc aacacaggca tgctcataag gaaaggttaa    60
aaaaagtaaa aggaactcgg caaaccttac cccgcctgtt                          100

<210> SEQ ID NO 93
<211> LENGTH: 100
<212> TYPE: DNA
<213> ORGANISM: Homo sapiens

<400> SEQUENCE: 93
atgaaactgt attactccta ctgttaaccc aacacaggca tgcccacaag gaaaggttaa    60
aaaaagtaaa aggaactcgg caaatcttac cccgcctgtt                          100

<210> SEQ ID NO 94
```

```
<211> LENGTH: 100
<212> TYPE: DNA
<213> ORGANISM: Homo sapiens

<400> SEQUENCE: 94
acaaaccggt gctacccata ctgttaaccc aacacaggca tgcttataag gaaaggttaa    60
aaaaagtaaa aggaactcgg caaatcttac cccgcctgtt                         100

<210> SEQ ID NO 95
<211> LENGTH: 100
<212> TYPE: DNA
<213> ORGANISM: Homo sapiens

<400> SEQUENCE: 95
caaatttatt attaccgata ctgttaatcc aacacaggca tgctctaagg aaaggttaaa    60
aaaaattaaa aggaactcgg caaatttac cctgcctgtt                          100

<210> SEQ ID NO 96
<211> LENGTH: 100
<212> TYPE: DNA
<213> ORGANISM: Homo sapiens

<400> SEQUENCE: 96
tgaaaccatt attacccaca ctgttaaccc aacacaggca tgcttacaag gaaaggttaa    60
aaaaagtaaa aggaactcag cgaatcttac ccctcctgtt                         100

<210> SEQ ID NO 97
<211> LENGTH: 100
<212> TYPE: DNA
<213> ORGANISM: Homo sapiens

<400> SEQUENCE: 97
taccaaaaac atcacctcta gcatcaccag tattagaggc accgcctgcc cagtgacaca    60
tgtttaacgg ccgcggtacc ctaaccgtgc aaaggtagca                         100

<210> SEQ ID NO 98
<211> LENGTH: 100
<212> TYPE: DNA
<213> ORGANISM: Homo sapiens

<400> SEQUENCE: 98
taccaaaaac atcacctcta gcattaacag tattagaggc actgcctacc cagtgacata    60
tgtttaacgg ccacagtatc ctgacagtgc acaggtagca                         100

<210> SEQ ID NO 99
<211> LENGTH: 100
<212> TYPE: DNA
<213> ORGANISM: Homo sapiens

<400> SEQUENCE: 99
taccaaaaac atcacctcta gcattaccag tattagagtc actgcctgcc cagtgacata    60
tgttcaacag ccgcggtatc ctgaccgtgc aaaggtagca                         100

<210> SEQ ID NO 100
<211> LENGTH: 100
<212> TYPE: DNA
<213> ORGANISM: Homo sapiens

<400> SEQUENCE: 100
taccaaaaac atcacctcta gcattaccag ttttagagtc actgcctgcc cggtgacata    60
```

```
tgttcaacgg ccatggtatc ctgaccgtgc aaaggtagca                 100
```

<210> SEQ ID NO 101
<211> LENGTH: 100
<212> TYPE: DNA
<213> ORGANISM: Homo sapiens

<400> SEQUENCE: 101

```
taccaaaaac atcacctcta gcattaccag tattagaggc accgcctgcc cagtgacata   60
tgtttaacgg ccgtggtacc ctaaccgtgc aaaggtagca                        100
```

<210> SEQ ID NO 102
<211> LENGTH: 100
<212> TYPE: DNA
<213> ORGANISM: Homo sapiens

<400> SEQUENCE: 102

```
taccaaaaac atcacctcta gcattaccag tattagaggc accgcctgcc cagtgacata   60
tgttgaatgg ccgcggcttt ctacgtctct aggggctgtg                        100
```

<210> SEQ ID NO 103
<211> LENGTH: 100
<212> TYPE: DNA
<213> ORGANISM: Homo sapiens

<400> SEQUENCE: 103

```
taccaaaaac atcacctcta gcattaccag tattagaggc actgcctgtc cagtgacata   60
tgttcgatgg ccgcagtatc ctgactgtgc aaaggtagca                        100
```

<210> SEQ ID NO 104
<211> LENGTH: 100
<212> TYPE: DNA
<213> ORGANISM: Homo sapiens

<400> SEQUENCE: 104

```
taccaaaaac atcacctcta gcattaccag tattagaggc actgcctacc cagtgactta   60
tgttcaatgg ccgtggtatc ctgaccgtgc aaaggtagca                        100
```

<210> SEQ ID NO 105
<211> LENGTH: 100
<212> TYPE: DNA
<213> ORGANISM: Homo sapiens

<400> SEQUENCE: 105

```
taccaaaaac atcacctcta gcattaccag tattagaggc actgcctgcc cagtgacata   60
tgttcaacga ccaccatatc ctgaccttgc aaaggtaaca                        100
```

<210> SEQ ID NO 106
<211> LENGTH: 100
<212> TYPE: DNA
<213> ORGANISM: Homo sapiens

<400> SEQUENCE: 106

```
taccaaaaac atcacctcta gcattattag tattagaggc gctgcctgcc cagtgacata   60
tgttcaacag ccacagtacc ctgagcgtgc aaaggtagca                        100
```

<210> SEQ ID NO 107
<211> LENGTH: 100
<212> TYPE: DNA

<213> ORGANISM: Homo sapiens

<400> SEQUENCE: 107
taccaaaaac atcacctcta gcattaccag tattaaaggc actgccttcc cagtgatata    60
tgttcaatgg ctgtggtatc ctgactgtgc aaaggtagca                         100

<210> SEQ ID NO 108
<211> LENGTH: 100
<212> TYPE: DNA
<213> ORGANISM: Homo sapiens

<400> SEQUENCE: 108
taccaaaaac atcaccccta gcattgctag tattagaggc actgcctgct cagtgacata    60
tgtttaaggg ttgcggtatc ctgaacttgc aaaggtagca                         100

<210> SEQ ID NO 109
<211> LENGTH: 100
<212> TYPE: DNA
<213> ORGANISM: Homo sapiens

<400> SEQUENCE: 109
taccaaaaac atcacctcta gcattaccag tattagaggc actgcctgcc cagtgacata    60
tgttcaacgg tggtggtatc ctgaccgtgc aaggtagcat                         100

<210> SEQ ID NO 110
<211> LENGTH: 100
<212> TYPE: DNA
<213> ORGANISM: Homo sapiens

<400> SEQUENCE: 110
taccaaaaac atcacctcta gcattaccag tattagaggc actgcctgcc cagtgacata    60
tgttcaacgg ccgcagtatc ctgaccatgt aaggtagcat                         100

<210> SEQ ID NO 111
<211> LENGTH: 100
<212> TYPE: DNA
<213> ORGANISM: Homo sapiens

<400> SEQUENCE: 111
tatcaaaaac atcacctcta gcattaccag tactagaggc accacctgcc cagtgacata    60
tgtttaatgg ctgcggtacc ctaaccgtgt aaaggtagca                         100

<210> SEQ ID NO 112
<211> LENGTH: 100
<212> TYPE: DNA
<213> ORGANISM: Homo sapiens

<400> SEQUENCE: 112
taccaaaaac atcacctctg acataactag tattagaggc actacctgcc cagtgacata    60
agtttaacag ccacagtatc ctgaccatgc taaggtagca                         100

<210> SEQ ID NO 113
<211> LENGTH: 100
<212> TYPE: DNA
<213> ORGANISM: Homo sapiens

<400> SEQUENCE: 113
taccaaaaac atcacctcta gcattactag taccagaggc aatgcctacc cagtgacgta    60
tgtttaaggg ctgcggtatc ttgaccatgc aaaggtagcc                         100

<210> SEQ ID NO 114
<211> LENGTH: 100
<212> TYPE: DNA
<213> ORGANISM: Homo sapiens

<400> SEQUENCE: 114
taatcacttg ttccttaaat agggacctgt atgaatggct ccacgagggt tcagctgtct    60
cttactttta accagtgaaa ttgacctgcc cgtgaagagg                         100

<210> SEQ ID NO 115
<211> LENGTH: 100
<212> TYPE: DNA
<213> ORGANISM: Homo sapiens

<400> SEQUENCE: 115
taatcacttg ttccctaaat agggacttgt atgaatggcc atatgaaggt tcagctgtct    60
cttacttttA atcagtgaaa ttgacctatt cgtgaagagg                         100

<210> SEQ ID NO 116
<211> LENGTH: 100
<212> TYPE: DNA
<213> ORGANISM: Homo sapiens

<400> SEQUENCE: 116
taatcgcttg ttccctaaat agggacttgt atgaatggac acacaagggt tcagctgtct    60
cttacttttA atcagtgaaa ttgacctatc tgtgaagagg                         100

<210> SEQ ID NO 117
<211> LENGTH: 100
<212> TYPE: DNA
<213> ORGANISM: Homo sapiens

<400> SEQUENCE: 117
tgatcacttg ttccttaaat agggacttgt atgaatggct cgacgaggtt tcagctgtct    60
cttactttca accactgcaa ctgacctgcc cgtgaagagg                         100

<210> SEQ ID NO 118
<211> LENGTH: 100
<212> TYPE: DNA
<213> ORGANISM: Homo sapiens

<400> SEQUENCE: 118
taatcacttg ttccttaaat agggacttgt atgaatgacc ccacgagggt tcagctgtct    60
cttacttcca accagtgaaa ctgacctgcc tgtgaagagg                         100

<210> SEQ ID NO 119
<211> LENGTH: 100
<212> TYPE: DNA
<213> ORGANISM: Homo sapiens

<400> SEQUENCE: 119
taatcacttg ttccctaaat agggacttat atgaatggcc acatgagggt tcagctgtct    60
cttacttttA atcagtgaaa ttgacgtatc catgaaaagg                         100

<210> SEQ ID NO 120
<211> LENGTH: 100
<212> TYPE: DNA
<213> ORGANISM: Homo sapiens

<400> SEQUENCE: 120
taatcacttg ttccttaaat agggacttgt atgaatggct ccatgagggt tcagctgtct    60
cttacttcca accagtgaaa ctgacctgcc catgaacagg                          100

<210> SEQ ID NO 121
<211> LENGTH: 100
<212> TYPE: DNA
<213> ORGANISM: Homo sapiens

<400> SEQUENCE: 121
taatcacttg ttccctaagt agggacttgt atgaatggcc acaccagggt ttagctgtct    60
cttactttca accagtgaaa ttgacctacc tatgaagagg                          100

<210> SEQ ID NO 122
<211> LENGTH: 100
<212> TYPE: DNA
<213> ORGANISM: Homo sapiens

<400> SEQUENCE: 122
taatcacttg ttccctaaat agggacttgt atgaatagcc acacaagggt tgagctgtct    60 cttacttta atcagtgaaa ttgacctatc catgaagagg                           100

<210> SEQ ID NO 123
<211> LENGTH: 100
<212> TYPE: DNA
<213> ORGANISM: Homo sapiens

<400> SEQUENCE: 123
taatcacttg ttccttaaat agggacttgt ctgaatggct ccacgagggt tcagctgtct    60
cttactttca accagtgaaa ttgacctgcc cgtgaagagg                          100

<210> SEQ ID NO 124
<211> LENGTH: 100
<212> TYPE: DNA
<213> ORGANISM: Homo sapiens

<400> SEQUENCE: 124
taatcatttg ttcccaaaat gggaacttcc atgaatggcc tcacaagggt ttaattgtct    60
cttacgttta atcagtgaaa ttgacctatc tgtggagagg                          100

<210> SEQ ID NO 125
<211> LENGTH: 100
<212> TYPE: DNA
<213> ORGANISM: Homo sapiens

<400> SEQUENCE: 125
taatcagttt ttccccaaat agggacctgt atgaatggcc acaagagggt ctgattgtct    60
cttaccttta gtcaatgaaa ttgacctacc catgaagagg                          100

<210> SEQ ID NO 126
<211> LENGTH: 100
<212> TYPE: DNA
<213> ORGANISM: Homo sapiens

<400> SEQUENCE: 126
cgggcatgac acagcaagac gagaagaccc tatggagctt taatttatta atgcaaacag    60
tacctaacaa acccacaggt cctaaactac caaacctgca                         100

```
<210> SEQ ID NO 127
<211> LENGTH: 100
<212> TYPE: DNA
<213> ORGANISM: Homo sapiens

<400> SEQUENCE: 127
cggacataat acaacaagac gagaagacca tatggagctt caatttacca atgcaaacaa      60
cacccaataa gcccacaggc tctaacctac caaacctgca                          100

<210> SEQ ID NO 128
<211> LENGTH: 100
<212> TYPE: DNA
<213> ORGANISM: Homo sapiens

<400> SEQUENCE: 128
cggacataat acaacaagac gagaagaccc taaggagctt taatttatga atgcaaacaa      60
gaccaaatag gcccgcaggc cctaaactac cagacctgcg                          100

<210> SEQ ID NO 129
<211> LENGTH: 100
<212> TYPE: DNA
<213> ORGANISM: Homo sapiens

<400> SEQUENCE: 129
ttaaaaattt cggttggggc gacctcggag cagaacccaa cctccgagca gtacatgcta      60
agacttcacc agtcaaagcg aactactata ctcaattgat                          100

<210> SEQ ID NO 130
<211> LENGTH: 100
<212> TYPE: DNA
<213> ORGANISM: Homo sapiens

<400> SEQUENCE: 130
ttaaaaattt cggctggggc gacctcggag tataacccaa cctccgagca acatatgctg      60
agacttcacc agtcaaaacg agttaccacg tacaattgat                          100

<210> SEQ ID NO 131
<211> LENGTH: 100
<212> TYPE: DNA
<213> ORGANISM: Homo sapiens

<400> SEQUENCE: 131
ttaaacattt cggttggggc gacctcggag tataacctaa cctccgagca acatatgctg      60
agactatacc agtcaaggcg aatatccaca tacaattgac                          100

<210> SEQ ID NO 132
<211> LENGTH: 100
<212> TYPE: DNA
<213> ORGANISM: Homo sapiens

<400> SEQUENCE: 132
ccaataactt gaccaacgga acaagttacc ctagggataa cagcgcaatc ctattctaga      60
gtccatatca acaatagggt ttacgacctc gatgttggat                          100

<210> SEQ ID NO 133
<211> LENGTH: 100
<212> TYPE: DNA
<213> ORGANISM: Homo sapiens

<400> SEQUENCE: 133
```

```
ccaatgattc gatcaacaga ataagttacc ctagggataa cagctcaatc ctattctaga    60
gttcatatcg acaataggt ttacgacctc gatgttggat                          100
```

<210> SEQ ID NO 134
<211> LENGTH: 100
<212> TYPE: DNA
<213> ORGANISM: Homo sapiens

<400> SEQUENCE: 134

```
ccaataattt gatcaacgga ataagttacc ttagggatag cagcgcaatc ccattctaga    60
atcagtattg acaatagagt ttacaacctc gatgttggat                         100
```

<210> SEQ ID NO 135
<211> LENGTH: 100
<212> TYPE: DNA
<213> ORGANISM: Homo sapiens

<400> SEQUENCE: 135

```
ccaataattt gatcaacgga acaagttacc ctagggataa cagcgcaatc ctattctaga    60
gtccatattg acaataggt ttacgacctc gatgttggat                          100
```

<210> SEQ ID NO 136
<211> LENGTH: 100
<212> TYPE: DNA
<213> ORGANISM: Homo sapiens

<400> SEQUENCE: 136

```
ccaataattt gatcaatgga ataagttatg ctagggataa cagtgcaatc ctattctaga    60
gtccatagcg acaataggga tgactacctc gatgctgaat                         100
```

<210> SEQ ID NO 137
<211> LENGTH: 100
<212> TYPE: DNA
<213> ORGANISM: Homo sapiens

<400> SEQUENCE: 137

```
ccaataattt gatcaacgga acaagttacc ctagagataa cagcgcaatc ctattctaga    60
gtccatatcg acaataggt ttacgacctc gatgttggat                          100
```

<210> SEQ ID NO 138
<211> LENGTH: 100
<212> TYPE: DNA
<213> ORGANISM: Homo sapiens

<400> SEQUENCE: 138

```
ccaataattc tatcaacagg ataagtgacc ctagggttaa gagtgcaatc ctattctagc    60
atccatatca acaacaggt ttacgacctt gatgttggat                          100
```

<210> SEQ ID NO 139
<211> LENGTH: 100
<212> TYPE: DNA
<213> ORGANISM: Homo sapiens

<400> SEQUENCE: 139

```
ccaataactt gttcaaggga ataagttact ctagggataa cagcacaatc ctattctaga    60
gtccatatcg acaataggt ttacgacctc ggtgttgtat                          100
```

<210> SEQ ID NO 140
<211> LENGTH: 100

```
<212> TYPE: DNA
<213> ORGANISM: Homo sapiens

<400> SEQUENCE: 140
ccaataattt gatcaacgga ataagttacc ctagggataa cagcacaatc ctattctaga    60
gttcatatcg agaatagggt ttacgacgtc gatgttggat                         100

<210> SEQ ID NO 141
<211> LENGTH: 100
<212> TYPE: DNA
<213> ORGANISM: Homo sapiens

<400> SEQUENCE: 141
ccaataattt gaccaacgga acaagttacc ctagtgataa cagtacaatc ctattctagg    60
gtccacatcg acagtagcat taacgacctc gatgttggat                         100

<210> SEQ ID NO 142
<211> LENGTH: 100
<212> TYPE: DNA
<213> ORGANISM: Homo sapiens

<400> SEQUENCE: 142
caagtagttt gagcaatgga acacgttacc ttagggatag cagtacaatc ctattctaga    60
atccgtatca gcaatagggt gtatgacttc gatattggat                         100

<210> SEQ ID NO 143
<211> LENGTH: 100
<212> TYPE: DNA
<213> ORGANISM: Homo sapiens

<400> SEQUENCE: 143
caaatagttt gaccaactga gcaagttacc ctagggataa caacacgatc ctattctaga    60
gtccatattg actatagggt ttacgatctc gatgttggat                         100

<210> SEQ ID NO 144
<211> LENGTH: 100
<212> TYPE: DNA
<213> ORGANISM: Homo sapiens

<400> SEQUENCE: 144
caggacatcc cgatggtgca gccgctatta aaggttcgtt tgttcaacga ttaaagtcct    60
acgtgatctg agttcagacc ggagtaatcc aggtcggttt                         100

<210> SEQ ID NO 145
<211> LENGTH: 100
<212> TYPE: DNA
<213> ORGANISM: Homo sapiens

<400> SEQUENCE: 145
caggacatcc aaatggtgta gccactatta agggtttgtc tgttcaaaga ttaaagtcct    60
atgtgatctg agttcagact agagtaatcc aggccggttt                         100

<210> SEQ ID NO 146
<211> LENGTH: 100
<212> TYPE: DNA
<213> ORGANISM: Homo sapiens

<400> SEQUENCE: 146
caggacatcc taatggtgta gctgctatca agggtttgtt tgttcaatga ttaaagtcct    60
```
acatgatctg agttcagacc ggagcaatcc aggtcagttt                                      100

<210> SEQ ID NO 147
<211> LENGTH: 100
<212> TYPE: DNA
<213> ORGANISM: Homo sapiens

<400> SEQUENCE: 147
gaggacatcc taatggtgta gccgctatta agggttcgtt tgtttaacgg ttaaagttct      60
atgtgatctg agttcagacc tgagtaatcc aggtcagttt                                      100

<210> SEQ ID NO 148
<211> LENGTH: 100
<212> TYPE: DNA
<213> ORGANISM: Homo sapiens

<400> SEQUENCE: 148
caggacatcc taatggtgta gctgctatca agggttcatt tgttcaatga ttaaagtcct      60
acgtggtctg agttcagacc ggagcaagcc aggtctggta                                      100

<210> SEQ ID NO 149
<211> LENGTH: 100
<212> TYPE: DNA
<213> ORGANISM: Homo sapiens

<400> SEQUENCE: 149
caggacatct taatgctgga gccgctatta agagtttgtt tgttcaacga ttaaagtcct      60
acgtgatctg aattcagacc agaataatcc aggtcagttc                                      100

<210> SEQ ID NO 150
<211> LENGTH: 100
<212> TYPE: DNA
<213> ORGANISM: Homo sapiens

<400> SEQUENCE: 150
caggacatcc taatggtgta gccgctatta agggttcatt tattcaatga ttaaagtcct      60
atgtgatctg atttcagacc agagtaatcc aggttggttt                                      100

<210> SEQ ID NO 151
<211> LENGTH: 100
<212> TYPE: DNA
<213> ORGANISM: Homo sapiens

<400> SEQUENCE: 151
caggacatcc taatggtgta gctgctgtca agggttcgtt tgtccaatga ttaaagtcct      60
acgtgatctg agttcagacc ggagcaatcc aggtctggta                                      100

<210> SEQ ID NO 152
<211> LENGTH: 100
<212> TYPE: DNA
<213> ORGANISM: Homo sapiens

<400> SEQUENCE: 152
gggacatcct aaatggtgta gccgctatta agggatcatt tgttcaatga ttaaagtcct      60
tcgtgatctg agttcagacc agagcaatcc aggttggttt                                      100

<210> SEQ ID NO 153
<211> LENGTH: 100
<212> TYPE: DNA
<213> ORGANISM: Homo sapiens

```
<400> SEQUENCE: 153
caggacgtcc taatggtgta gccgctaata agggttcgtt tgttcaatga tcaaagtcct    60
acatgatctg agttcagacc ggagtaatcc aggtcagttt                         100

<210> SEQ ID NO 154
<211> LENGTH: 100
<212> TYPE: DNA
<213> ORGANISM: Homo sapiens

<400> SEQUENCE: 154
caggacatcc taatggtgca gccgctatta agggttcgtt tgttcaatga ttagaatcct    60
acatgatctg agttcagatc ggagtaatcc aggtcggttt                         100

<210> SEQ ID NO 155
<211> LENGTH: 100
<212> TYPE: DNA
<213> ORGANISM: Homo sapiens

<400> SEQUENCE: 155
caggacatcc caatggtgca gccgctatta aaggttcgtt tgttcaacga ttagagtcct    60
atgtgatctg agttcagacc ggagtaatcc aggttggttt                         100

<210> SEQ ID NO 156
<211> LENGTH: 100
<212> TYPE: DNA
<213> ORGANISM: Homo sapiens

<400> SEQUENCE: 156
aaggacatgc taatggtgta gccagtatta aggattcttt tgttcagtga ttaaagtcct    60
acatgatttg agttcagacc agagtaaccc aggtcggttt                         100

<210> SEQ ID NO 157
<211> LENGTH: 100
<212> TYPE: DNA
<213> ORGANISM: Homo sapiens

<400> SEQUENCE: 157
ctatctactt caaattcctc cctgtacgaa aggacaagag aaataaggcc tacttcacaa    60
agcgccttcc cccgtaaatg atatcatctc aacttagtat                         100

<210> SEQ ID NO 158
<211> LENGTH: 100
<212> TYPE: DNA
<213> ORGANISM: Homo sapiens

<400> SEQUENCE: 158 tatcccaca cccacccaag aacagggttt gttaagatgg cagagcccgg taatcgcata     60
aaacttaaaa ctttacagtc agaggttcaa ttcctcttct                         100

<210> SEQ ID NO 159
<211> LENGTH: 100
<212> TYPE: DNA
<213> ORGANISM: Homo sapiens

<400> SEQUENCE: 159
catcacacac actattcaag aacaaggttt gttaagatgg cagagcccag caattgcata    60
aatcttaaaa ctttataatc agaggttcga ctcctcttct                         100
```

<210> SEQ ID NO 160
<211> LENGTH: 100
<212> TYPE: DNA
<213> ORGANISM: Homo sapiens

<400> SEQUENCE: 160
gaaatcacca cacacccaag aacagggttt cttaagatgg cggagcctgg caatagcata      60
aaacgtaaaa ctttacaatc aaaggttcaa ctcccttct                            100

<210> SEQ ID NO 161
<211> LENGTH: 100
<212> TYPE: DNA
<213> ORGANISM: Homo sapiens

<400> SEQUENCE: 161
tgtacccaca cccacccaag aacagggttt gttaagatgg cagaccccag caattgcata      60
aaatttaaaa ctttacaacc agaggttcaa cccctcttct                           100

<210> SEQ ID NO 162
<211> LENGTH: 100
<212> TYPE: DNA
<213> ORGANISM: Homo sapiens

<400> SEQUENCE: 162
taacaacata cccatggcca acctcctact cctcattgta cccattctaa tcgcaatggc      60
attcctaatg cttaccgaac gaaaaattct aggctatata                           100

<210> SEQ ID NO 163
<211> LENGTH: 100
<212> TYPE: DNA
<213> ORGANISM: Homo sapiens

<400> SEQUENCE: 163
taacaacatg tccataacta accttctact tcttattgta cctatcctaa tcgccatggc      60
attcctcatg ctaactgaat gaaaaatcct aggctacatg                           100

<210> SEQ ID NO 164
<211> LENGTH: 100
<212> TYPE: DNA
<213> ORGANISM: Homo sapiens

<400> SEQUENCE: 164
caactacgca aaggccccaa cgttgtaggc ccctacgggc tactacaacc cttcgctgac      60
gccataaaac tcttcaccaa agagcccta aaacccgcca                            100

<210> SEQ ID NO 165
<211> LENGTH: 100
<212> TYPE: DNA
<213> ORGANISM: Homo sapiens

<400> SEQUENCE: 165
caactatgca aaggatccaa tattttaggc ccctatggac tatttcaacc atttgctgat      60
gcaataaaac ttttcactaa agagaccta aaaccctcat                            100

<210> SEQ ID NO 166
<211> LENGTH: 100
<212> TYPE: DNA
<213> ORGANISM: Homo sapiens

<400> SEQUENCE: 166

```
caactatgca aaggacctaa cattgtaggt ccctatgggc tgcttcaacc agtcgttgat      60
gcaataaaac ttttcaccaa agaaacccta aggccctcaa                          100

<210> SEQ ID NO 167
<211> LENGTH: 100
<212> TYPE: DNA
<213> ORGANISM: Homo sapiens

<400> SEQUENCE: 167
caactacgca aagggcccaa tattgtaggc ccctatggac tattacaacc ttttgccgat      60
gccataaaac tctttaccaa agaatcctta aaaccctcaa                          100

<210> SEQ ID NO 168
<211> LENGTH: 100
<212> TYPE: DNA
<213> ORGANISM: Homo sapiens

<400> SEQUENCE: 168
catctaccat caccctctac atcaccgccc cgaccttagc tctcaccatc gctcttctac      60 tatgaaccccc ctccccata cccaaccccc tggtcaacct                          100

<210> SEQ ID NO 169
<211> LENGTH: 100
<212> TYPE: DNA
<213> ORGANISM: Homo sapiens

<400> SEQUENCE: 169
cgtcaactgt taccctctac atcactgccc caaccttagc cctctctatt gcccttctac      60
tatgaactcc cctccctata cctaaccccc tagttaatct                          100

<210> SEQ ID NO 170
<211> LENGTH: 100
<212> TYPE: DNA
<213> ORGANISM: Homo sapiens

<400> SEQUENCE: 170
caacctaggc ctcctattta ttctagccac ctctagccta gccgtttact caatcctctg      60
atcagggtga gcatcaaact caaactacgc cctgatcggc                          100

<210> SEQ ID NO 171
<211> LENGTH: 100
<212> TYPE: DNA
<213> ORGANISM: Homo sapiens

<400> SEQUENCE: 171
taatataggc ctcttattta ttctagccac atcaagccta gcagtctatt ccattctatg      60
atcaggataa gcatccaatt caaattatgt actgatcggc                          100

<210> SEQ ID NO 172
<211> LENGTH: 100
<212> TYPE: DNA
<213> ORGANISM: Homo sapiens

<400> SEQUENCE: 172
taatataggc ctcctatttta tactagccac atcaagccta gccgtctact ctattctatg     60
atcaggatga gcatctaatt caaattatgc actaatcggc                          100

<210> SEQ ID NO 173
```

```
<211> LENGTH: 100
<212> TYPE: DNA
<213> ORGANISM: Homo sapiens

<400> SEQUENCE: 173
taacttaggc cttctattca ttctggctac atccagccta gctgtctact ctatcctatg      60
atcaggatga gcatcaaact caaactatgc cctgatcggc                            100

<210> SEQ ID NO 174
<211> LENGTH: 100
<212> TYPE: DNA
<213> ORGANISM: Homo sapiens

<400> SEQUENCE: 174
gcactgcgag cagtagccca aacaatctca tatgaagtca ccctagccat cattctacta      60
tcaacattac taataagtgg ctcctttaac ctctccaccc                            100

<210> SEQ ID NO 175
<211> LENGTH: 100
<212> TYPE: DNA
<213> ORGANISM: Homo sapiens

<400> SEQUENCE: 175
gcattatgag cagttgccca aacaatttca tacgaagtta ccctagctat catcctatta      60
tcgatcctac taataagtgg ccaattcaat ctctgcaccc                            100

<210> SEQ ID NO 176
<211> LENGTH: 100
<212> TYPE: DNA
<213> ORGANISM: Homo sapiens

<400> SEQUENCE: 176
ttatcacaac acaagaacac ctctgattac tcctgccatc atgacccttg gcataatat       60 gatttatctc cacactagca gagaccaacc gaaccccctt                            100

<210> SEQ ID NO 177
<211> LENGTH: 100
<212> TYPE: DNA
<213> ORGANISM: Homo sapiens

<400> SEQUENCE: 177
gcatcacaat gccagaatta ctctgaccgc tcctaccatc atgaccctta gcatattat       60 gatttatttc cacactagca aaaactaacc gagccccttt                            100

<210> SEQ ID NO 178
<211> LENGTH: 100
<212> TYPE: DNA
<213> ORGANISM: Homo sapiens

<400> SEQUENCE: 178
ttatcacaat gcaagaattc ctctggccgc tcctaccatc atgacctctg gcataatat       60 gatttatctc cacgctggca gaaactaacc aagccccatt                            100

<210> SEQ ID NO 179
<211> LENGTH: 100
<212> TYPE: DNA
<213> ORGANISM: Homo sapiens

<400> SEQUENCE: 179
tcatcacaac acaagaattc ctctgactgc tcctaccatc atgccgccta gtcataatat      60
```
aatttatctc cccactagca gaaactaacc gagcccctt    100

<210> SEQ ID NO 180
<211> LENGTH: 100
<212> TYPE: DNA
<213> ORGANISM: Homo sapiens

<400> SEQUENCE: 180
tcattagaac acaagaacac ctctgactac tcctaacatc atgaccccta gctataatat    60
gatttatttc cacactagca gaaaccaatc gagctgcttt    100

<210> SEQ ID NO 181
<211> LENGTH: 100
<212> TYPE: DNA
<213> ORGANISM: Homo sapiens

<400> SEQUENCE: 181
cgaccttgcc gaaggggagt ccgaactagt ctcaggcttc aacatcgaat acgccgcagg    60 cccttcgcc ctattcttca tagccgaata cacaaacatt    100

<210> SEQ ID NO 182
<211> LENGTH: 100
<212> TYPE: DNA
<213> ORGANISM: Homo sapiens

<400> SEQUENCE: 182
tcagcaaggt caaagggagt ccgaactagt ctcaggcttc aacatcgaat acgccgcagg    60 cccttcgcc ctattcttca tagccgaata cacaaacatt    100

<210> SEQ ID NO 183
<211> LENGTH: 100
<212> TYPE: DNA
<213> ORGANISM: Homo sapiens

<400> SEQUENCE: 183
tgaccttact gaaggagaat cagaactagt ctcaggcttc aacattgaat atgctgcagg    60
cccattcgcc ctattctta tagccgaata cataaatatc    100

<210> SEQ ID NO 184
<211> LENGTH: 100
<212> TYPE: DNA
<213> ORGANISM: Homo sapiens

<400> SEQUENCE: 184
attataataa acaccctcac cactacaatc ttcctaggaa caacatatga cgcactctcc    60
cctgaactct acacaacata ttttgtcacc aagaccctac    100

<210> SEQ ID NO 185
<211> LENGTH: 100
<212> TYPE: DNA
<213> ORGANISM: Homo sapiens

<400> SEQUENCE: 185
attataataa acaccctcac cactacaatc ttcctaggaa caacatataa cgcactctcc    60
cctgaactct acacaacata ttttgtcacc aagaccctac    100

<210> SEQ ID NO 186
<211> LENGTH: 100
<212> TYPE: DNA

<213> ORGANISM: Homo sapiens

<400> SEQUENCE: 186

```
ttctaacctc cctgttctta tgaattcgaa cagcataccc ccgattccgc tacgaccaac      60
tcatacacct cctatgaaaa aacttcctac cactcaccct                           100
```

<210> SEQ ID NO 187
<211> LENGTH: 100
<212> TYPE: DNA
<213> ORGANISM: Homo sapiens

<400> SEQUENCE: 187

```
ttctgacctc cctgttctta tgaattcgaa cagcataccc ccgattccgc tacgaccaac      60
tcatacacct cctatgaaaa aacttcctac cactcaccct                           100
```

<210> SEQ ID NO 188
<211> LENGTH: 100
<212> TYPE: DNA
<213> ORGANISM: Homo sapiens

<400> SEQUENCE: 188

```
tcttaacctc cctatttta tgaattcgaa cagcttatcc ccaattctgc tatgattaac       60
ttatacatct cttatgaaaa aactttctac cacttacact                           100
```

<210> SEQ ID NO 189
<211> LENGTH: 100
<212> TYPE: DNA
<213> ORGANISM: Homo sapiens

<400> SEQUENCE: 189

```
tcttaacctc cctatttta tgaattcaaa cagcatatcc ccgtttcggc tacaatcaac       60
tcacacacct cctatgaaaa aatttttctac tacttacact                          100
```

<210> SEQ ID NO 190
<211> LENGTH: 100
<212> TYPE: DNA
<213> ORGANISM: Homo sapiens

<400> SEQUENCE: 190

```
ttctaaccgc cctgatttta tgaattcgaa cagcataccc ctgactgtgc tacaaccaac      60
tcatatatct cctatgaaaa aacttcctac cacttaaact                           100
```

<210> SEQ ID NO 191
<211> LENGTH: 100
<212> TYPE: DNA
<213> ORGANISM: Homo sapiens

<400> SEQUENCE: 191

```
tcctaacctc tctatttta tgaatccgaa cagcataccc ccgattccac tacgatcaac       60
tcatgtatct cttatgaaaa aatttcttac catttacact                           100
```

<210> SEQ ID NO 192
<211> LENGTH: 100
<212> TYPE: DNA
<213> ORGANISM: Homo sapiens

<400> SEQUENCE: 192

```
agcattactt atatgatatg tctccatacc cattacaatc tccagcattc cccctcaaac      60
ctaagaaata tgtctgataa aagagttact ttgatagagt                           100
```

<210> SEQ ID NO 193
<211> LENGTH: 100
<212> TYPE: DNA
<213> ORGANISM: Homo sapiens

<400> SEQUENCE: 193
agcattactt atatgatatg tctccatacc cattacaatc tccagcattc cccctcaaac    60
ctaagaaata tgtctgataa aagagttact ttgatagagt                         100

<210> SEQ ID NO 194
<211> LENGTH: 100
<212> TYPE: DNA
<213> ORGANISM: Homo sapiens

<400> SEQUENCE: 194
agcattctgt gtatgataca tctcaatacc catcataatc tccagcatcc caccccaaac    60
gtaagaaaca tgtctgacaa aagaattact ttgacagaat                         100

<210> SEQ ID NO 195
<211> LENGTH: 100
<212> TYPE: DNA
<213> ORGANISM: Homo sapiens

<400> SEQUENCE: 195
agcattctgt atatgacata tctcaatacc catcctaatc tccagcatcc cacctcaaat    60
gtaagaaata cggctgacaa aagaattact ttgatagagt                         100

<210> SEQ ID NO 196
<211> LENGTH: 100
<212> TYPE: DNA
<213> ORGANISM: Homo sapiens

<400> SEQUENCE: 196
ctatattttc atatgatata tttcaatatc catcacaatc tccagcatcc caccccaaat    60
gtaagaaata tgtctgacaa aagaattact ttgatagagt                         100

<210> SEQ ID NO 197
<211> LENGTH: 100
<212> TYPE: DNA
<213> ORGANISM: Homo sapiens

<400> SEQUENCE: 197
agcactactt atatgataca tctcaatatc cgctacaatt tccaacattc cccctaaac     60 ttaagaaata tgtctgacaa aagagtgact ttgatagagt                         100

<210> SEQ ID NO 198
<211> LENGTH: 100
<212> TYPE: DNA
<213> ORGANISM: Homo sapiens

<400> SEQUENCE: 198
aaataatagg agcttaaacc cccttatttc taggactatg agaatcgaac ccatccctga    60
gaatccaaaa ttctccgtgc cacctatcac accccatcct                         100

<210> SEQ ID NO 199
<211> LENGTH: 100
<212> TYPE: DNA
<213> ORGANISM: Homo sapiens

<400> SEQUENCE: 199
aaataatagg agtttaaatc cccttatttc taggactatg agaatcgaac ccatccctga    60
gaatccaaaa ttctccgtgc cacctatcac accccatcct    100

<210> SEQ ID NO 200
<211> LENGTH: 100
<212> TYPE: DNA
<213> ORGANISM: Homo sapiens

<400> SEQUENCE: 200
aaacaacaga ggttgaaatc ctcatatttc taggactata ggaattgaac ccatccctga    60
gaatccaaaa ttctccatgc tacctatcac accacgtcct    100

<210> SEQ ID NO 201
<211> LENGTH: 100
<212> TYPE: DNA
<213> ORGANISM: Homo sapiens

<400> SEQUENCE: 201
aaattataga ggtttaagtc ctcttatttg tagaattata ggaatcgaac ctaccctga    60 gaatccaaaa ttctctgtgc tacctaatac accacatcct    100

<210> SEQ ID NO 202
<211> LENGTH: 100
<212> TYPE: DNA
<213> ORGANISM: Homo sapiens

<400> SEQUENCE: 202
aaacaacaga ggatttcaac ctcttatttc tagaactata ggaattgaac ccaccctga    60 gaatccaaaa ttcccatgc tacctatcac accacgtcct    100

<210> SEQ ID NO 203
<211> LENGTH: 100
<212> TYPE: DNA
<213> ORGANISM: Homo sapiens

<400> SEQUENCE: 203
aaatagtaga ggtttaaacc ctcttatctc tagaactata ggaattgaac ctaaccctga    60
gaatccaaaa ttctccatgc tacctgtcac accacatcct    100

<210> SEQ ID NO 204
<211> LENGTH: 100
<212> TYPE: DNA
<213> ORGANISM: Homo sapiens

<400> SEQUENCE: 204
aaataataga ggttaaaatc ctcttatttc tagaactata ggaattgaac ctaccctga    60 taatccaaaa ttctccatgc cacctattac accacatcct    100

<210> SEQ ID NO 205
<211> LENGTH: 100
<212> TYPE: DNA
<213> ORGANISM: Homo sapiens

<400> SEQUENCE: 205
aaataataga ggtttgaatc ctcttatttc taggaccata ggaattgaac ctatccctga    60
gaatccaaaa ttctccgtgc cacgtgtcac accctatcct    100

```
<210> SEQ ID NO 206
<211> LENGTH: 100
<212> TYPE: DNA
<213> ORGANISM: Homo sapiens

<400> SEQUENCE: 206
aaagtaaggt cagctaaata agctatcggg cccatacccc gaaaatgttg gttataccct      60
tcccgtacta attaatcccc tggcccaacc cgtcatctac                           100

<210> SEQ ID NO 207
<211> LENGTH: 100
<212> TYPE: DNA
<213> ORGANISM: Homo sapiens

<400> SEQUENCE: 207
aaagtaaggt cagctaaata agctatcggg cccatacccc gaaaatgttg gttatatcct      60
tcccgtacta attaatcccc tggcccaacc cgtcatctac                           100

<210> SEQ ID NO 208
<211> LENGTH: 100
<212> TYPE: DNA
<213> ORGANISM: Homo sapiens

<400> SEQUENCE: 208
agagtaaggt cacctaaata aaccatcaga cccataccct gaaaatgttg gttacaccct      60
tcccatacta attaatccct tggctcaact tattattact                           100

<210> SEQ ID NO 209
<211> LENGTH: 100
<212> TYPE: DNA
<213> ORGANISM: Homo sapiens

<400> SEQUENCE: 209
aaagtaaggt cagctaaata agctatcagg cccatatccc aaaaatgttg gttacatcct      60
tcccatacta attaacctat tagctcagct tatcatctac                           100

<210> SEQ ID NO 210
<211> LENGTH: 100
<212> TYPE: DNA
<213> ORGANISM: Homo sapiens

<400> SEQUENCE: 210
aaggtaaggt cagctaaata agctatcagg cccatacccc gaaaatgttg gttataccct      60
tcccgtccta attaacccat aaggtcaact tattatttta                           100

<210> SEQ ID NO 211
<211> LENGTH: 100
<212> TYPE: DNA
<213> ORGANISM: Homo sapiens

<400> SEQUENCE: 211
agagtaaggt cagctaaata agctgttggg cccatacccc aaaaatgttg gttacaccct      60
tcccatggca attaatccct tagctcaact tgttatttcc                           100

<210> SEQ ID NO 212
<211> LENGTH: 100
<212> TYPE: DNA
<213> ORGANISM: Homo sapiens

<400> SEQUENCE: 212
```

```
agagcaaggt cagctaaata agctatcggg cccatacctc acaaatgtag gttacaccct      60
tcccgtacta attaatccct tagctcaact tagtatttct                           100

<210> SEQ ID NO 213
<211> LENGTH: 100
<212> TYPE: DNA
<213> ORGANISM: Homo sapiens

<400> SEQUENCE: 213
aaagtaaggt cagctaaata agctatcggg cccataccccc aaaaatgttg gtcatacccct    60 tcccatacta attaatccat tagcttggcc ttactatttt                          100

<210> SEQ ID NO 214
<211> LENGTH: 100
<212> TYPE: DNA
<213> ORGANISM: Homo sapiens

<400> SEQUENCE: 214
ggagtaaggt cagctaaata agctatcagg cccataccca gaaaatgttg gttatatcct      60
tcccgtacta atcaatccac tggcccaacc tgtcatctac                          100

<210> SEQ ID NO 215
<211> LENGTH: 100
<212> TYPE: DNA
<213> ORGANISM: Homo sapiens

<400> SEQUENCE: 215
aaattaaggt cagctaaata agctatcagg cccatacact aaaaatgttg gttatatcct      60
tcccaaagta attaatccat tagttcaact tattatctcc                          100

<210> SEQ ID NO 216
<211> LENGTH: 100
<212> TYPE: DNA
<213> ORGANISM: Homo sapiens

<400> SEQUENCE: 216
tctaccatct ttgcaggcac actcatcaca gcgctaagct cgcactgatt ttttacctga      60
gtaggcctag aaataaacat gctagctttt attccagttc                          100

<210> SEQ ID NO 217
<211> LENGTH: 100
<212> TYPE: DNA
<213> ORGANISM: Homo sapiens

<400> SEQUENCE: 217
tctaccatct ttgcaggcac actcatcaca gcgctaagct cgcactgatt ttttacctga      60
gtaggcctag aaataaacat gctagctttt attccagttc                          100

<210> SEQ ID NO 218
<211> LENGTH: 100
<212> TYPE: DNA
<213> ORGANISM: Homo sapiens

<400> SEQUENCE: 218
taaccaaaaa aataaaccct cgttccacag aagctgccat caagtatttc ctcacgcaag      60
caaccgcatc cataatcctt ctaatagcta tcctcttcaa                          100

<210> SEQ ID NO 219
<211> LENGTH: 100
```

```
<212> TYPE: DNA
<213> ORGANISM: Homo sapiens

<400> SEQUENCE: 219
taaccaaaaa aataaaccct cgttccacag aagctgccat caagtatttc ctcacgcaag    60
caaccgcatc cataatcctt ctaatagcta tcctcttcaa                         100

<210> SEQ ID NO 220
<211> LENGTH: 100
<212> TYPE: DNA
<213> ORGANISM: Homo sapiens

<400> SEQUENCE: 220
taattaaaaa aataaacccc cgctctacag aaactgctat caaatacttt ctcacataag    60
caaccacatc tataatcctc ataatagcta tcctctccaa                         100

<210> SEQ ID NO 221
<211> LENGTH: 100
<212> TYPE: DNA
<213> ORGANISM: Homo sapiens

<400> SEQUENCE: 221
caatatactc tccggacaat gaaccataac caatactacc aatcaatact catcattaat    60
aatcataatg gctatagcaa taaaactagg aatagccccc                         100

<210> SEQ ID NO 222
<211> LENGTH: 100
<212> TYPE: DNA
<213> ORGANISM: Homo sapiens

<400> SEQUENCE: 222
caatatactc tccggacaat gaaccataac caataccacc aatcaatact catcattaat    60
aatcataatg gctatagcaa taaaactagg aatagccccc                         100

<210> SEQ ID NO 223
<211> LENGTH: 100
<212> TYPE: DNA
<213> ORGANISM: Homo sapiens

<400> SEQUENCE: 223
caatgtactc tccggacaat gaaccacaac caacaccacc aacaaatact catcattaat    60
aatcacaaca gccctagtaa taaaactagg aatagcccct                         100

<210> SEQ ID NO 224
<211> LENGTH: 100
<212> TYPE: DNA
<213> ORGANISM: Homo sapiens

<400> SEQUENCE: 224
tttcacttct gagtcccaga ggttacccaa ggcacccctc tgacatccgg cctgcttctt    60
ctcacatgac aaaaactagc ccccatctca atcatatacc                         100

<210> SEQ ID NO 225
<211> LENGTH: 100
<212> TYPE: DNA
<213> ORGANISM: Homo sapiens

<400> SEQUENCE: 225
tttcacttct gagtcccaga ggttacccaa ggcacccctc tgacatccgg cctgctcctt    60
```
ctcacatgac aaaaactagc ccccatctca atcatatacc    100

<210> SEQ ID NO 226
<211> LENGTH: 100
<212> TYPE: DNA
<213> ORGANISM: Homo sapiens

<400> SEQUENCE: 226
tttcacttct gagtcccaga gaggacccaa ggaacttctc taatatctgg catacttctc    60
cttacatgac aaaaactagc ccctatctcg attatatttc    100

<210> SEQ ID NO 227
<211> LENGTH: 100
<212> TYPE: DNA
<213> ORGANISM: Homo sapiens

<400> SEQUENCE: 227
tttcacttct gagtcccaga ggtaacccaa ggaatctctt taacatctgg tatactttt    60 ctcacatgac aaaaactagc ccctatctcg atcatgtttc    100

<210> SEQ ID NO 228
<211> LENGTH: 100
<212> TYPE: DNA
<213> ORGANISM: Homo sapiens

<400> SEQUENCE: 228
tttcacttct gagttccaga agtaacccaa ggaacttctc taacatctgg catacttctc    60
ctcacgtgac aaaaactaac ccctatttca attcaattca    100

<210> SEQ ID NO 229
<211> LENGTH: 100
<212> TYPE: DNA
<213> ORGANISM: Homo sapiens

<400> SEQUENCE: 229
tttcacttct gagtcccaca gttaacccaa gaaacctctc taatttctgg catacttctc    60
ctcacatgac aaaaactagc ccctatctcg attatgtttc    100

<210> SEQ ID NO 230
<211> LENGTH: 100
<212> TYPE: DNA
<213> ORGANISM: Homo sapiens

<400> SEQUENCE: 230
tttcacttcc gagtcccaga agtaacccag ggaacttctc taatgtctgg catacttctc    60
ctcacatgac aaaaactagc ccctatctca attatatttc    100

<210> SEQ ID NO 231
<211> LENGTH: 100
<212> TYPE: DNA
<213> ORGANISM: Homo sapiens

<400> SEQUENCE: 231
ttccgtttct gagtcccaga agtcactcaa ggaacccctc taatatccag cctacttccc    60
ctcacatgac aaaaattagc ccctatttca attatatatc    100

<210> SEQ ID NO 232
<211> LENGTH: 100
<212> TYPE: DNA
<213> ORGANISM: Homo sapiens

<400> SEQUENCE: 232
aaatctctcc ctcactaaac gtaagccttc tcctcactct ctcaatctta tccatcatag    60
caggcagttg aggtggatta aaccaaaccc agctacgcaa                         100

<210> SEQ ID NO 233
<211> LENGTH: 100
<212> TYPE: DNA
<213> ORGANISM: Homo sapiens

<400> SEQUENCE: 233
aaatttctcc ctcattaaac gtaagccttc tcctcactct ttcaatctta tccatcatgg    60
caggcagttg aggtggatta aaccaaaccc aactacgcaa                         100

<210> SEQ ID NO 234
<211> LENGTH: 100
<212> TYPE: DNA
<213> ORGANISM: Homo sapiens

<400> SEQUENCE: 234
aatcttagca tactcctcaa ttacccacat aggatgaata atagcagttc taccgtacaa    60
ccctaacata accattctta atttaactat ttatattatc                         100

<210> SEQ ID NO 235
<211> LENGTH: 100
<212> TYPE: DNA
<213> ORGANISM: Homo sapiens

<400> SEQUENCE: 235
aatcttagca tactcctcaa ttacccacat aggatgaata acagcagttc taccgtacaa    60
ccctaacata accattctta atttaactat ttatattatc                         100

<210> SEQ ID NO 236
<211> LENGTH: 100
<212> TYPE: DNA
<213> ORGANISM: Homo sapiens

<400> SEQUENCE: 236
aatcctagcc tactcctcaa tcactcacat aggttgaata atagcagtac taatttatga    60
cccaaacatt accactctaa atctgattat ttaccttatc                         100

<210> SEQ ID NO 237
<211> LENGTH: 100
<212> TYPE: DNA
<213> ORGANISM: Homo sapiens

<400> SEQUENCE: 237
aatcctagca tactcctcaa tcacccatat aggctgaata atagcagtac tagcatacaa    60
cccaagtatc accattttca acctaatcat ctatatcatt                         100

<210> SEQ ID NO 238
<211> LENGTH: 100
<212> TYPE: DNA
<213> ORGANISM: Homo sapiens

<400> SEQUENCE: 238
ctaactacta ccgcattcct actactcaac ttaaactcca gcaccacgac cctactacta    60
tctcgcacct gaaacaagct aacatgacta acaccccttaa                        100

```
<210> SEQ ID NO 239
<211> LENGTH: 100
<212> TYPE: DNA
<213> ORGANISM: Homo sapiens

<400> SEQUENCE: 239
ctaactacta ccgcattcct actactcaac ttaaactcca gcaccacaac cctactacta      60
tctcgcacct gaaacaagct aacatgacta acacccttaa                          100

<210> SEQ ID NO 240
<211> LENGTH: 100
<212> TYPE: DNA
<213> ORGANISM: Homo sapiens

<400> SEQUENCE: 240
ctaacaacta ctgcattcct agcactcaat ctgaattcaa gcaccacagc cctattacta      60
tcccacgcct gaaacaaact aacatgatta atatccataa                          100

<210> SEQ ID NO 241
<211> LENGTH: 100
<212> TYPE: DNA
<213> ORGANISM: Homo sapiens

<400> SEQUENCE: 241
ctaacaacca ccacattcct ggtactcaac ttgaactcta gcactacaac cctactactg      60
tgccgcactt gaaataaact aacctgacta ataccccctaa                         100

<210> SEQ ID NO 242
<211> LENGTH: 100
<212> TYPE: DNA
<213> ORGANISM: Homo sapiens

<400> SEQUENCE: 242
ttccatccac cctcctctcc ctaggaggcc tgcccccgct aaccggcttt ttgcccaaat      60
gggccattat cgaagaattc acaaaaaaca atagcctcat                          100

<210> SEQ ID NO 243
<211> LENGTH: 100
<212> TYPE: DNA
<213> ORGANISM: Homo sapiens

<400> SEQUENCE: 243
ttccatccac cctcctctcc ctaggaggcc tgcccccgct aaccggcttt ttgcccaaat      60
gggccattat cgaagaattc acaaaaaaca atagcctcat                          100

<210> SEQ ID NO 244
<211> LENGTH: 100
<212> TYPE: DNA
<213> ORGANISM: Homo sapiens

<400> SEQUENCE: 244
tcccatctac cctactatca ctaggaggcc ttcccccact aactggcttt ctacccaaat      60
gatttatcat tgaagaattc acaaaaaata acaacctcat                          100

<210> SEQ ID NO 245
<211> LENGTH: 100
<212> TYPE: DNA
<213> ORGANISM: Homo sapiens

<400> SEQUENCE: 245
```

```
catccccacc atcatagcca ccatcaccct ccttaacctc tacttctacc tacgcctaat    60
ctactccacc tcaatcacac tactccccat atctaacaac                         100

<210> SEQ ID NO 246
<211> LENGTH: 100
<212> TYPE: DNA
<213> ORGANISM: Homo sapiens

<400> SEQUENCE: 246
catccccacc atcatagcca tcatcaccct ccttaacctc tacttctacc tgcgcctaat    60
ctactccacc tcaatcacac tactccctat atctaacaac                         100

<210> SEQ ID NO 247
<211> LENGTH: 100
<212> TYPE: DNA
<213> ORGANISM: Homo sapiens

<400> SEQUENCE: 247
tatccccact accatagcca ttattactct ctttaaccta tattttaca tacgcttaat     60 ctactctgct tcaattacac tattccccat atccaacaac                         100

<210> SEQ ID NO 248
<211> LENGTH: 100
<212> TYPE: DNA
<213> ORGANISM: Homo sapiens

<400> SEQUENCE: 248
gtaaaaataa aatgacagtt tgaacataca aacccaccc cattcctccc cacactcatc     60
gcccttacca cgctactcct acctatctcc cctttatac                          100

<210> SEQ ID NO 249
<211> LENGTH: 100
<212> TYPE: DNA
<213> ORGANISM: Homo sapiens

<400> SEQUENCE: 249
gtaaaaataa aatgacagtt tgaacacaca aacccaccc cattcctccc cacactcatc     60
gcccttacca cactgctcct acctatctcc cctttatgc                          100

<210> SEQ ID NO 250
<211> LENGTH: 100
<212> TYPE: DNA
<213> ORGANISM: Homo sapiens

<400> SEQUENCE: 250
gtaaaaataa aatgacaatt tgaaaataca aaatccacac cactcttccc cacactcact    60
gtccttacca ccctcctcct accaatctct ccacttacac                         100

<210> SEQ ID NO 251
<211> LENGTH: 100
<212> TYPE: DNA
<213> ORGANISM: Homo sapiens

<400> SEQUENCE: 251
taataatctt atagaaattt aggttaaata cagaccaaga gccttcaaag ccctcagtaa    60
gttgcaatac ttaatttctg caacagctaa ggactgcaaa                         100

<210> SEQ ID NO 252
```

```
<211> LENGTH: 100
<212> TYPE: DNA
<213> ORGANISM: Homo sapiens

<400> SEQUENCE: 252
taataatctt atagaaattt aggttaaata cagaccaaga gccttcaaag ccctcagtaa      60
gttgcaatac ttaatttctg caacagctaa ggactgcaaa                          100

<210> SEQ ID NO 253
<211> LENGTH: 100
<212> TYPE: DNA
<213> ORGANISM: Homo sapiens

<400> SEQUENCE: 253
accccactct gcatcaactg aacgcaaatc agccacttta attaagctaa gcccttacta     60
gaccaatggg acttaaaccc acaaacactt agttaacagc                          100

<210> SEQ ID NO 254
<211> LENGTH: 100
<212> TYPE: DNA
<213> ORGANISM: Homo sapiens

<400> SEQUENCE: 254
accccactct gcatcaactg aacgcaaatc agccacttta attaagctaa gcccttacta     60
gaccaatggg acttaaaccc acaaacactt agttaacagc                          100

<210> SEQ ID NO 255
<211> LENGTH: 100
<212> TYPE: DNA
<213> ORGANISM: Homo sapiens

<400> SEQUENCE: 255
attctactct gtatcaattg aacgcaaatc aatcacttta attaagctaa gcccttacta     60
gattgatggg acttaaaccc acgaacattt aattaacaga                          100

<210> SEQ ID NO 256
<211> LENGTH: 100
<212> TYPE: DNA
<213> ORGANISM: Homo sapiens

<400> SEQUENCE: 256
actctattct gcatcagttg aacgcaaata aaccacttta attaagctaa gcccttacta     60
gactggtgga attcaaaacc acgaaaattt agttaacagt                          100

<210> SEQ ID NO 257
<211> LENGTH: 100
<212> TYPE: DNA
<213> ORGANISM: Homo sapiens

<400> SEQUENCE: 257
actgtattct gcatcaattg aatgcaaatc aatcacttta attaagctaa gccatggcta     60
gactgttggg acttaaaccc atgaaaattt agctaacacc                          100

<210> SEQ ID NO 258
<211> LENGTH: 100
<212> TYPE: DNA
<213> ORGANISM: Homo sapiens

<400> SEQUENCE: 258
actctattct gcatcaattg aacacaaatc cgccacttta attaagctaa gcccttgcta     60
```

```
gattcgcaga attcaaaccc atgaaaattt agttaacagc                           100
```

<210> SEQ ID NO 259
<211> LENGTH: 100
<212> TYPE: DNA
<213> ORGANISM: Homo sapiens

<400> SEQUENCE: 259

```
actctattct gcatcagttg aacgcaaatc aaccacttta attaagctaa gtccttgcta    60
gatcggtgga attcaaaccc acaaaaattt agttaacagc                          100
```

<210> SEQ ID NO 260
<211> LENGTH: 100
<212> TYPE: DNA
<213> ORGANISM: Homo sapiens

<400> SEQUENCE: 260

```
accctacttt gcatctactg aacgcaaatc agccacttta attaagctaa gcccttgcta    60
gatcaatggg acttaaaccc acaaaaattt ggttaacagc                          100
```

<210> SEQ ID NO 261
<211> LENGTH: 100
<212> TYPE: DNA
<213> ORGANISM: Homo sapiens

<400> SEQUENCE: 261

```
taagcaccct aatcaactgg cttcaatcta cttctcccgc cgccgggaaa aaaggcggga    60
gaagccccgg caggtttgaa gctgcttctt cgaatttgca                          100
```

<210> SEQ ID NO 262
<211> LENGTH: 100
<212> TYPE: DNA
<213> ORGANISM: Homo sapiens

<400> SEQUENCE: 262

```
taagcaccct aatcaactgg cttcaatcta cttctcccgc cgccgggaaa aaaggcggga    60
gaagccccgg caggtttgaa gctgcttctt cgaatttgca                          100
```

<210> SEQ ID NO 263
<211> LENGTH: 100
<212> TYPE: DNA
<213> ORGANISM: Homo sapiens

<400> SEQUENCE: 263

```
attcaatatg aaaatcacct cggagctggt aaaagaggc ctaaccctg tctttagatt      60 tacagtccaa tgcttcactc agccatttta cctcaccccc                          100
```

<210> SEQ ID NO 264
<211> LENGTH: 100
<212> TYPE: DNA
<213> ORGANISM: Homo sapiens

<400> SEQUENCE: 264

```
attcaatatg aaaatcacct cagagctggt aaaagaggc ttaaccctg tctttagatt      60 tacagtccaa tgcttcactc agccatttta cctcaccccc                          100
```

<210> SEQ ID NO 265
<211> LENGTH: 100
<212> TYPE: DNA

<213> ORGANISM: Homo sapiens

<400> SEQUENCE: 265
attcaatatg aaaatcacct cagagctggt aaaaagaggc ttaacccctg tctttagatt    60
tacagtccaa tgcttcactc agccatttta cctcaccaga    100

<210> SEQ ID NO 266
<211> LENGTH: 100
<212> TYPE: DNA
<213> ORGANISM: Homo sapiens

<400> SEQUENCE: 266
actgatgttc gccgaccgtt gactattctc tacaaaccac aaagacattg gaacactata    60
cctattattc ggcgcatgag ctggagtcct aggcacagct    100

<210> SEQ ID NO 267
<211> LENGTH: 100
<212> TYPE: DNA
<213> ORGANISM: Homo sapiens

<400> SEQUENCE: 267
actgatgttc gccgaccgtt gactattctc tacaaaccac aaagacattg gaacactata    60
cctattattc ggcgcatgag ctggagtcct aggcacagct    100

<210> SEQ ID NO 268
<211> LENGTH: 100
<212> TYPE: DNA
<213> ORGANISM: Homo sapiens

<400> SEQUENCE: 268
actaatgttc gccaaccgct gactattctc aacaaatcat aaagatatcg gaacactata    60
tttattgttt ggtgcatgag ctggagtctt gggcacagcc    100

<210> SEQ ID NO 269
<211> LENGTH: 100
<212> TYPE: DNA
<213> ORGANISM: Homo sapiens

<400> SEQUENCE: 269
ctaagcctcc ttattcgagc cgagctgggc cagccaggca accttctagg taacgaccac    60
atctacaacg ttatcgtcac agcccatgca tttgtaataa    100

<210> SEQ ID NO 270
<211> LENGTH: 100
<212> TYPE: DNA
<213> ORGANISM: Homo sapiens

<400> SEQUENCE: 270
ctaagcctcc ttattcgagc cgaactgggc cagccaggca accttctagg taacgaccac    60
atctacaacg ttatcgtcac agcccatgca tttgtaataa    100

<210> SEQ ID NO 271
<211> LENGTH: 100
<212> TYPE: DNA
<213> ORGANISM: Homo sapiens

<400> SEQUENCE: 271
ttaagcctcc ttattcagac tgaactaggt caacctggca accttctagg taacgaccac    60
atctacaacg tcatcgtcac agcccacaca ttcttcataa    100

<210> SEQ ID NO 272
<211> LENGTH: 100
<212> TYPE: DNA
<213> ORGANISM: Homo sapiens

<400> SEQUENCE: 272
tcttcttcat agtaataccc atcataatcg gaggctttgg caactgacta gttcccctaa      60
taatcggtgc ccccgatatg gcgtttcccc gcataaacaa                          100

<210> SEQ ID NO 273
<211> LENGTH: 100
<212> TYPE: DNA
<213> ORGANISM: Homo sapiens

<400> SEQUENCE: 273
tcttcttcat agtaataccc atcataatcg gaggctttgg caactgacta gttcccctaa      60
taatcggtgc ccccgatatg gcgtttcccc gcataaacaa                          100

<210> SEQ ID NO 274
<211> LENGTH: 100
<212> TYPE: DNA
<213> ORGANISM: Homo sapiens

<400> SEQUENCE: 274
tcttctttat ggtaatacca atcataattg ggggtttcgg caactagcta gtccctctaa      60
taattggtgc acccgatatg gcattccccc ggataaatta                          100

<210> SEQ ID NO 275
<211> LENGTH: 100
<212> TYPE: DNA
<213> ORGANISM: Homo sapiens

<400> SEQUENCE: 275
tattctttat ggtaatacca atcataattg gaggtttcgg caactggcta gtccctctaa      60
taattggtgc acccgatatg acatttccct ggataaataa                          100

<210> SEQ ID NO 276
<211> LENGTH: 100
<212> TYPE: DNA
<213> ORGANISM: Homo sapiens

<400> SEQUENCE: 276 tcttttcat agtaatgtct atcataattg gaggttttgg caattgactg gtcccctga       60 taattggcgc ccctgacatg gcatttccct gcgtaaataa                          100

<210> SEQ ID NO 277
<211> LENGTH: 100
<212> TYPE: DNA
<213> ORGANISM: Homo sapiens

<400> SEQUENCE: 277
cataagcttc tgactcttac ctccctctct cctactcctg ctcgcatctg ctatagtgga      60
ggccggagca ggaacaggtt gaacagtcta ccctcccctta                         100

<210> SEQ ID NO 278
<211> LENGTH: 100
<212> TYPE: DNA
<213> ORGANISM: Homo sapiens

```
<400> SEQUENCE: 278
cataagcttc tgactcttac ccccctctct cctactcctg cttgcatctg ctatagtgga      60
ggccggcgca ggaacaggtt gaacagtcta ccctcccttg                           100

<210> SEQ ID NO 279
<211> LENGTH: 100
<212> TYPE: DNA
<213> ORGANISM: Homo sapiens

<400> SEQUENCE: 279
gcagggaact actcccaccc tggagcctcc gtagacctaa ccatcttctc cttacaccta      60
gcaggtgtct cctctatctt aggggccatc aatttcatca                           100

<210> SEQ ID NO 280
<211> LENGTH: 100
<212> TYPE: DNA
<213> ORGANISM: Homo sapiens

<400> SEQUENCE: 280
gcagggaact actcccaccc tggagcctcc gtagacctaa ccatcttctc cttacaccta      60
gcaggtatct cctctatctt aggagccatc aatttcatca                           100

<210> SEQ ID NO 281
<211> LENGTH: 100
<212> TYPE: DNA
<213> ORGANISM: Homo sapiens

<400> SEQUENCE: 281
gcaggaaact attcccatcc agaggcctct gtagacctaa ccattttctc ccttcatcta      60
gcaggtgtct cctctattct aggagctatt aatttcatca                           100

<210> SEQ ID NO 282
<211> LENGTH: 100
<212> TYPE: DNA
<213> ORGANISM: Homo sapiens

<400> SEQUENCE: 282
caacaattat caatataaaa cccccctgcca taacccaata ccaaacgccc ctcttcgtct     60
gatccgtcct aatcacagca gtcctacttc tcctatctct                           100

<210> SEQ ID NO 283
<211> LENGTH: 100
<212> TYPE: DNA
<213> ORGANISM: Homo sapiens

<400> SEQUENCE: 283
caacaattat taatataaaa cccccctgcca taacccaata ccaaacgccc cttttcgtct     60
gatccgtcct aatcacagca gtcttacttc tcctatctct                           100

<210> SEQ ID NO 284
<211> LENGTH: 100
<212> TYPE: DNA
<213> ORGANISM: Homo sapiens

<400> SEQUENCE: 284
ccacaattgt taatataaaa ccccccagcca tgtcccaata tcacacaccc ctcttcatct     60
gattagtcct aattacagca gttcttctac tcctttgtct                           100
```

```
<210> SEQ ID NO 285
<211> LENGTH: 100
<212> TYPE: DNA
<213> ORGANISM: Homo sapiens

<400> SEQUENCE: 285
ccacaattgt taatataaaa cccccagcca tgtcccaata tcacacaccc ctcttcatct      60
gattagtcct aattacagca gttcttctac tcctttgtct                          100

<210> SEQ ID NO 286
<211> LENGTH: 100
<212> TYPE: DNA
<213> ORGANISM: Homo sapiens

<400> SEQUENCE: 286
ccacaattat taacataaaa cccccctgcca tatatcaata ccaaacgccc ctctttgtct     60
gatctgtcct aatcacggca gtcctactcc tcctctccct                          100

<210> SEQ ID NO 287
<211> LENGTH: 100
<212> TYPE: DNA
<213> ORGANISM: Homo sapiens

<400> SEQUENCE: 287
ccacaattgt taatataaaa cccccagcca tgtcccaata tcacacaccc ctcttcatct      60
gattagtcct aattacagca gttcttctac tcctttgtct                          100

<210> SEQ ID NO 288
<211> LENGTH: 100
<212> TYPE: DNA
<213> ORGANISM: Homo sapiens

<400> SEQUENCE: 288
ccacaattgt taatataaaa cccccagcca tgtcccaata tcacacaccc ctcttcatct      60
aattagtcct aattacagca gttcttctac tcctttgtct                          100

<210> SEQ ID NO 289
<211> LENGTH: 100
<212> TYPE: DNA
<213> ORGANISM: Homo sapiens

<400> SEQUENCE: 289
cccagtccta gctgctggca tcactatact actaacagac cgcaacctca acaccacctt     60
cttcgacccc gccggaggag gagaccccat tctataccaa                          100

<210> SEQ ID NO 290
<211> LENGTH: 100
<212> TYPE: DNA
<213> ORGANISM: Homo sapiens

<400> SEQUENCE: 290
cccagtccta gccgctggca tcactatact actaacagac cgtaacctca acaccacctt     60
cttcgaccca gccggaggag gagaccccat tctataccaa                          100

<210> SEQ ID NO 291
<211> LENGTH: 100
<212> TYPE: DNA
<213> ORGANISM: Homo sapiens

<400> SEQUENCE: 291
```

```
cacctattct gattttcgg tcaccctgaa gtttatattc ttatcctacc aggcttcgga      60
ataatctccc atattgtaac ttactactcc ggaaaaaaag                          100
```

<210> SEQ ID NO 292
<211> LENGTH: 100
<212> TYPE: DNA
<213> ORGANISM: Homo sapiens

<400> SEQUENCE: 292

```
cacctattct gattttcgg tcaccctgaa gtttatattc tcatcctacc aggcttcgga      60
ataatctccc atattgtaac ttactactcc gggaaaaaaa                          100
```

<210> SEQ ID NO 293
<211> LENGTH: 100
<212> TYPE: DNA
<213> ORGANISM: Homo sapiens

<400> SEQUENCE: 293

```
cacttattct gattctctgg tcaccccgaa gtctgtatct tcatcctacc aggcttcagg      60
ataatttccc atatcacaac atactactct ggaaaaaaag                          100
```

<210> SEQ ID NO 294
<211> LENGTH: 100
<212> TYPE: DNA
<213> ORGANISM: Homo sapiens

<400> SEQUENCE: 294

```
catttattct gattctttgg tcaccctgaa gtttatatcc ttattctatc aggctttggg      60
atgatctccc atgtcgtgac gtattactct ggaaaaaagg                          100
```

<210> SEQ ID NO 295
<211> LENGTH: 100
<212> TYPE: DNA
<213> ORGANISM: Homo sapiens

<400> SEQUENCE: 295

```
cacctatttt gattctttgg tcaccctgaa gtctatattc tcatcctacc aggctttgga      60
ataatttctc acatcgtacc atattattcc ggaaagaaag                          100
```

<210> SEQ ID NO 296
<211> LENGTH: 100
<212> TYPE: DNA
<213> ORGANISM: Homo sapiens

<400> SEQUENCE: 296

```
catttattct gatttttggg tcaccccaaa gtctatatcc ttatcctacc aggtttcgga      60
ataatctccc atattgtaac atattattcc gggagaactc                          100
```

<210> SEQ ID NO 297
<211> LENGTH: 100
<212> TYPE: DNA
<213> ORGANISM: Homo sapiens

<400> SEQUENCE: 297

```
cacctattct gattttttgg ccaccccgaa gtttatattc ttatcctgcc aggcttcgga      60
ataatttccc atattgtaac ttactactcc ggaaaaaaag                          100
```

<210> SEQ ID NO 298
<211> LENGTH: 100

<210> SEQ ID NO 299
<211> LENGTH: 100
<212> TYPE: DNA
<213> ORGANISM: Homo sapiens

<400> SEQUENCE: 298
aaccatttgg atacataggt atggtctgag ctatgatatc aattggcttc ctagggttta    60
tcgtgtgagc acaccatata tttacagtag gaatagacgt                         100

<210> SEQ ID NO 299
<211> LENGTH: 100
<212> TYPE: DNA
<213> ORGANISM: Homo sapiens

<400> SEQUENCE: 299
aaccatttgg atacataggt atggtctgag ctatgatatc aattggcttc ctagggttta    60
tcgtgtgagc acaccatata tttacagtag gaatagacgt                         100

<210> SEQ ID NO 300
<211> LENGTH: 100
<212> TYPE: DNA
<213> ORGANISM: Homo sapiens

<400> SEQUENCE: 300
aaccatttgg gtatatgggc atagtatgag ccataatatc aattggcttc ttagggttta    60
tcgtatgggc ccaccacata tttacagtag gaatagatgt                         100

<210> SEQ ID NO 301
<211> LENGTH: 100
<212> TYPE: DNA
<213> ORGANISM: Homo sapiens

<400> SEQUENCE: 301
aaccatttgg gtacatgggc atggtctggg ctataatatc agttggcttc ctgggattca    60
ttgtgtgagc tcaccatatg ttcacagtgg gaatagacat                         100

<210> SEQ ID NO 302
<211> LENGTH: 100
<212> TYPE: DNA
<213> ORGANISM: Homo sapiens

<400> SEQUENCE: 302
acgggttcgg atatatggat atagtctgag ccatgatatc aattggtttc ctaggattta    60
ttgtatgggc ccaccccata tttacagtag gaatagacgt                         100

<210> SEQ ID NO 303
<211> LENGTH: 100
<212> TYPE: DNA
<213> ORGANISM: Homo sapiens

<400> SEQUENCE: 303
agccatttgg gtacatgggc atagtgtgag ccataatatc aattggcttc ttagggttta    60
ttgtatgggc tcaccacata tttacagtag gaacatatgt                         100

<210> SEQ ID NO 304
<211> LENGTH: 100
<212> TYPE: DNA
<213> ORGANISM: Homo sapiens

<400> SEQUENCE: 304
aaccatttgg ttatatagga atggtgtgag ccgtgatatt aattggtttt ctaggcttta    60
tcatatgggc tcatcgtata tttacaatag ggatagacat    100

<210> SEQ ID NO 305
<211> LENGTH: 100
<212> TYPE: DNA
<213> ORGANISM: Homo sapiens

<400> SEQUENCE: 305
agccatttgg gtatatgggc atagtatgag ccataatatc tattggcttc ttagggttta    60
ttgtatgagc acaccatata tttacagtag gaacagacat    100

<210> SEQ ID NO 306
<211> LENGTH: 100
<212> TYPE: DNA
<213> ORGANISM: Homo sapiens

<400> SEQUENCE: 306
aaccatttgg atatataggt atggtctgag ctatgatatc aattggcttc ctagggttta    60
ttgtgtgagc acaccatata tttacagtag gaatggacgt    100

<210> SEQ ID NO 307
<211> LENGTH: 100
<212> TYPE: DNA
<213> ORGANISM: Homo sapiens

<400> SEQUENCE: 307
aaccatttgg gtatatgggt atagtgtaag ccatagtatc agttgccttc ttggggttta    60
tcatatgggt ccaccacata tttacagtag gaatagatgt    100

<210> SEQ ID NO 308
<211> LENGTH: 100
<212> TYPE: DNA
<213> ORGANISM: Homo sapiens

<400> SEQUENCE: 308
aaccattcgg gtacataggt atggtctggg ctataatatc aattggcttc ctagggttta    60
ttgtatgagc ccatcatata ttcacagtag ggatagatgt    100

<210> SEQ ID NO 309
<211> LENGTH: 100
<212> TYPE: DNA
<213> ORGANISM: Homo sapiens

<400> SEQUENCE: 309
aaccattcgg atatataggt atggtctgag ctataatatc aattggtttc ttagggttta    60
ttgtgtgagc acaccatata tttacagtag gaatggacgt    100

<210> SEQ ID NO 310
<211> LENGTH: 100
<212> TYPE: DNA
<213> ORGANISM: Homo sapiens

<400> SEQUENCE: 310
agacacacga gcatatttca cctccgctac cataatcatc gctatcccca ccggcgtcaa    60
agtatttagc tgactcgcca cactccacgg aagcaatatg    100

<210> SEQ ID NO 311
<211> LENGTH: 100
<212> TYPE: DNA
<213> ORGANISM: Homo sapiens

<400> SEQUENCE: 311
agacacacga gcatatttca cctccgctac cataatcatc gctatcccca ccggcgtcaa    60
agtatttagc tgactcgcca cactccacgg aagcaatatg    100

<210> SEQ ID NO 312
<211> LENGTH: 100
<212> TYPE: DNA
<213> ORGANISM: Homo sapiens

<400> SEQUENCE: 312
agatacatga gcatatttca cctctgctac tataattatt gctattccta ctggtgtcaa    60
agtctttagc tggctagcta cacttcacag cagtagtatc    100

<210> SEQ ID NO 313
<211> LENGTH: 100
<212> TYPE: DNA
<213> ORGANISM: Homo sapiens

<400> SEQUENCE: 313
agatacacga gcctacttca cctccgctac tataattatc gccattccca ctggcgtcaa    60
agtatttagt tggctcgcta cgctccacgg aagtaacacc    100

<210> SEQ ID NO 314
<211> LENGTH: 100
<212> TYPE: DNA
<213> ORGANISM: Homo sapiens

<400> SEQUENCE: 314
ctcattgagc tgctgggaca cctccgctac cataatcatc gctatcccca ccggcgtcaa    60
agtatttagc tgactcgcta cactccacgg aagcaatatg    100

<210> SEQ ID NO 315
<211> LENGTH: 100
<212> TYPE: DNA
<213> ORGANISM: Homo sapiens

<400> SEQUENCE: 315
agacacacga gcctatttca cctccgctac cataatcatc gctatcccca ccagcgtcaa    60
agtatttagc tgactcgcta cactctacgg aagcaatatg    100

<210> SEQ ID NO 316
<211> LENGTH: 100
<212> TYPE: DNA
<213> ORGANISM: Homo sapiens

<400> SEQUENCE: 316
aaatgatctg ctgcagtgct ctgagcccta ggattcatct ttcttttcac cgtaggtggc    60
ctgactggca ttgtattagc aaactcatca ctagacatcg    100

<210> SEQ ID NO 317
<211> LENGTH: 100
<212> TYPE: DNA
<213> ORGANISM: Homo sapiens

<400> SEQUENCE: 317
aaatgatctg ctgcagtgct ctgagcccta ggatttattt ttcttttcac cgtaggtggc    60
ctgactggca ttgtattagc aaactcatca ctagacatcg    100

<210> SEQ ID NO 318
<211> LENGTH: 100
<212> TYPE: DNA
<213> ORGANISM: Homo sapiens

<400> SEQUENCE: 318
aaatgatctc cgcaatgtt ctgagccta ggattcatct ttcttttcac agtaggaggt    60
ctaattggca ttgtactagc taattcatca ctagatatta                        100

<210> SEQ ID NO 319
<211> LENGTH: 100
<212> TYPE: DNA
<213> ORGANISM: Homo sapiens

<400> SEQUENCE: 319
aaatggtcca ccgcagtact ctgagccta ggattcatct tccttttac agtgggtggc    60 ctaacggaca ttgtactagc aaactcatca ttagacatcg                        100

<210> SEQ ID NO 320
<211> LENGTH: 100
<212> TYPE: DNA
<213> ORGANISM: Homo sapiens

<400> SEQUENCE: 320
aaatgatctg ctgcggtgct ctgagccctg ggattcattt ttctcttcac tgtaggcggc    60
ctaactggca ttgtattagc aaactcatca ctagacatcg                        100

<210> SEQ ID NO 321
<211> LENGTH: 100
<212> TYPE: DNA
<213> ORGANISM: Homo sapiens

<400> SEQUENCE: 321
aagtgatctg ctgcagtact ctgagccta gggttcattt ttctcttcac tgtaggtggc    60
ctaaccggca ttgtactagc aaactcatca ttagacatcg                        100

<210> SEQ ID NO 322
<211> LENGTH: 100
<212> TYPE: DNA
<213> ORGANISM: Homo sapiens

<400> SEQUENCE: 322
tactacacga cacgtactac gttgtagctc acttccacta tgtcctatca ataggagctg    60
tatttgccat cataggaggc ttcattcact gatttcccct                        100

<210> SEQ ID NO 323
<211> LENGTH: 100
<212> TYPE: DNA
<213> ORGANISM: Homo sapiens

<400> SEQUENCE: 323
tactacacga cacgtactac gttgtagccc acttccacta tgtcctatca ataggagctg    60
tatttgccat cataggaggc ttcattcact gatttcccct                        100

<210> SEQ ID NO 324
<211> LENGTH: 100
<212> TYPE: DNA
<213> ORGANISM: Homo sapiens

<400> SEQUENCE: 324

```
tcttacacga cacatattat gttgtaggcc atttccacta tgtcctatca ataggcgcgg    60
tatttgccat cataggaggc tttgtccact gattccccccc                         100

<210> SEQ ID NO 325
<211> LENGTH: 100
<212> TYPE: DNA
<213> ORGANISM: Homo sapiens

<400> SEQUENCE: 325
ccttacatga cacatattat gttgtagccc atttccacta tgtcctatca ataggagcag    60
tactcgccat tataggaggc tttgtccact gattctcctt                          100

<210> SEQ ID NO 326
<211> LENGTH: 100
<212> TYPE: DNA
<213> ORGANISM: Homo sapiens

<400> SEQUENCE: 326
ttttacatga cacatattat gttgtagccc atttccatta agtcttatca ataggagccg    60
tatttgctat tataggaggc tttgtccact gattcccccct                         100

<210> SEQ ID NO 327
<211> LENGTH: 100
<212> TYPE: DNA
<213> ORGANISM: Homo sapiens

<400> SEQUENCE: 327
tactacatga tacatattat gttgtggccc actttcacta cgttctatca ataggagctg    60
tgttcaccat catgggggc ttcatccact gatttcccctt                          100

<210> SEQ ID NO 328
<211> LENGTH: 100
<212> TYPE: DNA
<213> ORGANISM: Homo sapiens

<400> SEQUENCE: 328
tactacacga cacatactac gtcgtagccc acttccacta cgtcctatca ataggagctg    60
tattcgccat cataggggc ttcattcact gatttccccct                          100

<210> SEQ ID NO 329
<211> LENGTH: 100
<212> TYPE: DNA
<213> ORGANISM: Homo sapiens

<400> SEQUENCE: 329
tactacacga cacatactac gtcgtagctc acttccatta cgtcctatca ataggagctg    60
tattcgccat cacaggaggt ttcattcact gatttccccct                         100

<210> SEQ ID NO 330
<211> LENGTH: 100
<212> TYPE: DNA
<213> ORGANISM: Homo sapiens

<400> SEQUENCE: 330
attctcaggc tacaccctag accaaaccta cgccaaaatc catttcacta tcatattcat    60
cggcgtaaat ctaactttct tcccacaaca ctttctcggc                          100

<210> SEQ ID NO 331
```

```
<211> LENGTH: 100
<212> TYPE: DNA
<213> ORGANISM: Homo sapiens

<400> SEQUENCE: 331
attctcaggc tacaccctag accaaaccta cgccaaaatc catttcgcta tcatattcat      60
cggcgtaaat ctaactttct tcccacaaca ctttctcggc                           100

<210> SEQ ID NO 332
<211> LENGTH: 100
<212> TYPE: DNA
<213> ORGANISM: Homo sapiens

<400> SEQUENCE: 332
attctcaggc tacacactcg gccaagctta tgccaaaatt cactttgcca tcatatttgt      60
aggcgtaaat ctaaccttct tcccgcagca ctttctcggc                           100

<210> SEQ ID NO 333
<211> LENGTH: 100
<212> TYPE: DNA
<213> ORGANISM: Homo sapiens

<400> SEQUENCE: 333
attctcaggc tacaccctag accaaaccta cgctaaaatc catttcgcta tcatattcat      60
cggcgtaaac ctaactttct tcccacaaca ctttcttggc                           100

<210> SEQ ID NO 334
<211> LENGTH: 100
<212> TYPE: DNA
<213> ORGANISM: Homo sapiens

<400> SEQUENCE: 334
ctatccggaa tgccccgacg ttactcggac taccccgatg catacaccac atgaaacatc      60
ctatcatctg taggctcatt catttctcta acagcagtaa                           100

<210> SEQ ID NO 335
<211> LENGTH: 100
<212> TYPE: DNA
<213> ORGANISM: Homo sapiens

<400> SEQUENCE: 335
ctatccggaa tgccccgacg ttactcggac tatcccgatg catacaccac atgaaatatc      60
ctatcatctg taggctcatt catttctcta acagcagtaa                           100

<210> SEQ ID NO 336
<211> LENGTH: 100
<212> TYPE: DNA
<213> ORGANISM: Homo sapiens

<400> SEQUENCE: 336
ttatctggaa taccccgatg ttattctgac taccccgacg catataccac gtgaaatatt      60
ttatcatctg taggctcatt catctcctta acagcagtaa                           100

<210> SEQ ID NO 337
<211> LENGTH: 100
<212> TYPE: DNA
<213> ORGANISM: Homo sapiens

<400> SEQUENCE: 337
ctatccggta tgcctcgatg ttactccaat tatcccgatg tatacaccac atgaaatatt      60
```
atttcatcca gaggctcatt tatttcccta acagcagtaa 100

<210> SEQ ID NO 338
<211> LENGTH: 100
<212> TYPE: DNA
<213> ORGANISM: Homo sapiens

<400> SEQUENCE: 338
ctatccagta tgccttgacg ttactccgat tatcctgatg catacaccac atgaaatatt 60
atctcatctg taggctcatt tatctcacta acagcagtta 100

<210> SEQ ID NO 339
<211> LENGTH: 100
<212> TYPE: DNA
<213> ORGANISM: Homo sapiens

<400> SEQUENCE: 339
ctatctgaga tgtcccgatg ttattccgac taccccgatg catataccac aggaaatatt 60
ttatcatctg taggctcatt catctcccta aaagcagtag 100

<210> SEQ ID NO 340
<211> LENGTH: 100
<212> TYPE: DNA
<213> ORGANISM: Homo sapiens

<400> SEQUENCE: 340
ctatctggaa taccccgacg ttactcggac taccccgatg catacaccac atgaaatatc 60
ctatcatctg taggctcatt catttcccta acagcagtaa 100

<210> SEQ ID NO 341
<211> LENGTH: 100
<212> TYPE: DNA
<213> ORGANISM: Homo sapiens

<400> SEQUENCE: 341
ctatctggaa taccccgacg ttactcggac taccccgatg catacaccac atgaaatatc 60
ctatcatctg taggctcatt catttcccta acagcagtaa 100

<210> SEQ ID NO 342
<211> LENGTH: 100
<212> TYPE: DNA
<213> ORGANISM: Homo sapiens

<400> SEQUENCE: 342
tattaataat tttcatgatt tgagaagcct tcgcttcgaa gcgaaaagtc ctaatagtag 60
aagaaccctc cataaacctg gagtgactat atggatgccc 100

<210> SEQ ID NO 343
<211> LENGTH: 100
<212> TYPE: DNA
<213> ORGANISM: Homo sapiens

<400> SEQUENCE: 343
tattaataat tttcataatt tgagaagcct tcgcttcgaa gcgaaaagtc ctaatagtag 60
aagaaccctc cataaacctg gagtgactat atggatgccc 100

<210> SEQ ID NO 344
<211> LENGTH: 100
<212> TYPE: DNA

<213> ORGANISM: Homo sapiens

<400> SEQUENCE: 344
tgctaataat tttcataacc tgagagacct tcgcttcaaa gcgaaaagtc ctaataaatg    60
agcaaccttc cactaaccta gagtggctgt agggatgccc    100

<210> SEQ ID NO 345
<211> LENGTH: 100
<212> TYPE: DNA
<213> ORGANISM: Homo sapiens

<400> SEQUENCE: 345
tattaataat tttcatgatt tgagaagcct tcgcttcaaa gcgaaaagtc ctaataatag    60
aagaaccctc cataaacctg gagtgactat atggatgcgc    100

<210> SEQ ID NO 346
<211> LENGTH: 100
<212> TYPE: DNA
<213> ORGANISM: Homo sapiens

<400> SEQUENCE: 346
cccaccctac cacacattcg aagaacccgt atacataaaa tctagacaaa aaggaagga    60 atcgaacccc ccaaagctgg tttcaagcca accccatggc    100

<210> SEQ ID NO 347
<211> LENGTH: 100
<212> TYPE: DNA
<213> ORGANISM: Homo sapiens

<400> SEQUENCE: 347
cccaccctac cacacattcg aagaacccgt atacataaaa tctagacaaa aaggaagga    60 atcgaacccc ccaaagctgg tttcaagcca accccatggc    100

<210> SEQ ID NO 348
<211> LENGTH: 100
<212> TYPE: DNA
<213> ORGANISM: Homo sapiens

<400> SEQUENCE: 348
tccaccctac catacgtttg aagaaccagt ctacataaaa cctagacgaa aaggaagga    60 atccaacccc ctaaaactgg tttcaagcca acctcataac    100

<210> SEQ ID NO 349
<211> LENGTH: 100
<212> TYPE: DNA
<213> ORGANISM: Homo sapiens

<400> SEQUENCE: 349
tccaccctac catacattta aagaaccagt ctacataaaa cctagacaaa aaggaagga    60 attgaacctc ctaaggctgg tttcaagcca gcctcataac    100

<210> SEQ ID NO 350
<211> LENGTH: 100
<212> TYPE: DNA
<213> ORGANISM: Homo sapiens

<400> SEQUENCE: 350
ctccatgact ttttcaaaaa ggtattagaa aaaccatttc ataactttgt caaagttaaa    60
ttataggcta aatcctatat atcttaatgg cacatgcagc    100

-continued

<210> SEQ ID NO 351
<211> LENGTH: 100
<212> TYPE: DNA
<213> ORGANISM: Homo sapiens

<400> SEQUENCE: 351
ctccatgact ttttcaaaaa gatattagaa aaaccatttc ataactttgt caaagttaaa       60
ttataggcta aatcctatat atcttaatgg cacatgcagc                           100

<210> SEQ ID NO 352
<211> LENGTH: 100
<212> TYPE: DNA
<213> ORGANISM: Homo sapiens

<400> SEQUENCE: 352
ctctgtgacc ttctcaataa gatattagtg aaattatttc ataactttgt caaagttaag       60
ttataggtta agccgtatat atcttaatgg cccatacagt                           100

<210> SEQ ID NO 353
<211> LENGTH: 100
<212> TYPE: DNA
<213> ORGANISM: Homo sapiens

<400> SEQUENCE: 353
ctctatgact ttttcaacaa gatattagaa aaattatttc ataactttgt caaagttaag       60
ttacaggtta agtcccatat atcttaatgg cacacgcagc                           100

<210> SEQ ID NO 354
<211> LENGTH: 100
<212> TYPE: DNA
<213> ORGANISM: Homo sapiens

<400> SEQUENCE: 354
ctctacaagt ttctcgataa gatattagta aaattatttc ataactttgt caaagttaag       60
ttataggtta agccctatat atcttaatgg cccatccagt                           100

<210> SEQ ID NO 355
<211> LENGTH: 100
<212> TYPE: DNA
<213> ORGANISM: Homo sapiens

<400> SEQUENCE: 355
ctctgtgact ttctcgataa gatattagca aattcattac gtaactttgt caaagttaag       60
ttataggcta aatcctatat gtcttaatgg ctcatccagt                           100

<210> SEQ ID NO 356
<211> LENGTH: 100
<212> TYPE: DNA
<213> ORGANISM: Homo sapiens

<400> SEQUENCE: 356
ctctatgact ctctcgataa gatattagta aaattattat ataactttgt caaagttaat       60
ttataggtta aatcctgtat gtcttaatgg ctcatccagt                           100

<210> SEQ ID NO 357
<211> LENGTH: 100
<212> TYPE: DNA
<213> ORGANISM: Homo sapiens

<400> SEQUENCE: 357
ctctatgact ttttcgataa gatattagta aaattatttc ctaactttgc caaagttaag    60
ttataagtta aaccctgtat atcttaatgg cccatccagc                         100

<210> SEQ ID NO 358
<211> LENGTH: 100
<212> TYPE: DNA
<213> ORGANISM: Homo sapiens

<400> SEQUENCE: 358
ccctatgact ttttcaacaa gatattagga aaactatttc ataacttcgt caaagttaag    60
ttacaggtta aaccccgtat atcttaatgg cacacgcagc                         100

<210> SEQ ID NO 359
<211> LENGTH: 100
<212> TYPE: DNA
<213> ORGANISM: Homo sapiens

<400> SEQUENCE: 359
gcaagtaggt ctacaagacg ctacttcccc tatcatagaa gagcttatca cctttcatga    60
tcacgccctc ataatcattt tccttatctg cttcctagtc                         100

<210> SEQ ID NO 360
<211> LENGTH: 100
<212> TYPE: DNA
<213> ORGANISM: Homo sapiens

<400> SEQUENCE: 360
gcaagtaggt ctacaagacg ctacttcccc tatcatagaa gagcttatca tctttcatga    60
tcacgccctc ataatcattt tccttatctg cttcctagtc                         100

<210> SEQ ID NO 361
<211> LENGTH: 100
<212> TYPE: DNA
<213> ORGANISM: Homo sapiens

<400> SEQUENCE: 361
ccaactaggc cttcaagatg ccacatcccc tataacagaa gagctaatcg ccttccatga    60
tcacgccatt ataatcatct tcctattcag cttcctagtt                         100

<210> SEQ ID NO 362
<211> LENGTH: 100
<212> TYPE: DNA
<213> ORGANISM: Homo sapiens

<400> SEQUENCE: 362
ccagctaggt cttcaagacg ccacatcccc tatcatagaa gagctaatcg ccttccatga    60
tcacgccctc ataatcatct ttcttatcag cttcctagtt                         100

<210> SEQ ID NO 363
<211> LENGTH: 100
<212> TYPE: DNA
<213> ORGANISM: Homo sapiens

<400> SEQUENCE: 363
ctgtatgccc ttttcctaac actcacaaca aaactaacta atactaacat ctcagacgct    60
caggaaatag aaaccgtctg aactatcctg cccgccatca                         100

```
<210> SEQ ID NO 364
<211> LENGTH: 100
<212> TYPE: DNA
<213> ORGANISM: Homo sapiens

<400> SEQUENCE: 364
ctgtacgccc ttttcctaac actcacaaca aaactaacta atactaacat ctcagacgct      60
caggaaatag aaaccgtctg aactatcctg cccgccatca                           100

<210> SEQ ID NO 365
<211> LENGTH: 100
<212> TYPE: DNA
<213> ORGANISM: Homo sapiens

<400> SEQUENCE: 365
tcctagtcct catcgccctc ccatccctac gcatccttta cataacagac gaggtcaacg      60
atccctccct taccatcaaa tcaattggcc accaatggta                           100

<210> SEQ ID NO 366
<211> LENGTH: 100
<212> TYPE: DNA
<213> ORGANISM: Homo sapiens

<400> SEQUENCE: 366
tcctagtcct tatcgccctc ccatccctac gcatccttta cataacagac gaggtcaacg      60
atccctcctt taccatcaaa tcaattggcc atcaatggta                           100

<210> SEQ ID NO 367
<211> LENGTH: 100
<212> TYPE: DNA
<213> ORGANISM: Homo sapiens

<400> SEQUENCE: 367
tcctagtcct aattgccctt ccatccctac gtatcctgta cgtaacagat gaaatcaatg      60
acccttcttt taccattaaa tcaatcggac accaatgata                           100

<210> SEQ ID NO 368
<211> LENGTH: 100
<212> TYPE: DNA
<213> ORGANISM: Homo sapiens

<400> SEQUENCE: 368
ctgaacctac gagtacaccg actacggcgg actaatcttc aactcctaca tacttccccc      60
attattccta gaaccaggcg acctgcgact ccttgacgtt                           100

<210> SEQ ID NO 369
<211> LENGTH: 100
<212> TYPE: DNA
<213> ORGANISM: Homo sapiens

<400> SEQUENCE: 369
ctgaacctac gaatacaccg actacggcgg actaatcttc aactcctaca tacttccccc      60
attattccta gaaccaggcg acctgcgact ccttgacgtt                           100

<210> SEQ ID NO 370
<211> LENGTH: 100
<212> TYPE: DNA
<213> ORGANISM: Homo sapiens

<400> SEQUENCE: 370
```

```
ctgaacctat gaatacacca attatggagg attaattttc aactcttata tacttccacc    60
actattctta gacccaagtg accttcgact tcttaaagtt                         100
```

<210> SEQ ID NO 371
<211> LENGTH: 100
<212> TYPE: DNA
<213> ORGANISM: Homo sapiens

<400> SEQUENCE: 371

```
gacaatcgag tagtactccc gattgaagcc cccattcgta taataattac atcacaagac    60
gtcttgcact catgagctgt ccccacatta ggcttaaaaa                         100
```

<210> SEQ ID NO 372
<211> LENGTH: 100
<212> TYPE: DNA
<213> ORGANISM: Homo sapiens

<400> SEQUENCE: 372

```
gacaatcgag tagtactccc ggttgaagcc cccattcgta taataattac atcacaagac    60
gtcttacact catgagctgt ccccacatta ggcttaaaaa                         100
```

<210> SEQ ID NO 373
<211> LENGTH: 100
<212> TYPE: DNA
<213> ORGANISM: Homo sapiens

<400> SEQUENCE: 373

```
gataatcgag tagtccttcc aattgaagcc cctgttcata taataattac atcacaagac    60
gtcctacact catgaactgt ccccacatta ggcttaaaaa                         100
```

<210> SEQ ID NO 374
<211> LENGTH: 100
<212> TYPE: DNA
<213> ORGANISM: Homo sapiens

<400> SEQUENCE: 374

```
cagatgcaat tcccggacgt ctaaaccaaa ccactttcac cgctacacga ccgggggtat    60
actacggtca atgctctgaa atctgtggag caaaccacag                         100
```

<210> SEQ ID NO 375
<211> LENGTH: 100
<212> TYPE: DNA
<213> ORGANISM: Homo sapiens

<400> SEQUENCE: 375

```
cagatgcaat tcccggacgt ctaaaccaaa ccactttcac tgctacacga ccaggggtat    60
actacggcca atgctctgaa atctgtggag caaaccagtt                         100
```

<210> SEQ ID NO 376
<211> LENGTH: 100
<212> TYPE: DNA
<213> ORGANISM: Homo sapiens

<400> SEQUENCE: 376

```
cagatgcaat ccccggacgc ctaaaccaaa ccacattcac cgccacacga ccaggagtat    60
actacggtca atggtcagaa atctgcagag ctagccacag                         100
```

<210> SEQ ID NO 377
<211> LENGTH: 100

```
<212> TYPE: DNA
<213> ORGANISM: Homo sapiens

<400> SEQUENCE: 377
cagatgtaat ccccggacgc ctaaaccaaa ccacattcac cgccatacga ccaggagtat      60
actacggtca atgctcagaa atctgcggag ctgaccatag                          100

<210> SEQ ID NO 378
<211> LENGTH: 100
<212> TYPE: DNA
<213> ORGANISM: Homo sapiens

<400> SEQUENCE: 378
tttcatgccc atcgtcctag aattaattcc cctaaaaatc tttgaaatag ggcccgtatt      60
taccctatag cacccctct accccctcta gagcccactg                           100

<210> SEQ ID NO 379
<211> LENGTH: 100
<212> TYPE: DNA
<213> ORGANISM: Homo sapiens

<400> SEQUENCE: 379
ttttatgccc atcgtcctag aattaattcc cctaaaaatc tttgaaatag ggcccgtatt      60
taccctatag cacccctct accccctcta gagcccactg                           100

<210> SEQ ID NO 380
<211> LENGTH: 100
<212> TYPE: DNA
<213> ORGANISM: Homo sapiens

<400> SEQUENCE: 380
taaagctaac ttagcattaa ccttttaagt taaagattaa gagaaccaac acctctttac      60
agtgaaatgc cccaactaaa tactaccgta tggcccacca                          100

<210> SEQ ID NO 381
<211> LENGTH: 100
<212> TYPE: DNA
<213> ORGANISM: Homo sapiens

<400> SEQUENCE: 381
taaagctaac ttagcattaa ccttttaagt taaagattaa gagaaccaac acctctttac      60
agtgaaatgc cccaactaaa tactaccgta tgacccacca                          100

<210> SEQ ID NO 382
<211> LENGTH: 100
<212> TYPE: DNA
<213> ORGANISM: Homo sapiens

<400> SEQUENCE: 382
ccgccgccgc cgcacattaa ccttttaagt taaagattaa gagaaccaac acctctttac      60
agtgaaatgc cccaactaaa tactaccgta tggcccacca                          100

<210> SEQ ID NO 383
<211> LENGTH: 100
<212> TYPE: DNA
<213> ORGANISM: Homo sapiens

<400> SEQUENCE: 383
tagagctgac ccagcattaa ccttttaagt taaagactaa gagaatcgct atctctttac      60
```

```
agtgacatgc ctcaactaga caccaccata tgacccacta                    100
```

<210> SEQ ID NO 384
<211> LENGTH: 100
<212> TYPE: DNA
<213> ORGANISM: Homo sapiens

<400> SEQUENCE: 384

```
taattacccc catactcctt acactattcc tcatcaccca actaaaaata ttaaacacaa    60
actaccacct acctccctca ccaaagccca taaaaataaa                        100
```

<210> SEQ ID NO 385
<211> LENGTH: 100
<212> TYPE: DNA
<213> ORGANISM: Homo sapiens

<400> SEQUENCE: 385

```
taattacccc catactcctt acactattcc tcatcaccca actaaaaata ttaaatacaa    60
attaccacct acctccctca ccaaagccca taaaaataaa                        100
```

<210> SEQ ID NO 386
<211> LENGTH: 100
<212> TYPE: DNA
<213> ORGANISM: Homo sapiens

<400> SEQUENCE: 386

```
taattgcccc catacttctt acactattcc tcatcactca gctaaaaata ttaaatacaa    60
attaccatct accccctca ccaaagccca taaaaataaa                         100
```

<210> SEQ ID NO 387
<211> LENGTH: 100
<212> TYPE: DNA
<213> ORGANISM: Homo sapiens

<400> SEQUENCE: 387

```
aaattataac aaaccctgag aaccaaaatg aacgaaaatc tgttcgcttc attcattgcc    60
cccacaatcc taggcctacc cgccgcagta ctgatcattc                        100
```

<210> SEQ ID NO 388
<211> LENGTH: 100
<212> TYPE: DNA
<213> ORGANISM: Homo sapiens

<400> SEQUENCE: 388

```
aaactataac aaaccctgag aaccaaaatg aacgaaaatc tgttcacttc attcattgcc    60
cccacaatcc taggcctacc cgccgcagta ctgatcattc                        100
```

<210> SEQ ID NO 389
<211> LENGTH: 100
<212> TYPE: DNA
<213> ORGANISM: Homo sapiens

<400> SEQUENCE: 389

```
aaactatagt aaaccctgag aaccaaagtg aacgaaaatc tgttcgcttc attcattgcc    60
cccacaatcc taggtctgcc cgccgcagta ctgatcattc                        100
```

<210> SEQ ID NO 390
<211> LENGTH: 100
<212> TYPE: DNA
<213> ORGANISM: Homo sapiens

<400> SEQUENCE: 390
aaaacataac aacccttgag aactaaaatg aacaaaaatc tgttcacctc atttatcgcc       60
ccaacaatcc tagggttacc cacagcagca ctaatcatct                            100

<210> SEQ ID NO 391
<211> LENGTH: 100
<212> TYPE: DNA
<213> ORGANISM: Homo sapiens

<400> SEQUENCE: 391
aaatcacaat aaaccctgag agccaaaatg aacgaaaatt tattcacttc attcattacc       60
cccacaattc taggcctacc tgctgcagta ccaatcatcc                            100

<210> SEQ ID NO 392
<211> LENGTH: 100
<212> TYPE: DNA
<213> ORGANISM: Homo sapiens

<400> SEQUENCE: 392
aaaacataac aacccttgac aactaaaatg aacgaaaatc tgctcacctc atttactgcc       60
ccgacaatcc tcggtttacc cgcagcagca ctaatcatct                            100

<210> SEQ ID NO 393
<211> LENGTH: 100
<212> TYPE: DNA
<213> ORGANISM: Homo sapiens

<400> SEQUENCE: 393
aaaccacaat aatcctttag agtcaaaatg aacgaaaatc tgtttacttc attcattgcc       60
cccacaattc taggccttcc agctgcagtg ccaatcgttc                            100

<210> SEQ ID NO 394
<211> LENGTH: 100
<212> TYPE: DNA
<213> ORGANISM: Homo sapiens

<400> SEQUENCE: 394
tatttccccc tctattgatc cccacctcca aatatctcat caacaaccga ctaatcacca       60
cccaacaatg actaatcaaa ctaacctcaa aacaaatgat                            100

<210> SEQ ID NO 395
<211> LENGTH: 100
<212> TYPE: DNA
<213> ORGANISM: Homo sapiens

<400> SEQUENCE: 395
tatttccccc tctattgatc cccacctcca aatatctcat caacaaccga ctaattacca       60
cccaacaatg actaatccaa ctaacctcaa aacaaatgat                            100

<210> SEQ ID NO 396
<211> LENGTH: 100
<212> TYPE: DNA
<213> ORGANISM: Homo sapiens

<400> SEQUENCE: 396
tatttccccc tctattgatc cccacctcca aatacctcat caacaaccga ctaattacca       60
cccaacaatg actaatccaa ctaacctcaa aacaaatgat                            100

<210> SEQ ID NO 397
<211> LENGTH: 100
<212> TYPE: DNA
<213> ORGANISM: Homo sapiens

<400> SEQUENCE: 397
tatttccccc cttactggtt ccaatttcca aatacctcat caacaactga ctaatcacta    60
cccaacaatg actaatccaa ctcatcttaa aacaaataat    100

<210> SEQ ID NO 398
<211> LENGTH: 100
<212> TYPE: DNA
<213> ORGANISM: Homo sapiens

<400> SEQUENCE: 398
agccatacac aacactaaag gacgaacctg atctcttata ctagtatcct taatcatttt    60
tattgccaca actaacctcc tcggactcct gcctcactca    100

<210> SEQ ID NO 399
<211> LENGTH: 100
<212> TYPE: DNA
<213> ORGANISM: Homo sapiens

<400> SEQUENCE: 399
agccatacac aacactaagg gacgaacctg atctcttata ctagtatcct taatcatttt    60
tattgccaca actaacctcc tcggactcct gcctcactca    100

<210> SEQ ID NO 400
<211> LENGTH: 100
<212> TYPE: DNA
<213> ORGANISM: Homo sapiens

<400> SEQUENCE: 400
agccatacac aacactaaag ggcgaacctg atctcttata ctagtatcct taatcatttt    60
tattgccaca actaatcttc tcgggctcct acgccgaggc    100

<210> SEQ ID NO 401
<211> LENGTH: 100
<212> TYPE: DNA
<213> ORGANISM: Homo sapiens

<400> SEQUENCE: 401
aatgatacat aacattaagg gacgaacctg gtcccttata ctaatctccc taattatttt    60
tattgccaca gctaatctcc ttggactctt accccactca    100

<210> SEQ ID NO 402
<211> LENGTH: 100
<212> TYPE: DNA
<213> ORGANISM: Homo sapiens

<400> SEQUENCE: 402
aacaataaat aacattaaag gacgaacctg atccctcatg ctaatatccc taattatctt    60
cattgctaca accaatctcc tcgggctctt gccccactca    100

<210> SEQ ID NO 403
<211> LENGTH: 100
<212> TYPE: DNA
<213> ORGANISM: Homo sapiens

<400> SEQUENCE: 403
tttacaccaa ccacccaact atctataaac ctagccatgg ccatcccctt atgagcgggc    60
gcagtgatta taggctttcg ctctaagatt aaaaatgccc                        100

<210> SEQ ID NO 404
<211> LENGTH: 100
<212> TYPE: DNA
<213> ORGANISM: Homo sapiens

<400> SEQUENCE: 404
tttacaccaa ccacccaact atctataaac ctagccatgg ccatcccctt atgagcgggc    60
gcagtgatta taggctttcg ctctaagatt aaaaatgccc                        100

<210> SEQ ID NO 405
<211> LENGTH: 100
<212> TYPE: DNA
<213> ORGANISM: Homo sapiens

<400> SEQUENCE: 405
tttacaccaa ctacccaacc atcaataaat ctagctacag caatcccctt atgagcaggc    60
acagtaatca caggcttccg ctttaaaact aaaaactcct                        100

<210> SEQ ID NO 406
<211> LENGTH: 100
<212> TYPE: DNA
<213> ORGANISM: Homo sapiens

<400> SEQUENCE: 406
tagcccactt cttaccacaa ggcacaccta caccccttat ccccatacta gttattatcg    60
aaaccatcag cctactcatt caaccaatag ccctggccgt                        100

<210> SEQ ID NO 407
<211> LENGTH: 100
<212> TYPE: DNA
<213> ORGANISM: Homo sapiens

<400> SEQUENCE: 407
tagcccactt cttaccacaa ggcacaccta caccccttat ccctatacta gttattatcg    60
aaaccatcag cctactcatt caaccaatag ccctggccgt                        100

<210> SEQ ID NO 408
<211> LENGTH: 100
<212> TYPE: DNA
<213> ORGANISM: Homo sapiens

<400> SEQUENCE: 408
tagctcactt ttaccacaa ggcacaccta taccacttat ccctatgcta gtgatcattg    60
aaactattag cctattcatt taaccaatgg caccagctgt                        100

<210> SEQ ID NO 409
<211> LENGTH: 100
<212> TYPE: DNA
<213> ORGANISM: Homo sapiens

<400> SEQUENCE: 409
tagctcactt cctaccacaa ggcacaccca tactacttac ccctatacta gtaatcatca    60
aaaccactag tctacttatt caaccaatgg cactagctgt                        100

<210> SEQ ID NO 410

```
<211> LENGTH: 100
<212> TYPE: DNA
<213> ORGANISM: Homo sapiens

<400> SEQUENCE: 410
tggctggctt tttaccacaa ggcacaccta tgccacttat ccctatacta gtaatcattg    60
aaaccattag cctatttatt caaccaatag cattagctgt                         100

<210> SEQ ID NO 411
<211> LENGTH: 100
<212> TYPE: DNA
<213> ORGANISM: Homo sapiens

<400> SEQUENCE: 411
tagcccatct cttgccacaa ggcacaccct caccccctcat tcccatacta attattatcc   60
aaaccatcag cctatttatc caaccaatag ccctagccat                         100

<210> SEQ ID NO 412
<211> LENGTH: 100
<212> TYPE: DNA
<213> ORGANISM: Homo sapiens

<400> SEQUENCE: 412
acgcctaacc gctaacatta ctgcaggcca cctactcatg cacctaattg gaagcgccac    60
cctagcaata tcaaccatta accttccctc tacacttatc                         100

<210> SEQ ID NO 413
<211> LENGTH: 100
<212> TYPE: DNA
<213> ORGANISM: Homo sapiens

<400> SEQUENCE: 413
acgcctaacc gctaacatta ctgcaggcca cctactcatg cacctaattg gaagcgccac    60
actagcaata tcaactatta accttccctc tacacttatc                         100

<210> SEQ ID NO 414
<211> LENGTH: 100
<212> TYPE: DNA
<213> ORGANISM: Homo sapiens

<400> SEQUENCE: 414
atcttcacaa ttctaattct actgactatc ctagaaatcg ctgtcgcctt aatccaagcc    60
tacgttttca cacttctagt aagcctctac ctgcacgaca                         100

<210> SEQ ID NO 415
<211> LENGTH: 100
<212> TYPE: DNA
<213> ORGANISM: Homo sapiens

<400> SEQUENCE: 415
atcttcacaa ttctaattct actgactatc ctagaaatcg ctgtcgcctt aatccaagcc    60 tacgtttta cacttctagt aagcctctac ctgcacgaca                          100

<210> SEQ ID NO 416
<211> LENGTH: 100
<212> TYPE: DNA
<213> ORGANISM: Homo sapiens

<400> SEQUENCE: 416
atcttcacaa ttttgatttt actgacgatt ctcgaaatcg ctgtcgccct gattctagcc    60
```

```
tatgttttca cactcctagt gagcctctac ctacatgaca                    100
```

<210> SEQ ID NO 417
<211> LENGTH: 100
<212> TYPE: DNA
<213> ORGANISM: Homo sapiens

<400> SEQUENCE: 417

```
acacataatg acccaccaat cacatgccta tcatatagta aaacccagcc catgacccct    60
aacaggggcc ctctcagccc tcctaatgac ctccggccta                        100
```

<210> SEQ ID NO 418
<211> LENGTH: 100
<212> TYPE: DNA
<213> ORGANISM: Homo sapiens

<400> SEQUENCE: 418

```
acacataatg acccaccaat cacatgccta tcatatagta aaacccagcc catggcccct    60
aacaggggcc ctctcagccc tcctaatgac ctccggccta                        100
```

<210> SEQ ID NO 419
<211> LENGTH: 100
<212> TYPE: DNA
<213> ORGANISM: Homo sapiens

<400> SEQUENCE: 419

```
acacataatg acccaccaaa cacatgccta ccgtatagtc aaacccagcc cctgacgact    60
gacaggagct ctctcagctc tcctaataac atctggcctg                        100
```

<210> SEQ ID NO 420
<211> LENGTH: 100
<212> TYPE: DNA
<213> ORGANISM: Homo sapiens

<400> SEQUENCE: 420

```
atacataatg acccaccaaa cacacaccta tcatttagtc aaacccagcc cttgaccatt    60
aacagggct ctctcagctc tcctaataac atccgccta                         100
```

<210> SEQ ID NO 421
<211> LENGTH: 100
<212> TYPE: DNA
<213> ORGANISM: Homo sapiens

<400> SEQUENCE: 421

```
acacataatg acccactata cacatgccta ccatatagtc aaacccagcc cctgaccact    60
aacaggagct ctctcatctc tcctaataac atctggcctg                        100
```

<210> SEQ ID NO 422
<211> LENGTH: 100
<212> TYPE: DNA
<213> ORGANISM: Homo sapiens

<400> SEQUENCE: 422

```
atacataatg acccaccaaa cacacgccta ccacatagtt aagcccagcc cttggccatt    60
aacaggagct ctctcagccc tcctaataac atctggccta                        100
```

<210> SEQ ID NO 423
<211> LENGTH: 100
<212> TYPE: DNA

<213> ORGANISM: Homo sapiens

<400> SEQUENCE: 423

| acacataatg acccaccaaa cacatgcttg ccatatagtc aaacccagcc cctgaccact | 60 |
| aacagaagct ctctcagctc tactaataac atctggcctg | 100 |

<210> SEQ ID NO 424
<211> LENGTH: 100
<212> TYPE: DNA
<213> ORGANISM: Homo sapiens

<400> SEQUENCE: 424

| atacataatg acccaccaga cacatgccta ccatagagtt gtacctagcc cttgaccact | 60 |
| aacaggagct ctctcggctc tcctaataac atctggccta | 100 |

<210> SEQ ID NO 425
<211> LENGTH: 100
<212> TYPE: DNA
<213> ORGANISM: Homo sapiens

<400> SEQUENCE: 425

| atacataatg gctcaccaat cacatgccta tcacatagta aaacccagcc catgacctct | 60 |
| aacaggggcc ctttcagccc tcctaatgac atccggccta | 100 |

<210> SEQ ID NO 426
<211> LENGTH: 100
<212> TYPE: DNA
<213> ORGANISM: Homo sapiens

<400> SEQUENCE: 426

| gccatgtgat ttcacttcca ctccataacg ctcctcatac taggcctact aaccaacaca | 60 |
| ctaaccatat accaatggtg gcgcgatgta acacgagaaa | 100 |

<210> SEQ ID NO 427
<211> LENGTH: 100
<212> TYPE: DNA
<213> ORGANISM: Homo sapiens

<400> SEQUENCE: 427

| gccatgtgat ttcacttcca ctccacaacc ctcctcatac taggcctact aaccaacaca | 60 |
| ctaaccatat accaatgatg gcgcgatgta acacgagaaa | 100 |

<210> SEQ ID NO 428
<211> LENGTH: 100
<212> TYPE: DNA
<213> ORGANISM: Homo sapiens

<400> SEQUENCE: 428

| gcacatacca aggccaccac acaccacctg tccaaaaagg ccttcgatac gggataatcc | 60 |
| tatttattac ctcagaagtt ttttcttcg caggattttt | 100 |

<210> SEQ ID NO 429
<211> LENGTH: 100
<212> TYPE: DNA
<213> ORGANISM: Homo sapiens

<400> SEQUENCE: 429

| gcacatacca aggccaccac acaccacctg tccagaaagg ccttcgatac gggataatcc | 60 |
| tatttattac ctcagaagtt ttttcttcg caggattttt | 100 |

<210> SEQ ID NO 430
<211> LENGTH: 100
<212> TYPE: DNA
<213> ORGANISM: Homo sapiens

<400> SEQUENCE: 430
gtacatttca aggccaccat acaacagttg tccaaaaagg cctccaatag ggaataattc    60
tatttattat ctcagaaata ttcttctttg ctggtttctt    100

<210> SEQ ID NO 431
<211> LENGTH: 100
<212> TYPE: DNA
<213> ORGANISM: Homo sapiens

<400> SEQUENCE: 431
gcacattcca aggccaccat acatcaatcg tccaaaaagg ccttcgatac agaataatct    60
tattcgttat ttcagaggtg tttttttccg ctggcttctt    100

<210> SEQ ID NO 432
<211> LENGTH: 100
<212> TYPE: DNA
<213> ORGANISM: Homo sapiens

<400> SEQUENCE: 432
gtacatttca aggccaccat acaacaattg tccaaaaagg catctgatat ggaatagtac    60
tatttattat ctcagaagta tttttctttg ctggattttt    100

<210> SEQ ID NO 433
<211> LENGTH: 100
<212> TYPE: DNA
<213> ORGANISM: Homo sapiens

<400> SEQUENCE: 433
gtacatttca agaccaccac acaacaacca tccaaaaagg cctctgatat ggaataatcc    60
tattcattat ttcagaagta tttttcttcg ccggattctt    100

<210> SEQ ID NO 434
<211> LENGTH: 100
<212> TYPE: DNA
<213> ORGANISM: Homo sapiens

<400> SEQUENCE: 434
gtacatacca agaccaccac acagtacccg tccaaaaagt ccttcggtat ggaataattt    60
tattcatcat ctcagaagtc tttttcttcg ctggattctt    100

<210> SEQ ID NO 435
<211> LENGTH: 100
<212> TYPE: DNA
<213> ORGANISM: Homo sapiens

<400> SEQUENCE: 435
gtacatacca aggccaccgc acaatacctg tccaaaaagg cctccaatac ggaataatgt    60
tcttcattat ttcagaagtc tttttcttcg ctggattctt    100

<210> SEQ ID NO 436
<211> LENGTH: 100
<212> TYPE: DNA
<213> ORGANISM: Homo sapiens

<400> SEQUENCE: 436
ctgagccttt taccactcca gcctagcccc tacccccaa ctaggagggc actggccccc      60
aacaggcatc accccgctaa atcccctaga agtcccactc                          100

<210> SEQ ID NO 437
<211> LENGTH: 100
<212> TYPE: DNA
<213> ORGANISM: Homo sapiens

<400> SEQUENCE: 437
ctgagccttt taccactcca gcctagctcc cacccccaa ctaggggac actggccccc      60 aacaggcatc accccgctaa atcccctaga agtcccactc                          100

<210> SEQ ID NO 438
<211> LENGTH: 100
<212> TYPE: DNA
<213> ORGANISM: Homo sapiens

<400> SEQUENCE: 438
ctgagcattc taccactcca gcctagcccc caccccctcaa ctaggaggac actgaccccc   60
aacaggcatc actccactca acccctaga agtcccactc                           100

<210> SEQ ID NO 439
<211> LENGTH: 100
<212> TYPE: DNA
<213> ORGANISM: Homo sapiens

<400> SEQUENCE: 439
ctaaacacat ccgtattact cgcatcagga gtatcaatca cctgagctca ccatagtcta    60
atagaaaaca accgaaacca aataattcaa gcactgctta                          100

<210> SEQ ID NO 440
<211> LENGTH: 100
<212> TYPE: DNA
<213> ORGANISM: Homo sapiens

<400> SEQUENCE: 440
ctaaacacat ccgtattact cgcatcaggg gtatcaatca cctgagctca ccatagtcta    60
atagaaaaca accgaaacca aataattcaa gcactgctta                          100

<210> SEQ ID NO 441
<211> LENGTH: 100
<212> TYPE: DNA
<213> ORGANISM: Homo sapiens

<400> SEQUENCE: 441
ctgaacacat ctgtattact tgcatcaggg gtttcaatta cttgagccca tcacagcata    60
atagaaaata atcgaaaaca agtaattcaa gcactacttt                          100

<210> SEQ ID NO 442
<211> LENGTH: 100
<212> TYPE: DNA
<213> ORGANISM: Homo sapiens

<400> SEQUENCE: 442
ccgaatacat ctgtattact tgcatcaggg gtttcaatta cctgagccca tcacagccta    60
atagaaaata atcgaaaaca aataattcaa gcactactta                          100

<210> SEQ ID NO 443
<211> LENGTH: 100
<212> TYPE: DNA
<213> ORGANISM: Homo sapiens

<400> SEQUENCE: 443
ccgaatacat ctgtattact tgcatcaggg gtttcaatta cctgagccca tcacagccta      60
atagaaaata atcgaaaaca aataattcaa gcactactta                           100

<210> SEQ ID NO 444
<211> LENGTH: 100
<212> TYPE: DNA
<213> ORGANISM: Homo sapiens

<400> SEQUENCE: 444
ctaaacacat ctgtactact cgcatcggga gtttcaatta cttgagctca ccatagccta      60
atagagaaca attgtaatca agcaattcaa gcactactta                           100

<210> SEQ ID NO 445
<211> LENGTH: 100
<212> TYPE: DNA
<213> ORGANISM: Homo sapiens

<400> SEQUENCE: 445
ttacaatttt actgggtctc tattttaccc tcctacaagc ctcagagtac ttcgagtctc      60
ccttcaccat ttccgacggc atctacggct caacattttt                           100

<210> SEQ ID NO 446
<211> LENGTH: 100
<212> TYPE: DNA
<213> ORGANISM: Homo sapiens

<400> SEQUENCE: 446
tgtagccaca ggcttccacg gacttcacgt cattattggc tcaactttcc tcactatctg      60
cttcatccgc caactaatat ttcactttac atccaaacat                           100

<210> SEQ ID NO 447
<211> LENGTH: 100
<212> TYPE: DNA
<213> ORGANISM: Homo sapiens

<400> SEQUENCE: 447
tatagctaca ggcttttcaca gacttcatgt cattattgga tcaatattcc tcactgtctg      60
ccttctccgc caattaaaat accactttac atctagtcat                           100

<210> SEQ ID NO 448
<211> LENGTH: 100
<212> TYPE: DNA
<213> ORGANISM: Homo sapiens

<400> SEQUENCE: 448
tatagtcaca ggttttcacg gacttcatgt tattatcaga tcaacatttc tcactatctg      60
cctcctccgc ccattaaaat tccactttac atccaaccac                           100

<210> SEQ ID NO 449
<211> LENGTH: 100
<212> TYPE: DNA
<213> ORGANISM: Homo sapiens

<400> SEQUENCE: 449

```
tatagctaca ggcttttatg gacttcacat cattattgga tcaactttcc ttactatctg    60
ccttctctgc caattaaaat accactttac atccagccat                         100

<210> SEQ ID NO 450
<211> LENGTH: 100
<212> TYPE: DNA
<213> ORGANISM: Homo sapiens

<400> SEQUENCE: 450
tacagccaca ggctttcatg gatttcatgt tattattgga tcaacatttc tcactatctg    60
cctcctccac caattaaaat tccactctac atccaatcac                         100

<210> SEQ ID NO 451
<211> LENGTH: 100
<212> TYPE: DNA
<213> ORGANISM: Homo sapiens

<400> SEQUENCE: 451
tatagccaca ggctttcatg gacttcacat cattattcgg tcaacatttc tcactatctg    60
cctcctctgc caactaaaat ttcactttac atctaaccac                         100

<210> SEQ ID NO 452
<211> LENGTH: 100
<212> TYPE: DNA
<213> ORGANISM: Homo sapiens

<400> SEQUENCE: 452
tgtagctacg ggcttccacg ggctccccgt catcattggt tcaacattcc ttactgtttg    60
ccttatccgc caactattat atcatttac atccaagtac                          100

<210> SEQ ID NO 453
<211> LENGTH: 100
<212> TYPE: DNA
<213> ORGANISM: Homo sapiens

<400> SEQUENCE: 453
cactttggct tcgaagccgc cgcctgatac tggcattttg tagatgtggt ttgactattt    60
ctgtatgtct ccatctattg atgagggtct tactctttta                         100

<210> SEQ ID NO 454
<211> LENGTH: 100
<212> TYPE: DNA
<213> ORGANISM: Homo sapiens

<400> SEQUENCE: 454
cactttgcct ttgaagccac tgcctgatat caacactttg tagatgtagt atgactattc    60
ttgtatgttt ctatttattg atgaggatct tactctttta                         100

<210> SEQ ID NO 455
<211> LENGTH: 100
<212> TYPE: DNA
<213> ORGANISM: Homo sapiens

<400> SEQUENCE: 455
cactttgcct ttgaaggtgc tgcctgatat tgacacttca tagatgtagt atgactattc    60
ttgtatgttt ctatttattg atgaggatct tactctttta                         100

<210> SEQ ID NO 456
<211> LENGTH: 100
```

-continued

```
<212> TYPE: DNA
<213> ORGANISM: Homo sapiens

<400> SEQUENCE: 456
cactttggct ttgaagccgc tgcctgatat tgacacttca tagatgtagt aggactattc    60
ttatacgtct ctttctactg atgaggatcc tactctttta                         100

<210> SEQ ID NO 457
<211> LENGTH: 100
<212> TYPE: DNA
<213> ORGANISM: Homo sapiens

<400> SEQUENCE: 457
cattttggct ttgaagccac cgcctgatat tgacactatg tagatgtagt atgactattc    60
tcatatattt ctatctactg atgagggtct tactctttta                         100

<210> SEQ ID NO 458
<211> LENGTH: 100
<212> TYPE: DNA
<213> ORGANISM: Homo sapiens

<400> SEQUENCE: 458
cactttgcct ttgaagttgc cgccggatat tgacactttg tagatgtagt atgactattc    60
ttatatgtct ctatctattg atgagggtcc tactctttta                         100

<210> SEQ ID NO 459
<211> LENGTH: 100
<212> TYPE: DNA
<213> ORGANISM: Homo sapiens

<400> SEQUENCE: 459
cactttgcct ttgaagccgc tgcctgatat cgacactttg tagatgtagt atgactattc    60
ttgtatgttt ctatttattg atgaggatct tactctttta                         100

<210> SEQ ID NO 460
<211> LENGTH: 100
<212> TYPE: DNA
<213> ORGANISM: Homo sapiens

<400> SEQUENCE: 460
cactttggct ttgaagccgc cacttaatat taacacttgg tagatgtagt atgactattc    60
ttatatgtct ctatctactg atgaggatcc tactcctttta                        100

<210> SEQ ID NO 461
<211> LENGTH: 100
<212> TYPE: DNA
<213> ORGANISM: Homo sapiens

<400> SEQUENCE: 461
tattttgaat ttgaagccac tgcctggtac tggcactttg tagacatagt atgtctattc    60
ctatatgttt ctatctattg atgaggatct tactctttta                         100

<210> SEQ ID NO 462
<211> LENGTH: 100
<212> TYPE: DNA
<213> ORGANISM: Homo sapiens

<400> SEQUENCE: 462
cactttggct ttgaagacgc cacctgatat tgacactttg tagatgtagt atgactattc    60
```

```
ttgtatattt ctatttactg atgaggatct tactctttta                        100
```

<210> SEQ ID NO 463
<211> LENGTH: 100
<212> TYPE: DNA
<213> ORGANISM: Homo sapiens

<400> SEQUENCE: 463

```
cactttggct ttgaagccgt ggcctgatat tgacactttg tagatgtagt atgactattc   60
ttctatattt ctatttactg atgaggatct tactctttta                        100
```

<210> SEQ ID NO 464
<211> LENGTH: 100
<212> TYPE: DNA
<213> ORGANISM: Homo sapiens

<400> SEQUENCE: 464

```
cactttggct ttgaagccac tgcctgatgt tgacactttg tagatgtagt atgactattc   60
ttatatgtct ctatctactg atgaggatcc tactctttta                        100
```

<210> SEQ ID NO 465
<211> LENGTH: 100
<212> TYPE: DNA
<213> ORGANISM: Homo sapiens

<400> SEQUENCE: 465

```
cactttgact ttgaagccgc cacctgatat tagcgcttcg cagatgtagt atgactattt   60
ttatacatct ctgtctactg atgagggtcc tactctttta                        100
```

<210> SEQ ID NO 466
<211> LENGTH: 100
<212> TYPE: DNA
<213> ORGANISM: Homo sapiens

<400> SEQUENCE: 466

```
cactttggct ttgaagccgc tgcctgatat tgacacttca tagatatagt aagactattc   60
ttatatgtct ctatctactg atgaggatcc tactctttta                        100
```

<210> SEQ ID NO 467
<211> LENGTH: 100
<212> TYPE: DNA
<213> ORGANISM: Homo sapiens

<400> SEQUENCE: 467

```
cacttcggct tcgaagccgc tgcttgatac tgacactttg tagatgtagt ttgactattc   60
ctatatgtct ctatctactg gtgaggatct tactctttta                        100
```

<210> SEQ ID NO 468
<211> LENGTH: 100
<212> TYPE: DNA
<213> ORGANISM: Homo sapiens

<400> SEQUENCE: 468

```
gtataaatag taccgttaac ttccaattaa ctagttttga caacattcaa aaaagagtaa   60
taaacttcgc cttaatttta ataatcaaca ccctcctagc                        100
```

<210> SEQ ID NO 469
<211> LENGTH: 100
<212> TYPE: DNA
<213> ORGANISM: Homo sapiens

<400> SEQUENCE: 469
gtatagacag taccactgac ttccaattaa ctagtttcga taacactcga aaaagagtaa    60
taaacctggc actagcccta acagtcaaca ccctcctggc                          100

<210> SEQ ID NO 470
<211> LENGTH: 100
<212> TYPE: DNA
<213> ORGANISM: Homo sapiens

<400> SEQUENCE: 470
cttactacta ataattatta catttgact accacaactc aacggctaca tagaaaaatc     60
caccccttac gagtgcggct tcgaccctat atccccgcc                           100

<210> SEQ ID NO 471
<211> LENGTH: 100
<212> TYPE: DNA
<213> ORGANISM: Homo sapiens

<400> SEQUENCE: 471 cgcgtcccctt tctccataaa attcttctta gtagctatta ccttcttatt atttgatcta   60
gaaattgccc tccttttacc cctaccatga gccctacaaa                          100

<210> SEQ ID NO 472
<211> LENGTH: 100
<212> TYPE: DNA
<213> ORGANISM: Homo sapiens

<400> SEQUENCE: 472
cgcattccct tctccataaa attcttcttg attgctatca cctttttatt atctgaccta    60
gaaattgccc tattactacc cctaccgtga gccctccaaa                          100

<210> SEQ ID NO 473
<211> LENGTH: 100
<212> TYPE: DNA
<213> ORGANISM: Homo sapiens

<400> SEQUENCE: 473
caactaacct gccactaata gttatgtcat ccctcttatt aatcatcatc ctagccctaa    60
gtctggccta tgagtgacta caaaaaggat tagactgagc                          100

<210> SEQ ID NO 474
<211> LENGTH: 100
<212> TYPE: DNA
<213> ORGANISM: Homo sapiens

<400> SEQUENCE: 474
cgaattggta tatagtttaa acaaaacgaa tgatttcgac tcattaaatt atgataatca    60
tatttaccaa atgcccctca tttacataaa tattatacta                          100

<210> SEQ ID NO 475
<211> LENGTH: 100
<212> TYPE: DNA
<213> ORGANISM: Homo sapiens

<400> SEQUENCE: 475
gcatttacca tctcacttct aggaatacta gtatatcgct cacacctcat atcctcccta    60
ctatgcctag aaggaataat actatcgctg ttcattatag                          100

<210> SEQ ID NO 476
<211> LENGTH: 100
<212> TYPE: DNA
<213> ORGANISM: Homo sapiens

<400> SEQUENCE: 476
gcatttacta tctcactttt gggaatacta atctactgct cacacctaat atcctccctg     60
ctatgcctag aagggataat gctatcacta ttcatcataa                          100

<210> SEQ ID NO 477
<211> LENGTH: 100
<212> TYPE: DNA
<213> ORGANISM: Homo sapiens

<400> SEQUENCE: 477
gcatatacca tatcacttct ggggatatta atctattgat cccacctgat atcatcccca     60
ctatgcctag aaggaataat attatcatta ttcatcataa                          100

<210> SEQ ID NO 478
<211> LENGTH: 100
<212> TYPE: DNA
<213> ORGANISM: Homo sapiens

<400> SEQUENCE: 478
gcatttacta cctcactgtt aggaatacta atctatcgct cacacctaac gtcctcccta     60
ctatgcctag aggggataat attatctcta ttcatcgtaa                          100

<210> SEQ ID NO 479
<211> LENGTH: 100
<212> TYPE: DNA
<213> ORGANISM: Homo sapiens

<400> SEQUENCE: 479
ctactctcat aaccctcaac acccactccc tcttagccaa tattgtgcct attgccatac     60
tagtctttgc cgcctgcgaa gcagcggtgg gcctagccct                          100

<210> SEQ ID NO 480
<211> LENGTH: 100
<212> TYPE: DNA
<213> ORGANISM: Homo sapiens

<400> SEQUENCE: 480
gtgtaatcat aaccctcaac acccactccc tcttagccaa tattgtacct atcaccatac     60
tagtctttgc tgcctgcaag cagcagtag gcctagccct                           100

<210> SEQ ID NO 481
<211> LENGTH: 100
<212> TYPE: DNA
<213> ORGANISM: Homo sapiens

<400> SEQUENCE: 481
actagtctca atctccaaca catatggcct agactacgta cataacctaa acctactcca     60
atgctaaaac taatcgtccc aacaattata ttactaccac                          100

<210> SEQ ID NO 482
<211> LENGTH: 100
<212> TYPE: DNA
<213> ORGANISM: Homo sapiens

<400> SEQUENCE: 482
actagtttca atctctaaca catatggtct agattacgta caaaacctac acttacttca    60
atactaaaaa ttattattcc aacaattata ctgttaccaa                         100

<210> SEQ ID NO 483
<211> LENGTH: 100
<212> TYPE: DNA
<213> ORGANISM: Homo sapiens

<400> SEQUENCE: 483
actagtttca atttccaaca catatggctt aaactatgtg cataacctaa atttacttcg    60
acggtaaaaa ttatcattcc aacaattata ctgctaccaa                         100

<210> SEQ ID NO 484
<211> LENGTH: 100
<212> TYPE: DNA
<213> ORGANISM: Homo sapiens

<400> SEQUENCE: 484
actagtttcc atctccaaca cctatagcct agactatgta tataacctaa atttacttcg    60
atgctaaaaa ttattattcc aacaattata ctgctaccaa                         100

<210> SEQ ID NO 485
<211> LENGTH: 100
<212> TYPE: DNA
<213> ORGANISM: Homo sapiens

<400> SEQUENCE: 485
cctagtctca atctccaacg cataaggcct agactatgta caaaatctaa atttactcca    60
atgccaaaaa ttattattcc aacaattata ctgttacaat                         100

<210> SEQ ID NO 486
<211> LENGTH: 100
<212> TYPE: DNA
<213> ORGANISM: Homo sapiens

<400> SEQUENCE: 486
actagtttca atctccaaca catacagcct agattatgta caaaatctaa atttacttca    60
atgctaaaag ttattattcc aacaattata ctgttaccac                         100

<210> SEQ ID NO 487
<211> LENGTH: 100
<212> TYPE: DNA
<213> ORGANISM: Homo sapiens

<400> SEQUENCE: 487
actagtctca atttctaaca gatacggtct agattatgta cataacttaa acttactcca    60
atgttaaaat taattatccc tacaatcata ctacttccaa                         100

<210> SEQ ID NO 488
<211> LENGTH: 100
<212> TYPE: DNA
<213> ORGANISM: Homo sapiens

<400> SEQUENCE: 488
actagtctca atctctaaca catatggcct agactacgta cataacctaa gcctactcca    60
atgctaaaac taatcatccc aacaatcata ttactaccac                         100

<210> SEQ ID NO 489

```
<211> LENGTH: 100
<212> TYPE: DNA
<213> ORGANISM: Homo sapiens

<400> SEQUENCE: 489
tgacatgact ttccaaaaag cacataattt gaatcaacac aaccacccac agcctaatta      60
ttagcatcat ccccctacta ttttttaacc aaatcaacaa                          100

<210> SEQ ID NO 490
<211> LENGTH: 100
<212> TYPE: DNA
<213> ORGANISM: Homo sapiens

<400> SEQUENCE: 490
taacatgatt ctccaaaaaa catataattt gaatcaacac aaccactcac agcctaatta      60
ttagcaccat ccccctacta ttttttaacc aaatcaacaa                          100

<210> SEQ ID NO 491
<211> LENGTH: 100
<212> TYPE: DNA
<213> ORGANISM: Homo sapiens

<400> SEQUENCE: 491
caacctattt agctgttccc caacctttc ctccgacccc ctaacaaccc ccctcctaat      60
actaactacc tgactcctac ccctcacaat catggcaagc                          100

<210> SEQ ID NO 492
<211> LENGTH: 100
<212> TYPE: DNA
<213> ORGANISM: Homo sapiens

<400> SEQUENCE: 492
caacctattt agctgctccc tatccttctc ctccgacccc ctaacgaccc ccctcctaat      60
actaactacc tgacttctac ccctcacaat catggcaagc                          100

<210> SEQ ID NO 493
<211> LENGTH: 100
<212> TYPE: DNA
<213> ORGANISM: Homo sapiens

<400> SEQUENCE: 493
caacgccact tatccagcga accactatca cgaaaaaaac tctacctctc tatactaatc      60
tccctacaaa tctccttaat tataacattc acagccacag                          100

<210> SEQ ID NO 494
<211> LENGTH: 100
<212> TYPE: DNA
<213> ORGANISM: Homo sapiens

<400> SEQUENCE: 494
cagcgccacc tatccaacga accactatca cgaaaaaaac tctacctctc tatgctaatc      60
tccctccaaa tctccttaat tataacattc acagccacgg                          100

<210> SEQ ID NO 495
<211> LENGTH: 100
<212> TYPE: DNA
<213> ORGANISM: Homo sapiens

<400> SEQUENCE: 495
aactaatcat attttatatc ttcttcgaaa ccacacttat ccccaccttg gctatcatca      60
```

```
cccgatgagg caaccagcca gaacgcctga acgcaggcac                          100
```

<210> SEQ ID NO 496
<211> LENGTH: 100
<212> TYPE: DNA
<213> ORGANISM: Homo sapiens

<400> SEQUENCE: 496

```
aactaattat attttatatt ctctttgaag ctacacttat ccccaccttta attattatta    60 cccgctgggg caaccaacca gaatgcctca atgcaagcac                          100
```

<210> SEQ ID NO 497
<211> LENGTH: 100
<212> TYPE: DNA
<213> ORGANISM: Homo sapiens

<400> SEQUENCE: 497

```
aactaattat attttatatt ctctttgaag ctacacttat ccctaccttta attatgatca    60 cccccctgagg taaccaacca gaacgcctca atgcaagctc                         100
```

<210> SEQ ID NO 498
<211> LENGTH: 100
<212> TYPE: DNA
<213> ORGANISM: Homo sapiens

<400> SEQUENCE: 498

```
atacttccta ttctacaccc tagtaggctc ccttccccta ctcatcgcac taatttacac    60
tcacaacacc ctaggctcac taaacattct actactcact                          100
```

<210> SEQ ID NO 499
<211> LENGTH: 100
<212> TYPE: DNA
<213> ORGANISM: Homo sapiens

<400> SEQUENCE: 499

```
ctcactgccc aagaactatc aaactcctga gccaacaact taatatgact agcttacaca    60 atagcttttta tagtaaagat acctctttac ggactccact                          100
```

<210> SEQ ID NO 500
<211> LENGTH: 100
<212> TYPE: DNA
<213> ORGANISM: Homo sapiens

<400> SEQUENCE: 500

```
tatgactccc taaagcccat gtcgaagccc ccatcgctgg gtcaatagta cttgccgcag    60
tactcttaaa actaggcggc tatggtataa tacgcctcac                          100
```

<210> SEQ ID NO 501
<211> LENGTH: 100
<212> TYPE: DNA
<213> ORGANISM: Homo sapiens

<400> SEQUENCE: 501

```
tgtgactccc taaagcccac gtagaagccc ctattgacgg ctcaatagta cttgcagcag    60
ttctcctaaa gctaggcggc tgtggtgtaa tatggcttac                          100
```

<210> SEQ ID NO 502
<211> LENGTH: 100
<212> TYPE: DNA

<213> ORGANISM: Homo sapiens

<400> SEQUENCE: 502
tatgacttcc taaagcccat gtagaaaccc ctattgctag ctcaatggta cttgcagcag    60
gactcctaaa actaggcggc tatggcataa cacgacttaa                         100

<210> SEQ ID NO 503
<211> LENGTH: 100
<212> TYPE: DNA
<213> ORGANISM: Homo sapiens

<400> SEQUENCE: 503
tgtgactccc tgaagcccac gtagaagccc ccattgccgg ctcaatagta cttgcagcag    60
tactcctaaa ataaggcggc tacggaatga tatggctcac                         100

<210> SEQ ID NO 504
<211> LENGTH: 100
<212> TYPE: DNA
<213> ORGANISM: Homo sapiens

<400> SEQUENCE: 504
tatgacttcc taaagctcat gtagaagccc ctattgcagg ctcaatagta cttagagcag    60
ttctcctaaa accaggcagc tacggcataa tatggcttac                         100

<210> SEQ ID NO 505
<211> LENGTH: 100
<212> TYPE: DNA
<213> ORGANISM: Homo sapiens

<400> SEQUENCE: 505
tatgacttcc taaagcccat gtacaagccc ctattgcagg ctcaatagta cttgcagcag    60
ttctcctaaa accaggcagc tatggcataa tacgggttac                         100

<210> SEQ ID NO 506
<211> LENGTH: 100
<212> TYPE: DNA
<213> ORGANISM: Homo sapiens

<400> SEQUENCE: 506
tgtgactccc aaaagcccat gtagaagccc ctattgccgg ctcaacagta cttgcagcgg    60
tactcctaaa actaggcggc tgcggtataa tacggcttac                         100

<210> SEQ ID NO 507
<211> LENGTH: 100
<212> TYPE: DNA
<213> ORGANISM: Homo sapiens

<400> SEQUENCE: 507
tatgactccc caaagcccag atagaagctc ctattgccgg ctcagtagta cttgcagcag    60
tactcctaaa actaggaggc tgcagtataa tatagcttac                         100

<210> SEQ ID NO 508
<211> LENGTH: 100
<212> TYPE: DNA
<213> ORGANISM: Homo sapiens

<400> SEQUENCE: 508
tatgactccc caaagcctac gtagaagccc ttattgccag ctcaatagta cttgcagcag    60
tactcctaaa gctaggtggc tatgatataa tatggcttac                         100

<210> SEQ ID NO 509
<211> LENGTH: 100
<212> TYPE: DNA
<213> ORGANISM: Homo sapiens

<400> SEQUENCE: 509
tatgactccc caaagcccac gtggaagccc ctattgctgg ctcaatagta cttgcagagg    60
tactcctaaa gctaggtggc tatggtatta tacggcttac                         100

<210> SEQ ID NO 510
<211> LENGTH: 100
<212> TYPE: DNA
<213> ORGANISM: Homo sapiens

<400> SEQUENCE: 510
actcattctc aaccccctga caaaacacat agcctacccc ttccttgtac tatccctatg    60
aggcataatt ataacaagct ccatctgcct acgacaaaca                         100

<210> SEQ ID NO 511
<211> LENGTH: 100
<212> TYPE: DNA
<213> ORGANISM: Homo sapiens

<400> SEQUENCE: 511
ccttatcctc agcccctaa cagaatatat agcctaccca ttcctcatat tatccctatg    60
aggaatggtt atgacaagct ctatttgtct acgacaaacc                         100

<210> SEQ ID NO 512
<211> LENGTH: 100
<212> TYPE: DNA
<213> ORGANISM: Homo sapiens

<400> SEQUENCE: 512
cctcatcctc agcccctaa tagaatatat atcctacccc ttcctcatac tatccttatg    60
aggaatagtt ataacaagct ctatttgtct aagacaaact                         100

<210> SEQ ID NO 513
<211> LENGTH: 100
<212> TYPE: DNA
<213> ORGANISM: Homo sapiens

<400> SEQUENCE: 513
ccttatcctc agcccctaa cagaacatat agcctacccc ttcttcatac tattcctatg    60
agggatagtt ataacaagct ctacttgtct gcgacaagcc                         100

<210> SEQ ID NO 514
<211> LENGTH: 100
<212> TYPE: DNA
<213> ORGANISM: Homo sapiens

<400> SEQUENCE: 514
gacctaaaat cgctcattgc atactcttca atcagccaca tagccctcgt agtaacagcc    60
attctcatcc aaaccccctg aagcttcacc ggcgcagtca                         100

<210> SEQ ID NO 515
<211> LENGTH: 100
<212> TYPE: DNA
<213> ORGANISM: Homo sapiens

<400> SEQUENCE: 515
ttctcataat cgcccacgga ctcacatcct cattactatt ctgcctagca aactcaaact    60
acgaacgcac tcacagtcgc atcataatcc tctctcaagg    100

<210> SEQ ID NO 516
<211> LENGTH: 100
<212> TYPE: DNA
<213> ORGANISM: Homo sapiens

<400> SEQUENCE: 516
acttcaaact ctactcccac taatagcttt ttgatgactt ctagcaagcc tcgctaacct    60
cgccttaccc cccactatta acctactggg agaactctct    100

<210> SEQ ID NO 517
<211> LENGTH: 100
<212> TYPE: DNA
<213> ORGANISM: Homo sapiens

<400> SEQUENCE: 517
ccttcaaata ctgcttccac taatagcctc ttgatgactt ctagcaaatc tcactaacct    60
tgccttaccc cctaccatta atctagtagg ataactcttt    100

<210> SEQ ID NO 518
<211> LENGTH: 100
<212> TYPE: DNA
<213> ORGANISM: Homo sapiens

<400> SEQUENCE: 518
ccttcaaact ctgcttccac taatagcctc ttgatgactt ctagcaaatc tcaccaacct    60
tgccctaccc cctaccatta atctaagagg agaactcttt    100

<210> SEQ ID NO 519
<211> LENGTH: 100
<212> TYPE: DNA
<213> ORGANISM: Homo sapiens

<400> SEQUENCE: 519
gcttcaaaca ctactcccac taatagcctt ttgatgactt agagcaaatc ttattaacct    60
tgccttaccc cccaccatta atctaatggg agaactcttt    100

<210> SEQ ID NO 520
<211> LENGTH: 100
<212> TYPE: DNA
<213> ORGANISM: Homo sapiens

<400> SEQUENCE: 520
tcttcaaaca ctactcccac taacagcctt ttgatgactt atagcaaacc ttactaacct    60
tgccttaccc cccaccacta atctaatagg agaactcttt    100

<210> SEQ ID NO 521
<211> LENGTH: 100
<212> TYPE: DNA
<213> ORGANISM: Homo sapiens

<400> SEQUENCE: 521
gtgctagtaa ccacgttctc ctgatcaaat atcactctcc tacttacagg actcaacata    60
ctagtcacag ccctatactc cctctacata tttaccacaa    100

```
<210> SEQ ID NO 522
<211> LENGTH: 100
<212> TYPE: DNA
<213> ORGANISM: Homo sapiens

<400> SEQUENCE: 522
cacaatgggg ctcactcacc caccacatta acaacataaa accctcattc acacgagaaa      60
acaccctcat gttcatacac ctatccccca ttctcctcct                           100

<210> SEQ ID NO 523
<211> LENGTH: 100
<212> TYPE: DNA
<213> ORGANISM: Homo sapiens

<400> SEQUENCE: 523
atccctcaac cccgacatca ttaccgggtt ttcctcttgt aaatatagtt taaccaaaac      60
atcagattgt gaatctgaca acagaggctt acgacccctt                           100

<210> SEQ ID NO 524
<211> LENGTH: 100
<212> TYPE: DNA
<213> ORGANISM: Homo sapiens

<400> SEQUENCE: 524
atttaccgag aaagctcaca agaactgcta actcatgccc ccatgtctaa caacatggct      60
ttctcaactt ttaaaggata acagctatcc attggtctta                           100

<210> SEQ ID NO 525
<211> LENGTH: 100
<212> TYPE: DNA
<213> ORGANISM: Homo sapiens

<400> SEQUENCE: 525
gtctaccgag aaagtgtaca agaactgcta actcatgccc ccatgcctag caacatggct      60
ttctcaactt tgaaaggatt agagtcatcc gttggtctta                           100

<210> SEQ ID NO 526
<211> LENGTH: 100
<212> TYPE: DNA
<213> ORGANISM: Homo sapiens

<400> SEQUENCE: 526
atctatggag aaagtatgtg agaactgcta actcattcct ccatgcctaa caacatggct      60
ttctcaactt ttaaaggatg agagtcatca gttggtctta                           100

<210> SEQ ID NO 527
<211> LENGTH: 100
<212> TYPE: DNA
<213> ORGANISM: Homo sapiens

<400> SEQUENCE: 527
atctaccaag aaattacgca aggacagcta acttgtgccc ccatgcctaa caacatggct      60
ttctcaactt ttaaagaatt agagttgtct attggtctta                           100

<210> SEQ ID NO 528
<211> LENGTH: 100
<212> TYPE: DNA
<213> ORGANISM: Homo sapiens

<400> SEQUENCE: 528
```

```
atttaccaag aaagtgtgca agaactgcta actcatgccc ccatgcctga caatatggct    60
ttctcaactt ttagaggata agagctatct gttggtccta                         100
```

<210> SEQ ID NO 529
<211> LENGTH: 100
<212> TYPE: DNA
<213> ORGANISM: Homo sapiens

<400> SEQUENCE: 529

```
atctacagag aaagtatgca agaattgcta agtcatgcac caatgcctaa caacatggct    60
ctctcaactt ttgaaggatt agagtcatcc tttggtctta                         100
```

<210> SEQ ID NO 530
<211> LENGTH: 100
<212> TYPE: DNA
<213> ORGANISM: Homo sapiens

<400> SEQUENCE: 530

```
atttactgag aaagtatgca agaactgcta actcatgccc ctgtgcctaa caacatggct    60
ttctcaagtt gtagaggata agagctatcc gttggtctta                         100
```

<210> SEQ ID NO 531
<211> LENGTH: 100
<212> TYPE: DNA
<213> ORGANISM: Homo sapiens

<400> SEQUENCE: 531

```
atttactgag aaagtatgca agaactgcta actcatgccc ccatgcctaa caacatggct    60
ttctcaagtt gtagaggata agagctatcc attggtctca                         100
```

<210> SEQ ID NO 532
<211> LENGTH: 100
<212> TYPE: DNA
<213> ORGANISM: Homo sapiens

<400> SEQUENCE: 532

```
atctaccaag aaagtatgca agaactgcta actcatgccc ccatgcctaa caatatggct    60
ttctcaactt ttaaaggatt ggagtcatcc gttggcctta                         100
```

<210> SEQ ID NO 533
<211> LENGTH: 100
<212> TYPE: DNA
<213> ORGANISM: Homo sapiens

<400> SEQUENCE: 533

```
atctaccaag aaattatgca agaactgcta actcacgccc ccatgcctaa caacatggct    60
ttctcaactt ttaaagaatt agaggtatcc attggtctta                         100
```

<210> SEQ ID NO 534
<211> LENGTH: 100
<212> TYPE: DNA
<213> ORGANISM: Homo sapiens

<400> SEQUENCE: 534

```
atatgccaag aaagtatgta agaactgcta actcatgccc ccatgcctaa caacatggtt    60
ctctcaactt ttaaaggatt agagttatcc attggtctta                         100
```

<210> SEQ ID NO 535
<211> LENGTH: 100

```
<212> TYPE: DNA
<213> ORGANISM: Homo sapiens

<400> SEQUENCE: 535
atctatggag aaagtatctg acaactgcta actcatgtcc ccatgtctaa caacatggct    60
ttctcaactt ttaaaggact agagtcatcc actggactta                        100

<210> SEQ ID NO 536
<211> LENGTH: 100
<212> TYPE: DNA
<213> ORGANISM: Homo sapiens

<400> SEQUENCE: 536
atctaccgag aaagtatgca agaactggta actcatgccc caatatataa caatatggca    60
ttctcaactt ttaaaggatt agagttaacc attggtctaa                        100

<210> SEQ ID NO 537
<211> LENGTH: 100
<212> TYPE: DNA
<213> ORGANISM: Homo sapiens

<400> SEQUENCE: 537
ggccccaaaa attttggtgc aactccaaat aaaagtaata accatgcaca ctactataac    60
caccctaacc ctgacttccc taattccccc catccttacc                        100

<210> SEQ ID NO 538
<211> LENGTH: 100
<212> TYPE: DNA
<213> ORGANISM: Homo sapiens

<400> SEQUENCE: 538
accctcgtta accctaacaa aaaaaactca taccccatt atgtaaaatc cattgtcgca     60
tccacctta ttatcagtct cttccccaca acaatattca                         100

<210> SEQ ID NO 539
<211> LENGTH: 100
<212> TYPE: DNA
<213> ORGANISM: Homo sapiens

<400> SEQUENCE: 539
tgtgcctaga ccaagaagtt attatctcga actgacactg agccacaacc caaacaaccc    60
agctctccct aagcttcaaa ctagactact tctccataat                        100

<210> SEQ ID NO 540
<211> LENGTH: 100
<212> TYPE: DNA
<213> ORGANISM: Homo sapiens

<400> SEQUENCE: 540
tatgcacaga ccaagaagtc attatctcaa actgacattg agtaacaaca caaactctca    60
aactctcact aagcttcaaa ccagactact tctccacaat                        100

<210> SEQ ID NO 541
<211> LENGTH: 100
<212> TYPE: DNA
<213> ORGANISM: Homo sapiens

<400> SEQUENCE: 541
attcatccct gtagcattgt tcgttacatg gtccatcata gaattctcac tgtgatatat    60
```
aaactcagac ccaaacatta atcagttctt caaatatcta        100

<210> SEQ ID NO 542
<211> LENGTH: 100
<212> TYPE: DNA
<213> ORGANISM: Homo sapiens

<400> SEQUENCE: 542
atttatcccc gtagcactat tcattacctg atctattgta aaattctcaa tatgatatat        60
aaactcagac cctaacatta atccattttt caaatatta        100

<210> SEQ ID NO 543
<211> LENGTH: 100
<212> TYPE: DNA
<213> ORGANISM: Homo sapiens

<400> SEQUENCE: 543
atttatccca gtagcactat ttgtcacctg atctattaga gaattctcaa tatggtatat        60
aaaatcagat cccaacatta atcaattttt caaatattta        100

<210> SEQ ID NO 544
<211> LENGTH: 100
<212> TYPE: DNA
<213> ORGANISM: Homo sapiens

<400> SEQUENCE: 544
gtttatccca gtagcagtat ttgttacctg atctattgta gaattctgaa tatgatacat        60
aaactcagac cctaacatta atcaattttt caaatactta        100

<210> SEQ ID NO 545
<211> LENGTH: 100
<212> TYPE: DNA
<213> ORGANISM: Homo sapiens

<400> SEQUENCE: 545
atttatccca gtggcactat ttgttacctg atctattgta gagttctcaa tatgatatat        60
aaactcagac cctaatacta atcaattttt caaatattta        100

<210> SEQ ID NO 546
<211> LENGTH: 100
<212> TYPE: DNA
<213> ORGANISM: Homo sapiens

<400> SEQUENCE: 546
ctcattttcc taattaccat actaatctta gttaccgcta acaacctatt ccaactgttc        60
atcggctgag agggcgtagg aattatatcc ttcttgctca        100

<210> SEQ ID NO 547
<211> LENGTH: 100
<212> TYPE: DNA
<213> ORGANISM: Homo sapiens

<400> SEQUENCE: 547
cttattttcc taatcaccat actaattcta gtcaccgcca acaacctatt tcaactcttc        60
atcggctgag agggcgtagg aatcatgtct ttcctactca        100

<210> SEQ ID NO 548
<211> LENGTH: 100
<212> TYPE: DNA
<213> ORGANISM: Homo sapiens

<400> SEQUENCE: 548
tcagttgatg atacgcccga gcagatgcca acacagcagc cattcaagca gtcctataca    60
accgtatcgg cgatatcggt ttcatcctcg ccttagcatg                          100

<210> SEQ ID NO 549
<211> LENGTH: 100
<212> TYPE: DNA
<213> ORGANISM: Homo sapiens

<400> SEQUENCE: 549
tcggttgatg gtatgctcga acagatgcca acacagcagc catcccagca atcctataca    60
accgtattgg cgacattggc ttcatcctag ccctagcatg                          100

<210> SEQ ID NO 550
<211> LENGTH: 100
<212> TYPE: DNA
<213> ORGANISM: Homo sapiens

<400> SEQUENCE: 550
atttatccta cactccaact catgagaccc acaacaaata gcccttctaa acgctaatcc    60
aagcctcacc ccactactag gcctcctcct agcagcagca                          100

<210> SEQ ID NO 551
<211> LENGTH: 100
<212> TYPE: DNA
<213> ORGANISM: Homo sapiens

<400> SEQUENCE: 551
attcctccta cactccaact catgagaacc acaagaaata ctcctcctaa acactaaccc    60
tgactttatt ccactactag gtttcctctt agcagcagca                          100

<210> SEQ ID NO 552
<211> LENGTH: 100
<212> TYPE: DNA
<213> ORGANISM: Homo sapiens

<400> SEQUENCE: 552
ggcaaatcag cccaattagg tctccacccc tgactcccct cagccataga aggccccacc    60
ccagtctcag ccctactcca ctcaagcact atagttgtag                          100

<210> SEQ ID NO 553
<211> LENGTH: 100
<212> TYPE: DNA
<213> ORGANISM: Homo sapiens

<400> SEQUENCE: 553
ggaaagtcag ctcaattcgg cctccatacc tgacttccat ccaccataga aggtccaacc    60
ccagtctcag ccctactcca ctccagcact atcgttatag                          100

<210> SEQ ID NO 554
<211> LENGTH: 100
<212> TYPE: DNA
<213> ORGANISM: Homo sapiens

<400> SEQUENCE: 554
ggaaagtcag ctaaattcaa cctccatccc tgactcccat ccgccataga aggcccaacc    60
ccagtctcgg ccctgctcca ctccagcact gtagttgtag                          100

```
<210> SEQ ID NO 555
<211> LENGTH: 100
<212> TYPE: DNA
<213> ORGANISM: Homo sapiens

<400> SEQUENCE: 555
ggaaaaacag cccaacttgg cctccactcc tcacttcctt ccgccatgga aggcccagcc      60
cctgtctcag ccctactcca ctctagtaat atagctgtgg                          100

<210> SEQ ID NO 556
<211> LENGTH: 100
<212> TYPE: DNA
<213> ORGANISM: Homo sapiens

<400> SEQUENCE: 556
ggaaagtcag ctcaattcag tctccatccc tgacttccat ctgctgtata aggcccaacc      60
gcagtctcag ctctactcca ctctagcact atagttgcag                          100

<210> SEQ ID NO 557
<211> LENGTH: 100
<212> TYPE: DNA
<213> ORGANISM: Homo sapiens

<400> SEQUENCE: 557
ggaaaatcag cccaatttgg cctccatcct tgacttccat cagctataga aggcccaaca      60
ccagtcacag ttctgctcca ttctagcaca atagttgtag                          100

<210> SEQ ID NO 558
<211> LENGTH: 100
<212> TYPE: DNA
<213> ORGANISM: Homo sapiens

<400> SEQUENCE: 558
ggaaaatcag ctcaattagg tcttcatccc tgactcccct cagccataga aggccctacc      60
cccatctcag ccctacttca ctcaagcccc atagttgtag                          100

<210> SEQ ID NO 559
<211> LENGTH: 100
<212> TYPE: DNA
<213> ORGANISM: Homo sapiens

<400> SEQUENCE: 559
ggaaagtcag ctcaatttgg cctctacccc tgacctcctt ccgccatgga aggtccaacc      60
ccagtctcag ccctactcca ctctagcgct gtagttgtag                          100

<210> SEQ ID NO 560
<211> LENGTH: 100
<212> TYPE: DNA
<213> ORGANISM: Homo sapiens

<400> SEQUENCE: 560
ggaaagtcag ctcaatttgg cctccacccc tgacttcctt ccaccatgga aggcccaacc      60
ccagcctcag ccgtactcca ctctagcact atagttgtag                          100

<210> SEQ ID NO 561
<211> LENGTH: 100
<212> TYPE: DNA
<213> ORGANISM: Homo sapiens

<400> SEQUENCE: 561
```

```
ggaaagtcag ctaaattcgg cctccatccc tgacttccat ccgccataga aggcccaacc    60
ccagcctcag ccctgctcca ctccagcact atagttgtag                         100

<210> SEQ ID NO 562
<211> LENGTH: 100
<212> TYPE: DNA
<213> ORGANISM: Homo sapiens

<400> SEQUENCE: 562
agcctcaaat agcagtttgg tctccacccc tgacttccct cggctataga aggcccaacc    60
ccagtttcag ccctactcca ctccagcact atagttgtgg                         100

<210> SEQ ID NO 563
<211> LENGTH: 100
<212> TYPE: DNA
<213> ORGANISM: Homo sapiens

<400> SEQUENCE: 563
ggaaagtcag ctcagttcag cctccatccc tgatttccat cagccataga aggcccagcc    60
ccagtctcag ccctactgca ctccagcact atagttgtag                         100

<210> SEQ ID NO 564
<211> LENGTH: 100
<212> TYPE: DNA
<213> ORGANISM: Homo sapiens

<400> SEQUENCE: 564
agcagatcag ctcaatttgg tctccacccc taactcctgt cagctataga agccccagca    60
cccatctcag ccctactcca ctctagcaca atagtggtag                         100

<210> SEQ ID NO 565
<211> LENGTH: 100
<212> TYPE: DNA
<213> ORGANISM: Homo sapiens

<400> SEQUENCE: 565
ggaaagtcag ctcaattcgg cctccatccc tgacttccat gcgccataga aggtcaaacc    60
ccaacctcag ccctactcca ctccagcact atagttgtag                         100

<210> SEQ ID NO 566
<211> LENGTH: 100
<212> TYPE: DNA
<213> ORGANISM: Homo sapiens

<400> SEQUENCE: 566
ggaaagtcag ctcaattcag cctccatccc tgacttccat cagccacaga aggcccaacc    60
ccagtctcag atctactcca ctccagcgct atagttgtag                         100

<210> SEQ ID NO 567
<211> LENGTH: 100
<212> TYPE: DNA
<213> ORGANISM: Homo sapiens

<400> SEQUENCE: 567
ggaaagtcag ctcaatttgg ccttcatccc tgacttcctt ccactgtaga aggcccaacc    60
ccagtttcag ccctactcca ctctagcact atagttgtac                         100

<210> SEQ ID NO 568
```

```
<211> LENGTH: 100
<212> TYPE: DNA
<213> ORGANISM: Homo sapiens

<400> SEQUENCE: 568
caggaatctt cttactcatc cgcttccacc ccctagcaga aaatagccca ctaatccaaa    60
ctctaacact atgcttaggc gctatcacca ctctgttcgc                         100

<210> SEQ ID NO 569
<211> LENGTH: 100
<212> TYPE: DNA
<213> ORGANISM: Homo sapiens

<400> SEQUENCE: 569
ctggagtctt cctactcatc cgctttcacc ccttggcaga aaacaaccca acaatccaaa    60
tcttcacact atgcctaggc gccaccacta ccctgtttgc                         100

<210> SEQ ID NO 570
<211> LENGTH: 100
<212> TYPE: DNA
<213> ORGANISM: Homo sapiens

<400> SEQUENCE: 570
ctggggtctt tctactcaac cgcttccacc ccttagcaga aaataaccca ccatccaaa     60 ctctcacact atgcctaggc gccaccacca ccctgttcgc                         100

<210> SEQ ID NO 571
<211> LENGTH: 100
<212> TYPE: DNA
<213> ORGANISM: Homo sapiens

<400> SEQUENCE: 571
agcagtctgc gcccttacac aaaatgacat caaaaaaatc gtagccttct ccacttcaag    60
tcaactagga ctcataatag ttacaatcgg catcaaccaa                         100

<210> SEQ ID NO 572
<211> LENGTH: 100
<212> TYPE: DNA
<213> ORGANISM: Homo sapiens

<400> SEQUENCE: 572
agcaatctgt gctttaacac aaaatgatat tgaaaaaatc gtagcactct ccacctcaag    60
tcaactaggc cttagaataa ccacaattgg cattaatcaa                         100

<210> SEQ ID NO 573
<211> LENGTH: 100
<212> TYPE: DNA
<213> ORGANISM: Homo sapiens

<400> SEQUENCE: 573
agcagtctgt gctcttacac aaaacgacat caaaaaaatt gtagccttct ccacttcgag    60
ccaactagga cttatagtag tcacaattgg catcaaccag                         100

<210> SEQ ID NO 574
<211> LENGTH: 100
<212> TYPE: DNA
<213> ORGANISM: Homo sapiens

<400> SEQUENCE: 574
agcagtctgt gctcttacac aaaatgacat caaaaaaatc gtagccttct ctacttcaag    60
```

```
ccaattagga ctcatggtag tcacaatcgg catcaaccaa                            100

<210> SEQ ID NO 575
<211> LENGTH: 100
<212> TYPE: DNA
<213> ORGANISM: Homo sapiens

<400> SEQUENCE: 575
agcaatttgt gctctaacac aaaatgtgat caacaaaatc gtagcattct ccacctcaag     60
tcaactaggc cttataatag ccacaatggg caagaatcaa                          100

<210> SEQ ID NO 576
<211> LENGTH: 100
<212> TYPE: DNA
<213> ORGANISM: Homo sapiens

<400> SEQUENCE: 576
agcaatttgt gctctaacac aaaatgttat caacaaaatc gtagcgttat ccacctcaag     60
tcaactaggc cttataatag tcacaactgg cattaatcaa                          100

<210> SEQ ID NO 577
<211> LENGTH: 100
<212> TYPE: DNA
<213> ORGANISM: Homo sapiens

<400> SEQUENCE: 577
agcgatctgc gctctgacac aaaatgatat ttaaaaaatc atagcgttct tcacctcaag     60
ccagctgggc cttataatag tcacaattgg cattaatcaa                          100

<210> SEQ ID NO 578
<211> LENGTH: 100
<212> TYPE: DNA
<213> ORGANISM: Homo sapiens

<400> SEQUENCE: 578
agcaatctgc gctctaacac aaaatgatat ttaaaaaatc atagcattct ccacctcaag     60
tcagctgggc cttacgatag tcacaattgg cattaatcag                          100

<210> SEQ ID NO 579
<211> LENGTH: 100
<212> TYPE: DNA
<213> ORGANISM: Homo sapiens

<400> SEQUENCE: 579
agcaatctgc actctaacac aaaatgacat ataaaaaatt gtggcatttt tcacctcgag     60
ttaactagga ctcataatag ttacaattgg tattaaccaa                          100

<210> SEQ ID NO 580
<211> LENGTH: 100
<212> TYPE: DNA
<213> ORGANISM: Homo sapiens

<400> SEQUENCE: 580
agcaatctgt gctctaacac aaaatgatat caaacaatg gtagcactct ccacttcaag      60
tcaactagac cttacaatac tcacaattga cattaatcaa                          100

<210> SEQ ID NO 581
<211> LENGTH: 100
<212> TYPE: DNA
```

<213> ORGANISM: Homo sapiens

<400> SEQUENCE: 581
ccacacctag cattcctgca catctgtacc cacgccttct tcaaagccat actatttatg    60
tgctccgggt ccatcatcca caaccttaac aatgaacaag                          100

<210> SEQ ID NO 582
<211> LENGTH: 100
<212> TYPE: DNA
<213> ORGANISM: Homo sapiens

<400> SEQUENCE: 582
ccacacctag cattccttca catctgcatc cacgcctttt aaaaagctat attatttata    60
tgttcaggct ccattatcca taacctcaat gatgaacaag                          100

<210> SEQ ID NO 583
<211> LENGTH: 100
<212> TYPE: DNA
<213> ORGANISM: Homo sapiens

<400> SEQUENCE: 583
ccacacctag cattcctaca catctgcacc cacgcctttt tcaaagttat attatttatg    60
tgttcaggat ccatcatcca cagcctcaac gatgaacaag                          100

<210> SEQ ID NO 584
<211> LENGTH: 100
<212> TYPE: DNA
<213> ORGANISM: Homo sapiens

<400> SEQUENCE: 584
ccacatctag catttctcca tatctgtaca catgcattct tcaaagctat gctgtttata    60
tgctccagat ccatcattca taaccttaat gatgaccagg                          100

<210> SEQ ID NO 585
<211> LENGTH: 100
<212> TYPE: DNA
<213> ORGANISM: Homo sapiens

<400> SEQUENCE: 585
ccatacctag cattcctaca catctgtacc catgctttct tcaaagccat attatttata    60
tgctccggat ccattattca taacctcaac aatgaacaag                          100

<210> SEQ ID NO 586
<211> LENGTH: 100
<212> TYPE: DNA
<213> ORGANISM: Homo sapiens

<400> SEQUENCE: 586
ccacacctag cattcctaca catttgcacc cacaccttt ttaaagctat attatttata     60
agttcaggat ccatcatcca taacctcaac aataaacaag                          100

<210> SEQ ID NO 587
<211> LENGTH: 100
<212> TYPE: DNA
<213> ORGANISM: Homo sapiens

<400> SEQUENCE: 587
gcacacctag cattcctaca tatctgcacc catgcctttt ctaaagctat attatttata    60
tgttcaggat ccatcaccca taacctcaac gatgaacaag                          100

<210> SEQ ID NO 588
<211> LENGTH: 100
<212> TYPE: DNA
<213> ORGANISM: Homo sapiens

<400> SEQUENCE: 588
ccacatctag cattccttca catgtgcacc cacacctttt ttaaagctat attatttata    60
tgctcaggct ccatcatcca caatctcaat gatgaacaag                         100

<210> SEQ ID NO 589
<211> LENGTH: 100
<212> TYPE: DNA
<213> ORGANISM: Homo sapiens

<400> SEQUENCE: 589
ccatatctag cattcctaca catctgtacc catgccttct ttaaagccat actattcata    60
tgctccggat ctatcattca taacctcaac aatgaataag                         100

<210> SEQ ID NO 590
<211> LENGTH: 100
<212> TYPE: DNA
<213> ORGANISM: Homo sapiens

<400> SEQUENCE: 590
ccacatctag cattccttca catctgtacc catgcctttt ttaaagctat ataatttata    60
tgttcagggt ccatcatcca taatctcaat gatgaacaag                         100

<210> SEQ ID NO 591
<211> LENGTH: 100
<212> TYPE: DNA
<213> ORGANISM: Homo sapiens

<400> SEQUENCE: 591
ccacacctag cattccttca catctgtatt catgcctttt ttaaagctat gttatttata    60
tgttcagagt ccatcatcca tagcctcaat gatgaacaac                         100

<210> SEQ ID NO 592
<211> LENGTH: 100
<212> TYPE: DNA
<213> ORGANISM: Homo sapiens

<400> SEQUENCE: 592
atattcgaaa ataggagga ctactcaaaa ccatacctct cacttcaacc tccctcacca     60
ttggcagcct agcattagca ggaatacctt tcctcacagg                          100

<210> SEQ ID NO 593
<211> LENGTH: 100
<212> TYPE: DNA
<213> ORGANISM: Homo sapiens

<400> SEQUENCE: 593
acattcgaaa ataggagga ctactcaaaa ttataccct cacttcaacc tccctcacca      60
ttggcagcct ggcacttgca ggaatgccct tcctcacggg                          100

<210> SEQ ID NO 594
<211> LENGTH: 100
<212> TYPE: DNA
<213> ORGANISM: Homo sapiens

```
<400> SEQUENCE: 594
acatctgaaa aataggagga ctattcaaga ctctactcct cacttcctcc tcccttatca        60
ttggcagcct cacacttaca ggtatgcctt tcctcacagg                             100

<210> SEQ ID NO 595
<211> LENGTH: 100
<212> TYPE: DNA
<213> ORGANISM: Homo sapiens

<400> SEQUENCE: 595
tttctactcc aaagaccaca tcatcgaaac cgcaaacata tcatacacaa acgcctgagc        60
cctatctatt actctcatcg ctacctccct gacaagcgcc                             100

<210> SEQ ID NO 596
<211> LENGTH: 100
<212> TYPE: DNA
<213> ORGANISM: Homo sapiens

<400> SEQUENCE: 596
cttttactct aaagacctta tcatcgaaac cgcaaataca tcatacacca acgcctgagc        60
cctttctatt actcttattg ccacctttt aacagctgtc                              100

<210> SEQ ID NO 597
<211> LENGTH: 100
<212> TYPE: DNA
<213> ORGANISM: Homo sapiens

<400> SEQUENCE: 597
cttctattcc atagacctca tcatcaaaac cgcaaatata tcatacacca acgcctgagc        60
cctatctatt actctcatcg ccacttccct aacaagcgcc                             100

<210> SEQ ID NO 598
<211> LENGTH: 100
<212> TYPE: DNA
<213> ORGANISM: Homo sapiens

<400> SEQUENCE: 598
cttttattct aaagacctca ttattgaaac tgcaaacaca tcatacacca acgcctgagc        60
cctttctatt actcttatcg caacctccct aacagctgtc                             100

<210> SEQ ID NO 599
<211> LENGTH: 100
<212> TYPE: DNA
<213> ORGANISM: Homo sapiens

<400> SEQUENCE: 599
tatagcactc gaataattct tctcacccta acaggtcaac ctcgcttccc cacccttact        60
aacattaacg aaaataaccc caccctacta aaccccatta                             100

<210> SEQ ID NO 600
<211> LENGTH: 100
<212> TYPE: DNA
<213> ORGANISM: Homo sapiens

<400> SEQUENCE: 600
aatagcactc gaataattct cctcacccta acaggccaac ctcgtttccc aaccctaacc       60
aacatcaacg aaacaaccc taccctgcta agccccatca                              100
```

<210> SEQ ID NO 601
<211> LENGTH: 100
<212> TYPE: DNA
<213> ORGANISM: Homo sapiens

<400> SEQUENCE: 601
aacgcctggc agccggaagc ctattcgcag gatttctcat tactaacaac atttcccccg    60
catccccctt ccaaacaaca atcccctct acctaaaact                          100

<210> SEQ ID NO 602
<211> LENGTH: 100
<212> TYPE: DNA
<213> ORGANISM: Homo sapiens

<400> SEQUENCE: 602
aacgcctaac aatcggaagc ctattcgcag gatttctcat caccagcaac attttcccca    60
catccatccc ccaaatgaca atcccacttc acttaaaact                          100

<210> SEQ ID NO 603
<211> LENGTH: 100
<212> TYPE: DNA
<213> ORGANISM: Homo sapiens

<400> SEQUENCE: 603
cacagccctc gctgtcactt tcctaggact tctaacagcc ctagacctca actacctaac    60
caacaaactt aaaataaaat ccccactatg cacattttat                          100

<210> SEQ ID NO 604
<211> LENGTH: 100
<212> TYPE: DNA
<213> ORGANISM: Homo sapiens

<400> SEQUENCE: 604
cacagcccta ggcatcacct tcctaggact tctgacagcc ctagacctca actacttaac    60
caacaaactc aaaataaaaa acccactgtg tacatttcac                          100

<210> SEQ ID NO 605
<211> LENGTH: 100
<212> TYPE: DNA
<213> ORGANISM: Homo sapiens

<400> SEQUENCE: 605
ttctccaaca tactcggatt ctaccctagc atcacacacc gcacaatccc ctatctaggc    60
cttcttacga gccaaaacct gcccctactc ctcctagacc                          100

<210> SEQ ID NO 606
<211> LENGTH: 100
<212> TYPE: DNA
<213> ORGANISM: Homo sapiens

<400> SEQUENCE: 606
taacctgact agaaaagcta ttacctaaaa caatttcaca gcaccaaatc tccacctcca    60
tcatcacctc aacccaaaaa ggcataatta aactttactt                          100

<210> SEQ ID NO 607
<211> LENGTH: 100
<212> TYPE: DNA
<213> ORGANISM: Homo sapiens

<400> SEQUENCE: 607

```
taacttgact agaaaaacta atacctaaaa caacctcaca gtaccaaacc tccgcctcca    60
tcatcacctc aactcaaaaa ggcataatca aactttactt                         100
```

<210> SEQ ID NO 608
<211> LENGTH: 100
<212> TYPE: DNA
<213> ORGANISM: Homo sapiens

<400> SEQUENCE: 608

```
cctctctttc ttcttcccac tcatcctaac cctactccta atcacataac ctattccccc    60
gagcaatctc aattacaata tatacaccaa caaacaatgt                         100
```

<210> SEQ ID NO 609
<211> LENGTH: 100
<212> TYPE: DNA
<213> ORGANISM: Homo sapiens

<400> SEQUENCE: 609

```
ttcctctttc ttcttcccac tcctcctaac cctcctccta atcacataac ctgttacccc    60
gagcactctc aattacaata tatacaccaa caaacaaggt                         100
```

<210> SEQ ID NO 610
<211> LENGTH: 100
<212> TYPE: DNA
<213> ORGANISM: Homo sapiens

<400> SEQUENCE: 610

```
tcaaccagta accactacta atcaacgccc ataatcatac aaagcccccg caccaatagg    60
atcctcccga atcaaccctg acccctctcc ttcataaatt                         100
```

<210> SEQ ID NO 611
<211> LENGTH: 100
<212> TYPE: DNA
<213> ORGANISM: Homo sapiens

<400> SEQUENCE: 611

```
tcaaccagca accaccacca atcaacactc ataattatag aaagcacccg cacccacaga    60
atcttcacga accaaccctg gcccctcacc ctcaaaaatt                         100
```

<210> SEQ ID NO 612
<211> LENGTH: 100
<212> TYPE: DNA
<213> ORGANISM: Homo sapiens

<400> SEQUENCE: 612

```
tcaaccagta actaccacca atcaatgccc gtaatcgtat aaagcccccg caccaatagg    60
atcctcccga atcaatgctg gcccctcccc ttcataaatt                         100
```

<210> SEQ ID NO 613
<211> LENGTH: 100
<212> TYPE: DNA
<213> ORGANISM: Homo sapiens

<400> SEQUENCE: 613

```
tcaaccagca actaccacca atcaacaccc ataattatat aaagcaccca cacccacaga    60
atcctcacga atcaaccctg tccccctcacc ctcaaaaacc                        100
```

<210> SEQ ID NO 614
<211> LENGTH: 100

-continued

<212> TYPE: DNA
<213> ORGANISM: Homo sapiens

<400> SEQUENCE: 614
tcaaccagca actaccacta gtcaacatcc ataatcatat aaagcacccg cacctataga    60
atcctcacga atcaaccctg acccctcacc atcaaaaatc    100

<210> SEQ ID NO 615
<211> LENGTH: 100
<212> TYPE: DNA
<213> ORGANISM: Homo sapiens

<400> SEQUENCE: 615
attcagcttc ctacactatt aaagtttacc acaaccacca ccccatcata ctctttcacc    60
cacagcacca atcctacctc catcgctaac cccactaaaa    100

<210> SEQ ID NO 616
<211> LENGTH: 100
<212> TYPE: DNA
<213> ORGANISM: Homo sapiens

<400> SEQUENCE: 616
attcaacttc ctacactatt aaaattcacc acaatcacca ccccatcata tttttttacc    60
cataacacta accccacttc tattgctaat cccactaaaa    100

<210> SEQ ID NO 617
<211> LENGTH: 100
<212> TYPE: DNA
<213> ORGANISM: Homo sapiens

<400> SEQUENCE: 617
cactcaccaa gacctcaacc cctgaccccc atgcctcagg atactcctca atagccatcg    60
ctgtagtata tccaaagaca accatcattc cccctaaata    100

<210> SEQ ID NO 618
<211> LENGTH: 100
<212> TYPE: DNA
<213> ORGANISM: Homo sapiens

<400> SEQUENCE: 618
cacttaccaa gacctcaatc cctgaccccc atgcctcagg atactcctca atagctattg    60
ctgtagtgta cccaaaaaca accattatac cccctaaata    100

<210> SEQ ID NO 619
<211> LENGTH: 100
<212> TYPE: DNA
<213> ORGANISM: Homo sapiens

<400> SEQUENCE: 619
aagttcctaa aacctcaata cttgatcctc atgcctcagg gtattcctca atagccatca    60
ccgcagtata tccaaaaaca accatcatcc ccccaaata    100

<210> SEQ ID NO 620
<211> LENGTH: 100
<212> TYPE: DNA
<213> ORGANISM: Homo sapiens

<400> SEQUENCE: 620
cactccctaa aacttcaatg cctgaccctc atgcctccgt gtattcctaa atagccatcg    60
ctgtagtata accaaaaaca actatcattc cgcgcaacta                          100

<210> SEQ ID NO 621
<211> LENGTH: 100
<212> TYPE: DNA
<213> ORGANISM: Homo sapiens

<400> SEQUENCE: 621
cactcaccaa gacttcaatt cctgaccccc atgtctcagg atactcctca atagccattg    60
ccatagtata tccaaaaaca accatcgtac ccccctagata                         100

<210> SEQ ID NO 622
<211> LENGTH: 100
<212> TYPE: DNA
<213> ORGANISM: Homo sapiens

<400> SEQUENCE: 622
aattaaaaaa actattaaac ccatataacc tcccccaaaa ttcagaataa taacacaccc    60
gaccacaccg ctaacaatca gtactaaacc cccataaata                          100

<210> SEQ ID NO 623
<211> LENGTH: 100
<212> TYPE: DNA
<213> ORGANISM: Homo sapiens

<400> SEQUENCE: 623
atttaaaaaa accattaaac ctatacaacc tcccccataa tttaaaataa tgatacaccc    60
aaccacacca ctaacaatca acactaagcc cccataaata                          100

<210> SEQ ID NO 624
<211> LENGTH: 100
<212> TYPE: DNA
<213> ORGANISM: Homo sapiens

<400> SEQUENCE: 624
attaaaaaaa accattaaac ccatataacc tcccccataa ttcagaataa taacacaccc    60
aactacacca ctaataatca atactatacc cccataaata                          100

<210> SEQ ID NO 625
<211> LENGTH: 100
<212> TYPE: DNA
<213> ORGANISM: Homo sapiens

<400> SEQUENCE: 625
ggagaaggct tagaagaaaa ccccacaaac cccattacta aacccacact caacagaaac    60
aaagcataca tcattattct cgcacggact acaaccacga                          100

<210> SEQ ID NO 626
<211> LENGTH: 100
<212> TYPE: DNA
<213> ORGANISM: Homo sapiens

<400> SEQUENCE: 626
ggagaaggct tagaagaaaa ccccacaaac cccattacta aaaccacact taacaaaaat    60
aaagcatatg tcattattct cgcacggact acaaccacga                          100

<210> SEQ ID NO 627
<211> LENGTH: 100
<212> TYPE: DNA
<213> ORGANISM: Homo sapiens

<400> SEQUENCE: 627
ggagaaggtt tagaagaaaa ccctacaaac cctattacta aagccacact taatgataat    60
aaagcatatg tgattaatcc cacatggatt acaaccacga                         100

<210> SEQ ID NO 628
<211> LENGTH: 100
<212> TYPE: DNA
<213> ORGANISM: Homo sapiens

<400> SEQUENCE: 628
ccaatgatat gaaaaaccat cgttgtattt caactacaag aacaccaatg accccaatac    60
gcaaaattaa cccctaata aaattaatta accactcatt                          100

<210> SEQ ID NO 629
<211> LENGTH: 100
<212> TYPE: DNA
<213> ORGANISM: Homo sapiens

<400> SEQUENCE: 629
ctaatgataa gaaaaaccat tgtcatattt caactataag aacactaatg accataatac    60
gtaaaacaaa tccactaata aaaatcatta attattcact                         100

<210> SEQ ID NO 630
<211> LENGTH: 100
<212> TYPE: DNA
<213> ORGANISM: Homo sapiens

<400> SEQUENCE: 630
ccaatgatat gaaaaaccat cgttgtattt caactacaag aacactaatg accccaacac    60
gcaaaaccaa ctcgttaata aaattaatta accactcatt                         100

<210> SEQ ID NO 631
<211> LENGTH: 100
<212> TYPE: DNA
<213> ORGANISM: Homo sapiens

<400> SEQUENCE: 631
ctaatggtat gaaaaaccat cattgtattt caactataag aacactaatg accaaaatat    60
gcacaacgca cctgctaata aaattatta gtcattcatt                          100

<210> SEQ ID NO 632
<211> LENGTH: 100
<212> TYPE: DNA
<213> ORGANISM: Homo sapiens

<400> SEQUENCE: 632
ccaatgatat gagaaaccat cattttattt cgactataag aacaccaatg accccaacat    60
gtaaaactaa tccactagta aaataatca accactcact                          100

<210> SEQ ID NO 633
<211> LENGTH: 100
<212> TYPE: DNA
<213> ORGANISM: Homo sapiens

<400> SEQUENCE: 633
catcgacctc cccaccccat ccaacatctc cgcatgatga aacttcggct cactccttgg    60
cgcctgcctg atcctccaaa tcaccacagg actattccta                         100

<210> SEQ ID NO 634
<211> LENGTH: 100
<212> TYPE: DNA
<213> ORGANISM: Homo sapiens

<400> SEQUENCE: 634
tattgatctc cccactccat ctaacatctc cacatgatga aacctcggct cacttcttgg        60
cgcctgccta accattcaaa tgatcacagg actattccta                             100

<210> SEQ ID NO 635
<211> LENGTH: 100
<212> TYPE: DNA
<213> ORGANISM: Homo sapiens

<400> SEQUENCE: 635
tattgatctc cccacaccat ccaacatctc tacatgatga aattttggct cacttcttgg        60
tgcctgctta attctccaga ccatcacagg attatttctg                             100

<210> SEQ ID NO 636
<211> LENGTH: 100
<212> TYPE: DNA
<213> ORGANISM: Homo sapiens

<400> SEQUENCE: 636
tatcgatctc cccgcccat ccaacatctc catatgatgg aacttcagct tgcttcttgg         60
tgcctgctta acccttcaaa ttattacagg actattccta                             100

<210> SEQ ID NO 637
<211> LENGTH: 100
<212> TYPE: DNA
<213> ORGANISM: Homo sapiens

<400> SEQUENCE: 637
catcgatctc cccactccat ctaatatctc tatatgatga aacctctgct cacttcttgg        60
cacctgctta ttccttcaaa tcatcacagg gctattccta                             100

<210> SEQ ID NO 638
<211> LENGTH: 100
<212> TYPE: DNA
<213> ORGANISM: Homo sapiens

<400> SEQUENCE: 638
gccatacact actcaccaga cgcctcaacc gccttttcat caatcgccca catcactcga        60
gacgtaaatt atggctgaat catccgctac cttcacgcca                             100

<210> SEQ ID NO 639
<211> LENGTH: 100
<212> TYPE: DNA
<213> ORGANISM: Homo sapiens

<400> SEQUENCE: 639
gccatacact aatcaccaga tgcttcaacc gccttctcat caatcgccca catcacctga        60
gacgtaaacc atggctgaat catccgctac ctccacgcta                             100

<210> SEQ ID NO 640
<211> LENGTH: 100
<212> TYPE: DNA
<213> ORGANISM: Homo sapiens

<400> SEQUENCE: 640

```
gctatacgct actcaccaga cgcctcaacc gccttctcct cagtcgtcca catcactcga    60
gatgtaaact atggctgaat catccgctac ctccatgcca                         100

<210> SEQ ID NO 641
<211> LENGTH: 100
<212> TYPE: DNA
<213> ORGANISM: Homo sapiens

<400> SEQUENCE: 641
gccatacact acacaccaga caccacaact gccttctctt caatggccca tattaatcga    60
gatgtgaact atggctgaat tatccactat ctccacacta                         100

<210> SEQ ID NO 642
<211> LENGTH: 100
<212> TYPE: DNA
<213> ORGANISM: Homo sapiens

<400> SEQUENCE: 642
atggcgcctc aatattcttt atctgcctct tcctacacat cgggcgaggc ctatattacg    60
gatcatttct ctactcagaa acctgaaaca tcggcattat                         100

<210> SEQ ID NO 643
<211> LENGTH: 100
<212> TYPE: DNA
<213> ORGANISM: Homo sapiens

<400> SEQUENCE: 643
atggcgcctc aatattttc atctgcctct tcctacatgt tggccgaggc ttatactatg     60
gatcatttat attcctagaa acctgaaata ttgattttt                          100

<210> SEQ ID NO 644
<211> LENGTH: 100
<212> TYPE: DNA
<213> ORGANISM: Homo sapiens

<400> SEQUENCE: 644
atggcgcttc catattttc atctgcctct tcttacacat tggctgaggt ttatactatg     60
gatcatttac atttctagaa acctgaaata tcggcattat                         100

<210> SEQ ID NO 645
<211> LENGTH: 100
<212> TYPE: DNA
<213> ORGANISM: Homo sapiens

<400> SEQUENCE: 645
acggtgcctc aatattcttc atctgcctct tcctacacat cggccgaggc ttatactatg    60
gctcattcct ctacctagaa acctgaaaca ttggtattat                         100

<210> SEQ ID NO 646
<211> LENGTH: 100
<212> TYPE: DNA
<213> ORGANISM: Homo sapiens

<400> SEQUENCE: 646
atggcccttc aacattcttc atctgcctct tcctacacgt cggcggaggc ttatattatg    60
ggtcattcgt acatttagaa acatgaaaca ctggcattat                         100

<210> SEQ ID NO 647
```

```
<211> LENGTH: 100
<212> TYPE: DNA
<213> ORGANISM: Homo sapiens

<400> SEQUENCE: 647
atggtgcttc aatattttc atctgcctct tcttacacat tggccaaggg ttatactacg      60
ggtcattact attcccagaa acctgaaata ttggcattat                          100

<210> SEQ ID NO 648
<211> LENGTH: 100
<212> TYPE: DNA
<213> ORGANISM: Homo sapiens

<400> SEQUENCE: 648
atggcgcctc aatattttc atctgcctct tcctacatat tggccgaggc ctgtactatg      60
gcttatttct ctacctagaa acctgaaaca ttggcatcat                          100

<210> SEQ ID NO 649
<211> LENGTH: 100
<212> TYPE: DNA
<213> ORGANISM: Homo sapiens

<400> SEQUENCE: 649
atgacgcttc aacattcttc atctgtctct tcctacactt tagccgaggc ttatattatg      60
gctcattcat atacttagaa aactgaaaca ttgacattat                          100

<210> SEQ ID NO 650
<211> LENGTH: 100
<212> TYPE: DNA
<213> ORGANISM: Homo sapiens

<400> SEQUENCE: 650
atggtgcctc aatattttc atctgcctct tcttacacat tggccaaggc ttatactatg      60
ggtcattcct atttctagaa acctgaaata ttggcattat                          100

<210> SEQ ID NO 651
<211> LENGTH: 100
<212> TYPE: DNA
<213> ORGANISM: Homo sapiens

<400> SEQUENCE: 651
cctcctgctt gcaactatag caacagcctt cataggctat gtcctcccgt gaggccaaat      60
atcattctga ggggccacag taattacaaa cttactatcc                          100

<210> SEQ ID NO 652
<211> LENGTH: 100
<212> TYPE: DNA
<213> ORGANISM: Homo sapiens

<400> SEQUENCE: 652
cctcttactc acaactatgg caacagcatt cataggctac ctgctcccat gaggccagat      60
atcattctga ggtgccacag taattacaaa tctactatcg                          100

<210> SEQ ID NO 653
<211> LENGTH: 100
<212> TYPE: DNA
<213> ORGANISM: Homo sapiens

<400> SEQUENCE: 653
tctcttgctt acaaccacag caacagcgtt tataggctat gtgcttccat gaggccaaat      60
```

```
atcactctga ggcgccacag taaccacaaa cctaatatca                         100

<210> SEQ ID NO 654
<211> LENGTH: 100
<212> TYPE: DNA
<213> ORGANISM: Homo sapiens

<400> SEQUENCE: 654
cctcctactc acaactatgg caacagcatt cataggctac gtgctcccat aaggccagat    60
atctttctga ggcactacag tagttacaaa tctactatca                         100

<210> SEQ ID NO 655
<211> LENGTH: 100
<212> TYPE: DNA
<213> ORGANISM: Homo sapiens

<400> SEQUENCE: 655
cctcttattc acaaccatag caacagcctt cataggctat gtcctcccat gaggccaaat    60
attcttctga ggagccacgg taattacgaa tctattgtcc                         100

<210> SEQ ID NO 656
<211> LENGTH: 100
<212> TYPE: DNA
<213> ORGANISM: Homo sapiens

<400> SEQUENCE: 656
cctcctactc ataaccacag caacagcatt tataggctat gtgcttccat gaggccagat    60
accattctga ggcactacag taatcacaaa cctactatca                         100

<210> SEQ ID NO 657
<211> LENGTH: 100
<212> TYPE: DNA
<213> ORGANISM: Homo sapiens

<400> SEQUENCE: 657
gctcctactc acaaccacag caacagcatt tataggctat gttcttccat gaggccaaat    60
atcattctga ggcgctaccg taaccacaaa cctactatca                         100

<210> SEQ ID NO 658
<211> LENGTH: 100
<212> TYPE: DNA
<213> ORGANISM: Homo sapiens

<400> SEQUENCE: 658
tctcctattc acaactatag caacaacatt cataggctat gtgctcccat gagcccaaat    60
atcattctga ggcactacag taattacaaa tttactatca                         100

<210> SEQ ID NO 659
<211> LENGTH: 100
<212> TYPE: DNA
<213> ORGANISM: Homo sapiens

<400> SEQUENCE: 659
cctcctactc acaactatgg caacagcatt cataggctac atgctcccat gaggccagat    60
atcattcgga ggcgctacag taattacaaa tctactatca                         100

<210> SEQ ID NO 660
<211> LENGTH: 100
<212> TYPE: DNA
```

<213> ORGANISM: Homo sapiens

<400> SEQUENCE: 660
cctcctcctc acaactatag taacagcatt catagcctat gtgctccggt gaggccaaat    60
atcattctga ggtgctacag taattataaa cctatcctca                         100

<210> SEQ ID NO 661
<211> LENGTH: 100
<212> TYPE: DNA
<213> ORGANISM: Homo sapiens

<400> SEQUENCE: 661
ctacctgctc acaactatag caaaagcatt cacaggatac atgctcccat gaggccagat    60
atcattctga ggcgctacaa taattacaaa tctactatca                         100

<210> SEQ ID NO 662
<211> LENGTH: 100
<212> TYPE: DNA
<213> ORGANISM: Homo sapiens

<400> SEQUENCE: 662
tgtcctgctc acaaccatag caacagcatt tataggctat gtacttccat gaggccaaat    60
atcattctga ggcgctacag tgattacaaa tctactatca                         100

<210> SEQ ID NO 663
<211> LENGTH: 100
<212> TYPE: DNA
<213> ORGANISM: Homo sapiens

<400> SEQUENCE: 663
ctcctactta acaactatag caacagcatt cataggctac gtgctcccat gaggccaaat    60
atcattctga ggtgctacag taattacaaa tctactatta                         100

<210> SEQ ID NO 664
<211> LENGTH: 100
<212> TYPE: DNA
<213> ORGANISM: Homo sapiens

<400> SEQUENCE: 664
gccatcccat acattgggac agacctagtt caatgaatct gaggaggcta ctcagtagac    60
agtcccaccc tcacacgatt ctttaccttt cacttcatct                         100

<210> SEQ ID NO 665
<211> LENGTH: 100
<212> TYPE: DNA
<213> ORGANISM: Homo sapiens

<400> SEQUENCE: 665
gccattccat acatcggaac agacctagtc caatgagtct gaggtggcta ctcagtagaa    60
agacccaccc tcacacgatt ctttaccttc cacttcattc                         100

<210> SEQ ID NO 666
<211> LENGTH: 100
<212> TYPE: DNA
<213> ORGANISM: Homo sapiens

<400> SEQUENCE: 666
gccatcccat atattggaac tgaccttgtc caatgaatcg gaggtggatt tccagttgac    60
aaagccactc ttacacgatt cttcgccttc cacttcatct                         100

<210> SEQ ID NO 667
<211> LENGTH: 100
<212> TYPE: DNA
<213> ORGANISM: Homo sapiens

<400> SEQUENCE: 667
gccatcccat atattggaac tgactttgta caatgaatct gaggggatt ctcatttgac      60 aaagccaccc tcacacgatt ttttgccttc catttcatct                          100

<210> SEQ ID NO 668
<211> LENGTH: 100
<212> TYPE: DNA
<213> ORGANISM: Homo sapiens

<400> SEQUENCE: 668
gccattccgt atattggaac tgaccttgtg caatgaatct gaggtggatt ttcagtagac     60
aaagccaccc ttacacgatt ttttgccttc cattttatct                          100

<210> SEQ ID NO 669
<211> LENGTH: 100
<212> TYPE: DNA
<213> ORGANISM: Homo sapiens

<400> SEQUENCE: 669 taccccttcat tattgcagcc ctagcagcac tccacctcct attcttgcac gaaacgggat    60
caaacaaccc cctaggaatc acctcccatt ccgataaaat                          100

<210> SEQ ID NO 670
<211> LENGTH: 100
<212> TYPE: DNA
<213> ORGANISM: Homo sapiens

<400> SEQUENCE: 670 tgcccttttat tattacagcc ttaacaaccc tacaccttct attcctacac gaaataggat    60
caaacaatcc cttaggcatc ccctcccatt ccgacaaaat                          100

<210> SEQ ID NO 671
<211> LENGTH: 100
<212> TYPE: DNA
<213> ORGANISM: Homo sapiens

<400> SEQUENCE: 671
caccttccac ccttactaca caatcaaaga cgccctcggc ttacttctct tccttctctc     60
cttaatgaca ttaacactat tctcaccaga cctcctaggc                          100

<210> SEQ ID NO 672
<211> LENGTH: 100
<212> TYPE: DNA
<213> ORGANISM: Homo sapiens

<400> SEQUENCE: 672
taccttccat ccttactaca caaccaaaga catcctaggc ctattccttt tcctcctcac     60
cctattaaca ctagtactat tctcaccaga cctcctgggc                          100

<210> SEQ ID NO 673
<211> LENGTH: 100
<212> TYPE: DNA
<213> ORGANISM: Homo sapiens

```
<400> SEQUENCE: 673
gacccagaca attataccct agccaacccc ttaaacaccc ctccccacat caagcccgaa      60
tgatatttcc tattcgccta cacaattctc cgatccgtcc                           100

<210> SEQ ID NO 674
<211> LENGTH: 100
<212> TYPE: DNA
<213> ORGANISM: Homo sapiens

<400> SEQUENCE: 674
gacccagaca actacaccct gactaacccc ctaaacaccc caccccacat caaacccgaa      60
tgatatttcc tattcgccta cgcaattctc cgatccattc                           100

<210> SEQ ID NO 675
<211> LENGTH: 100
<212> TYPE: DNA
<213> ORGANISM: Homo sapiens

<400> SEQUENCE: 675
gacccagaca actataccct agccaacccc ctaaacaccc caccccacat taaacccgaa      60
tgttactttc tattcgccta cgcaatccta cggtccattc                           100

<210> SEQ ID NO 676
<211> LENGTH: 100
<212> TYPE: DNA
<213> ORGANISM: Homo sapiens

<400> SEQUENCE: 676
ctaacaaact aggaggcgtc cttgccctat tactatccat cctcatccta gcaataatcc      60
ccatcctcca tatatccaaa caacaaagca taatatttcg                           100

<210> SEQ ID NO 677
<211> LENGTH: 100
<212> TYPE: DNA
<213> ORGANISM: Homo sapiens

<400> SEQUENCE: 677
ccaataaact aggaggcatt ctagcccttc tactatccat cctcatccta gcagcaattc      60
ctatactcca catatccaaa caacaaagca taatatttca                           100

<210> SEQ ID NO 678
<211> LENGTH: 100
<212> TYPE: DNA
<213> ORGANISM: Homo sapiens

<400> SEQUENCE: 678
ccaacaaact aggaggcgta ctggccctcc tactatcaat cctcatccta gcagcaattc      60
ccacacttca catgtccaaa caacaaagca taatattctg                           100

<210> SEQ ID NO 679
<211> LENGTH: 100
<212> TYPE: DNA
<213> ORGANISM: Homo sapiens

<400> SEQUENCE: 679
cccactaagc caatcacttt attgactcct agccgcagac ctcctcattc taacctgaat      60
cggaggacaa ccagtaagct acccttttac catcattgga                           100
```

```
<210> SEQ ID NO 680
<211> LENGTH: 100
<212> TYPE: DNA
<213> ORGANISM: Homo sapiens

<400> SEQUENCE: 680
cccattaagc caattcctat attgattcct agccacagac cttcttaccc taacctgaat      60
tggaggacaa ccagtgaact accccttcac taccatcgga                          100

<210> SEQ ID NO 681
<211> LENGTH: 100
<212> TYPE: DNA
<213> ORGANISM: Homo sapiens

<400> SEQUENCE: 681
caagtagcat ccgtactata cttcacaaca atcctaatcc taataccaac tatctcccta      60
attgaaaaca aaatactcaa atgggcctgt ccttgtagta                          100

<210> SEQ ID NO 682
<211> LENGTH: 100
<212> TYPE: DNA
<213> ORGANISM: Homo sapiens

<400> SEQUENCE: 682
caagtagcat ccgtactata cttcacgaca attttaatcc tcataccagc cacctcctca      60
atcgaaaata aaatactcaa atggacctgc ccctgtagta                          100

<210> SEQ ID NO 683
<211> LENGTH: 100
<212> TYPE: DNA
<213> ORGANISM: Homo sapiens

<400> SEQUENCE: 683
taaactaata caccagtctt gtaaaccgga gacgaaaacc ttttccaag gacaaatcag       60 agaaaaagtc tttaactcca ccattagcac ccaaagctaa                          100

<210> SEQ ID NO 684
<211> LENGTH: 100
<212> TYPE: DNA
<213> ORGANISM: Homo sapiens

<400> SEQUENCE: 684
taaaccaata caccggtctt gtaaactgga aatgaagact tccttccaag gacaaatcag      60
agaaaaagta cttgacttca ccatcagcac ccaaagctaa                          100

<210> SEQ ID NO 685
<211> LENGTH: 100
<212> TYPE: DNA
<213> ORGANISM: Homo sapiens

<400> SEQUENCE: 685
taaaccaata tattggtctt gtaaaccaga aatggagact ctctcccaag gacaactcag      60
agaaaaagta cttgacttca ccatcagcac ccaaagctaa                          100

<210> SEQ ID NO 686
<211> LENGTH: 100
<212> TYPE: DNA
<213> ORGANISM: Homo sapiens

<400> SEQUENCE: 686
```
gattctaatt taaactattc tctgttctttt catggggaag cagatttggg taccacccaa    60
gtattgactc acccatcaac aaccgctatg tatttcgtac    100

<210> SEQ ID NO 687
<211> LENGTH: 100
<212> TYPE: DNA
<213> ORGANISM: Homo sapiens

<400> SEQUENCE: 687
attactgcca gccaccatga atattgtacg gtaccataaa tacttgacca cctgtagtac    60
ataaaaaccc aacccacatc aaaccccccc cccccatgct    100

<210> SEQ ID NO 688
<211> LENGTH: 100
<212> TYPE: DNA
<213> ORGANISM: Homo sapiens

<400> SEQUENCE: 688
tacaagcaag tacagcaatc aaccttcaac tatcacacat caactgcaac tccaaagcca    60
cccctcaccc actaggatac caacaaacct acccacccett    100

<210> SEQ ID NO 689
<211> LENGTH: 100
<212> TYPE: DNA
<213> ORGANISM: Homo sapiens

<400> SEQUENCE: 689
aacagtacat agtacataaa gtcatttacc gtacatagca cattacagtc aaatcccttc    60
tcgtccccat ggatgacccc cctcagatag gggtcccttg    100

<210> SEQ ID NO 690
<211> LENGTH: 100
<212> TYPE: DNA
<213> ORGANISM: Homo sapiens

<400> SEQUENCE: 690
accaccatcc tccgtgaaat caatatcccg cacaagagtg ctactctcct cgctccgggc    60
ccataacact tgggggtagc taaagtgaac tgtatccgac    100

<210> SEQ ID NO 691
<211> LENGTH: 100
<212> TYPE: DNA
<213> ORGANISM: Homo sapiens

<400> SEQUENCE: 691
ttcaccatcc tctgtgaaat caatatcctg cagaagagtg ctactcttct tgatccaggt    60
ccataatact tgggggtagc tataatgaac tgtatccggc    100

<210> SEQ ID NO 692
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 692
acgttggatg ggtctattac cctattaatc ag    32

<210> SEQ ID NO 693

```
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 693
acgttggatg tctggggcca gcgtttca                                          28

<210> SEQ ID NO 694
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (8)..(8)
<223> OTHER INFORMATION: Inosine

<400> SEQUENCE: 694
gcgtgcanac cccccaga                                                    18

<210> SEQ ID NO 695
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 695
acgttggatg aggtctatca ccctattaac cac                                   33

<210> SEQ ID NO 696
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 696
acgttggatg tccggctcca gcgtctcg                                         28

<210> SEQ ID NO 697
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 697
acgttggatg gcctacatca gaccaaaata cttc                                  34

<210> SEQ ID NO 698
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 698
acgttggatg aacagtgtgg gtaataatgg tttca                                 35
```

<210> SEQ ID NO 699
<211> LENGTH: 26
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 699
actgacaatt aacagcccaa tatcta                                          26

<210> SEQ ID NO 700
<211> LENGTH: 32
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 700
acgttggatg ctgcgtcaga tcaaaacact ga                                   32

<210> SEQ ID NO 701
<211> LENGTH: 35
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 701
acgttggatg gacagtgagg gtaataatga cttgt                                35

<210> SEQ ID NO 702
<211> LENGTH: 34
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 702
acgttggatg tcatatacca aatttctccc tcat                                 34

<210> SEQ ID NO 703
<211> LENGTH: 34
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 703
acgttggatg gagtatgcta agattttgcg tagt                                 34

<210> SEQ ID NO 704
<211> LENGTH: 17
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 704
agccttctcc tcactct                                                    17

```
<210> SEQ ID NO 705
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 705
acgttggatg tcatatacca aatctctccc tcac                                34

<210> SEQ ID NO 706
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 706
acgttggatg gagtatgcta agattttgcg tagc                                34

<210> SEQ ID NO 707
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 707
acgttggatg cctatctctc ccagtcctag cc                                  32

<210> SEQ ID NO 708
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 708
acgttggatg gaatggggtc tcctcctccg gct                                 33

<210> SEQ ID NO 709
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 709
atcactatac tactaacaga ccg                                            23

<210> SEQ ID NO 710
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 710
acgttggatg cctatctctc ccagtcctag ct                                  32
```

```
<210> SEQ ID NO 711
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 711
acgttggatg aatggggtct cctcctccgg cg                                   32

<210> SEQ ID NO 712
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 712
acgttggatg ctccctaaaa gcagtagtgc                                      30

<210> SEQ ID NO 713
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 713
acgttggatg ctacagccac tctaggttag                                      30

<210> SEQ ID NO 714
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 714
tactattagg acttttcgct t                                               21

<210> SEQ ID NO 715
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 715
acgttggatg cattcatttc tctaacagca gtaatat                              37

<210> SEQ ID NO 716
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 716
acgttggatg catccatata gtcactccag gttta                                35

<210> SEQ ID NO 717
```

```
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 717
acgttggatg gatttcactt ccactccaca acc                          33

<210> SEQ ID NO 718
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 718
acgttggatg tcccgtatcg aaggcctttc                              30

<210> SEQ ID NO 719
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 719
ggcgtgttac atcgcgcca                                          19

<210> SEQ ID NO 720
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 720
acgttggatg gatttcactt ccactccata acg                          33

<210> SEQ ID NO 721
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 721
acgttggatg tcccgtatcg aaggcctttt                              30

<210> SEQ ID NO 722
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 722
acgttggatg tagctgctcc ctatccttc                               29

<210> SEQ ID NO 723
<211> LENGTH: 29
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 723
acgttggatg ttcgttggat aggtggcgc                                    29

<210> SEQ ID NO 724
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 724
cactcctaat actaactacc tgact                                        25

<210> SEQ ID NO 725
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 725
acgttggatg tagctgttcc ccaaccttt                                    29

<210> SEQ ID NO 726
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 726
acgttggatg ttcgctggat aagtggcgt                                    29

<210> SEQ ID NO 727
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 727
acgttggatg cggttgatgg tatgctcgaa                                   30

<210> SEQ ID NO 728
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 728
acgttggatg tgtaggagga atcatgctag ggct                              34

<210> SEQ ID NO 729
<211> LENGTH: 24
<212> TYPE: DNA
```

```
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (8)..(8)
<223> OTHER INFORMATION: Inosine

<400> SEQUENCE: 729
ggaagcantc ctatacaacc gtat                                          24

<210> SEQ ID NO 730
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 730
acgttggatg cagttgatga tacgcccgag                                    30

<210> SEQ ID NO 731
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 731
acgttggatg tgtaggataa atcatgctaa ggcg                               34

<210> SEQ ID NO 732
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 732
acgttggatg cacagcccta ggcatcacc                                     29

<210> SEQ ID NO 733
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 733
acgttggatg gtgaaatgta cacagtgggt t                                  31

<210> SEQ ID NO 734
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 734
cagccctaga cctcaactac                                               20
```

<210> SEQ ID NO 735
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 735
acgttggatg cacagccctc gctgtcact                                    29

<210> SEQ ID NO 736
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 736
acgttggatg ataaaatgtg catagtgggg a                                 31

<210> SEQ ID NO 737
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 737
acgttggatg cccagacaac tacaccctga ct                                32

<210> SEQ ID NO 738
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 738
acgttggatg gcctcctagt ttattgggaa t                                 31

<210> SEQ ID NO 739
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 739
gaataggaaa tatcattcgg g                                            21

<210> SEQ ID NO 740
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 740
acgttggatg cccagacaat tataccctag cc                                32

<210> SEQ ID NO 741

```
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 741
acgttggatg gcctcctagt ttgttaggga c                                31

<210> SEQ ID NO 742
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (8)..(8)
<223> OTHER INFORMATION: Inosine

<400> SEQUENCE: 742
gcgtgcanac cccccagac                                              19

<210> SEQ ID NO 743
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (8)..(8)
<223> OTHER INFORMATION: Inosine

<400> SEQUENCE: 743
gcgtgcanac cccccagat                                              19

<210> SEQ ID NO 744
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 744
actgacaatt aacagcccaa tatctac                                     27

<210> SEQ ID NO 745
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 745
actgacaatt aacagcccaa tatctat                                     27

<210> SEQ ID NO 746
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 746
agccttctcc tcactctc                                                  18

<210> SEQ ID NO 747
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 747
agccttctcc tcactctt                                                  18

<210> SEQ ID NO 748
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 748
atcactatac tactaacaga ccgc                                           24

<210> SEQ ID NO 749
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 749
atcactatac tactaacaga ccgt                                           24

<210> SEQ ID NO 750
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 750
tactattagg acttttcgct tc                                             22

<210> SEQ ID NO 751
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 751
tactattagg acttttcgct tt                                             22

<210> SEQ ID NO 752
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 752
ggcgtgttac atcgcgccac                                          20

<210> SEQ ID NO 753
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 753
ggcgtgttac atcgcgccat                                          20

<210> SEQ ID NO 754
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 754
cactcctaat actaactacc tgactc                                   26

<210> SEQ ID NO 755
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 755
cactcctaat actaactacc tgactt                                   26

<210> SEQ ID NO 756
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (8)..(8)
<223> OTHER INFORMATION: Inosine

<400> SEQUENCE: 756
ggaagcantc ctatacaacc gtatc                                    25

<210> SEQ ID NO 757
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (8)..(8)
<223> OTHER INFORMATION: Inosine

<400> SEQUENCE: 757
ggaagcantc ctatacaacc gtatct                                   26

<210> SEQ ID NO 758

```
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 758
cagccctaga cctcaactac c                                              21

<210> SEQ ID NO 759
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 759
cagccctaga cctcaactac t                                              21

<210> SEQ ID NO 760
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 760
gaataggaaa tatcattcgg gc                                             22

<210> SEQ ID NO 761
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 761
gaataggaaa tatcattcgg gt                                             22

<210> SEQ ID NO 762
<211> LENGTH: 101
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 762
ggtctattac cctattaatc agtcacggga gctctccatg catttggtat tttaatctgg    60
ggggtgtgca cgcgatagca ttgtgaaacg ctggccccag a                       101

<210> SEQ ID NO 763
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (11)..(11)
<223> OTHER INFORMATION: a, c, t, g, unknown or other

<400> SEQUENCE: 763
``` tctgggggt ntgcacgc                                                   18

<210> SEQ ID NO 764
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 764
aggtctatca ccctattaac cactcacggg agctctccat gcatttggta ttttcgtctg      60
gggggtgtgc acgcgatagc attgcgagac gctggagccg ga                       102

<210> SEQ ID NO 765
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (11)..(11)
<223> OTHER INFORMATION: a, c, t, g, unknown or other

<400> SEQUENCE: 765 tctgggggt ntgcacgc                                                   18

<210> SEQ ID NO 766
<211> LENGTH: 86
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 766
gcctacatca gaccaaaata cttcactgac aattaacagc ccaatatcta taaataatca     60
atgaaaccat tattcccac actgtt                                          86

<210> SEQ ID NO 767
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 767
actgacaatt aacagcccaa tatcta                                         26

<210> SEQ ID NO 768
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 768
ctgcgtcaga tcaaaacact gaactgacaa ttaacagccc aatatctaca atcaaccaac     60
aagtcattat taccctcact gtc                                            83

<210> SEQ ID NO 769
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 769
actgacaatt aacagcccaa tatcta                                         26

<210> SEQ ID NO 770
<211> LENGTH: 124
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 770
tcatatacca aatttctccc tcattaaacg taagccttct cctcactctt tcaatcttat    60
ccatcatggc aggcagttga ggtggattaa accaaaccca actacgcaaa atcttagcat   120
actc                                                                124

<210> SEQ ID NO 771
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 771
agccttctcc tcactct                                                   17

<210> SEQ ID NO 772
<211> LENGTH: 124
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 772
tcatatacca aatctctccc tcactaaacg taagccttct cctcactctc tcaatcttat    60
ccatcatagc aggcagttga ggtggattaa accaaaccca gctacgcaaa atcttagcat   120
actc                                                                124

<210> SEQ ID NO 773
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 773
agccttctcc tcactct                                                   17

<210> SEQ ID NO 774
<211> LENGTH: 101
<212> TYPE: DNA
<213> ORGANISM: Artificial Sequence
<220> FEATURE:
<223> OTHER INFORMATION: Description of Artificial Sequence: Synthetic

```
              polynucleotide

<400> SEQUENCE: 774
cctatctctc ccagtcctag ccgctggcat cactatacta ctaacagacc gtaacctcaa    60
caccaccttc ttcgacccag ccggaggagg agaccccatt c                       101

<210> SEQ ID NO 775
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 775
atcactatac tactaacaga ccg                                            23

<210> SEQ ID NO 776
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 776
cctatctctc ccagtcctag ctgctggcat cactatacta ctaacagacc gcaacctcaa    60
caccaccttc ttcgaccccg ccggaggagg agaccccatt                         100

<210> SEQ ID NO 777
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 777
atcactatac tactaacaga ccg                                            23

<210> SEQ ID NO 778
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 778
ctccctaaaa gcagtagtgc taataatttt cataacctga gagaccttcg cttcaaagcg    60
aaaagtccta ataatgagc aaccttccac taacctagag tggctgtag               109

<210> SEQ ID NO 779
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 779
aagcgaaaag tcctaatagt a                                              21

<210> SEQ ID NO 780
```

<211> LENGTH: 121
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 780
cattcatttc tctaacagca gtaatattaa taattttcat aatttgagaa gccttcgctt      60
cgaagcgaaa agtcctaata gtagaagaac cctccataaa cctggagtga ctatatggat     120
g                                                                    121

<210> SEQ ID NO 781
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 781
aagcgaaaag tcctaatagt a                                               21

<210> SEQ ID NO 782
<211> LENGTH: 121
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 782
cattcatttc tctaacagca gtaatattaa taattttcat gatttgagaa gccttcgctt      60
cgaagcgaaa agtcctaata gtagaagaac cctccataaa cctggagtga ctatatggat     120
g                                                                    121

<210> SEQ ID NO 783
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 783
aagcgaaaag tcctaatagt a                                               21

<210> SEQ ID NO 784
<211> LENGTH: 147
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 784
gatttcactt ccactccaca accctcctca tactaggcct actaaccaac acactaacca      60
tataccaatg atggcgcgat gtaacacgag aaagcacata ccaaggccac cacacaccac     120
ctgtccagaa aggccttcga tacggga                                        147

<210> SEQ ID NO 785
<211> LENGTH: 17
<212> TYPE: DNA

<213> ORGANISM: Artificial Sequence
<220> FEATURE:
<223> OTHER INFORMATION: Description of Artificial Sequence: Synthetic
      primer

<400> SEQUENCE: 785
tggcgcgatg taacacg                                                17

<210> SEQ ID NO 786
<211> LENGTH: 147
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 786
gatttcactt ccactccata acgctcctca tactaggcct actaaccaac acactaacca    60
tataccaatg gtggcgcgat gtaacacgag aaagcacata ccaaggccac cacacaccac   120
ctgtccaaaa aggccttcga tacggga                                      147

<210> SEQ ID NO 787
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 787
tggcgcgatg taacacg                                                17

<210> SEQ ID NO 788
<211> LENGTH: 112
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 788
tagctgctcc ctatccttct cctccgaccc cctaacgacc cccctcctaa tactaactac    60
ctgacttcta cccctcacaa tcatggcaag ccagcgccac ctatccaacg aa           112

<210> SEQ ID NO 789
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 789
ctcctaatac taactacctg act                                          23

<210> SEQ ID NO 790
<211> LENGTH: 112
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 790
tagctgttcc ccaacctttt cctccgaccc cctaacaacc cccctcctaa tactaactac    60
ctgactccta cccctcacaa tcatggcaag ccaacgccac ttatccagcg aa            112

<210> SEQ ID NO 791
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 791
ctcctaatac taactacctg act                                            23

<210> SEQ ID NO 792
<211> LENGTH: 111
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 792
cggttgatgg tatgctcgaa cagatgccaa cacagcagcc atcccagcaa tcctatacaa    60
ccgtattggc gacattggct tcatcctagc cctagcatga ttcctcctac a            111

<210> SEQ ID NO 793
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (6)..(6)
<223> OTHER INFORMATION: a, c, t, g, unknown or other

<400> SEQUENCE: 793
aagcantcct atacaaccgt at                                             22

<210> SEQ ID NO 794
<211> LENGTH: 111
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 794
cagttgatga tacgcccgag cagatgccaa cacagcagcc attcaagcag tcctatacaa    60
ccgtatcggc gatatcggtt tcatcctcgc cttagcatga tttatcctac a            111

<210> SEQ ID NO 795
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (6)..(6)
<223> OTHER INFORMATION: a, c, t, g, unknown or other

<400> SEQUENCE: 795
aagcantcct atacaaccgt at                                             22

<210> SEQ ID NO 796
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 796
cacagcccta ggcatcacct tcctaggact tctgacagcc ctagacctca actacttaac    60
caacaaactc aaaataaaaa acccactgtg tacatttcac                         100

<210> SEQ ID NO 797
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 797
cagccctaga cctcaactac                                                20

<210> SEQ ID NO 798
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 798
cacagccctc gctgtcactt tcctaggact tctaacagcc ctagacctca actacctaac    60
caacaaactt aaaataaaat ccccactatg cacattttat                         100

<210> SEQ ID NO 799
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 799
cagccctaga cctcaactac                                                20

<210> SEQ ID NO 800
<211> LENGTH: 115
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 800
cccagacaac tacaccctga ctaaccccct aaacacccca ccccacatca aacccgaatg    60
atatttccta ttcgcctacg caattctccg atccattccc aataaactag gaggc        115

<210> SEQ ID NO 801
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 801
cccgaatgat atttcctatt c                                      21

<210> SEQ ID NO 802
<211> LENGTH: 115
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 802
cccagacaat tataccctag ccaacccctt aaacacccct ccccacatca agcccgaatg      60
atatttccta ttcgcctaca caattctccg atccgtccct aacaaactag gaggc         115

<210> SEQ ID NO 803
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 803
cccgaatgat atttcctatt c                                      21

<210> SEQ ID NO 804
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 804
acgttggatg gatctaaaac actctttac                              29

<210> SEQ ID NO 805
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 805
acgttggatg tcacacgatt aacccaagtc                             30

<210> SEQ ID NO 806
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 806
acgttggatg ttgtgtagag ttcaggggag                             30

<210> SEQ ID NO 807
<211> LENGTH: 30
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 807
acgttggatg ctacaatctt cctaggaaca                                    30

<210> SEQ ID NO 808
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 808
acgttggatg gaggagtatg ctaagatttt                                    30

<210> SEQ ID NO 809
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 809
acgttggatg cagttgaggt ggattaaacc                                    30

<210> SEQ ID NO 810
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 810
acgttggatg ctactccacc tcaatcacac                                    30

<210> SEQ ID NO 811
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 811
acgttggatg cattttattt ttacgttgtt aga                                33

<210> SEQ ID NO 812
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 812
acgttggatg aggccatcaa tttcatcaca                                    30

<210> SEQ ID NO 813
<211> LENGTH: 28
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 813
acgttggatg gggttatggc aggggggtt                                28

<210> SEQ ID NO 814
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 814
acgttggatg ccggcgtcaa agtatttagc                               30

<210> SEQ ID NO 815
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 815
acgttggatg atttcatatt gcttccgtgg                               30

<210> SEQ ID NO 816
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 816
acgttggatg gcctaatgtg gggacagc                                 28

<210> SEQ ID NO 817
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 817
acgttggatg taataattac atcacaagac                               30

<210> SEQ ID NO 818
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 818
acgttggatg cttcattcat tgcccccaca                               30

<210> SEQ ID NO 819
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 819
acgttggatg gaatgatcag tactgcggcg                                              30

<210> SEQ ID NO 820
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 820
acgttggatg cgccttaatc caagcctac                                               29

<210> SEQ ID NO 821
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 821
acgttggatg gcaggtagag gcttactaga                                              30

<210> SEQ ID NO 822
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 822
acgttggatg gggatatagg gtcgaagccg                                              30

<210> SEQ ID NO 823
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 823
acgttggatg ggctacatag aaaaatccac                                              30

<210> SEQ ID NO 824
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 824
acgttggatg gatctaaaac actctttac                                               29

<210> SEQ ID NO 825
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 825
aaaacactct ttacgccgg                                              19

<210> SEQ ID NO 826
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 826
aaaacactct ttacgccggc                                             20

<210> SEQ ID NO 827
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 827
aaaacactct ttacgccggt                                             20

<210> SEQ ID NO 828
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 828
acgttggatg ttgtgtagag ttcaggggag                                  30

<210> SEQ ID NO 829
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 829
ttcaggggag agtgcgt                                                17

<210> SEQ ID NO 830
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 830
ttcaggggag agtgcgtc                                               18

<210> SEQ ID NO 831
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 831
```
ttcaggggag agtgcgtt                                                 18

<210> SEQ ID NO 832
<211> LENGTH: 30
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 832
acgttggatg gaggagtatg ctaagatttt                                    30

<210> SEQ ID NO 833
<211> LENGTH: 20
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 833
tatgctaaga ttttgcgtag                                               20

<210> SEQ ID NO 834
<211> LENGTH: 21
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 834
tatgctaaga ttttgcgtag c                                             21

<210> SEQ ID NO 835
<211> LENGTH: 21
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 835
tatgctaaga ttttgcgtag t                                             21

<210> SEQ ID NO 836
<211> LENGTH: 30
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 836
acgttggatg ctactccacc tcaatcacac                                    30

<210> SEQ ID NO 837
<211> LENGTH: 18
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 837
ctcaatcaca ctactccc                                          18

<210> SEQ ID NO 838
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 838
ctcaatcaca ctactcccc                                         19

<210> SEQ ID NO 839
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 839
ctcaatcaca ctactccct                                         19

<210> SEQ ID NO 840
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 840
acgttggatg aggccatcaa tttcatcaca                             30

<210> SEQ ID NO 841
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 841
atcaatttca tcacaacaat tat                                    23

<210> SEQ ID NO 842
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 842
atcaatttca tcacaacaat tatc                                   24

<210> SEQ ID NO 843
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 843
atcaatttca tcacaacaat tatt                                   24

<210> SEQ ID NO 844
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 844
acgttggatg ccggcgtcaa agtatttagc                                      30

<210> SEQ ID NO 845
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 845
agtatttagc tgactcgc                                                   18

<210> SEQ ID NO 846
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 846
agtatttagc tgactcgcc                                                  19

<210> SEQ ID NO 847
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 847
agtatttagc tgactcgct                                                  19

<210> SEQ ID NO 848
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 848
acgttggatg gcctaatgtg gggacagc                                        28

<210> SEQ ID NO 849
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 849
gggacagctc atgagtg                                                    17

<210> SEQ ID NO 850
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 850
gggacagctc atgagtgc                                                    18

<210> SEQ ID NO 851
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 851
gggacagctc atgagtgt                                                    18

<210> SEQ ID NO 852
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 852
acgttggatg cttcattcat tgcccccaca                                       30

<210> SEQ ID NO 853
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 853
gcccccacaa tcctagg                                                     17

<210> SEQ ID NO 854
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 854
gcccccacaa tcctaggc                                                    18

<210> SEQ ID NO 855
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 855
gcccccacaa tcctaggt                                                    18

```
<210> SEQ ID NO 856
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 856
acgttggatg cgccttaatc caagcctac                                         29

<210> SEQ ID NO 857
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 857
atccaagcct acgtttt                                                      17

<210> SEQ ID NO 858
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 858
atccaagcct acgttttc                                                     18

<210> SEQ ID NO 859
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 859
atccaagcct acgttttt                                                     18

<210> SEQ ID NO 860
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 860
acgttggatg gggatatagg gtcgaagccg                                        30

<210> SEQ ID NO 861
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 861
atatagggtc gaagccgca                                                    19

<210> SEQ ID NO 862
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 862
atatagggtc gaagccgcac                                               20

<210> SEQ ID NO 863
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 863
atatagggtc gaagccgcat                                               20

<210> SEQ ID NO 864
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 864
tgatctaaaa cactctttac gccggtttct attgacttgg gttaatcgtg tga          53

<210> SEQ ID NO 865
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 865
aaaacactct ttacgccgg                                                19

<210> SEQ ID NO 866
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 866
tgatctaaaa cactctttat gccggtttct attgacttgg gttaatcgtg tga          53

<210> SEQ ID NO 867
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 867
aaaacactct ttacgccgg                                                19

<210> SEQ ID NO 868
<211> LENGTH: 53
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 868
tcacacgatt aacccaagtc aatagaagcc ggcgtaaaga gtgttttaga tca        53

<210> SEQ ID NO 869
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 869
ccggcgtaaa gagtgtttt                                              19

<210> SEQ ID NO 870
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 870
ctacaatctt cctaggaaca acatataacg cactctcccc tgaactctac acaa       54

<210> SEQ ID NO 871
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 871
acgcactctc ccctgaa                                                17

<210> SEQ ID NO 872
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 872
ctacaatctt cctaggaaca acatatgacg cactctcccc tgaactctac acaa       54

<210> SEQ ID NO 873
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 873
acgcactctc ccctgaa                                                17

<210> SEQ ID NO 874
<211> LENGTH: 54
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 874
cagttgaggt ggattaaacc aaacccaact acgcaaaatc ttagcatact cctc          54

<210> SEQ ID NO 875
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 875
ctacgcaaaa tcttagcata                                                20

<210> SEQ ID NO 876
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 876
cagttgaggt ggattaaacc aaacccagct acgcaaaatc ttagcatact cctc          54

<210> SEQ ID NO 877
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 877
ctacgcaaaa tcttagcata                                                20

<210> SEQ ID NO 878
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 878
ctactccacc tcaatcacac tactccctat atctaacaac gtaaaaataa aatg          54

<210> SEQ ID NO 879
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 879
ctcaatcaca ctactccc                                                  18

<210> SEQ ID NO 880
<211> LENGTH: 54
<212> TYPE: DNA
<213> ORGANISM: Artificial Sequence
```

<220> FEATURE:
<223> OTHER INFORMATION: Description of Artificial Sequence: Synthetic
      oligonucleotide

<400> SEQUENCE: 880
ctactccacc tcaatcacac tactccccat atctaacaac gtaaaaataa aatg          54

<210> SEQ ID NO 881
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 881
ctcaatcaca ctactccc                                                  18

<210> SEQ ID NO 882
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 882
gccatcaatt tcatcacaac aattattaat ataaaacccc ctgccataac cc            52

<210> SEQ ID NO 883
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 883
atcaatttca tcacaacaat tat                                            23

<210> SEQ ID NO 884
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 884
gccatcaatt tcatcacaac aattatcaat ataaaacccc ctgccataac cc            52

<210> SEQ ID NO 885
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 885
atcaatttca tcacaacaat tat                                            23

<210> SEQ ID NO 886
<211> LENGTH: 54
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 886
ccggcgtcaa agtatttagc tgactcgcca cactccacgg aagcaatatg aaat          54

<210> SEQ ID NO 887
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 887
agtatttagc tgactcgc                                                  18

<210> SEQ ID NO 888
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 888
ccggcgtcaa agtatttagc tgactcgcta cactccacgg aagcaatatg aaat          54

<210> SEQ ID NO 889
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 889
agtatttagc tgactcgc                                                  18

<210> SEQ ID NO 890
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 890
ccggcgtcaa agtatttagc tgactcgcca cactccacgg aagcaatatg aaat          54

<210> SEQ ID NO 891
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 891
agtatttagc tgactcgc                                                  18

<210> SEQ ID NO 892
<211> LENGTH: 53
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 892
taataattac atcacaagac gtcttacact catgagctgt ccccacatta ggc    53

<210> SEQ ID NO 893
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 893
cactcatgag ctgtccc    17

<210> SEQ ID NO 894
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 894
gcctaatgtg gggacagctc atgagtgtaa gacgtcttgt gatgtaatta tta    53

<210> SEQ ID NO 895
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 895
gggacagctc atgagtg    17

<210> SEQ ID NO 896
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 896
taataattac atcacaagac gtcttgcact catgagctgt ccccacatta ggc    53

<210> SEQ ID NO 897
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 897
cactcatgag ctgtccc    17

<210> SEQ ID NO 898
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 898
cttcattcat tgcccccaca atcctaggcc tacccgccgc agtactgatc attc        54

<210> SEQ ID NO 899
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 899
gcccccacaa tcctagg                                                 17

<210> SEQ ID NO 900
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 900
cttcattcat tgcccccaca atcctaggtc tgcccgccgc agtactgatc attc        54

<210> SEQ ID NO 901
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 901
gcccccacaa tcctagg                                                 17

<210> SEQ ID NO 902
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 902
cttcattcat tgcccccaca atcctaggcc tacccgccgc agtactgatc attc        54

<210> SEQ ID NO 903
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 903
gcccccacaa tcctagg                                                 17

<210> SEQ ID NO 904
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 904
ctgtcgcctt aatccaagcc tacgtttta cacttctagt aagcctctac ctgc     54

<210> SEQ ID NO 905
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 905
atccaagcct acgtttt     17

<210> SEQ ID NO 906
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 906
ctgtcgcctt aatccaagcc tacgttttca cacttctagt aagcctctac ctgc     54

<210> SEQ ID NO 907
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 907
atccaagcct acgtttt     17

<210> SEQ ID NO 908
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 908
tacatagaaa aatccacccc ttacgaatgc ggcttcgacc ctatatcccc cgc     53

<210> SEQ ID NO 909
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 909
tgcggcttcg accctatat     19

<210> SEQ ID NO 910
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 910

```
tacatagaaa aatccacccc ttacgagtgc ggcttcgacc ctatatcccc cgc         53
```

<210> SEQ ID NO 911
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 911

```
tgcggcttcg accctatat                                              19
```

<210> SEQ ID NO 912
<211> LENGTH: 75
<212> TYPE: DNA
<213> ORGANISM: Pan troglodytes

<400> SEQUENCE: 912

```
gatcacaggt ctatcaccct attaaccagt cacgggagcc ttccatgcat ttggtatttt  60
cgtctggggg gtgtg                                                  75
```

<210> SEQ ID NO 913
<211> LENGTH: 75
<212> TYPE: DNA
<213> ORGANISM: Homo sapiens

<400> SEQUENCE: 913

```
gatcacaggt ctatcaccct attaaccact cacgggagct ctccatgcat ttggtatttt  60
cgtctggggg gtatg                                                  75
```

<210> SEQ ID NO 914
<211> LENGTH: 75
<212> TYPE: DNA
<213> ORGANISM: Pan troglodytes

<400> SEQUENCE: 914

```
cacgcgatag cattgcgaaa cgctggcccc ggagcaccct atgtcgcagt atctgtcttt  60
gattcctgcc ccatt                                                  75
```

<210> SEQ ID NO 915
<211> LENGTH: 75
<212> TYPE: DNA
<213> ORGANISM: Homo sapiens

<400> SEQUENCE: 915

```
cacgcgatag cattgcgaga cgctggagcc ggagcaccct atgtcgcagt atctgtcttt  60
gattcctgcc tcatc                                                  75
```

<210> SEQ ID NO 916
<211> LENGTH: 75
<212> TYPE: DNA
<213> ORGANISM: Pan troglodytes

<400> SEQUENCE: 916

```
gtattattta tcgcacctac gttcaatatt acgacctagc atacctacta aagtgtgttg  60
attaattaat gcttg                                                  75
```

<210> SEQ ID NO 917
<211> LENGTH: 75

```
<212> TYPE: DNA
<213> ORGANISM: Homo sapiens

<400> SEQUENCE: 917
ctattattta tcgcacctac gttcaatatt acaggcgaac atacttacta aagtgtgtta    60
attaattaat gcttg                                                    75

<210> SEQ ID NO 918
<211> LENGTH: 75
<212> TYPE: DNA
<213> ORGANISM: Homo sapiens

<400> SEQUENCE: 918
taggacataa taataacaat tgaatgtctg cacagccact ttccacacag acatcataac    60
aaaaaatttc cacca                                                    75

<210> SEQ ID NO 919
<211> LENGTH: 75
<212> TYPE: DNA
<213> ORGANISM: Pan troglodytes

<400> SEQUENCE: 919
cacaaacccc cccttccccc cggccacagc actcaaacaa atctctgcca aaccccaaaa    60
acaaagaacc cagac                                                    75

<210> SEQ ID NO 920
<211> LENGTH: 75
<212> TYPE: DNA
<213> ORGANISM: Homo sapiens

<400> SEQUENCE: 920
aaccccccct cccccgcttc tggccacagc acttaaacac atctctgcca aaccccaaaa    60
acaaagaacc ctaac                                                    75

<210> SEQ ID NO 921
<211> LENGTH: 75
<212> TYPE: DNA
<213> ORGANISM: Pan troglodytes

<400> SEQUENCE: 921
gccagcctag ccagacttca aatttcatct ttaggcggta tgcactttta acagtcaccc    60
ctcaattaac atgcc                                                    75

<210> SEQ ID NO 922
<211> LENGTH: 75
<212> TYPE: DNA
<213> ORGANISM: Homo sapiens

<400> SEQUENCE: 922
accagcctaa ccagatttca aattttatct tttggcggta tgcactttta acagtcaccc    60
cccaactaac acatt                                                    75

<210> SEQ ID NO 923
<211> LENGTH: 75
<212> TYPE: DNA
<213> ORGANISM: Homo sapiens

<400> SEQUENCE: 923
attttcccct cccactccca tactactaat ctcatcaata caaccccgc ccatcctacc     60
```

```
cagcacacac acacc                                                          75

<210> SEQ ID NO 924
<211> LENGTH: 75
<212> TYPE: DNA
<213> ORGANISM: Homo sapiens

<400> SEQUENCE: 924
gctgctaacc ccatacccg aaccaaccaa accccaaaga caccccccac agtttatgta          60
gcttacctcc tcaaa                                                          75

<210> SEQ ID NO 925
<211> LENGTH: 75
<212> TYPE: DNA
<213> ORGANISM: Pan troglodytes

<400> SEQUENCE: 925
gcaatacact gaaatgttt cgacgggttt acatcacccc ataaacaaac aggtttggtc          60
ctagcctttc tatta                                                          75

<210> SEQ ID NO 926
<211> LENGTH: 75
<212> TYPE: DNA
<213> ORGANISM: Homo sapiens

<400> SEQUENCE: 926
gcaatacact gaaatgttt agacgggctc acatcacccc ataaacaaat aggtttggtc          60
ctagcctttc tatta                                                          75

<210> SEQ ID NO 927
<211> LENGTH: 75
<212> TYPE: DNA
<213> ORGANISM: Homo sapiens

<400> SEQUENCE: 927
gctcttagta agattacaca tgcaagcatc cccgttccag tgagttcacc ctctaaatca         60
ccacgatcaa aagga                                                          75

<210> SEQ ID NO 928
<211> LENGTH: 75
<212> TYPE: DNA
<213> ORGANISM: Pan troglodytes

<400> SEQUENCE: 928
acaagtatca agcacgcagc aatgcagctc aaaacgctta gcctagccac accccacgg          60 gagacagcag tgata                                                          75

<210> SEQ ID NO 929
<211> LENGTH: 75
<212> TYPE: DNA
<213> ORGANISM: Homo sapiens

<400> SEQUENCE: 929
acaagcatca agcacgcagc aatgcagctc aaaacgctta gcctagccac accccacgg          60 gaaacagcag tgatt                                                          75

<210> SEQ ID NO 930
<211> LENGTH: 75
<212> TYPE: DNA
<213> ORGANISM: Pan troglodytes
```

<400> SEQUENCE: 930
aacctttagc aataaacgaa agtttaacta agccatacta acctcagggt tggtcaattt    60
cgtgctagcc accgc                                                    75

<210> SEQ ID NO 931
<211> LENGTH: 75
<212> TYPE: DNA
<213> ORGANISM: Homo sapiens

<400> SEQUENCE: 931
aacctttagc aataaacgaa agtttaacta agctatacta accccagggt tggtcaattt    60
cgtgccagcc accgc                                                    75

<210> SEQ ID NO 932
<211> LENGTH: 75
<212> TYPE: DNA
<213> ORGANISM: Pan troglodytes

<400> SEQUENCE: 932
ggtcatacga ttaacccaag tcaatagaaa ccggcgtaaa gagtgtttta gatcaccccc    60
ccataaagct aaaat                                                    75

<210> SEQ ID NO 933
<211> LENGTH: 75
<212> TYPE: DNA
<213> ORGANISM: Homo sapiens

<400> SEQUENCE: 933
ggtcacacga ttaacccaag tcaatagaag ccggcgtaaa gagtgtttta gatcaccccc    60
tccccaataa agcta                                                    75

<210> SEQ ID NO 934
<211> LENGTH: 75
<212> TYPE: DNA
<213> ORGANISM: Pan troglodytes

<400> SEQUENCE: 934
aaattcacct gagttgtaaa aaactccagc tgatacaaaa taaactacga aagtggcttt    60
aacacatctg aatac                                                    75

<210> SEQ ID NO 935
<211> LENGTH: 75
<212> TYPE: DNA
<213> ORGANISM: Homo sapiens

<400> SEQUENCE: 935
aaactcacct gagttgtaaa aaactccagt tgacacaaaa tagactacga aagtggcttt    60
aacatatctg aacac                                                    75

<210> SEQ ID NO 936
<211> LENGTH: 75
<212> TYPE: DNA
<213> ORGANISM: Pan troglodytes

<400> SEQUENCE: 936
acaatagcta agacccaaac tgggattaga taccccacta tgcttagccc taaacttcaa    60
cagttaaatt aacaa                                                    75

```
<210> SEQ ID NO 937
<211> LENGTH: 75
<212> TYPE: DNA
<213> ORGANISM: Homo sapiens

<400> SEQUENCE: 937
acaatagcta agacccaaac tgggattaga taccccacta tgcttagccc taaacctcaa      60
cagttaaatc aacaa                                                      75

<210> SEQ ID NO 938
<211> LENGTH: 75
<212> TYPE: DNA
<213> ORGANISM: Pan troglodytes

<400> SEQUENCE: 938
aactgctcgc cagaacacta cgagccacag cttaaaactc aaaggacctg gcggtgcttc      60
atatccctct agagg                                                      75

<210> SEQ ID NO 939
<211> LENGTH: 75
<212> TYPE: DNA
<213> ORGANISM: Homo sapiens

<400> SEQUENCE: 939
aactgctcgc cagaacacta cgagccacag cttaaaactc aaaggacctg gcggtgcttc      60
atatccctct agagg                                                      75

<210> SEQ ID NO 940
<211> LENGTH: 75
<212> TYPE: DNA
<213> ORGANISM: Pan troglodytes

<400> SEQUENCE: 940
agcctgttct gtaatcgata aaccccgatc aacctcaccg cctcttgctc agcctatata      60
ccgccatctt cagca                                                      75

<210> SEQ ID NO 941
<211> LENGTH: 75
<212> TYPE: DNA
<213> ORGANISM: Homo sapiens

<400> SEQUENCE: 941
agcctgttct gtaatcgata aaccccgatc aacctcacca cctcttgctc agcctatata      60
ccgccatctt cagca                                                      75

<210> SEQ ID NO 942
<211> LENGTH: 75
<212> TYPE: DNA
<213> ORGANISM: Pan troglodytes

<400> SEQUENCE: 942
aaccctgatg aaggttacaa agtaagcaca agtacccacg taaagacgtt aggtcaaggt      60
gtagcctatg aggtg                                                      75

<210> SEQ ID NO 943
<211> LENGTH: 75
<212> TYPE: DNA
<213> ORGANISM: Homo sapiens

<400> SEQUENCE: 943
```

-continued aaccctgatg aaggctacaa agtaagcgca agtacccacg taaagacgtt aggtcaaggt    60
gtagcccatg aggtg                                                    75

<210> SEQ ID NO 944
<211> LENGTH: 75
<212> TYPE: DNA
<213> ORGANISM: Pan troglodytes

<400> SEQUENCE: 944
gcaagaaatg ggctacattt tctaccccag aaaattacga taaccccttat gaaacctaag   60 ggtcaaaggt ggatt                                                    75

<210> SEQ ID NO 945
<211> LENGTH: 75
<212> TYPE: DNA
<213> ORGANISM: Homo sapiens

<400> SEQUENCE: 945
gcaagaaatg ggctacattt tctaccccag aaaactacga tagcccttat gaaacttaag    60
ggtcgaaggt ggatt                                                    75

<210> SEQ ID NO 946
<211> LENGTH: 75
<212> TYPE: DNA
<213> ORGANISM: Pan troglodytes

<400> SEQUENCE: 946
tagcagtaaa ctaagagtag agtgcttagt tgaacagggc cctgaagcgc gtacacaccg    60
cccgtcaccc tcctc                                                    75

<210> SEQ ID NO 947
<211> LENGTH: 75
<212> TYPE: DNA
<213> ORGANISM: Homo sapiens

<400> SEQUENCE: 947
tagcagtaaa ctaagagtag agtgcttagt tgaacagggc cctgaagcgc gtacacaccg    60
cccgtcaccc tcctc                                                    75

<210> SEQ ID NO 948
<211> LENGTH: 75
<212> TYPE: DNA
<213> ORGANISM: Homo sapiens

<400> SEQUENCE: 948
aagtatactt caaggacat ttaactaaaa cccctacgca tttatataga ggagacaagt     60
cgtaacatgg taagt                                                    75

<210> SEQ ID NO 949
<211> LENGTH: 75
<212> TYPE: DNA
<213> ORGANISM: Pan troglodytes

<400> SEQUENCE: 949
gtactggaaa gtgcacttgg acgaaccaga gtgtagctta acataaagca cccaacttac    60
acttaggaga tttca                                                    75

<210> SEQ ID NO 950

```
<211> LENGTH: 75
<212> TYPE: DNA
<213> ORGANISM: Homo sapiens

<400> SEQUENCE: 950
gtactggaaa gtgcacttgg acgaaccaga gtgtagctta acacaaagca cccaacttac      60
acttaggaga tttca                                                      75

<210> SEQ ID NO 951
<211> LENGTH: 75
<212> TYPE: DNA
<213> ORGANISM: Pan troglodytes

<400> SEQUENCE: 951
actcaacttg accactctga gccaaaccta gccccaaacc ccctccaccc tactaccaaa      60
caaccttaac caaac                                                      75

<210> SEQ ID NO 952
<211> LENGTH: 75
<212> TYPE: DNA
<213> ORGANISM: Homo sapiens

<400> SEQUENCE: 952
acttaacttg accgctctga gctaaaccta gccccaaacc cactccacct tactaccaga      60
caaccttagc caaac                                                      75

<210> SEQ ID NO 953
<211> LENGTH: 75
<212> TYPE: DNA
<213> ORGANISM: Pan troglodytes

<400> SEQUENCE: 953
catttaccca aataaagtat aggcgataga aattgtaaac cggcgcaata gacatagtac      60
cgcaagggaa agatg                                                      75

<210> SEQ ID NO 954
<211> LENGTH: 75
<212> TYPE: DNA
<213> ORGANISM: Homo sapiens

<400> SEQUENCE: 954
catttaccca aataaagtat aggcgataga aattgaaacc tggcgcaata gatatagtac      60
cgcaagggaa agatg                                                      75

<210> SEQ ID NO 955
<211> LENGTH: 75
<212> TYPE: DNA
<213> ORGANISM: Pan troglodytes

<400> SEQUENCE: 955
aaaaattata cccaagcata atacagcaag gactaacccc tgtacctttt gcataatgaa      60
ttaactagaa ataac                                                      75

<210> SEQ ID NO 956
<211> LENGTH: 75
<212> TYPE: DNA
<213> ORGANISM: Homo sapiens

<400> SEQUENCE: 956
aaaaattata accaagcata atatagcaag gactaacccc tatacctttct gcataatgaa      60
```

```
ttaactagaa ataac                                                       75

<210> SEQ ID NO 957
<211> LENGTH: 75
<212> TYPE: DNA
<213> ORGANISM: Pan troglodytes

<400> SEQUENCE: 957
tttgcaaaga gaaccaaagc taagacccccc gaaaccagac gagctaccta agaacagcta    60
aaagagcaca cccgt                                                       75

<210> SEQ ID NO 958
<211> LENGTH: 75
<212> TYPE: DNA
<213> ORGANISM: Homo sapiens

<400> SEQUENCE: 958
tttgcaagga gagccaaagc taagacccccc gaaaccagac gagctaccta agaacagcta    60
aaagagcaca cccgt                                                       75

<210> SEQ ID NO 959
<211> LENGTH: 75
<212> TYPE: DNA
<213> ORGANISM: Pan troglodytes

<400> SEQUENCE: 959
ctatgtagca aaatagtggg aagatttata ggtagaggcg acaaacctac cgagcctggt     60
gatagctggt tgtcc                                                       75

<210> SEQ ID NO 960
<211> LENGTH: 75
<212> TYPE: DNA
<213> ORGANISM: Homo sapiens

<400> SEQUENCE: 960
ctatgtagca aaatagtggg aagatttata ggtagaggcg acaaacctac cgagcctggt     60
gatagctggt tgtcc                                                       75

<210> SEQ ID NO 961
<211> LENGTH: 75
<212> TYPE: DNA
<213> ORGANISM: Pan troglodytes

<400> SEQUENCE: 961
aagatagaat cttagttcaa ctttaaattt acctacagaa ccctctaaat cccttgtaa      60 acttaactgt tagtc                                                       75

<210> SEQ ID NO 962
<211> LENGTH: 75
<212> TYPE: DNA
<213> ORGANISM: Homo sapiens

<400> SEQUENCE: 962
aagatagaat cttagttcaa ctttaaattt gcccacagaa ccctctaaat cccttgtaa      60 atttaactgt tagtc                                                       75

<210> SEQ ID NO 963
<211> LENGTH: 75
<212> TYPE: DNA
```

<213> ORGANISM: Pan troglodytes

<400> SEQUENCE: 963
caaagaggaa cagctctta gacactagga aaaaaccttg taaagagagt aaaaaattta    60
acacccatag taggc    75

<210> SEQ ID NO 964
<211> LENGTH: 75
<212> TYPE: DNA
<213> ORGANISM: Homo sapiens

<400> SEQUENCE: 964
caaagaggaa cagctctttg gacactagga aaaaaccttg tagagagagt aaaaaattta    60
acacccatag taggc    75

<210> SEQ ID NO 965
<211> LENGTH: 75
<212> TYPE: DNA
<213> ORGANISM: Pan troglodytes

<400> SEQUENCE: 965
ctaaaagcag ccaccaatta agaaagcgtt caagctcaac acccacaacc ttaaagatcc    60
caaacataca accga    75

<210> SEQ ID NO 966
<211> LENGTH: 75
<212> TYPE: DNA
<213> ORGANISM: Homo sapiens

<400> SEQUENCE: 966
ctaaaagcag ccaccaatta agaaagcgtt caagctcaac acccactacc taaaaaatcc    60
caaacatata actga    75

<210> SEQ ID NO 967
<211> LENGTH: 75
<212> TYPE: DNA
<213> ORGANISM: Pan troglodytes

<400> SEQUENCE: 967
actccttaca cccaattgga ccaatctatt accccataga agaactaatg ttagtataag    60
taacatgaaa acatt    75

<210> SEQ ID NO 968
<211> LENGTH: 75
<212> TYPE: DNA
<213> ORGANISM: Homo sapiens

<400> SEQUENCE: 968
actcctcaca cccaattgga ccaatctatc accctataga agaactaatg ttagtataag    60
taacatgaaa acatt    75

<210> SEQ ID NO 969
<211> LENGTH: 75
<212> TYPE: DNA
<213> ORGANISM: Pan troglodytes

<400> SEQUENCE: 969
ctcctccgca taagcctaca tcagaccaaa atattaaact gacaattaac agcctaatat    60
ctacaatcaa ccaac    75

<210> SEQ ID NO 970
<211> LENGTH: 75
<212> TYPE: DNA
<213> ORGANISM: Homo sapiens

<400> SEQUENCE: 970
ctcctccgca taagcctgcg tcagattaaa acactgaact gacaattaac agcccaatat    60
ctacaatcaa ccaac    75

<210> SEQ ID NO 971
<211> LENGTH: 75
<212> TYPE: DNA
<213> ORGANISM: Pan troglodytes

<400> SEQUENCE: 971
aagccattat taccccgct gttaacccaa cacaggcatg cccacaagga aaggttaaaa    60
aaagtaaaag gaact    75

<210> SEQ ID NO 972
<211> LENGTH: 75
<212> TYPE: DNA
<213> ORGANISM: Homo sapiens

<400> SEQUENCE: 972
aagtcattat taccctcact gtcaacccaa cacaggcatg ctcataagga aaggttaaaa    60
aaagtaaaag gaact    75

<210> SEQ ID NO 973
<211> LENGTH: 75
<212> TYPE: DNA
<213> ORGANISM: Pan troglodytes

<400> SEQUENCE: 973
cggcaaatct taccccgcct gtttaccaaa aacatcacct ctagcattac cagtattaga    60
ggcaccgcct gcccg    75

<210> SEQ ID NO 974
<211> LENGTH: 75
<212> TYPE: DNA
<213> ORGANISM: Homo sapiens

<400> SEQUENCE: 974
cggcaaatct taccccgcct gtttaccaaa aacatcacct ctagcatcac cagtattaga    60
ggcaccgcct gccca    75

<210> SEQ ID NO 975
<211> LENGTH: 75
<212> TYPE: DNA
<213> ORGANISM: Pan troglodytes

<400> SEQUENCE: 975
gtgacatatg tttaacggcc gcggtaccct aaccgtgcaa aggtagcata atcacttgtt    60 ccttaaaatag ggact    75

<210> SEQ ID NO 976
<211> LENGTH: 75
<212> TYPE: DNA
<213> ORGANISM: Homo sapiens -continued

<400> SEQUENCE: 976
gtgacacatg tttaacggcc gcggtaccct aaccgtgcaa aggtagcata atcacttgtt    60
ccttaaatag ggacc                                                    75

<210> SEQ ID NO 977
<211> LENGTH: 75
<212> TYPE: DNA
<213> ORGANISM: Pan troglodytes

<400> SEQUENCE: 977
tgtatgaatg gctccacgag ggtttagctg tctcttactt tcaaccagtg aaattgacct    60
acccgtgaag aggcg                                                    75

<210> SEQ ID NO 978
<211> LENGTH: 75
<212> TYPE: DNA
<213> ORGANISM: Homo sapiens

<400> SEQUENCE: 978
tgtatgaatg gctccacgag ggttcagctg tctcttactt ttaaccagtg aaattgacct    60
gcccgtgaag aggcg                                                    75

<210> SEQ ID NO 979
<211> LENGTH: 75
<212> TYPE: DNA
<213> ORGANISM: Pan troglodytes

<400> SEQUENCE: 979
ggcataacat aacaagacga gaagacccta tggagcttta attcattaat gcaaacaata    60
cttaacaaac ctaca                                                    75

<210> SEQ ID NO 980
<211> LENGTH: 75
<212> TYPE: DNA
<213> ORGANISM: Homo sapiens

<400> SEQUENCE: 980
ggcataacac agcaagacga gaagacccta tggagcttta atttattaat gcaaacagta    60
cctaacaaac ccaca                                                    75

<210> SEQ ID NO 981
<211> LENGTH: 75
<212> TYPE: DNA
<213> ORGANISM: Pan troglodytes

<400> SEQUENCE: 981
ggtcctaaac tattaaacct gcattaaaaa tttcggttgg ggcgacctcg agcacaacc     60 caacctccga gcaat                                                    75

<210> SEQ ID NO 982
<211> LENGTH: 75
<212> TYPE: DNA
<213> ORGANISM: Homo sapiens

<400> SEQUENCE: 982
ggtcctaaac taccaaacct gcattaaaaa tttcggttgg ggcgacctcg agcagaacc     60 caacctccga gcagt                                                    75

```
<210> SEQ ID NO 983
<211> LENGTH: 75
<212> TYPE: DNA
<213> ORGANISM: Pan troglodytes

<400> SEQUENCE: 983
acatgctaag acctcaccag tcaaagcgaa ttactacatc caattgatcc aatgacttga    60
ccaacggaac aagtt                                                    75

<210> SEQ ID NO 984
<211> LENGTH: 75
<212> TYPE: DNA
<213> ORGANISM: Homo sapiens

<400> SEQUENCE: 984
acatgctaag acttcaccag tcaaagcgaa ctactatact caattgatcc ataacttga     60 ccaacggaac aagtt                                                    75

<210> SEQ ID NO 985
<211> LENGTH: 75
<212> TYPE: DNA
<213> ORGANISM: Pan troglodytes

<400> SEQUENCE: 985
accctaggga taacagcgca atcctattcc agagtccata tcaacaatag ggtttacgac    60
ctcgatgttg gatca                                                    75

<210> SEQ ID NO 986
<211> LENGTH: 75
<212> TYPE: DNA
<213> ORGANISM: Homo sapiens

<400> SEQUENCE: 986
accctaggga taacagcgca atcctattct agagtccata tcaacaatag ggtttacgac    60
ctcgatgttg gatca                                                    75

<210> SEQ ID NO 987
<211> LENGTH: 75
<212> TYPE: DNA
<213> ORGANISM: Pan troglodytes

<400> SEQUENCE: 987
ggacatcccg atggtgcagc cgctattaaa ggttcgtttg ttcaacgatt aaagtcctac    60
gtgatctgag ttcag                                                    75

<210> SEQ ID NO 988
<211> LENGTH: 75
<212> TYPE: DNA
<213> ORGANISM: Homo sapiens

<400> SEQUENCE: 988
ggacatcccg atggtgcagc cgctattaaa ggttcgtttg ttcaacgatt aaagtcctac    60
gtgatctgag ttcag                                                    75

<210> SEQ ID NO 989
<211> LENGTH: 75
<212> TYPE: DNA
<213> ORGANISM: Homo sapiens
<220> FEATURE:
<221> NAME/KEY: modified_base
<222> LOCATION: (32)..(32)
```

<223> OTHER INFORMATION: a, c, t, g, unknown or other

<400> SEQUENCE: 989

```
accggagtaa tccaggtcgg tttctatcta cnttcaaatt cctccctgta cgaaaggaca    60
agagaaataa ggcct                                                    75
```

<210> SEQ ID NO 990
<211> LENGTH: 75
<212> TYPE: DNA
<213> ORGANISM: Pan troglodytes

<400> SEQUENCE: 990

```
acttcacaaa gcgccttccc caataaatga tattatctca atttagcgcc atgccaacac    60
ccactcaaga acaga                                                    75
```

<210> SEQ ID NO 991
<211> LENGTH: 75
<212> TYPE: DNA
<213> ORGANISM: Homo sapiens

<400> SEQUENCE: 991

```
acttcacaaa gcgccttccc ccgtaaatga tatcatctca acttagtatt atacccacac    60
ccacccaaga acagg                                                    75
```

<210> SEQ ID NO 992
<211> LENGTH: 75
<212> TYPE: DNA
<213> ORGANISM: Pan troglodytes

<400> SEQUENCE: 992

```
gtttgttaag atggcagagc ccggtaattg cataaaactt aaaactttac aatcagaggt    60
tcaattcctc ttctt                                                    75
```

<210> SEQ ID NO 993
<211> LENGTH: 75
<212> TYPE: DNA
<213> ORGANISM: Homo sapiens

<400> SEQUENCE: 993

```
gtttgttaag atggcagagc ccggtaatcg cataaaactt aaaactttac agtcagaggt    60
tcaattcctc ttctt                                                    75
```

<210> SEQ ID NO 994
<211> LENGTH: 75
<212> TYPE: DNA
<213> ORGANISM: Pan troglodytes

<400> SEQUENCE: 994

```
gacaacacac ccatgaccaa cctcctactc ctcattgtac ccatcctaat cgcaatagca    60
ttcctaatgc taacc                                                    75
```

<210> SEQ ID NO 995
<211> LENGTH: 75
<212> TYPE: DNA
<213> ORGANISM: Homo sapiens

<400> SEQUENCE: 995

```
aacaacatac ccatggccaa cctcctactc ctcattgtac ccattctaat cgcaatggca    60
ttcctaatgc ttacc                                                    75
```

<210> SEQ ID NO 996
<211> LENGTH: 75
<212> TYPE: DNA
<213> ORGANISM: Pan troglodytes

<400> SEQUENCE: 996
gaacgaaaaa ttctaggcta catacaacta cgcaaaggtc ccaacattgt aggtccttac    60
gggctattac agccc    75

<210> SEQ ID NO 997
<211> LENGTH: 75
<212> TYPE: DNA
<213> ORGANISM: Homo sapiens

<400> SEQUENCE: 997
gaacgaaaaa ttctaggcta tatacaacta cgcaaaggcc ccaacgttgt aggcccctac    60
gggctactac aaccc    75

<210> SEQ ID NO 998
<211> LENGTH: 75
<212> TYPE: DNA
<213> ORGANISM: Pan troglodytes

<400> SEQUENCE: 998
ttcgctgacg ccataaaact cttcactaaa gaacccttaa aaccctccac ttcaaccatt    60
accctctaca tcacc    75

<210> SEQ ID NO 999
<211> LENGTH: 75
<212> TYPE: DNA
<213> ORGANISM: Homo sapiens

<400> SEQUENCE: 999
ttcgctgacg ccataaaact cttcaccaaa gagcccctaa aacccgccac atctaccatc    60
accctctaca tcacc    75

<210> SEQ ID NO 1000
<211> LENGTH: 75
<212> TYPE: DNA
<213> ORGANISM: Pan troglodytes

<400> SEQUENCE: 1000
gccccaaccc tagccctcac cattgccctc ttactatgaa ccccctccc catacccaac    60 cccctagtca atctc    75

<210> SEQ ID NO 1001
<211> LENGTH: 75
<212> TYPE: DNA
<213> ORGANISM: Homo sapiens

<400> SEQUENCE: 1001
gccccgacct tagctctcac catcgctctt ctactatgaa cccccctccc catacccaac    60
cccctggtca acctc    75

<210> SEQ ID NO 1002
<211> LENGTH: 75
<212> TYPE: DNA
<213> ORGANISM: Pan troglodytes

<400> SEQUENCE: 1002
aacttaggcc tcctatttat tctagccacc tccagcctag ccgtttactc aatcctctga    60
tcagggtgag catca                                                    75

<210> SEQ ID NO 1003
<211> LENGTH: 75
<212> TYPE: DNA
<213> ORGANISM: Homo sapiens

<400> SEQUENCE: 1003
aacctaggcc tcctatttat tctagccacc tctagcctag ccgtttactc aatcctctga    60
tcagggtgag catca                                                    75

<210> SEQ ID NO 1004
<211> LENGTH: 75
<212> TYPE: DNA
<213> ORGANISM: Pan troglodytes

<400> SEQUENCE: 1004
aactcgaact acgccttaat cggtgcacta cgagcagtag cccaaacaat ctcatacgaa    60
gtcactctag ccatt                                                    75

<210> SEQ ID NO 1005
<211> LENGTH: 75
<212> TYPE: DNA
<213> ORGANISM: Homo sapiens

<400> SEQUENCE: 1005
aactcaaact acgccctgat cggcgcactg cgagcagtag cccaaacaat ctcatatgaa    60
gtcaccctag ccatc                                                    75

<210> SEQ ID NO 1006
<211> LENGTH: 75
<212> TYPE: DNA
<213> ORGANISM: Pan troglodytes

<400> SEQUENCE: 1006
atcctactgt caacgctact aataagtggc tccttcaatc tctctaccct tgtcacaaca    60
caagagcacc tctga                                                    75

<210> SEQ ID NO 1007
<211> LENGTH: 75
<212> TYPE: DNA
<213> ORGANISM: Homo sapiens

<400> SEQUENCE: 1007
attctactat caacattact aataagtggc tcctttaacc tctccaccct tatcacaaca    60
caagaacacc tctga                                                    75

<210> SEQ ID NO 1008
<211> LENGTH: 75
<212> TYPE: DNA
<213> ORGANISM: Pan troglodytes

<400> SEQUENCE: 1008
ctaatcctgc caacatgacc cctggccata atatgattta tctctacact agcagagacc    60
aaccgaactc ccttc                                                    75

```
<210> SEQ ID NO 1009
<211> LENGTH: 75
<212> TYPE: DNA
<213> ORGANISM: Homo sapiens

<400> SEQUENCE: 1009
ttactcctgc catcatgacc cttggccata atatgattta tctccacact agcagagacc    60
aaccgaaccc ccttc                                                    75

<210> SEQ ID NO 1010
<211> LENGTH: 75
<212> TYPE: DNA
<213> ORGANISM: Pan troglodytes

<400> SEQUENCE: 1010
gaccttactg aaggagaatc tgaactagtc tcaggcttta atatcgagta tgccgcaggc    60 cccttttgccc tattt                                                   75

<210> SEQ ID NO 1011
<211> LENGTH: 75
<212> TYPE: DNA
<213> ORGANISM: Homo sapiens

<400> SEQUENCE: 1011
gaccttgccg aagggagtc cgaactagtc tcaggcttca acatcgaata cgccgcaggc    60
cccttcgccc tattc                                                    75

<210> SEQ ID NO 1012
<211> LENGTH: 75
<212> TYPE: DNA
<213> ORGANISM: Pan troglodytes

<400> SEQUENCE: 1012
ttcatagccg aatacataaa cattattata ataaacaccc tcactgctac aatcttccta    60
ggagcaacat acaat                                                    75

<210> SEQ ID NO 1013
<211> LENGTH: 75
<212> TYPE: DNA
<213> ORGANISM: Homo sapiens

<400> SEQUENCE: 1013
ttcatagccg aatacacaaa cattattata ataaacaccc tcaccactac aatcttccta    60
ggaacaacat atgac                                                    75

<210> SEQ ID NO 1014
<211> LENGTH: 75
<212> TYPE: DNA
<213> ORGANISM: Pan troglodytes

<400> SEQUENCE: 1014
actcactccc ctgaactcta cacgacatat tttgtcacca aagctctact tctaacctcc    60
ctgttcctat gaatt                                                    75

<210> SEQ ID NO 1015
<211> LENGTH: 75
<212> TYPE: DNA
<213> ORGANISM: Homo sapiens

<400> SEQUENCE: 1015
```

```
gcactctccc ctgaactcta cacaacatat tttgtcacca agaccctact tctaacctcc    60
ctgttcttat gaatt                                                    75

<210> SEQ ID NO 1016
<211> LENGTH: 75
<212> TYPE: DNA
<213> ORGANISM: Pan troglodytes

<400> SEQUENCE: 1016
cgaacagcat atccccgatt tcgctacgac cagctcatac acctcctatg aaaaaacttc    60
ctaccactca cccta                                                    75

<210> SEQ ID NO 1017
<211> LENGTH: 75
<212> TYPE: DNA
<213> ORGANISM: Homo sapiens

<400> SEQUENCE: 1017
cgaacagcat accccgatt ccgctacgac caactcatac acctcctatg aaaaaacttc     60
ctaccactca cccta                                                    75

<210> SEQ ID NO 1018
<211> LENGTH: 75
<212> TYPE: DNA
<213> ORGANISM: Pan troglodytes

<400> SEQUENCE: 1018
gcatcactca tgtgatatat ctccataccc actacaatct ccagcatccc ccctcaaacc    60
taagaaatat gtctg                                                    75

<210> SEQ ID NO 1019
<211> LENGTH: 75
<212> TYPE: DNA
<213> ORGANISM: Homo sapiens

<400> SEQUENCE: 1019
gcattactta tatgatatgt ctccataccc attacaatct ccagcattcc ccctcaaacc    60
taagaaatat gtctg                                                    75

<210> SEQ ID NO 1020
<211> LENGTH: 75
<212> TYPE: DNA
<213> ORGANISM: Pan troglodytes

<400> SEQUENCE: 1020
ataaaagaat tactttgata gagtaaataa taggagttca aatcccctta tttctaggac    60
tataagaatc gaact                                                    75

<210> SEQ ID NO 1021
<211> LENGTH: 75
<212> TYPE: DNA
<213> ORGANISM: Homo sapiens

<400> SEQUENCE: 1021
ataaaagagt tactttgata gagtaaataa taggagctta aaccccctta tttctaggac    60
tatgagaatc gaacc                                                    75

<210> SEQ ID NO 1022
<211> LENGTH: 75
```

```
<212> TYPE: DNA
<213> ORGANISM: Pan troglodytes

<400> SEQUENCE: 1022
catccctgag aatccaaaat tctccgtgcc acctatcaca ccccatccta aagtaaggtc    60
agctaaataa gctat                                                    75

<210> SEQ ID NO 1023
<211> LENGTH: 75
<212> TYPE: DNA
<213> ORGANISM: Homo sapiens

<400> SEQUENCE: 1023
catccctgag aatccaaaat tctccgtgcc acctatcaca ccccatccta aagtaaggtc    60
agctaaataa gctat                                                    75

<210> SEQ ID NO 1024
<211> LENGTH: 75
<212> TYPE: DNA
<213> ORGANISM: Pan troglodytes

<400> SEQUENCE: 1024
cgggcccata ccccgaaaat gttggttaca cccttcccgt actaattaat cccctagccc    60
aacccatcat ctact                                                    75

<210> SEQ ID NO 1025
<211> LENGTH: 75
<212> TYPE: DNA
<213> ORGANISM: Homo sapiens

<400> SEQUENCE: 1025
cgggcccata ccccgaaaat gttggttata cccttcccgt actaattaat cccctggccc    60
aacccgtcat ctact                                                    75

<210> SEQ ID NO 1026
<211> LENGTH: 75
<212> TYPE: DNA
<213> ORGANISM: Pan troglodytes

<400> SEQUENCE: 1026
ctaccatcct tacaggcacg ctcattacag cgctaagctc acactgattt ttcacctgag    60
taggcctaga aataa                                                    75

<210> SEQ ID NO 1027
<211> LENGTH: 75
<212> TYPE: DNA
<213> ORGANISM: Homo sapiens

<400> SEQUENCE: 1027
ctaccatctt tgcaggcaca ctcatcacag cgctaagctc gcactgattt tttacctgag    60
taggcctaga aataa                                                    75

<210> SEQ ID NO 1028
<211> LENGTH: 75
<212> TYPE: DNA
<213> ORGANISM: Pan troglodytes

<400> SEQUENCE: 1028
atatactagc ttttatccca atcctaacca aaaaaataag cccccgctcc acagaagccg    60
```
ccatcaaata ctttc 75

<210> SEQ ID NO 1029
<211> LENGTH: 75
<212> TYPE: DNA
<213> ORGANISM: Homo sapiens

<400> SEQUENCE: 1029
acatgctagc ttttattcca gttctaacca aaaaaataaa ccctcgttcc acagaagctg 60
ccatcaagta tttcc 75

<210> SEQ ID NO 1030
<211> LENGTH: 75
<212> TYPE: DNA
<213> ORGANISM: Pan troglodytes

<400> SEQUENCE: 1030
tcacacaagc aactgcgtcc ataattctcc tgatagctat cctctccaac agcatactct 60
ccggacaatg aacca 75

<210> SEQ ID NO 1031
<211> LENGTH: 75
<212> TYPE: DNA
<213> ORGANISM: Homo sapiens

<400> SEQUENCE: 1031
tcacgcaagc aaccgcatcc ataatccttc taatagctat cctcttcaac aatatactct 60
ccggacaatg aacca 75

<210> SEQ ID NO 1032
<211> LENGTH: 75
<212> TYPE: DNA
<213> ORGANISM: Pan troglodytes

<400> SEQUENCE: 1032
taaccaatac taccaatcaa tactcatcat taataattat aatagcaatg gcaataaaac 60
taggaatagc cccct 75

<210> SEQ ID NO 1033
<211> LENGTH: 75
<212> TYPE: DNA
<213> ORGANISM: Homo sapiens

<400> SEQUENCE: 1033
taaccaatac taccaatcaa tactcatcat taataatcat aatagctata gcaataaaac 60
taggaatagc cccct 75

<210> SEQ ID NO 1034
<211> LENGTH: 75
<212> TYPE: DNA
<213> ORGANISM: Pan troglodytes

<400> SEQUENCE: 1034
ttcacttttg agttccagaa gttacccaag gcaccccct aatatccggc ctactcctcc 60
tcacatgaca aaaat 75

<210> SEQ ID NO 1035
<211> LENGTH: 75
<212> TYPE: DNA
<213> ORGANISM: Homo sapiens

```
<400> SEQUENCE: 1035
ttcacttctg agtcccagag gttacccaag gcacccctct gacatccggc ctgcttcttc    60
tcacatgaca aaaac                                                    75

<210> SEQ ID NO 1036
<211> LENGTH: 75
<212> TYPE: DNA
<213> ORGANISM: Pan troglodytes

<400> SEQUENCE: 1036
tagcccctat ttcaattata taccaaatct cctcatcact gaacgtaaac cttctcctca    60 cccttttcaat cttgt                                                   75

<210> SEQ ID NO 1037
<211> LENGTH: 75
<212> TYPE: DNA
<213> ORGANISM: Homo sapiens

<400> SEQUENCE: 1037
tagcccccat ctcaatcata taccaaatct ctccctcact aaacgtaagc cttctcctca    60
ctctctcaat cttat                                                    75

<210> SEQ ID NO 1038
<211> LENGTH: 75
<212> TYPE: DNA
<213> ORGANISM: Pan troglodytes

<400> SEQUENCE: 1038
ccattatagc aggcagctga ggcggactaa accaaaccca actacgcaaa atcctagcat    60
actcctcaat caccc                                                    75

<210> SEQ ID NO 1039
<211> LENGTH: 75
<212> TYPE: DNA
<213> ORGANISM: Homo sapiens

<400> SEQUENCE: 1039
ccatcatagc aggcagttga ggtggattaa accaaaccca gctacgcaaa atcttagcat    60
actcctcaat taccc                                                    75

<210> SEQ ID NO 1040
<211> LENGTH: 75
<212> TYPE: DNA
<213> ORGANISM: Pan troglodytes

<400> SEQUENCE: 1040
acataggctg aataatagca gtcctaccat ataaccctaa cataaccatt cttaatttaa    60
ccatttacat catcc                                                    75

<210> SEQ ID NO 1041
<211> LENGTH: 75
<212> TYPE: DNA
<213> ORGANISM: Homo sapiens

<400> SEQUENCE: 1041
acataggatg aataatagca gttctaccgt acaaccctaa cataaccatt cttaatttaa    60
ctatttatat tatcc                                                    75
```

<210> SEQ ID NO 1042
<211> LENGTH: 75
<212> TYPE: DNA
<213> ORGANISM: Pan troglodytes

<400> SEQUENCE: 1042
taactactac cgcatttctg ctactcaact taaactccag caccacaacc ctactactat    60
ctcgcacctg aaaca                                                    75

<210> SEQ ID NO 1043
<211> LENGTH: 75
<212> TYPE: DNA
<213> ORGANISM: Homo sapiens

<400> SEQUENCE: 1043
taactactac cgcattccta ctactcaact taaactccag caccacgacc ctactactat    60
ctcgcacctg aaaca                                                    75

<210> SEQ ID NO 1044
<211> LENGTH: 75
<212> TYPE: DNA
<213> ORGANISM: Pan troglodytes

<400> SEQUENCE: 1044
agctaacatg attaactccc ctaattccat ccaccctcct ctccctagga ggcctacccc    60
cactaactgg cttct                                                    75

<210> SEQ ID NO 1045
<211> LENGTH: 75
<212> TYPE: DNA
<213> ORGANISM: Homo sapiens

<400> SEQUENCE: 1045
agctaacatg actaacaccc ttaattccat ccaccctcct ctccctagga ggcctgcccc    60
cgctaaccgg ctttt                                                    75

<210> SEQ ID NO 1046
<211> LENGTH: 75
<212> TYPE: DNA
<213> ORGANISM: Pan troglodytes

<400> SEQUENCE: 1046
tacccaaatg agttatcatc gaagaattca caaaaaataa tagcctcatc atccccacca    60
tcatagccat catca                                                    75

<210> SEQ ID NO 1047
<211> LENGTH: 75
<212> TYPE: DNA
<213> ORGANISM: Homo sapiens

<400> SEQUENCE: 1047
tgcccaaatg ggccattatc gaagaattca caaaaaacaa tagcctcatc atccccacca    60
tcatagccac catca                                                    75

<210> SEQ ID NO 1048
<211> LENGTH: 75
<212> TYPE: DNA
<213> ORGANISM: Pan troglodytes

<400> SEQUENCE: 1048

```
ctctccttaa cctctatttc tacctacgcc taatctactc cacctcaatt acactacttc    60
ccatatctaa taacg                                                    75

<210> SEQ ID NO 1049
<211> LENGTH: 75
<212> TYPE: DNA
<213> ORGANISM: Homo sapiens

<400> SEQUENCE: 1049
ccctccttaa cctctacttc tacctacgcc taatctactc cacctcaatc acactactcc    60
ccatatctaa caacg                                                    75

<210> SEQ ID NO 1050
<211> LENGTH: 75
<212> TYPE: DNA
<213> ORGANISM: Pan troglodytes

<400> SEQUENCE: 1050
taaaaataaa atgacaattc gaacatacaa aacccacccc cttcctccct acactcatca    60
cccttaccac actgc                                                    75

<210> SEQ ID NO 1051
<211> LENGTH: 75
<212> TYPE: DNA
<213> ORGANISM: Homo sapiens

<400> SEQUENCE: 1051
taaaaataaa atgacagttt gaacatacaa aacccacccc attcctcccc acactcatcg    60
cccttaccac gctac                                                    75

<210> SEQ ID NO 1052
<211> LENGTH: 75
<212> TYPE: DNA
<213> ORGANISM: Pan troglodytes

<400> SEQUENCE: 1052
ttctacccat ctcccccttc atactaataa tcttatagaa atttaggtta agcacagacc    60
aagagccttc aaagc                                                    75

<210> SEQ ID NO 1053
<211> LENGTH: 75
<212> TYPE: DNA
<213> ORGANISM: Homo sapiens

<400> SEQUENCE: 1053
tcctacctat ctcccctttt atactaataa tcttatagaa atttaggtta aatacagacc    60
aagagccttc aaagc                                                    75

<210> SEQ ID NO 1054
<211> LENGTH: 75
<212> TYPE: DNA
<213> ORGANISM: Pan troglodytes

<400> SEQUENCE: 1054
cctcagcaag ttacaatact taatttctgc aacaactaag gactgcaaaa ccccactctg    60
catcaactga acgca                                                    75

<210> SEQ ID NO 1055
```

```
<211> LENGTH: 75
<212> TYPE: DNA
<213> ORGANISM: Homo sapiens

<400> SEQUENCE: 1055
cctcagtaag ttgcaatact taatttctgt aacagctaag gactgcaaaa ccccactctg    60
catcaactga acgca                                                    75

<210> SEQ ID NO 1056
<211> LENGTH: 75
<212> TYPE: DNA
<213> ORGANISM: Pan troglodytes

<400> SEQUENCE: 1056
aatcagccac tttaattaag ctaagcccct actagattaa tgggacttaa acccacaaac    60
atttagttaa cagct                                                    75

<210> SEQ ID NO 1057
<211> LENGTH: 75
<212> TYPE: DNA
<213> ORGANISM: Homo sapiens

<400> SEQUENCE: 1057
aatcagccac tttaattaag ctaagcccct actagaccaa tgggacttaa acccacaaac    60
acttagttaa cagct                                                    75

<210> SEQ ID NO 1058
<211> LENGTH: 75
<212> TYPE: DNA
<213> ORGANISM: Pan troglodytes

<400> SEQUENCE: 1058
aaacacccta atcaactggc ttcaatctac ttctcccgcc gcaagaaaaa aaggcgggag    60
aagccccggc aggtt                                                    75

<210> SEQ ID NO 1059
<211> LENGTH: 75
<212> TYPE: DNA
<213> ORGANISM: Homo sapiens

<400> SEQUENCE: 1059
aagcacccta atcaactggc ttcaatctac ttctcccgcc gccgggaaaa aaggcgggag    60
aagccccggc aggtt                                                    75

<210> SEQ ID NO 1060
<211> LENGTH: 75
<212> TYPE: DNA
<213> ORGANISM: Pan troglodytes

<400> SEQUENCE: 1060
tgaagctgct tcttcgaatt tgcaattcaa tatgaaaatc acctcagagc tggtaaaaag    60
aggcttaacc cctgt                                                    75

<210> SEQ ID NO 1061
<211> LENGTH: 75
<212> TYPE: DNA
<213> ORGANISM: Homo sapiens

<400> SEQUENCE: 1061
tgaagctgct tcttcgaatt tgcaattcaa tatgaaaatc acctcggagc tggtaaaaag    60
```
aggcctaacc cctgt                                                            75

<210> SEQ ID NO 1062
<211> LENGTH: 75
<212> TYPE: DNA
<213> ORGANISM: Homo sapiens

<400> SEQUENCE: 1062
ctttagattt acagtccaat gcttcactca gccattttac ctcaccccca ctgatgttcg            60
ccgaccgttg actat                                                            75

<210> SEQ ID NO 1063
<211> LENGTH: 75
<212> TYPE: DNA
<213> ORGANISM: Pan troglodytes

<400> SEQUENCE: 1063
tctctacaaa ccacaaagat attggaacac tatacctact attcggtgca tgagctggag            60
tcctgggcac agccc                                                            75

<210> SEQ ID NO 1064
<211> LENGTH: 75
<212> TYPE: DNA
<213> ORGANISM: Homo sapiens

<400> SEQUENCE: 1064
tctctacaaa ccacaaagac attggaacac tatacctatt attcggcgca tgagctggag            60
tcctaggcac agctc                                                            75

<210> SEQ ID NO 1065
<211> LENGTH: 75
<212> TYPE: DNA
<213> ORGANISM: Pan troglodytes

<400> SEQUENCE: 1065
taagtctcct tattcgggct gaactaggcc aaccaggcaa cctcctaggt aatgaccaca            60
tctacaatgt catcg                                                            75

<210> SEQ ID NO 1066
<211> LENGTH: 75
<212> TYPE: DNA
<213> ORGANISM: Homo sapiens

<400> SEQUENCE: 1066
taagcctcct tattcgagcc gagctgggcc agccaggcaa ccttctaggt aacgaccaca            60
tctacaacgt tatcg                                                            75

<210> SEQ ID NO 1067
<211> LENGTH: 75
<212> TYPE: DNA
<213> ORGANISM: Pan troglodytes

<400> SEQUENCE: 1067
tcacagccca tgcattcgta ataatcttct tcatagtaat gcctattata atcggaggct            60
ttggcaactg gctag                                                            75

<210> SEQ ID NO 1068
<211> LENGTH: 75
<212> TYPE: DNA

<210> SEQ ID NO 1068
<211> LENGTH: 75
<212> TYPE: DNA
<213> ORGANISM: Homo sapiens

<400> SEQUENCE: 1068
tcacagccca tgcatttgta ataatcttct tcatagtaat acccatcata atcggaggct    60
ttggcaactg actag    75

<210> SEQ ID NO 1069
<211> LENGTH: 75
<212> TYPE: DNA
<213> ORGANISM: Pan troglodytes

<400> SEQUENCE: 1069
ttcccttgat aattggtgcc cccgacatgg cattccccg cataaacaac ataagcttct    60
ggctcctgcc ccctt    75

<210> SEQ ID NO 1070
<211> LENGTH: 75
<212> TYPE: DNA
<213> ORGANISM: Homo sapiens

<400> SEQUENCE: 1070
ttcccctaat aatcggtgcc cccgatatgg cgtttccccg cataaacaac ataagcttct    60
gactcttacc tccct    75

<210> SEQ ID NO 1071
<211> LENGTH: 75
<212> TYPE: DNA
<213> ORGANISM: Pan troglodytes

<400> SEQUENCE: 1071
ctctcctact tctacttgca tctgccatag tagaagccgg cgcgggaaca ggttgaacag    60
tctaccctcc cttag    75

<210> SEQ ID NO 1072
<211> LENGTH: 75
<212> TYPE: DNA
<213> ORGANISM: Homo sapiens

<400> SEQUENCE: 1072
ctctcctact cctgctcgca tctgctatag tggaggccgg agcaggaaca ggttgaacag    60
tctaccctcc cttag    75

<210> SEQ ID NO 1073
<211> LENGTH: 75
<212> TYPE: DNA
<213> ORGANISM: Pan troglodytes

<400> SEQUENCE: 1073
cgggaaacta ctcgcatcct ggagcctccg tagacctaac catcttctcc ttacatctgg    60
caggcatctc ctcta    75

<210> SEQ ID NO 1074
<211> LENGTH: 75
<212> TYPE: DNA
<213> ORGANISM: Homo sapiens

<400> SEQUENCE: 1074
cagggaacta ctcccaccct ggagcctccg tagacctaac catcttctcc ttacacctag    60
caggtgtctc ctcta    75

<210> SEQ ID NO 1075
<211> LENGTH: 75
<212> TYPE: DNA
<213> ORGANISM: Pan troglodytes

<400> SEQUENCE: 1075

```
tcctaggagc cattaacttc atcacaacaa ttattaatat aaaacctcct gccatgaccc     60
aataccaaac ccccc                                                     75
```

<210> SEQ ID NO 1076
<211> LENGTH: 75
<212> TYPE: DNA
<213> ORGANISM: Homo sapiens

<400> SEQUENCE: 1076

```
tcttaggggc catcaatttc atcacaacaa ttatcaatat aaaaccccct gccataaccc     60
aataccaaac gcccc                                                     75
```

<210> SEQ ID NO 1077
<211> LENGTH: 75
<212> TYPE: DNA
<213> ORGANISM: Pan troglodytes

<400> SEQUENCE: 1077

```
tcttcgtctg atccgtccta atcacagcag tcttacttct cctatccctc ccagtcctag     60
ctgctggcat cacca                                                     75
```

<210> SEQ ID NO 1078
<211> LENGTH: 75
<212> TYPE: DNA
<213> ORGANISM: Homo sapiens

<400> SEQUENCE: 1078

```
tcttcgtctg atccgtccta atcacagcag tcctacttct cctatctctc ccagtcctag     60
ctgctggcat cacta                                                     75
```

<210> SEQ ID NO 1079
<211> LENGTH: 75
<212> TYPE: DNA
<213> ORGANISM: Pan troglodytes

<400> SEQUENCE: 1079

```
tactattgac agatcgtaac ctcaacacta ccttcttcga cccagccggg ggaggagacc     60
ctattctata tcaac                                                     75
```

<210> SEQ ID NO 1080
<211> LENGTH: 75
<212> TYPE: DNA
<213> ORGANISM: Homo sapiens

<400> SEQUENCE: 1080

```
tactactaac agaccgcaac ctcaacacca ccttcttcga ccccgccgga ggaggagacc     60
ccattctata ccaac                                                     75
```

<210> SEQ ID NO 1081
<211> LENGTH: 75
<212> TYPE: DNA
<213> ORGANISM: Pan troglodytes

<400> SEQUENCE: 1081
acttattctg attttttggc cacccgaag tttatattct tatcctacca ggcttcggaa    60
taatttccca cattg    75

<210> SEQ ID NO 1082
<211> LENGTH: 75
<212> TYPE: DNA
<213> ORGANISM: Homo sapiens

<400> SEQUENCE: 1082
acctattctg attttcggt caccctgaag tttatattct tatcctacca ggcttcggaa    60
taatctccca tattg    75

<210> SEQ ID NO 1083
<211> LENGTH: 75
<212> TYPE: DNA
<213> ORGANISM: Pan troglodytes

<400> SEQUENCE: 1083
taacttatta ctccggaaaa aaagaaccat ttggatatat aggcatggtt tgagctataa    60
tatcaattgg cttcc    75

<210> SEQ ID NO 1084
<211> LENGTH: 75
<212> TYPE: DNA
<213> ORGANISM: Homo sapiens

<400> SEQUENCE: 1084
taacttacta ctccggaaaa aaagaaccat ttggatacat aggtatggtc tgagctatga    60
tatcaattgg cttcc    75

<210> SEQ ID NO 1085
<211> LENGTH: 75
<212> TYPE: DNA
<213> ORGANISM: Pan troglodytes

<400> SEQUENCE: 1085
tagggtttat cgtgtgagca caccatatat ttacagtagg gatagacgta gacacccgag    60
cctatttcac ctccg    75

<210> SEQ ID NO 1086
<211> LENGTH: 75
<212> TYPE: DNA
<213> ORGANISM: Homo sapiens

<400> SEQUENCE: 1086
tagggtttat cgtgtgagca caccatatat ttacagtagg aatagacgta gacacacgag    60
catatttcac ctccg    75

<210> SEQ ID NO 1087
<211> LENGTH: 75
<212> TYPE: DNA
<213> ORGANISM: Pan troglodytes

<400> SEQUENCE: 1087
ctaccataat cattgctatt cctaccggcg tcaaagtatt cagctgactc gctacacttc    60
acggaagcaa tatga    75

```
<210> SEQ ID NO 1088
<211> LENGTH: 75
<212> TYPE: DNA
<213> ORGANISM: Homo sapiens

<400> SEQUENCE: 1088
ctaccataat catcgctatc cccaccggcg tcaaagtatt tagctgactc gccacactcc    60
acggaagcaa tatga                                                    75

<210> SEQ ID NO 1089
<211> LENGTH: 75
<212> TYPE: DNA
<213> ORGANISM: Pan troglodytes

<400> SEQUENCE: 1089
aatgatctgc cgcagtactc tgagccctag ggtttatctt tctcttcacc gtaggtggcc    60
taaccggcat tgtac                                                    75

<210> SEQ ID NO 1090
<211> LENGTH: 75
<212> TYPE: DNA
<213> ORGANISM: Homo sapiens

<400> SEQUENCE: 1090
aatgatctgc tgcagtgctc tgagccctag gattcatctt tcttttcacc gtaggtggcc    60
tgactggcat tgtat                                                    75

<210> SEQ ID NO 1091
<211> LENGTH: 75
<212> TYPE: DNA
<213> ORGANISM: Pan troglodytes

<400> SEQUENCE: 1091
tagcaaactc atcattagac atcgtgctac acgacacata ctacgtcgta gcccacttcc    60
actacgttct atcaa                                                    75

<210> SEQ ID NO 1092
<211> LENGTH: 75
<212> TYPE: DNA
<213> ORGANISM: Homo sapiens

<400> SEQUENCE: 1092
tagcaaactc atcactagac atcgtactac acgacacgta ctacgttgta gcccacttcc    60
actatgtcct atcaa                                                    75

<210> SEQ ID NO 1093
<211> LENGTH: 75
<212> TYPE: DNA
<213> ORGANISM: Pan troglodytes

<400> SEQUENCE: 1093
taggagctgt attcgccatc ataggaggct tcattcactg attccccta ttctcaggct    60 ataccctaga ccaaa                                                    75

<210> SEQ ID NO 1094
<211> LENGTH: 75
<212> TYPE: DNA
<213> ORGANISM: Homo sapiens

<400> SEQUENCE: 1094
```

```
taggagctgt atttgccatc ataggaggct tcattcactg atttccccta ttctcaggct    60
acaccctaga ccaaa                                                    75

<210> SEQ ID NO 1095
<211> LENGTH: 75
<212> TYPE: DNA
<213> ORGANISM: Pan troglodytes

<400> SEQUENCE: 1095
cctatgccaa atccaatttt gccatcatgt tcattggcgt aaacctaacc ttcttcccac    60
agcacttcct tggcc                                                    75

<210> SEQ ID NO 1096
<211> LENGTH: 75
<212> TYPE: DNA
<213> ORGANISM: Homo sapiens

<400> SEQUENCE: 1096
cctacgccaa atccatttc actatcatat tcatcggcgt aaatctaact ttcttcccac     60
aacactttct cggcc                                                    75

<210> SEQ ID NO 1097
<211> LENGTH: 75
<212> TYPE: DNA
<213> ORGANISM: Pan troglodytes

<400> SEQUENCE: 1097
tatctgggat gccccgacgt tactcggact accccgatgc atacaccaca tgaaatgtcc    60
tatcatccgt aggct                                                    75

<210> SEQ ID NO 1098
<211> LENGTH: 75
<212> TYPE: DNA
<213> ORGANISM: Homo sapiens

<400> SEQUENCE: 1098
tatccggaat gccccgacgt tactcggact accccgatgc atacaccaca tgaaacatcc    60
tatcatctgt aggct                                                    75

<210> SEQ ID NO 1099
<211> LENGTH: 75
<212> TYPE: DNA
<213> ORGANISM: Pan troglodytes

<400> SEQUENCE: 1099
catttatctc cctgacagca gtaatattaa taattttcat gatttgagaa gcctttgctt    60
caaaacgaaa agtcc                                                    75

<210> SEQ ID NO 1100
<211> LENGTH: 75
<212> TYPE: DNA
<213> ORGANISM: Homo sapiens

<400> SEQUENCE: 1100
cattcatttc tctaacagca gtaatattaa taattttcat gatttgagaa gccttcgctt    60
cgaagcgaaa agtcc                                                    75

<210> SEQ ID NO 1101
<211> LENGTH: 75
```

```
<212> TYPE: DNA
<213> ORGANISM: Pan troglodytes

<400> SEQUENCE: 1101
taatagtaga agagccctcc gcaaacctgg aatgactata tggatgcccc ccaccctacc    60
acacattcga agaac                                                    75

<210> SEQ ID NO 1102
<211> LENGTH: 75
<212> TYPE: DNA
<213> ORGANISM: Homo sapiens

<400> SEQUENCE: 1102
taatagtaga agaaccctcc ataaacctgg agtgactata tggatgcccc ccaccctacc    60
acacattcga agaac                                                    75

<210> SEQ ID NO 1103
<211> LENGTH: 75
<212> TYPE: DNA
<213> ORGANISM: Pan troglodytes

<400> SEQUENCE: 1103
ccgtatacat aaaatctaga caaaaaagga aggaatcgaa ccccctaaag ctggtttcaa    60
gccaacccca tgacc                                                    75

<210> SEQ ID NO 1104
<211> LENGTH: 75
<212> TYPE: DNA
<213> ORGANISM: Homo sapiens

<400> SEQUENCE: 1104
ccgtatacat aaaatctaga caaaaaagga aggaatcgaa cccccaaag ctggtttcaa     60 gccaacccca tggcc                                                    75

<210> SEQ ID NO 1105
<211> LENGTH: 75
<212> TYPE: DNA
<213> ORGANISM: Pan troglodytes

<400> SEQUENCE: 1105
tccatgactt tttcaaaaag atattagaaa aactatttca taactttgtc aaagttaaat    60
tacaggttaa ccccc                                                    75

<210> SEQ ID NO 1106
<211> LENGTH: 75
<212> TYPE: DNA
<213> ORGANISM: Homo sapiens

<400> SEQUENCE: 1106
tccatgactt tttcaaaaag gtattagaaa aaccatttca taactttgtc aaagttaaat    60
tataggctaa atcct                                                    75

<210> SEQ ID NO 1107
<211> LENGTH: 75
<212> TYPE: DNA
<213> ORGANISM: Pan troglodytes

<400> SEQUENCE: 1107
gtatatctta atggcacatg cagcgcaagt aggtctacaa gatgctactt ccctatcat     60
```
agaagaactt attat    75

<210> SEQ ID NO 1108
<211> LENGTH: 75
<212> TYPE: DNA
<213> ORGANISM: Homo sapiens

<400> SEQUENCE: 1108
atatatctta atggcacatg cagcgcaagt aggtctacaa gacgctactt cccctatcat    60
agaagagctt atcac    75

<210> SEQ ID NO 1109
<211> LENGTH: 75
<212> TYPE: DNA
<213> ORGANISM: Pan troglodytes

<400> SEQUENCE: 1109
ctttcacgac catgccctca taattatctt tctcatctgc tttctagtcc tatacgccct    60
tttcctaaca ctcac    75

<210> SEQ ID NO 1110
<211> LENGTH: 75
<212> TYPE: DNA
<213> ORGANISM: Homo sapiens

<400> SEQUENCE: 1110
ctttcatgat cacgccctca taatcatttt ccttatctgc ttcctagtcc tgtatgccct    60
tttcctaaca ctcac    75

<210> SEQ ID NO 1111
<211> LENGTH: 75
<212> TYPE: DNA
<213> ORGANISM: Pan troglodytes

<400> SEQUENCE: 1111
aacaaaacta actaatacta gtatttcaga cgcccaggaa atagaaaccg tctgaactat    60
cctgcccgcc atcat    75

<210> SEQ ID NO 1112
<211> LENGTH: 75
<212> TYPE: DNA
<213> ORGANISM: Homo sapiens

<400> SEQUENCE: 1112
aacaaaacta actaatacta acatctcaga cgctcaggaa atagaaaccg tctgaactat    60
cctgcccgcc atcat    75

<210> SEQ ID NO 1113
<211> LENGTH: 75
<212> TYPE: DNA
<213> ORGANISM: Pan troglodytes

<400> SEQUENCE: 1113
cctagtcctt attgccctac catccctgcg tatcctttac ataacagacg aggtcaacga    60
cccctccttt actat    75

<210> SEQ ID NO 1114
<211> LENGTH: 75
<212> TYPE: DNA
<213> ORGANISM: Homo sapiens

```
<400> SEQUENCE: 1114
cctagtcctc atcgccctcc catccctacg catcctttac ataacagacg aggtcaacga    60 tccctcccctt accat                                                    75

<210> SEQ ID NO 1115
<211> LENGTH: 75
<212> TYPE: DNA
<213> ORGANISM: Pan troglodytes

<400> SEQUENCE: 1115
taaatcaatc ggccatcaat gatattgaac ctacgaatac accgactacg gcgggctaat    60
cttcaactcc tacat                                                     75

<210> SEQ ID NO 1116
<211> LENGTH: 75
<212> TYPE: DNA
<213> ORGANISM: Homo sapiens

<400> SEQUENCE: 1116
caaatcaatt ggccaccaat ggtactgaac ctacgagtac accgactacg gcggactaat    60
cttcaactcc tacat                                                     75

<210> SEQ ID NO 1117
<211> LENGTH: 75
<212> TYPE: DNA
<213> ORGANISM: Pan troglodytes

<400> SEQUENCE: 1117
actcccccca ttatttctag aaccaggtga tctacgactc cttgacgttg ataaccgagt    60
ggtcctccca gttga                                                     75

<210> SEQ ID NO 1118
<211> LENGTH: 75
<212> TYPE: DNA
<213> ORGANISM: Homo sapiens

<400> SEQUENCE: 1118
acttccccca ttattcctag aaccaggcga cctgcgactc cttgacgttg acaatcgagt    60
agtactcccg attga                                                     75

<210> SEQ ID NO 1119
<211> LENGTH: 75
<212> TYPE: DNA
<213> ORGANISM: Pan troglodytes

<400> SEQUENCE: 1119 agccccgtt cgtataataa ttacatcaca agatgttcta cactcatgag ctgttcccac     60
attaggccta aaaac                                                     75

<210> SEQ ID NO 1120
<211> LENGTH: 75
<212> TYPE: DNA
<213> ORGANISM: Homo sapiens

<400> SEQUENCE: 1120
agcccccatt cgtataataa ttacatcaca agacgtcttg cactcatgag ctgtccccac    60
attaggctta aaaac                                                     75
```

<210> SEQ ID NO 1121
<211> LENGTH: 75
<212> TYPE: DNA
<213> ORGANISM: Pan troglodytes

<400> SEQUENCE: 1121

```
agacgcaatt cccggacgcc taaaccaaac cactttcacc gccacacgac caggagtata      60
ctacggccaa tgctc                                                      75
```

<210> SEQ ID NO 1122
<211> LENGTH: 75
<212> TYPE: DNA
<213> ORGANISM: Homo sapiens

<400> SEQUENCE: 1122

```
agatgcaatt cccggacgtc taaaccaaac cactttcacc gctacacgac cgggggtata      60
ctacggtcaa tgctc                                                      75
```

<210> SEQ ID NO 1123
<211> LENGTH: 75
<212> TYPE: DNA
<213> ORGANISM: Pan troglodytes

<400> SEQUENCE: 1123

```
agaaatctgt ggagcaaacc acagttttat acccatcgtc ctagaattaa tccctctaaa      60
aatctttgaa atagg                                                      75
```

<210> SEQ ID NO 1124
<211> LENGTH: 75
<212> TYPE: DNA
<213> ORGANISM: Homo sapiens

<400> SEQUENCE: 1124

```
tgaaatctgt ggagcaaacc acagtttcat gcccatcgtc ctagaattaa ttcccctaaa      60
aatctttgaa atagg                                                      75
```

<210> SEQ ID NO 1125
<211> LENGTH: 75
<212> TYPE: DNA
<213> ORGANISM: Homo sapiens

<400> SEQUENCE: 1125

```
gcccgtattt accctatagc acccccctcta cccccctctag agcccactgt aaagctaact    60
tagcattaac cttttt                                                     75
```

<210> SEQ ID NO 1126
<211> LENGTH: 75
<212> TYPE: DNA
<213> ORGANISM: Pan troglodytes

<400> SEQUENCE: 1126

```
aagttaaaga ttaagaggac cgacacctct ttacagtgaa atgccccaac taaataccgc      60
cgtatgaccc accat                                                      75
```

<210> SEQ ID NO 1127
<211> LENGTH: 75
<212> TYPE: DNA
<213> ORGANISM: Homo sapiens

<400> SEQUENCE: 1127

```
aagttaaaga ttaagagaac caacacctct ttacagtgaa atgccccaac taaatactac    60
cgtatggccc accat                                                     75

<210> SEQ ID NO 1128
<211> LENGTH: 75
<212> TYPE: DNA
<213> ORGANISM: Pan troglodytes

<400> SEQUENCE: 1128 aattacccccc atactcctga cactatttct cgtcacccaa ctaaaaatat taaattcaaa   60
ttaccatcta ccccc                                                     75

<210> SEQ ID NO 1129
<211> LENGTH: 75
<212> TYPE: DNA
<213> ORGANISM: Homo sapiens

<400> SEQUENCE: 1129 aattacccccc atactcctta cactattcct catcacccaa ctaaaaatat taaacacaaa   60
ctaccaccta cctcc                                                     75

<210> SEQ ID NO 1130
<211> LENGTH: 75
<212> TYPE: DNA
<213> ORGANISM: Pan troglodytes

<400> SEQUENCE: 1130
ctcaccaaaa cccataaaaa taaaaaacta caataaaccc tgagaaccaa aatgaacgaa    60
aatctattcg cttca                                                     75

<210> SEQ ID NO 1131
<211> LENGTH: 75
<212> TYPE: DNA
<213> ORGANISM: Homo sapiens

<400> SEQUENCE: 1131
ctcaccaaag cccataaaaa taaaaaatta taacaaaccc tgagaaccaa aatgaacgaa    60
aatctgttcg cttca                                                     75

<210> SEQ ID NO 1132
<211> LENGTH: 75
<212> TYPE: DNA
<213> ORGANISM: Pan troglodytes

<400> SEQUENCE: 1132
ttcgctgccc ccacaatcct aggcttaccc gccgcagtac taatcattct attccccccct  60 ctactggtcc ccact                                                     75

<210> SEQ ID NO 1133
<211> LENGTH: 75
<212> TYPE: DNA
<213> ORGANISM: Homo sapiens

<400> SEQUENCE: 1133
ttcattgccc ccacaatcct aggcctaccc gccgcagtac tgatcattct atttcccccct  60 ctattgatcc ccacc                                                     75

<210> SEQ ID NO 1134
```

```
<211> LENGTH: 75
<212> TYPE: DNA
<213> ORGANISM: Pan troglodytes

<400> SEQUENCE: 1134
tctaaacatc tcatcaacaa ccgactaatt accacccaac aatgactaat tcaactgacc    60
tcaaaacaaa taata                                                    75

<210> SEQ ID NO 1135
<211> LENGTH: 75
<212> TYPE: DNA
<213> ORGANISM: Homo sapiens

<400> SEQUENCE: 1135
tccaaatatc tcatcaacaa ccgactaatc accacccaac aatgactaat caaactaacc    60
tcaaaacaaa tgata                                                    75

<210> SEQ ID NO 1136
<211> LENGTH: 75
<212> TYPE: DNA
<213> ORGANISM: Pan troglodytes

<400> SEQUENCE: 1136
actatacaca gcactaaagg acgaacctga tctctcatac tagtatcctt aatcattttt    60
attaccacaa ccaat                                                    75

<210> SEQ ID NO 1137
<211> LENGTH: 75
<212> TYPE: DNA
<213> ORGANISM: Homo sapiens

<400> SEQUENCE: 1137
accatacaca acactaaagg acgaacctga tctcttatac tagtatcctt aatcattttt    60
attgccacaa ctaac                                                    75

<210> SEQ ID NO 1138
<211> LENGTH: 75
<212> TYPE: DNA
<213> ORGANISM: Pan troglodytes

<400> SEQUENCE: 1138
cttcttgggc ttctacccca ctcattcaca ccaaccaccc aactatctat aaacctagcc    60
atggctatcc cccta                                                    75

<210> SEQ ID NO 1139
<211> LENGTH: 75
<212> TYPE: DNA
<213> ORGANISM: Homo sapiens

<400> SEQUENCE: 1139
ctcctcggac tcctgcctca ctcatttaca ccaaccaccc aactatctat aaacctagcc    60
atggccatcc cctta                                                    75

<210> SEQ ID NO 1140
<211> LENGTH: 75
<212> TYPE: DNA
<213> ORGANISM: Pan troglodytes

<400> SEQUENCE: 1140
tgagcaggcg cagtagtcat aggctttcgc tttaagacta aaaatgccct agcccacttc    60
```
ttaccgcaag gcaca                                                          75

<210> SEQ ID NO 1141
<211> LENGTH: 75
<212> TYPE: DNA
<213> ORGANISM: Homo sapiens

<400> SEQUENCE: 1141
tgagcgggca cagtgattat aggctttcgc tctaagatta aaaatgccct agcccacttc         60
ttaccacaag gcaca                                                          75

<210> SEQ ID NO 1142
<211> LENGTH: 75
<212> TYPE: DNA
<213> ORGANISM: Pan troglodytes

<400> SEQUENCE: 1142
cctacacccc ttatccccat actagttatc atcgaaacta ttagcctact cattcaacca         60
atagccttag ccgta                                                          75

<210> SEQ ID NO 1143
<211> LENGTH: 75
<212> TYPE: DNA
<213> ORGANISM: Homo sapiens

<400> SEQUENCE: 1143
cctacacccc ttatccccat actagttatt atcgaaacca tcagcctact cattcaacca         60
atagccctgg ccgta                                                          75

<210> SEQ ID NO 1144
<211> LENGTH: 75
<212> TYPE: DNA
<213> ORGANISM: Pan troglodytes

<400> SEQUENCE: 1144
cgtctaaccg ctaacattac tgcaggccac ctactcatgc acctaattgg aagcgccaca         60
ctagcattat caact                                                          75

<210> SEQ ID NO 1145
<211> LENGTH: 75
<212> TYPE: DNA
<213> ORGANISM: Homo sapiens

<400> SEQUENCE: 1145
cgcctaaccg ctaacattac tgcaggccac ctactcatgc acctaattgg aagcgccacc         60
ctagcaatat caacc                                                          75

<210> SEQ ID NO 1146
<211> LENGTH: 75
<212> TYPE: DNA
<213> ORGANISM: Pan troglodytes

<400> SEQUENCE: 1146
atcaatctac cctatgcact cattatcttc acaattctaa tcctactgac tattctagag         60
atcgccgtcg cctta                                                          75

<210> SEQ ID NO 1147
<211> LENGTH: 75
<212> TYPE: DNA

<213> ORGANISM: Homo sapiens

<400> SEQUENCE: 1147
attaaccttc cctctacact tatcatcttc acaattctaa ttctactgac tatcctagaa    60
atcgctgtcg cctta                                                    75

<210> SEQ ID NO 1148
<211> LENGTH: 75
<212> TYPE: DNA
<213> ORGANISM: Pan troglodytes

<400> SEQUENCE: 1148
atccaagcct acgtttttac acttctagtg agcctctacc tgcacgacaa cacataatga    60
cccaccaatc acatg                                                    75

<210> SEQ ID NO 1149
<211> LENGTH: 75
<212> TYPE: DNA
<213> ORGANISM: Homo sapiens

<400> SEQUENCE: 1149
atccaagcct acgttttcac acttctagta agcctctacc tgcacgacaa cacataatga    60
cccaccaatc acatg                                                    75

<210> SEQ ID NO 1150
<211> LENGTH: 75
<212> TYPE: DNA
<213> ORGANISM: Pan troglodytes

<400> SEQUENCE: 1150
cctaccacat agtaaaaccc agcccatgac ccctaacagg ggccctctcg gccctcctaa    60
taacctccgg cctgg                                                    75

<210> SEQ ID NO 1151
<211> LENGTH: 75
<212> TYPE: DNA
<213> ORGANISM: Homo sapiens

<400> SEQUENCE: 1151
cctatcatat agtaaaaccc agcccatgac ccctaacagg ggccctctca gccctcctaa    60
tgacctccgg cctag                                                    75

<210> SEQ ID NO 1152
<211> LENGTH: 75
<212> TYPE: DNA
<213> ORGANISM: Pan troglodytes

<400> SEQUENCE: 1152
ccatatgatt ccacttctac tccacaacac tactcacact aggcttacta actaacacat    60
tgaccatata tcaat                                                    75

<210> SEQ ID NO 1153
<211> LENGTH: 75
<212> TYPE: DNA
<213> ORGANISM: Homo sapiens

<400> SEQUENCE: 1153
ccatgtgatt tcacttccac tccataacgc tcctcatact aggcctacta accaacacac    60
taaccatata ccaat                                                    75

<210> SEQ ID NO 1154
<211> LENGTH: 75
<212> TYPE: DNA
<213> ORGANISM: Pan troglodytes

<400> SEQUENCE: 1154
gatgacgcga tgttatacga gaaggcacat accaaggcca ccacacacca cccgtccaaa    60
aaggtctccg atatg                                                    75

<210> SEQ ID NO 1155
<211> LENGTH: 75
<212> TYPE: DNA
<213> ORGANISM: Homo sapiens

<400> SEQUENCE: 1155
gatggcgcga tgtaacacga gaaagcacat accaaggcca ccacacacca cctgtccaaa    60
aaggccttcg atacg                                                    75

<210> SEQ ID NO 1156
<211> LENGTH: 75
<212> TYPE: DNA
<213> ORGANISM: Pan troglodytes

<400> SEQUENCE: 1156
ggataattct ttttattacc tcagaagttt ttttctttgc aggattttt tgagctttct    60 accactccag cctag                                                    75

<210> SEQ ID NO 1157
<211> LENGTH: 75
<212> TYPE: DNA
<213> ORGANISM: Homo sapiens

<400> SEQUENCE: 1157
ggataatcct atttattacc tcagaagttt ttttcttcgc aggatttttc tgagcctttt    60
accactccag cctag                                                    75

<210> SEQ ID NO 1158
<211> LENGTH: 75
<212> TYPE: DNA
<213> ORGANISM: Pan troglodytes

<400> SEQUENCE: 1158
cccctacccc ccagctagga ggacactggc ccccaacagg tattacccca ctaaatcccc    60
tagaagtccc actcc                                                    75

<210> SEQ ID NO 1159
<211> LENGTH: 75
<212> TYPE: DNA
<213> ORGANISM: Homo sapiens

<400> SEQUENCE: 1159
cccctacccc ccaattagga gggcactggc ccccaacagg catcaccccg ctaaatcccc    60
tagaagtccc actcc                                                    75

<210> SEQ ID NO 1160
<211> LENGTH: 75
<212> TYPE: DNA
<213> ORGANISM: Pan troglodytes

<400> SEQUENCE: 1160
taaacacatc tgtattactc gcatcaggag tatcaattac ttgagcccat cacagcttaa     60
tagaaaataa ccgaa                                                      75

<210> SEQ ID NO 1161
<211> LENGTH: 75
<212> TYPE: DNA
<213> ORGANISM: Homo sapiens

<400> SEQUENCE: 1161
taaacacatc cgtattactc gcatcaggag tatcaatcac ctgagctcac catagtctaa     60
tagaaaacaa ccgaa                                                      75

<210> SEQ ID NO 1162
<211> LENGTH: 75
<212> TYPE: DNA
<213> ORGANISM: Pan troglodytes

<400> SEQUENCE: 1162
accaaataat tcaagcactg cttattacga ttctactagg tctttatttt accctcctac     60
aagcctcaga atatt                                                      75

<210> SEQ ID NO 1163
<211> LENGTH: 75
<212> TYPE: DNA
<213> ORGANISM: Homo sapiens

<400> SEQUENCE: 1163
accaaataat tcaagcactg cttattacaa ttttactggg tctctatttt accctcctac     60
aagcctcaga gtact                                                      75

<210> SEQ ID NO 1164
<211> LENGTH: 75
<212> TYPE: DNA
<213> ORGANISM: Pan troglodytes

<400> SEQUENCE: 1164
tcgaatcccc ttttaccatt tccgatggca tctacggctc aacattcttt gtagccacag     60
gcttccacgg actcc                                                      75

<210> SEQ ID NO 1165
<211> LENGTH: 75
<212> TYPE: DNA
<213> ORGANISM: Homo sapiens

<400> SEQUENCE: 1165
tcgagtctcc cttcaccatt tccgacggca tctacggctc aacatttttt gtagccacag     60
gcttccacgg acttc                                                      75

<210> SEQ ID NO 1166
<211> LENGTH: 75
<212> TYPE: DNA
<213> ORGANISM: Pan troglodytes

<400> SEQUENCE: 1166
acgtcattat tggatcaact ttcctcacta tctgcctcat ccgccaacta atatttcact     60
tcacatccaa acatc                                                      75

```
<210> SEQ ID NO 1167
<211> LENGTH: 75
<212> TYPE: DNA
<213> ORGANISM: Homo sapiens

<400> SEQUENCE: 1167
acgtcattat tggctcaact ttcctcacta tctgcttcat ccgccaacta atatttcact    60
ttacatccaa acatc                                                    75

<210> SEQ ID NO 1168
<211> LENGTH: 75
<212> TYPE: DNA
<213> ORGANISM: Pan troglodytes

<400> SEQUENCE: 1168
acttcggctt tcaagccgcc gcctgatact gacacttcgt agatgtagtc tgactatttc    60
tatatgtctc tattt                                                    75

<210> SEQ ID NO 1169
<211> LENGTH: 75
<212> TYPE: DNA
<213> ORGANISM: Homo sapiens

<400> SEQUENCE: 1169
actttggctt cgaagccgcc gcctgatact ggcattttgt agatgtggtt tgactatttc    60
tgtatgtctc catct                                                    75

<210> SEQ ID NO 1170
<211> LENGTH: 75
<212> TYPE: DNA
<213> ORGANISM: Pan troglodytes

<400> SEQUENCE: 1170
actgatgagg atcttactct tttagtataa gtagtaccgt taacttccaa ttaactagtt    60
ttgacaacat tcaaa                                                    75

<210> SEQ ID NO 1171
<211> LENGTH: 75
<212> TYPE: DNA
<213> ORGANISM: Homo sapiens

<400> SEQUENCE: 1171
attgatgagg gtcttactct tttagtataa atagtaccgt taacttccaa ttaactagtt    60
ttgacaacat tcaaa                                                    75

<210> SEQ ID NO 1172
<211> LENGTH: 75
<212> TYPE: DNA
<213> ORGANISM: Pan troglodytes

<400> SEQUENCE: 1172
aaagagtaat aaacttcgtc ctaattttaa taaccaatac ccttctagcc ctactactga    60
taattatcac attct                                                    75

<210> SEQ ID NO 1173
<211> LENGTH: 75
<212> TYPE: DNA
<213> ORGANISM: Homo sapiens

<400> SEQUENCE: 1173
```

-continued

```
aaagagtaat aaacttcgcc ttaattttaa taatcaacac cctcctagcc ttactactaa    60
taattattac atttt                                                     75

<210> SEQ ID NO 1174
<211> LENGTH: 75
<212> TYPE: DNA
<213> ORGANISM: Pan troglodytes

<400> SEQUENCE: 1174
gactaccaca actcaacagc tacatagaaa aatctacccc ttacgaatgt ggcttcgacc    60
ctatatcccc cgccc                                                     75

<210> SEQ ID NO 1175
<211> LENGTH: 75
<212> TYPE: DNA
<213> ORGANISM: Homo sapiens

<400> SEQUENCE: 1175
gactaccaca actcaacggc tacatagaaa aatccacccc ttacgagtgc ggcttcgacc    60
ctatatcccc cgccc                                                     75

<210> SEQ ID NO 1176
<211> LENGTH: 75
<212> TYPE: DNA
<213> ORGANISM: Pan troglodytes

<400> SEQUENCE: 1176
gcgtcccctt ctccataaaa ttttcctag tagccatcac cttcctatta tttgacctag     60
aaattgccct cctat                                                     75

<210> SEQ ID NO 1177
<211> LENGTH: 75
<212> TYPE: DNA
<213> ORGANISM: Homo sapiens

<400> SEQUENCE: 1177
gcgtcccttt ctccataaaa ttcttcttag tagctattac cttcttatta tttgatctag    60
aaattgccct cctt                                                      75

<210> SEQ ID NO 1178
<211> LENGTH: 75
<212> TYPE: DNA
<213> ORGANISM: Pan troglodytes

<400> SEQUENCE: 1178
tgcccttacc ttgagcccta caaacggcca acctaccact aatagtcaca tcatccctct    60
tattaattac tatcc                                                     75

<210> SEQ ID NO 1179
<211> LENGTH: 75
<212> TYPE: DNA
<213> ORGANISM: Homo sapiens

<400> SEQUENCE: 1179 taccctacc atgagcccta caaacaacta acctgccact aatagttatg tcatccctct     60
tattaatcat catcc                                                     75

<210> SEQ ID NO 1180
<211> LENGTH: 75
```

```
<212> TYPE: DNA
<213> ORGANISM: Pan troglodytes

<400> SEQUENCE: 1180
tagccctaag cctcgcctac gaatgattac aaaaagggtt agactgaacc gaattggtat     60
atagtttaaa taaaa                                                      75

<210> SEQ ID NO 1181
<211> LENGTH: 75
<212> TYPE: DNA
<213> ORGANISM: Homo sapiens

<400> SEQUENCE: 1181
tagccctaag tctggcctat gagtgactac aaaaaggatt agactgaacc gaattggtat     60
atagtttaaa caaaa                                                      75

<210> SEQ ID NO 1182
<211> LENGTH: 75
<212> TYPE: DNA
<213> ORGANISM: Pan troglodytes

<400> SEQUENCE: 1182
cgaatgattt cgactcatta aattatgata atcatattta ccaaatgccc cttatttata     60
taaatattat actag                                                      75

<210> SEQ ID NO 1183
<211> LENGTH: 75
<212> TYPE: DNA
<213> ORGANISM: Homo sapiens

<400> SEQUENCE: 1183
cgaatgattt cgactcatta aattatgata atcatattta ccaaatgccc ctcatttaca     60
taaatattat actag                                                      75

<210> SEQ ID NO 1184
<211> LENGTH: 75
<212> TYPE: DNA
<213> ORGANISM: Pan troglodytes

<400> SEQUENCE: 1184
catttaccat ctcacttcta ggaatactag tatatcgctc acacctaata tcttccctac     60
tatgcctaga aggaa                                                      75

<210> SEQ ID NO 1185
<211> LENGTH: 75
<212> TYPE: DNA
<213> ORGANISM: Homo sapiens

<400> SEQUENCE: 1185
catttaccat ctcacttcta ggaatactag tatatcgctc acacctcata tcctccctac     60
tatgcctaga aggaa                                                      75

<210> SEQ ID NO 1186
<211> LENGTH: 75
<212> TYPE: DNA
<213> ORGANISM: Pan troglodytes

<400> SEQUENCE: 1186
taatactatc actgttcatc atagccaccc tcataaccct caatactcac tccctcttag     60
```

```
ccaatattgt accca                                              75

<210> SEQ ID NO 1187
<211> LENGTH: 75
<212> TYPE: DNA
<213> ORGANISM: Homo sapiens

<400> SEQUENCE: 1187
taatactatc gctgttcatt atagctactc tcataaccct caacacccac tccctcttag    60
ccaatattgt gccta                                              75

<210> SEQ ID NO 1188
<211> LENGTH: 75
<212> TYPE: DNA
<213> ORGANISM: Pan troglodytes

<400> SEQUENCE: 1188
tcaccatact agtctttgct gcctgcgaag cagcagtagg tctagcacta ctagtttcaa    60
tctctaacac atatg                                              75

<210> SEQ ID NO 1189
<211> LENGTH: 75
<212> TYPE: DNA
<213> ORGANISM: Homo sapiens

<400> SEQUENCE: 1189
ttgccatact agtctttgcc gcctgcgaag cagcggtggg cctagcccta ctagtctcaa    60
tctccaacac atatg                                              75

<210> SEQ ID NO 1190
<211> LENGTH: 75
<212> TYPE: DNA
<213> ORGANISM: Pan troglodytes

<400> SEQUENCE: 1190
gcttagacta cgtacataac ctaaacctac tccaatgcta aaactaatca tcccgacaat    60
tatattacta ccact                                              75

<210> SEQ ID NO 1191
<211> LENGTH: 75
<212> TYPE: DNA
<213> ORGANISM: Homo sapiens

<400> SEQUENCE: 1191
gcctagacta cgtacataac ctaaacctac tccaatgcta aaactaatcg tcccaacaat    60
tatattacta ccact                                              75

<210> SEQ ID NO 1192
<211> LENGTH: 75
<212> TYPE: DNA
<213> ORGANISM: Pan troglodytes

<400> SEQUENCE: 1192
aacatgattc tctaaaaaac gtataatttg aatcaacaca accactcaca gcctaattat    60
cagcaccatt ccctt                                              75

<210> SEQ ID NO 1193
<211> LENGTH: 75
<212> TYPE: DNA
<213> ORGANISM: Homo sapiens
```

<400> SEQUENCE: 1193
gacatgactt tccaaaaaac acataatttg aatcaacaca accacccaca gcctaattat    60
tagcatcatc cctct                                                    75

<210> SEQ ID NO 1194
<211> LENGTH: 75
<212> TYPE: DNA
<213> ORGANISM: Pan troglodytes

<400> SEQUENCE: 1194 actattttt aaccaaatta acaacaacct attcagctgt tccctgccct tctcctccga    60 cccccttaaca actcc                                                   75

<210> SEQ ID NO 1195
<211> LENGTH: 75
<212> TYPE: DNA
<213> ORGANISM: Homo sapiens

<400> SEQUENCE: 1195 actattttt aaccaaatca acaacaacct atttagctgt tccccaacct tttcctccga    60
ccccctaaca acccc                                                    75

<210> SEQ ID NO 1196
<211> LENGTH: 75
<212> TYPE: DNA
<213> ORGANISM: Pan troglodytes

<400> SEQUENCE: 1196
cctcctaata ttaactgctt gacttctacc cctcacaatc atagcaagcc agcgccacct    60
atccaacgaa ccact                                                    75

<210> SEQ ID NO 1197
<211> LENGTH: 75
<212> TYPE: DNA
<213> ORGANISM: Homo sapiens

<400> SEQUENCE: 1197
cctcctaata ctaactacct gactcctacc cctcacaatc atggcaagcc aacgccactt    60
atccagtgaa ccact                                                    75

<210> SEQ ID NO 1198
<211> LENGTH: 75
<212> TYPE: DNA
<213> ORGANISM: Pan troglodytes

<400> SEQUENCE: 1198
atcacgaaaa aaactctacc tctccatgct aatttccctc caaatctcct taattataac    60
attctcggcc acaga                                                    75

<210> SEQ ID NO 1199
<211> LENGTH: 75
<212> TYPE: DNA
<213> ORGANISM: Homo sapiens

<400> SEQUENCE: 1199
atcacgaaaa aaactctacc tctctatact aatctcccta caaatctcct taattataac    60
attcacagcc acaga                                                    75

<210> SEQ ID NO 1200
<211> LENGTH: 75
<212> TYPE: DNA
<213> ORGANISM: Pan troglodytes

<400> SEQUENCE: 1200
gctaattata ttttatatct tcttcgaaac cacacttatc cccaccctgg ctatcatcac    60
ccgatggggt aacca    75

<210> SEQ ID NO 1201
<211> LENGTH: 75
<212> TYPE: DNA
<213> ORGANISM: Homo sapiens

<400> SEQUENCE: 1201
actaatcata ttttatatct tcttcgaaac cacacttatc cccaccttgg ctatcatcac    60
ccgatgaggc aacca    75

<210> SEQ ID NO 1202
<211> LENGTH: 75
<212> TYPE: DNA
<213> ORGANISM: Pan troglodytes

<400> SEQUENCE: 1202
accagaacgc ctgaacgcag gtacatactt cctattctat accctagtag gctccctccc    60
cctactcatc gcact    75

<210> SEQ ID NO 1203
<211> LENGTH: 75
<212> TYPE: DNA
<213> ORGANISM: Homo sapiens

<400> SEQUENCE: 1203
gccagaacgc ctgaacgcag gcacatactt cctattctac accctagtag gctcccttcc    60
cctactcatc gcact    75

<210> SEQ ID NO 1204
<211> LENGTH: 75
<212> TYPE: DNA
<213> ORGANISM: Pan troglodytes

<400> SEQUENCE: 1204
aatctatacc cacaacaccc taggctcact aaatatccta ttactcactc ttacaaccca    60
agaactatca aacac    75

<210> SEQ ID NO 1205
<211> LENGTH: 75
<212> TYPE: DNA
<213> ORGANISM: Homo sapiens

<400> SEQUENCE: 1205
aatttacact cacaacaccc taggctcact aaacattcta ctactcactc tcactgccca    60
agaactatca aactc    75

<210> SEQ ID NO 1206
<211> LENGTH: 75
<212> TYPE: DNA
<213> ORGANISM: Pan troglodytes

<400> SEQUENCE: 1206

```
ctgagccaac aacttaatat gactagcgta cacgatggct ttcatggtaa aaataccctt    60
ttacggactc cacct                                                    75

<210> SEQ ID NO 1207
<211> LENGTH: 75
<212> TYPE: DNA
<213> ORGANISM: Homo sapiens

<400> SEQUENCE: 1207
ctgagccaac aacttaatat gactagctta cacaatagct tttatagtaa agatacctct    60
ttacggactc cactt                                                    75

<210> SEQ ID NO 1208
<211> LENGTH: 75
<212> TYPE: DNA
<213> ORGANISM: Pan troglodytes

<400> SEQUENCE: 1208
atgactccct aaagcccatg tcgaagcccc tattgccggg tcaatggtac ttgctgcagt    60
actcttaaaa ttagg                                                    75

<210> SEQ ID NO 1209
<211> LENGTH: 75
<212> TYPE: DNA
<213> ORGANISM: Homo sapiens

<400> SEQUENCE: 1209
atgactccct aaagcccatg tcgaagcccc catcgctggg tcaatagtac ttgccgcagt    60
actcttaaaa ctagg                                                    75

<210> SEQ ID NO 1210
<211> LENGTH: 75
<212> TYPE: DNA
<213> ORGANISM: Pan troglodytes

<400> SEQUENCE: 1210
tggctatggc ataatacgcc tcacactcat cctcaacccc ctaacaaaac atatagccta    60
tcccttcctc atgtt                                                    75

<210> SEQ ID NO 1211
<211> LENGTH: 75
<212> TYPE: DNA
<213> ORGANISM: Homo sapiens

<400> SEQUENCE: 1211
cggctatggt ataatacgcc tcacactcat tctcaacccc ctgacaaaac acatagccta    60
ccccttcctt gtact                                                    75

<210> SEQ ID NO 1212
<211> LENGTH: 75
<212> TYPE: DNA
<213> ORGANISM: Pan troglodytes

<400> SEQUENCE: 1212
gtccttatga ggtataatca taacaagctc catctgcctg cgacaaacag acctaaaatc    60
gctcattgca taccc                                                    75

<210> SEQ ID NO 1213
```

```
<211> LENGTH: 75
<212> TYPE: DNA
<213> ORGANISM: Homo sapiens

<400> SEQUENCE: 1213
atccctatga ggcataatta taacaagctc catctgccta cgacaaacag acctaaaatc      60
gctcattgca tactc                                                      75

<210> SEQ ID NO 1214
<211> LENGTH: 75
<212> TYPE: DNA
<213> ORGANISM: Pan troglodytes

<400> SEQUENCE: 1214
ttcagtcagc cacatagccc tcgtagtaac agccattctc atccaaaccc cctgaagctt      60
caccggcgca attat                                                      75

<210> SEQ ID NO 1215
<211> LENGTH: 75
<212> TYPE: DNA
<213> ORGANISM: Homo sapiens

<400> SEQUENCE: 1215
ttcaatcagc cacatagccc tcgtagtaac agccattctc atccaaaccc cctgaagctt      60
caccggcgca gtcat                                                      75

<210> SEQ ID NO 1216
<211> LENGTH: 75
<212> TYPE: DNA
<213> ORGANISM: Pan troglodytes

<400> SEQUENCE: 1216
cctcataatc gcccacggac ttacatcctc attattatcc tgcctagcaa actcaaatta      60
tgaacgcacc cacag                                                      75

<210> SEQ ID NO 1217
<211> LENGTH: 75
<212> TYPE: DNA
<213> ORGANISM: Homo sapiens

<400> SEQUENCE: 1217
tctcataatc gcccacgggc ttacatcctc attactattc tgcctagcaa actcaaacta      60
cgaacgcact cacag                                                      75

<210> SEQ ID NO 1218
<211> LENGTH: 75
<212> TYPE: DNA
<213> ORGANISM: Pan troglodytes

<400> SEQUENCE: 1218
tcgcatcata attctctccc aaggacttca aactctactc ccactaatag cctttttgatg    60 actcctggca agcct                                                      75

<210> SEQ ID NO 1219
<211> LENGTH: 75
<212> TYPE: DNA
<213> ORGANISM: Homo sapiens

<400> SEQUENCE: 1219
tcgcatcata atcctctctc aaggacttca aactctactc ccactaatag cttttttgatg    60
```

```
acttctagca agcct                                                            75

<210> SEQ ID NO 1220
<211> LENGTH: 75
<212> TYPE: DNA
<213> ORGANISM: Pan troglodytes

<400> SEQUENCE: 1220
cgctaacctc gccctacccc ctaccattaa tctcctaggg gaactctccg tgctagtaac          60
ctcattctcc tgatc                                                            75

<210> SEQ ID NO 1221
<211> LENGTH: 75
<212> TYPE: DNA
<213> ORGANISM: Homo sapiens

<400> SEQUENCE: 1221
cgctaacctc gccttacccc ccactattaa cctactggga gaactctctg tgctagtaac          60
cacgttctcc tgatc                                                            75

<210> SEQ ID NO 1222
<211> LENGTH: 75
<212> TYPE: DNA
<213> ORGANISM: Pan troglodytes

<400> SEQUENCE: 1222
aaataccact ctcctactca caggattcaa catactaatc acagccctgt actccctcta          60
catgtttacc acaac                                                            75

<210> SEQ ID NO 1223
<211> LENGTH: 75
<212> TYPE: DNA
<213> ORGANISM: Homo sapiens

<400> SEQUENCE: 1223
aaatatcact ctcctactta caggactcaa catactagtc acagccctat actccctcta          60
catatttacc acaac                                                            75

<210> SEQ ID NO 1224
<211> LENGTH: 75
<212> TYPE: DNA
<213> ORGANISM: Pan troglodytes

<400> SEQUENCE: 1224
acaatgaggc tcactcaccc accacattaa tagcataaag ccctcattca cacgagaaaa          60
cactctcata ttttt                                                            75

<210> SEQ ID NO 1225
<211> LENGTH: 75
<212> TYPE: DNA
<213> ORGANISM: Homo sapiens

<400> SEQUENCE: 1225
acaatggggc tcactcaccc accacattaa caacataaaa ccctcattca cacgagaaaa          60
caccctcatg ttcat                                                            75

<210> SEQ ID NO 1226
<211> LENGTH: 75
<212> TYPE: DNA
```

<213> ORGANISM: Pan troglodytes

<400> SEQUENCE: 1226

```
acacctatcc cccatcctcc ttctatccct caatcctgat atcatcactg gattcacctc    60
ctgtaaatat agttt                                                     75
```

<210> SEQ ID NO 1227
<211> LENGTH: 75
<212> TYPE: DNA
<213> ORGANISM: Homo sapiens

<400> SEQUENCE: 1227

```
acacctatcc cccattctcc tcctatccct caaccccgac atcattaccg ggttttcctc    60
ttgtaaatat agttt                                                     75
```

<210> SEQ ID NO 1228
<211> LENGTH: 75
<212> TYPE: DNA
<213> ORGANISM: Pan troglodytes

<400> SEQUENCE: 1228

```
aaccaaaaca tcagattgtg aatctgacaa cagaggctca cgacccctta tttaccgaga    60
aagcttataa gaact                                                     75
```

<210> SEQ ID NO 1229
<211> LENGTH: 75
<212> TYPE: DNA
<213> ORGANISM: Homo sapiens

<400> SEQUENCE: 1229

```
aaccaaaaca tcagattgtg aatctgacaa cagaggctta cgacccctta tttaccgaga    60
aagctcacaa gaact                                                     75
```

<210> SEQ ID NO 1230
<211> LENGTH: 75
<212> TYPE: DNA
<213> ORGANISM: Pan troglodytes

<400> SEQUENCE: 1230

```
gctaactcgt attcccatgc ctaacaacat ggctttctca acttttaaag gataacagtt    60
atccattggt cttag                                                     75
```

<210> SEQ ID NO 1231
<211> LENGTH: 75
<212> TYPE: DNA
<213> ORGANISM: Homo sapiens

<400> SEQUENCE: 1231

```
gctaactcat gccccatgt ctaacaacat ggctttctca acttttaaag gataacagct     60
atccattggt cttag                                                     75
```

<210> SEQ ID NO 1232
<211> LENGTH: 75
<212> TYPE: DNA
<213> ORGANISM: Pan troglodytes

<400> SEQUENCE: 1232

```
gccccaaaaa ttttggtgca actccaaata aaagtaataa ccatgtatgc taccataacc    60
accttagccc taact                                                     75
```

<210> SEQ ID NO 1233
<211> LENGTH: 75
<212> TYPE: DNA
<213> ORGANISM: Homo sapiens

<400> SEQUENCE: 1233
gccccaaaaa ttttggtgca actccaaata aaagtaataa ccatgcacac tactataacc    60
accctaaccc tgact    75

<210> SEQ ID NO 1234
<211> LENGTH: 75
<212> TYPE: DNA
<213> ORGANISM: Pan troglodytes

<400> SEQUENCE: 1234
tccttaattc ccccatcct cggcgccctc attaaccta acaaaaaaaa ctcatacccc    60
cattacgtga aatcc    75

<210> SEQ ID NO 1235
<211> LENGTH: 75
<212> TYPE: DNA
<213> ORGANISM: Homo sapiens

<400> SEQUENCE: 1235
tccctaattc ccccatcct taccaccctc gttaaccta acaaaaaaaa ctcatacccc    60
cattatgtaa aatcc    75

<210> SEQ ID NO 1236
<211> LENGTH: 75
<212> TYPE: DNA
<213> ORGANISM: Pan troglodytes

<400> SEQUENCE: 1236
attatcgcat ccacctttat cattagcctt ttccccacaa caatattcat atgcctagac    60
caagaaacta ttatc    75

<210> SEQ ID NO 1237
<211> LENGTH: 75
<212> TYPE: DNA
<213> ORGANISM: Homo sapiens

<400> SEQUENCE: 1237
attgtcgcat ccacctttat tatcagtctc ttccccacaa caatattcat gtgcctagac    60
caagaagtta ttatc    75

<210> SEQ ID NO 1238
<211> LENGTH: 75
<212> TYPE: DNA
<213> ORGANISM: Pan troglodytes

<400> SEQUENCE: 1238
tcgaactgac actgagcaac aacccaaaca acccaactct ccctgagctt taaactagac    60
tatttctcca taaca    75

<210> SEQ ID NO 1239
<211> LENGTH: 75
<212> TYPE: DNA
<213> ORGANISM: Homo sapiens

```
<400> SEQUENCE: 1239
tcgaactgac actgagccac aacccaaaca acccagctct ccctaagctt caaactagac      60
tacttctcca taata                                                      75

<210> SEQ ID NO 1240
<211> LENGTH: 75
<212> TYPE: DNA
<213> ORGANISM: Pan troglodytes

<400> SEQUENCE: 1240
tttatccccg tagcactgtt cgttacatga tccatcatag aattctcact atgatatata      60
gactcagacc ccaac                                                      75

<210> SEQ ID NO 1241
<211> LENGTH: 75
<212> TYPE: DNA
<213> ORGANISM: Homo sapiens

<400> SEQUENCE: 1241
ttcatccctg tagcattgtt cgttacatgg tccatcatag aattctcact gtgatatata      60
aactcagacc caaac                                                      75

<210> SEQ ID NO 1242
<211> LENGTH: 75
<212> TYPE: DNA
<213> ORGANISM: Pan troglodytes

<400> SEQUENCE: 1242
atcaaccaat tcttcaaata cttacttatc ttcctaatta ctatactaat cctagtcacc      60
gctaacaacc tattc                                                      75

<210> SEQ ID NO 1243
<211> LENGTH: 75
<212> TYPE: DNA
<213> ORGANISM: Homo sapiens

<400> SEQUENCE: 1243
attaatcagt tcttcaaata tctactcatc ttcctaatta ccatactaat cttagttacc      60
gctaacaacc tattc                                                      75

<210> SEQ ID NO 1244
<211> LENGTH: 75
<212> TYPE: DNA
<213> ORGANISM: Pan troglodytes

<400> SEQUENCE: 1244
caactcttca tcggctgaga aggcgtagga attatatcct ttctactcat tagctgatgg      60
tacgcccgaa cagat                                                      75

<210> SEQ ID NO 1245
<211> LENGTH: 75
<212> TYPE: DNA
<213> ORGANISM: Homo sapiens

<400> SEQUENCE: 1245
caactgttca tcggctgaga gggcgtagga attatatcct tcttgctcat cagttgatga      60
tacgcccgag cagat                                                      75
```

```
<210> SEQ ID NO 1246
<211> LENGTH: 75
<212> TYPE: DNA
<213> ORGANISM: Pan troglodytes

<400> SEQUENCE: 1246
gccaacacag cagccatcca agcaatccta tataaccgta tcggtgatat tggttttgtc    60
ctagccctag catga                                                    75

<210> SEQ ID NO 1247
<211> LENGTH: 75
<212> TYPE: DNA
<213> ORGANISM: Homo sapiens

<400> SEQUENCE: 1247
gccaacacag cagccattca agcaatccta tacaaccgta tcggcgatat cggtttcatc    60
ctcgccttag catga                                                    75

<210> SEQ ID NO 1248
<211> LENGTH: 75
<212> TYPE: DNA
<213> ORGANISM: Pan troglodytes

<400> SEQUENCE: 1248
tttctcctac actccaactc atgagatcca caacaaataa tcctcctaag tactaataca    60
gaccttactc cacta                                                    75

<210> SEQ ID NO 1249
<211> LENGTH: 75
<212> TYPE: DNA
<213> ORGANISM: Homo sapiens

<400> SEQUENCE: 1249
tttatcctac actccaactc atgagaccca caacaaatag cccttctaaa cgctaatcca    60
agcctcaccc cacta                                                    75

<210> SEQ ID NO 1250
<211> LENGTH: 75
<212> TYPE: DNA
<213> ORGANISM: Pan troglodytes

<400> SEQUENCE: 1250
ctaggcttcc tcctagcagc agcaggcaaa tcagctcaac taggccttca cccctgactc    60
ccctcagcca tagaa                                                    75

<210> SEQ ID NO 1251
<211> LENGTH: 75
<212> TYPE: DNA
<213> ORGANISM: Homo sapiens

<400> SEQUENCE: 1251
ctaggcctcc tcctagcagc agcaggcaaa tcagcccaat taggtctcca ccectgactc    60 ccctcagcca tagaa                                                    75

<210> SEQ ID NO 1252
<211> LENGTH: 75
<212> TYPE: DNA
<213> ORGANISM: Pan troglodytes

<400> SEQUENCE: 1252
```

```
ggccctaccc ctgtttcagc cctactccac tcaagcacca tagtcgtagc aggaatcttc    60
ctactcatcc gcttc                                                     75

<210> SEQ ID NO 1253
<211> LENGTH: 75
<212> TYPE: DNA
<213> ORGANISM: Homo sapiens

<400> SEQUENCE: 1253
ggccccaccc cagtctcagc cctactccac tcaagcacta tagttgtagc aggaatcttc    60
ttactcatcc gcttc                                                     75

<210> SEQ ID NO 1254
<211> LENGTH: 75
<212> TYPE: DNA
<213> ORGANISM: Pan troglodytes

<400> SEQUENCE: 1254
taccccctag cagagaataa cccactaatc caaactctca cgctatgcct aggcgctatc    60
accaccctat tcgca                                                     75

<210> SEQ ID NO 1255
<211> LENGTH: 75
<212> TYPE: DNA
<213> ORGANISM: Homo sapiens

<400> SEQUENCE: 1255 cacccctag cagaaaatag cccactaatc caaactctaa cactatgctt aggcgctatc     60
accactctgt tcgca                                                     75

<210> SEQ ID NO 1256
<211> LENGTH: 75
<212> TYPE: DNA
<213> ORGANISM: Pan troglodytes

<400> SEQUENCE: 1256
gcagtctgcg ccctcacaca aaatgacatc aaaaaaatcg tggccttctc cacttcaagc    60
caactaggac tcata                                                     75

<210> SEQ ID NO 1257
<211> LENGTH: 75
<212> TYPE: DNA
<213> ORGANISM: Homo sapiens

<400> SEQUENCE: 1257
gcagtctgcg cccttacaca aaatgacatc aaaaaaatcg tagccttctc cacttcaagt    60
caactaggac tcata                                                     75

<210> SEQ ID NO 1258
<211> LENGTH: 75
<212> TYPE: DNA
<213> ORGANISM: Pan troglodytes

<400> SEQUENCE: 1258
atagttacaa tcggtatcaa ccaaccacac ctagcattcc ttcacatctg cacccacgct    60
ttcttcaaag ccata                                                     75

<210> SEQ ID NO 1259
<211> LENGTH: 75
```

```
<212> TYPE: DNA
<213> ORGANISM: Homo sapiens

<400> SEQUENCE: 1259
atagttacaa tcggcatcaa ccaaccacac ctagcattcc tgcacatctg tacccacgcc    60
ttcttcaaag ccata                                                    75

<210> SEQ ID NO 1260
<211> LENGTH: 75
<212> TYPE: DNA
<213> ORGANISM: Pan troglodytes

<400> SEQUENCE: 1260
ctattcatat gctccggatc cattattcac aacctcaata atgagcaaga cattcgaaaa    60
ataggaggat tactc                                                    75

<210> SEQ ID NO 1261
<211> LENGTH: 75
<212> TYPE: DNA
<213> ORGANISM: Homo sapiens

<400> SEQUENCE: 1261
ctatttatgt gctccgggtc catcatccac aaccttaaca atgaacaaga tattcgaaaa    60
ataggaggac tactc                                                    75

<210> SEQ ID NO 1262
<211> LENGTH: 75
<212> TYPE: DNA
<213> ORGANISM: Pan troglodytes

<400> SEQUENCE: 1262
aaaaccatac ccctcacttc aacctccctc accattggga gcctagcatt agcaggaata    60
cccttcctca caggt                                                    75

<210> SEQ ID NO 1263
<211> LENGTH: 75
<212> TYPE: DNA
<213> ORGANISM: Homo sapiens

<400> SEQUENCE: 1263
aaaaccatac ctctcacttc aacctccctc accattggca gcctagcatt agcaggaata    60
cctttcctca caggt                                                    75

<210> SEQ ID NO 1264
<211> LENGTH: 75
<212> TYPE: DNA
<213> ORGANISM: Pan troglodytes

<400> SEQUENCE: 1264
ttctactcca aagacctcat catcgaaacc gctaacatat catacacaaa cgcctgagcc    60
ctatctatta ctctc                                                    75

<210> SEQ ID NO 1265
<211> LENGTH: 75
<212> TYPE: DNA
<213> ORGANISM: Homo sapiens

<400> SEQUENCE: 1265
ttctactcca aagaccacat catcgaaacc gcaaacatat catacacaaa cgcctgagcc    60
```
ctatctatta ctctc                                                          75

<210> SEQ ID NO 1266
<211> LENGTH: 75
<212> TYPE: DNA
<213> ORGANISM: Pan troglodytes

<400> SEQUENCE: 1266
atcgccacct ctctgacaag cgcctacagc acccgaataa tcctcctcac cctaacaggt    60
caacctcgct tccca                                                          75

<210> SEQ ID NO 1267
<211> LENGTH: 75
<212> TYPE: DNA
<213> ORGANISM: Homo sapiens

<400> SEQUENCE: 1267
atcgctacct ccctgacaag cgcctatagc actcgaataa ttcttctcac cctaacaggt    60
caacctcgct tcccc                                                          75

<210> SEQ ID NO 1268
<211> LENGTH: 75
<212> TYPE: DNA
<213> ORGANISM: Pan troglodytes

<400> SEQUENCE: 1268
accctcacca acattaacga aaacaacccc actctgttaa atcccattaa acgcctaacc    60
attggaagct tattt                                                          75

<210> SEQ ID NO 1269
<211> LENGTH: 75
<212> TYPE: DNA
<213> ORGANISM: Homo sapiens

<400> SEQUENCE: 1269
acccttacta acattaacga aaataacccc accctactaa accccattaa acgcctggca    60
gccggaagcc tattc                                                          75

<210> SEQ ID NO 1270
<211> LENGTH: 75
<212> TYPE: DNA
<213> ORGANISM: Homo sapiens

<400> SEQUENCE: 1270
gcaggatttc tcattactaa caacatttcc cccgcatccc ccttccaaac aacaatcccc    60
ctctacctaa aactc                                                          75

<210> SEQ ID NO 1271
<211> LENGTH: 75
<212> TYPE: DNA
<213> ORGANISM: Pan troglodytes

<400> SEQUENCE: 1271
acagccctag gcgttacttc cctaggactt ctaacagccc tagacctcaa ttacctaacc    60
agcaagctca aaata                                                          75

<210> SEQ ID NO 1272
<211> LENGTH: 75
<212> TYPE: DNA
<213> ORGANISM: Homo sapiens

<400> SEQUENCE: 1272
acagccctcg ctgtcacttt cctaggactt ctaacagccc tagacctcaa ctacctaacc    60
aacaaactta aaata                                                     75

<210> SEQ ID NO 1273
<211> LENGTH: 75
<212> TYPE: DNA
<213> ORGANISM: Pan troglodytes

<400> SEQUENCE: 1273
aaatccccac tatatacatt tcacttctct aatatactcg gattctaccc taacattata    60
caccgctcga tcccc                                                     75

<210> SEQ ID NO 1274
<211> LENGTH: 75
<212> TYPE: DNA
<213> ORGANISM: Homo sapiens

<400> SEQUENCE: 1274
aaatccccac tatgcacatt ttatttctcc aacatactcg gattctaccc tagcatcaca    60
caccgcacaa tcccc                                                     75

<210> SEQ ID NO 1275
<211> LENGTH: 75
<212> TYPE: DNA
<213> ORGANISM: Pan troglodytes

<400> SEQUENCE: 1275
tatctaggcc ttcttacaag ccaaaaccta cccctacttc ttctagacct gacctgacta    60
gagaaactat tacct                                                     75

<210> SEQ ID NO 1276
<211> LENGTH: 75
<212> TYPE: DNA
<213> ORGANISM: Homo sapiens

<400> SEQUENCE: 1276
tatctaggcc ttcttacgag ccaaaacctg cccctactcc tcctagacct aacctgacta    60
gaaaagctat tacct                                                     75

<210> SEQ ID NO 1277
<211> LENGTH: 75
<212> TYPE: DNA
<213> ORGANISM: Pan troglodytes

<400> SEQUENCE: 1277
aaaacaattt cacagtacca aatctccgct tccattacca cctcaaccca aaaaggcatg    60
atcaaacttt atttc                                                     75

<210> SEQ ID NO 1278
<211> LENGTH: 75
<212> TYPE: DNA
<213> ORGANISM: Homo sapiens

<400> SEQUENCE: 1278
aaaacaattt cacagcacca aatctccacc tccatcatca cctcaaccca aaaaggcata    60
attaaacttt acttc                                                     75

<210> SEQ ID NO 1279
<211> LENGTH: 75
<212> TYPE: DNA
<213> ORGANISM: Pan troglodytes

<400> SEQUENCE: 1279
ctctcttttt tcttccctct catcttaacc ttactcctaa tcacataacc tattcccccg    60
agcaatctca atcac    75

<210> SEQ ID NO 1280
<211> LENGTH: 75
<212> TYPE: DNA
<213> ORGANISM: Homo sapiens

<400> SEQUENCE: 1280
ctctctttct tcttcccact catcctaacc ctactcctaa tcacataacc tattcccccg    60
agcaatctca attac    75

<210> SEQ ID NO 1281
<211> LENGTH: 75
<212> TYPE: DNA
<213> ORGANISM: Pan troglodytes

<400> SEQUENCE: 1281
aatgtataca ccaacaaaca atgtccaacc agtaactact actaaccaac gcccataatc    60
atataaggcc cccgc    75

<210> SEQ ID NO 1282
<211> LENGTH: 75
<212> TYPE: DNA
<213> ORGANISM: Homo sapiens

<400> SEQUENCE: 1282
aatatataca ccaacaaaca atgttcaacc agtaactact actaatcaac gcccataatc    60
atacaaagcc cccgc    75

<210> SEQ ID NO 1283
<211> LENGTH: 75
<212> TYPE: DNA
<213> ORGANISM: Pan troglodytes

<400> SEQUENCE: 1283
accaatagga tcctcccgaa tcagccctgg cccctcccct tcataaatta ttcaacttcc    60
cacgctatta aaatt    75

<210> SEQ ID NO 1284
<211> LENGTH: 75
<212> TYPE: DNA
<213> ORGANISM: Homo sapiens

<400> SEQUENCE: 1284
accaatagga tcctcccgaa tcaaccctga cccctctcct tcataaatta ttcagcttcc    60
tacactatta aagtt    75

<210> SEQ ID NO 1285
<211> LENGTH: 75
<212> TYPE: DNA
<213> ORGANISM: Pan troglodytes

<400> SEQUENCE: 1285

```
taccacaacc accatcccat catacccttt tacccataac actaatccta cctccatcgc    60
cagtcctact aaaac                                                     75

<210> SEQ ID NO 1286
<211> LENGTH: 75
<212> TYPE: DNA
<213> ORGANISM: Homo sapiens

<400> SEQUENCE: 1286
taccacaacc accaccccat catactcttt cacccacagc accaatccta cctccatcgc    60
taaccccact aaaac                                                     75

<210> SEQ ID NO 1287
<211> LENGTH: 75
<212> TYPE: DNA
<213> ORGANISM: Pan troglodytes

<400> SEQUENCE: 1287
actaaccaaa acctcaaccc ctgaccccca tgcctcagga tactcctcaa tagccatagc    60
cgtagtatac ccaaa                                                     75

<210> SEQ ID NO 1288
<211> LENGTH: 75
<212> TYPE: DNA
<213> ORGANISM: Homo sapiens

<400> SEQUENCE: 1288
actcaccaag acctcaaccc ctgaccccca tgcctcagga tactcctcaa tagccatcgc    60
tgtagtatat ccaaa                                                     75

<210> SEQ ID NO 1289
<211> LENGTH: 75
<212> TYPE: DNA
<213> ORGANISM: Pan troglodytes

<400> SEQUENCE: 1289
aacaaccatt attccccca aataaattaa aaaaaccatt aaacctatat aacctccccc     60
ataattcaaa atgat                                                     75

<210> SEQ ID NO 1290
<211> LENGTH: 75
<212> TYPE: DNA
<213> ORGANISM: Homo sapiens

<400> SEQUENCE: 1290
gacaaccatc attccccta aataaattaa aaaactatt aaacccatat aacctccccc      60
aaaattcaga ataat                                                     75

<210> SEQ ID NO 1291
<211> LENGTH: 75
<212> TYPE: DNA
<213> ORGANISM: Pan troglodytes

<400> SEQUENCE: 1291
ggcacaccca actacaccac taacaatcaa tactaaaccc ccataaatgg gagaaggctt    60
agaagaaaac cccac                                                     75

<210> SEQ ID NO 1292
```

```
<211> LENGTH: 75
<212> TYPE: DNA
<213> ORGANISM: Homo sapiens

<400> SEQUENCE: 1292
aacacacccg accacaccgc taacaatcaa tactaaaccc ccataaatag gagaaggctt    60
agaagaaaac cccac                                                    75

<210> SEQ ID NO 1293
<211> LENGTH: 75
<212> TYPE: DNA
<213> ORGANISM: Pan troglodytes

<400> SEQUENCE: 1293
aaaccctatc actaaactca cactcaataa aaataaagca tatgtcatta ttctcgcacg    60
gactacaacc acgac                                                    75

<210> SEQ ID NO 1294
<211> LENGTH: 75
<212> TYPE: DNA
<213> ORGANISM: Homo sapiens

<400> SEQUENCE: 1294
aaaccccatt actaaaccca cactcaacag aaacaaagca tacatcatta ttctcgcacg    60
gactacaacc acgac                                                    75

<210> SEQ ID NO 1295
<211> LENGTH: 75
<212> TYPE: DNA
<213> ORGANISM: Pan troglodytes

<400> SEQUENCE: 1295
caatgatatg aaaaccatc gttgtatttc aactacaaga acaccaatga ccccgacacg     60
caaaattaac ccact                                                    75

<210> SEQ ID NO 1296
<211> LENGTH: 75
<212> TYPE: DNA
<213> ORGANISM: Homo sapiens

<400> SEQUENCE: 1296
caatgatatg aaaaccatc gttgtatttc aactacaaga acaccaatga ccccaatacg     60
caaaactaac ccct                                                     75

<210> SEQ ID NO 1297
<211> LENGTH: 75
<212> TYPE: DNA
<213> ORGANISM: Pan troglodytes

<400> SEQUENCE: 1297
aataaaatta attaatcact catttatcga cctcccaccc ccatccaaca tttccgcatg    60
atggaacttc ggctc                                                    75

<210> SEQ ID NO 1298
<211> LENGTH: 75
<212> TYPE: DNA
<213> ORGANISM: Homo sapiens

<400> SEQUENCE: 1298
aataaaatta attaaccact cattcatcga cctccccacc ccatccaaca tctccgcatg    60
```

```
atgaaacttc ggctc                                                     75

<210> SEQ ID NO 1299
<211> LENGTH: 75
<212> TYPE: DNA
<213> ORGANISM: Pan troglodytes

<400> SEQUENCE: 1299
acttctcggc gcctgcctaa tccttcaaat taccacagga ttattcctag ctatacacta   60
ctcaccagac gcctc                                                     75

<210> SEQ ID NO 1300
<211> LENGTH: 75
<212> TYPE: DNA
<213> ORGANISM: Homo sapiens

<400> SEQUENCE: 1300
actccttggc gcctgcctga tcctccaaat caccacagga ctattcctag ccatgcacta   60
ctcaccagac gcctc                                                     75

<210> SEQ ID NO 1301
<211> LENGTH: 75
<212> TYPE: DNA
<213> ORGANISM: Pan troglodytes

<400> SEQUENCE: 1301
aaccgccttc tcgtcgatcg cccacatcac ccgagacgta aactatggtt ggatcatccg   60
ctacctccac gctaa                                                     75

<210> SEQ ID NO 1302
<211> LENGTH: 75
<212> TYPE: DNA
<213> ORGANISM: Homo sapiens

<400> SEQUENCE: 1302
aaccgccttt tcatcaatcg cccacatcac tcgagacgta aattatggct gaatcatccg   60
ctaccttcac gccaa                                                     75

<210> SEQ ID NO 1303
<211> LENGTH: 75
<212> TYPE: DNA
<213> ORGANISM: Pan troglodytes

<400> SEQUENCE: 1303
cggcgcctca atatttttta tctgcctctt cctacacatc ggccgaggtc tatattacgg   60
ctcatttctc tacct                                                     75

<210> SEQ ID NO 1304
<211> LENGTH: 75
<212> TYPE: DNA
<213> ORGANISM: Homo sapiens

<400> SEQUENCE: 1304
tggcgcctca atattcttta tctgcctctt cctacacatc gggcgaggcc tatattacgg   60
atcatttctc tactc                                                     75

<210> SEQ ID NO 1305
<211> LENGTH: 75
<212> TYPE: DNA
```

<213> ORGANISM: Pan troglodytes

<400> SEQUENCE: 1305
agaaacctga aacattggca ttatcctctt gctcacaacc atagcaacag cctttatggg     60
ctatgtcctc ccatg     75

<210> SEQ ID NO 1306
<211> LENGTH: 75
<212> TYPE: DNA
<213> ORGANISM: Homo sapiens

<400> SEQUENCE: 1306
agaaacctga aacatcggca ttatcctcct gcttgcaact atagcaacag ccttcatagg     60
ctatgtcctc ccgtg     75

<210> SEQ ID NO 1307
<211> LENGTH: 75
<212> TYPE: DNA
<213> ORGANISM: Pan troglodytes

<400> SEQUENCE: 1307
aggccaaata tccttctgag gagccacagt aattacaaac ctactgtccg ctatcccata     60
catcggaaca gacct     75

<210> SEQ ID NO 1308
<211> LENGTH: 75
<212> TYPE: DNA
<213> ORGANISM: Homo sapiens

<400> SEQUENCE: 1308
aggccaaata tcattctgag gggccacagt aattacaaac ttactatccg ccatcccata     60
cattgggaca gacct     75

<210> SEQ ID NO 1309
<211> LENGTH: 75
<212> TYPE: DNA
<213> ORGANISM: Pan troglodytes

<400> SEQUENCE: 1309
ggtccagtga gtctgaggag gctactcagt agacagccct acccttacac gattcttcac     60
cttccacttt atctt     75

<210> SEQ ID NO 1310
<211> LENGTH: 75
<212> TYPE: DNA
<213> ORGANISM: Homo sapiens

<400> SEQUENCE: 1310
agttcaatga atctgaggag gctactcagt agacagtccc accctcacac gattctttac     60
ctttcacttc atctt     75

<210> SEQ ID NO 1311
<211> LENGTH: 75
<212> TYPE: DNA
<213> ORGANISM: Pan troglodytes

<400> SEQUENCE: 1311
acccttcatc atcacagccc taacaacact tcatctccta ttcttacacg aaacaggatc     60
aaataacccc ctagg     75

<210> SEQ ID NO 1312
<211> LENGTH: 75
<212> TYPE: DNA
<213> ORGANISM: Homo sapiens

<400> SEQUENCE: 1312
gcccttcatt attgcagccc tagcaacact ccacctccta ttcttgcacg aaacgggatc    60
aaacaacccc ctagg                                                    75

<210> SEQ ID NO 1313
<211> LENGTH: 75
<212> TYPE: DNA
<213> ORGANISM: Pan troglodytes

<400> SEQUENCE: 1313
aatcacctcc cactccgaca aaattacctt ccacccctac tacacaatca aagatatcct    60
tggcttattc ctttt                                                    75

<210> SEQ ID NO 1314
<211> LENGTH: 75
<212> TYPE: DNA
<213> ORGANISM: Homo sapiens

<400> SEQUENCE: 1314
aatcacctcc cattccgata aaatcacctt ccaccctttac tacacaatca aagacgccct    60
cggcttactt ctctt                                                    75

<210> SEQ ID NO 1315
<211> LENGTH: 75
<212> TYPE: DNA
<213> ORGANISM: Pan troglodytes

<400> SEQUENCE: 1315
cctccttatc ctaatgacat taacactatt ctcaccaggc ctcctaggcg atccagacaa    60
ctatacccta gctaa                                                    75

<210> SEQ ID NO 1316
<211> LENGTH: 75
<212> TYPE: DNA
<213> ORGANISM: Homo sapiens

<400> SEQUENCE: 1316
ccttctctcc ttaatgacat taacactatt ctcaccagac ctcctaggcg acccagacaa    60
ttatacccta gccaa                                                    75

<210> SEQ ID NO 1317
<211> LENGTH: 75
<212> TYPE: DNA
<213> ORGANISM: Pan troglodytes

<400> SEQUENCE: 1317 cccccctaaac accccacccc acattaaacc cgagtgatac tttctatttg cctacacaat    60
cctccgatcc atccc                                                    75

<210> SEQ ID NO 1318
<211> LENGTH: 75
<212> TYPE: DNA
<213> ORGANISM: Homo sapiens

```
<400> SEQUENCE: 1318
ccccttaaac accctcccc acatcaagcc cgaatgatat ttcctattcg cctacacaat    60
tctccgatcc gtccc                                                    75

<210> SEQ ID NO 1319
<211> LENGTH: 75
<212> TYPE: DNA
<213> ORGANISM: Pan troglodytes

<400> SEQUENCE: 1319
caacaaacta ggaggcgtcc tcgccctact actatctatc ctaatcctaa cagcaatccc    60
tgtcctccac acatc                                                    75

<210> SEQ ID NO 1320
<211> LENGTH: 75
<212> TYPE: DNA
<213> ORGANISM: Homo sapiens

<400> SEQUENCE: 1320
taacaaacta ggaggcgtcc ttgccctatt actatccatc ctcatcctag caataatccc    60
catcctccat atatc                                                    75

<210> SEQ ID NO 1321
<211> LENGTH: 75
<212> TYPE: DNA
<213> ORGANISM: Pan troglodytes

<400> SEQUENCE: 1321
caaacaacaa agcataatat ttcgcccact aagccaactg ctttactgac tcctagccac    60
agacctcctc atcct                                                    75

<210> SEQ ID NO 1322
<211> LENGTH: 75
<212> TYPE: DNA
<213> ORGANISM: Homo sapiens

<400> SEQUENCE: 1322
caaacaacaa agcataatat ttcgcccact aagccaatca ctttattgac tcctagccgc    60
agacctcctc attct                                                    75

<210> SEQ ID NO 1323
<211> LENGTH: 75
<212> TYPE: DNA
<213> ORGANISM: Pan troglodytes

<400> SEQUENCE: 1323
aacctgaatc ggaggacaac cagtaagcta ccccttcatc accatcggac aaatagcatc    60
cgtattatac ttcac                                                    75

<210> SEQ ID NO 1324
<211> LENGTH: 75
<212> TYPE: DNA
<213> ORGANISM: Homo sapiens

<400> SEQUENCE: 1324
aacctgaatc ggaggacaac cagtaagcta ccctttacc atcattggac aagtagcatc    60
cgtactatac ttcac                                                    75
```

```
<210> SEQ ID NO 1325
<211> LENGTH: 75
<212> TYPE: DNA
<213> ORGANISM: Pan troglodytes

<400> SEQUENCE: 1325
aacaatccta atcctaatac caatcgcctc tctaatcgaa acaaaatac ttgaatgaac      60 ctgcccttgt agtat                                                     75

<210> SEQ ID NO 1326
<211> LENGTH: 75
<212> TYPE: DNA
<213> ORGANISM: Homo sapiens

<400> SEQUENCE: 1326
aacaatccta atcctaatac caactatctc cctaattgaa acaaaatac tcaaatgggc      60 ctgtccttgt agtat                                                     75

<210> SEQ ID NO 1327
<211> LENGTH: 75
<212> TYPE: DNA
<213> ORGANISM: Pan troglodytes

<400> SEQUENCE: 1327
aaactaatac accggtcttg taaaccggaa acgaaaactt tcttccaagg acaaatcaga    60
gaaaaagtaa ttaac                                                    75

<210> SEQ ID NO 1328
<211> LENGTH: 75
<212> TYPE: DNA
<213> ORGANISM: Homo sapiens

<400> SEQUENCE: 1328
aaactaatac accagtcttg taaaccggag atgaaaacct ttttccaagg acaaatcaga    60
gaaaaagtct ttaac                                                    75

<210> SEQ ID NO 1329
<211> LENGTH: 75
<212> TYPE: DNA
<213> ORGANISM: Pan troglodytes

<400> SEQUENCE: 1329
ttcaccatca gcacccaaag ctaagattct aatttaaact attctctgtt ctttcatggg    60
gaagcaaatt taggt                                                    75

<210> SEQ ID NO 1330
<211> LENGTH: 75
<212> TYPE: DNA
<213> ORGANISM: Homo sapiens

<400> SEQUENCE: 1330
tccaccatta gcacccaaag ctaagattct aatttaaact attctctgtt ctttcatggg    60
gaagcagatt tgggt                                                    75

<210> SEQ ID NO 1331
<211> LENGTH: 75
<212> TYPE: DNA
<213> ORGANISM: Homo sapiens

<400> SEQUENCE: 1331
```

```
accacccaag tattgactca cccatcaaca accgctatgt atttcgtaca ttactgccag    60
ccaccatgaa tattg                                                    75

<210> SEQ ID NO 1332
<211> LENGTH: 75
<212> TYPE: DNA
<213> ORGANISM: Homo sapiens

<400> SEQUENCE: 1332
tacggtacca taaatacttg accacctgta gtacataaaa acccaatcca catcaaaacc    60
ccctccccat gctta                                                    75

<210> SEQ ID NO 1333
<211> LENGTH: 75
<212> TYPE: DNA
<213> ORGANISM: Homo sapiens

<400> SEQUENCE: 1333
caagcaagta cagcaatcaa ccctcaacta tcacacatca actgcaactc caaagccacc    60
cctcacccac tagga                                                    75

<210> SEQ ID NO 1334
<211> LENGTH: 75
<212> TYPE: DNA
<213> ORGANISM: Pan troglodytes

<400> SEQUENCE: 1334
taccaacaga cctatctccc cttgacagaa catagtacat acaaccatac accgtacata    60
gcacattaca gtcaa                                                    75

<210> SEQ ID NO 1335
<211> LENGTH: 75
<212> TYPE: DNA
<213> ORGANISM: Homo sapiens

<400> SEQUENCE: 1335
taccaacaaa cctacccacc cttaacagta catagtacat aaagccattt accgtacata    60
gcacattaca gtcaa                                                    75

<210> SEQ ID NO 1336
<211> LENGTH: 75
<212> TYPE: DNA
<213> ORGANISM: Pan troglodytes

<400> SEQUENCE: 1336
acccctcctc gccccacgg atgctccccc tcagatagga atcccttggt caccatcctc     60
cgtgaaatca atatc                                                    75

<210> SEQ ID NO 1337
<211> LENGTH: 75
<212> TYPE: DNA
<213> ORGANISM: Homo sapiens

<400> SEQUENCE: 1337
atcccttctc gtccccatgg atgacccccc tcagataggg gtcccttgac caccatcctc    60
cgtgaaatca atatc                                                    75

<210> SEQ ID NO 1338
<211> LENGTH: 75
```

```
<212> TYPE: DNA
<213> ORGANISM: Pan troglodytes

<400> SEQUENCE: 1338
tcccgcacaa gagtgactct cctcgctccg ggcccataac atctgggggt agctaaagtg      60
aactgtatcc gacat                                                       75

<210> SEQ ID NO 1339
<211> LENGTH: 75
<212> TYPE: DNA
<213> ORGANISM: Homo sapiens

<400> SEQUENCE: 1339
ccgcacaaga gtgctactct cctcgctccg ggcccataac acttgggggt agctaaagtg      60
aactgtatcc gacat                                                       75

<210> SEQ ID NO 1340
<211> LENGTH: 75
<212> TYPE: DNA
<213> ORGANISM: Pan troglodytes

<400> SEQUENCE: 1340
gatcacaggt ctatcaccct attaaccagt cacgggagcc ttccatgcat ttggtatttt      60
cgtctggggg gtgtg                                                       75

<210> SEQ ID NO 1341
<211> LENGTH: 75
<212> TYPE: DNA
<213> ORGANISM: Homo sapiens

<400> SEQUENCE: 1341
gatcacaggt ctatcaccct attaaccact cacgggagct ctccatgcat ttggtatttt      60
cgtctggggg gtatg                                                       75

<210> SEQ ID NO 1342
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1342
acgttggatg caaggcatgc ctgtatactc                                       30

<210> SEQ ID NO 1343
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1343
acgttggatg gtaacaacgc agagctcagg                                       30

<210> SEQ ID NO 1344
<211> LENGTH: 28
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 1344
aggcctgtat actctctcct gttatcct                                              28

<210> SEQ ID NO 1345
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1345
acgttggatg gaagctcctc cttgctcttc                                            30

<210> SEQ ID NO 1346
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1346
acgttggatg ggaaaaacta gagaaagagc                                            30

<210> SEQ ID NO 1347
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1347
ggctgctgca gggcttttat ttc                                                   23

<210> SEQ ID NO 1348
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1348
acgttggatg tagaggtgat acacttaccg                                            30

<210> SEQ ID NO 1349
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1349
acgttggatg gaccaaagaa gtaaacactg                                            30

<210> SEQ ID NO 1350
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 1350
catttccctc caaacac                                                  17

<210> SEQ ID NO 1351
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1351
acgttggatg cctcccggcc acagagtgtg                                    30

<210> SEQ ID NO 1352
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1352
acgttggatg ggatgacaaa gatgccaggc                                    30

<210> SEQ ID NO 1353
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1353
cccgccctcc ctcagagcca                                               20

<210> SEQ ID NO 1354
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1354
acgttggatg aagggaacag gagtgagtg                                     29

<210> SEQ ID NO 1355
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1355
acgttggatg tcttccagtc cctgatctgg                                    30

<210> SEQ ID NO 1356
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1356
```
ttaatgccaa ccatgggata gtgtgag                                    27

<210> SEQ ID NO 1357
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1357
acgttggatg gggtttgctg aagatggcgg                                 30

<210> SEQ ID NO 1358
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1358
acgttggatg ctgctcgcca gaacactacg                                 30

<210> SEQ ID NO 1359
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1359
ggcggtatat aggctgagca agagg                                      25

<210> SEQ ID NO 1360
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1360
acgttggatg gtccctattt aaggaacaag                                 30

<210> SEQ ID NO 1361
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1361
acgttggatg ctcggcaaat cttaccccgc                                 30

<210> SEQ ID NO 1362
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1362
gtcaggcggt gcctctaata ctggt                                              25

<210> SEQ ID NO 1363
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1363
acgttggatg ggtgattttc atattgaatt g                                       31

<210> SEQ ID NO 1364
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1364
acgttggatg caccctaatc aactggcttc                                         30

<210> SEQ ID NO 1365
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1365
gacggggctt ctcccgcctt tttt                                               24

<210> SEQ ID NO 1366
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1366
acgttggatg ttttgaaaaa gtcatggagg                                         30

<210> SEQ ID NO 1367
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1367
acgttggatg tgactatatg gatgccccccc                                        30

<210> SEQ ID NO 1368
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1368
ggcttgaaac cagcttt                                                       17

<210> SEQ ID NO 1369
<211> LENGTH: 30
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 1369
acgttggatg gcacacctac accccttatc                                    30

<210> SEQ ID NO 1370
<211> LENGTH: 30
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 1370
acgttggatg gtggcgcttc caattaggtg                                    30

<210> SEQ ID NO 1371
<211> LENGTH: 21
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 1371
ctactcattc aaccaatagc c                                             21

<210> SEQ ID NO 1372
<211> LENGTH: 31
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 1372
acgttggatg ctgaaccgaa ttggtatata g                                  31

<210> SEQ ID NO 1373
<211> LENGTH: 30
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 1373
acgttggatg aggtgtgagc gatatactag                                    30

<210> SEQ ID NO 1374
<211> LENGTH: 18
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 1374
tatttaccaa atgcccct                                                 18

<210> SEQ ID NO 1375
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 1375
acgttggatg gtaatagata gggctcaggc                                      30

<210> SEQ ID NO 1376
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 1376
acgttggatg ctcacttcaa cctccctcac                                      30

<210> SEQ ID NO 1377
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 1377
ctgagtagaa acctgtgagg aa                                              22

<210> SEQ ID NO 1378
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 1378
acgttggatg caccatcctc cgtgaaatc                                       29

<210> SEQ ID NO 1379
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 1379
acgttggatg ggttaatagg gtgatagacc                                      30

<210> SEQ ID NO 1380
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 1380
gagctccggg cccataaca                                                  19

```
<210> SEQ ID NO 1381
<211> LENGTH: 29
<212> TYPE: DNA
<213> ORGANISM: Pan troglodytes

<400> SEQUENCE: 1381
aggcctgtat actctctcct gttatcctg                                    29

<210> SEQ ID NO 1382
<211> LENGTH: 29
<212> TYPE: DNA
<213> ORGANISM: Pan troglodytes

<400> SEQUENCE: 1382
aggcctgtat actctctcct gttatcctt                                    29

<210> SEQ ID NO 1383
<211> LENGTH: 24
<212> TYPE: DNA
<213> ORGANISM: Pan troglodytes

<400> SEQUENCE: 1383
ggctgctgca gggcttttat ttcg                                         24

<210> SEQ ID NO 1384
<211> LENGTH: 24
<212> TYPE: DNA
<213> ORGANISM: Pan troglodytes

<400> SEQUENCE: 1384
ggctgctgca gggcttttat ttct                                         24

<210> SEQ ID NO 1385
<211> LENGTH: 18
<212> TYPE: DNA
<213> ORGANISM: Pan troglodytes

<400> SEQUENCE: 1385
catttccctc caaacacc                                                18

<210> SEQ ID NO 1386
<211> LENGTH: 18
<212> TYPE: DNA
<213> ORGANISM: Pan troglodytes

<400> SEQUENCE: 1386
catttccctc caaacacg                                                18

<210> SEQ ID NO 1387
<211> LENGTH: 21
<212> TYPE: DNA
<213> ORGANISM: Pan troglodytes

<400> SEQUENCE: 1387
cccgccctcc ctcagagcca c                                            21

<210> SEQ ID NO 1388
<211> LENGTH: 21
<212> TYPE: DNA
<213> ORGANISM: Pan troglodytes

<400> SEQUENCE: 1388
cccgccctcc ctcagagcca g                                            21
```

<210> SEQ ID NO 1389
<211> LENGTH: 28
<212> TYPE: DNA
<213> ORGANISM: Pan troglodytes

<400> SEQUENCE: 1389
ttaatgccaa ccatgggata gtgtgaga        28

<210> SEQ ID NO 1390
<211> LENGTH: 28
<212> TYPE: DNA
<213> ORGANISM: Pan troglodytes

<400> SEQUENCE: 1390
ttaatgccaa ccatgggata gtgtgagt        28

<210> SEQ ID NO 1391
<211> LENGTH: 26
<212> TYPE: DNA
<213> ORGANISM: Pan troglodytes

<400> SEQUENCE: 1391
ggcggtatat aggctgagca agaggc        26

<210> SEQ ID NO 1392
<211> LENGTH: 26
<212> TYPE: DNA
<213> ORGANISM: Pan troglodytes

<400> SEQUENCE: 1392
ggcggtatat aggctgagca agaggt        26

<210> SEQ ID NO 1393
<211> LENGTH: 26
<212> TYPE: DNA
<213> ORGANISM: Pan troglodytes

<400> SEQUENCE: 1393
gtcaggcggt gcctctaata ctggta        26

<210> SEQ ID NO 1394
<211> LENGTH: 26
<212> TYPE: DNA
<213> ORGANISM: Pan troglodytes

<400> SEQUENCE: 1394
gtcaggcggt gcctctaata ctggtg        26

<210> SEQ ID NO 1395
<211> LENGTH: 25
<212> TYPE: DNA
<213> ORGANISM: Pan troglodytes

<400> SEQUENCE: 1395
gacggggctt ctcccgcctt ttttc        25

<210> SEQ ID NO 1396
<211> LENGTH: 25
<212> TYPE: DNA
<213> ORGANISM: Pan troglodytes

<400> SEQUENCE: 1396
gacggggctt ctcccgcctt ttttt        25

<210> SEQ ID NO 1397
<211> LENGTH: 18
<212> TYPE: DNA
<213> ORGANISM: Pan troglodytes

<400> SEQUENCE: 1397
ggcttgaaac cagcttta                                         18

<210> SEQ ID NO 1398
<211> LENGTH: 18
<212> TYPE: DNA
<213> ORGANISM: Pan troglodytes

<400> SEQUENCE: 1398
ggcttgaaac cagctttg                                         18

<210> SEQ ID NO 1399
<211> LENGTH: 22
<212> TYPE: DNA
<213> ORGANISM: Pan troglodytes

<400> SEQUENCE: 1399
ctactcattc aaccaatagc cc                                    22

<210> SEQ ID NO 1400
<211> LENGTH: 22
<212> TYPE: DNA
<213> ORGANISM: Pan troglodytes

<400> SEQUENCE: 1400
ctactcattc aaccaatagc ct                                    22

<210> SEQ ID NO 1401
<211> LENGTH: 19
<212> TYPE: DNA
<213> ORGANISM: Pan troglodytes

<400> SEQUENCE: 1401
tatttaccaa atgcccctc                                        19

<210> SEQ ID NO 1402
<211> LENGTH: 19
<212> TYPE: DNA
<213> ORGANISM: Pan troglodytes

<400> SEQUENCE: 1402
tatttaccaa atgcccctt                                        19

<210> SEQ ID NO 1403
<211> LENGTH: 23
<212> TYPE: DNA
<213> ORGANISM: Pan troglodytes

<400> SEQUENCE: 1403
ctgagtagaa acctgtgagg aaa                                   23

<210> SEQ ID NO 1404
<211> LENGTH: 23
<212> TYPE: DNA
<213> ORGANISM: Pan troglodytes

<400> SEQUENCE: 1404

```
ctgagtagaa acctgtgagg aag                                              23

<210> SEQ ID NO 1405
<211> LENGTH: 20
<212> TYPE: DNA
<213> ORGANISM: Pan troglodytes

<400> SEQUENCE: 1405
gagctccggg cccataacac                                                  20

<210> SEQ ID NO 1406
<211> LENGTH: 20
<212> TYPE: DNA
<213> ORGANISM: Pan troglodytes

<400> SEQUENCE: 1406
gagctccggg cccataacat                                                  20

<210> SEQ ID NO 1407
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1407
acgttggatg caaggcatgc ctgtatactc                                       30

<210> SEQ ID NO 1408
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1408
acgttggatg gtaacaacgc agagctcagg                                       30

<210> SEQ ID NO 1409
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1409
acgttggatg gaagctcctc cttgctcttc                                       30

<210> SEQ ID NO 1410
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1410
acgttggatg ggaaaaacta gagaaagagc                                       30

<210> SEQ ID NO 1411
<211> LENGTH: 30
<212> TYPE: DNA
<213> ORGANISM: Artificial Sequence
```

<220> FEATURE:
<223> OTHER INFORMATION: Description of Artificial Sequence: Synthetic
      primer

<400> SEQUENCE: 1411
acgttggatg tagaggtgat acacttaccg                                    30

<210> SEQ ID NO 1412
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1412
acgttggatg gaccaaagaa gtaaacactg                                    30

<210> SEQ ID NO 1413
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1413
acgttggatg cctcccggcc acagagtgtg                                    30

<210> SEQ ID NO 1414
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1414
acgttggatg ggatgacaaa gatgccaggc                                    30

<210> SEQ ID NO 1415
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1415
acgttggatg aagggaacag gagtgagtg                                     29

<210> SEQ ID NO 1416
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1416
acgttggatg tcttccagtc cctgatctgg                                    30

<210> SEQ ID NO 1417
<211> LENGTH: 30
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 1417
acgttggatg gggtttgctg aagatggcgg                                        30

<210> SEQ ID NO 1418
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1418
acgttggatg ctgctcgcca gaacactacg                                        30

<210> SEQ ID NO 1419
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1419
acgttggatg gtccctattt aaggaacaag                                        30

<210> SEQ ID NO 1420
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1420
acgttggatg ctcggcaaat cttaccccgc                                        30

<210> SEQ ID NO 1421
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1421
acgttggatg ggtgattttc atattgaatt g                                      31

<210> SEQ ID NO 1422
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1422
acgttggatg caccctaatc aactggcttc                                        30

<210> SEQ ID NO 1423
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 1423
acgttggatg ttttgaaaaa gtcatggagg                                      30

<210> SEQ ID NO 1424
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1424
acgttggatg tgactatatg gatgcccccc                                      30

<210> SEQ ID NO 1425
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1425
acgttggatg gcacacctac accccttatc                                      30

<210> SEQ ID NO 1426
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1426
acgttggatg gtggcgcttc caattaggtg                                      30

<210> SEQ ID NO 1427
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1427
acgttggatg gtaatagata gggctcaggc                                      30

<210> SEQ ID NO 1428
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1428
acgttggatg ctcacttcaa cctccctcac                                      30

<210> SEQ ID NO 1429
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1429
acgttggatg caccatcctc cgtgaaatc                29

<210> SEQ ID NO 1430
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1430
acgttggatg ggttaatagg gtgatagacc                30

<210> SEQ ID NO 1431
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1431
aggcctgtat actctctcct gttatcct                28

<210> SEQ ID NO 1432
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1432
aggcctgtat actctctcct gttatcctg                29

<210> SEQ ID NO 1433
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1433
ggctgctgca gggcttttat ttc                23

<210> SEQ ID NO 1434
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1434
ggctgctgca gggcttttat ttcg                24

<210> SEQ ID NO 1435
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 1435
catttccctc caaacac                                                  17

<210> SEQ ID NO 1436
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1436
catttccctc caaacacc                                                 18

<210> SEQ ID NO 1437
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1437
cccgccctcc ctcagagcca                                               20

<210> SEQ ID NO 1438
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1438
cccgccctcc ctcagagcca c                                             21

<210> SEQ ID NO 1439
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1439
ttaatgccaa ccatgggata gtgtgag                                       27

<210> SEQ ID NO 1440
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1440
ttaatgccaa ccatgggata gtgtgaga                                      28

<210> SEQ ID NO 1441
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1441
```
ggcggtatat aggctgagca agagg                                          25

<210> SEQ ID NO 1442
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1442
ggcggtatat aggctgagca agaggc                                         26

<210> SEQ ID NO 1443
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1443
gtcaggcggt gcctctaata ctggt                                          25

<210> SEQ ID NO 1444
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1444
gtcaggcggt gcctctaata ctggta                                         26

<210> SEQ ID NO 1445
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1445
gacggggctt ctcccgcctt tttt                                           24

<210> SEQ ID NO 1446
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1446
gacggggctt ctcccgcctt ttttc                                          25

<210> SEQ ID NO 1447
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1447

```
ggcttgaaac cagcttt                                                    17

<210> SEQ ID NO 1448
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1448
ggcttgaaac cagcttta                                                   18

<210> SEQ ID NO 1449
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1449
ctactcattc aaccaatagc c                                               21

<210> SEQ ID NO 1450
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1450
ctactcattc aaccaatagc cc                                              22

<210> SEQ ID NO 1451
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1451
ctgagtagaa acctgtgagg aa                                              22

<210> SEQ ID NO 1452
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1452
ctgagtagaa acctgtgagg aaa                                             23

<210> SEQ ID NO 1453
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1453
gagctccggg cccataaca                                                  19
```

<210> SEQ ID NO 1454
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1454
gagctccggg cccataacac                                          20

<210> SEQ ID NO 1455
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1455
aggcctgtat actctctcct gttatcctt                                29

<210> SEQ ID NO 1456
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1456
ggctgctgca gggcttttat ttct                                     24

<210> SEQ ID NO 1457
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1457
catttccctc caaacacg                                            18

<210> SEQ ID NO 1458
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1458
cccgccctcc ctcagagcca g                                        21

<210> SEQ ID NO 1459
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1459
ttaatgccaa ccatgggata gtgtgagt                                 28

<210> SEQ ID NO 1460
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1460
ggcggtatat aggctgagca agaggt                                          26

<210> SEQ ID NO 1461
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1461
gtcaggcggt gcctctaata ctggtg                                          26

<210> SEQ ID NO 1462
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1462
gacggggctt ctcccgcctt ttttt                                           25

<210> SEQ ID NO 1463
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1463
ggcttgaaac cagctttg                                                   18

<210> SEQ ID NO 1464
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1464
ctactcattc aaccaatagc ct                                              22

<210> SEQ ID NO 1465
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1465
ctgagtagaa acctgtgagg aag                                             23

```
<210> SEQ ID NO 1466
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1466
gagctccggg cccataacat                                                   20
```